US008637482B2

(12) United States Patent
Feinstein et al.

(10) Patent No.: US 8,637,482 B2
(45) Date of Patent: Jan. 28, 2014

(54) METHODS FOR TREATING CHRONIC KIDNEY DISEASE

(75) Inventors: Elena Feinstein, Rehovot (IL); Svetlana Adamsky, Gedera (IL); Shai Erlich, Belmont, CA (US); Bruce Molitoris, Indianapolis, IN (US)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

(21) Appl. No.: 13/376,766

(22) PCT Filed: Jun. 7, 2010

(86) PCT No.: PCT/US2010/037565

§ 371 (c)(1), (2), (4) Date: Feb. 22, 2012

(87) PCT Pub. No.: WO2010/144336

PCT Pub. Date: Dec. 16, 2010

(65) Prior Publication Data

US 2012/0141378 A1 Jun. 7, 2012

Related U.S. Application Data

(60) Provisional application No. 61/184,937, filed on Jun. 8, 2009, provisional application No. 61/235,381, filed on Aug. 20, 2009.

(51) Int. Cl.

| | |
|---|---|
| ***A61K 48/00*** | (2006.01) |
| ***C12Q 1/68*** | (2006.01) |
| ***C07H 21/04*** | (2006.01) |
| ***C07H 21/02*** | (2006.01) |

(52) U.S. Cl.

USPC ............... 514/44; 435/6; 536/23.1; 536/24.3; 536/24.31; 536/24.33

(58) Field of Classification Search

None

See application file for complete search history.

(56) References Cited

U.S. PATENT DOCUMENTS

| | | | |
|---|---|---|---|
| 7,842,674 | B2 | 11/2010 | Feinstein |
| 8,148,342 | B2 | 4/2012 | Feinstein |
| 2006/0069056 | A1 | 3/2006 | Feinstein |
| 2008/0085324 | A1 * | 4/2008 | Dworkin et al. .............. 424/600 |
| 2008/0090765 | A1 | 4/2008 | Schmidt-Ott et al. |
| 2008/0108583 | A1 | 5/2008 | Feinstein |
| 2008/0269156 | A1 | 10/2008 | Feinstein et al. |
| 2009/0105173 | A1 | 4/2009 | Feinstein |
| 2010/0029746 | A1 | 2/2010 | Feinstein |
| 2010/0222409 | A1 | 9/2010 | Kalinski |
| 2012/0184597 | A1 | 7/2012 | Feinstein |

FOREIGN PATENT DOCUMENTS

| | | |
|---|---|---|
| WO | WO2007/084684 | 7/2007 |
| WO | WO 2009/032915 A2 | 3/2009 |
| WO | WO20091116037 | 9/2009 |

OTHER PUBLICATIONS

Molitoris et al., (2003) "Transitioning to Therapy in Ischemic Acute Renal Failure". J Am Soc Nephrol, 14: 265-267.

Molitoris et al., (2009) "siRNA Targeted to p53 Attenuates Ischemic and Cisplatin-Induced Acute Kidney Injury". J Am Soc Nephrol, 20: 1754-1764.

International Preliminary Report on Patentability issued by the International Searching Authority (ISA/US) on Dec. 12, 2011 in connection with International Application No. PCT/US2010/037565.

Notification of Transmittal of the International Search Report and the Written Opinion of the International Searching Authority, or the Declaration, including an International Search Report and Written Opinion of the International Searching Authority, mailed Oct. 15, 2010 in connection with PCT International Application No. PCT/US2010/037565, filed Jun. 7, 2010.

Official Communication pursuant to Rules 161/162 issued on Jan. 19, 2012, in connection with European Patent Application No. 10786615.4, filed on Jun. 7, 2010.

Response to Official Communication pursuant to Rules 161/162, filed on Jul. 24, 2012, in connection with European Patent Application No. 10786615.4, filed on Jun. 7, 2010.

Amended Claims in Response to Official Communication pursuant to Rules 161/162, filed on Jul. 24, 2012, in connection with European Patent Application No. 10786615.4, filed on Jun. 7, 2010.

English translation of Office Action dated Apr. 26, 2013, issued in connection with Chinese Patent Application No. 201080028245.5, filed on Jun. 7, 2010.

English translation of Response to Office Action dated Apr. 28, 2013, as filed on Jul. 11, 2013, in connection with Chinese Patent Application No. 201080028245.5, filed on Jun. 7, 2010.

Supplementary European Search Report dated Jul. 3, 2013, issued in connection with European Patent Application No. 10786615.4.

Carol Jacobson et al., Cardiovascular Nursing Practice, Chapter 16, p. 850.

Krenitsky and Rosner, "Nutritional Support for Patients with Acute Kidney Injury: How Much Protein is Enough or Too Much?", Practical Gastroenterology, Jun. 2011, pp. 28-42.

http://www.childrenshospital.org/az/Site2937/mainpageS2937P1.html, Aug. 8, 2013.

12) http://www.patient.co.uk/doctor/acute-kidney-injury, Aug. 8, 2013.

* cited by examiner

*Primary Examiner* — Amy Bowman

(74) *Attorney, Agent, or Firm* — John P. White; Cooper & Dunham LLP

(57) ABSTRACT

The present invention relates to methods for treating chronic kidney disease (CKD) including methods for preventing or delaying onset of CKD and methods for preventing exacerbation and progression of CKD. In particular embodiments, the invention provides methods for treating a subject at risk of developing CKD comprising administering to the subject a composition comprising a) a therapeutically effective amount of at least one oligonucleotide compound which inhibits the expression of a human target gene associated with the kidney disease; and b) a pharmaceutically acceptable excipient or carrier, or mixtures thereof, thereby reducing the risk of CKD in the subject.

15 Claims, 9 Drawing Sheets high salt diet | regular diet

Tubular necrosis

Tubular dilation

Casts

Glomerular damage

Interstitial cellular infiltrate

Interstitial fibrosis

METHODS FOR TREATING CHRONIC KIDNEY DISEASE

RELATED APPLICATION

This application is a §371 national stage of PCT International Application No. PCT/US2010/037565, filed Jun. 7, 2010, claiming priority of United States Provisional Patent Applications Nos. 61/184937, filed 8 Jun. 2009 and 61/235381, filed 20 Aug. 2009, the contents of each of which are hereby incorporated by reference into this application.

Throughout this application various patents and publications are cited. The disclosures of these documents in their entireties are hereby incorporated by reference into this application to more fully describe the state of the art to which this invention pertains.

REFERENCE TO SEQUENCE LISTING

This application incorporates-by-reference nucleotide and/or amino acid sequences which are present in the file named "111207_2094_83628_Substitute_Sequence_Listing_GC .txt," which is 458 kilobytes in size, and which was created Dec. 6, 2011 in the IBM-PC machine format, having an operating system compatibility with MS-Windows, which is contained in the text file filed Dec. 7, 2011 as part of this application.

FIELD OF THE INVENTION

The present invention relates to methods for treating chronic kidney disease (CKD) including methods for preventing or delaying onset of CKD and methods for preventing exacerbation and progression of CKD. In particular embodiments, the invention provides methods for treating a subject at risk of developing CKD comprising administering to the subject a composition comprising a) a therapeutically effective amount of at least one oligonucleotide compound which inhibits the expression of a human target gene associated with the kidney disease; and b) a pharmaceutically acceptable excipient or carrier, or mixtures thereof, thereby reducing the risk of CKD in the subject.

BACKGROUND OF THE INVENTION

Chronic Kidney Disease

Chronic kidney disease (CKD) is a worldwide public health problem and is recognized as a common condition that is associated with an increased risk of cardiovascular disease and end stage renal disease (ESRD).

The Kidney Disease Outcomes Quality Initiative (K/DOQI) of the National Kidney Foundation (NKF) defines chronic kidney disease as either kidney damage or a decreased kidney glomerular filtration rate (GFR) for three or more months. Other markers of CKD are also known and used for diagnosis. In general, the destruction of renal mass with irreversible sclerosis and loss of nephrons leads to a progressive decline in GFR and eventually ESRD.

Recently, the K/DOQI published a classification of the stages of CKD, as follows:

Stage 1: Kidney damage with normal or increased GFR (>90 mL/min/1.73 $m^2$)

Stage 2: Mild reduction in GFR (60-89 mL/min/1.73 $m^2$)

Stage 3: Moderate reduction in GFR (30-59 mL/min/1.73 $m^2$)

Stage 4: Severe reduction in GFR (15-29 mL/min/1.73 $m^2$)

Stage 5: Kidney failure (GFR <15 mL/min/1.73 $m^2$ or dialysis)

In stages 1 and 2 CKD, GFR alone does not confirm the diagnosis. Other markers of kidney damage, including abnormalities in the composition of blood or urine or abnormalities in imaging tests, should be relied upon.

Pathophysiology of CKD

Approximately 1 million nephrons are present in each kidney, each contributing to the total GFR. Irrespective of the etiology of renal injury, with progressive destruction of nephrons, the kidney is able to maintain GFR by hyperfiltration and compensatory hypertrophy of the remaining healthy nephrons. This nephron adaptability allows for continued normal clearance of plasma solutes so that substances such as urea and creatinine start to show significant increases in plasma levels only after total GFR has decreased to 50%, when the renal reserve has been exhausted. The plasma creatinine value will approximately double with a 50% reduction in GFR. Therefore, a doubling in plasma creatinine from a baseline value of 0.6 mg/dL to 1.2 mg/dL in a patient actually represents a loss of 50% of functioning nephron mass.

The residual nephron hyperfiltration and hypertrophy, although beneficial for the reasons noted, is thought to represent a major cause of progressive renal dysfunction. This is believed to occur because of increased glomerular capillary pressure, which damages the capillaries and leads initially to focal and segmental glomerulosclerosis and eventually to global glomerulosclerosis. This hypothesis has been based on studies of five-sixths nephrectomized rats, which develop lesions that are similar to those observed in humans with CKD.

The two most common causes of chronic kidney disease are diabetes and hypertension. Other factors include acute insults from nephrotoxins, including radiocontrast agents, or decreased perfusion (ischemia); sepsis; Proteinuria; Increased renal ammoniagenesis with interstitial injury; Hyperlipidemia; Hyperphosphatemia with calcium phosphate deposition; Decreased levels of nitrous oxide and smoking In the United States, the incidence and prevalence of CKD is rising, with poor outcomes and high cost to the health system. Kidney disease is the ninth leading cause of death in the US. The high rate of mortality has led the US Surgeon General's mandate for America's citizenry, Healthy People 2010, to contain a chapter focused on CKD. The objectives of this chapter are to articulate goals and to provide strategies to reduce the incidence, morbidity, mortality, and health costs of chronic kidney disease in the United States. The burden of chronic kidney disease can be assessed by multiple criteria, all of which underscore the need for improved detection, treatment, and monitoring of clinical and fiscal outcomes. Reducing renal failure will require additional public health efforts, including effective preventive strategies and early detection and treatment of chronic kidney disease.

The incidence rates of end-stage renal disease (ESRD) have also increased steadily internationally since 1989. The United States has the highest incident rate of ESRD, followed by Japan. Japan has the highest prevalence per million population, followed by the US.

The mortality rates associated with hemodialysis are striking and indicate that the life expectancy of patients entering into hemodialysis is markedly shortened. At every age, patients with ESRD on dialysis have significantly increased mortality when compared with nondialysis patients and individuals without kidney disease. At age 60 years, a healthy person can expect to live for more than 20 years, whereas the life expectancy of a 60-year-old patient starting hemodialysis is closer to 4 years (Aurora and Verelli, May 21, 2009.

Chronic Renal Failure: Treatment & Medication. Emedicine. http://emedicine.medscape.com/articte/238798-treatment).

International Patent Publication Nos. WO 2006/035434, WO 2008/104978, WO 2008/106102, and WO 2009/001359 assigned to one of the assignees of the present invention relate to methods of treating acute kidney disease including acute renal failure following cardiac surgery.

Methods and compositions useful for treating CKD and for attenuating progression of CKD would be of great therapeutic value.

SUMMARY OF THE INVENTION

According to one aspect the present invention provides a method of treating or preventing kidney damage in a subject at risk of chronic kidney disease (CKD) associated with exposure to a recurrence of renal insults comprising administering to the subject a therapeutically effective dose of a compound which inhibits a target gene associated with kidney damage wherein the oligonucleotide compound is administered to the subject within 24 hours of the renal insult. In some embodiments the compound is an oligonucleotide compound. In some embodiments the oligonucleotide compound inhibits expreession of a target gene.

According to another aspect the present invention provides a method of attenuating progression of chronic kidney disease (CKD) in a subject at risk of CKD progression resulting from exposure to a recurrence of renal insults comprising administering to the subject a therapeutically effective dose of an oligonucleotide compound which down regulates expression of a target gene associated with kidney injury wherein the oligonucleotide compound is administered to the subject within 24 hours of each renal insult. In some embodiments the kidney insult results in acute renal insult including acute kidney injury (AKI).

In various embodiments a subject at risk of chronic kidney disease (CKD) or CKD progression is a subject having any one or more of Type 1 or Type 2 diabetes mellitus, high blood pressure (hypertension), high cholesterol, heart disease, liver disease, amyloidosis, Sickle cell disease, Systemic Lupus erythematosus, glomerulonephritis, polycystic kidney disease, atherosclerosis, vascular diseases such as arteritis, vasculitis, or fibromuscular dysplasia or a subject that is about to undergo radiographical examination (i.e. administration of a radiocontrast agent) or a subject that uses nephrotoxic medications, including, without being limited to, analgesics such as acetaminophen (Tylenol®) and non-steroidal anti-inflammatory drugs (NSAIDs) (e.g. ibuprofen (Motrin®, Advil®)) that can cause analgesic nephropathy when used regularly over long durations of time.

In another aspect the present invention relates to a method of attentuating the severity of kidney damage resulting from renal insult in a subject suffering from chronic kidney disease (CKD) comprising administering to the subject a therapeutically effective dose of an oligonucleotide compound which inhibits expression of a target gene associated with renal ischemia, thereby attenuating kidney damage. In some embodiments kidney damage is AKI.

In other embodiments provided is a method to prevent progression of CKD resulting from acute kidney injury or insult in a subject suffering from CKD comprising administering to the subject a therapeutically effective dose of an oligonucleotide compound which inhibits expression of a target gene associated with renal ischemia, thereby preventing progression of CKD.

In some embodiments of the methods of the present invention, the renal insult is selected from surgery including cardiovascular surgery, exposure to radiocontrast agent, myoglobinuria, ischemia/reperfusion injury, urinary tract obstruction exposure to nephrotoxins, including contrast agents including radiocontrast agents; decreased perfusion; proteinuria; increased renal ammoniagenesis with interstitial injury; hyperlipidemia; hyperphosphatemia with calcium phosphate deposition. In some embodiments the renal insult is selected from ischemia/reperfusion, sepsis and exposure to a radiocontrast agent.

In certain embodiments ischemia/reperfusion injury ensues during or following cardiovascular surgery or cardiopulmonary surgery. Myoglobinurea results from myoglobin, which acts as an endogenous nephrotoxin by both direct proximal tubule cell (PTC) injury and renal vasoconstriction. A recurrence or plurality of renal insults refers to 2, 3, 4, 5 or more renal insults of the same or different types.

In some embodiments the oligonucleotide is administered to the subject within (i.e. prior to, simultaneously with or post) 72 hours, within 48 hours, within 24 hours, within 16 hours, within 8 hours, within 4 hours pre or post renal insult and preferably at about 72 hours pre to about to about 8 hours post renal insult. In some embodiments the oligonucleotide is administered 0 to 4 hours post renal insult. In some embodiments the oligonucleotide is administered to the subject in proximity of the renal insult. in proximity refers to within one hour of renal insult, within 50, 45, 40, 35, 30, 25, 20, 15, 10, 5, 4, 3, 2 minutes or 1 minute post renal insult.

In various embodiments the oligonucleotide compound is selected from the group consisting of unmodified or chemically modified siRNA, shRNA, an aptamer, an antisense molecule, miRNA, and a ribozyme. In the presently preferred embodiments the inhibitor is chemically modified siRNA.

In some embodiments the target gene is a human gene whose expression is up regulated after renal insult. In some embodiments the target gene associated with kidney injury, kidney damage, renal ischemia is selected from a gene having an mRNA sequence set forth in Table 1, infra. A non-limiting example of target genes include p53, tumor protein p53 binding protein 2 (TP53BP2); leucine-rich repeats and death domain containing (LRDD); cytochrome b-245, alpha polypeptide (CYBA, p22phox); activating transcription factor 3 (ATF3); caspase 2, apoptosis-related cysteine peptidase (CASP2); NADPH oxidase 3 (NOX3); harakiri, BCL2 interacting protein (HRK, BID3); complement component 1, q subcomponent binding protein (C1QBP); BCL2/adenovirus E1B 19 kDa interacting protein 3 (BNIP3); mitogen-activated protein kinase 8 (MAPK8, JNK1); mitogen-activated protein kinase 14 (MAPK14, p38); ras-related C3 botulinum toxin substrate 1 (rho family, small GTP binding protein RAC1); glycogen synthase kinase 3 beta (GSK3B); purinergic receptor P2X, ligand-gated ion channel, 7 (P2RX7); transient receptor potential cation channel, subfamily M, member 2 (TRPM2); poly (ADP-ribose) glycohydrolase (PARG); CD38 molecule (CD38); STEAP family member 4 (STEAP4); bone morphogenetic protein 2 (BMP2); gap junction protein, alpha 1, 43 kDa (connexin 43,GJA1); TYRO protein tyrosine kinase binding protein (TYROBP); connective tissue growth factor (CTGF); secreted phosphoprotein 1 (osteopontin, SPP1); ras homolog gene family, member A (RHOA); dual oxidase 1 (DUOX1), NOX1, NOX2 (gp91phox, CYBB), NOX4, NOX5, DUOX2 and associated proteins, NOXO1, NOXO2 (p47phox, NCF1) NOXA1, NOXA2 (p67phox, NCF2) and p40phox (NCF4), ASPP1, CTDS, CAPNS1, REDD1, REDD2, HTRA2, KEAP1, SHC1, ZNHIT1, LGALS3, HI95, TGFb-1, ACE, MCP-1, CDK, MIF, ECE-1, ET-1, TSA, Smad2, Smad3, ALK5, STAT3, PTGDS, TLR2. In some embodiments the target gene is selected from p53 and CASP2. Without being bound to theory, any one or more of the aforementioned genes is upregulated by renal insult and inhibition of this upregulation of one or more of those genes in the kidney protects the renal cells from damage including ischemic injury.

In another aspect the present invention provides a method of preventing the development of chronic kidney disease (CKD) in a subject at risk of developing CKD resulting from exposure to a plurality of renal insults comprising administering to the subject a therapeutically effective dose of an oligonucleotide compound which inhibits expression of a gene associated with renal ischemia wherein the oligonucleotide compound is administered to the subject within 16 hours of the renal insult.

In yet another aspect the present invention provides a method of preventing chronic kidney disease (CKD) from occurring in a subject which may be predisposed or at risk of developing CKD resulting from exposure to a plurality of renal insults comprising administering to the subject a therapeutically effective dose of an oligonucleotide compound which inhibits expression of a gene associated with renal ischemia wherein the oligonucleotide compound is administered to the subject within 16 hours of the renal insult. Methods include sustained delivery and controlled delivery for local or systemic delivery including delivery of siRNA using for example a delivery vehicle including pump, a slow or sustained release composition or an implant comprising a siRNA depot. The delivery vehicle comprises natural and synthetic materials or a combination of natural and synthetic materials.

Kits for the treatment or prevention of chronic kidney disease (CKD) are also provided. In some embodiments the invention provides a kit for the treatment or prevention of chronic kidney disease (CKD) associated with exposure to a radiocontrast agent. In some embodiments a kit includes a package containing a therapeutically effective dose of an oligonucleotide compound which inhibits expression of a gene associated with kidney damage in an amount effective to prevent radiocontrast agent induced kidney damage and a radiocontrast agent in an amount effective to perform a radiographical examination. In certain embodiments an oligonucleotide compound is included as a separate individual preparation and a radiocontrast agent as a separate individual preparation. In some embodiments, an oligonucleotide compound and a radiocontrast agent are combined as a single composition. In some embodiments, an oligonucleotide compound preparation and a radiocontrast agent preparation are provided in different forms (e.g. one preparation is a liquid and the other preparation is a freeze-dried preparation). In some embodiments, a kit further includes instructions for use.

In various embodiments the present invention provides a method employing a double stranded oligoribonucleotide compound that inhibits expression of a target gene associated with AKI and progression to CKD. In various embodiment the target gene is a gene associated with ischemia/reperfusion injury (IRI). In certain preferred embodiments the target gene is selected from the genes listed in Table 1, set forth hereinbelow. In particular embodiments the double stranded oligoribonucleotide compounds are chemically modified siRNA.

In some embodiments the siRNA compound is chemically modified according to the following structure:

5'$(N)_x$-Z3'(antisense strand)

3'Z'-$(N')_y$-z"5'(sense strand)

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein Z and Z' may be present or absent, but if present is independently 1-5 consecutive nucleotides covalently attached at the 3' terminus of the strand in which it is present;

wherein z" may be present or absent, but if present is a capping moiety covalently attached at the 5' terminus of (N') y;

each of x and y is independently an integer between 18 and 40;

wherein the sequence of (N')y is substantially complementary to the sequence of (N)x; and wherein (N)x comprises an antisense sequence substantially complementary to from about 18 to about 40 consecutive ribonucleotides present in an mRNA shown in Table 1, set forth in any one of SEQ ID NOS:1-115.

In some embodiments the covalent bond joining each consecutive N or N' is a phosphodiester bond. In various embodiments all the covalent bonds are phosphodiester bonds.

In various embodiments the compound comprises ribonucleotides wherein x=y and each of x and y is 19, 20, 21, 22 or 23. In some embodiments x=y=23. In other embodiments x=y=19.

In some embodiments the compound is blunt ended, for example wherein both Z and Z' are absent. In an alternative embodiment, the compound comprises at least one 3' overhang, wherein at least one of Z or Z' is present. Z and Z' can independently comprise one or more covalently linked modified or non-modified nucleotides, for example inverted dT or dA; dT, LNA, mirror nucleotide and the like. In some embodiments each of Z and Z' are independently selected from dT and dTdT.

In some embodiments each of (N)x and (N')y consist of unmodified nucleotides.

In some embodiments N or N' comprises a modification in the sugar residue of one or more ribonucleotides. In other embodiments the compound comprises at least one ribonucleotide modified in the sugar residue. In some embodiments the compound comprises a modification at the 2' position of the sugar residue. In some embodiments the modification in the 2' position comprises the presence of an amino, a fluoro, an alkoxy or an alkyl moiety. In certain embodiments the 2' modification comprises a methoxy moiety (also known as 2'-O-methyl; 2'-O-Me; 2'-O—$CH_3$). In some embodiments in each of (N)x and (N')y the ribonucleotides alternate between modified ribonucleotides and unmodified ribonucleotides each modified ribonucleotide being modified so as to have a 2'-O-methyl on its sugar and the ribonucleotide located at the middle position of (N)x being unmodified and the ribonucleotide located at the middle position of (N')y being modified. In some embodiments the preferred compound is I5, which targets p53.

In some embodiments the siRNA compound comprises modified alternating ribonucleotides in one or both of the antisense and the sense strands. In other embodiments the compound comprises modified alternating ribonucleotides in the antisense strand (N)x only. In certain embodiments the middle ribonucleotide of the antisense strand is not modified; e.g. ribonucleotide in position 10 in a 19-mer strand or position 12 in a 23-mer strand.

In additional embodiments the compound comprises modified ribonucleotides in alternating positions wherein each N at the 5' and 3' termini of $(N)_x$ are modified in their sugar residues, and each N' at the 5' and 3' termini of $(N')_y$ are unmodified in their sugar residues. In some embodiments, neither $(N)_x$ nor $(N')_y$ are phosphorylated at the 3' and 5' termini. In other embodiments either or both $(N)_x$ and $(N')_y$ are phosphorylated at the 3' termini.

In some embodiments (N)x comprises modified and unmodified ribonucleotides, each modified ribonucleotide having a 2'-O-methyl on its sugar, wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide. In some embodiments, (N)x comprises 2'O Me modified ribonucleotides at positions 2, 4, 6, 8, 11, 13, 15, 17 and 19. In other embodiments (N)x comprises 2'O Me modified ribonucleotides at positions 1, 3, 5, 7, 9, 11, 13, 15, 17 and 19.

In some embodiments the unconventional moiety is selected from a mirror nucleotide and a nucleotide joined to an adjacent nucleotide by a 2'-5' internucleotide phosphate bond. In some embodiments the mirror nucleotide is selected from an L-ribonucleotide (L-RNA) and an L-deoxyribonucleotide (L-DNA). In some embodiments (N')y comprises at least one unconventional moiety.

In one embodiment of the above structure, the compound comprises at least one mirror nucleotide at one or both termini in (N')y. In various embodiments the compound comprises two consecutive mirror nucleotides, one at the 3' penultimate position and one at the 3' terminus in (N')y. In one preferred embodiment x=y=19 and (N')y comprises an L-DNA at position 18.

In some embodiments x=y=19 and (N')y, consists of unmodified ribonucleotides at positions 1-17 and 19 and one L-DNA at the 3' penultimate position (position 18). In other embodiments x=y=19 and (N')y consists of unmodified ribonucleotides at position 1-16 and 19 and two consecutive L-DNA at the 3' penultimate position (positions 17 and 18).

In another embodiment of the above structure, (N')y further comprises one or more nucleotides containing an intra-sugar bridge at one or both termini.

BRIEF DESCRIPTION OF THE FIGURES

FIGS. 9A-9C relate to acute injury parameters tubular necrosis (9A), tubular dialation (9B) and casts (9C). FIGS. 9D-9H relate to chronic injury parameters glomerular damage (9D), interstitial cellular infiltrate (9E); interstitial fibrosis (9F), tubular atrophy or dilation (9G) and vasculopathy (9H).

DETAILED DESCRIPTION OF THE INVENTION

Figure 1:
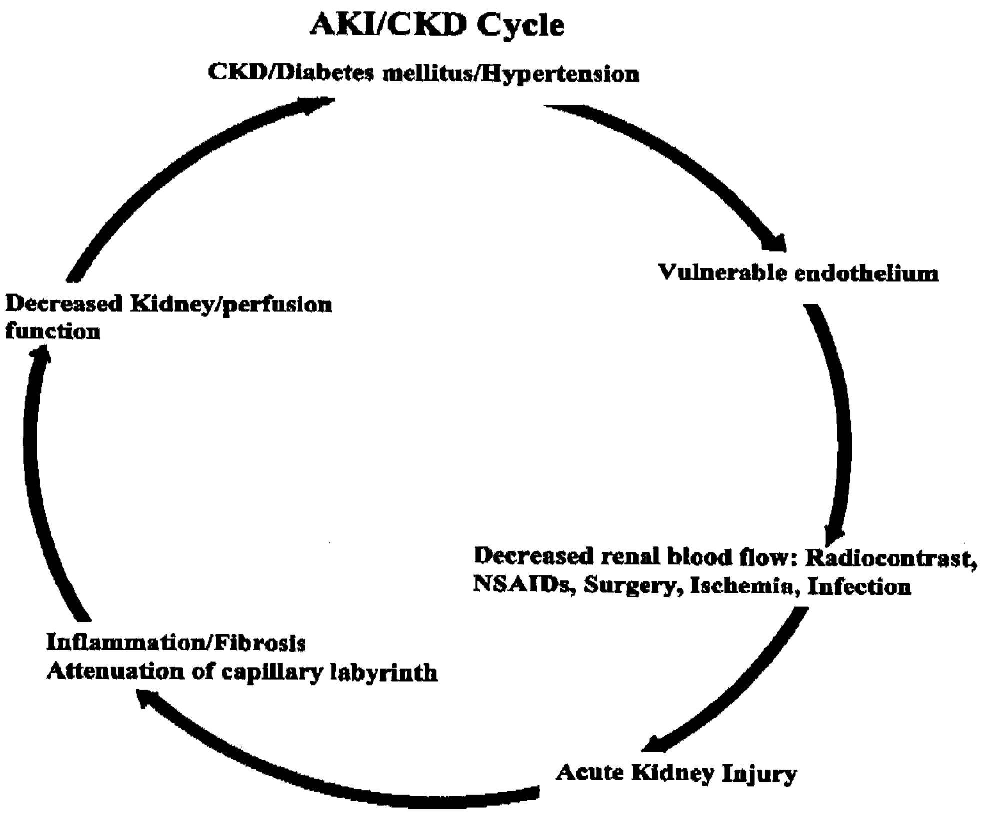
FIG. 1 provides a proposed vicious circle of mutual reinforcement between AKI and CKD in the development of ESRD (from: B. Molitoris (2008) "Contrast nephropathy: are short-term outcome measures adequate for quantification of long-term renal risk", Nat Clin Pract Nephrol. 2008 4:594-5.)

The present invention relates in general to a method of attenuating the progression of chronic kidney disease or preventing exacerbation of CKD progression in a subject at risk thereof. The method employs generally compounds which down-regulate expression of various target genes associated with acute kidney injury and in particular with ischemic reperfusion injury. The method employs chemically modified small interfering RNA oligonucleotides (siRNAs), possessing structures and modifications which may increase activity, increase stability, and or minimize toxicity, reduce off target effect or reduce innate immune response when compared to the unmodified compound.

Table 1, below, sets forth the gene identification number (gi) with an NCBI accession number for non-limiting examples of target genes. The table sets forth the respective mRNA sequences, the gi number (gene identifier number) and the sequence identifier number (SEQ ID NO) for the corresponding mRNA.

TABLE 1

Non-limiting list of target genes

| Gene | Full name and Human Gene ID |
|---|---|
| REDD1 | DDIT4, DNA-damage-inducible transcript 4<br>gi\|56676369\|ref\|NM_019058 (SEQ ID NO: 1) |
| REDD2 | DNA-damage-inducible transcript 4-like<br>gi\|34222182\|ref\|NM_145244 (SEQ ID NO: 2) |
| TP53BP2<br>(ASPP2) | tumor protein p53 binding protein, 2<br>gi\|112799848\|ref\|NM_001031685.2 (SEQ ID NO: 3)<br>gi\|112799845\|ref\|NM_005426.2 (SEQ ID NO: 4): |
| LRDD | leucine-rich repeats and death domain containing<br>gi\|61742781\|ref\|NM_018494.3 (SEQ ID NO: 5)<br>gi\|61742783\|ref\|NM_145886.2 (SEQ ID NO: 6)<br>gi\|61742785\|ref\|NM_145887.2 (SEQ ID NO: 7) |

TABLE 1-continued

| Non-limiting list of target genes | |
|---|---|
| Gene | Full name and Human Gene ID |
| CYBA | cytochrome b-245, alpha polypeptide<br>gi\|68509913\|ref\|NM_000101.2\|(SEQ ID NO: 8) |
| ATF3 | activating transcription factor 3<br>gi\|95102484\|ref\|NM_001030287.2\|v.3 (SEQ ID NO: 9)<br>gi\|71902534\|ref\|NM_001674.2\|v. 1 (SEQ ID NO: 10)<br>gi\|95102482\|ref\|NM_001040619.1\|(SEQ ID NO: 11) |
| CASP2 | caspase 2, apoptosis-related cysteine peptidase<br>gi\|39995058\|ref\|NM_032982.2 (SEQ ID NO: 12)<br>gi\|39995060\|ref\|NM_032983.2 (SEQ ID NO: 13) |
| NOX3 | NADPH oxidase 3<br>Gi\|11136625\|ref\|NM_015718.1 (SEQ ID NO: 14) |
| HRK | harakiri<br>gi\|4504492\|ref\|NM_003806.1 (SEQ ID NO: 15) |
| C1QBP | complement component 1, q subcomponent binding protein<br>gi\|28872801\|ref\|NM_001212.3 (SEQ ID NO: 16) |
| BNIP3 | BCL2/adenovirus E1B 19 kDa interacting protein 3<br>Gi\|7669480\|ref\|NM_004052.2 (SEQ ID NO: 17) |
| MAPK8 | mitogen-activated protein kinase 8<br>gi\|20986493\|ref\|NM_002750.2 v.2 (SEQ ID NO: 18)<br>gi\|20986522\|ref\|NM_139049.1 v. 1 (SEQ ID NO: 19)<br>gi\|20986518\|ref\|NM_139046.1 v.3 (SEQ ID NO: 20)<br>gi\|20986520\|ref\|NM_139047.1 v.4 (SEQ ID NO: 21) |
| MAPK14 | mitogen-activated protein kinase 14<br>gi\|20986511\|ref\|NM_139012.1 v.2 (SEQ ID NO: 22)<br>gi\|20986515\|ref\|NM_139014.1 v. 4 (SEQ ID NO: 23)<br>gi\|4503068\|ref\|NM_001315.1 v.1 (SEQ ID NO: 24)<br>gi\|20986513\|ref\|NM_139013.1 v.3 (SEQ ID NO: 25) |
| Rac1 | ras-related C3 botulinum toxin substrate 1 (rho family, small GTP binding protein)<br>gi\|156071511\|ref\|NM_018890.3 (SEQ ID NO: 26)<br>gi\|156071503\|ref\|NM_006908.4 (SEQ ID NO: 27) |
| GSK3B | glycogen synthase kinase 3 beta<br>gi\|21361339\|ref\|NM_002093.2 (SEQ ID NO: 28)<br>gi\|225903436\|ref\|NM_001146156.1 (SEQ ID NO: 29) |
| P2RX7 | purinergic receptor P2X, ligand-gated ion channel, 7<br>gi\|34335273\|ref\|NM_002562.4 (SEQ ID NO: 30) |
| TRPM2 | transient receptor potential cation channel, subfamily M, member 2<br>gi\|67906812\|ref\|NM_003307.3 v. L (SEQ ID NO: 31) |
| PARG | poly (ADP-ribose) glycohydrolase<br>gi\|70610135\|ref\|NM_003631.2 (SEQ ID NO: 32) |
| CD38 | CD38 molecule<br>Gi\|38454325\|ref\|NM_001775.2 (SEQ ID NO: 33) |
| STEAP4 | STEAP family member 4<br>Gi\|13375867\|ref\|NM_024636.1 (SEQ ID NO: 34) |
| BMP2 | bone morphogenetic protein 2<br>gi\|80861484\|ref\|NM_001200.2 (SEQ ID NO: 35) |
| GJA1 | gap junction protein, alpha 1, 43 kDa<br>gi\|4755136\|ref\|NM_000165.2 (SEQ ID NO: 36) |
| TYROBP | TYRO protein tyrosine kinase binding protein<br>gi\|291045273\|ref\|NM_001173515.1 variant 4 (SEQ ID NO: 37)<br>gi\|291045270\|ref\|NM_198125.2\|variant 2 (SEQ ID NO: 38)<br>gi\|291045269\|ref\|NM_003332.3\|variant 1 (SEQ ID NO: 39)<br>gi\|291045271\|ref\|NM_001173514.1 variant 3 (SEQ ID NO: 40) |
| CTGF | connective tissue growth factor<br>gi\|4503122\|ref\|NM_001901.1 (SEQ ID NO: 41) |
| SPP1 | secreted phosphoprotein 1<br>gi\|91206461\|ref\|NM_001040058.1 (SEQ ID NO: 42)<br>gi\|38146097\|ref\|NM_000582.2 (SEQ ID NO: 43)<br>gi\|91598938\|ref\|NM_001040060.1 (SEQ ID NO: 44) |
| RHOA | ras homolog gene family member A<br>gi\|50593005\|ref\|NM_001664.2 (SEQ ID NO: 45) |
| DUOX1 | dual oxidase 1<br>gi\|28872749\|ref\|NM_017434.3 (SEQ ID NO: 46)<br>gi\|28872750\|ref\|NM_175940.1 (SEQ ID NO: 47) |
| NOX4 | NADPH oxidase 4<br>gi\|219842344\|ref\|NM_016931.3\|v. 1 (SEQ ID NO: 48)<br>gi\|219842345\|ref\|NM_001143836.1\|v. 1 (SEQ ID NO: 49)<br>gi\|219842347\|ref\|NM_001143837.1\|v. 1 (SEQ ID NO: 50) |
| NOX1 | NADPH oxidase 1<br>(gi: 21614529, NM_007052 isoform 1L; SEQ ID NO: 51)<br>(gi: 7669509, NM_013955 isoform 1Lv; SEQ ID NO: 52) |
| NOX2 (gp91pho, CYBB) | NADPH oxidase 2<br>(gi: 6996020, NM_000397; SEQ ID NO: 53) |
| NOX5 | NADPH oxidase 5<br>(gi: 20127623, NM_024505; SEQ ID NO: 54) |

TABLE 1-continued

| Non-limiting list of target genes | |
|---|---|
| Gene | Full name and Human Gene ID |
| DUOX2 | Dual oxidase 2<br>(gi: 132566531, NM_014080; SEQ ID NO: 55) |
| NOXO1 | NADPH oxidase organizer 1<br>(gi: 34222190, variant a, NM_144603, SEQ ID NO: 56)<br>(gi: 41281810, variant b, NM_172167; SEQ ID NO: 57)<br>(gi: 41281827, variant c, NM_172168; SEQ ID NO: 58) |
| NCF1 (p47phox, NOXO2) | NADPH oxidase organizer 2<br>(gi: 115298671, NM_000265; SEQ ID NO: 59) |
| NOXA1 | NADPH oxidase activator 1<br>(gi: 41393186, NM_006647; SEQ ID NO: 60) |
| NCF2 (p67phox, NOXA2) | NADPH oxidase activator 2<br>(gi: 67189969, NM_000433; SEQ ID NO: 61)<br>(gi\|189083741\|ref\|NM_001127651.1\|v.2 (SEQ ID NO: 62) |
| ASPP1 | protein phosphatase 1, regulatory (inhibitor) subunit 13B (PPP1R13B)<br>gi\|121114286\|ref\|NM_015316.2\| (SEQ ID NO: 63) |
| CTSD | Cathepsin D<br>gi\|23110949\|ref\|NM_001909.3\| (SEQ ID NO: 64) |
| CAPNS1 | Calpain small subunit 1<br>gi\|51599152\|ref\|NM_001749.2\|Variant 1 (SEQ ID NO: 65)<br>gi\|51599150\|ref\|NM_001003962.1\|variant 2 (SEQ ID NO: 66) |
| p53 (TP53) | tumor protein p53<br>gi\|187830767\|ref\|NM_000546.4\|variant 1 (SEQ ID NO: 67)<br>gi\|187830776\|ref\|NM_001126112.1\|variant 2 (SEQ ID NO: 68)<br>gi\|187830854\|ref\|NM_001126114.1\|variant 3 (SEQ ID NO: 69)<br>gi\|187830822\|ref\|NM_001126113.1\|variant 4 (SEQ ID NO: 70)<br>gi\|187830893\|ref\|NM_001126115.1\|variant 5 (SEQ ID NO: 71)<br>gi\|187830900\|ref\|NM_001126116.1\|variant 6 (SEQ ID NO: 72)<br>gi\|187830908\|ref\|NM_001126117.1\|variant 7 (SEQ ID NO: 73) |
| HTRA2 | Htra serine peptidase 2<br>var 1 gi: 73747817, NM_013247 (SEQ ID NO: 74)<br>var 2 gi: 73747818, NM_145074 (SEQ ID NO: 75) |
| KEAP1 | Kelch-like ECH-associated protein 1<br>var 1 gi: 45269144 NM_203500 (SEQ ID NO: 76)<br>var 2 gi: 45269143 NM_012289 (SEQ ID NO: 77) |
| SHC1 | Src homology 2 domain containing) transforming prot. 1<br>gi\|194239661\|ref\|NM_183001.4\|(SEQ ID NO: 78<br>gi\|194239660\|ref\|NM_003029.4\|(SEQ ID NO: 79)<br>gi\|194239663\|ref\|NM_001130040.1\| (SEQ ID NO: 80)<br>gi\|194239667\|ref\|NM_001130041.1\| (SEQ ID NO: 81) |
| ZNHIT1 | Zn finger HIT type 1<br>gi: 37594439\|; NM_006349 (SEQ ID NO: 82) |
| LGALS3 | lectin galactoside-binding soluble 3<br>var 1 gi: 115430222 NM_002306 (SEQ ID NO: 83)<br>var 2 gi: 115430224 NR_003225 (SEQ ID NO: 84)<br>var 3 gi\|294345474\|ref\|NM_001177388.1\| (SEQ ID NO: 85) |
| HI95 | Sestrin2<br>gi: 32454742 NM_031459 (SEQ ID NO: 86) |
| TGFb-1 | transforming growth factor beta-1<br>gi: 63025221 NM_000660 (SEQ ID NO: 87) |
| ACE | angiotensin-converting enzyme<br>transcript variant 2: gi\|23238213\|ref\|NM_152830.1\| (SEQ ID NO: 88)<br>transcript variant 1, gi\|23238217\|ref\|NM_000789.2\| (SEQ ID NO: 89) |
| CCL2 | *Homo sapiens* chemokine (C-C motif) ligand 2 (CCL2), mRNA<br>gi\|56119169\|ref\|NM_002982.3\| (SEQ ID NO: 90) |
| CDK1 (CDC2) | *Homo sapiens* cell division cycle 2, G1 to S and G2 to M (CDC2),<br>gi\|195927038\|ref\|NM_001786.3\|v.1 (SEQ ID NO: 91)<br>gi\|195927039\|ref\|NM_033379.3\|v.2 (SEQ ID NO: 92)<br>gi\|195927040\|ref\|NM_001130829.1\|v.3 (SEQ ID NO: 93) |
| MIF | macrophage inhibitory factor<br>gi: 4505184 NM_002415 (SEQ ID NO: 94) |
| ECE-1 | endothelin converting enzyme<br>gi\|164519130\|ref\|NM_001397.2\|variant 1, (SEQ ID NO: 95)<br>gi\|164519139\|ref\|NM_001113349.1\| (SEQ ID NO: 96)<br>gi\|164519135\|ref\|NM_001113347.1\| (SEQ ID NO: 97)<br>gi\|164519137\|ref\|NM_001113348.1\| (SEQ ID NO: 98) |
| ET-1 (EDN1) | *Homo sapiens* endothelin 1, mRNA<br>gi\|154800436\|ref\|NM_001955.3\| (SEQ ID NO: 99) |
| TSA (LY6E) | (Thymic shared antigen1)<br>*Homo sapiens* lymphocyte antigen 6 complex, locus E (LY6E), mRNA<br>variant 1, gi\|187827163\|ref\|NM_002346.2\| (SEQ ID NO: 100)<br>variant 2, gi\|187761330\|ref\|NM_001127213.1\| (SEQ ID NO: 101) |
| Smad2 | *Homo sapiens* SMAD family member 2 (SMAD2), mRNA<br>variant 1, gi\|118572580\|ref\|NM_005901.4\| (SEQ ID NO: 102)<br>variant 2, gi\|118572581\|ref\|NM_001003652.2 (SEQ ID NO: 103)<br>gi\|209693425\|ref\|NM_001135937.1\|var 3 (SEQ ID NO: 104) |

TABLE 1-continued

| Non-limiting list of target genes | |
|---|---|
| Gene | Full name and Human Gene ID |
| Smad3 | *Homo sapiens* SMAD family member 3 (SMAD3), mRNA variant 1, gi\|52352808\|ref\|NM_005902.3 (SEQ ID NO: 105) gi\|223029439\|ref\|NM_001145102.1\|v.2 (SEQ ID NO: 106) gi\|223029441\|ref\|NM_001145103.1\|v.3 (SEQ ID NO: 107) gi\|223029443\|ref\|NM_001145104.1\|v.4 (SEQ ID NO: 108) |
| TGFBR1 | *Homo sapiens* transforming growth factor, beta receptor 1, mRNA (ALK5, activin-receptor like kinase) transcript variant 1, gi\|66346739\|ref\|NM_004612.2\| (SEQ ID NO: 109) ranscript variant 2, gi\|195963411\|ref\|NM_001130916.1\| (SEQ ID NO: 110) |
| STAT3 | *Homo sapiens* signal transducer and activator of transcription 3 (acute-phase response factor) (STAT3), mRNA transcript variant 1, gi\|47080104\|ref\|NM_139276.2\| (SEQ ID NO: 111) transcript variant 2 gi\|47080105\|ref\|NM_003150.3\| (SEQ ID NO: 112) transcript variant 3 gi\|47458819\|ref\|NM_213662.1\| (SEQ ID NO: 113) |
| PTGDS | *Homo sapiens* prostaglandin D2 synthase 21 kDa (brain) (PTGDS), mRNA gi\|38505192\|ref\|NM_000954.5\| (SEQ ID NO: 114) |
| TLR2 | *Homo sapiens* toll-like receptor 2 (TLR2), mRNA gi\|68160956\|ref\|NM_003264.3\| (SEQ ID NO: 115) |

Definitions

For convenience certain terms employed in the specification, examples and claims are described herein.

It is to be noted that, as used herein, the singular forms “a”, “an” and “the” include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

An “inhibitor” is a compound, which is capable of reducing (partially or fully) or down regulating the expression of a gene or the activity of the product of such gene to an extent sufficient to achieve a desired biological or physiological effect. The term “inhibitor” as used herein refers to one or more of an oligonucleotide inhibitor, including siRNA, shRNA, synthetic shRNA; miRNA, antisense RNA and DNA and ribozymes.

A “siRNA inhibitor” is a compound which is capable of reducing the expression of a gene or the activity of the product of such gene to an extent sufficient to achieve a desired biological or physiological effect. The term “siRNA inhibitor” as used herein refers to one or more of a siRNA, shRNA, synthetic shRNA; miRNA Inhibition may also be referred to as down-regulation or, for RNAi, silencing.

The term “inhibit” or “down regulate” as used herein refers to reducing the expression of a gene or the activity of the product of such gene to an extent sufficient to achieve a desired biological or physiological effect. Inhibition or down regulation may be complete or partial.

As used herein, the term “inhibition” or “down-regulation” of a target gene means reduction of the gene expression (transcription or translation) or polypeptide activity of a gene selected from the group consisiting of any one of SEQ ID NO:1-115 or an SNP (single nucleotide polymorphism) or other variants thereof. The gi number for the mRNA of each target gene is set forth in Table 1. The polynucleotide sequence of the target mRNA sequence, refers to the mRNA sequences set forth herein, or any homologous sequences thereof preferably having at least 70% identity, more preferably 80% identity, even more preferably 90% or 95% identity to any one of mRNA set forth herein. Therefore, polynucleotide which have undergone mutations, alterations or modifications as described herein are encompassed in the present invention. The terms “mRNA polynucleotide sequence” and “mRNA” are used interchangeably.

As used herein, the terms “polynucleotide” and “nucleic acid” may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs. Throughout this application, mRNA sequences are set forth as representing the corresponding genes.

“Oligonucleotide” or “oligomer” refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds of the present invention encompass molecules comprising deoxyribonucleotides, ribonucleotides, modified deoxyribonucleotides, modified ribonucleotides and combinations thereof.

“Nucleotide” is meant to encompass deoxyribonucleotides and ribonucleotides, which may be natural or synthetic, and or modified or unmodified. Modifications include changes to the sugar moiety, the base moiety and or the linkages between ribonucleotides in the oligoribonucleotide. As used herein, the term “ribonucleotide” encompasses natural and synthetic, unmodified and modified ribonucleotides. Modifications include changes to the sugar moiety, to the base moiety and/or to the linkages between ribonucleotides in the oligonucleotide.

Analogs of, or modifications to, a nucleotide/oligonucleotide are preferably employed with the present invention, provided that said analog or modification does not substantially adversely affect the function of the nucleotide/oligonucleotide. In some embodiments a chemical modification results in an increase in activity or stability or a reduction in off-target effects or induction of innate immune responses. Acceptable modifications include modifications of the sugar moiety, modifications of the base moiety, modifications in the internucleotide linkages and combinations thereof.

The nucleotides can be selected from naturally occurring or synthetic modified bases. Naturally occurring bases include adenine, guanine, cytosine, thymine and uracil.

Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, compounds comprising nucleotide analogs can be prepared wherein the structure of one or more nucleotide is fundamentally altered and better suited as therapeutic or experimental reagents. An example of a nucleotide analog is a peptide nucleic acid (PNA) wherein the deoxyribose (or ribose) phosphate backbone in DNA (or RNA is replaced with a polyamide backbone which is similar to that found in peptides. PNA analogs have been shown to be resistant to enzymatic degradation and to have extended lives in vivo and in vitro.

Possible modifications to the sugar residue are manifold and include 2'-O alkyl, locked nucleic acid (LNA), glycol nucleic acid (GNA), threose nucleic acid (TNA), arabinoside, altritol (ANA) and other, 6-membered sugars including morpholinos, and cyclohexinyls.

LNA compounds are disclosed in International Patent Publication Nos. WO 00/47599, WO 99/14226, and WO 98/39352. Examples of siRNA compounds comprising LNA nucleotides are disclosed in Elmen et al., (NAR 2005. 33(1): 439-447) and in International Patent Publication No. WO 2004/083430.

Backbone modifications, such as ethyl (resulting in a phospho-ethyl triester); propyl (resulting in a phospho-propyl triester); and butyl (resulting in a phospho-butyl triester) are also possible. Other backbone modifications include polymer backbones, cyclic backbones, acyclic backbones, thiophosphate-D-ribose backbones, amidates, phosphonoacetate derivatives. Certain structures include siRNA compounds having one or a plurality of 2'-5' internucleotide linkages (bridges or backbone).

Additional modifications which may be present in the molecules of the present invention include nucleoside modifications such as artificial nucleic acids, peptide nucleic acid (PNA), morpholino and locked nucleic acid (LNA), glycol nucleic acid (GNA), threose nucleic acid (TNA), arabinoside, and mirror nucleoside (for example, beta-L-deoxynucleoside instead of beta-D-deoxynucleoside). Further, said molecules may additionally contain modifications on the sugar, such as 2'-alkyl, 2'-fluoro, 2'-deoxy-2'-fluoro, 2'O-allyl, 2'-amine and 2'-alkoxy. Additional sugar modifications are discussed herein.

Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks.

siRNAs and RNA Interference

RNA interference (RNAi) is a phenomenon involving double-stranded (ds) RNA-dependent gene specific posttranscriptional silencing. Originally, attempts to study this phenomenon and to manipulate mammalian cells experimentally were frustrated by an active, non-specific antiviral defense mechanism which was activated in response to long dsRNA molecules (Gil et al. Apoptosis, 2000. 5:107-114). Later it was discovered that synthetic duplexes of 21 nucleotide RNAs could mediate gene specific RNAi in mammalian cells, without the stimulation of the generic antiviral defense mechanisms (see Elbashir et al. Nature 2001, 411:494-498 and Caplen et al. PNAS USA 2001, 98:9742-9747). As a result, small interfering RNAs (siRNAs), which are short double-stranded RNAs, have become powerful tools in attempting to understand gene function. Thus RNA interference (RNAi) refers to the process of sequence-specific post-transcriptional gene silencing in mammals mediated by small interfering RNAs (siRNAs) (Fire et al, Nature 1998. 391, 806) or microRNAs (miRNA; Ambros, Nature 2004 431: 7006, 350-55; and Bartel, Cell. 2004. 116(2):281-97). The corresponding process in plants is commonly referred to as specific post transcriptional gene silencing or RNA silencing and is referred to as quelling in fungi.

A siRNA is a double-stranded RNA molecule which inhibits or down regulates, either partially or fully, a gene or the expression of a gene/mRNA of its endogenous or cellular counterpart, or of an exogenous gene such as a viral nucleic acid. The mechanism of RNA interference is detailed infra.

Several studies have revealed that siRNA therapeutics are effective in vivo in both mammals and in humans. Bitko et al., have shown that specific siRNA molecules directed against the respiratory syncytial virus (RSV) nucleocapsid N gene are effective in treating mice when administered intranasally (Bitko et al., Nat. Med. 2005, 11(1):50-55). siRNA has recently been successfully used for inhibition in primates (Tolentino et al., Retina 2004. 24(1):132-138). For a review of the use of siRNA as therapeutics, see for example Batik (J. Mol. Med. 2005. 83: 764-773) or Dykxhoorn et al (2006. Gene Ther. 13:541-552).

siRNA Structures

The selection and synthesis of siRNA corresponding to known genes has been widely reported; (see for example Ui-Tei et al., J Biomed Biotech. 2006; 2006: 65052; Chalk et al., BBRC. 2004, 319(1): 264-74; Sioud & Leirdal, Met. Mol Biol.; 2004, 252:457-69; Levenkova et al., Bioinform. 2004, 20(3):430-2; Ui-Tei et al., NAR. 2004, 32(3):936-48).

For examples of the use of, and production of, modified siRNA see, for example, Braasch et al., Biochem. 2003, 42(26):7967-75; Chiu et al., RNA, 2003, 9(9):1034-48; PCT publications WO 2004/015107 (atugen AG) and WO 02/44321 (Tuschl et al). U.S. Pat. Nos. 5,898,031 and 6,107,094, teach chemically modified oligomers. US Patent Publication Nos. 2005/0080246 and 2005/0042647 relate to oligomeric compounds having an alternating motif and dsRNA compounds having chemically modified internucleoside linkages, respectively.

Other modifications have been disclosed. The inclusion of a 5'-phosphate moiety was shown to enhance activity of siRNAs in *Drosophila* embryos (Boutla, et al., Curr. Biol. 2001, 11:1776-1780) and is required for siRNA function in human HeLa cells (Schwarz et al., Mol. Cell, 2002, 10:537-48). Amarzguioui et al., (NAR, 2003, 31(2):589-95) showed that siRNA activity depended on the positioning of the 2'-O-methyl modifications. Holen et al (NAR. 2003, 31(9):2401-07) report that an siRNA having small numbers of 2'-O-methyl modified nucleosides gave good activity compared to wild type but that the activity decreased as the numbers of 2'-O-methyl modified nucleosides was increased. Chiu and Rana (RNA. 2003, 9:1034-48) teach that incorporation of 2'-O-methyl modified nucleosides in the sense or antisense strand (fully modified strands) severely reduced siRNA activity relative to unmodified siRNA. The placement of a 2'-O-methyl group at the 5'-terminus on the antisense strand was reported to severely limit activity whereas placement at the 3'-terminus of the antisense and at both termini of the sense strand was tolerated (Czauderna et al., NAR. 2003, 31(11):2705-16; WO 2004/015107). The molecules of the present invention offer an advantage in that they are non-toxic and may be formulated as pharmaceutical compositions for treatment of various diseases.

International Patent Publication No. WO 2008/050329 to the assignee of the present invention and hereby incorporated in its entirely relates to siRNA compounds, compositions comprising same and to methods of use thereof for treating diseases and disorders related to expression of proapoptotic genes. U.S. Ser. No. 11/655,610 relates to methods of treating hearing impairment by inhibiting a pro-apoptotic gene in general and p53 in particular.

Oligonucleotides

The present invention provides methods employing oligonucleotide inhibitors including double-stranded oligonucleotides (e.g. siRNA), which down-regulate the expression of a desired gene. A siRNA is a duplex oligoribonucleotide in which the sense strand is derived from the mRNA sequence of the desired gene, and the antisense strand is complementary to the sense strand. In general, some deviation from the target mRNA sequence is tolerated without compromising the siRNA activity (see e.g. Czauderna et al., NAR. 2003, 31(11): 2705-2716). Without being bound by theory, an siRNA of the invention inhibits gene expression on a post-transcriptional level with or without destroying the mRNA; siRNA may target the mRNA for specific cleavage and degradation and/or may inhibit translation from the targeted message.

In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid which is mRNA transcribed from a target gene, and the second strand comprises a ribonucleotide sequence at least partially complementary to the first strand and wherein said first strand and or said second strand comprises a one or more chemically modified ribonucleotides and or unconventional moieties.

In one embodiment the siRNA compound comprises at least one ribonucleotide comprising a 2' modification on the sugar moiety ("2' sugar modification"). In certain embodiments the compound comprises 2'O-alkyl or 2'-fluoro or 2'O-allyl or any other 2' modification, optionally on alternate positions. Other stabilizing modifications are also possible (e.g. terminal modifications). In some embodiments a preferred 2'O-alkyl is 2'O-methyl (methoxy, 2' OMe) sugar modification.

In some embodiments the backbone of the oligonucleotides is modified and comprises phosphate-D-ribose entities but may also contain thiophosphate-D-ribose entities, triester, thioate, 2'-5' bridged backbone (also may be referred to as 5'-2'), PACE and the like.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me riboU, N3-Me riboT, N3-Me-dC, N3-Me-dT, N1-Me-dG, N1-Me-dA, N3-ethyl-dC, N3-Me-dC. In some embodiments the non-base pairing nucleotide analog is a ribonucleotide. In other embodiments it is a deoxyribonucleotide. In addition, analogues of polynucleotides may be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to enzymatic degradation and to enhance stability in vivo and in vitro. Other useful modifications include polymer backbones, cyclic backbones, acyclic backbones, thiophosphate-D-ribose backbones, triester backbones, thioate backbones, 2'-5' bridged backbone, artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). The compounds of the present invention can be synthesized using one or more inverted nucleotides, for example inverted thymidine or inverted adenine (see, for example, Takei, et al., 2002, JBC 277(26):23800-06).

Additional modifications include terminal modifications on the 5' and/or 3' part of the oligonucleotides and are also known as capping moieties. Such terminal modifications are selected from a nucleotide, a modified nucleotide, a lipid, a peptide, a sugar and an inverted abasic moiety.

What is sometimes referred to in the present invention as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide.

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; bridged nucleic acids including LNA and ethylene bridged nucleic acids. In some embodiments of the present invention a preferred unconventional moiety is an abasic ribose moiety, an abasic deoxyribose moiety, a deoxyribonucleotide, a mirror nucleotide, and a nucleotide joined to an adjacent nucleotide by a 2'-5' internucleotide phosphate bond.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide), also referred to as L-RNA in the case of a mirror ribonucleotide, and "spiegelmer". The nucleotide can be a ribonucleotide or a deoxyribonucleotide and may further comprise at least one sugar, base and or backbone modification. See U.S. Pat. No. 6,586,238. Also, U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU)).

The term "capping moiety" as used herein includes abasic ribose moiety, abasic deoxyribose moiety, modifications to abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'O-Me nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain preferred capping moieties are abasic ribose or abasic deoxyribose moieties; inverted abasic ribose or abasic deoxyribose moieties; C6-amino-Pi; a mirror nucleotide including L-DNA and L-RNA.

A further end modification is a biotin group. Such biotin group may preferably be attached to either the most 5' or the most 3' nucleotide of the first and/or second strand or to both ends. In a more preferred embodiment the biotin group is coupled to a polypeptide or a protein. It is also within the scope of the present invention that the polypeptide or protein is attached through any of the other aforementioned end modifications.

The various end modifications as disclosed herein are preferably located at the ribose moiety of a nucleotide of the nucleic acid according to the present invention. More particularly, the end modification may be attached to or replace any of the OH-groups of the ribose moiety, including but not limited to the 2'OH, 3'OH and 5'OH position, provided that the nucleotide thus modified is a terminal nucleotide. Inverted abasic or abasic are nucleotides, either deoxyribonucleotides or ribonucleotides which do not have a nucleobase moiety (for example see Sternberger, et al., (2002). Antisense Nucleic Acid Drug Dev, 12, 131-43).

Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate.

Bridged nucleic acids include LNA (2'-O,4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged nucleic acid adenosine 3' monophosphate, 2'-O,4'-C-ethylene bridged nucleic acid 5-methyl-cytidine 3' monophosphate, 2'-O,4'-C-ethylene bridged nucleic acid guanosine 3' monophosphate, 5-methyl-uridine (or thymidine) 3' monophosphate).

In certain embodiments the complementarity between said first strand and the target nucleic acid is perfect. In some embodiments, the strands are substantially complementary, i.e. having one, two or up to three mismatches between said first strand and the target nucleic acid. Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

In some embodiments the first strand and the second strand of the compound are linked by a loop structure, which is comprised of a non-nucleic acid polymer such as, inter alia, polyethylene glycol. Alternatively, the loop structure is comprised of a nucleic acid, including modified and non-modified ribonucleotides and modified and non-modified deoxyribonucleotides.

In further embodiments, the 5'-terminus of the first strand of the siRNA is linked to the 3'-terminus of the second strand, or the 3'-terminus of the first strand is linked to the 5'-terminus of the second strand, said linkage being via a nucleic acid linker typically having a length between 2-100 nucleobases, preferably about 2 to about 30 nucleobases.

In preferred embodiments the methods of the invention employ oligonucleotide compounds having alternating ribonucleotides modified in at least one of the antisense and the sense strands of the compound, for 19 mer and 23 mer oligomers the ribonucleotides at the 5' and 3' termini of the antisense strand are modified in their sugar residues, and the ribonucleotides at the 5' and 3' termini of the sense strand are unmodified in their sugar residues. For 21 mer oligomers the ribonucleotides at the 5' and 3' termini of the sense strand are modified in their sugar residues, and the ribonucleotides at the 5' and 3' termini of the antisense strand are unmodified in their sugar residues, or may have an optional additional modification at the 3' terminus. As mentioned above, it is preferred that the middle nucleotide of the antisense strand is unmodified.

According to one preferred embodiment of the invention, the antisense and the sense strands of the oligonucleotide/siRNA are phosphorylated at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

Any siRNA sequence can be prepared having any of the modifications/structures disclosed herein. The compound comprising a combination of sequence plus structure is useful in the treatment of the conditions disclosed herein.

Structural Motifs

In some embodiments of the present invention the oligonucleotide inhibitor is chemically modified siRNA according to one of the following modifications set forth in Structures (A)-(P) or as tandem siRNA or RNAstar.

In one aspect the present invention provides a compound set forth as Structure (A):

5'$(N)_x$-Z3'(antisense strand)

3'Z'-$(N')_y$5'(sense strand) (A)

wherein each of N and N' is a nucleotide selected from an unmodified ribonucleotide, a modified ribonucleotide, an unmodified deoxyribonucleotide and a modified deoxyribonucleotide;

wherein each of $(N)_x$ and $(N')_y$ is an oligonucleotide in which each consecutive N or N' is joined to the next N or N' by a covalent bond;

wherein each of x and y is an integer between 18 and 40;

wherein each of Z and Z' may be present or absent, but if present is 1-5 consecutive nucleotides covalently attached at the 3' terminus of the strand in which it is present;

wherein the sequence of $(N')_y$ is a sequence substantially complementary to (N)x; and wherein the sequence of $(N)_x$ comprises an antisense sequence substantially complementary to from about 18 to about 40 consecutive ribonucleotides in an mRNA of a target gene associated with acute kidney injury.

In certain embodiments the present invention provides a compound having structure (B)

5'$(N)_x$-Z3'(antisense strand)

3'Z'-$(N')_y$5'(sense strand) (B)

wherein each of $(N)_x$ and $(N')_y$ is an oligomer in which each consecutive N or N' is an unmodified ribonucleotide or a modified ribonucleotide joined to the next N or N' by a covalent bond;

wherein each of Z and Z' may be present or absent, but if present is 1-5 consecutive nucleotides covalently attached at the 3' terminus of the strand in which it is present;

wherein each of x and y=19, 21 or 23 and $(N)_x$ and $(N')_Y$ are fully complementary wherein alternating ribonucleotides in each of $(N)_x$ and $(N')_y$ are modified to result in a 2'-O-methyl modification in the sugar residue of the ribonucleotides;

wherein the sequence of $(N')_y$ is a sequence substantially complementary to (N)x; and wherein the sequence of $(N)_x$ comprises an antisense sequence substantially complementary to the substantially complementary to from about 18 to about 40 consecutive ribonucleotides in an mRNA of a target gene associated with acute kidney injury.

In some embodiments each of $(N)_x$ and $(N')_y$ is independently phosphorylated or non-phosphorylated at the 3' and 5' termini.

In certain embodiments wherein each of x and y=19 or 23, each N at the 5' and 3' termini of $(N)_x$ is modified; and each N' at the 5' and 3' termini of $(N')_y$ is unmodified.

In certain embodiments wherein each of x and y=21, each N at the 5' and 3' termini of $(N)_x$ is unmodified; and each N' at the 5' and 3' termini of $(N)_y$ is modified.

In particular embodiments, when x and y=19, the siRNA is modified such that a 2'-O-methyl (2'-OMe) group is present on the first, third, fifth, seventh, ninth, eleventh, thirteenth, fifteenth, seventeenth and nineteenth nucleotide of the antisense strand $(N)_x$, and whereby the very same modification, i.e. a 2'-OMe group, is present at the second, fourth, sixth, eighth, tenth, twelfth, fourteenth, sixteenth and eighteenth nucleotide of the sense strand $(N')_y$. In various embodiments these particular siRNA compounds are blunt ended at both termini.

In some embodiments, the present invention provides a compound having Structure (C):

5'(N)x-Z3'antisense strand

3'Z'-(N')y5'sense strand (C)

wherein each of N and N' is a nucleotide independently selected from an unmodified ribonucleotide, a modified ribonucleotide, an unmodified deoxyribonucleotide and a modified deoxyribonucleotide;

wherein each of (N)x and (N')y is an oligomer in which each consecutive nucleotide is joined to the next nucleotide by a covalent bond and each of x and y is an integer between 18 and 40;

wherein in (N)x the nucleotides are unmodified or (N)x comprises alternating modified ribonucleotides and unmodified ribonucleotides; each modified ribonucleotide being modified so as to have a 2'-O-methyl on its sugar and the ribonucleotide located at the middle position of (N)x being modified or unmodified preferably unmodified;

wherein (N')y comprises unmodified ribonucleotides further comprising one modified nucleotide at a terminal or penultimate position, wherein the modified nucleotide is selected from the group consisting of a mirror nucleotide, a bicyclic nucleotide, a 2'-sugar modified nucleotide, an altritol nucleotide, or a nucleotide joined to an adjacent nucleotide by an internucleotide linkage selected from a 2'-5' phosphodiester bond, a P-alkoxy linkage or a PACE linkage;

wherein if more than one nucleotide is modified in (N')y, the modified nucleotides may be consecutive;

wherein each of Z and Z' may be present or absent, but if present is 1-5 deoxyribonucleotides covalently attached at the 3' terminus of any oligomer to which it is attached;

wherein the sequence of $(N')_y$ comprises a sequence substantially complementary to (N)x; and wherein $(N)_x$ comprises an antisense sequence substantially complementary to from about 18 to about 40 consecutive ribonucleotides in an mRNA of a target gene associated with acute kidney injury.

In particular embodiments, x=y=19 and in (N)x each modified ribonucleotide is modified so as to have a 2'-O-methyl on its sugar and the ribonucleotide located at the middle of (N)x is unmodified. Accordingly, in a compound wherein x=19, (N)x comprises 2'-O-methyl sugar modified ribonucleotides at positions 1, 3, 5, 7, 9, 11, 13, 15, 17 and 19. In other embodiments, (N)x comprises 2'O Me modified ribonucleotides at positions 2, 4, 6, 8, 11, 13, 15, 17 and 19 and may further comprise at least one abasic or inverted abasic unconventional moiety for example in position 5. In other embodiments, (N)x comprises 2'O Me modified ribonucleotides at positions 2, 4, 8, 11, 13, 15, 17 and 19 and may further comprise at least one abasic or inverted abasic unconventional moiety for example in position 6. In other embodiments, (N)x comprises 2'O Me modified ribonucleotides at positions 2, 4, 6, 8, 11, 13, 17 and 19 and may further comprise at least one abasic or inverted abasic unconventional moiety for example in position 15. In other embodiments, (N)x comprises 2'O Me modified ribonucleotides at positions 2, 4, 6, 8, 11, 13, 15, 17 and 19 and may further comprise at least one abasic or inverted abasic unconventional moiety for example in position 14. In other embodiments, (N)x comprises 2'O Me modified ribonucleotides at positions 1, 2, 3, 7, 9, 11, 13, 15, 17 and 19 and may further comprise at least one abasic or inverted abasic unconventional moiety for example in position 5. In other embodiments, (N)x comprises 2'O Me modified ribonucleotides at positions 1, 2, 3, 5, 7, 9, 11, 13, 15, 17 and 19 and may further comprise at least one abasic or inverted abasic unconventional moiety for example in position 6. In other embodiments, (N)x comprises 2'O Me modified ribonucleotides at positions 1, 2, 3, 5, 7, 9, 11, 13, 17 and 19 and may further comprise at least one abasic or inverted abasic unconventional moiety for example in position 15. In other embodiments, (N)x comprises 2'O Me modified ribonucleotides at positions 1, 2, 3, 5, 7, 9, 11, 13, 15, 17 and 19 and may further comprise at least one abasic or inverted abasic unconventional moiety for example in position 14. In other embodiments, (N)x comprises 2'OMe modified ribonucleotides at positions 2, 4, 6, 7, 9, 11, 13, 15, 17 and 19 and may further comprise at least one abasic or inverted abasic unconventional moiety for example in position 5. In other embodiments, (N)x comprises 2'OMe modified ribonucleotides at positions 1, 2, 4, 6, 7, 9, 11, 13, 15, 17 and 19 and may further comprise at least one abasic or inverted abasic unconventional moiety for example in position 5. In other embodiments, (N)x comprises 2'O Me modified ribonucleotides at positions 2, 4, 6, 8, 11, 13, 14, 16, 17 and 19 and may further comprise at least one abasic or inverted abasic unconventional moiety for example in position 15. In other embodiments, (N)x comprises 2'OMe modified ribonucleotides at positions 1, 2, 3, 5, 7, 9, 11, 13, 14, 16, 17 and 19 and may further comprise at least one abasic or inverted abasic unconventional moiety for example in position 15. In other embodiments, (N)x comprises 2'OMe modified ribonucleotides at positions 2, 4, 6, 8, 11, 13, 15, 17 and 19 and may further comprise at least one abasic or inverted abasic unconventional moiety for example in position 7. In other embodiments, (N)x comprises 2'OMe modified ribonucleotides at positions 2, 4, 6, 11, 13, 15, 17 and 19 and may further comprise at least one abasic or inverted abasic unconventional moiety for example in position 8.

In yet other embodiments (N)x comprises at least one nucleotide mismatch relative to the one of the genes. In certain preferred embodiments, (N)x comprises a single nucleotide mismatch on position 5, 6, or 14. In one embodiment of Structure (C), at least two nucleotides at either or both the 5' and 3' termini of (N')y are joined by a 2'-5' phosphodiester bond. In certain preferred embodiments x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and three nucleotides at the 3' terminus of (N')y are joined by two 2'-5' phosphodiester bonds (set forth herein as Structure I). In other preferred embodiments, x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and four consecutive nucleotides at the 5' terminus of (N')y are joined by three 2'-5' phosphodiester bonds. In a further embodiment, an additional nucleotide located in the middle position of (N)y may be modified with 2'-O-methyl on its sugar. In another preferred embodiment, in (N)x the nucleotides alternate between 2'-O-methyl modified ribonucleotides and unmodified ribonucleotides, and in (N')y four consecutive nucleotides at the 5' terminus are joined by three 2'-5' phosphodiester bonds and the 5' terminal nucleotide or two or three consecutive nucleotides at the 5' terminus comprise 3'-O-methyl modifications.

In certain preferred embodiments of Structure C, x=y=19 and in (N')y the nucleotide in at least one position comprises a mirror nucleotide, a deoxyribonucleotide and a nucleotide joined to an adjacent nucleotide by a 2'-5' internucleotide bond.

In certain preferred embodiments of Structure C, x=y=19 and (N')y comprises a mirror nucleotide. In various embodiments the mirror nucleotide is an L-DNA nucleotide. In certain embodiments the L-DNA is L-deoxyribocytidine. In some embodiments (N')y comprises L-DNA at position 18. In other embodiments (N')y comprises L-DNA at positions 17 and 18. In certain embodiments (N')y comprises L-DNA substitutions at positions 2 and at one or both of positions 17 and 18. In certain embodiments (N')y further comprises a 5' terminal cap nucleotide such as 5'-O-methyl DNA or an abasic or inverted abasic moiety as an overhang.

In yet other embodiments (N')y comprises a DNA at position 15 and L-DNA at one or both of positions 17 and 18. In that structure, position 2 may further comprise an L-DNA or an abasic unconventional moiety.

Other embodiments of Structure C are envisaged wherein x=y=21 or wherein x=y=23; in these embodiments the modifications for (N')y discussed above instead of being on positions 15, 16, 17, 18 are on positions 17, 18, 19, 20 for 21 mer and on positions 19, 20, 21, 22 for 23 mer; similarly the modifications at one or both of positions 17 and 18 are on one or both of positions 19 or 20 for the 21 mer and one or both of positions 21 and 22 for the 23 mer. All modifications in the 19 mer are similarly adjusted for the 21 and 23 mer.

According to various embodiments of Structure (C), in (N')y 2, 3, 4, 5, 6, 7, 8, 9, 10, 11, 12, 13 or 14 consecutive ribonucleotides at the 3' terminus are linked by 2'-5' internucleotide linkages. In one preferred embodiment, four consecutive nucleotides at the 3' terminus of (N')y are joined by three 2'-5' phosphodiester bonds, wherein one or more of the 2'-5' nucleotides which form the 2'-5' phosphodiester bonds further comprises a 3'-O-methyl sugar modification. Preferably the 3' terminal nucleotide of (N')y comprises a 2'-O-methyl sugar modification. In certain preferred embodiments of Structure C, x=y=19 and in (N')y two or more consecutive nucleotides at positions 15, 16, 17, 18 and 19 comprise a nucleotide joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In some embodiments the nucleotides at positions 17 and 18 in (N')y are joined by a 2'-5' internucleotide bond. In other embodiments the nucleotides at positions 16, 17, 18, 16-17, 17-18, or 16-18 in (N')y are joined by a 2'-5' internucleotide bond.

In certain embodiments (N')y comprises an L-DNA at position 2 and 2'-5' internucleotide bonds at positions 16-17, 17-18, or 16-18. In certain embodiments (N')y comprises 2'-5' internucleotide bonds at positions 16-17, 17-18, or 16-18 and a 5' terminal cap nucleotide.

According to various embodiments of Structure (C), in (N')y 2, 3, 4, 5, 6, 7, 8, 9, 10, 11, 12, 13 or 14 consecutive nucleotides at either terminus or 2-8 modified nucleotides at each of the 5' and 3' termini are independently mirror nucleotides. In some embodiments the mirror nucleotide is an L-ribonucleotide. In other embodiments the mirror nucleotide is an L-deoxyribonucleotide. The mirror nucleotide may further be modified at the sugar or base moiety or in an internucleotide linkage.

In one preferred embodiment of Structure (C), the 3' terminal nucleotide or two or three consecutive nucleotides at the 3' terminus of (N')y are L-deoxyribonucleotides.

In other embodiments of Structure (C), in (N')y 2, 3, 4, 5, 6, 7, 8, 9, 10, 11, 12, 13 or 14 consecutive ribonucleotides at either terminus or 2-8 modified nucleotides at each of the 5' and 3' termini are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe). In one series of preferred embodiments, three, four or five consecutive nucleotides at the 5' terminus of (N')y comprise the 2'-OMe modification. In another preferred embodiment, three consecutive nucleotides at the 3' terminus of (N')y comprise the 2'-O-methyl modification.

In some embodiments of Structure (C), in (N')y 2, 3, 4, 5, 6, 7, 8, 9, 10, 11, 12, 13 or 14 consecutive ribonucleotides at either or 2-8 modified nucleotides at each of the 5' and 3' termini are independently bicyclic nucleotide. In various embodiments the bicyclic nucleotide is a locked nucleic acid (LNA). A 2'-O,4'-C-ethylene-bridged nucleic acid (ENA) is a species of LNA (see below).

In various embodiments (N')y comprises modified nucleotides at the 5' terminus or at both the 3' and 5' termini.

In some embodiments of Structure (C), at least two nucleotides at either or both the 5' and 3' termini of (N')y are joined by P-ethoxy backbone modifications. In certain preferred embodiments x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle position of (N)x being unmodified; and four consecutive nucleotides at the 3' terminus or at the 5' terminus of (N')y are joined by three P-ethoxy backbone modifications. In another preferred embodiment, three consecutive nucleotides at the 3' terminus or at the 5' terminus of (N')y are joined by two P-ethoxy backbone modifications.

In some embodiments of Structure (C), in (N')y 2, 3, 4, 5, 6, 7 or 8, consecutive ribonucleotides at each of the 5' and 3' termini are independently mirror nucleotides, nucleotides joined by 2'-5' phosphodiester bond, 2' sugar modified nucleotides or bicyclic nucleotide. In one embodiment, the modification at the 5' and 3' termini of (N')y is identical. In one preferred embodiment, four consecutive nucleotides at the 5' terminus of (N')y are joined by three 2'-5' phosphodiester bonds and three consecutive nucleotides at the 3' terminus of (N')y are joined by two 2'-5' phosphodiester bonds. In another embodiment, the modification at the 5' terminus of (N')y is different from the modification at the 3' terminus of (N')y. In one specific embodiment, the modified nucleotides at the 5' terminus of (N')y are mirror nucleotides and the modified nucleotides at the 3' terminus of (N')y are joined by 2'-5' phosphodiester bond. In another specific embodiment, three consecutive nucleotides at the 5' terminus of (N')y are LNA nucleotides and three consecutive nucleotides at the 3' terminus of (N')y are joined by two 2'-5' phosphodiester bonds. In (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified, or the ribonucleotides in (N)x being unmodified.

In another embodiment of Structure (C), the present invention provides a compound wherein x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; three nucleotides at the 3' terminus of (N')y are joined by two 2'-5' phosphodiester bonds and three nucleotides at the 5' terminus of (N')y are LNA such as ENA.

In another embodiment of Structure (C), five consecutive nucleotides at the 5' terminus of (N')y comprise the 2'-O-methyl sugar modification and two consecutive nucleotides at the 3' terminus of (N')y are L-DNA.

In yet another embodiment, the present invention provides a compound wherein x=y=19 or x=y=23; (N)x consists of unmodified ribonucleotides; three consecutive nucleotides at the 3' terminus of (N')y are joined by two 2'-5' phosphodiester bonds and three consecutive nucleotides at the 5' terminus of (N')y are LNA such as ENA.

According to other embodiments of Structure (C), in (N')y the 5' or 3' terminal nucleotide, or 2, 3, 4, 5 or 6 consecutive nucleotides at either termini or 1-4 modified nucleotides at each of the 5' and 3' termini are independently phosphonocarboxylate or phosphinocarboxylate nucleotides (PACE nucleotides). In some embodiments the PACE nucleotides are deoxyribonucleotides. In some preferred embodiments in (N')y, 1 or 2 consecutive nucleotides at each of the 5' and 3' termini are PACE nucleotides.

In some embodiments, the present invention provides a compound having Structure (D):

5'(N)x-Z3' antisense strand

3'Z'-(N')y5' sense strand (D)

wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein (N)x comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein (N')y comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein $(N)_x$ comprises an antisense sequence substantially complementary to from about 18 to about 40 consecutive ribonucleotides in an mRNA of a target gene associated with acute kidney injury.

In one embodiment of Structure (D), x=y=19 or x=y=23; (N)x comprises unmodified ribonucleotides in which two consecutive nucleotides linked by one 2'-5' internucleotide linkage at the 3' terminus; and (N')y comprises unmodified ribonucleotides in which two consecutive nucleotides linked by one 2'-5' internucleotide linkage at the 5' terminus.

In some embodiments, x=y=19 or x=y=23; (N)x comprises unmodified ribonucleotides in which three consecutive nucleotides at the 3' terminus are joined together by two 2'-5' phosphodiester bonds; and (N')y comprises unmodified ribonucleotides in which four consecutive nucleotides at the 5' terminus are joined together by three 2'-5' phosphodiester bonds (set forth herein as Structure II).

According to various embodiments of Structure (D) 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are linked by 2'-5' internucleotide linkages.

According to one preferred embodiment of Structure (D), four consecutive nucleotides at the 5' terminus of (N')y are joined by three 2'-5' phosphodiester bonds and three consecutive nucleotides at the 3' terminus of (N')x are joined by two 2'-5' phosphodiester bonds. Three nucleotides at the 5' terminus of (N')y and two nucleotides at the 3' terminus of (N')x may also comprise 3'-O-methyl modifications.

According to various embodiments of Structure (D), 2, 3, 4, 5, 6, 7, 8, 9, 10, 11, 12, 13 or 14 consecutive nucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently mirror nucleotides. In some embodiments the mirror is an L-ribonucleotide. In other embodiments the mirror nucleotide is L-deoxyribonucleotide.

In other embodiments of Structure (D), 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In one preferred embodiment of Structure (D), five consecutive nucleotides at the 5' terminus of (N')y comprise a 2'OMe sugar modification and five consecutive nucleotides at the 3' terminus of (N')x comprise the 2'OMe sugar modification. In another preferred embodiment of Structure (D), ten consecutive nucleotides at the 5' terminus of (N')y comprise the 2'OMe sugar modification and five consecutive nucleotides at the 3' terminus of (N')x comprise the 2'OMe sugar modification. In another preferred embodiment of Structure (D), thirteen consecutive nucleotides at the 5' terminus of (N')y comprise the 2'OMe sugar modification and five consecutive nucleotides at the 3' terminus of (N')x comprise the 2'-O-methyl modification.

In some embodiments of Structure (D), in (N')y 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently a bicyclic nucleotide. In various embodiments the bicyclic nucleotide is a locked nucleic acid (LNA) such as a 2'-O,4'-C-ethylene-bridged nucleic acid (ENA).

In various embodiments of Structure (D), (N')y comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a 2'-5' phosphodiester bond, a P-alkoxy linkage or a PACE linkage;

In various embodiments of Structure (D), (N)x comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a 2'-5' phosphodiester bond, a P-alkoxy linkage or a PACE linkage;

In embodiments wherein each of the 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In one specific embodiment of Structure (D), five consecutive nucleotides at the 5' terminus of (N')y comprise the 2'OMe sugar modification and two consecutive nucleotides at the 3' terminus of (N')y are L-DNA. In addition, the compound may further comprise five consecutive 2'OMe sugar modified nucleotides at the 3' terminus of (N')x.

In various embodiments of Structure (D), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (E):

5'(N)x-Z3'antisense strand

3'Z'-(N')y5'sense strand (E)

wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein (N)x comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein (N')y comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of (N')y is a sequence substantially complementary to (N)x; and wherein the sequence of (N)x comprises an antisense sequence substantially complementary to from about 18 to about 40 consecutive ribonucleotides in an mRNA of a target gene associated with acute kidney injury.

In certain preferred embodiments the ultimate nucleotide at the 5' terminus of (N)x is unmodified.

According to various embodiments of Structure (E) 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are linked by 2'-5' internucleotide linkages.

According to various embodiments of Structure (E), 2, 3, 4, 5, 6, 7, 8, 9, 10, 11, 12, 13 or 14 consecutive nucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive nucleotides starting at the ultimate or penultimate position of the 3' terminus of (N')y are independently mirror nucleotides. In some embodiments the mirror is an L-ribonucleotide. In other embodiments the mirror nucleotide is L-deoxyribonucleotide.

In other embodiments of Structure (E), 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In some embodiments of Structure (E), in (N')y 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are independently a bicyclic nucleotide. In various embodiments the bicyclic nucleotide is a locked nucleic acid (LNA) such as a 2'-O,4'-C-ethylene-bridged nucleic acid (ENA).

In various embodiments of Structure (E), (N')y comprises modified nucleotides selected from a bicyclic nucleotide, a 2' sugar modified nucleotide, a mirror nucleotide, an altritol nucleotide, a nucleotide joined to an adjacent nucleotide by a P-alkoxy backbone modification or a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In various embodiments of Structure (E), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where both 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (E), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (F):

5'(N)x-Z3'antisense strand

3'Z'-(N')y5'sense strand (F)

wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein each of (N)x and (N')y comprise unmodified ribonucleotides in which each of (N)x and (N')y independently comprise one modified nucleotide at the 3' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a nucleotide joined to an adjacent nucleotide by a 2'-5' phosphodiester bond;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence substantially complementary to from about 18 to about 40 consecutive ribonucleotides in an mRNA of a target gene associated with acute kidney injury.

In some embodiments of Structure (F), x=y=19 or x=y=23; (N')y comprises unmodified ribonucleotides in which two consecutive nucleotides at the 3' terminus comprises two consecutive mirror deoxyribonucleotides; and (N)x comprises unmodified ribonucleotides in which one nucleotide at the 3' terminus comprises a mirror deoxyribonucleotide (set forth as Structure III).

According to various embodiments of Structure (F) 2, 3, 4, 5, 6, 7, 8, 9, 10, 11, 12, 13 or 14 consecutive ribonucleotides independently beginning at the ultimate or penultimate position of the 3' termini of (N)x and (N')y are linked by 2'-5' internucleotide linkages.

According to one preferred embodiment of Structure (F), three consecutive nucleotides at the 3' terminus of (N')y are joined by two 2'-5' phosphodiester bonds and three consecutive nucleotides at the 3' terminus of (N')x are joined by two 2'-5' phosphodiester bonds.

According to various embodiments of Structure (F), 2, 3, 4, 5, 6, 7, 8, 9, 10, 11, 12, 13 or 14 consecutive nucleotides independently beginning at the ultimate or penultimate position of the 3' termini of (N)x and (N')y are independently mirror nucleotides. In some embodiments the mirror nucleotide is an L-ribonucleotide. In other embodiments the mirror nucleotide is an L-deoxyribonucleotide.

In other embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In some embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently a bicyclic nucleotide. In various embodiments the bicyclic nucleotide is a locked nucleic acid (LNA) such as a 2'-O,4'-C-ethylene-bridged nucleic acid (ENA).

In various embodiments of Structure (F), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at both the 3' and 5' termini.

In various embodiments of Structure (F), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (F), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (G):

5'(N)x-Z3' antisense strand

3'Z'-(N')y5'sense strand (G)

wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein each of (N)x and (N')y comprise unmodified ribonucleotides in which each of (N)x and (N')y independently comprise one modified nucleotide at the 5' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a nucleotide joined to an adjacent nucleotide by a 2'-5' phosphodiester bond;

wherein for (N)x the modified nucleotide is preferably at penultimate position of the 5' terminal;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence substantially complementary to from about 18 to about 40 consecutive ribonucleotides in an mRNA of a target gene associated with acute kidney injury.

In some embodiments of Structure (G), x=y=19 or x=y=23.

According to various embodiments of Structure (G) 2, 3, 4, 5, 6, 7, 8, 9, 10, 11, 12, 13 or 14 consecutive ribonucleotides independently beginning at the ultimate or penultimate position of the 5' termini of (N)x and (N')y are linked by 2'-5' internucleotide linkages. For (N)x the modified nucleotides preferably starting at the penultimate position of the 5' terminal.

According to various embodiments of Structure (G), 2, 3, 4, 5, 6, 7, 8, 9, 10, 11, 12, 13 or 14 consecutive nucleotides independently beginning at the ultimate or penultimate position of the 5' termini of (N)x and (N')y are independently mirror nucleotides. In some embodiments the mirror nucleotide is an L-ribonucleotide. In other embodiments the mirror nucleotide is an L-deoxyribonucleotide. For (N)x the modified nucleotides preferably starting at the penultimate position of the 5' terminal.

In other embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe). In some preferred embodiments the consecutive modified nucleotides preferably begin at the penultimate position of the 5' terminus of (N)x.

In one preferred embodiment of Structure (G), five consecutive ribonucleotides at the 5' terminus of (N')y comprise a 2'OMe sugar modification and one ribonucleotide at the 5' penultimate position of (N')x comprises a 2'OMe sugar modification. In another preferred embodiment of Structure (G), five consecutive ribonucleotides at the 5' terminus of (N')y comprise 2'OMe sugar modification and two consecutive ribonucleotides at the 5' terminal position of (N')x comprise a 2'OMe sugar modification.

In some embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are bicyclic nucleotides. In various embodiments the bicyclic nucleotide is a locked nucleic acid (LNA) such as a 2'-O,4'-C-ethylene-bridged nucleic acid (ENA). In some preferred embodiments the consecutive modified nucleotides preferably begin at the penultimate position of the 5' terminus of (N)x.

In various embodiments of Structure (G), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In various embodiments of Structure (G), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond. In various embodiments of Structure (G), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (H):

5'(N)x-Z3' antisense strand

3'Z'-(N')y5' sense strand (H)

wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein (N)x comprises unmodified ribonucleotides further comprising one modified nucleotide at the 3' terminal or penultimate position or the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein (N')y comprises unmodified ribonucleotides further comprising one modified nucleotide at an internal position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of $(N')_y$ is a sequence substantially complementary to (N)x; and wherein the sequence of $(N)_x$ comprises an antisense sequence substantially complementary to from about 18 to about 40 consecutive ribonucleotides in an mRNA of a target gene associated with acute kidney injury.

In one embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or both termini of (N)x are independently 2' sugar modified nucleotides, bicyclic nucleotides, mirror nucleotides, altritol nucleotides or nucleotides joined to an adjacent nucleotide by a 2'-5' phosphodiester bond and 2, 3, 4, 5, 6, 7, 8, 9, 10, 11, 12, 13 or 14 consecutive internal ribonucleotides in (N')y are independently 2' sugar modified nucleotides, bicyclic nucleotides, mirror nucleotides, altritol nucleotides or nucleotides joined to an adjacent nucleotide by a 2'-5' phosphodiester bond. In some embodiments the 2' sugar modification comprises the presence of an amino, a fluoro, an alkoxy or an alkyl moiety. In certain embodiments the 2' sugar modification comprises a methoxy moiety (2'-OMe).

In another embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or 2-8 consecutive nucleotides at each of 5' and 3' termini of (N')y are independently 2' sugar modified nucleotides, bicyclic nucleotides, mirror nucleotides, altritol nucleotides or nucleotides joined to an adjacent nucleotide by a 2'-5' phosphodiester bond, and 2, 3, 4, 5, 6, 7, 8, 9, 10, 11, 12, 13 or 14 consecutive internal ribonucleotides in (N)x are independently 2' sugar modified nucleotides, bicyclic nucleotides, mirror nucleotides, altritol nucleotides or nucleotides joined to an adjacent nucleotide by a 2'-5' phosphodiester bond.

In one embodiment wherein each of 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (H), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In one preferred embodiment of Structure (H), x=y=19; three consecutive ribonucleotides at the 9-11 nucleotide positions 9-11 of (N')y comprise 2'OMe sugar modification and five consecutive ribonucleotides at the 3' terminal position of (N')x comprise 2'OMe sugar modification.

For all the above Structures (A)-(H), in various embodiments x=y and each of x and y is 19, 20, 21, 22 or 23. In certain embodiments, x=y=19. In yet other embodiments x=y=23. In additional embodiments the compound comprises modified ribonucleotides in alternating positions wherein each N at the 5' and 3' termini of (N)x are modified in their sugar residues and the middle ribonucleotide is not modified, e.g. ribonucleotide in position 10 in a 19-mer strand, position 11 in a 21 mer and position 12 in a 23-mer strand.

In some embodiments where x=y=21 or x=y=23 the position of modifications in the 19 mer are adjusted for the 21 and 23 mers with the proviso that the middle nucleotide of the antisense strand is preferably not modified.

In some embodiments, neither (N)x nor (N')y are phosphorylated at the 3' and 5' termini. In other embodiments either or both (N)x and (N')y are phosphorylated at the 3' termini. In yet another embodiment, either or both (N)x and (N')y are phosphorylated at the 3' termini using non-cleavable phosphate groups. In yet another embodiment, either or both (N)x and (N')y are phosphorylated at the terminal 2' termini position using cleavable or non-cleavable phosphate groups. These particular siRNA compounds are also blunt ended and are non-phosphorylated at the termini; however, comparative experiments have shown that siRNA compounds phosphorylated at one or both of the 3'-termini have similar activity in vivo compared to the non-phosphorylated compounds.

In certain embodiments for all the above-mentioned Structures, the compound is blunt ended, for example wherein both Z and Z' are absent. In an alternative embodiment, the compound comprises at least one 3' overhang, wherein at least one of Z or Z' is present. Z and Z' independently comprises one or more covalently linked modified or non-modified nucleotides, for example inverted dT or dA; dT, LNA, mirror nucleotide and the like. In some embodiments each of Z and Z' are independently selected from dT and dTdT. siRNA in which Z and/or Z' is present have similar activity and stability as siRNA in which Z and Z' are absent.

In certain embodiments for all the above-mentioned Structures, the compound comprises one or more phosphonocarboxylate and/or phosphinocarboxylate nucleotides (PACE nucleotides). In some embodiments the PACE nucleotides are deoxyribonucleotides and the phosphinocarboxylate nucleotides are phosphinoacetate nucleotides. Examples of PACE nucleotides and analogs are disclosed in U.S. Pat. Nos. 6,693,187 and 7,067,641, both incorporated herein by reference.

In certain embodiments for all the above-mentioned Structures, the compound comprises one or more locked nucleic acids (LNA) also defined as bridged nucleic acids or bicyclic nucleotides. Preferred locked nucleic acids are 2'-O,4'-C-ethylene nucleosides (ENA) or 2'-O,4'-C-methylene nucleosides. Other examples of LNA and ENA nucleotides are disclosed in WO 98/39352, WO 00/47599 and WO 99/14226, all incorporated herein by reference.

In certain embodiments for all the above-mentioned Structures, the compound comprises one or more altritol monomers (nucleotides), also defined as 1,5 anhydro-2-deoxy-D-altrito-hexitol (see for example, Allart, et al., 1998. *Nucleosides & Nucleotides* 17:1523-1526; Herdewijn et al., 1999. *Nucleosides & Nucleotides* 18:1371-1376; Fisher et al., 2007, *NAR* 35(4):1064-1074; all incorporated herein by reference).

The present invention explicitly excludes compounds in which each of N and/or N' is a deoxyribonucleotide (D-A, D-C, D-G, D-T). In certain embodiments (N)x and (N')y may comprise independently 1, 2, 3, 4, 5, 6, 7, 8, 9 or more deoxyribonucleotides. In certain embodiments the present invention provides a compound wherein each of N is an unmodified ribonucleotide and the 3' terminal nucleotide or 2, 3, 4, 5, 6, 7, 8, 9, 10, 11, 12, 13 or 14 consecutive nucleotides at the 3' terminus of (N')y are deoxyribonucleotides. In yet other embodiments each of N is an unmodified ribonucleotide and the 5' terminal nucleotide or 2, 3, 4, 5, 6, 7, 8, 9, 10, 11, 12, 13 or 14 consecutive nucleotides at the 5' terminus of (N')y are deoxyribonucleotides. In further embodiments the 5' terminal nucleotide or 2, 3, 4, 5, 6, 7, 8, or 9 consecutive nucleotides at the 5' terminus and 1, 2, 3, 4, 5, or 6 consecutive nucleotides at the 3' termini of (N)x are deoxyribonucleotides and each of N' is an unmodified ribonucleotide. In yet further embodiments (N)x comprises unmodified ribonucleotides and 1 or 2, 3 or 4 consecutive deoxyribonucleotides independently at each of the 5' and 3' termini and 1 or 2, 3, 4, 5 or 6 consecutive deoxyribonucleotides in internal positions; and each of N' is an unmodified ribonucleotide. In certain embodiments the 3' terminal nucleotide or 2, 3, 4, 5, 6, 7, 8, 9, 10, 11, 12 13 or 14 consecutive nucleotides at the 3' terminus of (N')y and the terminal 5' nucleotide or 2, 3, 4, 5, 6, 7, 8, 9, 10, 11, 12 13 or 14 consecutive nucleotides at the 5' terminus of (N)x are deoxyribonucleotides. The present invention excludes compounds in which each of N and/or N' is a deoxyribonucleotide. In some embodiments the 5' terminal nucleotide of N or 2 or 3 consecutive of N and 1, 2, or 3 of N' is a deoxyribonucleotide. Certain examples of active DNA/RNA siRNA chimeras are disclosed in US patent publication 2005/0004064, and Ui-Tei, 2008 (NAR 36(7):2136-2151) incorporated herein by reference in their entirety.

Unless otherwise indicated, in preferred embodiments of the structures discussed herein the covalent bond between each consecutive N or N' is a phosphodiester bond.

An additional novel molecule provided by the present invention is an oligonucleotide comprising consecutive nucleotides wherein a first segment of such nucleotides encode a first inhibitory RNA molecule, a second segment of such nucleotides encode a second inhibitory RNA molecule, and a third segment of such nucleotides encode a third inhibitory RNA molecule. Each of the first, the second and the third segment may comprise one strand of a double stranded RNA and the first, second and third segments may be joined together by a linker. Further, the oligonucleotide may comprise three double stranded segments joined together by one or more linker Thus, one molecule provided by the present invention is an oligonucleotide comprising consecutive nucleotides which encode three inhibitory RNA molecules; said oligonucleotide may possess a triple stranded structure, such that three double stranded arms are linked together by one or more linker, such as any of the linkers presented hereinabove. This molecule forms a "star"-like structure, and may also be referred to herein as RNAstar. Such structures are disclosed in PCT patent publication WO 2007/091269, assigned to the assignee of the present invention and incorporated herein in its entirety by reference.

A covalent bond refers to an internucleotide linkage linking one nucleotide monomer to an adjacent nucleotide monomer. A covalent bond includes for example, a phosphodiester bond, a phosphorothioate bond, a P-alkoxy bond, a P-carboxy bond and the like. The normal internucleoside linkage of RNA and DNA is a 3' to 5' phosphodiester linkage. In certain preferred embodiments a covalent bond is a phosphodiester bond. Covalent bond encompasses non-phosphorous-containing internucleoside linkages, such as those disclosed in WO 2004/041924 inter alia. Unless otherwise indicated, in preferred embodiments of the structures discussed herein the covalent bond between each consecutive N or N' is a phosphodiester bond.

For all of the structures above, in some embodiments the oligonucleotide sequence of (N)x is fully complementary to the oligonucleotide sequence of (N')y. In other embodiments (N)x and (N')y are substantially complementary. In certain embodiments (N)x is fully complementary to a target sequence. In other embodiments (N)x is substantially complementary to a target sequence.

In some embodiments, neither (N)x nor (N')y are phosphorylated at the 3' and 5' termini. In other embodiments either or both (N)x and (N')y are phosphorylated at the 3' termini (3' Pi). In yet another embodiment, either or both (N)x and (N')y are phosphorylated at the 3' termini with non-cleavable phosphate groups. In yet another embodiment, either or both (N)x and (N')y are phosphorylated at the terminal 2' termini position using cleavable or non-cleavable phosphate groups. Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks.

In one aspect the present invention provides a compound having Structure (I):

5'(N)x-Z3'(antisense strand)

3'Z'-(N')y-z"5'(sense strand) (I)

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein Z and Z' may be present or absent, but if present is independently 1-5 consecutive nucleotides or non-nucleotide moieties covalently attached at the 3' terminus of the strand in which it is present;

wherein z" may be present or absent, but if present is a capping moiety covalently attached at the 5' terminus of (N')y;

wherein x=18 to 27;

wherein y=18 to 27;

wherein (N)x comprises modified and unmodified ribonucleotides, each modified ribonucleotide having a 2'-O-methyl on its sugar, wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide;

wherein in (N')y at least one unconventional moiety is present, which unconventional moiety may be an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond; and wherein the sequence of $(N)_y$ is a sequence having complementarity to (N)x; and wherein the sequence of $(N)_x$ comprises an antisense sequence having complementarity to from about 18 to about 27 consecutive ribonucleotides in an mRNA of a target gene associated with acute kidney injury.

In some embodiments x=y=19. In other embodiments x=y=23. In some embodiments the at least one unconventional moiety is present at positions 15, 16, 17, or 18 in (N')y. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments an L-DNA moiety is present at position 17, position 18 or positions 17 and 18.

In other embodiments the unconventional moiety is an abasic moiety. In various embodiments (N')y comprises at least five abasic ribose moieties or abasic deoxyribose moieties.

In yet other embodiments (N')y comprises at least five abasic ribose moieties or abasic deoxyribose moieties and at least one of N' is an LNA.

In some embodiments (N)x comprises nine alternating modified ribonucleotides. In other embodiments of Structure (I) (N)x comprises nine alternating modified ribonucleotides further comprising a 2'O modified nucleotide at position 2. In some embodiments (N)x comprises 2'O Me modified ribonucleotides at the odd numbered positions 1, 3, 5, 7, 9, 11, 13, 15, 17, 19. In other embodiments (N)x further comprises a 2'O Me modified ribonucleotide at one or both of positions 2 and 18. In yet other embodiments (N)x comprises 2'O Me modified ribonucleotides at positions 2, 4, 6, 8, 11, 13, 15, 17, 19.

In various embodiments z" is present and is selected from an abasic ribose moiety, a deoxyribose moiety; an inverted abasic ribose moiety, a deoxyribose moiety; C6-amino-Pi; a mirror nucleotide.

In another aspect the present invention provides a compound having Structure (J) set forth below:

5'(N)x-Z3'(antisense strand)

3'Z'-(N')y-z"5'(sense strand) (J)

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein Z and Z' may be present or absent, but if present is independently 1-5 consecutive nucleotides covalently attached at the 3' terminus of the strand in which it is present;

wherein z" may be present or absent but if present is a capping moiety covalently attached at the 5' terminus of (N')y;

wherein x=18 to 27;

wherein y=18 to 27;

wherein (N)x comprises modified or unmodified ribonucleotides, and optionally at least one unconventional moiety;

wherein in (N')y at least one unconventional moiety is present, which unconventional moiety may be an abasic ribose moiety, an abasic deoxyribose moiety, a modified or unmodified deoxyribonucleotide, a mirror nucleotide, a non-base pairing nucleotide analog or a nucleotide joined to an adjacent nucleotide by a 2'-5' internucleotide phosphate bond; and wherein the sequence of $(N)_3$/is a sequence having complementarity to (N)x; and wherein the sequence of $(N)_x$ comprises an antisense sequence having complementarity to from about 18 to about 27 consecutive ribonucleotides in an mRNA of a target gene associated with acute kidney injury.

In some embodiments x=y=19. In other embodiments x=y=23. In some preferred embodiments (N)x comprises modified and unmodified ribonucleotides, and at least one unconventional moiety.

In some embodiments in (N)x the N at the 3' terminus is a modified ribonucleotide and (N)x comprises at least 8 modified ribonucleotides. In other embodiments at least 5 of the at least 8 modified ribonucleotides are alternating beginning at the 3' end. In some embodiments (N)x comprises an abasic moiety in one of positions 5, 6, 7, 8, 9, 10, 11, 12, 13, 14 or 15.

In some embodiments the at least one unconventional moiety in (N')y is present at positions 15, 16, 17, or 18. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments an L-DNA moiety is present at position 17, position 18 or positions 17 and 18. In other embodiments the at least one unconventional moiety in (N')y is an abasic ribose moiety or an abasic deoxyribose moiety.

In yet another aspect the present invention provides a compound having Structure (K) set forth below:

5'$(N)_x$-Z3'(antisense strand)

3'Z'-$(N')_y$-z"5'(sense strand) (K)

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein Z and Z' may be present or absent, but if present is independently 1-5 consecutive nucleotides covalently attached at the 3' terminus of the strand in which it is present;

wherein z" may be present or absent but if present is a capping moiety covalently attached at the 5' terminus of (N')y;

wherein x=18 to 27;

wherein y=18 to 27;

wherein (N)x comprises a combination of modified or unmodified ribonucleotides and unconventional moieties, any modified ribonucleotide having a 2'-O-methyl on its sugar;

wherein (N')y comprises modified or unmodified ribonucleotides and optionally an unconventional moiety, any modified ribonucleotide having a 2'OMe on its sugar;

wherein the sequence of $(N)_y$ is a sequence having complementarity to (N)x; and wherein the sequence of $(N)_x$ comprises an antisense sequence having complementarity to from about 18 to about 27 consecutive ribonucleotides in an mRNA of a target gene associated with acute kidney injury.

In some embodiments x=y=19. In other embodiments x=y=23. In some preferred embodiments the at least one unconventional moiety is present in (N)x and is an abasic ribose moiety or an abasic deoxyribose moiety. In other embodiments the at least one unconventional moiety is present in (N)x and is a non-base pairing nucleotide analog. In various embodiments (N')y comprises unmodified ribonucleotides. In some embodiments (N)x comprises at least five abasic ribose moieties or abasic deoxyribose moieties or a combination thereof. In certain embodiments (N)x and/or (N')y comprise modified ribonucleotides which do not base pair with corresponding modified or unmodified ribonucleotides in (N')y and/or (N)x.

In various embodiments the present invention provides an siRNA set forth in Structure (L):

5'$(N)_x$-Z3'(antisense strand)

3'Z'-$(N')_y$5'(sense strand) (L)

wherein each of N and N' is a nucleotide selected from an unmodified ribonucleotide, a modified ribonucleotide, an unmodified deoxyribonucleotide and a modified deoxyribonucleotide;

wherein each of $(N)_x$ and $(N')_y$ is an oligonucleotide in which each consecutive N or N' is joined to the next N or N' by a covalent bond;

wherein Z and Z' are absent;

wherein x=y=19;

wherein in (N')y the nucleotide in at least one of positions 15, 16, 17, 18 and 19 comprises a nucleotide selected from an abasic unconventional moiety, a mirror nucleotide, a deoxyribonucleotide and a nucleotide joined to an adjacent nucleotide by a 2'-5' internucleotide bond;

wherein (N)x comprises alternating 2'OMe sugar modified ribonucleotides and unmodified ribonucleotides so as to have 2'OMe sugar modified ribonucleotide at the middle position of (N)x; and wherein the sequence of $(N)_y$ is a sequence having complementarity to (N)x; and wherein the sequence of $(N)_x$ comprises an antisense having complementarity to from about 18 to about 40 consecutive ribonucleotides in an mRNA of a target gene associated with acute kidney injury.

In some embodiments of Structure (L), in (N')y the nucleotide in one or both of positions 17 and 18 comprises a modified nucleotide selected from an abasic unconventional moiety, a mirror nucleotide and a nucleotide joined to an adjacent nucleotide by a 2'-5' internucleotide bond. In some embodiments the mirror nucleotide is selected from L-DNA and L-RNA. In various embodiments the mirror nucleotide is L-DNA.

In various embodiments (N')y comprises a modified nucleotide at position 15 wherein the modified nucleotide is selected from a mirror nucleotide and a deoxyribonucleotide.

In certain embodiments (N')y further comprises a modified nucleotide or pseudo nucleotide at position 2 wherein the pseudo nucleotide may be an abasic unconventional moiety and the modified nucleotide is optionally a mirror nucleotide.

In various embodiments the antisense strand (N)x comprises 2'O-Me modified ribonucleotides at the odd numbered positions (5' to 3'; positions 1, 3, 5, 7, 9, 11, 13, 15, 17, 19). In some embodiments (N)x further comprises 2'O-Me modified ribonucleotides at one or both positions 2 and 18. In other embodiments (N)x comprises 2'O Me modified ribonucleotides at positions 2, 4, 6, 8, 11, 13, 15, 17, 19.

Other embodiments of Structures (L) are envisaged wherein x=y=21 or wherein x=y=23; in these embodiments the modifications for (N')y discussed above instead of being in positions 17 and 18 are in positions 19 and 20 for 21-mer oligonucleotide and 21 and 22 for 23-mer oligonucleotide; similarly the modifications in positions 15, 16, 17, 18 or 19 are in positions 17, 18, 19, 20 or 21 for the 21-mer oligonucleotide and positions 19, 20, 21, 22, or 23 for the 23-mer oligonucleotide. The 2'O Me modifications on the antisense strand are similarly adjusted. In some embodiments (N)x comprises 2'O Me modified ribonucleotides at the odd numbered positions (5' to 3'; positions 1, 3, 5, 7, 9, 12, 14, 16, 18, 20 for the 21-mer oligonucleotide [nucleotide at position 11 unmodified] and 1, 3, 5, 7, 9, 11, 13, 15, 17, 19, 21, 23 for the 23-mer oligonucleotide [nucleotide at position 12 unmodified]. In other embodiments (N)x comprises 2'O Me modified ribonucleotides at positions 2, 4, 6, 8, 10, 12, 14, 16, 18, 20 [nucleotide at position 11 unmodified for the 21-mer oligonucleotide and at positions 2, 4, 6, 8, 10, 13, 15, 17, 19, 21, 23 for the 23-mer oligonucleotide [nucleotide at position 12 unmodified].

In some embodiments (N')y further comprises a 5' terminal cap nucleotide. In various embodiments the terminal cap moiety is selected from an abasic unconventional moiety, an inverted abasic unconventional moiety, an L-DNA nucleotide, and a C6-imine phosphate (C6 amino linker with phosphate at terminus).

In other embodiments the present invention provides a compound having Structure (M) set forth below:

5'(N)ₓ-Z3'(antisense strand)

3'Z'-(N')ᵧ5'(sense strand)  (M)

wherein each of N and N' is selected from a pseudo-nucleotide and a nucleotide;

wherein each nucleotide is selected from an unmodified ribonucleotide, a modified ribonucleotide, an unmodified deoxyribonucleotide and a modified deoxyribonucleotide;

wherein each of $(N)_x$ and $(N')_y$ is an oligonucleotide in which each consecutive N or N' is joined to the next N or N' by a covalent bond;

wherein Z and Z' are absent;

wherein x=18 to 27;

wherein y=18 to 27;

wherein the sequence of $(N)_y$ is a sequence having complementarity to (N)x; and wherein the sequence of $(N)_x$ comprises an antisense sequence having complementarity to from about 18 to about 27 consecutive ribonucleotides in an mRNA of a target gene associated with acute kidney injury.

In other embodiments the present invention provides a double stranded compound having Structure (N) set forth below:

5'(N)ₓ-Z3'(antisense strand)

3'Z'-(N')ᵧ5'(sense strand)  (N)

wherein each of N and N' is a nucleotide selected from an unmodified ribonucleotide, a modified ribonucleotide, an unmodified deoxyribonucleotide and a modified deoxyribonucleotide;

wherein each of $(N)_x$ and $(N')_y$ is an oligonucleotide in which each consecutive N or N' is joined to the next N or N' by a covalent bond;

wherein Z and Z' are absent;

wherein each of x and y is an integer between 18 and 40;

wherein the sequence of $(N)_y$ is a sequence having complementarity to (N)x; and wherein the sequence of $(N)_x$ comprises an antisense sequence having complementarity to from about 18 to about 40 consecutive ribonucleotides in an antisense sequence to the mRNA of a target gene associated with acute kidney injury;

wherein (N)x, (N')y or (N)x and (N')y comprise non base-pairing modified nucleotides such that (N)x and (N')y form less than 15 base pairs in the double stranded compound.

In other embodiments the present invention provides a compound having Structure (O) set forth below:

5'(N)ₓ-Z3'(antisense strand)

3'Z'-(N')ᵧ5'(sense strand)  (O)

wherein each of N is a nucleotide selected from an unmodified ribonucleotide, a modified ribonucleotide, an unmodified deoxyribonucleotide and a modified deoxyribonucleotide;

wherein each of N' is a nucleotide analog selected from a six membered sugar nucleotide, seven membered sugar nucleotide, morpholino moiety, peptide nucleic acid and combinations thereof;

wherein each of $(N)_x$ and $(N')_y$ is an oligonucleotide in which each consecutive N or N' is joined to the next N or N' by a covalent bond;

wherein Z and Z' are absent;

wherein each of x and y is an integer between 18 and 40;

wherein the sequence of $(N)_y$ is a sequence having complementarity to (N)x; and wherein the sequence of $(N)_x$ comprises an antisense sequence having complementarity to from about 18 to about 40 consecutive ribonucleotides in an mRNA of a target gene associated with acute kidney injury.

In other embodiments the present invention provides a compound having Structure (P) set forth below:

5'(N)ₓ-Z3'(antisense strand)

3'Z'-(N')ᵧ5'(sense strand)  (P)

wherein each of N and N' is a nucleotide selected from an unmodified ribonucleotide, a modified ribonucleotide, an unmodified deoxyribonucleotide and a modified deoxyribonucleotide;

wherein each of $(N)_x$ and $(N')_y$ is an oligonucleotide in which each consecutive N or N' is joined to the next N or N' by a covalent bond;

wherein Z and Z' are absent;

wherein each of x and y is an integer between 18 and 40;

wherein one of N or N' in an internal position of (N)x or (N')y or one or more of N or N' at a terminal position of (N)x or (N')y comprises an abasic moiety or a 2' modified nucleotide;

wherein the sequence of $(N)_y$ is a sequence having complementarity to (N)x; and wherein the sequence of $(N)_x$ comprises an antisense sequence having complementarity to from about 18 to about 40 consecutive ribonucleotides in an mRNA of a target gene associated with acute kidney injury.

In various embodiments (N')y comprises a modified nucleotide at position 15 wherein the modified nucleotide is selected from a mirror nucleotide and a deoxyribonucleotide.

In certain embodiments (N')y further comprises a modified nucleotide at position 2 wherein the modified nucleotide is selected from a mirror nucleotide and an abasic unconventional moiety.

In various embodiments the antisense strand (N)x comprises 2'O-Me modified ribonucleotides at the odd numbered positions (5' to 3'; positions 1, 3, 5, 7, 9, 11, 13, 15, 17, 19). In some embodiments $(N)_x$ further comprises 2'O-Me modified ribonucleotides at one or both positions 2 and 18. In other embodiments (N)x comprises 2'O Me modified ribonucleotides at positions 2, 4, 6, 8, 11, 13, 15, 17, 19.

An additional novel molecule provided by the present invention is an oligonucleotide comprising consecutive nucleotides wherein a first segment of such nucleotides encode a first inhibitory RNA molecule, a second segment of such nucleotides encode a second inhibitory RNA molecule, and a third segment of such nucleotides encode a third inhibitory RNA molecule. Each of the first, the second and the third segment may comprise one strand of a double stranded RNA and the first, second and third segments may be joined together by a linker. Further, the oligonucleotide may comprise three double stranded segments joined together by one or more linker Thus, one molecule employed in the methods of the present invention is an oligonucleotide comprising consecutive nucleotides which encode three inhibitory RNA molecules; said oligonucleotide may possess a triple stranded structure, such that three double stranded arms are linked together by one or more linker, such as any of the linkers presented hereinabove. This molecule forms a "star"-like structure, and may also be referred to herein as RNAstar and described in PCT Patent Publication WO 2007/091269 assigned to one of the assignees of the presnet application.

Said triple-stranded oligonucleotide may be an oligoribonucleotide having the general structure:

5'Oligo1(sense)LINKER A Oligo2(sense)3'

3'Oligo1(antisense)LINKER B Oligo3(sense)5'

3'Oligo3(antisense)LINKER C Oligo2(antisense)5' or

5'Oligo1(sense)LINKER A Oligo2(antisense)3'

3'Oligo1(antisense)LINKER B Oligo3(sense)5'

3'Oligo3(antisense)LINKER C Oligo2(sense)5' or

5'Oligo1(sense)LINKER A Oligo3(antisense)3'

3'Oligo1(antisense)LINKER B Oligo2(sense)5'

5'Oligo3(sense)LINKER C Oligo2(antisense)3' wherein one or more of linker A, linker B or linker C is present; any combination of two or more oligonucleotides and one or more of linkers A-C is possible, so long as the polarity of the strands and the general structure of the molecule remains. Further, if two or more of linkers A-C are present, they may be identical or different.

Thus, a triple-armed structure is formed, wherein each arm comprises a sense strand and complementary antisense strand (i.e. Oligo1 antisense base pairs to Oligo1 sense etc.). The triple armed structure may be triple stranded, whereby each arm possesses base pairing.

Further, the above triple stranded structure may have a gap instead of a linker in one or more of the strands. Such a molecule with one gap is technically quadruple stranded and not triple stranded; inserting additional gaps or nicks will lead to the molecule having additional strands. Preliminary results obtained by the inventors of the present invention indicate that said gapped molecules are more active in inhibiting certain target genes than the similar but non-gapped molecules. This may also be the case for nicked molecules.

According to one preferred embodiment of the invention, the antisense and the sense strands of the siRNA are phosphorylated only at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

The invention further provides a vector capable of expressing any of the aforementioned oligoribonucleotides in a cell after which appropriate modification may be made. In preferred embodiment the cell is a mammalian cell, preferably a human cell.

Methods of Treatment

In one embodiment, the present invention relates to a method for the treatment of a subject in need of treatment for attenuation of CKD progression which is associated with expression of one or more of the target genes of Table 1, comprising administering to the subject an amount of an oligonucleotide inhibitor, which reduces, down regulates or inhibits expression or upregulation of one or more of those genes.

A number of conditions can cause permanent damage to the kidneys and/or affect the function of the kidneys and lead to CKD. The most common causes of CKD in adults are:

a) Diabetes. Diabetic nephropathy (DN) is a common complication of diabetes;
b) High blood pressure. Untreated or poorly treated high blood pressure is a major cause of CKD;
c) Aging kidneys. There appears to be an age-related decline in kidney function;
d) Acute or chronic kidney ischemia (this is the model we used in rats and you are using in humans);
e) sepsis.

Other less common conditions that can lead to CKD include diseases of the glomeruli, such as glomerulonephritis (inflammation of the glomeruli in the kidneys); renal artery stenosis (narrowing), haemolytic-uraemic syndrome, polycystic kidney disease, blockages to the flow of urine, drug and toxin-induced kidney damage, and repeated kidney infections.

In some embodiments, the present invention relates to a method for the treatment of a subject in need of treating chronic kidney disease (CKD) which is associated with expression of one or more of the target genes of Table 1, supra, comprising administering to the subject an amount of an oligonucleotide inhibitor, which prevents upregulation or overexpression of one or more of those genes in a kidney of the subject. In certain embodiments the upregulation or overexpression of one or more of the target genes is in response to renal insult or injury. In some embodiments the renal insult is an acute renal insult including acute kidney injury (AKI). In various embodiments of the invention treatment includes preventing or delaying onset of CKD and preventing exacerbation and progression of CKD.

In preferred embodiments the subject being treated is a warm-blooded animal and, in particular, mammals including non-human primate and human.

The methods of the invention comprise administering to the subject one or more inhibitory compounds which down-regulate expression of the target genes of Table 1; and in particular siRNA in a therapeutically effective dose so as to thereby treat the subject.

In various embodiments the inhibitor is selected from the group consisting of siRNA, shRNA, an aptamer, an antisense molecule, miRNA, and a ribozyme. In the presently preferred embodiments the inhibitor is siRNA. In preferred embodiments the siRNA is a chemically synthesized, modified compound.

The term "treatment" refers to both therapeutic treatment and prophylactic or preventative measures, wherein the object is to prevent or delay the onset of CKD, attenuate, prevent or slow down CKD or progression or severity of CKD as listed above. Those in need of treatment include those already experiencing the disease or condition, those prone to CKD, and those in which CKD is to be prevented; for example in a subject exposed to repetitive renal insults, including renal insults due to nephrotoxic drugs, such as, without being limited to, antibiotics (e.g. aminoglycosides), chemotherapeutic drugs (e.g. Cisplatin), immunosuppressant drugs (e.g. Cyclosporin A, Tacrolimus (also FK-506 or Fujimycin)) and radiocontrast agents, or ischemia-reperfusion injury (IRI). According to various embodiments of the present invention the oligonucleotide inhibitor is administered before, during or subsequent to the exposure to the renal insult, preferably subsequent to the insult. In some embodiments the oligonucleotide inhibitor is a siRNA compound. In various embodiments the siRNA is administered to the subject at about 4 hours post renal insult. In cases where treatment is for the purpose of prevention, then the present invention relates to a method for delaying the onset of or averting the development of the CKD. In some embodiments CKD develops in response to repetitive renal insults including repetitive acute kidney injury (AKI).

Acute renal failure (ARF), also known as acute kidney injury (AKI), is a rapid loss of renal function due to kidney damage and resulting in retention of nitrogenous (urea and creatinine) and non-nitrogenous waste products in the blood. Depending on the severity and duration of the renal dysfunction, this accumulation is accompanied by metabolic disturbances, such as metabolic acidosis (acidification of the blood) and hyperkalaemia (elevated serum potassium levels), changes in body fluid balance, and effects on many other organ systems. It can be characterized by oliguria or anuria (decrease or cessation of urine production).

Glomerular filtration rate "GFR" describes the flow rate of filtered fluid across the glomeruli. The assessment of GFR is the most commonly used test of renal function. In some embodiments the method of attenuating progression of CKD or preventing exacerbation of CKD is measured as an increase of about 5%, 10%, 20%, 30%, 40% or more in GFR in a treated subject when compared to the untreated subject.

Creatinine clearance rate (CCr, mL/min/1.73 $m^2$) is the volume of blood plasma that is cleared of creatinine per unit time and is a useful measure for approximating the true GFR.

SCr (mg/dL) relates to serum creatinine levels. In some embodiments the method of attenuating progression of CKD or preventing exacerbation of CKD is measured as an decrease of about 5%, 10%, 20%, 30%, 40% or more in SCr in a treated subject when compared to the untreated subject.

In some embodiments the method of the invention relates to a method of treating CKD induced by repetitive acute kidney injury (AKI) insults, in particular acute renal failure due to ischemia in post surgical patients, acute renal failure due to chemotherapy treatment such as cisplatin administration, sepsis-associated acute renal failure, nephrotoxin induced AKI including radiocontrast media induced AKI. Contrast induced AKI (CIAKI) (also known as contrast-induced nephropathy) relates to the induction of AKI by intravascular administration of iodinated contrast media, for example in patients undergoing angiography, and in particular coronary angiography. In another embodiment the method of the invention relates to the prevention of CKD in high-risk patients undergoing major cardiac surgery or vascular surgery. The patients are at risk of developing acute renal failure which in some cases progresses to CKD. Those patients are identified using various scoring methods such as the Cleveland Clinic algorithm or that developed by US Academic Hospitals (QMMI) and by Veterans' Administration (CICSS).

In another preferred embodiment, the methods of the present invention relate to treating or preventing CKD in a subject induced by treatment of the subject with a nephrotoxin including a diuretic, a β-blocker, a vasodilator agent, an ACE inhibitor, an immunosuppressant (e.g. cyclosporin), an aminoglycoside antibiotic (e.g. gentamicin), an antifungal (e.g. amphotericin B), a chemotherapeutic agent (e.g. cisplatin), radiocontrast media, an antibody (e.g. immunoglobulin), mannitol, a NSAID (e.g. aspirin, ibuprofen, diclofenac), cyclophosphamide, methotrexate, aciclovir, polyethylene glycol, β-lactam antibiotics, vancomycin, rifampicin, sulphonamides, ciprofloxacin, ranitidine, cimetidine, furosemide, thiazides, phenyloin, penicillamine, lithium salts, fluoride, demeclocycline, foscarnet, aristolochic acid, an anti-oxidant, a calcium channel blocker, a vasoactive substance, a growth factors, an anti-inflammatory agents and more.

In the majority of hospitalized ARF patients, ARF is caused by acute tubular necrosis (ATN), which results from ischemic, septic and/or nephrotoxic insults. Renal hypoperfusion is caused by hypovolemic, cardiogenic and septic shock, by administration of vasoconstrictive drugs or renovascular injury. Nephrotoxins include exogenous toxins, such as radiocontrast media, aminoglycosides and cisplatin and cisplatin-like compounds, as well as endogenous toxins, such as myoglobin. Without wishing to be bound to theory, recent studies support the theory that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum. It has been suggested that apoptotic tubule cell death may be more predictive of functional changes than necrotic cell death (Komarov et al., Science 1999, 10; 285(5434):1733-7); Supavekin et al., Kidney Int. 2003, 63(5):1714-24).

A "contrast agent," as used herein, refers to a compound employed to improve the visibility of internal body structures in an image, such as an X-ray image or a scanning image (e.g., CAT (Computerized Axial Tomography) scan, MRI (Magnetic Resonance Imaging) scan). The term contrast agent is also referred to herein as a radiocontrast agent. Contrast agents are employed in various diagnostic (e.g. embolism; cardiac catheterization) and therapeutic procedures. Contrast-induced nephropathy (CIN) remains the primary risk factor in the use of contrast agents. Patients with pre-existing renal failure and diabetes are at particularly high risk. Moreover, CIN is associated with significant in-hospital and long-term morbidity and mortality.

Additional mechanisms that contribute to the development of AKI: ischemia, vasoconstriction, toxic injury related to selected endogenous substances (e.g. myoglobin in rhabdomyolysis due to crush injury and extensive blunt trauma), radiocontrast (iodinated and IV contrast for radiological examination including CT angiography, cardiac arteriography), phosphate nephropathy due to bowel preparation for colonoscopy with sodium phosphate, nephrotoxic drugs (e.g., NSAIDs, aminoglycoside antibiotics, gentamycin and penicillin, amphotericin B), microcirculatory changes, as observed with sepsis and other inflammatory states, hemolysis, diagnostic cardiac catheterization, femoral arteriography especially in aged or diabetic patients, percutaneous coronary intervention (PCI), coronary artery bypass grafting (CABG), sepsis, thoracoabdominal aortic surgery, aortic aneurysim repair for example for infra-renal aortic abdominal surgery or thoracic or thoracoabdominal aortic surgery.

Preexisting conditions predicting severity and long term outcome of AKI patients with coronary arthery disease (CAD), heart failure, diabetes, vascular complications (e.g. atheroembolic disease and renal vein thrombosis), HIV-infected patients, gender, older age (>60), pre-existing chronic kidney disease or underlying renal insufficiency, volume depletion, hepatitis co-infection, liver disease, hepatorenal syndrome, cancer patients, patients with serious water and electrolyte metabolism disturbances, patients with hematological and non-hematological malignancies, cirrhosis, COPD, severe burns, pericarditis and pancreatitis.

Intrinsic Damage to the Kidney:

toxins or medication (e.g. some NSAIDs, aminoglycoside antibiotics, iodinated contrast, lithium, phosphate nephropathy due to bowel preparation for colonoscopy with sodium phosphates)

rhabdomyolysis (breakdown of muscle tissue)—the resultant release of myoglobin in the blood affects the kidney; it can be caused by injury (especially crush injury and extensive blunt trauma), statins, stimulants and some other drugs hemolysis (breakdown of red blood cells)—the hemoglobin damages the tubules; it may be caused by various conditions such as sickle-cell disease, and lupus erythematosus multiple myeloma, either due to hypercalcemia or "cast nephropathy" (multiple myeloma can also cause chronic renal failure by a different mechanism)

acute glomerulonephritis which may be due to a variety of causes, such as anti glomerular basement membrane disease/

Goodpasture's syndrome, Wegener's granulomatosis or acute lupus nephritis with systemic lupus erythematosus Post-renal (obstructive causes in the urinary tract) due to medication interfering with normal emptying of bladder (e.g. anticholinergics), benign prostatic hypertrophy or prostate cancer, kidney stones, abdominal malignancy (e.g. ovarian cancer, colorectal cancer), obstructed urinary catheter, drugs that can cause crystalluria and drugs that can lead to myoglobinuria & cystitis.

In conclusion, currently there is no satisfactory mode of therapy for the prevention and/or treatment of CKD induced by recurring acute insults to the kidney, and there is a need therefore to develop novel compounds for this purpose.

Pharmaceutical Compositions

While it may be possible for the compounds of the present invention to be administered as the raw chemical, it is preferable to present them as a pharmaceutical composition. Accordingly the present invention provides a method employing a pharmaceutical composition comprising one or more of the oligonucleotide compounds of the invention; and a pharmaceutically acceptable carrier. This composition may comprise a mixture of two or more different siRNA compounds.

In some embodiments the pharmaceutical composition comprises at least one siRNA compound of the invention covalently or non-covalently bound to one or more siRNA compounds of the invention in an amount effective to inhibit the target genes of the present invention; and a pharmaceutically acceptable carrier. The compound may be processed intracellularly by endogenous cellular complexes to produce one or more oligoribonucleotides of the invention.

The invention further provides a pharmaceutical composition comprising a pharmaceutically acceptable carrier and one or more of the compounds of the invention in an amount effective to inhibit expression in a cell of a human target gene of the present invention, the compound comprising a sequence $(N)_x$ which is substantially complementary to the sequence of a target nucleic acid.

"Having complementarity" or "substantially complementary" refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

Additionally, the invention provides a method of inhibiting the expression of the target genes of the present invention by at least 40%, preferably by 50%, 60% or 70%, more preferably by 75%, 80% or 90% as compared to a control comprising contacting an mRNA transcript of the target gene of the present invention with one or more of the compounds of the invention.

In one embodiment the oligoribonucleotide is inhibiting one or more of the target genes of the present invention, whereby the inhibition is selected from the group comprising inhibition of gene function, inhibition of polypeptide and inhibition of mRNA expression.

In one embodiment the compound inhibits the target polypeptide, whereby the inhibition is selected from the group comprising inhibition of function (which may be examined by an enzymatic assay or a binding assay with a known interactor of the native gene/polypeptide, inter alia), inhibition of protein (which may be examined by Western blotting, ELISA or immuno-precipitation, inter alia) and inhibition of mRNA expression (which may be examined by Northern blotting, quantitative RT-PCR, in-situ hybridisation or microarray hybridisation, inter alia).

Additionally, the invention provides a method of treating or preventing kidney damage in a subject at risk of CKD associated with activation or upregulation or overexpression of one or more of the target genes of the present invention, the method comprising administering to the subject a compound of the invention in a therapeutically effective dose thereby treating or preventing kidney damage in the subject.

In additional embodiments the invention provides a method of treating a subject at risk of developing CKD accompanied by or associated with or resulting from an elevated level of one or more of the target genes of the present invention, the method comprising administering to the subject a compound of the invention in a therapeutically effective dose thereby reducing the risk of developing CKD in the subject.

Delivery

The siRNA compound useful in methods of the invention is administered as the compound per se (i.e. as naked siRNA) or as pharmaceutically acceptable salt and is administered alone or as an active ingredient in combination with one or more pharmaceutically acceptable carrier, solvent, diluent, excipient, adjuvant and vehicle. In some embodiments, the siRNA molecules useful in methods of the present invention are delivered to the target tissue by direct application of the naked molecules prepared with a carrier or a diluent.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

However, in some embodiments the siRNA molecules of the invention are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al., FEBS Let. 2003, 539:111-115; Xia et al., Nat. Biotech. 2002, 20:1006-1010; Reich et al., Mol. Vision 2003, 9: 210-216; Sorensen et al., J. Mol. Biol. 2003. 327: 761-766; Lewis et al., Nat. Gen. 2002, 32: 107-108 and Simeoni et al., NAR 2003, 31, 11: 2717-2724). siRNA has recently been successfully used for inhibition of gene expression in primates (see for example, Tolentino et al., Retina 24(4):660).

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Other such implants, delivery systems, and modules are well known to those skilled in the art. The siRNAs or pharmaceutical compositions of the present invention are administered and dosed in accordance with good medical practice, taking into account the clinical condition of the individual subject, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

In general, the active dose of compound for humans is in the range of from 1 ng/kg to about 20-100 mg/kg body weight per day, preferably about 0.01 mg to about 2-10 mg/kg body weight per day, in a regimen of a single dose or multiple doses, e.g. or two doses or three or more doses, administered within 24 hours of each renal insult. The siRNA compounds useful in methods of the present invention can be administered by any of the conventional routes of administration. The compounds are administered orally, subcutaneously or parenterally including intravenous, intraarterial, intramuscular, intraperitoneally, and intranasal administration as well as intrathecal and infusion techniques. Implants of the compounds are also useful. Liquid forms are prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, as well as similar pharmaceutical vehicles. In a particular embodiment, the administration comprises intravenous administration.

Pharmaceutical compositions that include the nucleic acid molecule disclosed herein may be administered once daily, qid, tid, bid, QD, or at any interval and for any duration that is medically appropriate. However, the composition may also be dosed in dosage units containing two, three, four, five, six or more sub-doses administered at appropriate intervals throughout the day.

In some embodiments the dosage unit is compounded for a single dose over several days, e.g., using a conventional sustained release formulation which provides sustained and consistent release of the dsRNA over a several day period. Sustained release formulations are well known in the art. In certain embodiments the methods of the invention include administering one or more siRNA compound or compounds to the subject for sustained or controlled delivery. The methods of the present invention rely primarily on parenteral administration routes and more specifically on implant depots or depot injections, which provide for prolonged release of the biological agent into the circulatory system. Devices for use in these parenteral delivery systems include non-injectable and injectable devices. Non-injectable devices include an implant such as a siRNA depot implant, or similar device. Known depot implants include, but are not limited to, synthetic and natural materials including solid biodegradable and non-biodegradable polymer devices including foams, gels, matrices, and the like comprising one or more of dextran, fibrin, hyaluronate, chitosan and the like as well as a pump and micropump systems also known in the art. Injectable devices include bolus injections (release and dissipation of the compound subsequent to injection), and repository or depot injections, which provide a storage reservoir or depot at the site of injection, allowing for sustained release of the biological agent over time.

The present invention also provides for a process of preparing a pharmaceutical composition useful in a method according to present invention, which comprises:

- providing one or more double stranded compound of the invention; and
- admixing said compound with a pharmaceutically acceptable carrier.

The present invention also provides for a process of preparing a pharmaceutical composition, useful in a method according to present invention, which comprises admixing one or more siRNA compounds accroding to present invention with a pharmaceutically acceptable carrier.

In a preferred embodiment, the siRNA compound used in the preparation of a pharmaceutical composition, useful in a method according to present invention, is admixed with a carrier in a pharmaceutically effective dose. In a particular embodiment the siRNA compound, useful in a method of the present invention is conjugated to a steroid, vitamin or to a lipid or to another suitable molecule e.g. to cholesterol.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

General Methods in Molecular Biology

Standard molecular biology techniques known in the art and not specifically described were generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry can be used for detection of cells containing specific DNA and mRNA sequences (Testoni et al., 1996, Blood 87:3822.) Methods of performing RT-PCR are also well known in the art.

Example 1

Generation of Sequences for Active siRNA Compounds to Target Genes and Production of the siRNAs Using proprietary algorithms and the known sequence of the target genes, the sequences of many potential siRNAs were generated. In addition to the algorithm, some of the 23-mer oligomer sequences were generated by 5' and/or 3' extension of the 19-mer sequences. The sequences that have been generated using this method are fully complementary to the corresponding mRNA sequence.

Sequence listing: The sequence listing for this application (SEQ ID NO:1-SEQ ID NO:119) has been submitted electronically as sequence listing file entitled "209-

PCT1_ST25.txt" created Jun. 7, 2010, 459 kb. Applicants hereby incorporate by reference the sequence listing into the instant specification.

Example 2

In Vitro Testing of siRNA Compounds

1. General

About 1.5-2×$10^5$ test cells (HEPG2 or PC3 cells for siRNA targeting the human gene) were seeded per well in 6 wells plate (70-80% confluent).

After 24 h cells were transfected with siRNA oligomers using Lipofectamine™ 2000 reagent (Invitrogene) at final concentration of 500 pM, 5 nM, 20 nM or 40 nM. The cells were incubated at 37° C. in a $CO_2$ incubator for 72 h.

As positive control for cells transfection PTEN-Cy3 labeled siRNA oligos were used. As negative control for siRNA activity GFP siRNA oligos were used.

About 72 h after transfection cells were harvested and RNA was extracted from cells. Transfection efficiency was tested by fluorescent microscopy.

The percent of inhibition of gene expression using specific siRNAs was determined using qPCR analysis of target gene in cells expressing the endogenous gene.

The inhibitory activity of the compounds of the present invention on target genes or binding of the compounds of the present invention to target genes may be used to determine the interaction of an additional compound with the target polypeptide, e.g., if the additional compound competes with the oligonucleotides of the present invention for inhibition of a target gene, or if the additional compound rescues said inhibition. The inhibition or activation is tested by various means, such as, inter alia, assaying for the product of the activity of the target polypeptide or displacement of binding compound from the target polypeptide in radioactive or fluorescent competition assays.

Example 3 siP53 Compounds

QM5 is a chemically modified siRNA compound which targets rat and mouse p53 and is the disclosed of International Patent Publication WO 2006/035434, assigned to one of the assignees of the present invention. QM5. The compound has two separate strands, sense (SEN; passenger) and antisense (AS; guide), each comprising alternating unmodified ribonucleotides (upper case letters) and 2'-methoxy(2'-O-Me; 2'-O—$CH_3$) sugar modified ribonucleotides (lower case letters) on both strands forming a specific pattern as shown herein below:

```
Sense (passenger) sequence
                                    (SEQ ID NO: 116
5' GaAgAaAaUuUcCgCaAaA 3'

Antisense (guide) sequence
                                   (SEQ ID NO: 117)
3' cUuCuUuUaAaGgCgUuUu 5'
```

The I5 compound is a 19-mer blunt-ended nucleic acid duplex that targets human p53, a gene that plays a pivotal role in the stress-response apoptotic pathway. The compound has two separate strands, sense (SEN) and antisense (AS), each comprising alternating unmodified ribonucleotides (upper case letters) and 2'-methoxy(2'OMe) sugar modified ribonucleotides (lower case letters) on both strands forming a specific pattern as shown herein below:

```
Sense (passenger) sequence
                                   (SEQ ID NO: 118)
5' GaGaAuAuUuCaCcCuUcA 3'

Antisense (guide) sequence
                                   (SEQ ID NO: 119)
3' cUcUuAuAaAgUgGgAaGu 5'
```

For treating or preventing kidney damage in a human subject at risk of chronic kidney disease (CKD) associated with exposure to a recurrence of renal insults a therapeutically effective dose of I5 is administered to the subject within 24 hours of each renal insult thereby treating CKD. 15 is the subject of WO 2006/035434, assigned to one of the assignees of the present invention.

Example 4

Model Systems of CKD

The following animal models were implemented to support the methods of the invention (1) preventing CKD development in a subject at risk of CKD due to multiple renal insults (supported by example 4-1;

(2) preventing acceleration/progression of CKD development by AKI episodes in a subject with a CKD background (supported by Example 4-2); and (3) attenuating the severity of AKI on the background of CKD (supported by Example 4-2).

Example 4-1

Bilateral Kidney Arterial Clamp CKD Model

This animal model is useful in assessing the test compounds for prevention of CKD or attenuation of CKD progression resulting from repetitive AKI/ARF insults.

Repetitive AKI/ARF insults often results in the exacerbation of chronic kidney disease (CKD), progression of CKD or development of CKD (see FIG. 1). ARF is a clinical syndrome characterized by rapid deterioration of renal function that occurs within days. Without being bound by theory the acute kidney injury may be the result of renal ischemia-reperfusion injury such as renal ischemia-reperfusion injury in patients undergoing major surgery such as major cardiac surgery. The principal feature of ARF is an abrupt decline in glomerular filtration rate (GFR), resulting in the retention of nitrogenous wastes (urea, creatinine) in the blood. Recent studies, support that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum.

Figure 2:
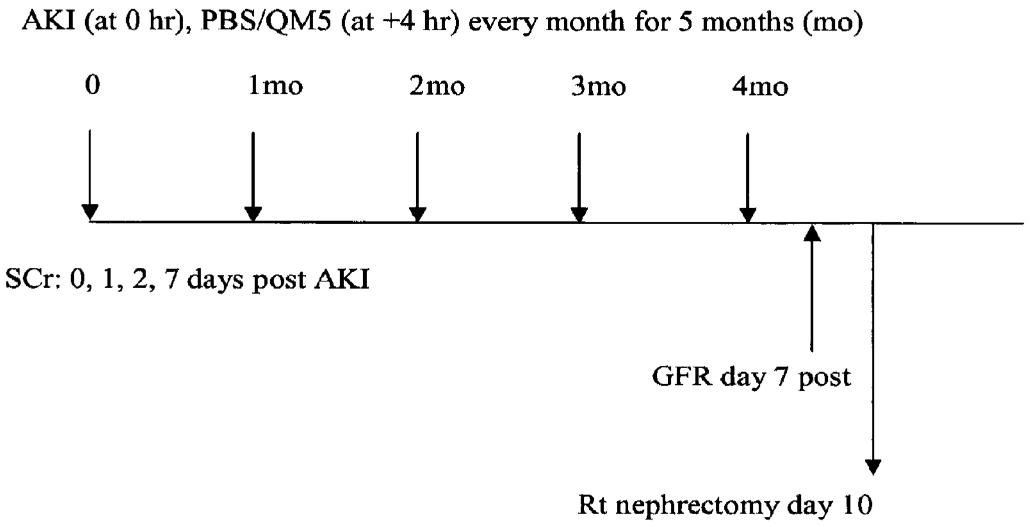
FIG. 2 provides an outline of the study design as described in Example 2, hereinbelow.

The rat model for CKD comprises repetitive (5 times) ischemia-reperfusion-induced ARF as follows and as shown in FIG. 2:

Ischemia-reperfusion injury was induced in rats following 45 minutes bilateral kidney arterial clamp and subsequent release of the clamp to allow 24 hours of reperfusion. PBS or QM5 (rat siP53) (12 mg/kg) were injected i.v. into individual experimental animals 4 hours post clamp. ARF progression was monitored by measurement of serum creatinine (SCr) levels before (baseline) and 24 hrs, 2 days and 7 days post surgery. The treatment (I/R injury, QM5, SCr measurement) was repeated for four more cycles at 30-day intervals, for a total of five cycles. At 7 days post $5^{th}$ cycle 24 hour creatinine clearance (CrCl) metabolic cage and urine protein were measured. The right kidneys were surgically removed 2 days after metabolic cage (day 10 post $5^{th}$ cycle) and the kidney was histologically analyzed for CKD. At 3 weeks post right nephrectomy the left kidney was exteriorized and studied in vivo using intravital two-photon microscopy (for Cy3-siRNa uptake and retention).

Results

Age-matched untreated rats had much more uniform uptake and distribution of the Cy3 labeled siRNA. Twenty-four hours after the initial injection, reduction in cellular levels of the siRNA was visible. Also tubular lumens were generally more open with only a few collapsed lumens visible.

Saline treated CKD rats had much more heterogeneous distribution (patchy) and uptake of the siRNA. Tubules could be seen with thin epithelia and the lumen greatly distended. Uptake in tubular cells did occur, but at a lower level than surrounding tubular cells with more normal morphology. Degradation of the labeled siRNA appeared slower in these rats as there appeared to be greater residual fluorescence than in age-matched untreated rats at 24 hours.

QM5 treated CKD rats displayed uptake and distribution characteristics that were intermediary between the control age-matched untreated and saline treated CKD groups. Overall uptake was more homogeneous when viewing individual fields. Cystic tubules were still present on occasion. Overall, QM5 aided in the uniform delivery of the Cy3-labeled siRNA to the tubular epithelia, this was more readily apparent in Rat #4. Metabolism of siRNA at 24 hr was also intermediate between age-matched untreated rats and saline treated ischemic rats. Under physiological conditions, in age-matched untreated rats Cy3-labeled siRNA, following intravenous injection, was rapidly filtered across the glomerulus and taken up selectively by proximal tubule cells (PTC). Total cellular and cytosolic accumulation in proximal tubule cells was quantified using threshold analysis and revealed a maximum at 120 minutes with a rapid decay over the next four hours. The biological activity of the siRNA correlated closely to the fluorescent half life.

Figure 3:
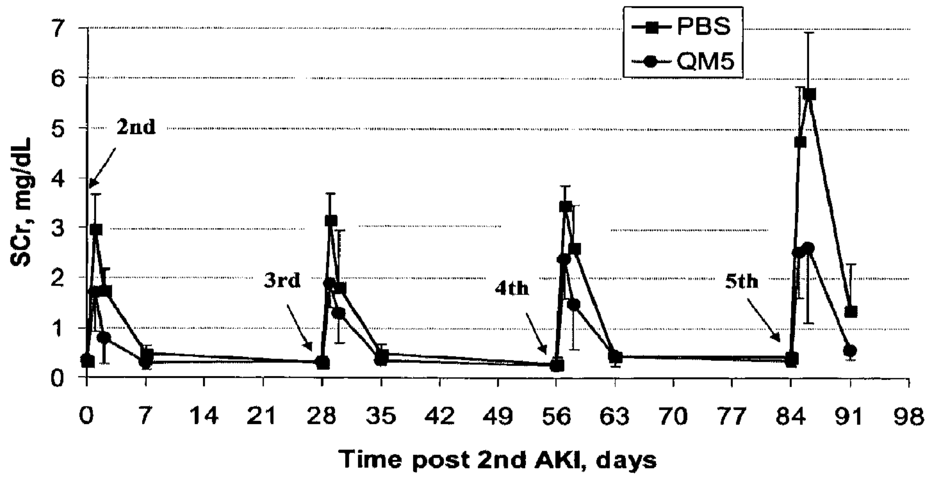
FIG. 3 shows the effect of p53 siRNA on kidney function following repetitive ischemic injury.

FIG. 3 shows the effect of p53 siRNA on kidney function following repetitive ischemic injury. Serum creatinine levels prior to each ischemia (AKI) cycle, and at days 1, 2, and 7 post each ischemia cycle in rats treated with PBS or siP53 (QM5) (12 mg/kg) given i.v. at 4 hrs post each ischemia (AKI). Data represent the mean±SD (n=10/group).

Figure 4:
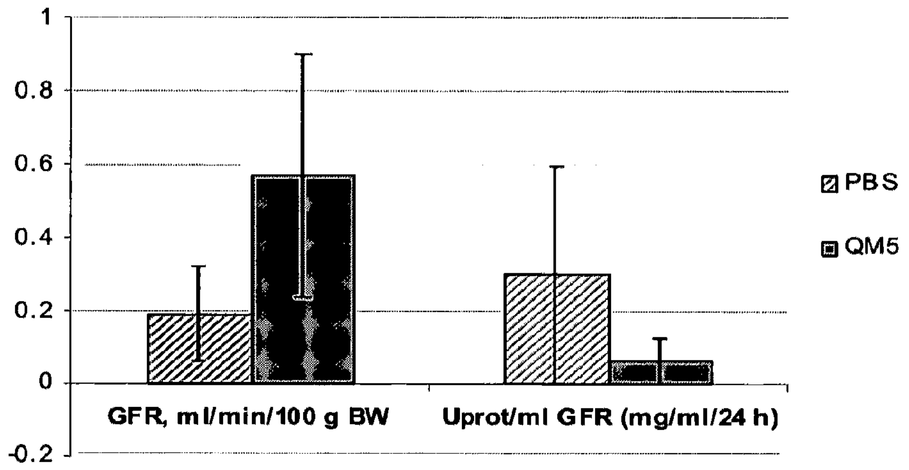
FIG. 4 shows that siP53 protects GFR and minimizes proteinuria.

FIG. 4 shows that siP53 protects GFR and minimizes proteinuria. Measurements from PBS treated animals are shown by hatched columns, while QM5 treated animals are solid coumns.

Table 2 hereinbelow shows the effect of siP53 on kidney function following five monthly cycles of ischemic injury: siP53 protects glomerular filtration rate and minimizes proteinuria. Glomerular filtration rate (GFR) and proteinuria (Uprot) were measured at 7 days following last (5th) AKI cycle by 24 hrs urine collection and tail blood collection. Groups: PBS—rats were treated with PBS given i.v. at 4 hrs post each ischemic injury; QM5—siP53 (12 mg/kg) given i.v. at 4 hrs post each ischemic injury. Data represent means±SD (n=10/group)

TABLE 2

| | Injury score, mean/group (n = 10) ± SD | | |
|---|---|---|---|
| Histopatholgy scoring parameters | PBS | QM5 | p-value |
| Glomerular Damage | 0.1 + 0.3 | 0.1 + 0.3 | 1 |
| Interstitial Cellular Infiltrate | 1.2 + 0.4 | 0.5 + 0.5 | 0.008 |
| Interstitial fibrosis | 1.3 + 0.5 | 0.9 + 0.6 | 0.12 |
| Tubular status | 1.4 + 0.5 | 0.8 + 0.6 | 0.04 |
| Vasculopathy | 0.1 + 0.3 | 0 | 0.37 |
| Total Chronic injury score | 4.1 + 0.7 | 2.3 + 1.2 | 0.02 |
| Tubular necrosis | 0.1 + 0.3 | 0 | 0.37 |
| Tubular dilation | 1.4 + 0.5 | 0.8 + 0.6 | 0.04 |
| Casts | 1.3 + 1.3 | 0.5 + 0.5 | 0.16 |
| Total Acute injury score | 2.8 + 1.8 | 1.3 + 0.9 | 0.05 |
| Total pathology score Chronic + acute | 6.9 + 3.3 | 3.6 + 1.8 | 0.02 |

Figure 5:
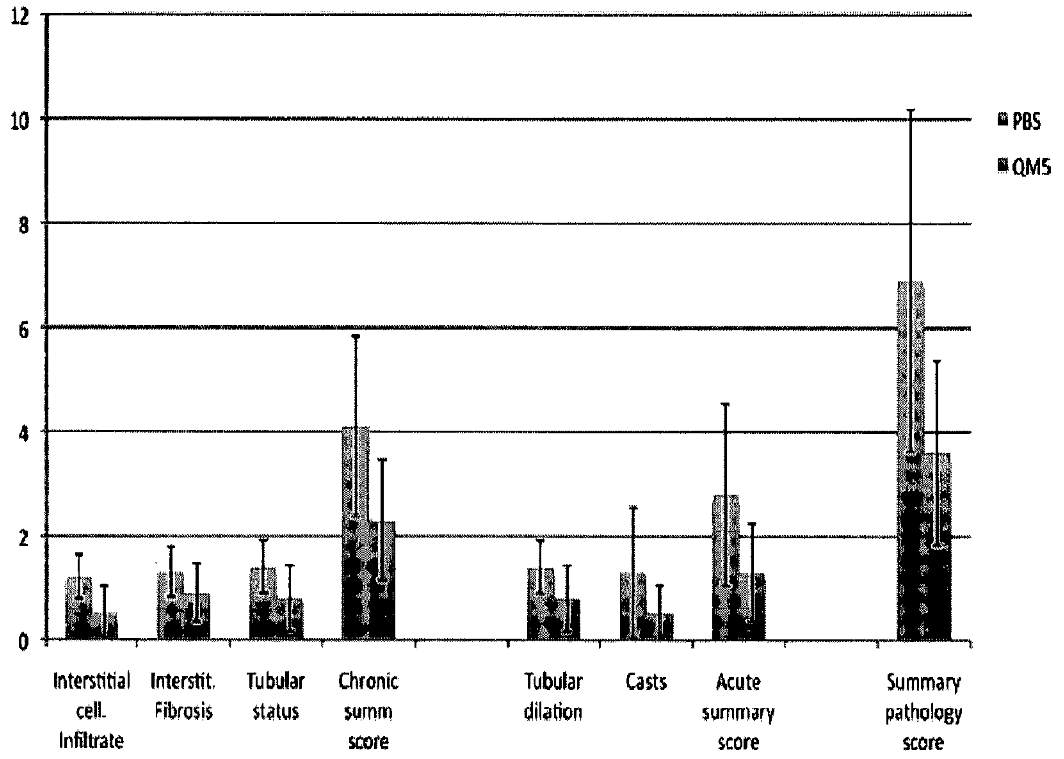
FIG. 5. Effect of siP53 (12 mg/kg) on histology after five monthly cycles of ischemic injury.

FIG. 5 shows histopathology scoring of right kidney procured 10 days post fifth AKI cycle. At 10 days post last (5th) ischemic injury, the rats (treated with PBS or siP53 at 4 hrs post each monthly ischemic injury) were subjected to right nephrectomy. Harvested right kidney sections were blindly analyzed by board-certified pathologist. At least two representative kidney sections were analyzed for each rat. The parameters of acute (tubular necrosis, tubular dilation, casts) and chronic (glomerular damage, interstitial cellular infiltrate, interstitial fibrosis, tubular status and vasculopathy) damage were analyzed. Total acute and total chronic injury scores are a sums of all chronic or acute damage parameters respectively. Total pathology score is a sum of acute and chronic injury scores for each rat. Grading of pathological changes was performed according to the following scoring system:

Grade 0—no pathological changes; Grade 1—feature involves 1 to 10% of the area (mild and focal); Grade 2—feature involves 10 to 25% of the area (moderate and multifocal); Grade 3—feature involves 25 to 75% of the area (diffuse damage without damage of normal architecture); Grade 4—feature involves more than 75% of the area (diffuse damage with prominent damage of normal kidney architecture). Data represent the mean±SD (n=10/group).

Example 4-2

Uninephrectomy and High Salt Diet

This animal model is useful in assessing the test compounds for reduction/attenuation of AKI/ARF in a CKD background thereby providing a model for preventing exacerbation or progression of CKD by recurring AKI/ARF insults in CKD patients and in attenuating the severity of AKI in patients suffereing from CKD who undergo a proceedure or event likely to cause AKI.

Figure 6:
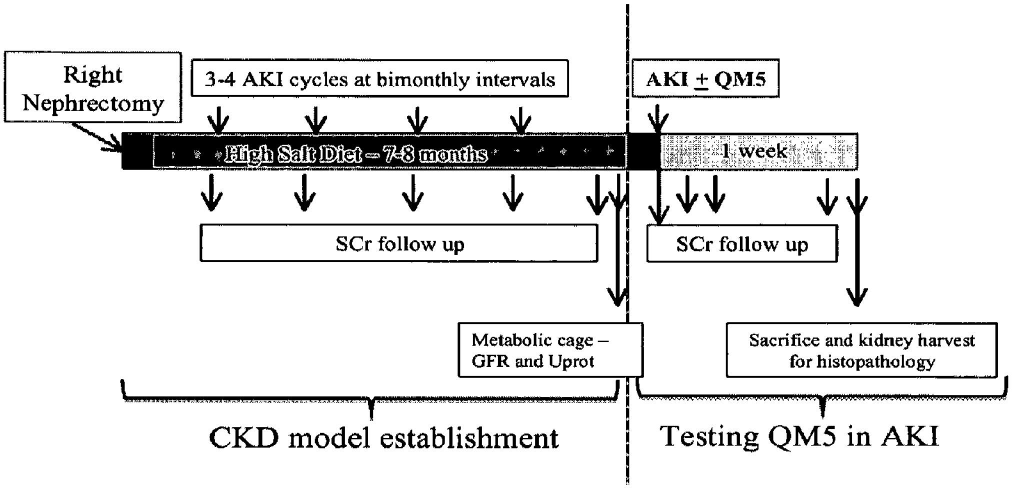
FIG. 6 provides the study design for a CKD model established by nephrectomy and multiple AKI induction at bimonthly intervals. CKD was induced by subjecting rats to uninephrectomy and multiple AKI (3-4 over a period of 7-8 months) and feeding them with high salt (Na, sodium) diet.

FIG. 6 shows the study design used to establish CKD. In summary, SD rats were subjected to right nephrectomy, followed by 3 or 4 repetitive bimonthly cycles of AKI (until SCr and GFR rates were at CKD levels). The first AKI cycle comprised a left pedicle clamp for a period of 45 minutes, whereas all following AKIs comprised a 30 minute clamp. Throughout the entire period, the rats were fed a high salt diet. After 3 or 4 cycles, the following kidney function parameters were evaluated: serum creatinine (SCr), GFR and urine protein.

Animal was considered to have moderate to severe CKD when serum creatinine (SCr) levels were above 0.8 mg/ml and glomerular filtration rate (GFR) was less than 0.60 ml/min/100 gr. In addition, 3 rats were uninephrectomized and fed with regular diet for the same total period of time as above (7-8 months). At the end of this period, their SCr, GFR and Uprot were evaluated. Results are shown in Table 3, hereinbelow:

TABLE 3

| | SCr, mg/ml | GFR, ml/min/ 100 g BW | Uprot, mg/24 h |
|---|---|---|---|
| Normal rats (historical and published data) | 0.2-0.3 | 0.8-0.9* | |
| Uninephr rats after 3 AKI cycles (N = 3), HS diet | 1.13 ± 0.05 | 0.16 ± 0.03 | 221 ± 21 |
| Uninephr rats after 4 AKI cycles (N = 4), HS diet | 0.98 ± 0.17 | 0.19 ± 0.03 | 646 ± 160 |

*Zaladek-Gil et al (1999), Braz J Med Biol Res, 32: 107-113; Chamberlain et al, (2007) Exp Physiol, 92: 251-262

Figure 7:
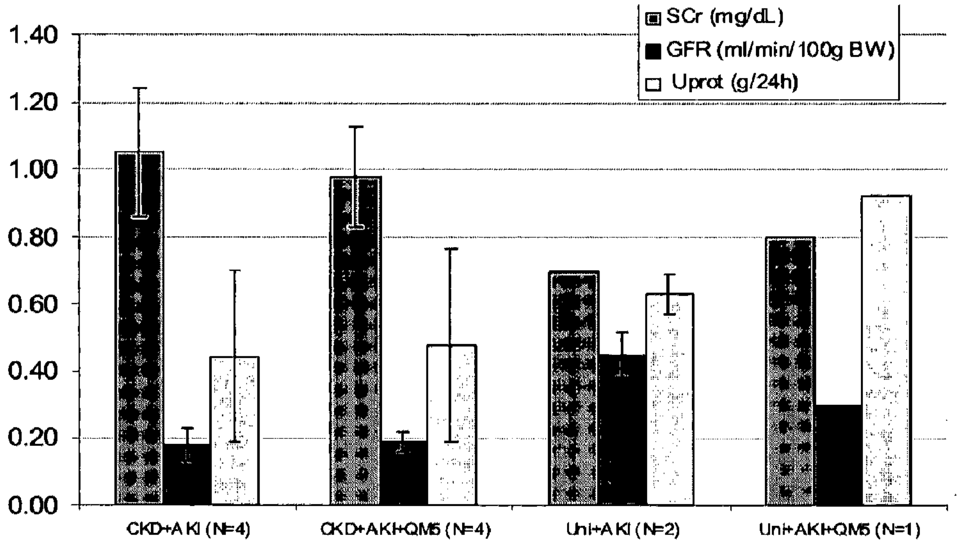
FIG. 7 shows pretreatment kidney function parameters after 7-8 months of feeding either a high or low Na diet. Serum creatinine, GFR and Urine protein were similar in rats treated with QM5 siRNA or carrier only. High Na diet resulted in more rapid progression of CKD, loss of GFR but not proteinuria.
Figure 8:
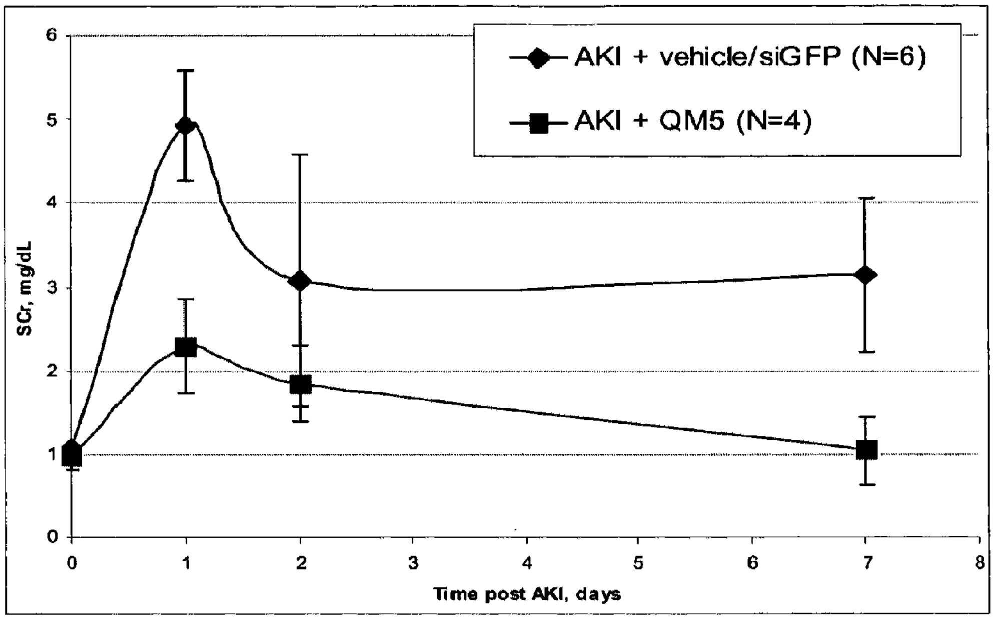
FIG. 8 shows the efficacy of QM5 (siP53) on prevention of AKI in CKD induced animals.
Figure 9A:
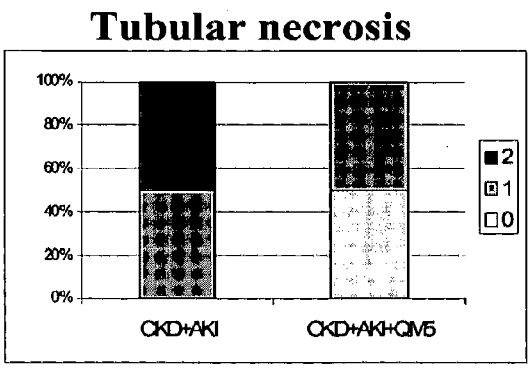
FIGS. 9A-9H show the histopatholgy evaluation at termination of the CKD study outlined in FIG. 6 and described in Example 2.2.
Figure 9B:
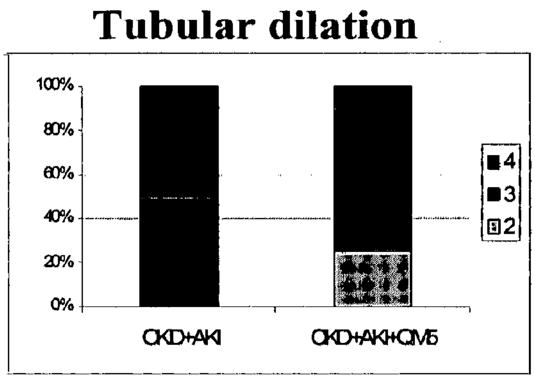
Figure 9C:
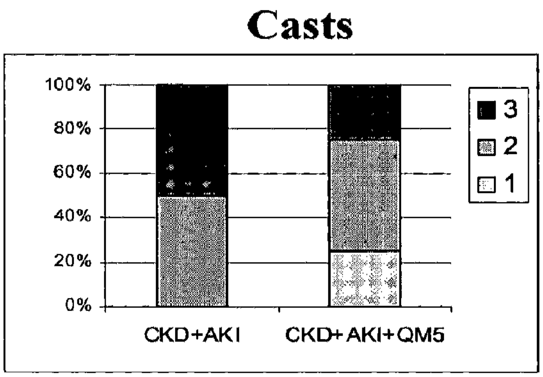
Figure 9D:
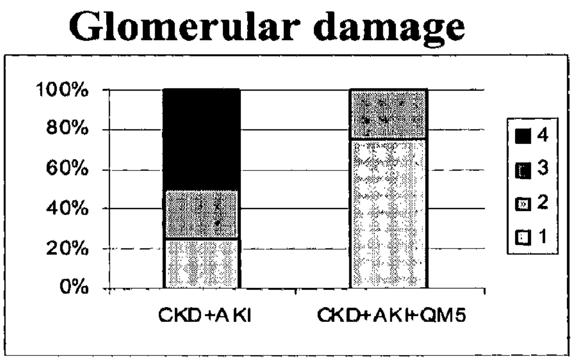
Figure 9E:
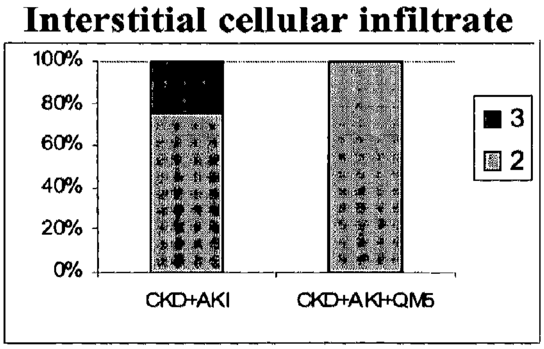
Figure 9F:
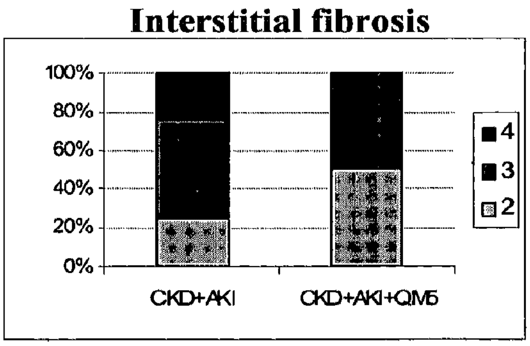
Figure 9G:
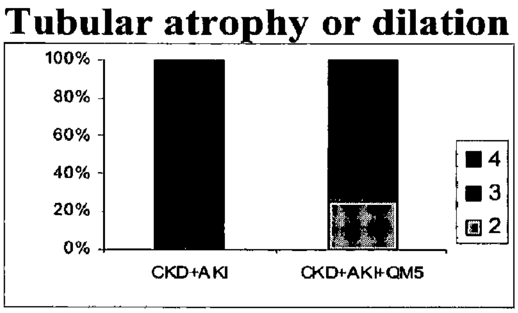
Figure 9H:
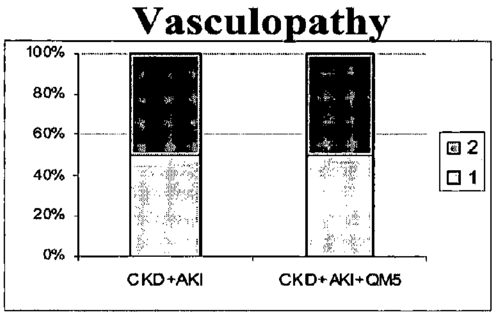

FIG. 7 shows kidney function parameters in group sorted animals prior to AKI/ARF insults and prior to siP53 treatment). The results show that uninephrectomized animals exposed to a high salt diet exhibit more severe CKD than uninephrectomized animals exposed to a normal diet as measured by SCr, GFR and urine protein (Uprot) levels. CKD and control animals received siP53 or siGFP (12 mg/kg) or vehicle by i.v. injection at 4 hours post last AKI insult. FIG. 8 shows the effect of siP53 (QM5) on prevention of AKI insult in animals with CKD.

FIGS. 9A-9H show histopathological parameters for acute injury (9A-9C) and chronic injury (9D-9H). The scoring system for histopathology was as follows: 0: none; 1: mild and focal; 2: moderate and multifocal; 3: diffuse without damage of normal architecture; 4: diffuse with prominent damage of normal architecture. All acute parameters, tubular necrosis, tubular dilation and urinary casts were improved in siP53 treated animals. The chromic injury parameters glomerular damage, interstitial infitrate, interstitial fibrosis and tubular atrophy were reduced in treated animals.

Figure 10:
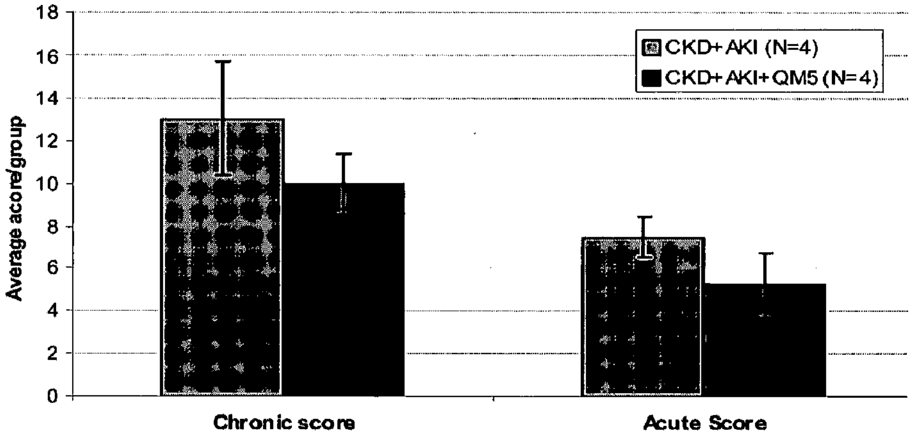
FIG. 10 shows results of histopathogy evaluation at termination and records the average acute and chronic injury scores in treated vs untreated group.

Average histopathology scores for acute and chronic injury in treated and untreated animals are shown in FIG. 10.

While certain embodiments of the invention have been illustrated and described, it will be clear that the invention is not limited to the embodiments described herein. Modifications, changes, variations, substitutions and equivalents will be apparent to those skilled in the art without departing from scope of the present invention as described by the claims, which follow.

The invention claimed is:

1. A method of treating a subject having chronic kidney disease (CKD) resulting from exposure to a recurring renal insult, comprising administering to the subject a therapeutically effective dose of an oligonucleotide compound which down-regulates expression of a target gene associated with kidney injury, wherein the target gene is a p53 gene, the sequence of which is set forth in any one of SEQ ID Nos: 67-73 or a CASP2 gene, the sequence of which is set forth in any one of SEQ ID Nos: 12 or 13, wherein the oligonucleotide compound is administered to the subject in proximity of the renal insult, thereby treating chronic kidney disease (CKD) in the subject.

2. The method according to claim 1, wherein the oligonucleotide compound is administered to the subject within about 72 hrs before the renal insult to 8 hrs after the renal insult.

3. The method according to claim 2, wherein the oligonucleotide compound is administered to the subject within about 4 hours of the renal insult.

4. The method according to claim 2, wherein the oligonucleotide compound is administered to the subject within about 0.5 hours of the renal insult.

5. The method according to claim 2, wherein the oligonucleotide is administered to the subject at about 0-4 hours post the renal insult.

6. The method according to claim 1, wherein the renal insult is associated with one or more of surgery including cardiovascular surgery; exposure to myoglobinuria, ischemia/reperfusion injury; sepsis; urinary tract obstruction; exposure to a nephrotoxin including a nephrotoxic radiocontrast imaging agent, an antibiotic or a chemotherapeutic agent; proteinuria; increased renal ammoniagenesis with interstitial injury; hyperlipidemia; hyperphosphatemia with calcium phosphate deposition.

7. The method according to claim 6, wherein the renal insult is associated with ischemia/reperfusion injury or exposure to a nephrotoxin or both.

8. The method according to claim 7, wherein the renal insult is associated with ischemia/reperfusion ensuing during or following cardiovascular surgery or cardiopulmonary surgery.

9. The method according to claim 6, wherein the renal insult is associated with myoglobinuria.

10. The method according to claim 6, wherein the renal insult is associated with a nephrotoxin.

11. The method according to claim 1, wherein the oligonucleotide compound is selected from the group consisting of an unmodified siRNA, a chemically modified siRNA, shRNA, an aptamer, an antisense molecule, miRNA, and a ribozyme.

12. The method according to claim 11, wherein the oligonucleotide compound is chemically modified siRNA.

13. The method according to claim 12, wherein the siRNA has a general double stranded structure:

$$5'(N)_x\text{- Z }3'\text{(antisense strand)}$$

$$3'Z'\text{-}(N')_y\text{-}z''5'\text{(sense strand)}$$

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein Z and Z' may be present or absent, but if present is independently 1-5 consecutive nucleotides or non-nucleotide moiety covalently attached at the 3' terminus of the strand in which it is present;

wherein z" may be present or absent, but if present is a capping moiety covalently attached at the 5' terminus of (N')y;

each of x and y is idependently an integer between 18 and 40;

wherein the sequence of (N')y is substantially complementary to the sequence of (N)x; and wherein (N)x comprises an antisense sequence substantially complementary to from about 18 to about 40 consecutive ribonucleotides present in an mRNA of Table 1 set forth in any one of SEQ ID NO:1-115.

14. The method according to claim 13, wherein the siRNA is the I5 siRNA compound.

15. The method of claim 1, wherein the attenuating progression of chronic kidney disease comprises attenuating the severity of the renal insults.

* * * * *

SEQUENCE LISTING

```
<160> NUMBER OF SEQ ID NOS: 119

<210> SEQ ID NO 1
<211> LENGTH: 1752
<212> TYPE: RNA
<213> ORGANISM: HUMAN

<400> SEQUENCE: 1

agggcgcagc aggccaaggg ggaggugcga gcguggaccu gggacggguc ugggcggcuc      60

ucggugguug gcacggguuc gcacacccau ucaagcggca ggacgcacuu gucuuagcag     120

uucucgcuga ccgcgcuagc ugcggcuucu acgcuccggc acucugaguu caucagcaaa     180

cgcccuggcg ucuguccuca ccaugccuag ccuuugggac cgcuucucgu cgucguccac     240

cuccucuucg cccucguccu ugccccgaac ucccaccccca gaucggccgc cgcgcucagc    300

cugggggucg gcgacccggg aggaggggguu ugaccgcucc acgagccugg agagcucgga    360

cugcgagucc cuggacagca gcaacagugg cuucgggccg gaggaagaca cggcuuaccu     420

ggaugggggug ucguugcccg acuucgagcu gcucagugac ccugaggaug aacacuugug    480

ugccaaccug augcagcugc ugcaggagag ccuggcccag gcgcggcugg gcucucgacg     540

cccugcgcgc cugcugaugc cuagccaguu gguaagccag gugggcaaag aacuacugcg     600

ccuggccuac agcgagccgu gcggccugcg gggggcgcug cuggacgucu gcguggagca     660

gggcaagagc ugccacagcg ugggccagcu ggcacucgac cccagccugg ugcccaccuu     720

ccagcugacc cucgugcugc gccuggacuc acgacucugg cccaagaucc aggggcuguu     780

uagcuccgcc aacucucccu uccucccugg cuucagccag ucccugacgc ugagcacugg     840

cuuccgaguc aucaagaaga agcuguacag cucggaacag cugcucauug aggaguguug     900

aacuucaacc ugagggggcc gacagugccc uccaagacag agacgacuga acuuuugggg     960

uggagacuag aggcaggagc ugagggacug auuccugugg uuggaaaacu gaggcagcca    1020

ccuaaggugg aggugggggga auaguguuuc ccaggaagcu cauugaguug ugugcgggug   1080

gcugugcauu ggggacacau accccucagu acuguagcau gaaacaaagg cuuaggggcc    1140
```

-continued

```
aacaaggcuu ccagcuggau guguguguag cauguaccuu auuauuuuug uuacugacag   1200

uuaacagugg ugugacaucc agagagcagc ugggcugcuc ccgccccagc ccggcccagg   1260

gugaaggaag aggcacgugc uccucagagc agccggaggg aggggggagg ucggaggucg   1320

uggagguggu uuguguaucu uacuggucug aagggaccaa gugguuugu uguuuguuuu   1380

guaucuuguu uuucugaucg gagcaucacu acugaccugu uguaggcagc uaucuuacag   1440

acgcaugaau guaagaguag gaaggggugg gugucaggga ucacuuggga ucuuugacac   1500

uugaaaaauu acaccuggca gcugcguuua agccuucccc caucguguac ugcagaguug   1560

agcuggcagg ggaggggcug agaggguggg ggcuggaacc ccuccccggg aggagugcca   1620

ucugggucuu ccaucuagaa cuguuuacau gaagauaaga uacucacugu ucaugaauac   1680

acuugauguu caaguauuaa gaccuaugca auauuuuuua cuuuucuaau aaacauguuu   1740

guuaaaacag uu                                                       1752
```

<210> SEQ ID NO 2
<211> LENGTH: 2607
<212> TYPE: RNA
<213> ORGANISM: HUMAN

<400> SEQUENCE: 2

```
agccggcgca ggguggccgg ggagggguga gcagggugcc gcuggcugcu ggggucugca     60

ggucaccgag uccccaggag aggggacucc uaagaagcca ccugccugug uuuacccggc    120

agcgagcgcg caggcccccg cgaacuccug gcagcgcuca ggaaaggccg uugcgccucg    180

cgaaggaaac agagccguug accauggiug caacuggcag uuugagcagc aagaacccgg    240

ccagcauuuc agaauugcug gacuguggcu aucacccaga gagccugcua agugauuuug    300

acuacuggga uuauguuguu ccugaaccca accucaacga gguaaauauu gaggaaucaa    360

cuugccagaa uuugguuaaa augcuggaga acugucuguc caaaucaaag caaacuaaac    420

uugguugcuc aaagguccuu gucccugaga aacugaccca gagaauugcu caagaugucc    480

ugcggcuuuc cucaacggag cccugcggcu ugcgagguug uguuaugcac gugaacuugg    540

aaauugaaaa uguauguaaa aagcuggaua ggauugugug ugauucuagc gucguaccua    600

cuuuugagcu uacacuugug uuuaagcagg agaacugcuc auggacuagc uucagggacu    660

uuuucuuuag uagaggucgc uucuccucug guuucaggag aacucugauc cucagcucag    720

gauuucgacu uguuaagaaa aaacuuuacu cacugauugg aacaacagug auugaagggu    780

ccuaaaaagg gaaaauauau aaagauuauu ucaugauugg guaguaaaac uauucagcua    840

gucagcuaaa gucauuugua guuugcccca ccugcccuaa auaagaaacc ccaaauguag    900

ucucuuuucu uucuguguuu cacauucaua gcaacugcag cuaacaggcu gauuuucugg    960

ccuuuggaga agugauucaa aauaguguag auuuucugca uagaucccau uuuuguacag   1020

aauugaaugg gauggaauag guaagcaaaa guagaagccc auuugaguuu uacauuugau   1080

uccacaauuu gguuucaggu aggcuuggua auagacuaua uaaaccagau uugccuauuu   1140

ugauuuucau auggcuuuuu uuucucuaag uuuucagagg auuuuuuaaa ucacagaauc   1200

auacuaaaug auauuuagcc uaucaaaacu uccaaaagcc cacaccacca guuccugacu   1260

caaauuugaa ggguuuuuag acaggaaggu aggauuaagu aggugaguuu aauuaaagcu   1320

uaacccuagg uaagaguaaa ugagaaauau uacggcaaua auggaacugc uucacuguuu   1380

cuuggugacu uccucacucu aauguuuuaa agaggcaaca aaagcuugug gugccauuuc   1440

aguaaccacg guguuguuuu agaugccuuu auaagcucag uuuccccugu ucuuaagugu   1500
```

-continued

```
ugaauacugu cuuuaaacua gaaaaaugca aaauauugaa cugauauuuu ugugugguagu   1560

ugauuacucu uccauugagu gaaugaugaa uaccugugag gauaggaaau uaguucugag   1620

aucuaguccc ucucugauuc acuuaguaau cuauccucuu uucaguauua caugugcuua   1680

aucucagaug aaccauuuca ccauggcagu guuaucucau cucugggcuu uucugggaau   1740

ugaaguaucu cuccuuaacc ccaauuguca aggguaguag cuguauacua ccacuuugaa   1800

uuauugaaac gggucaauuu acgaagucug cauuggcuau ggagauaugg uuuauaguac   1860

agccuagaga augaaacuca ccguccagau aaccaugcau gcacccagau uuuuuccacc   1920

uuggauaccu gucacuaggg aauaauaaag gccuuauuuu uugucuuauu ccaacuaagu   1980

agaucauuau cucuuuccuu uuuuauguua augagagaau uuagccucca cucaacaaug   2040

uucaauucag caaggcuuuc auauccuugc ugugggucgu ggauaaggag cuuauucagg   2100

uuuccugccc uagcuauuag cuccacuuca caugcuggag accggcguag ggacagaugu   2160

auucauccug guguuacuga aaaacaggug ugauccuguu acugauacua uaagugaccu   2220

aaaaugucac uguucaaauu agccaguguu cuaacaaacu aaacucuuca aaugcuugga   2280

aagauacuac aaagccaauc uuuauagaau ugggccaaga uaaaucaaug uuguuuugca   2340

ugucuauugu uaagcuccaa agguucacug uguuucugcc gcuguccugg aguugucacc   2400

acugacuggg caaggcuucu ugggcaucga uguagaacug uuguccuuuu uccacuaaca   2460

guuaucuuug acucucuugc cuguuaugcu uacaaaaugg ugauggcuua uggaaggcug   2520

uuaaauuaau auuccuguua aaggaaauua aaguuugucu auuuuugaca auaaaacauu   2580

auauauuuuu aaaaaaaaaa aaaaaaa                                       2607
```

<210> SEQ ID NO 3
<211> LENGTH: 4670
<212> TYPE: RNA
<213> ORGANISM: HUMAN

<400> SEQUENCE: 3

```
gcuggggccc gacccgggau uaguugguuu cggagcggag gagggagccc cgaccgucac     60

gagcgucgaa gagacaaagc cgcgucaggg ggcccggccg gggcggggga gcccggggcu    120

uguuggugcc ccagcccgcg cggagggccc uucggacccg cgcgccgccg cugccgccgc    180

cgccgccucg caacaggucc gggcggccuc gcucuccgcu ccccuccccc gcauccgcga    240

cccuccgggg caccucagcu cggccggggc cgcagucugg ccacccgcuu ccaugcgguu    300

cgggguccaag augaugccga uguuucuuac cguguaucuc aguaacaaug agcagcacuu    360

cacagaaguu ccaguuacuc cagaaacaau augcagagac gugguggauc ugugcaaaga    420

acccggcgag agugauugcc auuuggcuga aguguggugu ggcucugaac guccaguugc    480

ggauaaugag cgaauguuug auguucuuca acgauuugga agucagagga acgaaguucg    540

cuucuuccuu cgucaugaac gccccccugg cagggacauu gugaguggac caagaucuca    600

ggauccaagu uuaaaaagaa augguguaaa aguuccuggu gaauaucgaa gaaaggagaa    660

cgguguuaau aguccuagga uggaucugac ucuugcugaa cuucaggaaa uggcaucucg    720

ccagcagcaa cagauugaag cccagcaaca auugcuggca acuaaggaac agcgcuuaaa    780

guuuuugaaa caacaagauc agcgacaaca gcaacaaguu gcugagcagg agaaacuuaa    840

aaggcuaaaa gaaauagcug agaaucagga agcuaagcua aaaaaaguga gagcacuuaa    900

aggccacgug gaacagaaga gacuaagcaa ugggaaacuu guggaggaaa uugaacagau    960

gaauaauuug uuccagcaaa aacagaggga gcucguccug gcugugucaa aaguagaaga   1020
```

-continued

```
acugaccagg cagcuagaga ugcucaagaa cggcaggauc gacagccacc augacaauca   1080
gucugcagug gcugagcuug aucgccucua uaaggagcug cagcuaagaa acaaauugaa   1140
ucaagagcag aaugccaagc uacaacaaca gagggagugu uugaauaagc guaauucaga   1200
aguggcaguc auggauaagc guguuaauga gcugagggac cggcugugga agaagaaggc   1260
agcucuacag caaaaagaaa aucuaccagu uucaucugau ggaaaucuuc cccagcaagc   1320
cgcgucagcc ccaagccgug uggcugcagu agguccuau auccagucgu cuacuaugcc   1380
ucggaugccc ucaaggccug aauugcuggu gaagccagcc cugccggaug guuccuuggu   1440
cauucaggcu ucagaggggc cgaugaaaau acagacacug cccaacauga gaucuggggc   1500
ugcuucacaa acuaaaggcu cuaaaaucca uccaguuggc ccugauugga guccuucaaa   1560
ugcagaucuu uucccaagcc aaggcucugc uucuguaccu caaagcacug ggaaugcucu   1620
ggaucaaguu gaugauggag agguuccgcu gagggagaaa gagaagaaag ugcguccguu   1680
cucaauguuu gaugcaguag accaguccaa ugccccaccu uccuuuggua cucugaggaa   1740
gaaccagagc agugaagaua ucuugcggga ugcucagguu gcaaauaaaa auguggcuaa   1800
aguaccaccu ccuguuccua caaaaccaaa acagauuaau uugccuuauu uuggacaaac   1860
uaaucagcca ccuucagaca uuaagccaga cggaaguucu cagcaguugu caacaguugu   1920
uccguccaug ggaacuaaac caaaaccagc agggcagcag ccgagagugc ugcuaucucc   1980
cagcauaccu ucgguuggcc aagaccagac ccuuucucca gguucuaagc aagaaagucc   2040
accugcugcu gccguccggc ccuuuacucc ccagccuucc aaagacaccu uacuuccacc   2100
cuucagaaaa ccccagaccg uggcagcaag uucaauauau uccauguaua cgcaacagca   2160
ggcgccagga aaaaacuucc agcaggcugu gcagagcgcg uugaccaaga cucauaccag   2220
agggccacac uuuucaagug uauaugguaa gccuguaauu gcugcugccc agaaucaaca   2280
gcagcaccca gagaacauuu auuccaauag ccagggcaag ccuggcaguc cagaaccuga   2340
aacagagccu guuucuucag uucaggagaa ccaugaaaac gaaagaauuc cucggccacu   2400
cagcccaacu aaauuacugc cuuucuuauc uaauccuuac cgaaaccaga gugaugcuga   2460
ccuagaagcc uuacgaaaga aacugucuaa cgcaccaagg ccucuaaaga aacguaguuc   2520
uauuacagag ccagaggguc cuaaugggcc aaauauucag aagcuuuuau aucagaggac   2580
caccauagcg gccauggaga ccaucucugu cccaucauac ccauccaagu cagcuucugu   2640
gacugccagc ucagaaagcc caguagaaau ccagaaucca uauuuacaug uggagcccga   2700
aaaggaggug gucucucugg uuccugaauc auuguccccca gaggaugugg ggaaugccag   2760
uacagagaac agugacaugc cagcuccuuc uccaggccuu gauuaugagc cugagggagu   2820
cccagacaac agcccaaauc uccagaauaa cccagaagaa ccaaauccag aggcuccaca   2880
ugugcuugau guguaccugg aggaguaccc uccauaccca cccccaccau acccaucugg   2940
ggagccugaa gggcccggag aagacucggu gagcaugcgc ccgccugaaa ucaccgggca   3000
ggucucucug ccuccuggua aaaggacaaa cuugcguaaa acuggcucag agcguaucgc   3060
ucauggaaug agggugaaau ucaaccccccu ugcuuuacug cuagauucgu cuuuggaggg   3120
agaauuugac cuuguacaga gaauuauuua ugagguugau gacccaagcc uccccaauga   3180
ugaaggcauc acggcucuuc acaaugcugu gugugcaggc cacacagaaa ucguuaaguu   3240
ccugguacag uuuggguguaa auguaaaugc ugcugauagu gauggaugga cuccauuaca   3300
uugugcugcc ucauguaaca acguccaagu guguaaguuu uugguggagu caggagccgc   3360
uguguuugcc augaccuaca gugacaugca gacugcugca gauaagugcg aggaaaugga   3420
```

```
ggaaggcuac acucagugcu cccaauuucu uuauggaguu caggagaaga ugggcauaau   3480
gaauaaagga gucauuuaug cgcuuuggga uuaugaaccu cagaaugaug augagcugcc   3540
caugaaagaa ggagacugca ugacaaucau ccacagggaa gacgaagaug aaaucgaaug   3600
guggugggcg cgccuuaaug auaaggaggg auauguucca cguaacuugc ugggacugua   3660
cccaagaauu aaaccaagac aaaggagcuu ggccugaaac uuccacacag aauuuuaguc   3720
aaugaagaau uaaucucugu uaagaagaag uaauacgauu auuuuuggca aaaauuucac   3780
aagacuuauu uuaaugacaa uguagcuuga aagcgaugaa gaaugucucu agaagagaau   3840
gaaggauuga agaauucacc auuagaggac auuuagcgug augaaauaaa gcaucuacgu   3900
cagcaggcca uacuguguug gggcaaaggu gucccgugua gcacucagau aaguauacag   3960
cgacaauccu guuuucuaca agaauccugu cuaguaaaua ggaucauuua uugggcaguu   4020
gggaaaucag cucucugucc uguugagugu uuucagcagc ugcuccuaaa ccaguccucc   4080
ugccagaaag gaccagugcc gucacaucgc ugucucugau uguccccggc accagcaggc   4140
ccuugggggg cucaccugaa ggcucgaagg cacugcacac uuguauauug ucagugaaga   4200
acuguuaguu gguugucagu gaacaauaac uuuauuauau gaguuuuugu agcaucuuaa   4260
gaauuauaca uauguuugaa auauugaaac uaagcuacgg uaccaguaau uagauguaga   4320
aucuuguuug uaggcugaau uuuaaucugu auuuauuguc uuuuguaucu cagaaauuag   4380
aaacuugcua cagacuuacc cguaauauuu gucaagauca uagcugacuu uaaaaacagu   4440
uguaauaaac uuuuugaugc uagcuguuua cugguuuuug uuuuugaugu cauaaauaga   4500
ccuuguuuaa uagucacaag ccguugggau aucauaccca gcugaaaaag aacaaacugc   4560
uuaacauaag uauauguauc guaauaagag uuuuuuacca gcuaagugau ucaauguaag   4620
ugguuuuuaa aauaaaauac uguagagauc auggugaaaa aaaaaaaaaa              4670
```

<210> SEQ ID NO 4
<211> LENGTH: 4802
<212> TYPE: RNA
<213> ORGANISM: HUMAN

<400> SEQUENCE: 4

```
gcuggggccc gacccgggau uaguugguuu cggagcggag gagggagccc cgaccgucac     60
gagcgucgaa gagacaaagc cgcgucaggg ggcccggccg gggcggggga gcccggggcu    120
uguuggugcc ccagcccgcg cggagggccc uucggacccg cgcgccgccg cugccgccgc    180
cgccgccucg caacaggucc gggcggccuc gcucuccgcu ccccuccccc gcauccgcga    240
cccuccgggg caccucagcu cggccggggc cgcagucugg ccacccgcuu ccaugcgguu    300
cggguccaag augaugccga uguuucuuac cguguaucuc aguaacaaug agcagcacuu    360
cacagaaguu ccaguuacuc cagaaacaau augcagagac gugguggauc ugugcaaaga    420
acccggcgag agugauugcc auuuggcuga agugugguggu ggcucuguag agauagaguu    480
ucaucauguu ggccaggaug gucucgaucu ccugaccuug ugauccgccu gccucggccu    540
cccaaagugc uggauuacag gugugagcca ccacgaucag ccucuagugu uuaaaaaaga    600
acguccaguu gcggauaaug agcgaauguu ugauguucuu caacgauuug gaagucagag    660
gaacgaaguu cgcuucuucc uucgucauga acgcccccu ggcagggaca uugugagugg    720
accaagaucu caggauccaa guuuaaaaag aaauggugua aaaguuccug gugaauaucg    780
aagaaaggag aacgguguua auaguccuag gauggaucug acucuugcug aacuucagga    840
aauggcaucu cgccagcagc aacagauuga agcccagcaa caauugcugg caacuaagga    900
```

-continued

```
acagcgcuua aaguuuuuga aacaacaaga ucagcgacaa cagcaacaag uugcugagca    960
ggagaaacuu aaaaggcuaa aagaaauagc ugagaaucag gaagcuaagc uaaaaaaagu   1020
gagagcacuu aaaggccacg uggaacagaa gagacuaagc aaugggaaac uuguggagga   1080
aauugaacag augaauaauu uguuccagca aaaacagagg gagcucgucc uggcugugucc  1140
aaaaguagaa gaacugacca ggcagcuaga gaugcucaag aacggcagga ucgacagcca   1200
ccaugacaau cagucugcag uggcugagcu ugaucgccuc uauaaggagc ugcagcuaag   1260
aaacaaauug aaucaagagc agaaugccaa gcuacaacaa cagagggagu guuugaauaa   1320
gcguaauuca gaaguggcag ucauggauaa gcguguuaau gagcugaggg accggcugug   1380
gaagaagaag gcagcucuac agcaaaaaga aaaucuacca guuucaucug auggaaaucu   1440
uccccagcaa gccgcgucag ccccaagccg uguggcugca guaggucccu auauccaguc   1500
gucuacuaug ccucggaugc ccucaaggcc ugaauugcug gugaagccag cccugccgga   1560
ugguuccuug gucauucagg cuucagaggg gccgaugaaa auacagacac ugcccaacau   1620
gagaucuggg gcugcuucac aaacuaaagg cucuaaaauc cauccaguug gcccugauug   1680
gaguccuuca aaugcagauc uuuucccaag ccaaggcucu gcuucuguac cucaaagcac   1740
ugggaaugcu cuggaucaag uugaugaugg agagguuccg cugagggaga aagagaagaa   1800
agugcguccg uucucaaugu uugaugcagu agaccagucc aaugccccac cuuccuuugg   1860
uacucugagg aagaaccaga gcagugaaga uaucuugcgg gaugcucagg uugcaaauaa   1920
aaauguggcu aaaguaccac cuccuguucc uacaaaacca aaacagauua auuugccuua   1980
uuuuggacaa acuaaucagc caccuucaga cauuaagcca gacggaaguu cucagcaguu   2040
gucaacaguu guuccgucca ugggaacuaa accaaaacca gcagggcagc agccgagagu   2100
gcugcuaucu cccagcauac cuucgguugg ccaagaccag acccuuucuc cagguucuaa   2160
gcaagaaagu ccaccugcug cugccguccg gcccuuuacu ccccagccuu ccaaagacac   2220
cuuacuucca cccuucagaa aaccccagac cguggcagca aguucaauau auuccaugua   2280
uacgcaacag caggcgccag gaaaaaacuu ccagcaggcu gugcagagcg cguugaccaa   2340
gacucauacc agagggccac acuuuucaag uguauauggu aagccuguaa uugcugcugc   2400
ccagaaucaa cagcagcacc cagagaacau uuauuccaau agccagggca agccuggcag   2460
uccagaaccu gaaacagagc cuguuucuuc aguucaggag aaccaugaaa acgaaagaau   2520
uccucggcca cucagcccaa cuaaauuacu gccuuucuua ucuaauccuu accgaaacca   2580
gagugaugcu gaccuagaag ccuuacgaaa gaaacugucu aacgcaccaa ggccucuaaa   2640
gaaacguagu ucuauuacag agccagaggg uccuaauggg ccaaauauuc agaagcuuuu   2700
auaucagagg accaccauag cggccaugga gaccaucucu gucccaucau acccauccaa   2760
gucagcuucu gugacugcca gcucagaaag cccaguagaa auccagaauc cauauuuaca   2820
uguggagccc gaaaaggagg uggucucucu gguuccugaa ucauuguccc cagaggaugu   2880
ggggaaugcc aguacagaga acagugacau gccagcuccu ucuccaggcc uugauuauga   2940
gccugaggga gucccagaca acagcccaaa ucuccagaau aacccagaag aaccaaaucc   3000
agaggcucca caugugcuug auguguaccu ggaggaguac ccuccauacc cacccccacc   3060
auacccaucu ggggagccug aagggcccgg agaagacucg gugagcaugc gcccgccuga   3120
aaucaccggg caggucucuc ugccuccugg uaaaaggaca aacuugcgua aaacuggcuc   3180
agagcguauc gcucauggaa ugagggugaa auucaacccc cuugcuuuac ugcuagauuc   3240
gucuuuggag ggagaauuug accuuguaca gagaauuauu uaugagguug augacccaag   3300
```

```
ccuccccaau gaugaaggca ucacggcucu ucacaaugcu gugugugcag gccacacaga   3360

aaucguuaag uuccugguac aguuuggugu aaauguaaau gcugcugaua gugauggaug   3420

gacuccauua cauugugcug ccucauguaa caacguccaa guguguaagu uuuuggugga   3480

gucaggagcc gcuguguuug ccaugaccua cagugacaug cagacugcug cagauaagug   3540

cgaggaaaug gaggaaggcu acacucagug cucccaauuu cuuuauggag uucaggagaa   3600

gaugggcaua augaauaaag gagucauuua ugcgcuuugg gauuaugaac cucagaauga   3660

ugaugagcug cccaugaaag aaggagacug caugacaauc auccacaggg aagacgaaga   3720

ugaaaucgaa ugguggugggg cgcgccuuaa ugauaaggag ggauauguuc cacguaacuu   3780

gcugggacug uacccaagaa uuaaaccaag acaaaggagc uuggccugaa acuuccacac   3840

agaauuuuag ucaaugaaga auuaaucucu guuaagaaga aguaauacga uuauuuuugg   3900

caaaaauuuc acaagacuua uuuuaaugac aauguagcuu gaaagcgaug aagaaugucu   3960

cuagaagaga augaaggauu gaagaauuca ccauuagagg acauuuagcg ugaugaaaua   4020

aagcaucuac gucagcaggc cauacugugu uggggcaaag gugucccgug uagcacucag   4080

auaaguauac agcgacaauc cuguuuucua caagaauccu gucuaguaaa uaggaucauu   4140

uauugggcag uugggaaauc agcucucugu ccuguugagu guuuucagca gcugcuccua   4200

aaccaguccu ccugccagaa aggaccagug ccgucacauc gcugucucug auugucccccg   4260

gcaccagcag gcccuugggg ggcucaccug aaggcucgaa ggcacugcac acuuguauau   4320

ugucagugaa gaacuguuag uugguuguca gugaacaaua acuuuauuau augaguuuuu   4380

guagcaucuu aagaauuaua cauauguuug aaauauugaa acuaagcuac gguaccagua   4440

auuagaugua gaaucuuguu uguaggcuga auuuuaaucu guauuuauug ucuuuuguau   4500

cucagaaauu agaaacuugc uacagacuua cccguaauau uugucaagau cauagcugac   4560

uuuaaaaaca guuguaauaa acuuuuugau gcuagcuguu uacugguuuu uguuuuugau   4620

gucauaaaua gaccuuguuu aauagucaca agccguuggg auaucauacc cagcugaaaa   4680

agaacaaacu gcuuaacaua aguauaugua ucguaaauag aguuuuuuac cagcuaagug   4740

auucaaugua aguggguuuu aaaauaaaau acuguagaga ucauggugaa aaaaaaaaaa   4800

aa                                                                  4802
```

<210> SEQ ID NO 5
<211> LENGTH: 3046
<212> TYPE: RNA
<213> ORGANISM: HUMAN

<400> SEQUENCE: 5

```
gccggcggga ucccaggcgc cgagcgcccg cugagcagcc acccuuugcg cgccgccugc     60

agcgcagcuu ccccgggcgc ugccuggaca ggccugccug cgugcuggga caugucuggc    120

cuccaaggac cgucggugggg cgauggcugc aacgguggag gggccagagc uggaggcagc    180

ugcugccgca ggagaugcuu cagaggauuc ggacgcaggg uccagggcgc ugccuuuccu    240

gggcggcaac cggcugagcu uggaccugua ccccgggggc ugccagcagc ugcugcaccu    300

gugugccag cagccucugc agcugcugca ggugggaauuc uugcgucuga gcacucacga    360

ggacccucag cugcuggagg ccacccuggc ccagcugccu cagagccugu ccugccuccg    420

cucccugguc cucaaagggu cgaucuggga ccucggaccc uggcucugag ggccacaucc    480

gccucccccc uucccaggag ggcaacgccg ggacacacug ggugccuguc uccggggugc    540

ccugaccaac cugcccgcug gucugagugg ccuggcccau cuggcccacc uggaccugag    600
```

-continued

```
cuucaacagc cuggagacac ugccggccug uguccugcag augcgagguc ugggugcgcu    660
cuugcugucu cacaacugcc ucucugagcu gccugaggcu cugggggccc uccccgcccu    720
caccuuccuc acagugacac acaaccgccu gcagacgcug cccccagcac ugggggcccu    780
auccacccug cagcgccucg aucucucuca gaaucugcug gacacgcuac cuccugagau    840
uggaggccug ggcagccucc uggagcucaa ccuggccucc aaccggcugc agagccuccc    900
agccucucug gcgggacuuc gguccuugcg gcuccuuguc cugcacagca accuccuggc    960
cucugugcca gcugacuugg cccgccuucc acuccucacc cggcucgacc ugagggacaa   1020
ccagcuccgg gaccugcccc cugagcugcu agacgccccc uuugugcgcc ugcaggggaa   1080
cccccugggu gaggccucgc cagacgcccc gaguucacca guggcagccc ucauuccaga   1140
aaugcccaga cuguuccuga ccucagauuu ggacagcuuu ccugugaccc cucaaggcug   1200
cucagugacc cuggccugug gcguccgccu gcaguuccca gcgggagcca ccgccacccc   1260
caucaccauc cgcuaucggc ugcugcugcc ggagccaggc cucguccccc ugggucccca   1320
ugacgcccug cucagccaug ugcuggagcu gcagccccau gggguggccu uccagcagga   1380
uguggggcug uggcugcucu ucaccccacc gcaggcccgg cgcugccgug aaguggugga   1440
caggacccgg aaugacaaca gcugggguga ccuggagacc uaccuggagg aagaggcacc   1500
ccagcggcuc ugggcucacu gccaggugcc ccacuucucc ugguuccuug ugguuucccg   1560
cccugugucc aaugccugcc uggugccacc ggaggggaca cugcugugcu ccucggguca   1620
uccuggggu c aaagucaucu uccccccugg ggccacugag gagccucguc gagucuccau   1680
gcagguggug cgcauggcug gccgagagcu gcaggcccuc cugggagaac cagaggcugc   1740
agugagcccc cugcugugcc ugucacagag cgguccccc agcuuccucc aaccggucac   1800
cgugcagcug ccucugcccu cuggcaucac aggccucagu cuggaccgcu cccgccugca   1860
ccuguuguac ugggcccuc cugcagccac cugggaugac aucacagcuc agguggucccu   1920
ggagcucacc caccuguacu ggcucuggua caccaccaag aacugugugg gaggccuggc   1980
ucggaaggcc ugggagcggc ugcggcugca ccgugugaac cucaucgcuc ugcagcggcg   2040
ccgggacccu gagcaggucc ugcugcagug ccugccccga aacaaggugg acgccacccu   2100
ucggcggcug cuggagcggu accggggccc cgagcccucu gacacggugg agauguucga   2160
gggcgaagag uucuuugcgg ccuucgagcg cggcaucgac guggaugcug accgcccuga   2220
cuguguggag ggcagaaucu gcuuugucuu cuacucgcac cugaagaaug ugaaggaggu   2280
auacgugacc accacucugg accgggaggc ucaggcugug cggggccagg uguccuucua   2340
ccguggcgcg gugccugugc gggugcccga ggaggcugag gcugcccggc agaggaaggg   2400
cgcagacgcc cuguggaugg ccacucugcc caucaagcug ccgagacuuc gaggguccga   2460
ggggccacgg cgggggcug gccucuccuu ggcacccuug aaucugggag augccgagac   2520
cggcuuucug acgcagagca accugcugag uguggcuggg cgucugggguc uggacuggcc   2580
agccguggcc cugcaccugg gggugucuua ccgggaggug cagcgcaucc ggcacgaguu   2640
ccgggaugau cuggaugagc agauccguca caugcucuuc uccugggcug agcgccaggc   2700
ugggcagcca ggggcugugg ggcuccuggu gcaggcccug gagcagagug accggcagga   2760
cguggcugaa gaggugcgcg cagucuugga gcucggccgc cgcaaguacc aggacagcau   2820
ccgacgcaug ggcuuggccc ccaaggaccc cgcucugccu ggcuccucgg cuccacagcc   2880
cccagagccu gcccaggccu aggccccaca gacuuuuagg cuggcccaga uauuccccag   2940
uggaugggca gagcccccac cuucaagucu cuccagugug uggggacggg ucccugugag   3000
```

-continued caacaaaacu gcacuguuuc uuucaccuca aaaaaaaaaa aaaaaa 3046

<210> SEQ ID NO 6
<211> LENGTH: 3025
<212> TYPE: RNA
<213> ORGANISM: HUMAN

<400> SEQUENCE: 6
gccggcggga ucccaggcgc cgagcgcccg cugagcagcc acccuuugcg cgccgccugc 60
agcgcagcuu ccccgggcgc ugccuggaca ggccugccug cgugcuggga caugucuggc 120
cuccaaggac cgucgguggg cgauggcugc aacgguggag gggccagagc uggaggcagc 180
ugcugccgca ggagaugcuu cagaggauuc ggacgcaggg uccagggcgc ugccuuuccu 240
gggcggcaac cggcugagcu uggaccugua ccccgggggc ugccagcagc ugcugcaccu 300 gugugucag cagccucugc agcugcugca gguggaauuc uugcgucuga gcacucacga 360
ggacccucag cugcuggagg ccacccuggc ccagcugccu cagagccugu ccugccuccg 420
cucccugguc cucaaaggag ggcaacgccg ggacacacug ggugccuguc uccgggggugc 480 ccugaccaac cugcccgcug gucugagugg ccuggcccau cuggcccacc uggaccugag 540
cuucaacagc cuggagacac ugccggccug uguccugcag augcgagguc ugggugcgcu 600
cuugcugucu cacaacugcc ucucugagcu gccugaggcu cugggggccc uccccgcccu 660
caccuuccuc acagugacac acaaccgccu gcagacgcug cccccagcac ugggggcccu 720
auccacccug cagcgccucg aucucucuca gaaucugcug gacacgcuac cuccugagau 780
uggaggccug ggcagccucc uggagcucaa ccuggccucc aaccggcugc agagccuccc 840
agccucucug gcgggacuuc gguccuugcg gcuccuuguc cugcacagca accuccuggc 900
cucugugcca gcugacuugg cccgccuucc acuccucacc cggcucgacc ugagggacaa 960
ccagcuccgg gaccugcccc cugagcugcu agacgccccc uuugugcgcc ugcaggggaa 1020
cccccugggu gaggccucgc cagacgcccc gaguucacca guggcagccc ucauuccaga 1080
aaugcccaga cuguuccuga ccucagauuu ggacagcuuu ccugugaccc cucaaggcug 1140
cucagugacc cuggccugug gcguccgccu gcaguuccca gcgggagcca ccgccacccc 1200
caucaccauc cgcuaucggc ugcugcugcc ggagccaggc cucguccccc uggguccuca 1260
ugacgcccug cucagccaug ugcuggagcu gcagccccau gggguggccu uccagcagga 1320
uguggggcug uggcugcucu ucaccccacc gcaggcccgg cgcugccgug aaguggugu 1380 caggacccgg aaugacaaca gcugggguga ccuggagacc uaccuggagg aagaggcacc 1440
ccagcggcuc ugggcucacu gccaggugcc ccacuucucc ugguuccuug ugguuucccg 1500 cccuguguc aaugccugcc uggugccacc ggaggggaca cugcugugcu ccucggguca 1560 uccuggggguc aaagucaucu uccccccugg ggccacugag gagccucguc gagucuccau 1620
gcagguggug cgcauggcug gccgagagcu gcaggcccuc cugggagaac cagaggcugc 1680
agugagcccc cugcugugcc ugucacagag cggucccccc agcuuccucc aaccggucac 1740
cgugcagcug ccucugcccu cuggcaucac aggccucagu cuggaccgcu cccgccugca 1800
ccuguuguac ugggccccuc cugcagccac cugggaugac aucacagcuc agguggcuccu 1860 ggagcucacc caccuguacg cacgcuucca ggucacacac uucuccuggu acuggcucug 1920
guacaccacc aagaacugug ugggaggccu ggcucggaag gccugggagc ggcugcggcu 1980
gcaccgugug aaccucaucg cucugcagcg gcgccgggac ccugagcagg uccugcugca 2040
gugccugccc cgaaacaagg uggacgccac ccuucggcgg cugcuggagc gguaccgggg 2100

-continued

```
ccccgagccc ucugacacgg uggagauguu cgagggcgaa gaguucuuug cggccuucga   2160

gcgcggcauc gacguggaug cugaccgccc ugacugugug gagggcagaa ucugcuuugu   2220

cuucuacucg caccugaaga augugaagga gguauacgug accaccacuc uggaccggga   2280

ggcucaggcu gugcggggcc aggugucuu cuaccguggc gcggugccug ugcgggugcc   2340

cgaggaggcu gaggcugccc ggcagaggaa gggcgcagac gcccugugga uggccacucu   2400

gcccaucaag cugccgagac uucgagggc cgaggggcca cggcgggggg cuggccucuc   2460

cuuggcaccc uugaaucugg gagaugccga gaccggcuuu cugacgcaga gcaaccugcu   2520

gagugugcu gggcgucugg gucuggacug gccagccgug gcccugcacc ugggggguguc   2580

cuaccgggag gugcagcgca uccggcacga guuccgggau gaucuggaug agcagauccg   2640

ucacaugcuc uucuccuggg cugagcgcca ggcugggcag ccaggggcug uggggcuccu   2700

ggugcaggcc cuggagcaga gugaccggca ggacguggcu gaagaggugc gcgcagucuu   2760

ggagcucggc cgccgcaagu accaggacag cauccgacgc augggcuugg cccccaagga   2820

ccccgcucug ccuggcuccu cggcuccaca gcccccagag ccugcccagg ccuaggcccc   2880

acagacuuuu aggcuggccc agauauuccc caguggaugg gcagagcccc caccuucaag   2940

ucucuccagu guguggggac ggguccugu gagcaacaaa acugcacugu uucuuucacc   3000

ucaaaaaaaa aaaaaaaaaa aaaaa                                         3025
```

<210> SEQ ID NO 7
<211> LENGTH: 2902
<212> TYPE: RNA
<213> ORGANISM: HUMAN

<400> SEQUENCE: 7

```
gcuuccccgg gcgcugccug gacaggccug ccugcgugcu gggacauguc uggccuccaa     60

ggaccgucgg ugggcgaugg cugcaacggu ggaggggcca gagcuggagg cagcugcugc    120

cgcaggagau gcuucagagg auucggacgc agggccagg gcgcugccuu uccugggcgg    180

caaccggcug agcuuggacc uguaccccgg gggcugccag cagcugcugc accugugugu    240

ccagcagccu cugcagcugc ugcaggugga auucuugcgu cugagcacuc acgaggaccc    300

ucagcugcug gaggccaccc uggcccagcu gccucagagc cuguccugcc uccgcucccu    360

gguccucaaa ggagggcaac gccgggacac acugggugcc ugucuccggg gugcccugac    420

caaccugccc gcuggucuga guggccuggc ccaucuggcc caccuggacc ugagcuucaa    480

cagccuggag acacugccgg ccugugucc u gcagaugcga ggucugggug cgcucuugcu    540

gucucacaac ugccucucug agcugccuga ggcucugggg gcccucccg cccucaccuu    600

ccucacagug acacacaacc gccugcagac gcugccccca gcacuggggg cccuauccac    660

ccugcagcgc cucgaucucu cucagaaucu gcuggacacg cuaccuccug agauuggagg    720

ccugggcagc cuccuggagc ucaaccuggc cuccaaccgg cugcagagcc ucccagccuc    780

ucuggcggga cuucggucu ugcggcuccu uguccugcac agcaaccucc uggccucugu    840

gccagcugac uuggcccgcc uuccacuccu cacccggcuc gaccugaggg acaaccagcu    900

ccgggaccug cccccugagc ugcuagacgc ccccuuugug cgccugcagg ggaacccccu    960

gggugaggcc ucgccagacg ccccgaguuc accaguggca gcccucauuc cagaaaugcc   1020

cagacuguuc cugaccucag auuuggacag cuuuccugug accccucaag gcugcucagu   1080

gacccuggcc uguggcgucc gccugcaguu cccagcggga gccaccgcca cccccaucac   1140

cauccgcuau cggcugcugc ugccggagcc aggccucguc ccccugggguc cucaugacgc   1200
```

-continued

```
ccugcucagc caugugcugg agcugcagcc ccaugggug gccuuccagc aggauguggg   1260

gcuguggcug cucuucaccc caccgcaggc ccggcgcugc cgugaagugg uggucaggac   1320

ccggaaugac aacagcuggg gugaccugga gaccuaccug gaggaagagg caccccagcg   1380

gcucugggcu cacugccagg ugccccacuu cuccugguuc cuugugguuu cccgcccugu   1440

guccaaugcc ugccuggugc caccggaggg gacacugcug ugcuccucgg gucauccugg   1500

ggucaaaguc aucuuccccc cuggggccac ugaggagccu cgucgagucu ccaugcaggu   1560

ggugcgcaug gcuggccgag agcugcaggc ccuccuggga gaaccagagg cugcagugag   1620

cccccugcug ugccugucac agagcggucc ccccagcuuc cuccaaccgg ucaccgugca   1680

gcugccucug cccucuggca ucacaggccu cagucuggac cgcucccgcc ugcaccuguu   1740

guacugggcc ccuccugcag ccaccuggga ugacaucaca gcucaggugg uccuggagcu   1800

cacccaccug uacgcacgcu uccaggucac acacuucucc ugguacuggc ucugguacac   1860

caccaagaac ugugugggag gccuggcucg gaaggccugg gagcggcugc ggcugcaccg   1920

ugugaaccuc aucgcucugc agcggcgccg ggacccugag cagguccugc ugcagugccu   1980

gccccgaaac aagguggacg ccacccuucg gcggcugcug gagcgguacc ggggccccga   2040

gcccucugac acgguggaga uguucgaggg cgaagaguuc uuugcggccu ucgagcgcgg   2100

caucgacgug gaugcugacc gcccugacug uguggagggc agaaucugcu uugucuucua   2160

cucgcaccug aagaauguga aggaggugue cuucuaccgu ggcgcggugc cugugcgggu   2220

gcccgaggag gcugaggcug cccggcagag gaagggcgca gacgcccugu ggauggccac   2280

ucugcccauc aagcugccga gacuucgagg guccgagggg ccacggcggg gggcuggccu   2340

cuccuuggca cccuugaauc ugggagaugc cgagaccggc uuucugacgc agagcaaccu   2400

gcugagugug gcugggcguc ugggucugga cuggccagcc guggcccugc accugggggu   2460

guccuaccgg gaggugcagc gcauccggca cgaguuccgg gaugaucugg augagcagau   2520

ccgucacaug cucuucuccu gggcugagcg ccaggcuggg cagccagggg cuguggggcu   2580

ccuggugcag gcccuggagc agagugaccg gcaggacgug gcugaagagg ugcgcgcagu   2640

cuuggagcuc ggccgccgca aguaccagga cagcauccga cgcaugggcu uggcccccaa   2700

ggaccccgcu cugccuggcu ccucggcucc acagccccca gagccugccc aggccuaggc   2760

cccacagacu uuuaggcugg cccagauauu ccccagugga ugggcagagc ccccaccuuc   2820

aagucucucc agugugugg gacggguccc ugugagcaac aaaacugcac uguuucuuuc   2880

accucaaaaa aaaaaaaaaa aa                                            2902
```

<210> SEQ ID NO 8
<211> LENGTH: 743
<212> TYPE: RNA
<213> ORGANISM: HUMAN

<400> SEQUENCE: 8

```
cgcgccuagc agugucccag ccggguucgu gucgccaugg ggcagaucga gugggccaug     60

ugggccaacg aacaggcgcu ggcguccggc cugauccuca ucaccggggg caucguggcc    120

acagcugggc gcuucaccca gugguacuuu ggugccuacu ccauuguggc gggcguguuu    180

gugugccugc uggaguaccc ccgggggaag aggaagaagg gcuccaccau ggagcgcugg    240

ggacagaagu acaugaccgc cgguggugaag cuguucgggc ccuuuaccag gaauuacuau    300

guucgggccg uccugcaucu ccugcucucg gugcccgccg gcuuccugcu ggccaccauc    360

cuugggaccg ccugccuggc cauugcgagc ggcaucuacc uacuggcggc ugugcguggc    420
```

-continued gagcagugga cgcccaucga gcccaagccc cgggagcggc cgcagaucgg aggcaccauc 480
aagcagccgc ccagcaaccc cccgccgcgg cccccggccg aggcccgcaa gaagcccagc 540
gaggaggagg cugcgguggc ggcgggggga cccccgggag gucccccaggu caaccccauc 600 ccggugaccg acgaggucgu gugaccucgc cccggaccug cccucccgcc aggugcaccc 660
accugcaaua aaugcagcga agccgggaaa aaaaaaaaaa aaaaaaaaaa aaaaaaaaaa 720
aaaaaaaaaa aaaaaaaaaa aaa 743

<210> SEQ ID NO 9
<211> LENGTH: 1914
<212> TYPE: RNA
<213> ORGANISM: HUMAN

<400> SEQUENCE: 9
aguugaccaa ccaugccuug aggauaaaau ggaugggauc agaugggaag augugacaag 60
aagagaaauc cuccucuaua uaggaugcuc ugcuguuucc uaaggauuuu cagcaccuug 120
ccccaaaauc aaaaugaugc uucaacaccc aggccagguc ucugccucgg aagugagugc 180
uucugccauc guccccugcc uguccccucc ugggucacug guguuugagg auuuugcuaa 240
ccugacgccc uuugucaagg aagagcugag guuugccauc cagaacaagc accucugcca 300
ccggaugucc ucugcgcugg aaucagucac ugucagcgac agaccccucg ggguguccau 360
cacaaaagcc gagguagccc cugaagaaga ugaaaggaaa aagaggcgac gagaaagaaa 420
uaagauugca gcugcaaagu gccgaaacaa gaagaaggag aagacggagu gccugcagaa 480
agagucggag aagcuggaaa gugugaaugc ugaacugaag gcucagauug aggagcucaa 540
gaacgagaag cagcauuuga uauacaugcu caaccuucau cggcccacgu guauuguccg 600
ggcucagaau gggaggacuc cagaagauga gagaaaccuc uuuauccaac agauaaaaga 660
aggaacauug cagagcuaag cagucguggu augggggcga cuggggaguc cucauugaau 720
ccucauuuua uacccaaaac ccugaagcca uuggagagcu gucuuccugu guaccucuag 780
aaucccagca gcagagaacc aucaaggcgg gagggccugc agugauucag caggcccuuc 840
ccauucugcc ccagaguggg ucuuggacca gggcaagugc aucuuugccu caacuccagg 900
auuuaggccu uaacacacug gccauucuua uguuccagau ggcccccagc ugguguccug 960
cccgccuuuc aucuggauuc uacaaaaaac caggaugccc accguuagga uucaggcagc 1020
agugucugua ccucgggugg gagggauggg gccaucuccu ucaccguggc uaccauuguc 1080
acucguaggg gauguggagu gagaacagca uuuagugaag uugugcaacg gccaggguug 1140
ugcuuucuag caaauaugcu guuaugucca gaaauugugu gugcaagaaa acuaggcaau 1200
guacucuucc gauguuugug ucacacaaca cugaugugac uuuuauaugc uuuuucucag 1260
aucugguuuc uaagaguuuu ggggggcggg gcugucacca cgugcaguau cucaagauau 1320
ucagguggcc agaagagcuu gucagcaaga ggaggacaga auucucccag cguuaacaca 1380
aaauccaugg gcaguaugau ggcagguccu cuguugcaaa cucaguucca aagucacagg 1440
aagaaagcag aaaguucaac uuccaaaggg uuaggacucu ccacucaaug ucuuagguca 1500
ggaguugugu cuaggcugga agagccaaag aauauuccau uuuccuuucc uugugguuga 1560
aaaccacagu caguggagag auguuuggaa accacaguca guggagccug ggugguaccc 1620
aggcuuuagc auuauuggau gucaauagca uuguuuuugu cauguagcug uuuuaagaaa 1680
ucuggcccag gguguuugca gcugugagaa gucacucaca cuggccacaa ggacgcuggc 1740
uacugucuau uaaaauucug auguuucugu gaaauucuca gaguguuuaa uuguacucaa 1800
ugguaucauu acaauuuucu guaagagaaa auauuacuua uuuauccuag uauuccuaac 1860
cugucagaau aauaaauauu ggaaccaaga caugguaaaa aaaaaaaaaa aaaa 1914

<210> SEQ ID NO 10
<211> LENGTH: 2049
<212> TYPE: RNA
<213> ORGANISM: HUMAN

<400> SEQUENCE: 10
cgggaagcua uuaauagcau uacgucagcc ugggacuggc aacacggagu aaacgaccgc 60
gccgccagcc ugagggcuau aaaaggggug augcaacgcu cuccaagcca cagucgcacg 120
cagccaggcg cgcacugcac agcucucuuc ucucgccgcc gcccgagcgc acccuucagc 180
ccgcgcgccg gccgugaguc cucggugcuc gcccgccggc cagacaaaca gcccgcccga 240
ccccgucccg acccuggccg ccccgagcgg agccuggagc aaaaugaugc uucaacaccc 300
aggccagguc ucugccucgg aagugagugc uucugccauc guccccugcc uguccccucc 360
ugggucacug guguuugagg auuuugcuaa ccugacgccc uuugucaagg aagagcugag 420
guuugccauc cagaacaagc accucugcca ccggaugucc ucugcgcugg aaucagucac 480
ugucagcgac agaccccucg ggguguccau cacaaaagcc gagguagccc cugaagaaga 540
ugaaaggaaa aagaggcgac gagaaagaaa uaagauugca gcugcaaagu gccgaaacaa 600
gaagaaggag aagacggagu gccugcagaa agagucggag aagcuggaaa gugugaaugc 660
ugaacugaag gcucagauug aggagcucaa gaacgagaag cagcauuuga uauacaugcu 720
caaccuucau cggcccacgu guauuguccg ggcucagaau gggaggacuc cagaagauga 780
gagaaaccuc uuuauccaac agauaaaaga aggaacauug cagagcuaag cagucguggu 840 auggggcga cuggggaguc cucauugaau ccucauuuua uacccaaaac ccugaagcca 900
uuggagagcu gucuuccugu guaccucuag aaucccagca gcagagaacc aucaaggcgg 960
gagggccugc agugauucag caggcccuuc ccauucugcc ccagaguggg ucuuggacca 1020
gggcaagugc aucuuugccu caacuccagg auuuaggccu uaacacacug gccauucuua 1080
uguuccagau ggcccccagc uggugucug cccgccuuuc aucuggauuc uacaaaaaac 1140
caggaugccc accguuagga uucaggcagc agugucugua ccucgggugg gagggauggg 1200
gccaucuccu ucaccguggc uaccauuguc acucguaggg gauguggagu gagaacagca 1260
uuuagugaag uugugcaacg gccaggguug ugcuuucuag caaauaugcu guuaugucca 1320
gaaauugugu gugcaagaaa acuaggcaau guacucuucc gauguuugug ucacacaaca 1380
cugaugugac uuuuauaugc uuuuucucag aucugguuuc uaagaguuuu gggggcggg 1440 gcugucacca cgugcaguau cucaagauau ucagguggcc agaagagcuu gucagcaaga 1500
ggaggacaga auucucccag cguuaacaca aaauccaugg gcaguaugau ggcagguccu 1560
cuguugcaaa cucaguucca aagucacagg aagaaagcag aaaguucaac uuccaaaggg 1620
uuaggacucu ccacucaaug ucuuagguca ggaguugugu cuaggcugga agagccaaag 1680
aauauuccau uuuccuuucc uuguguuga aaaccacagu caguggagag auguuuggaa 1740
accacaguca guggagccug gguguacccc aggcuuuagc auuauuggau gucaauagca 1800
uuguuuuugu cauguagcug uuuuaagaaa ucuggcccag gguguuugca gcugugagaa 1860
gucacucaca cuggccacaa ggacgcuggc uacugucuau uaaaaauucug auguuucugu 1920 gaaauucuca gaguguuuaa uuguacucaa ugguaucauu acaauuuucu guaagagaaa 1980
auauuacuua uuuauccuag uauuccuaac cugucagaau aauaaauauu ggaaccaaga 2040

-continued caugguaaa 2049

<210> SEQ ID NO 11
<211> LENGTH: 2361
<212> TYPE: RNA
<213> ORGANISM: HUMAN

<400> SEQUENCE: 11
cgggaagcua uuaauagcau uacgucagcc ugggacuggc aacacggagu aaacgaccgc 60
gccgccagcc ugagggcuau aaaaggggug augcaacgcu cuccaagcca cagucgcacg 120
cagccaggcg cgcacugcac agcucucuuc ucucgccgcc gcccgagcgc acccuucagc 180
ccgcgcgccg gccgugaguc cucggugcuc gcccgccggc cagacaaaca gcccgcccga 240
ccccgucccg acccuggccg ccccgagcgg agccuggagc aaaaugaugc uucaacaccc 300
aggccagguc ucugccucgg aagugagugc uucugccauc guccccugcc uguccccucc 360
ugggucacug guguuugagg auuuugcuaa ccugacgccc uuugucaagg aagagcugag 420
guuugccauc cagaacaagc accucugcca ccggaugucc ucugcgcugg aaucagucac 480
ugucagcgac agaccccucg ggguguccau cacaaaagcc gagguagccc cugaagaaga 540
ugaaaggaaa aagaggcgac gagaaagaaa uaagauugca gcugcaaagu gccgaaacaa 600
gaagaaggag aagacggagu gccugcagaa acucccaagg cccuuuuggg uccagaagac 660
cugcauaugg gcuguugacu caugcaaaug agguaucuga acugcagcuu caguauuagc 720
agagccacag gccgccucug uggcaucacc aggguuucuc ugaagaagag ggucugcauu 780
uuccuaaacc cagugcugcu cucccaucuc ccaucuuccu cucgcagcuu gaugagcccc 840 ggug➝guccc agguacaccc cugcauccag gcagcagccc aggccacccc cuccucacug 900
gcccuuggcu ccuuucuuga ugccucuguu gcuugucccc caggagucgg agaagcugga 960
aagugugaau gcugaacuga aggcucagau ugaggagcuc aagaacgaga agcagcauuu 1020
gauauacaug cucaaccuuc aucggcccac guguauuguc cgggcucaga augggaggac 1080
uccagaagau gagagaaacc ucuuuaucca acagauaaaa gaaggaacau ugcagagcua 1140
agcagucgug guaugggggc gacuggggag uccucauuga auccucauuu uauacccaaa 1200
acccugaagc cauuggagag cugucuuccu guguaccucu agaaucccag cagcagagaa 1260
ccaucaaggc gggagggccu gcagugauuc agcaggcccu ucccauucug ccccagagug 1320
ggucuuggac cagggcaagu gcaucuuugc cucaacucca ggauuuaggc cuuaacacac 1380
uggccauucu uauguuccag auggccccca gcuggugucc ugcccgccuu ucaucuggau 1440
ucuacaaaaa accaggaugc ccaccguuag gauucaggca gcagugucug uaccucgggu 1500
gggagggaug gggccaucuc cuucaccgug gcuaccauug ucacucguag gggaugugga 1560
gugagaacag cauuuaguga aguugugcaa cggccagggu ugugcuuucu agcaaauaug 1620
cuguuauguc cagaaauugu gugugcaaga aaacuaggca auguacucuu ccgauguuug 1680
ugucacacaa cacugaugug acuuuuauau gcuuuuucuc agaucugguu ucuaagaguu 1740
uuggggggcg gggcugucac cacgugcagu aucucaagau auucaggugg ccagaagagc 1800
uugucagcaa gaggaggaca gaauucuccc agcguuaaca caaaauccau gggcaguaug 1860
auggcagguc cucuguugca aacucaguuc caaagucaca ggaagaaagc agaaaguuca 1920
acuuccaaag gguuaggacu cuccacucaa ugucuuaggu caggaguugu gucuaggcug 1980
gaagagccaa agaauauucc auuuuccuuu ccuuguggu gaaaaccaca gucaguggag 2040
agauguuugg aaaccacagu caguggagcc uggguggiac ccaggcuuua gcauuauugg 2100

-continued augucaauag cauuguuuuu gucauguagc uguuuuaaga aaucuggccc agggguguuug 2160 cagcugugag aagucacuca cacuggccac aaggacgcug gcuacugucu auuaaaauuc 2220
ugauguuucu gugaaauucu cagaguguuu aauuguacuc aaugguauca uuacaauuuu 2280
cuguaagaga aaauauuacu uauuuauccu aguauuccua accugucaga auaauaaaua 2340
uuggaaccaa gacaugguaa a 2361

<210> SEQ ID NO 12
<211> LENGTH: 4145
<212> TYPE: RNA
<213> ORGANISM: HUMAN

<400> SEQUENCE: 12 gggugccug gugugugggc gcggcagggc gcaggcgcag gcgcagugug cguccgcguc 60
ugaggggagg gauguggggg aagcgacggc ccccgguuug uuugggcugu gggcggugcg 120
cagcggagag cccgggaaaa gcgggaaaug gcggcgccga gcgcggggguc uugguccacc 180 uuccagcaca aggagcugau ggccgcugac aggggacgca ggauauuggg agugugugggc 240 augcauccuc aucaucagga aacucuaaaa aagaaccgag uggugcuagc caaacagcug 300
uuguugagcg aauuguuaga acaucuucug gagaaggaca ucaucaccuu ggaaaugagg 360
gagcucaucc aggccaaagu gggcaguuuc agccagaaug uggaacuccu caacuugcug 420
ccuaagaggg guccccaagc uuuugaugcc uucugugaag cacugaggga gaccaagcaa 480
ggccaccugg aggauauguu gcucaccacc cuuucugggc uucagcaugu acucccaccg 540
uugagcugug acuacgacuu gagucucccu uuuccggugu gugaguccug uccccuuuac 600
aagaagcucc gccugucgac agauacugug gaacacuccc uagacaauaa agaugguccu 660
gucugccuuc aggugaagcc uugcacuccu gaauuuuauc aaacacacuu ccagcuggca 720
uauagguugc agucucggcc ucguggccua gcacuggugu ugagcaaugu gcacuucacu 780
ggagagaaag aacuggaauu ucgcucugga ggggaugugg accacaguac ucuagucacc 840
cucuucaagc uuuugggcua ugacguccau guucuaugug accagacugc acaggaaaug 900
caagagaaac ugcagaauuu ugcacaguua ccugcacacc gagucacgga cuccugcauc 960
guggcacucc ucucgcaugg uguggagggc gccaucuaug guguggaugg gaaacugcuc 1020
cagcuccaag agguuuuuca gcucuuugac aacgccaacu gcccaagccu acagaacaaa 1080
ccaaaaaugu ucuucaucca ggccugccgu ggagaugaga cugaucgugg gguugaccaa 1140
caagauggaa agaaccacgc aggaucccu gggugcgagg agagugaugc cgguaaagaa 1200
aaguugccga agaugagacu gcccacgcgc ucagacauga uaugcggcua ugccugccuc 1260
aaagggacug ccgccaugcg gaacaccaaa cgagguuccu gguacaucga ggcucuugcu 1320
caaguguuuu cugagcgggc uugugauaug cacguggccg acaugcuggu uaaggugaac 1380
gcacuuauca aggaucggga agguuaugcu ccuggcacag aauuccaccg gugcaaggag 1440
augucugaau acugcagcac ucugugccgc caccucuacc uguucccagg acacccuccc 1500
acaugauguc accuccccau cauccacgcc aaguggaagc cacuggacca caggaggugu 1560
gauagagccu uugaucuuca ggaugcacgg uuucuguucu gccccccucag ggaugugga 1620 aucucccaga cuuguuuccu gugcccauca ucucugccuu ugagugugggg acuccaggcc 1680 agcuccuuuu cugugaagcc cuuugccugu agagccagcc uugguuggac cuauugccag 1740
gaauguuuca gcugcaguug aagagccuga caagugaagu uguaaacaca gugugguuau 1800
ggggagaggg cauauaaauu ccccauauuu guguucaguu ccagcuuuug uagauggcac 1860

-continued

```
uuuagugauu gcuuuuauua cauuaguuaa gaugucugag agaccaucuc cuaucuuuua   1920

uuucauucau auccuccgcc cuuuuugucc uagagugaga guuuggaagg uguccaaauu   1980

uaauguagac auuaucuuuu ggcucugaag aagcaaacau gacuagagac gcaccuugcu   2040

gcagugucca gaagcggccu gugcguuccc uucaguacug cagcgccacc caguggaagg   2100

acacucuugg cucguuuggg cucaaggcac cgcagccugu cagccaacau ugccuugcau   2160

uuguaccuua uugaucuuug cccauggaag ucucaaagau cuuucguugg uuguuucucu   2220

gagcuuuguu acugaaauga gccucguggg gagcaucaga gaaggccagg aagaauggug   2280

uguuucccua gacucuguaa ccaccucucu gucuuuuucc uuccugagaa acguccaucu   2340

cucucccuua cuauucccac uuucauucaa ucaaccugca cuucauaucu agauuucuag   2400

aaaagcuucc uagcuuaucu cccugcuuca uaucucuccc uucuuuaccu ucauuucauc   2460

cuguuggcug cugccaccaa aucugucuag aauccugcuu uacaggauca uguaaaugcu   2520

caaagaugua auguaguucu uuguuccugc uuucucuuuc aguauuaaac ucuccuuuga   2580

uauuaugugg cuuuuauuuc agugccauac auguuauugu uuucaaccua gaaaccuuua   2640

ucccugcuua ucugaaacuu cccaacuucc cuguucuuua agacuuuuuu uuuuuuuuuu   2700

uuuuuuuuug agacagaguc ucgcucuguc gcccaggcug gagggcagug gcacgaucuc   2760

agcucacugc aagcuccaac ucccggguuc acgccauucu ccugccucag ccuuccaagu   2820

agcugggacu acaggugccc gccaccgugc ccggcuaauu uuuuuguauu uuuaguagag   2880

acaggguuuc accauguuag ccgggauggu cuugaucucc ugaccucaug auccacccac   2940

cucagccucc caaaguguug ggauuacagg cgugagccac ugcgcccggg caagaccuuu   3000

uuuuaaaaaa aaaaaaaaaa aaacuuccau ucuuucuucc uccagucugu ucucacauaa   3060

cagaguaguu uugguuuuua auuuuuuuug guuguuugcu guuuuuuguu uuuuaaggug   3120

aguucucacu auguuucuca gacuggucuc gaacuccugg ccucaagcca ucuucccgcc   3180

ucagccucuc aaauagcugg gcuuacaggc augagccacc acaccuggcc aggauuuggu   3240

uguuuaaaua uaaaucugau cacccccccug cuuagaaccc uucugcuuuc uauuaccccu   3300

cauuuaaaau guaaacucuu caccuugguu uaugagaacu gguucuugcc uuccccuuga   3360

accucauuaa augguagauuu cuugcuaagc uccagcccga gugguucucc cucagcuucu   3420

aauuuugugc ucuuuccugc ccuuuuccug ggccuucuca gcucuccacc cccaccacuc   3480

uugacucagg ugguguccuu cuuccucaag ucuugacaau ucccgggccc uucaguccccu   3540

gagcagucua cuucuguguc ugucaccaca ucuugucuuu uccccucauu gcauuuauug   3600

caguuuauau auaugcuacu uuuacuuguu cauuucuguc uccccuacca ggcuguaaau   3660

gagggcagaa accuuguuug uuuuauucac caucauguac caagugcuug gcacauagug   3720

ggccuucauu aaauguuugu ugaauaaaag agggaagaag gcaagccaac cuuagcuaca   3780

auccuaccuu uugauaaaau guuccuuuug acaauauaca cggauuauua uuuguacuuu   3840

guuuuuccau guguuuugcu uuuauccacu ggcauuuuua gcuccuugaa gacauaucau   3900

gugugagaua acuuccuuca caucucccau ggucccuagc aaaaugcuag gccuguagua   3960

gucaaggugc ucaauaaaua uuuguuuggg ugguuuguga gccuugcugc caaguccugc   4020

cuuugggucg acauaguaug gaaguauuug agagagagaa ccuuuccacu cccacugcca   4080

ggauuuugua uugccaucgg gugccaaaua aaugcucaua uuuauuaaaa aaaaaaaaaa   4140

aaaaa                                                               4145
```

<210> SEQ ID NO 13

-continued

<211> LENGTH: 3927
<212> TYPE: RNA
<213> ORGANISM: HUMAN

<400> SEQUENCE: 13
gggugcccug gugugugggc gcggcagggc gcaggcgcag gcgcagugug cguccgcguc 60
ugaggggagg gauguggggg aagcgacggc ccccgguuug uuugggcugu gggcggugcg 120
cagcggagag cccgggaaaa gcgggaaaug gcggcgccga gcgcggggguc uugguccacc 180 uuccagcaca aggagcugau ggccgcugac aggggacgca ggauauuggg agugugugggc 240 augcauccuc aucaucagga aacucuaaaa aagaaccgag uggugcuagc caaacagcug 300
uuguugagcg aauuguuaga acaucuucug gagaaggaca ucaucaccuu ggaaaugagg 360
gagcucaucc aggccaaagu gggcaguuuc agccagaaug uggaacuccu caacuugcug 420
ccuaagaggg guccccaagc uuuugaugcc uucugugaag ccuugcacuc cugaauuuua 480
ucaaacacac uuccagcugg cauauagguu gcagucucgg ccucguggcc uagcacuggu 540
guugagcaau gugcacuuca cuggagagaa agaacuggaa uuucgcucug gaggggaugu 600
ggaccacagu acucuaguca cccucuucaa gcuuuugggc uaugacgucc auguucuaug 660
ugaccagacu gcacaggaaa ugcaagagaa acugcagaau uuugcacagu uaccugcaca 720
ccgagucacg gacuccugca ucguggcacu ccucucgcau ggugugggagg gcgccaucua 780 uggugugggau gggaaacugc uccagcucca agagguuuuu cagcucuuug acaacgccaa 840
cugcccaagc cuacagaaca aaccaaaaau guucuucauc caggccugcc guggagauga 900
gacugaucgu gggguugacc aacaagaugg aaagaaccac gcaggauccc cugggugcga 960
ggagagugau gccgguaaag aaaaguugcc gaagaugaga cugcccacgc gcucagacau 1020
gauaugcggc uaugccugcc ucaaagggac ugccgccaug cggaacacca aacgagguuc 1080
cugguacauc gaggcucuug cucaagugu uucugagcgg gcuugugaua ugcacguggc 1140
cgacaugcug guuaagguga acgcacuuau caaggaucgg gaagguuaug cuccuggcac 1200
agaauuccac cggugcaagg agaugucuga auacugcagc acucugugcc gccaccucua 1260
ccuguuccca ggacacccuc ccacaugaug ucaccucccc aucauccacg ccaaguggaa 1320
gccacuggac cacaggaggu gugauagagc cuuugaucuu caggaugcac gguuucuguu 1380
cugcccccuc agggaugugg gaaucuccca gacuuguuuc cugugcccau caucucugcc 1440
uuugagugug ggacuccagg ccagcuccuu uucugugaag cccuuugccu guagagccag 1500
ccuugguugg accuauugcc aggaauguuu cagcugcagu ugaagagccu gacaagugaa 1560
guuguaaaca cagugugguu auggggagag ggcauauaaa uuccccauau uuguguucag 1620
uuccagcuuu uguagauggc acuuuaguga uugcuuuuau uacauuaguu aagaugucug 1680
agagaccauc uccuaucuuu uauuucauuc auauccuccg cccuuuuugu ccuagaguga 1740
gaguuuggaa ggguguccaaa uuuaauguag acauuaucuu uuggcucuga agaagcaaac 1800
augacuagag acgcaccuug cugcaguguc cagaagcggc cugugcguuc ccuucaguac 1860
ugcagcgcca cccaguggaa ggacacucuu ggcucguuug ggcucaaggc accgcagccu 1920
gucagccaac auugccuugc auuuguaccu uauugaucuu ugcccaugga agucucaaag 1980
aucuuucguu gguuguuucu cugagcuuug uuacugaaau gagccucgug gggagcauca 2040
gagaaggcca ggaagaaugg uguguuuccc uagacucugu aaccaccucu cugucuuuuu 2100
ccuuccugag aaacguccau cucucucccu uacuauuccc acuuucauuc aaucaaccug 2160
cacuucauau cuagauuucu agaaaagcuu ccuagcuuau cucccugcuu cauaucucuc 2220

-continued

```
ccuucuuuac cuucauuuca uccuguuggc ugcugccacc aaaucugucu agaauccugc   2280

uuuacaggau cauguaaaug cucaaagaug uaauguaguu cuuuguuccu gcuuucucuu   2340

ucaguauuaa acucuccuuu gauauuaugu ggcuuuuauu ucagugccau acauguuauu   2400

guuuucaacc uagaaaccuu uaucccugcu uaucugaaac uucccaacuu cccuguucuu   2460

uaagacuuuu uuuuuuuuuu uuuuuuuuuu ugagacagag ucucgcucug ucgcccaggc   2520

uggagggcag uggcacgauc ucagcucacu gcaagcucca acucccgggu ucacgccauu   2580

cuccugccuc agccuuccaa guagcuggga cuacaggugc ccgccaccgu gcccggcuaa   2640

uuuuuuugua uuuuuaguag agacaggguu ucaccauguu agccgggaug gucuugaucu   2700

ccugaccuca ugauccaccc accucagccu cccaaagugu ugggauuaca ggcgugagcc   2760

acugcgcccg ggcaagaccu uuuuuuaaaa aaaaaaaaaa aaaaacuucc auucuuucuu   2820

ccuccagucu guucucacau aacagaguag uuuugguuuu uaauuuuuuu ugguuguuug   2880

cuguuuuuug uuuuuuaagg ugaguucuca cuauguuucu cagacugguc ucgaacuccu   2940

ggccucaagc caucuucccg ccucagccuc ucaaauagcu gggcuuacag gcaugagcca   3000

ccacaccugg ccaggauuug guuguuuaaa uauaaaucug aucacccccc ugcuuagaac   3060

ccuucugcuu ucuauuaccc cucauuuaaa auguaaacuc uucaccuugg uuuaugagaa   3120

cugguucuug ccuuccccuu gaaccucauu aaauggugau uucuugcuaa gcuccagccc   3180

gaguggucuc cucucagcuu cuaauuuugu gcucuuuccu gcccuuuucc ugggccuucu   3240

cagcucucca cccccaccac ucuugacuca gguggugucc uucuuccuca agucuugaca   3300

auucccgggc ccuucagucc cugagcaguc uacuucugug ucugucacca caucuugucu   3360

uuuccccuca uugcauuuau ugcaguuuau auauaugcua cuuuuacuug uucauuucug   3420

ucuccccuac caggcuguaa augagggcag aaaccuuguu uguuuuauuc accaucaugu   3480

accaagugcu uggcacauag ugggccuuca uuaaauguuu guugaauaaa agagggaaga   3540

aggcaagcca accuuagcua caauccuacc uuuugauaaa auguuccuuu ugacaauaua   3600

cacggauuau uauuuguacu uuguuuuucc auguguuuug cuuuuaucca cuggcauuuu   3660

uagcuccuug aagacauauc augugugaga uaacuuccuu cacaucuccc auggucccua   3720

gcaaaaugcu aggccuguag uagucaaggu gcucaauaaa uauuuguuug ggugguuugu   3780

gagccuugcu gccaaguccu gccuuugggu cgacauagua uggaaguauu ugagagagag   3840

aaccuuucca cucccacugc caggauuuug uauugccauc gggugccaaa uaaaugcuca   3900

uauuuauuaa aaaaaaaaaa aaaaaaa                                       3927
```

<210> SEQ ID NO 14
<211> LENGTH: 2044
<212> TYPE: RNA
<213> ORGANISM: HUMAN

<400> SEQUENCE: 14

```
caaagacaaa auaauuuacu agggaagccc uuacuaacga cccaacaucc agacacaggu     60

gagggagaag aaauuuccug acagccgaag agcaacaagu aucaugaugg ggugcuggau    120

uuugaaugag ggucucucca ccauauuagu acucucaugg cugggaauaa auuuuuaucu    180

guuuauugac acguucuacu gguaugaaga ggaggagucu uuccauuaca cacgaguuau    240

uuuggguuca acacuggcuu gggcacgagc auccgcacug ugccugaauu uuaacugcau    300

gcuaauucua auaccuguca gucgaaaccu uauuucauuc auaagaggaa caaguauuug    360

cugcagagga ccguggagga ggcaauuaga caaaaaccuc agauuucaca aacuggucgc    420
```

-continued

```
cuaugggaua gcuguuaaug caaccaucca caucguggcg cauuucuuca accuggaacg    480

cuaccacugg agccaguccg aggaggccca gggacuucug gccgcacuuu ccaagcuggg    540

caacaccccu aacgagagcu accucaaccc uguccggacc uuccccacaa acacaaccac    600

ugaauugcua aggacaauag caggcgucac cggucuggug aucucucugg cuuuagucuu    660

gaucaugacc ucgucaacug aguucaucag acaggccucc uaugaguugu ucugguacac    720

acaccauguu uucaucgucu ucuuucucag ccuggccauc caugggacgg gucggauugu    780

ucgaggccaa acccaagaca gucucucucu gcacaacauc accuucugua gagaccgcua    840

ugcagaaugg cagacagugg cccaaugccc cgugccucaa uuuucuggca aggaacccuc    900

ggcuuggaaa uggauuuuag gcccuguggu cuuguaugca ugugaaagaa uaauuagguu    960

cuggcgauuu caacaagaag uugucauuac caagguggua agccaccccu cuggaguccu   1020

ggaacuucac augaaaaagc guggcuuuaa aauggcgcca gggcaguaca ucuuggugca   1080

gugcccagcc auaucuucgc uggaguggca ccccuucacc cuuaccucug ccccccagga   1140

ggacuuuuuc agcgugcaca uccgggcagc aggagacugg acagcagcgc uacuggaggc   1200

cuuuggggca gagggacagg cccuccagga gcccuggagc cugccaaggc uggcagugga   1260

cgggcccuuu ggaacugccc ugacagaugu auuucacuac ccagugugug ugugcguugc   1320

cgcggggauc ggagucacuc ccuucgcugc ucuucugaaa ucuauauggu acaaaugcag   1380

ugaggcacag accccacuga agcugagcaa gguguauuuc uacuggauuu gccgggaugc   1440

aagagcuuuu gagugguuug cugaucucuu acucucccug gaaacacgga ugagugagca   1500

ggggaaaacu cacuuucuga guuaucauau auuucuuacc ggcugggaug aaaaucaggc   1560

ucuucacaua gcuuuacacu gggacgaaaa uacugacgug auuacaggcu uaaagcagaa   1620

gaccuucuau gggaggccca acuggaacaa ugaguucaag cagauugccu acaaucaccc   1680

cagcagcagu auuggcgugu ucuucugugg accuaaagcu cucucgagga cacuucaaaa   1740

gaugugccac uuguauucau cagcugaccc cagagguguu cauuucuauu acaacaagga   1800

gagcuucuag acuuuggagg ucaaguccag gcauuguguu uucaaucaag uuauugauuc   1860

caaagaacuc caccaggaau uccugugacg gccuguugau augagcuccc aguugggaac   1920

uggugaauaa uaauuaacua uugugaacag uacacuauac cauacuuccu uagcuuauaa   1980

auaacauguc auauacaaca gaacaaaaac auuuacugaa auuaaaauau auuauguuuc   2040

ucaa                                                                2044
```

<210> SEQ ID NO 15
<211> LENGTH: 716
<212> TYPE: RNA
<213> ORGANISM: HUMAN

<400> SEQUENCE: 15

```
gaaacuuggu guccagggga ggcccccggc ggcuggagcg cggcggcagc gggcgcagag     60

gccggaggga gaggaggcga ggggcggccc gagcgcgggg cgggagcgag gccagcgguc    120

augugcccgu gcccccugca ccgcggccgc ggcccccccgg ccgugugcgc cugcagcgcg    180

ggucgccugg ggcugcgcuc guccgccgcg cagcucaccg ccgcccggcu caaggcgcua    240

ggcgacgagc ugcaccagcg caccaugugg cggcgccgcg cgcggagccg gagggcgccg    300

gcgcccggcg cgcuccccac cuacuggccu uggcugugcg cggccgcgca gguggcggcg    360

cuggcggccu ggcugcucgg caggcggaac uuguaggaac gcggggcuuc uuggugggc    420

cggagccgag acccagccgg agcgagcaac agguugguga aaacccugug uccuuggaga    480
```

```
aagcugguuc ccguuuucca gagggggagc ccagagcuug aaaggccgcg guuggcacuu    540

cgagaaggaa guggagagua aagacagcgc cuggagcgau cguagaaaca cagaauggga    600

cuggggaagc ccuuuggaaa uccagcugca gaaacagaca ccccaaugcu auuuacauac    660

agcucuauau auauaaaaaa agaaaauaug aauauuaaaa aaaaaaaaaa aaaaaa        716
```

<210> SEQ ID NO 16
<211> LENGTH: 1163
<212> TYPE: RNA
<213> ORGANISM: HUMAN

<400> SEQUENCE: 16

```
ccggcggcgc cucaggucgc ggggcgccua ggccuggguu guccuuugca ucugcacgug     60

uucgcagucg uuuccgcgau gcugccucug cugcgcugcg ugccccgugu gcugggcucc    120

uccgucgccg gccuccgcgc ugccgcgccc gccucgccuu uccggcagcu ccugcagccg    180

gcaccccggc ugugcacccg gcccuucggg cugcucagcg ugcgcgcagg uuccgagcgg    240

cggccgggcc uccugcggcc ucgcggaccc ugcgccugug gcuguggcug cggcucgcug    300

cacaccgacg gagacaaagc uuuuguugau uuccugagug augaaauuaa ggaggaaaga    360

aaaauucaga agcauaaaac ccucccuaag augucuggag guugggagcu ggaacugaau    420

gggacagaag cgaaauuagu gcggaaaguu gccggggaaa aaaucacggu cacuuucaac    480

auuaacaaca gcaucccacc aacauuugau ggugaggagg aacccucgca agggcagaag    540

guugaagaac aggagccuga acugacauca acucccaauu ucgugguuga aguuauaaag    600

aaugaugaug gcaagaaggc ccuuguguug gacugucauu auccagagga ugagguugga    660

caagaagacg aggcugagag ugacaucuuc ucuaucaggg aaguuagcuu ucaguccacu    720

ggcgagucug aauggaagga uacuaauuau acacucaaca cagauuccuu ggacugggcc    780

uuauaugacc accuaaugga uuuccuugcc gaccgagggg uggacaacac uuuugcagau    840

gagcuggugg agcucagcac agcccuggag caccaggagu acauuacuuu ucuugaagac    900

cucaagaguu uugucaagag ccaguagagc agacagaugc ugaaagccau aguuucaugg    960

caggcuuugg ccagugaaca aauccuacuc ugaagcuaga caugugcuuu gaaaugauua   1020

ucauccuaau aucauggggg aaaaaauacc aaauuuaaau uauauguuuu guguucucau   1080

uuauuaucau uuuuuucugu acaaaucuau uauuucuaga uuuuuguaua acaugauaga   1140

cauaaaauug guuuaucucc ucc                                           1163
```

<210> SEQ ID NO 17
<211> LENGTH: 1535
<212> TYPE: RNA
<213> ORGANISM: HUMAN

<400> SEQUENCE: 17

```
ccuccgcuca guccgggagc gcacgugggc cgcggcgcuc cgaccuccgc uuucccaccg     60

cccgcagcug aagcacaucc cgcagcccgg cgcggacucc gaucgccgca guugcccucu    120

ggcgccaugu cgcagaacgg agcgcccggg augcaggagg agagccugca gggcuccugg    180

guagaacugc acuucagcaa uaaugggaac gggggcagcg uuccagccuc gguuucuauu    240

uauaauggag acauggaaaa aauacugcug gacgcacagc augagucugg acggaguagc    300

uccaagagcu cucacuguga cagcccaccu cgcucgcaga caccacaaga uaccaacagg    360

gcuucugaaa cagauaccca uagcauugga gagaaaaaca gcucacaguc ugaggaagau    420

gauauugaaa gaaggaaaga aguugaaagc aucuugaaga aaaacucaga uuggauaugg    480
```

gauuggucaa gucggccgga aaauauuccc cccaaggagu uccucuuuaa acacccgaag 540
cgcacggcca cccucagcau gaggaacacg agcgucauga agaaaggggg cauauucucu 600
gcagaauuuc ugaaaguuuu ccuuccaucu cugcugcucu cucauuugcu ggccaucgga 660
uuggggaucu auauuggaag gcgucugaca accuccacca gcaccuuuug augaagaacu 720
ggagucugac uugguucguu aguggauuac uucugagcuu gcaacauagc ucacugaaga 780
gcuguuagau ccuggggugg ccacgucacu uguguuuauu uguucuguaa augcugcguu 840
ccuaauuuag uaaaauaaaa gaauagacac uaaaaucaug uugaucuaua auuacaccua 900
ugggaucaau aagcauguca gacugauuaa ugucuacugu gaaaauuugg uaguaaauuu 960
ucauuugaua uuagauauaa auaucugaau auaaauaauu uuaauauacu agucaugaug 1020 uguuguuguau uuuaaaaauu aucugcaacc uuaauucagc ugaaguacuu uauauuucaa 1080
aagaaugaau aacauugaua auaaaaucgc uacuuuaagg gguuugucca aaauaaauau 1140
uguggccuua uauaucacac uauuguagaa aguauuauuu aauuuaaaug gaugcagguu 1200
gucuacuaaa gaaagauuau auauaacuau gcuaauuguu cauaaucaac agaaaccaag 1260
auagagcuac aaacucagcu guacaguucg uacacuaaac ucuucuugcu uuugcauuau 1320
aaggaauuaa gucuccgauu auuaggugau cacccuggau gaucaguuuu cugcugaagg 1380
caccuacuca guaucuuuuc cucuuuauca cucugcauug gugaauuuaa uccucuccuu 1440
uguguucaac uuuugugugc uuuuaaaauc agcuuuauuc uaagcaaauc ugugucuacu 1500
uuaaaaaacu ggaaauggaa aaaaaaauaa aucuu 1535

<210> SEQ ID NO 18
<211> LENGTH: 1417
<212> TYPE: RNA
<213> ORGANISM: HUMAN

<400> SEQUENCE: 18
auuaauugcu ugccaucaug agcagaagca agcgugacaa caauuuuuau aguguagaga 60
uuggagauuc uacauucaca guccugaaac gauaucagaa uuuaaaaccu auaggcucag 120
gagcucaagg aauaguaugc gcagcuuaug augccauucu ugaaagaaau guugcaauca 180
agaagcuaag ccgaccauuu cagaaucaga cucaugccaa gcgggccuac agagagcuag 240
uucuuaugaa auguguuaau cacaaaaaua uaauuggccu uuugaauguu uucacaccac 300
agaaaucccu agaagaauuu caagauguuu acauagucau ggagcucaug gaugcaaauc 360
uuugccaagu gauucagaug gagcuagauc augaaagaau guccuaccuu cucuaucaga 420 ugcuguguggg aaucaagcac cuucauucug cuggaauuau ucaucgggac uuaaagccca 480
guaauauagu aguaaaaucu gauugcacuu ugaagauucu ugacuucggu cuggccagga 540
cugcaggaac gaguuuuaug augacgccuu auguagugac ucgcuacuac agagcacccg 600
aggucauccu uggcaugggc uacaaggaaa acguggauuu auggucugug ggugcauua 660 ugggagaaau gguuugccac aaaauccucu uuccaggaag ggacuauauu gaucagugga 720
auaaaguuau ugaacagcuu ggaacaccau guccugaauu caugaagaaa cugcaaccaa 780
caguaaggac uuacguugaa aacagaccua aauaugcugg auauagcuuu gagaaacucu 840
ucccugaugu ccuuuuccca gcugacucag aacacaacaa acuuaaagcc agucaggcaa 900
gggauuuguu auccaaaaug cugguaauag augcaucuaa aaggaucucu guagaugaag 960
cucuccaaca cccguacauc aaugucuggu augauccuuc ugaagcagaa gcuccaccac 1020
caaagauccc ugacaagcag uuagaugaaa gggaacacac aauagaagag uggaaagaau 1080

-continued ugauauauaa ggaaguuaug gacuuggagg agagaaccaa gaauggaguu auacgggggc 1140
agcccucucc uuuagcacag gugcagcagu gaucaauggc ucucagcauc caucaucauc 1200
gucgucuguc aaugaugugu cuucaauguc aacagauccg acuuuggccu cugauacaga 1260
cagcagucua gaagcagcag cugggccucu gggcugcugu agaugacuac uugggccauc 1320 ggggggug g agggaugggg agucgguuag ucauugauag aacuacuuug aaaacaauuc 1380
aguggucuua uuuuugggug auuuuucaaa aaaugua 1417

<210> SEQ ID NO 19
<211> LENGTH: 1412
<212> TYPE: RNA
<213> ORGANISM: HUMAN

<400> SEQUENCE: 19
auuaauugcu ugccaucaug agcagaagca agcgugacaa caauuuuuau aguguagaga 60
uuggagauuc uacauucaca guccugaaac gauaucagaa uuuaaaaccu auaggcucag 120
gagcucaagg aauaguaugc gcagcuuaug augccauucu ugaaagaaau guugcaauca 180
agaagcuaag ccgaccauuu cagaaucaga cucaugccaa gcgggccuac agagagcuag 240
uucuuaugaa auguguuaau cacaaaaaua uaauuggccu uuugaauguu uucacaccac 300
agaaaucccu agaagaauuu caagauguuu acauagucau ggagcucaug gaugcaaauc 360
uuugccaagu gauucagaug gagcuagauc augaaagaau guccuaccuu cucuaucaga 420
ugcugugugg aaucaagcac cuucauucug cuggaauuau ucaucgggac uuaaagccca 480
guaauauagu aguaaaaucu gauugcacuu ugaagauucu ugacuucggu cuggccagga 540
cugcaggaac gaguuuuaug augacgccuu auguagugac ucgcuacuac agagcacccg 600
aggucauccu uggcaugggc uacaaggaaa acguggauuu auggucugug gggugcauua 660
ugggagaaau gguuugccac aaaauccucu uuccaggaag ggacuauauu gaucagugga 720
auaaaguuau ugaacagcuu ggaacaccau guccugaauu caugaagaaa cugcaaccaa 780
caguaaggac uuacguugaa aacagaccua aauaugcugg auauagcuuu gagaaacucu 840
ucccugaugu ccuuuuccca gcugacucag aacacaacaa acuuaaagcc agucaggcaa 900
gggauuuguu auccaaaaug cugguaauag augcaucuaa aaggaucucu guagaugaag 960
cucuccaaca cccguacauc aaugucuggu augauccuuc ugaagcagaa gcuccaccac 1020
caaagauccc ugacaagcag uuagaugaaa gggaacacac aauagaagag uggaaagaau 1080
ugauauauaa ggaaguuaug gacuuggagg agagaaccaa gaauggaguu auacgggggc 1140
agcccucucc uuuaggugca gcagugauca auggcucuca gcauccauca ucaucgucgu 1200
cugucaauga ugugucuuca augucaacag auccgacuuu ggccucugau acagacagca 1260
gucuagaagc agcagcuggg ccucugggcu gcuguagaug acuacuuggg ccaucggggg 1320
gugggaggga uggggagucg guuagucauu gauagaacua cuuugaaaac aauucagugg 1380
ucuuauuuuu gggugauuuu ucaaaaaaug ua 1412

<210> SEQ ID NO 20
<211> LENGTH: 1417
<212> TYPE: RNA
<213> ORGANISM: HUMAN

<400> SEQUENCE: 20
auuaauugcu ugccaucaug agcagaagca agcgugacaa caauuuuuau aguguagaga 60
uuggagauuc uacauucaca guccugaaac gauaucagaa uuuaaaaccu auaggcucag 120
gagcucaagg aauaguaugc gcagcuuaug augccauucu ugaaagaaau guugcaauca 180
agaagcuaag ccgaccauuu cagaaucaga cucaugccaa gcgggccuac agagagcuag 240
uucuuaugaa auguguuaau cacaaaaaua uaauuggccu uuugaauguu uucacaccac 300
agaaaucccu agaagaauuu caagauguuu acauagucau ggagcucaug gaugcaaauc 360
uuugccaagu gauucagaug gagcuagauc augaaagaau guccuaccuu cucuaucaga 420
ugcugugugg aaucaagcac cuucauucug cuggaauuau ucaucgggac uuaaagccca 480
guaauauagu aguaaaaucu gauugcacuu ugaagauucu ugacuucggu cuggccagga 540
cugcaggaac gaguuuuaug augacgccuu auguagugac ucgcuacuac agagcacccg 600
aggucauccu uggcaugggc uacaaggaaa acguugacau uuggucaguu gggugcauca 660
ugggagaaau gaucaaaggu gguguuuugu ucccagguac agaucauauu gaucagugga 720
auaaaguuau ugaacagcuu ggaacaccau guccugaauu caugaagaaa cugcaaccaa 780
caguaaggac uuacguugaa aacagaccua aauaugcugg auauagcuuu gagaaacucu 840
ucccugaugu ccuuuuccca gcugacucag aacacaacaa acuuaaagcc agucaggcaa 900
gggauuuguu auccaaaaug cugguaauag augcaucuaa aaggaucucu guagaugaag 960
cucuccaaca cccguacauc aaugucuggu augauccuuc ugaagcagaa gcuccaccac 1020
caaagauccc ugacaagcag uuagaugaaa gggaacacac aauagaagag uggaaagaau 1080
ugauauauaa ggaaguuaug gacuuggagg agagaaccaa gaauggaguu auacgggggc 1140
agcccucucc uuuagcacag gugcagcagu gaucaauggc ucucagcauc caucaucauc 1200
gucgucuguc aaugaugugu cuucaauguc aacagauccg acuuuggccu cugauacaga 1260
cagcagucua gaagcagcag cugggccucu gggcugcugu agaugacuac uugggccauc 1320 ggggggu ggg agggaugggg agucgguuag ucauugauag aacuacuuug aaaacaauuc 1380
aguggucuua uuuuugggug auuuuucaaa aaaugua 1417

<210> SEQ ID NO 21
<211> LENGTH: 1412
<212> TYPE: RNA
<213> ORGANISM: HUMAN

<400> SEQUENCE: 21
auuaauugcu ugccaucaug agcagaagca agcgugacaa caauuuuuau aguguagaga 60
uuggagauuc uacauucaca guccugaaac gauaucagaa uuuaaaaccu auaggcucag 120
gagcucaagg aauaguaugc gcagcuuaug augccauucu ugaaagaaau guugcaauca 180
agaagcuaag ccgaccauuu cagaaucaga cucaugccaa gcgggccuac agagagcuag 240
uucuuaugaa auguguuaau cacaaaaaua uaauuggccu uuugaauguu uucacaccac 300
agaaaucccu agaagaauuu caagauguuu acauagucau ggagcucaug gaugcaaauc 360
uuugccaagu gauucagaug gagcuagauc augaaagaau guccuaccuu cucuaucaga 420
ugcugugugg aaucaagcac cuucauucug cuggaauuau ucaucgggac uuaaagccca 480
guaauauagu aguaaaaucu gauugcacuu ugaagauucu ugacuucggu cuggccagga 540
cugcaggaac gaguuuuaug augacgccuu auguagugac ucgcuacuac agagcacccg 600
aggucauccu uggcaugggc uacaaggaaa acguugacau uuggucaguu gggugcauca 660
ugggagaaau gaucaaaggu gguguuuugu ucccagguac agaucauauu gaucagugga 720
auaaaguuau ugaacagcuu ggaacaccau guccugaauu caugaagaaa cugcaaccaa 780
caguaaggac uuacguugaa aacagaccua aauaugcugg auauagcuuu gagaaacucu 840

-continued

```
ucccugaugu ccuuuuccca gcugacucag aacacaacaa acuuaaagcc agucaggcaa    900
gggauuuguu auccaaaaug cugguaauag augcaucuaa aaggaucucu guagaugaag    960
cucuccaaca cccguacauc aaugucuggu augauccuuc ugaagcagaa gcuccaccac   1020
caaagauccc ugacaagcag uuagaugaaa gggaacacac aauagaagag uggaaagaau   1080
ugauauauaa ggaaguuaug gacuuggagg agagaaccaa gaauggaguu auacgggggc   1140
agcccucucc uuuaggugca gcagugauca auggcucuca gcauccauca ucaucgucgu   1200
cugucaauga ugugucuuca augucaacag auccgacuuu ggccucugau acagacagca   1260
gucuagaagc agcagcuggg ccucugggcu gcuguagaug acuacuuggg ccaucggggg   1320
gugggaggga uggggagucg guuagucauu gauagaacua cuuugaaaac aauucagugg   1380
ucuuauuuuu gggugauuuu ucaaaaaaug ua                                 1412
```

<210> SEQ ID NO 22
<211> LENGTH: 4353
<212> TYPE: RNA
<213> ORGANISM: HUMAN

<400> SEQUENCE: 22

```
uucucucacg aagccccgcc cgcggagagg uuccauauug gguaaaaucu cggcucucgg     60
agagucccgg gagcuguucu cgcgagagua cugcgggagg cucccguuug cuggcucuug    120
gaaccgcgac cacuggagcc uuagcgggcg cagcagcugg aacgggagua cugcgacgca    180
gcccggaguc ggccuuguag gggcgaaggu gcagggagau cgcggcgggc gcagucuuga    240
gcgccggagc gcgucccugc ccuuagcggg gcuugcccca gucgcagggg cacauccagc    300
cgcugcggcu gacagcagcc gcgcgcgcgg gagucugcgg ggucgcggca gccgcaccug    360
cgcgggcgac cagcgcaagg uccccgcccg gcugggcggg cagcaagggc cggggagagg    420
gugcgggugc aggcgggggc cccacagggc caccuucuug cccggcggcu gccgcuggaa    480
aaugucucag gagaggccca cguucuaccg gcaggagcug aacaagacaa ucugggaggu    540
gcccgagcgu uaccagaacc ugucuccagu gggcucuggc gccuauggcu cugugugugc    600
ugcuuuugac acaaaaacgg gguuacgugu ggcagugaag aagcucucca gaccauuuca    660
guccaucauu caugcgaaaa gaaccuacag agaacugcgg uuacuuaaac auaugaaaca    720
ugaaaaugug auuggucugu uggacguuuu uacaccugca aggucucugg aggaauucaa    780
ugauguguau cuggugaccc aucucauggg ggcagaucug aacaacauug ugaaauguca    840
gaagcuuaca gaugaccaug uucaguuccu uaucuaccaa auucuccgag gucuaaagua    900
uauacauuca gcugacauaa uucacaggga ccuaaaaccu aguaaucuag cugugaauga    960
agacugugag cugaagauuc uggauuuugg acuggcucgg cacacagaug augaaaugac   1020
aggcuacgug gccacuaggu gguacagggc uccugagauc augcugaacu ggaugcauua   1080
caaccagaca guugauauuu ggucaguggg augcauaaug gccgagcugu ugacuggaag   1140
aacauuguuu ccugguacag accauauuga ucaguugaag cucauuuuaa gacucguugg   1200
aaccccaggg gcugagcuuu ugaagaaaau cuccucagag ucugcaagaa acuauauuca   1260
gucuuugacu cagaugccga agaugaacuu ugcgaaugua uuuauuggug ccaaucccu    1320
ggcugucgac uugcuggaga agaugcuugu auuggacuca gauaagagaa uuacagcggc   1380
ccaagcccuu gcacaugccu acuuugcuca guaccacgau ccugaugaug aaccaguggc   1440
cgauccuuau gaucaguccu uugaaagcag ggaccuccuu auagaugagu ggaaaagccu   1500
gaccuaugau gaagucauca gcuuugugcc accaccccuu gaccaagaag agauggaguc   1560
```

-continued

```
cugagcaccu gguuucuguu cuguugaucc cacuucacug ugaggggaag gccuuuucac   1620
gggaacucuc caaauauuau ucaagugccu cuuguugcag agauuucccuc cauggugggaa   1680
gggggugugc gugcgugugc gugcguguua gugugugugc augugugugu cugucuuugu   1740
gggaggguaa gacaauauga acaaacuaug aucacaguga cuuuacagga gguuguggau   1800
gcuccagggc agccuccacc uugcucuucu uucugagagu uggcucaggc agacaagagc   1860
ugcuguccuu uuaggaauau guucaaugca aaguaaaaaa auaugaauug uccccaaucc   1920
cggucaugcu uuugccacuu uggcuucucc ugugacccca ccuugacggu ggggcguaga   1980
cuugacaaca ucccacagug gcacggagag aaggcccaua ccuucugguu gcuucagacc   2040
ugacaccguc ccucagugau acguacagcc aaaaaggacc aacuggcuuc ugugcacuag   2100
ccugugauua acuugcuuag uaugguucuc agaucuugac aguauauuug aaacuguaaa   2160
uauguuugug ccuuaaaagg agagaagaaa guguagauag uuaaaagacu gcagcugcug   2220
aaguucugag ccgggcaagu cgagagggcu guuggacagc ugcuugugg cccggaguaa   2280
ucaggcagcc uucauaggcg gucaugugug caugugagca caugcguaua ugugcgucuc   2340
ucuuucuccc ucaccccag guguugccau uucucugcuu acccuucacc uuuggugcag   2400
agguuucuug aauaucugcc ccaguaguca gaagcagguu cuugauguca uguacuuccu   2460
guguacucuu uauuucuagc agagugagga uguguuuugc acgucuugcu auuugagcau   2520
gcacagcugc uuguccugcu cucuucagga ggcccuggug ucaggcaggu uugccaguga   2580
agacuucuug gguaguuuag aucccauguc accucagcug auauuauggc aagugauauc   2640
accucucuuc agccccuagu gcuauucugu guugaacaca auugauacuu caggugcuuu   2700
ugaugugaaa aucaugaaaa gaggaacagg uggauguaua gcauuuuuau ucaugccauc   2760
uguuuucaac caacuauuuu ugaggaauua ucaugggaaa agaccagggc uuuucccagg   2820
aauaucccaa acuucggaaa caaguuauuc ucuucacucc caauaacuaa ugcuaagaaa   2880
ugcugaaaau caaaguaaaa aauuaaagcc cauaaggcca gaaacuccuu uugcugucuu   2940
ucucuaaaua ugauuacuuu aaaauaaaaa aguaacaagg ugucuuuucc acuccuaugg   3000
aaaagggucu ucuuggcagc uuaacauuga cuucuugguu uggggagaaa uaaauuuugu   3060
uucagaauuu uguauauugu aggaauccuu ugagaaugug auuccuuuug augggggagaa   3120
agggcaaauu auuuuaauau uuuguauuuu caacuuuaua aagauaaaau auccucaggg   3180
guggagaagu gucguuuuca uaacuugcug aauuucaggc auuuuguucu acaugaggac   3240
ucauauauuu aagccuuuug uguaaauaaga aaguauaaag ucacuuccag uguuggcugu   3300
gugacagaau cuuguauuug ggccaaggug uuuccauuuc ucaaucagug cagugauaca   3360
uguacuccag agggacaggg uggaccccu gagucaacug gagcaagaag gaaggaggca   3420
gacugauggc gauucccucu cacccgggac ucuccccuu ucaaggaaag ugaaccuuua   3480
aaguaaaggc cucaucuccu uuauugcagu ucaaauccuc accauccaca gcaagaugaa   3540
uuuuaucagc cauguuuggu uguaaaugcu cgugugauuu ccuacagaaa uacugcucug   3600
aauauuuugu aauaaagguc uuugcacaug ugaccacaua cguguuagga ggcugcaugc   3660
ucuggaagcc uggacucuaa gcuggagcuc uuggaagagc ucuucgguuu cugagcauaa   3720
ugcucccauc uccugauuuc ucugaacaga aaacaaaaga gagaaugagg gaaauugcua   3780
uuuuauuugu auucaugaac uuggcuguaa ucaguuaugc cguauaggau gucagacaau   3840
accacugguu aaaauaaagc cuauuuuuca aauuuaguga guuucucaag uuuauuauau   3900
uuuucucuug uuuuuauuua augcacaaua uggcauuaua ucaauauccu uuaaacugug   3960
```

accuggcaua cuugucugac agaucuuaau acuacuccua acauuuagaa aauguugaua 4020
aagcuucuua guuguacauu uuuuggugaa gaguauccag gucuuugcug uggaugggua 4080
aagcaaagag caaaugaacg aaguauuaag cauuggggcc ugucuuaucu acacucgagu 4140
guaagagugg ccgaaaugac agggcucagc agacuguggc cugagggcca aaucuggccc 4200
accaccuguu ugguguagcc ugcuaagaau ggcuuuuaca uuuuuaaaug guugggaaag 4260
aaaaaaaaag aaguaguaga uuuuguagca ugugauguaa guaauguaaa acuuaaauuc 4320
caguauccau aaauaaaguu uuaugagaac aga 4353

<210> SEQ ID NO 23
<211> LENGTH: 4274
<212> TYPE: RNA
<213> ORGANISM: HUMAN

<400> SEQUENCE: 23
uucucucacg aagccccgcc cgcggagagg uuccauauug gguaaaaucu cggcucucgg 60
agagucccgg gagcuguucu cgcgagagua cugcgggagg cucccguuug cuggcucuug 120
gaaccgcgac cacuggagcc uuagcgggcg cagcagcugg aacgggagua cugcgacgca 180
gcccggaguc ggccuuguag gggcgaaggu gcagggagau cgcggcgggc gcagucuuga 240
gcgccggagc gcgucccugc ccuuagcggg gcuugcccca gucgcagggg cacauccagc 300
cgcugcggcu gacagcagcc gcgcgcgcgg gagucugcgg ggucgcggca gccgcaccug 360
cgcgggcgac cagcgcaagg uccccgcccg gcugggcggg cagcaagggc cggggagagg 420
gugcgggugc aggcgggggc cccacagggc caccuucuug cccggcggcu gccgcuggaa 480
aaugucucag gagaggccca cguucuaccg gcaggagcug aacaagacaa ucugggaggu 540
gcccgagcgu uaccagaacc ugucuccagu gggcucuggc gccuauggcu cugugugugc 600
ugcuuuugac acaaaaacgg gguuacgugu ggcagugaag aagcucucca gaccauuuca 660
guccaucauu caugcgaaaa gaaccuacag agaacugcgg uuacuuaaac auaugaaaca 720
ugaaaaugug auuggucugu uggacguuuu uacaccugca aggucucugg aggaauucaa 780
ugauguguau cuggugaccc aucucauggg ggcagaucug aacaacauug ugaaauguca 840
gaagcuuaca gaugaccaug uucaguuccu uaucuaccaa auucuccgag gucuaaagua 900
uauacauuca gcugacauaa uucacaggga ccuaaaaccu aguaaucuag cugugaauga 960
agacugugag cugaagauuc uggauuuugg acuggcucgg cacacagaug augaaaugac 1020
aggcuacgug gccacuaggu gguacagggc uccugagauc augcugaacu ggaugcauua 1080
caaccagaca guugauauuu ggucaguggg augcauaaug gccgagcugu ugacuggaag 1140
aacauuguuu ccugguacag accauauuga ucaguugaag cucauuuuaa gacucguugg 1200
aaccccaggg gcugagcuuu ugaagaaaau cuccucagag ucucugucga cuugcuggag 1260
aagaugcuug uauuggacuc agauaagaga auuacagcgg cccaagcccu ugcacaugcc 1320
uacuuugcuc aguaccacga uccugaugau gaaccagugg ccgauccuua ugaucagucc 1380
uuugaaagca gggaccuccu uauagaugag uggaaaagcc ugaccuauga ugaagucauc 1440
agcuuugugc caccaccccu ugaccaagaa gagauggagu ccugagcacc ugguuucugu 1500
ucuguugauc ccacuucacu gugaggggaa ggccuuuuca cgggaacucu ccaaauauua 1560
uucaagugcc ucuuguugca gagauuuccu ccauggugga agggggugug cgugcgugug 1620
cgugcguguu agugugugug caugugugug ucugucuuug ugggagggua agacaauaug 1680
aacaaacuau gaucacagug acuuuacagg agguugugga ugcuccaggg cagccuccac 1740

-continued

```
cuugcucuuc uuucugagag uuggcucagg cagacaagag cugcuguccu uuuaggaaua   1800
uguucaaugc aaaguaaaaa aauaugaauu guccccaauc ccggucaugc uuuugccacu   1860
uuggcuucuc cugugacccc accuugacgg uggggcguag acuugacaac aucccacagu   1920
ggcacggaga gaaggcccau accuucuggu ugcuucagac cugacaccgu cccucaguga   1980
uacguacagc caaaaaggac caacuggcuu cugugcacua gccugugauu aacuugcuua   2040
guaugguucu cagaucuuga caguauauuu gaaacuguaa auauguuugu gccuuaaaag   2100
gagagaagaa aguguagaua guuaaaagac ugcagcugcu gaaguucuga gccgggcaag   2160
ucgagagggc uguuggacag cugcuugugg gcccggagua aucaggcagc cuucauaggc   2220
ggucaugugu gcaugugagc acaugcguau augugcgucu cucuuucucc cucacccccca   2280
gguguugcca uuucucugcu uacccuucac cuuuggugca gagguuucuu gaauaucugc   2340
cccaguaguc agaagcaggu ucuugauguc auguacuucc uguguacucu uuauuucuag   2400
cagagugagg auguguuuug cacgucuugc uauuugagca ugcacagcug cuuguccugc   2460
ucucuucagg aggcccuggu gucaggcagg uuugccagug aagacuucuu ggguaguuua   2520
gaucccaugu caccucagcu gauauuaugg caagugauau caccucucuu cagccccuag   2580
ugcuauucug uguugaacac aauugauacu ucaggugcuu uugaugugaa aaucaugaaa   2640
agaggaacag guggauguau agcauuuuua uucaugccau cuguuuucaa ccaacuauuu   2700
uugaggaauu aucaugggaa aagaccaggg cuuuucccag gaauauccca aacuucggaa   2760
acaaguuauu cucuucacuc ccaauaacua augcuaagaa augcugaaaa ucaaaguaaa   2820
aaauuaaagc ccauaaggcc agaaacuccu uuugcugucu uucucuaaau augauuacuu   2880
uaaaauaaaa aaguaacaag gugucuuuuc cacuccuaug gaaaagggc uucuuggcag   2940
cuuaacauug acuucuuggu uuggggagaa auaaauuuug uuucagaauu uuguauauug   3000
uaggaauccu uugagaaugu gauuccuuuu gauggggaga aagggcaaau uauuuuaaua   3060
uuuuguauuu ucaacuuuau aaagauaaaa uauccucagg gguggagaag ugucguuuuc   3120
auaacuugcu gaauuucagg cauuuuguuc uacaugagga cucauauauu uaagccuuuu   3180
guguaauaag aaaguauaaa gucacuucca guguuggcug ugugacagaa ucuuguauuu   3240
gggccaaggu guuuccauuu cucaaucagu gcagugauac auguacucca gagggacagg   3300
guggaccccc ugagucaacu ggagcaagaa ggaaggaggc agacugaugg cgauucccuc   3360
ucacccggga cucuccccu uucaaggaaa gugaaccuuu aaaguaaagg ccucaucucc   3420
uuuauugcag uucaaauccu caccauccac agcaagauga auuuuaucag ccauguuugg   3480
uuguaaaugc ucgugugauu uccuacagaa auacugcucu gaauauuuug uaauaaaggu   3540
cuuugcacau gugaccacau acguguuagg aggcugcaug cucuggaagc cuggacucua   3600
agcuggagcu cuuggaagag cucuucgguu ucugagcaua augcucccau cucccugauuu   3660
cucugaacag aaaacaaaag agagaaugag ggaaauugcu auuuuauuug uauucaugaa   3720
cuuggcugua aucaguuaug ccguauagga ugucagacaa uaccacuggu uaaaauaaag   3780
ccuauuuuuc aaauuuagug aguuucucaa guuuauuaua uuuuucucuu guuuuuauuu   3840
aaugcacaau auggcauuau aucaauaucc uuuaaacugu gaccuggcau acuugucuga   3900
cagaucuuaa uacuacuccu aacauuuaga aaauguugau aaagcuucuu aguuguacau   3960
uuuuugguga agaguaucca ggucuuugcu guggaugggu aaagcaaaga gcaaaugaac   4020
gaaguauuaa gcauuggggc cugucuuauc uacacucgag uguaagagug gccgaaauga   4080
cagggcucag cagacugugg ccugagggcc aaaucuggcc caccaccugu uugguguagc   4140
```

cugcuaagaa uggcuuuuac auuuuuaaau gguugggaaa gaaaaaaaaa gaaguaguag 4200
auuuuguagc augugaugua aguaauguaa aacuuaaauu ccaguaucca uaaauaaagu 4260
uuuaugagaa caga 4274

<210> SEQ ID NO 24
<211> LENGTH: 4353
<212> TYPE: RNA
<213> ORGANISM: HUMAN

<400> SEQUENCE: 24
uucucucacg aagccccgcc cgcggagagg uuccauauug gguaaaaucu cggcucucgg 60
agagucccgg gagcuguucu cgcgagagua cugcgggagg cucccguuug cuggcucuug 120
gaaccgcgac cacuggagcc uuagcgggcg cagcagcugg aacgggagua cugcgacgca 180
gcccggaguc ggccuuguag ggcgaaggu gcagggagau cgcggcgggc gcagucuuga 240
gcgccggagc gcgucccugc ccuuagcggg gcuugcccca gucgcagggg cacauccagc 300
cgcugcggcu gacagcagcc gcgcgcgcgg gagucugcgg ggucgcggca gccgcaccug 360
cgcgggcgac cagcgcaagg uccccgcccg gcugggcggg cagcaagggc cggggagagg 420
gugcgggugc aggcgggggc cccacagggc caccuucuug cccggcggcu gccgcuggaa 480
aaugucucag gagaggccca cguucuaccg gcaggagcug aacaagacaa ucugggaggu 540
gcccgagcgu uaccagaacc ugucuccagu gggcucuggc gccuauggcu cugugugugc 600
ugcuuuugac acaaaaacgg gguuacgugu ggcagugaag aagcucucca gaccauuuca 660
guccaucauu caugcgaaaa gaaccuacag agaacugcgg uuacuuaaac auaugaaaca 720
ugaaaaugug auuggucugu uggacguuuu uacaccugca aggucucugg aggaauucaa 780
ugauguguau cuggugaccc aucucauggg ggcagaucug aacaacauug ugaaauguca 840
gaagcuuaca gaugaccaug uucaguuccu uaucuaccaa auucuccgag gucuaaagua 900
uauacauuca gcugacauaa uucacaggga ccuaaaaccu aguaaucuag cugugaauga 960
agacugugag cugaagauuc uggauuuugg acuggcucgg cacacagaug augaaaugac 1020
aggcuacgug gccacuaggu gguacagggc uccugagauc augcugaacu ggaugcauua 1080
caaccagaca guugauauuu ggucaguggg augcauaaug gccgagcugu ugacuggaag 1140
aacauuguuu ccugguacag accauauuaa ccagcuucag cagauuaugc gucugacagg 1200
aacacccccc gcuuaucuca uuaacaggau gccaagccau gaggcaagaa acuauauuca 1260
gucuuugacu cagaugccga agaugaacuu ugcgaaugua uuuauuggug ccaaucccu 1320 ggcugucgac uugcuggaga agaugcuugu auuggacuca gauaagagaa uuacagcggc 1380
ccaagcccuu gcacaugccu acuuugcuca guaccacgau ccugaugaug aaccagugc 1440 cgauccuuau gaucaguccu uugaaagcag ggaccuccuu auagaugagu ggaaaagccu 1500
gaccuaugau gaagucauca gcuuugugcc accaccccuu gaccaagaag agauggaguc 1560
cugagcaccu gguuucuguu cuguugaucc cacuucacug ugaggggaag gccuuuucac 1620
gggaacucuc caaauauuau ucaagugccu cuuguugcag agauuuccuc cauggugaa 1680 ggggguguc gugcgugugc gugcguguua gugugugugc augugugugu cugucuuugu 1740
gggaggguaa gacaauauga acaaacuaug aucacaguga cuuuacagga gguuguggau 1800
gcuccagggc agccuccacc uugcucuucu uucugagagu uggcucaggc agacaagagc 1860
ugcuguccuu uuaggaauau guucaaugca aaguaaaaaa auaugaauug uccccaaucc 1920
cggucaugcu uuugccacuu uggcuucucc ugugacccca ccuugacggu ggggcguaga 1980

-continued

```
cuugacaaca ucccacagug gcacggagag aaggcccaua ccuucugguu gcuucagacc   2040
ugacaccguc ccucagugau acguacagcc aaaaaggacc aacuggcuuc ugugcacuag   2100
ccugugauua acuugcuuag uaugguucuc agaucuugac aguauauuug aaacuguaaa   2160
uauguuugug ccuuaaaagg agagaagaaa guguagauag uuaaaagacu gcagcugcug   2220
aaguucugag ccgggcaagu cgagagggcu guuggacagc ugcuugiggg cccggaguaa   2280
ucaggcagcc uucauaggcg gucaugugug caugugagca caugcguaua ugugcgucuc   2340
ucuuucuccc ucacccccag guguugccau uucucugcuu acccuucacc uuuggugcag   2400
agguuucuug aauaucugcc ccaguaguca gaagcagguu cuugauguca uguacuuccu   2460
guguacucuu uauuucuagc agagugagga uguguuuugc acgucuugcu auuugagcau   2520
gcacagcugc uuguccugcu cucuucagga ggcccuggug ucaggcaggu uugccaguga   2580
agacuucuug gguaguuuag aucccauguc accucagcug auauuauggc aagugauauc   2640
accucucuuc agccccuagu gcuauucugu guugaacaca auugauacuu caggugcuuu   2700
ugaugugaaa aucaugaaaa gaggaacagg uggauguaua gcauuuuuau ucaugccauc   2760
uguuuucaac caacuauuuu ugaggaauua ucaugggaaa agaccagggc uuuucccagg   2820
aauaucccaa acuucggaaa caaguuauuc ucuucacucc caauaacuaa ugcuaagaaa   2880
ugcugaaaau caaaguaaaa aauuaaagcc cauaaggcca gaaacuccuu uugcugucuu   2940
ucucuaaaua ugauuacuuu aaaauaaaaa aguaacaagg ugucuuuucc acuccuaugg   3000
aaaagggucu ucuuggcagc uuaacauuga cuucuugguu uggggagaaa uaaauuuugu   3060
uucagaauuu uguauauugu aggaauccuu ugagaaugug auuccuuuug augggggagaa  3120
agggcaaauu auuuuaauau uuuguauuuu caacuuuaua aagauaaaau auccucaggg   3180
guggagaagu gucguuuuca uaacuugcug aauuucaggc auuuuguucu acaugaggac   3240
ucauauauuu aagccuuuug uguaauaaga aaguauaaag ucacuuccag uguuggcugu   3300
gugacagaau cuuguauuug ggccaaggug uuuccauuuc ucaaucagug cagugauaca   3360
uguacuccag agggacaggg uggacccccu gagucaacug gagcaagaag gaaggaggca   3420
gacugauggc gauucccucu cacccgggac ucucccccuu ucaaggaaag ugaaccuuua   3480
aaguaaaggc cucaucuccu uuauugcagu ucaaauccuc accauccaca gcaagaugaa   3540
uuuuaucagc cauguuuggu uguaaaugcu cgugugauuu ccuacagaaa uacugcucug   3600
aauauuuugu aauaaagguc uuugcacaug ugaccacaua cguguuagga ggcugcaugc   3660
ucuggaagcc uggacucuaa gcuggagcuc uuggaagagc ucuucgguuu cugagcauaa   3720
ugcucccauc uccugauuuc ucugaacaga aaacaaaaga gagaaugagg gaaauugcua   3780
uuuuauuugu auucaugaac uuggcuguaa ucaguuaugc cguauaggau gucagacaau   3840
accacugguu aaaauaaagc cuauuuuuca aauuuaguga guuucucaag uuuauuauau   3900
uuuucucuug uuuuuauuua augcacaaua uggcauuaua ucaauauccu uuaaacugug   3960
accuggcaua cuugucugac agaucuuaau acuacuccua acauuuagaa aauguugaua   4020
aagcuucuua guuguacauu uuuuggugaa gaguauccag gucuuugcug uggaugggua   4080
aagcaaagag caaaugaacg aaguauuaag cauuggggcc ugucuuaucu acacucgagu   4140
guaagagugg ccgaaaugac agggcucagc agacuguggc cugagggcca aaucuggccc   4200
accaccuguu ugguguagcc ugcuaagaau ggcuuuuaca uuuuuaaaug guugggaaag   4260
aaaaaaaaag aaguaguaga uuuuguagca ugugauguaa guaauguaaa acuuaaauuc   4320
caguauccau aaauaaaguu uuaugagaac aga                                4353
```

<210> SEQ ID NO 25
<211> LENGTH: 1431
<212> TYPE: RNA
<213> ORGANISM: HUMAN

<400> SEQUENCE: 25

```
uucucucacg aagccccgcc cgcggagagg uuccauauug gguaaaaucu cggcucucgg     60

agagucccgg gagcuguucu cgcgagagua cugcgggagg cucccguuug cuggcucuug    120

gaaccgcgac cacuggagcc uuagcgggcg cagcagcugg aacgggagua cugcgacgca    180

gcccggaguc ggccuuguag ggcgaaggu gcagggagau cgcggcgggc gcagucuuga    240

gcgccggagc gcgucccugc ccuuagcggg gcuugcccca gucgcagggg cacauccagc    300

cgcugcggcu gacagcagcc gcgcgcgcgg gagucugcgg ggucgcggca gccgcaccug    360

cgcgggcgac cagcgcaagg uccccgcccg gcugggcggg cagcaagggc cggggagagg    420

gugcgggugc aggcgggggc cccacagggc caccuucuug cccggcggcu gccgcuggaa    480

aaugucucag gagaggccca cguucuaccg gcaggagcug aacaagacaa ucugggaggu    540

gcccgagcgu uaccagaacc ugucuccagu gggcucuggc gccuauggcu cugugugugc    600

ugcuuuugac acaaaaacgg gguuacgugu ggcagugaag aagcucucca gaccauuuca    660

guccaucauu caugcgaaaa gaaccuacag agaacugcgg uuacuuaaac auaugaaaca    720

ugaaaaugug auuggucugu uggacguuuu uacaccugca aggucucugg aggaauucaa    780

ugauguguau cuggugaccc aucucauggg ggcagaucug aacaacauug ugaaauguca    840

gaagcuuaca gaugaccaug uucaguuccu uaucuaccaa auucuccgag gucuaaagua    900

uauacauuca gcugacauaa uucacaggga ccuaaaaccu aguaaucuag cugugaauga    960

agacugugag cugaagauuc uggauuuugg acuggcucgg cacacagaug augaaaugac   1020

aggcuacgug gccacuaggu gguacagggc uccugagauc augcugaacu ggaugcauua   1080

caaccagaca guugauauuu ggucaguggg augcauaaug gccgagcugu ugacuggaag   1140

aacauuguuu ccugguacag accauauuga ucaguugaag cucauuuuaa gacucguugg   1200

aaccccaggg gcugagcuuu ugaagaaaau cuccucagag ucugcaagaa acuauauuca   1260

gucuuugacu cagaugccga agaugaacuu ugcgaaugua uuuauuggug ccaaucccca   1320

ggguaaguug accauauauc cucaccucau ggauauugaa uugguuauga uauaaauugg   1380

ggauuugaag aagaguuucu ccuuuugacc aaauaaagua ccauuaguug a            1431
```

<210> SEQ ID NO 26
<211> LENGTH: 2398
<212> TYPE: RNA
<213> ORGANISM: HUMAN

<400> SEQUENCE: 26

```
gggaggccgg augugagugg agcggccauu uccuguuucu cugcaguuuu ccucagcuuu     60

ggguggugc cgcugccggg caucggcuuc caguccgcgg agggcgaggc ggcguggaca    120

gcggccccgg cacccagcgc cccgccgccc gcaagccgcg cgcccguccg ccgcgccccg    180

agcccgccgc uuccuaucuc agcgcccugc cgccgccgcc gcggcccagc gagcggcccu    240

gaugcaggcc aucaagugug ugguggguggg agacggagcu guagguaaaa cuugccuacu    300

gaucaguuac acaaccaaug cauuuccugg agaauauauc ccuacugucu uugacaauua    360

uucugccaau guuaugguag auggaaaacc ggugaaucug ggcuuauggg auacagcugg    420

acaagaagau uaugacagau uacgccccu auccuauccg caaacaguug gagaaacgua    480
```

-continued cgguaaggau auaaccuccc ggggcaaaga caagccgauu gccgaugugu ucuuaauuug 540
cuuuucccuu gugaguccug caucauuuga aaauguccgu gcaaaguggu auccugaggu 600
gcggcaccac ugucccaaca cucccaucau ccuaguggga acuaaacuug aucuuaggga 660
ugauaaagac acgaucgaga aacugaagga gaagaagcug acucccauca ccuauccgca 720
gggucuagcc auggcuaagg agauuggugc uguaaaauac cuggagugcu cggcgcucac 780
acagcgaggc cucaagacag uguuugacga agcgauccga gcaguccucu gcccgccucc 840
cgugaagaag aggaagagaa aaugccugcu guuguaaaug ucucagcccc ucguucuugg 900
uccugucccu uggaaccuuu guacgcuuug cucaaaaaaa aacaaaaaaa aaaaacaaaa 960
aaaaaaaaca acgguggagc cuucgcacuc aaugccaacu uuuuguuaca gauuaauuuu 1020
uccauaaaac cauuuuuuga accaaucagu aauuuuaagg uuuuguuugu ucuaaaugua 1080
agaguucaga cucacauucu auuaaaauuu agcccuaaaa ugacaagccu ucuuaaagcc 1140
uuauuuuuca aaagcgcccc ccccauucuu guucagauua agaguugcca aaauaccuuc 1200
ugaacuacac ugcauuguug ugccgagaac accgagcacu gaacuuugca aagaccuucg 1260
ucuuugagaa gacgguagcu ucugcaguua ggaggugcag acacuugcuc uccuauguag 1320
uucucagaug cguaaagcag aacagccucc cgaaugaagc guugccauug aacucaccag 1380
ugaguuagca gcacguguuc ccgacauaac auuguacugu aauggaguga gcguagcagc 1440
ucagcucuuu ggaucagucu uugugauuuc auagcgaguu uucugaccag cuuuugcgga 1500
gauuuugaac agaacugcua uuuccucuaa ugaagaauuc uguuuagcug ugggugugcc 1560 gggugggggug ugugugauca aaggacaaag acaguauuuu gacaaaauac gaaguggaga 1620
uuuacacuac auuguacaag gaaugaaagu gucacgggua aaaacucuaa aagguuaauu 1680
ucugucaaau gcaguagaug augaaagaaa gguugguauu aucaggaaau guuuucuuaa 1740
gcuuuuccuu ucucuuacac cugccaugcc uccccaaauu gggcauuuaa uucaucuuua 1800
aacugguugu ucuguuaguc gcuaacuuag uaagugcuuu ucuuauagaa ccccuucuga 1860
cugagcaaua ugccuccuug uauuauaaaa ucuuucugau aaugcauuag aagguuuuuu 1920
ugucgauuag uaaaagugcu uuccauguua cuuuauucag agcuaauaag ugcuuuccuu 1980
aguuuucuag uaacuaggug uaaaaaucau guguugcagc uuuauaguuu uuaaaauauu 2040
uuagauaauu cuuaaacuau gaaccuucuu aacaucacug ucuugccaga uuaccgacac 2100
ugucacuuga ccaauacuga ccccucuuuac cucgcccacg cggacacacg ccuccuguag 2160
ucgcuuugcc uauugauguu ccuuugggguc ugugagguuc uguaaacugu gcuagugcug 2220
acgauguucu guacaacuua acucacuggc gagaauacag cgugggaccc uucagccacu 2280
acaacagaau uuuuuaaauu gacaguugca gaauugugga guguuuuuac auugaucuuu 2340
ugcuaaugca auuagcauua uguuuugcau guaugacuua auaaauccuu gaaucaua 2398

<210> SEQ ID NO 27
<211> LENGTH: 2341
<212> TYPE: RNA
<213> ORGANISM: HUMAN

<400> SEQUENCE: 27
gggaggccgg augugagugg agcggccauu uccuguuucu cugcaguuuu ccucagcuuu 60
gggugguggc cgcugccggg caucggcuuc caguccgcgg agggcgaggc ggcguggaca 120
gcggccccgg cacccagcgc cccgccgccc gcaagccgcg cgcccguccg ccgcgccccg 180
agcccgccgc uuccuaucuc agcgcccugc cgccgccgcc gcggcccagc gagcggcccu 240

```
gaugcaggcc aucaagugug ugguggugggg agacggagcu guagguaaaa cuugccuacu    300

gaucaguuac acaaccaaug cauuuccugg agaauauauc ccuacugucu uugacaauua    360

uucugccaau guuaugguag auggaaaacc ggugaaucug ggcuuauggg auacagcugg    420

acaagaagau uaugacagau uacgcccccu auccuauccg caaacagaug uguucuuaau    480

uugcuuuucc cuugugaguc cugcaucauu ugaaaauguc cgugcaaagu gguauccuga    540

ggugcggcac cacuguccca acacucccau cauccuagug ggaacuaaac uugaucuuag    600

ggaugauaaa gacacgaucg agaaacugaa ggagaagaag cugacuccca ucaccuaucc    660

gcagggucua gccauggcua aggagauugg ugcuguaaaa uaccuggagu gcucggcgcu    720

cacacagcga ggccucaaga caguguuuga cgaagcgauc cgagcagucc ucugcccgcc    780

ucccgugaag aagaggaaga gaaaaugccu gcuguuguaa augucucagc cccucguucu    840

ugguccuguc ccuuggaacc uuuguacgcu uugcucaaaa aaaaacaaaa aaaaaaaaca    900

aaaaaaaaaa acaacggugg agccuucgca cucaaugcca acuuuuuguu acagauuaau    960

uuuuccauaa aaccauuuuu ugaaccaauc aguaauuuua agguuuuguu uguucuaaau   1020

guaagaguuc agacucacau ucuauuaaaa uuuagcccua aaaugacaag ccuucuuaaa   1080

gccuuauuuu ucaaaagcgc cccccccauu cuuguucaga uuaagaguug ccaaaauacc   1140

uucugaacua cacugcauug uugugccgag aacaccgagc acugaacuuu gcaaagaccu   1200

ucgucuuuga gaagacggua gcuucugcag uuaggaggug cagacacuug cucuccuaug   1260

uaguucucag augcguaaag cagaacagcc ucccgaauga agcguugcca uugaacucac   1320

cagugaguua gcagcacgug uucccgacau aacauuguac uguaauggag ugagcguagc   1380

agcucagcuc uuuggaucag ucuuugugau uucauagcga guuuucugac cagcuuuugc   1440

ggagauuuug aacagaacug cuauuuccuc uaaugaagaa uucuguuuag cugugggugu   1500

gccgggugggg gugugugugua ucaaaggaca aagacaguau uuugacaaaa uacgaagugg   1560

agauuuacac uacauuguac aaggaaugaa agugucacgg guaaaaacuc uaaaagguua   1620

auuucuguca aaugcaguag augaugaaag aaagguuggu auuaucagga aauguuuucu   1680

uaagcuuuuc cuuucucuua caccugccau gccuccccaa auugggcauu uaauucaucu   1740

uuaaacuggu uguucuguua gucgcuaacu uaguaagugc uuuucuuaua gaaccccuuc   1800

ugacugagca auaugccucc uuguauuaua aaaucuuucu gauaaugcau uagaagguuu   1860

uuuugucgau uaguaaaagu gcuuuccaug uuacuuuauu cagagcuaau aagugcuuuc   1920

cuuaguuuuc uaguaacuag guguaaaaau caugugugc agcuuuauag uuuuuaaaau   1980

auuuuagaua auucuuaaac uaugaaccuu cuuaacauca cugucuugcc agauuaccga   2040

cacugucacu ugaccaauac ugacccucuu uaccucgccc acgcggacac acgccuccug   2100

uagucgcuuu gccuauugau guuccuuugg gucugugagg uucuguaaac ugugcuagug   2160

cugacgaugu ucuguacaac uuaacucacu ggcgagaaua cagcguggga cccuucagcc   2220

acuacaacag aauuuuuuaa auugacaguu gcagaauugu ggaguguuuu uacauugauc   2280

uuuugcuaau gcaauuagca uuauguuuug cauguaugac uuaauaaauc cuugaaucau   2340

a                                                                    2341
```

<210> SEQ ID NO 28
<211> LENGTH: 7134
<212> TYPE: RNA
<213> ORGANISM: HUMAN

<400> SEQUENCE: 28

-continued cgggcuugug ccgccgccgc cgccgccgcc gcccgggcca agugacaaag gaaggaagga 60
agcgaggagg agccggcccc gcagccgcug acagggcucu gggcuggggc aaagcgcgga 120
cacuuccuga gcgggcaccg agcagagccg aggggcggga gggcggccga gcuguugccg 180
cggacggggg agggggcccc gagggacgga agcgguugcc ggguucccau guccccggcg 240
aauggggaac agucgaggag ccgcugccug ggucugaag ggagcugccu ccgccaccgc 300
cauggccgcu ggauccagcc gccgccugca gcugcuccug gcgcaaugag gagaggagcc 360
gccgccaccg ccaccgcccg ccucugacug acucgcgacu ccgccgcccu cuaguucgcc 420
gggccccugc cgucagcccg ccggaucccg cggcuugccg gagcugcagc guuucccguc 480
gcaucuccga gccacccccu cccucccucu cccucccucc uacccauccc ccuuucucuu 540
caagcgugag acucgugauc cuuccgccgc uucccuucuu cauugacucg gaaaaaaaau 600
ccccgaggaa aauauaauau ucgaaguacu cauuuucaau caaguauuug cccccguuuc 660
acgugauaca uauuuuuuua ggauuugccc ucucuuuucu cuccucccag gaaagggagg 720
ggaaagaauu guauuuuuuc ccaaguccua aaucaucuau auguuaaaua uccgugccga 780
ucugucuuga aggagaaaua uaucgcuugu uuuguuuuuu auaguauaca aaaggaguga 840
aaagccaaga ggacgaaguc uuuuucuuuu ucuucugugg gagaacuuaa ugcugcauuu 900
aucguuaacc uaacacccca acauaaagac aaaaggaaga aaaggaggaa ggaaggaaaa 960
ggugauucgc gaagagagug aucaugucag ggcggcccag aaccaccucc uuugcggaga 1020
gcugcaagcc ggugcagcag ccuucagcuu uuggcagcau gaaaguuagc agagacaagg 1080
acggcagcaa ggugacaaca gugguggcaa cuccugggca ggguccagac aggccacaag 1140
aagucagcua uacagacacu aaagugauug gaaauggauc auuuggugug guauaucaag 1200
ccaaacuuug ugauucagga gaacuggucg ccaucaagaa aguauugcag gacaagagau 1260
uuaagaaucg agagcuccag aucaugagaa agcuagauca cuguaacaua guccgauugc 1320
guuauuucuu cuacuccagu ggugagaaga aagaugaggu cuaucuuaau cuggugcugg 1380
acuauguucc ggaaacagua uacagaguug ccagacacua uagucgagcc aaacagacgc 1440
ucccugugau uuaugucaag uuguauaugu aucagcuguu ccgaaguuua gccuauaucc 1500
auuccuuugg aaucugccau cgggauauua aaccgcagaa ccucuuguug gauccugaua 1560
cugcuguauu aaaacucugu gacuuuggaa gugcaaagca gcugguccga ggagaaccca 1620
auguuucgua uaucuguucu cgguacuaua gggcaccaga guugaucuuu ggagccacug 1680
auuauaccuc uaguauagau guauggucug cuggcugugu guuggcugag cuguuacuag 1740
gacaaccaau auuuccaggg gauaguggug uggaucaguu gguagaaaua aucaaggucc 1800
ugggaacucc aacaagggag caaaucagag aaaugaaccc aaacuacaca gaauuuaaau 1860
ucccucaaau uaaggcacau ccuuggacua aggauucguc aggaacagga cauuucaccu 1920
caggagugcg ggucuuccga ccccgaacuc caccggaggc aauugcacug uguagccguc 1980
ugcuggagua uacaccaacu gcccgacuaa caccacugga agcuugugca cauucauuuu 2040
uugaugaauu acgggaccca aaugucaaac uaccaaaugg gcgagacaca ccugcacucu 2100
ucaacuucac cacucaagaa cugucaagua auccaccucu ggcuaccauc cuuauuccuc 2160
cucaugcucg gauucaagca gcugcuucaa cccccacaaa ugccacagca gcgucagaug 2220
cuaauacugg agaccgugga cagaccaaua augcugcuuc ugcaucagcu uccaacucca 2280
ccugaacagu cccgagcagc cagcugcaca ggaaaaacca ccaguuacuu gagugucacu 2340
cagcaacacu ggucacguuu ggaaagaaua uuaaaaagag aaaaaaaucc uguucauuuu 2400

-continued

```
aguguucaau uuuuuuauua uuauuguugu ucuuauuuaa ccuuguaaaa uaucuauaaa   2460

uacaaaccaa uuucauugua uucucacuuu gagggagauc cagggggugg gaggggguugu   2520

ggggaggggg aaagcggagc acuagaacau acaaucucuc ucccacgaca aucuuuuuuu   2580

auuaaaaguc ugcuguugua uacuuuaaaa acaggacucc ugccucaugc cccuuccaca   2640

aaagaagaaa accuuuuucu gugcugaugg guuuuuuuga acuuuguuuu cuuuuaaagu   2700

cuagugugag acuuugguau agugcacagc uugaaauugg uugggagcuu agcagguaua   2760

acucaacggg gacuuaaaug ucacuuguaa aauuaaucca uaucuucggg uauuuauaga   2820

cuugccuuug gcauguuggu ggcaggugug gcagacaaag aaauguguau cauucguaac   2880

ccagggaggu caauaaaguu uggaacucua cagggaagau ucuuaguaga uuuguuaagg   2940

uuuuguuuug cucucaguua gugcuaguga uguagaggcu uguacaggag gcugccagag   3000

gggaagcagc aagcaagacu caggcacaca ugcucuacag guggcucuuu guuugccuga   3060

ccaaaguucu uugcaaaucu uagcacaguu ucaaacuagu gaccugggag gagauggaag   3120

ggguguugag caggcugagc uagcugcuga ggucaaaggc ugaugagccc agaggaaggg   3180

gacaggucag ggauacaucu caccacugug aauaaguuug uccagauuuu uuucuaaagu   3240

uacuucccuu ggaaagauac acuugagagg acauuguagu uaaauaaugu gaacuguaac   3300

agucaucuac ugguuuauuu uucauauuuu uuaauugaaa auugagcuug cagaaauagc   3360

cacauucuac acauaguucu aauuuuaaau ccaaaucuag aaucuguauu uaauuuguuu   3420

uuuaaccuca ugcuuuuuac auuuauuuau ugaugcaugu cagaugguag aaauauuaaa   3480

aacuacacau cagaaugaua cagucacuua uaccugcuga cuuuauagga aagcugauga   3540

uauaaaugug uguauauaug uuauauauac auauauucaa uacugccuuu uuuuuugucu   3600

acaguaucaa aauugacugg uugaagcaug agaagaaugu uucccccaca cccaguuaag   3660

aguuuuugug ucuguuuucu uuguguauca gugaacgaug uuaagaauca gucucucuuu   3720

uugaagaaaa agcaauauuc cuuggaaagc aaggagaauu gaaggacuau guuugccgug   3780

aggaaauaga uuuucaugac uaguuuguuu uauacuuuua agguuggcau cuaugugggc   3840

cuuauauacu cuaaaaugaa cuuuagucac cuuggugcuu augggccauu acuugaccua   3900

ugaaucuuua aggcacaauc aguuguacuu uacauuuaaa gaucacuuga gugauggccg   3960

ccuuucccuc cuacccgcuc cuuccccaca ugccuuccaa gguuagcugg uaacuguagg   4020

gcugcagagc ugagcccaug guugugugua acuugcccuc acccuccuca uugccaccuu   4080

aggucacuuu augggucucg uccuccagag gguucggaag uggagucugu uggcagcccu   4140

ccugcaggcc cuagcacccu guccugcucc uuaacugugu gugugacucu ccaagagagu   4200

uguccugccu gcugaaguga accaguaccc agaaagacaa cugugagcca ucuugguuuu   4260

cacucgcugu uuagcugagg ucuugggcca caaaaggggu uucacaaacc ucuggauaua   4320

ucagaguuua ugagaaagga aacaugcuca gucaaaccaa aucaaacaaa uugaauuuua   4380

uguuuuauaa agugcuucug aaagcuaaga uuugaaagaa gucugaaauc aaaguauuug   4440

gcagcauaac uccuuaaagg uaguggcguu gauagaccau uuucagacag aauuuauaaa   4500

gaaucugaaa aggcaggucu gugauagaga aauggaccug cauucagauc caacugccca   4560

gcaagcguuu ggaugcagac acugcucugg acgugguaua cuccccagag uccauaaaaa   4620

ucagugcuua uuuuaggaaa cagguugccc cccacaacug ggguaaaaga agagagaaaa   4680

gucacgcuuu ucucucauuu cauugugugu gcaugugugc gugugugugu gugugugugu   4740

gugcugagau gugugauuuu ucuuucucaa ggaucauggu gggaucacag aacucuuuua   4800
```

-continued

```
uacaagugag auccaggucu cugaauaucu uuuuguauau aauaauaaua aaaagcuccu   4860
caccaaauuc aagcuuguac auuauauuuu cuuucugugu uuuuaaauuu aaguuuuauu   4920
guuuuguaug uaaauaugug gacccaggaa cuguuauuaa ugagcaaaaa guuacuguuc   4980
agggcaguga uucuguuuaa uaaucagaca aaauguagac gagcuuuuua aagccauaua   5040
guuuuaacuc uguacaguag guaccggccu guauuauugu aacaauaacu cuagcaaugu   5100
auaguguauc uauauaguuu ggagugccuu cgcuuccaug uguuuuuuuu uuuaauuugu   5160
ucuuuuuuaa auuuuaauug guuuccuuua uccaugucuc ccuguccacc cccuuucccu   5220
uugaaauaau aacucacuca uaacaguauc uuugccccuu ccacaguuaa guuucaguga   5280
uaccauacuc aggaguggga agaggaaauc auauucguaa uuucauuucg uugaagcccu   5340
gccuuuguuu ugguucugaa ugucuuuccu ccucgguagc agugagaccg guuucauuuc   5400
auacuuaguc cauucaggga cuuaguguag caccagggag cccuagagcu ggaggauauc   5460
gaauagauua aauuuugcuc gucucuucca caagcccuaa ccaugggucu uaaaaacagc   5520
agauucuggg agccuuccau gcucucucuc ucuccucuuu uaucuacuuc ccucccaaau   5580
gagagaguga cagagaauug uuuuuuuaua aaucgaaguu ucuuaauagu aucagguuuu   5640
gauacgucag uggucuaaaa ugcuauagug caauuacuag caguuacugc acggagugcc   5700
accgugccaa uagaggacug uuguuuuaac aagggaacuc uuagcccauu uccucccucc   5760
cgccaucucu acccuugcuc aaugaaauau cauuuuaauu ucuuuuaaaa aaaaucaguu   5820
uaauucuuac ugugugccca acacgaaggc cuuuuuugaa agaaaaaauag aauguuuugc   5880
cucaaaguag uccauauaaa augucuugaa uagaagaaaa aacuaccaaa ccaaagguua   5940
cuauuuuuga aacaucgugu guucauucca gcaaggcaga agacugcacc uucuuuccag   6000
ugacaugcug ugucauuuuu uuuaaguccu cuuaauuuuu agacacauuu uugguuuaug   6060
uuuuaacaau guaugccuaa ccagucaucu ugucugcacc aaugcaaagg uuucugagag   6120
gaguauucuc uaucccugug gauaugaaga cacuggcauu ucaucuauuu uucccuuucc   6180
uuuuuaaagg auuuaacuuu ggaaucuucc aaaggaaguu uggccaaugc cagaucccca   6240
ggaauuuggg ggguuuucuu ucuuuucaac ugaaauugua ucugauuccu acuguucaug   6300
uuagugauca ucuaaucaca gagccaaaca cuuuucuccc cugugugga aaguagguau   6360
gcuuuacaau aaaaucuguc uuuucuggua gaaaccugag ccacugaaaa uaaaagagac   6420
aacuagaagc acaguagagu cccagacuga gaucuaccuu ugagaggcuu ugaaaguaau   6480
cccuggggguu uggauuauuu ucacaagggu uaugccguuu uauucaaguu uguugcuccg   6540
uuuugcaccu cugcaauaaa agcaaaauga caaccaguac auaaggggguu agcuugacaa   6600
aguagacuuc cuuguguuaa uuuuuaaguu uuuuuuuccu uaacuauauc ugucuacagg   6660
cagauacaga uaguuguaug aaaaucugcu ugccuguaaa auuugcauuu auaaaugugu   6720
ugccgaugga ucacuugggc cuguacacau accaauuagc gugaccacuu ccaucuuaaa   6780
aacaaaccua aaaaacaaaa uuuauuauau auauauauau auauauauaa aggacugugg   6840
guuguauaca aacuauugca aacacuugug caaaucuguc uugauauaaa ggaaaagcaa   6900
aaucuguaua acauuauuac uacuugaaug ccucugugac ugauuuuuuu uucauuuuaa   6960
auauaaacuu uuuugugaaa aguaugcuca auguuuuuuu ucccuuuccc cauucccuug   7020
uaaauacauu uuguucuaug ugacuugguu uggaaauagu uaacugguac uguaauuugc   7080
auuaaauaaa aaguagguua gccuggaaau gaaauuaaaa aaaaaaaaaa aaaa         7134
```

<210> SEQ ID NO 29

-continued

<211> LENGTH: 7095
<212> TYPE: RNA
<213> ORGANISM: HUMAN

<400> SEQUENCE: 29
cgggcuugug ccgccgccgc cgccgccgcc gcccgggcca agugacaaag gaaggaagga 60
agcgaggagg agccggcccc gcagccgcug acagggcucu gggcuggggc aaagcgcgga 120
cacuuccuga gcgggcaccg agcagagccg aggggcggga gggcggccga gcuguugccg 180
cggacggggg agggggcccc gagggacgga agcgguugcc ggguucccau guccccggcg 240 aaugggggaac agucgaggag ccgcugccug ggucugaag ggagcugccu ccgccaccgc 300
cauggccgcu ggauccagcc gccgccugca gcugcuccug gcgcaaugag gagaggagcc 360
gccgccaccg ccaccgcccg ccucugacug acucgcgacu ccgccgcccu cuaguucgcc 420
gggccccugc cgucagcccg ccggaucccg cggcuugccg gagcugcagc guuucccguc 480
gcaucuccga gccacccccu cccucccucu cccucccucc uacccauccc ccuuucucuu 540
caagcgugag acucgugauc cuuccgccgc uucccuucuu cauugacucg gaaaaaaaau 600
ccccgaggaa aauauaauau ucgaaguacu cauuuucaau caaguauuug cccccguuuc 660
acgugauaca uauuuuuuua ggauuugccc ucucuuuucu cuccucccag gaaagggagg 720
ggaaagaauu guauuuuuuc ccaaguccua aaucaucuau auguuaaaua uccgugccga 780
ucugucuuga aggagaaaua uaucgcuugu uuuguuuuuu auaguauaca aaaggaguga 840
aaagccaaga ggacgaaguc uuuuucuuuu ucuucugugg gagaacuuaa ugcugcauuu 900
aucguuaacc uaacacccca acauaaagac aaaaggaaga aaaggaggaa ggaaggaaaa 960
ggugauucgc gaagagagug aucaugucag ggcggcccag aaccaccucc uuugcggaga 1020
gcugcaagcc ggugcagcag ccuucagcuu uuggcagcau gaaaguuagc agagacaagg 1080
acggcagcaa ggugacaaca gugguggcaa cuccugggca ggguccagac aggccacaag 1140
aagucagcua uacagacacu aaagugauug gaaauggauc auuuggugug guauaucaag 1200
ccaaacuuug ugauucagga gaacuggucg ccaucaagaa aguauugcag gacaagagau 1260
uuaagaaucg agagcuccag aucaugagaa agcuagauca cuguaacaua guccgauugc 1320
guuauuucuu cuacuccagu ggugagaaga aagaugaggu cuaucuuaau cuggugcugg 1380
acuauguucc ggaaacagua uacagaguug ccagacacua uagucgagcc aaacagacgc 1440
ucccugugau uuaugucaag uuguauaugu aucagcuguu ccgaaguuua gccuauaucc 1500
auuccuuugg aaucugccau cgggauauua aaccgcagaa ccucuuguug gauccugaua 1560
cugcuguauu aaaacucugu gacuuuggaa gugcaaagca gcugguccga ggagaaccca 1620
auguuucgua uaucuguucu cgguacuaua gggcaccaga guugaucuuu ggagccacug 1680
auuauaccuc uaguauagau guauggucug cuggcugugu guuggcugag cuguuacuag 1740
gacaaccaau auuuccaggg gauaguggug uggaucaguu gguagaaaua aucaaggucc 1800
ugggaacucc aacaagggag caaaucagag aaaugaaccc aaacuacaca gaauuuaaau 1860
ucccucaaau uaaggcacau ccuuggacua aggucuuccg accccgaacu ccaccggagg 1920
caauugcacu guguagccgu cugcuggagu auacaccaac ugcccgacua acaccacugg 1980
aagcuugugc acauucauuu uuugaugaau uacgggaccc aaaugucaaa cuaccaaaug 2040
ggcgagacac accugcacuc uucaacuuca ccacucaaga acugucaagu aauccaccuc 2100
uggcuaccau ccuuauuccu ccucaugcuc ggauucaagc agcugcuuca acccccacaa 2160
augccacagc agcgucagau gcuaauacug gagaccgugg acagaccaau aaugcugcuu 2220

-continued

```
cugcaucagc uuccaacucc accugaacag ucccgagcag ccagcugcac aggaaaaacc   2280
accaguuacu ugagugucac ucagcaacac uggucacguu uggaaagaau auuaaaaaga   2340
gaaaaaaauc cuguucauuu uaguguucaa uuuuuuuauu auuauuguug uucuuauuua   2400
accuuguaaa auaucuauaa auacaaacca auuucauugu auucucacuu ugagggagau   2460
ccaggggggug ggaggggguug uggggagggg gaaagcggag cacuagaaca uacaaucucu   2520
cucccacgac aaucuuuuuu uauuaaaagu cugcuguugu auacuuuaaa aacaggacuc   2580
cugccucaug ccccuuccac aaaagaagaa aaccuuuuuc ugugcugaug gguuuuuuug   2640
aacuuuguuu ucuuuuaaag ucuaguguga gacuuuggua uagugcacag cuugaaauug   2700
guugggagcu uagcagguau aacucaacgg ggacuuaaau gucacuugua aaauuaaucc   2760
auaucuucgg guauuuauag acuugccuuu ggcauguugg uggcaggugu ggcagacaaa   2820
gaaaugugua ucauucguaa cccagggagg ucaauaaagu uuggaacucu acagggaaga   2880
uucuuaguag auuuguuaag guuuuguuuu gcucucaguu agugcuagug auguagaggc   2940
uuguacagga ggcugccaga ggggaagcag caagcaagac ucaggcacac augcucuaca   3000
gguggcucuu uguuugccug accaaaguuc uuugcaaauc uuagcacagu uucaaacuag   3060
ugaccuggga ggagauggaa ggggguguuga gcaggcugag cuagcugcug aggucaaagg   3120
cugaugagcc cagaggaagg ggacagguca gggauacauc ucaccacugu gaauaaguuu   3180
guccagauuu uuuucuaaag uuacuucccu uggaaagaua cacuugagag gacauuguag   3240
uuaaauaaug ugaacuguaa cagucaucua cugguuuauu uuucauauuu uuuaauugaa   3300
aauugagcuu gcagaaauag ccacauucua cacauaguuc uaauuuuaaa uccaaaucua   3360
gaaucuguau uuaauuuguu uuuuaaccuc augcuuuuua cauuuauuua uugaugcaug   3420
ucagauggua gaaauauuaa aaacuacaca ucagaaugau acagucacuu auaccugcug   3480
acuuuauagg aaagcugaug auauaaaugu guguauauau guuauauaua cauauauuca   3540
auacugccuu uuuuuuuguc uacaguauca aaauugacug guugaagcau gagaagaaug   3600
uuucccccac acccaguuaa gaguuuuugu gucuguuuuc uuuguguauc agugaacgau   3660
guuaagaauc agucucucuu uuugaagaaa aagcaauauu ccuuggaaag caaggagaau   3720
ugaaggacua uguuugccgu gaggaaauag auuuucauga cuaguuuguu uuauacuuuu   3780
aagguuggca ucuauguggg ccuuauauac ucuaaaauga acuuuaguca ccuuggugcu   3840
uaugggccau uacuugaccu augaaucuuu aaggcacaau caguuguacu uuacauuuaa   3900
agaucacuug agugauggcc gccuuucccu ccuacccgcu ccuuccccac augccuucca   3960
agguuagcug guaacuguag ggcugcagag cugagcccau gguugugugu aacuugcccu   4020
cacccuccuc auugccaccu uaggucacuu uaugggucuc guccuccaga ggguucggaa   4080
guggagucug uuggcagccc uccugcaggc ccuagcaccc uguccugcuc cuuaacugug   4140
ugugugacuc uccaagagag uuguccugcc ugcugaagug aaccaguacc cagaaagaca   4200
acugugagcc aucuugguuu ucacucgcug uuuagcugag gucuugggcc acaaaagggg   4260
uuucacaaac cucuggauau aucagaguuu augagaaagg aaacaugcuc agucaaacca   4320
aaucaaacaa auugaauuuu auguuuuaua aagugcuucu gaaagcuaag auuugaaaga   4380
agucugaaau caaaguauuu ggcagcauaa cuccuuaaag guaguggcgu ugauagacca   4440
uuuucagaca gaauuuauaa agaaucugaa aaggcagguc ugugauagag aaauggaccu   4500
gcauucagau ccaacugccc agcaagcguu uggaugcaga cacugcucug gacgugguau   4560
acuccccaga guccauaaaa aucagugcuu auuuuaggaa acagguugcc ccccacaacu   4620
```

-continued

```
gggguaaaag aagagagaaa agucacgcuu uucucucauu ucauugugug ugcaugugug   4680
cgugugugug ugugugugug ugugcugaga ugugugauuu uucuuucuca aggaucaugg   4740
ugggaucaca gaacucuuuu auacaaguga gauccagguc ucugaauauc uuuuuguaua   4800
uaauaauaau aaaaagcucc ucaccaaauu caagcuugua cauuauauuu ucuuucugug   4860
uuuuuaaauu uaaguuuuau uguuuuguau guaaauaugu ggacccagga acuguuauua   4920
augagcaaaa aguuacuguu cagggcagug auucuguuua auaaucagac aaaauguaga   4980
cgagcuuuuu aaagccauau aguuuuaacu cuguacagua gguaccggcc uguauuauug   5040
uaacaauaac ucuagcaaug uauaguguau cuauauaguu uggagugccu ucgcuuccau   5100
guguuuuuuu uuuuaauuug uucuuuuuua aauuuuaauu gguuuccuuu auccaugucu   5160
cccuguccac ccccuuuccc uuugaaauaa uaacucacuc auaacaguau cuuugccccu   5220
uccacaguua aguuucagug auaccauacu caggaguggg aagaggaaau cauauucgua   5280
auuucauuuc guugaagccc ugccuuuguu uugguucuga augucuuucc uccucgguag   5340
cagugagacc gguuucauuu cauacuuagu ccauucaggg acuuagugua gcaccaggga   5400
gcccuagagc uggaggauau cgaauagauu aaauuuugcu cgucucuucc acaagcccua   5460
accaugggguc uuaaaaacag cagauucugg gagccuucca ugcucucucu cucuccucuu   5520
uuaucuacuu cccucccaaa ugagagagug acagagaauu guuuuuuuau aaaucgaagu   5580
uucuuaauag uaucagguuu ugauacguca guggucuaaa augcuauagu gcaauuacua   5640
gcaguuacug cacggagugc caccgugcca auagaggacu guuguuuuaa caagggaacu   5700
cuuagcccau uuccucccuc ccgccaucuc uacccuugcu caaugaaaua ucauuuuaau   5760
uucuuuuaaa aaaaaucagu uuaauucuua cugugugccc aacacgaagg ccuuuuuuga   5820
aagaaaaaua gaauguuuug ccucaaagua guccauauaa aaugucuuga auagaagaaa   5880
aaacuaccaa accaaagguu acuauuuuug aaacaucgug uguucauucc agcaaggcag   5940
aagacugcac cuucuuucca gugacaugcu gugucauuuu uuuuaagucc ucuuaauuuu   6000
uagacacauu uuugguuuau guuuuaacaa uguaugccua accagucauc uugucugcac   6060
caaugcaaag guuucugaga ggaguauucu cuaucccugu ggauaugaag acacuggcau   6120
uucaucuauu uuucccuuuc cuuuuuaaag gauuuaacuu uggaaucuuc caaaggaagu   6180
uuggccaaug ccagaucccc aggaauuugg gggguuuucu uucuuuucaa cugaaauugu   6240
aucugauucc uacuguucau guuagugauc aucuaaucac agagccaaac acuuuucucc   6300
ccugugugga aaaguaggua ugcuuuacaa uaaaaucugu cuuuucuggu agaaaccuga   6360
gccacugaaa auaaaagaga caacuagaag cacaguagag ucccagacug agaucuaccu   6420
uugagaggcu uugaaaguaa ucccuggggu uuggauuauu uucacaaggg uuaugccguu   6480
uuauucaagu uuguugcucc guuuugcacc ucugcaauaa aagcaaaaug acaaccagua   6540
cauaaggggu uagcuugaca aaguagacuu ccuuguguua auuuuuaagu uuuuuuuucc   6600
uuaacuauau cugucuacag gcagauacag auaguuguau gaaaaucugc uugccuguaa   6660
aauuugcauu uauaaaugug uugccgaugg aucacuuggg ccuguacaca uaccaauuag   6720
cgugaccacu uccaucuuaa aaacaaaccu aaaaaaacaaa auuuauuaua uauauauaua   6780
uauauauaua aaggacugug gguuguauac aaacuauugc aaacacuugu gcaaaucugu   6840
cuugauauaa aggaaaagca aaaucuguau aacauuauua cuacuugaau gccucugua   6900
cugauuuuuu uuucauuuua aauauaaacu uuuuugugaa aaguaugcuc aauguuuuuu   6960
uucccuuucc ccauucccuu guaaauacau uuuguucuau gugacuuggu uuggaaauag   7020
```

-continued

```
uuaacuggua cuguaauuug cauuaaauaa aaaguagguu agccuggaaa ugaaauuaaa   7080

aaaaaaaaaa aaaaa                                                    7095


<210> SEQ ID NO 30
<211> LENGTH: 3155
<212> TYPE: RNA
<213> ORGANISM: HUMAN

<400> SEQUENCE: 30

guuucauuuu gcaguuacug ggagggggcu ugcuguggcc cugucaggaa gaguagagcu     60

cugguccagc uccgcgcagg gagggaggcu gucaccaugc cggccugcug cagcugcagu    120

gauguuuucc aguaugagac gaacaaaguc acucggaucc agagcaugaa uuauggcacc    180

auuaaguggu ucuuccacgu gaucaucuuu uccuacguuu gcuuugcucu ggugagugac    240

aagcuguacc agcggaaaga gccugucauc aguucugugc acaccaaggu gaaggggaua    300

gcagagguga aagaggagau cguggagaau ggagugaaga aguuggugca cagugucuuu    360

gacaccgcag acuacaccuu cccuuugcag gggaacucuu ucuucgugau gacaaacuuu    420

cucaaaacag aaggccaaga gcagcgguug ugucccgagu aucccacccg caggacgcuc    480

uguuccucug accgagguug uaaaaaggga uggauggacc cgcagagcaa aggaauucag    540

accggaaggu guguagugua ugaagggaac cagaagaccu gugaagucuc ugccuggugc    600

cccaucgagg caguggaaga ggcccccccgg ccugcucucu ugaacagugc cgaaaacuuc    660

acugugcuca ucaagaacaa uaucgacuuc cccggccaca acuacaccac gagaaacauc    720

cugccagguu uaaacaucac uuguaccuuc cacaagacuc agaauccaca gugucccauu    780

uuccgacuag gagacaucuu ccgagaaaca ggcgauaauu uuucagaugu ggcaauucag    840

ggcggaauaa ugggcauuga gaucuacugg gacugcaacc uagaccguug guuccaucac    900

ugccguccca aauacaguuu ccgucgccuu gacgacaaga ccaccaacgu guccuuguac    960

ccuggcuaca acuucagaua cgccaaguac uacaaggaaa acaauguuga gaaacggacu   1020

cugauaaaag ucuucgggau ccguuuugac auccugguuu uuggcaccgg aggaaaauuu   1080

gacauuaucc agcugguugu guacaucggc ucaacccucu ccuacuucgg ucuggccgcu   1140

guguucaucg acuuccucau cgacacuuac uccaguaacu gcugucgcuc ccauauuuau   1200

cccuggugca agugcuguca gcccugugug gucaacgaau acuacuacag gaagaagugc   1260

gaguccauug uggagccaaa gccgacauua aaguaugugu ccuuugugga ugaaucccac   1320

auuaggaugg ugaaccagca gcuacuaggg agaagucugc aagaugucaa gggccaagaa   1380

gucccaagac cugcgaugga cuucacagau uuguccaggc ugccccuggc ccuccaugac   1440

acacccccga uuccuggaca accagaggag auacagcugc uuagaaagga ggcgacuccu   1500

agauccaggg auagccccgu cuggugccag uguggaagcu gccucccauc ucaacucccu   1560

gagagccaca ggugccugga ggagcugugc ugccggaaaa agccgggggc cugcaucacc   1620

accucagagc uguucaggaa gcugguccug uccagacacg uccugcaguu ccuccugcuc   1680

uaccaggagc ccuugcuggc gcuggaugug gauuccacca acagccggcu gcggcacugu   1740

gccuacaggu gcuacgccac cuggcgcuuc ggcucccagg acauggcuga cuuugccaac   1800

cugcccagcu gcugccgcug gaggauccgg aaagaguuuc cgaagaguga agggcaguac   1860

aguggcuuca agaguccuua cugaagccag gcaccguggc ucacgucugu aaucccagcg   1920

cuuugggagg ccgaggcagg cagaucaccu gaggucggga guuggagacc cgccuggcua   1980

acaaggcgaa auccugucug uacuaaaaau acaaaaauca gccagacaug guggcaugca   2040
```

-continued ccugcaaucc cagcuacucg ggaggcugag gcacaagaau cacuugaacc cgggaggcag 2100
agguuguagu gagcccagau ugugccacug cucuccagcc ugggaggcac agcaaacugu 2160
cccccaaaaa aaaaaaagag uccuuaccaa uagcaggggc ugcaguagcc auguuaacau 2220
gacauuuacc agcaacuuga acuucaccug caaagcucug uggccacauu uucagccaaa 2280
gggaaauaug cuuucaucuu cuguugcucu cugugucuga gagcaaagug accugguuaa 2340
acaaaccaga aucccucuac auggacucag agaaaagaga uugagaugua agucucaacu 2400
cuguccccag gaaguugugu gacccuaggc cucucaccuc ugugccucug ucuccuuguu 2460
gcccaacuac uaucucagag auauugugag gacaaauuga gacagugcac augaacuguc 2520
uuuuaaugug uaaagaucua caugaaugca aaacauuuca uuaugagguc agacuaggau 2580
aauguccaac uaaaaacaaa cccuuuucau ccuggcugga gaauguggag aacuaaaggu 2640
ggccacaaau ucuuugacac ucaagucccc caagaccuaa ggguuuuauc uccuccccuu 2700
gaauaugggu ggcucugauu gcuuuaucca aaaguggaag ugacauugug ucaguuucag 2760
auccugaucu uaagaggcug acagcuucua cuugcugucc cuuggaacuc uugcuaucgg 2820
ggaagccaga cgccauuuaa aagucugccu auccuggcca ggugugguggcucacaccug 2880 uaaucccagc acuuugggag accaaggcgg gcggaucacu uaaagucagg aguccaagac 2940
cagacucgcc aacauggu ga aaccguaucu cuaauaaaaa uacaaaaauu agcugggcau 3000
ggugcgggca ccuguagucc uagcuaucaa gaggcugaga caggagaaac acuugaaccu 3060
gggaggugga gguugcauug agcugagauc gugccacugc acuccaggcu gggugacaga 3120
gcgagacucc aucucaaaaa aaaaaaaaag aaaaa 3155

<210> SEQ ID NO 31
<211> LENGTH: 5876
<212> TYPE: RNA
<213> ORGANISM: HUMAN

<400> SEQUENCE: 31
caaccacccc augugucucu agaaccccag uguagcgagc uggagagagg acuguccuga 60
gggcagcagg ccugguugca gcuggcgugg gggucucaga auggagcccu cagcccugag 120
gaaagcuggc ucggagcagg aggagggcuu ugaggggcug cccagaaggg ucacugaccu 180
ggggaugguc uccaaucucc ggcgcagcaa cagcagccuc uucaagagcu ggaggcuaca 240
gugccccuuc ggcaacaaug acaagcaaga aagccucagu ucguggauuc cugaaaacau 300
caagaagaaa gaaugcgugu auuuugugga aaguuccaaa cugucugaug cugggaaggu 360
ggugugucag uguggcuaca cgcaugagca gcacuuggag gaggcuacca agccccacac 420
cuuccagggc acacaguggg acccaaagaa acauguccag gagaugccaa ccgaugccuu 480
uggcgacauc gucuucacgg gccugagcca gaaggugaaa aaguacgucc gagucuccca 540
ggacacgccc uccagcguga ucuaccaccu caugacccag cacugggggc uggacguccc 600
caaucucuug aucucgguga ccgggggggc caagaacuuc aacaugaagc cgcggcugaa 660
gagcauuuuc cgcagaggcc uggucaaggu ggcucagacc acaggggccu ggaucaucac 720 agggggguccc cacaccggcg ucaugaagca gguaggcgag gcggugcggg acuucagccu 780
gagcagcagc uacaaggaag gcgagcucau caccaucgga gucgccaccu ggggcacugu 840
ccaccgccgc gagggccuga uccaucccac gggcagcuuc cccgccgagu acauacugga 900
ugaggauggc caagggaacc ugaccugccu agacagcaac cacucucacu ucauccucgu 960
ggacgacggg acccacggcc aguacggggu ggagauuccu cugaggacca ggcuggagaa 1020

-continued

```
guucauaucg gagcagacca aggaaagagg aggugugggcc aucaagaucc ccaucgugug   1080
cgugggugcug gagggcggcc cgggcacguu gcacaccauc gacaacgcca ccaccaacgg   1140
caccccccugu gugguugugg agggcucggg ccgcguggcc gacgucauug cccaggugggc   1200
caaccugccu gucucggaca ucacuaucuc ccugauccag cagaaacuga gcguguucuu   1260
ccaggagaug uuugagaccu ucacggaaag caggauuguc gaguggacca aaaagaucca   1320
agauaucguc cggaggcggc agcugcugac ugucuuccgg gaaggcaagg auggucagca   1380
ggacguggau guggccaucu ugcaggccuu gcugaaagcc ucacggagcc aagaccacuu   1440
uggccacgag aacugggacc accagcugaa acuggcagug gcauggaauc gcguggacau   1500
ugcccgcagu gagaucuuca uggaugagug gcaguggaag ccuucagauc ugcacccccac   1560
gaugacagcu gcacucaucu ccaacaagcc ugaguuugug aagcucuucc uggagaacgg   1620
ggugcagcug aaggaguuug ucaccuggga caccuugcuc uaccuguacg agaaccugga   1680
ccccuccugc cuguuccaca gcaagcugca gaaggugcug guggaggauc ccgagcgccc   1740
ggcuugcgcg cccgcggcgc cccgccugca gaugcaccac guggcccagg ugcugcggga   1800
gcugcugggg gacuucacgc agccgcuuua uccccggccc cggcacaacg accggcugcg   1860
gcuccugcug cccguucccc acgucaagcu caacgugcag ggagugagcc uccgguccccu   1920
cuacaagcgu uccucaggcc augugaccuu caccauggac cccauccgug accuucucau   1980
uugggccauu guccagaacc gucgggagcu ggcaggaauc aucugggcuc agagccagga   2040
cugcaucgca gcggccuugg ccugcagcaa gauccugaag gaacugucca aggaggagga   2100
ggacacggac agcucggagg agaugcuggc gcuggcggag gaguaugagc acagagccau   2160
cgggggucuuc accgagugcu accggaagga cgaagagaga gcccagaaac ugcucacccg   2220
cguguccgag gccuggggga agaccaccug ccugcagcuc gcccuggagg ccaaggacau   2280
gaaguuugug ucucacgggg gcauccaggc cuuccugacc aaggugugggu ggggccagcu   2340
cuccguggac aaugggcugu ggcgugugac ccugugcaug cuggccuucc cgcugcuccu   2400
caccggccuc aucuccuuca gggagaagag gcugcaggau gugggcaccc ccgcggcccg   2460
cgcccgugcc uucuucaccg cacccguggu ggucuuccac cugaacaucc ucuccuacuu   2520
cgccuuccuc ugccuguucg ccuacgugcu cauggugggac uuccagccug ugcccuccug   2580
gugcgagugu gccaucuacc ucuggcucuu cuccuuggug ugcgaggaga ugcggcagcu   2640
cuucuaugac ccugacgagu gcgggcugau gaagaaggca gccuuguacu ucagugacuu   2700
cuggaauaag cuggacgucg gcgcaaucuu gcucuucgug gcagggcuga ccugcaggcu   2760
caucccggcg acgcuguacc ccgggcgcgu cauccucucu cuggacuuca uccuguucug   2820
ccuccggcuc augcacauuu uuaccaucag uaagacgcug gggcccaaga ucaucauugu   2880
gaagcggaug augaaggacg ucuucuucuu ccucuuccug cuggcugugu ggguggguguc   2940
cuucgggggug gccaagcagg ccauccucau ccacaacgag cgccgggugg acuggcuguu   3000
ccgagggggcc gucuaccacu ccuaccucac caucuucggg cagaucccgg gcuacaucga   3060
cggugugaac uucaacccgg agcacugcag ccccaauggc accgaccccu acaagccuaa   3120
gugccccgag agcgacgcga cgcagcagag gccggccuuc ccugaguggc ugacgguccu   3180
ccuacucugc cucuaccugc ucuucaccaa cauccugcug cucaaccucc ucaucgccau   3240
guucaacuac accuuccagc aggugcagga gcacacggac cagauuugga aguuccagcg   3300
ccaugaccug aucgaggagu accacggccg ccccgccgcg ccgcccccccu ucauccuccu   3360
cagccaccug cagcucuuca ucaagagggu gguccugaag acuccggcca agaggcacaa   3420
```

-continued

```
gcagcucaag aacaagcugg agaagaacga ggaggcggcc cugcuauccu gggagaucua   3480
ccugaaggag aacuaccucc agaaccgaca guuccagcaa aagcagcggc ccgagcagaa   3540
gaucgaggac aucagcaaua agguugacgc cauggugac cugcuggacc uggacccacu   3600
gaagaggucg ggcuccaugg agcagagguu ggccucccug gaggagcagg uggcccagac   3660
agcccgagcc cugcacugga ucgugaggac gcugcgggcc agcggcuuca gcucggaggc   3720
ggacgucccc acucuggccu cccagaaggc cgcggaggag ccggaugcug agccgggagg   3780
caggaagaag acggaggagc cgggcgacag cuaccacgug aaugcccggc accuccucua   3840
ccccaacugc ccugucacgc gcuuccccgu gcccaacgag aaggugcccu gggagacgga   3900
guuccugauc uaugacccac ccuuuuacac ggcagagagg aaggacgcgg ccgccaugga   3960
ccccauggga gacacccugg agccacuguc cacgauccag uacaacgugg uggauggccu   4020
gagggaccgc cggagcuucc acgggccgua cacagugcag gccggguugc cccugaaccc   4080
caugggccgc acaggacugc gugggcgcgg gagccucagc ugcuucggac ccaaccacac   4140
gcuguacccc auggucacgc gguggaggcg gaacgaggau ggagccaucu gcaggaagag   4200
cauaaagaag augcuggaag ugcuggugu gaagcucccu cucuccgagc acugggcccu   4260
gccuggggc ucccgggagc caggggagau gcuaccucgg aagcugaagc ggauccuccg   4320
gcaggagcac uggccgucuu uugaaaacuu gcugaagugc ggcauggagg uguacaaagg   4380
cuacauggau gacccgagga acacggacaa ugccuggauc gagacggugg ccgucagcgu   4440
ccacuuccag gaccagaaug acguggagcu gaacaggcug aacucuaacc ugcacgccug   4500
cgacucgggg gccuccaucc gauggcaggu gguggacagg cgcaucccac ucuaugcgaa   4560
ccacaagacc cuccuccaga aggcagccgc ugaguucggg gcucacuacu gacugugccc   4620
ucaggcuggg cggcuccagu ccauagacgu uccccccaga aaccagggcu ucucucuccu   4680
gagccuggcc aggacucagg cuguuccugg gcccugcaca ugauggggu ugguggaccc   4740
agugccccuc acggcugccg caagucugcu gcagaugacc ucaugaacug gaagggguca   4800
aggugacccg ggaggagagc ucaagacagg gcacaggcua cucagagcug aggggcccu   4860
gggacccuug gccaucaggc gaggggcugg gccugugcag cugggcccuu ggccagaguc   4920
cacucccuuc cuggcugugu caccccgagc agcucaucca ccauggaggu cauuggccug   4980
aggcaaguuc cccggagagu cggggucccc uguggcccc ucaggccuau gucugugagg   5040
aaggggcccu gccacucucc ccaagagggc cuccauguuu cgaggugccu caacauggag   5100
ccuugccugg ccugggcuag gggcacuguc ugaacuccug acugucagga uaaacuccgu   5160
gggggguacag gagcccagac aaagcccagg ccugucaaga gacgcagagg gccccugcca   5220
ggguuggccc cagggacccu gggacgaggc ugcagaagcu cucccucccu acucccuggg   5280
agccacgugc uggccaugug gccagggacg gcaugagcag gaggcgggga cgugggggcc   5340
uucugguuug gugucaacag cucacaggag cgugaaccau gagggcccuc aggaggggaa   5400
cgugguaaaa cccaagacau uaaaucugcc aucucaggcc uggcuggcuc uucugugcuu   5460
uccacaaaua aaguuccuga cacguccagg gccaggggcu gugugacggc ugccugaagu   5520
ucuccucgau cccccgguga gcuuccugca gccuguggau guccugcagc cccucagccc   5580
uacccccaag uuucuccucu gacccaucag cucccugucu ucauuuuccu aaaccugggc   5640
uccagcaucg uccccaagcc caccaggcca ggaugcaggc auccacaugc ccuccuccuu   5700
ggcuuccccu gcgugguggu gccaaugugc ccuggcaccc cugcagaggc uccggaugga   5760
gccuggggcu gccuggccac ugagcacugg ccgaggugau gcccacccuu cccuggacag   5820
```

-continued gccucugucu uccaccugac ccaaagcucu cuagccaccc ccuuguccccc agguau 5876

<210> SEQ ID NO 32
<211> LENGTH: 4276
<212> TYPE: RNA
<213> ORGANISM: HUMAN

<400> SEQUENCE: 32 cgguggugggg aaagugaacg aaucccgaau caaagcggcg cauugaggca ggugggggugc 60 caguggaaga gagaaagcag gcgaguguuu acggccugac uugggaggcc ggcggaucag 120
caauugcaga agcaggcagc ggcagagagg gaauggugca ggcaggcgcu gagaaggacg 180
cgcaguccau cucucucagg uuagugaaau gaggcucucc gcccggggcc ggcccgggga 240
cagugcgcug cugguccccag caugaaugcg ggccccggcu gugaacccug caccaagcga 300
ccccgcuggg gcgccgcuac aacuucgccg gcugcuucgg acgcccggag cuuucccagc 360
aggcagaggc gcguccucga ccccaaggac gcucacgugc aguucagggu cccaccgucc 420
ucgccagccu gcgucccagg gcgggcggga cagcacagag gcagcgccac cucgcuuguu 480
uucaaacaaa agacuauuac caguuggaug gacacuaaag gaaucaagac agcggaauca 540
gaaaguuugg auaguaaaga aaacaacaau acaagaauag aauccaugau gaguucugua 600
caaaaagaua acuuuuacca acauaaugua gaaaaauuag aaaauguuuc ucagcuaagu 660
cuugauaagu cacccacuga aaaaaguaca caguauuuga accagcauca gacugcagca 720
auguguaagu ggcaaaauga agggaaacac acggagcagc uuuuggaaag ugaaccucaa 780
acaguaaccc ugguaccaga gcaguuuagu aaugcuaaca uugaucgguc accucaaaau 840
gaugaucaca gugacacaga uagugaagag aauagagaca aucaacaguu ucucacaacu 900
guaaagcuug caaaugcaaa gcagacuacg gaagaugaac aggccagaga agccaaaagc 960
caccagaagu gcagcaaguc uugcgauccu ggggaagacu gugcaaguug ucagcaagau 1020
gagauagaug uggugccaga gaguccauug ucagauguug gcucugagga uguugguacu 1080
gggccaaaaa augacaacaa auugacuaga caagaaaguu gccuaggaaa uucuccucca 1140
uuugagaagg aaagugaacc cgagucaccg auggaugugg auaauucuaa aaauaguugu 1200
caagacucag aagcagauga ggagacaagu ccagguuuug augaacaaga agaugguagu 1260
uccucccaaa cagcaaauaa accuucaagg uuccaagcaa gagacgcuga cauugaauuu 1320
aggaaacggu acucuacuaa gggcggugaa guuagauuac auuuccaauu ugaaggagga 1380
gagagucgca cuggaaugaa ugauuuaaau gcuaaacuac cuggaaauau uucuagccug 1440
aauguagaau gcagaaauuc uaagcaacau ggaaaaaagg auucuaaaau cacagaucau 1500
uucaugagac ugcccaaagc agaggacaga agaaaagaac agugggaaac caaacaucaa 1560
agaacagaaa ggaagauccc uaaauacguu ccaccucacc uuucuccaga uaagaagugg 1620
cuuggaacuc ccauugagga gaugagaaga augccucggu gugggauccg gcugccucuc 1680
uugagaccau cugccaauca cacaguaacu auucggguag aucuuuugcg agcaggagaa 1740
guuccuaaac cuuuuccaac acauuauaaa gauuuguggg auaacaagca uguuaaaaug 1800
ccuuguucag aacaaaauuu guacccagug gaagaugaga auggugagcg aacugcgggg 1860 agccggugggg agcucauuca gacugcacuu cucaacaaau uuacacgacc ccaaaacuug 1920
aaggaugcua uucugaaaua caauguggca uauucuaaga aaugggacuu uacagcuuug 1980
aucgauuucu gggauaaggu acuugaagaa gcagaagcuc aacauuuaua ucaguccauc 2040
uugccugaua uggugaaaau ugcacucugu cugccaaaua uuugcaccca gccaauacca 2100

-continued

```
cuccugaaac agaagaugaa ucauuccauc acaaugucgc aggaacagau ugccagucuu   2160

uuagcuaaug cuuucuucug cacauuucca cgacgaaaug cuaagaugaa aucggaguau   2220

ucuaguuacc cagacauuaa cuucaaucga uuguuugagg gacguucauc aaggaaaccg   2280

gagaaacuua aaacgcucuu cugcuacuuu agaagaguca cagagaaaaa accuacuggg   2340

uuggugacau uuacaagaca gagucuugaa gauuuuccag aaugggaaag augugaaaaa   2400

cccuugacac gauugcaugu cacuuacgaa gguaccauag aagaaaaugg ccaaggcaug   2460

cuacaggugg auuuugcaaa ucguuuuguu ggagguggug uaaccagugc aggacuugug   2520

caagaagaaa uccgcuuuuu aaucaauccu gaguugauua uuucacggcu cuucacugag   2580

gugcuggauc acaaugaaug ucuaauuauc acagguacug agcaguacag ugaauacaca   2640

ggcuaugcug agacauaucg uugguccegg agccacgaag augggaguga aagggacgac   2700

uggcagcggc gcugcacuga gaucguugcc aucgaugcuc uucacuucag acgcuaccuc   2760

gaucaguuug ugccugagaa aaugagacgc gagcugaaca aggcuuacug uggauuucuc   2820

cguccuggag uuucuucaga gaaucuuucu gcaguggcca caggaaacug gggcuguggu   2880

gccuuugggg gugaugccag guuaaaagcc uuaauacaga uauuggcagc ugcugcagcu   2940

gagcgagaug ugguuuauuu caccuuuggg gacucagaau ugaugagaga cauuuacagc   3000

augcacauuu uccuuacuga aaggaaacuc acuguuggag auguguauaa gcuguugcua   3060

cgauacuaca augaagaaug cagaaacugu uccacccccug gaccagacau caagcuuuau   3120

ccauucauau accaugcugu cgaguccugu gcagagaccg cugaccauuc agggcaaagg   3180

acagggaccu gaggagccga gcgaauagca ucuccuccca ccucccacca gagacguccu   3240

guuugagcug ucagguguaa uauaugaauu gacuuaaguu aauauaaaug uguacauaau   3300

ccacauuugu agucaaggac gcaaucucuu ccacacaugu gcaguuguca guugguacau   3360

cuaaacuccc uccauccuga cucacgugga cuuagauaug uuuuguuucu auuuucuucu   3420

auuucaguuu uucauucuuu gauguuuauu ucuuuugucc aucagaucuc uugugaaauc   3480

ccauggaagg uugugcucag ccugucgggu cucuuucuuc cugcccauau auuauaccag   3540

uugcuucugc agcccgcaga ugccagcgau gccaggaaac aaguugaaau ccaggaaucu   3600

cuuuaacuga uuuugcuaaa aaucucccug ugagccuucc acucaacucu uaauaugcuu   3660

gcauuguuua aguuuuuaaa uucugaaaau uaauaauuag gguuuuuuuc auauguguug   3720

cauaaugcaa accuccuagg uuaaaauagu uucuuuauuu aagauagaau aauuuccaga   3780

aauuguacuu uugagguauc auuuuuaucu guaaugguuu gucugucuuu uuuccucuga   3840

ucaguauuuu uuuauaccag uuuuggagac uggcugagau gaaaggaaau guggaauaaa   3900

aggagguuuu ccugaugugg uguaaagaaa acagauucaa gagaauugaa gauuuuuuuu   3960

guuucuuggu acuuuuuucu uuuuaaauua ggacuaaugu uucuuuugug gugcuugagg   4020

cauauucaua uaaccaaagu uugagaacug ggaacuucau gcugauuugu acauauugaa   4080

guuucucugg uauucaaagg uuauauagug aaugaauuuu cauuaauaaa ucacuuuguc   4140

agaaacuccc auaucaucua uauuuuauau auguauauau aaacguaugc ucuuuaagug   4200

ugucuauaug ugagcacaua aaaucuaaau aaaauuggac uggugggaaa caaaaaaaaa   4260

aaaaaaaaaa aaaaaa                                                   4276
```

<210> SEQ ID NO 33
<211> LENGTH: 1494
<212> TYPE: RNA
<213> ORGANISM: HUMAN

<400> SEQUENCE: 33
agugaaacag aaggggaggu gcaguuucag aacccagcca gccucucucu ugcugccuag 60
ccuccugccg gccucaucuu cgcccagcca accccgccug gagcccuaug gccaacugcg 120
aguucagccc ggguguccggg gacaaacccu gcugccggcu cucuaggaga gcccaacucu 180
gucuuggcgu caguauccug guccugaucc ucgucguggu gcucgcggug gucgucccga 240
gguggcgcca gcaguggagc gguccgggca ccaccaagcg cuuucccgag accguccugg 300
cgcgaugcgu caaguacacu gaaauucauc cugagaugag acauguagac ugccaaagug 360
uaugggaugc uuucaagggu gcauuuauuu caaaacaucc uugcaacauu acugaagaag 420
acuaucagcc acuaaugaag uugggaacuc agaccguacc uugcaacaag auucuucuuu 480
ggagcagaau aaaagaucug gcccaucagu ucacacaggu ccagcgggac auguucaccc 540
uggaggacac gcugcuaggc uaccuugcug augaccucac auggugugu gaauucaaca 600 cuuccaaaau aaacuaucaa ucuugcccag acuggagaaa ggacugcagc aacaacccug 660
uuucaguauu cuggaaaacg guuuccgca gguuugcaga agcugccugu gauguggucc 720
augugaugcu caauggaucc cgcaguaaaa ucuuugacaa aaacagcacu uuugggagug 780
uggaagucca uaauuugcaa ccagagaagg uucagacacu agaggccugg gugauacaug 840
guggaagaga agauuccaga gacuuaugcc aggaucccac cauaaaagag cuggaaucga 900
uuauaagcaa aaggaauauu caauuuuccu gcaagaauau cuacagaccu gacaaguuuc 960
uucagugugu gaaaaauccu gaggauucau cuugcacauc ugagaucuga gccagucgcu 1020
gugguuguuu uagcuccuug acuccuugug guuuauguca ucauacauga cucagcauac 1080
cugcuggugc agagcugaag auuuuggagg guccuccaca auaaggucaa ugccagagac 1140
ggaagccuuu uuccccaaag ucuuaaaaua acuuauauca ucagcauacc uuuauuguga 1200
ucuaucaaua gucaagaaaa auuauuguau aagauuagaa ugaaaauugu auguuaaguu 1260
acuucacuuu aauucucaug ugauccuuuu auguuauuua uauauuggua acauccuuuc 1320
uauugaaaaa ucaccacacc aaaccucucu uauuagaaca ggcaagugaa gaaaagugaa 1380
ugcucaaguu uuucagaaag cauuacauuu ccaaaugaau gaccuuguug caugauguau 1440
uuuuguaccc uuccuacaga uagucaaacc auaaacuuca uggucauggg uaaa 1494

<210> SEQ ID NO 34
<211> LENGTH: 4454
<212> TYPE: RNA
<213> ORGANISM: HUMAN

<400> SEQUENCE: 34
agcgcugagc ugcaggcgcg gcgaaacuuc ccucuacccg cccggcccgc ggcgcgcacc 60
guuggcgcug gacgcuuccu ccuuggaagc gccucucccu caguuaugga gaaaacuugu 120
auagaugcac uuccucuuac uaugaauucu ucagaaaagc aagagacugu auguauuuuu 180
ggaacuggug auuuuggaag aucacuggga uugaaaaugc uccagugugg uuauucuguu 240
guuuuuggaa gucgaaaccc ccagaagacc acccuacugc ccagugugc agaagucuug 300 agcuauucag aagcagccaa gaagucuggc aucauaauca uagcaaucca cagagagcau 360
uaugauuuuc ucacagaauu aacugagguu cucaauggaa aaauauuggu agacaucagc 420
aacaaccuca aaaucaauca auauccagaa ucuaaugcag aguaccuugc ucauuuggug 480
ccaggagccc acgugguaaa agcauuuaac accaucucag ccugggcucu ccagucagga 540
gcacuggaug caagucggca gguguuugug uguggaaaug acagcaaagc caagcaaaga 600

-continued

```
gugauggaua uuguucguaa ucuuggacuu acuccaaugg aucaaggauc acucauggca    660

gccaaagaaa uugaaaagua cccccugcag cuauuuccaa uguggagguu ccccuucuau    720

uugucugcug ugcugugugu cuucuuguuu uucuauugug uuauaagaga cguaaucuac    780

ccuuauguuu augaaaagaa agauaauaca uuucguaugg cuauuuccau uccaaaucgu    840

aucuuuccaa uaacagcacu uacacugcuu gcuuugguuu accucccugg uguuauugcu    900

gccauucuac aacuguaccg aggcacaaaa uaccgucgau ucccagacug gcuugaccac    960

uggaugcuuu gccgaaagca gcuuggcuug guagcucugg gauuugccuu ccuucauguc   1020

cucuacacac uugugauucc uauucgauau uauguacgau ggagauuggg aaacuuaacc   1080

guuacccagg caauacucaa gaaggagaau ccauuuagca ccuccucagc cuggcucagu   1140

gauucauaug uggcuuuggg aauacuuggg uuuuuucugu uuguacucuu gggaaucacu   1200

ucuuugccau cuguuagcaa ugcagucaac uggagagagu uccgauuugu ccaguccaaa   1260

cugggguuau ugacccugau cuuguguaca gcccacaccc ugguguacgg ugggaagaga   1320

uuccucagcc cuucaaaucu cagaugguau cuuccugcag ccuacguguu agggcuuauc   1380

auuccuugca cugugcuggu gaucaaguuu guccuaauca ugccaugugu agacaacacc   1440

cuuacaagga uccgccaggg cugggaaagg aacucaaaac acuagaaaaa gcauugaaug   1500

gaaaaucaau auuuaaaaca aaguucaauu uagcuggauu ucugaacuau gguuuugaau   1560

guuuaaagaa gaaugauggg uacaguuagg aaaguuuuuu ucuuacaccg ugacugaggg   1620

aaacauugcu ugucuuugag aaauugacug acauacugga agagaacacc auuuuaucuc   1680

agguuaguga agaaucagug caggucccug acucuuauuu ucccagaggc cauggagcug   1740

agauugagac uagccuugug guuucacacu aaagaguuuc cuuguuaugg gcaacaugca   1800

ugaccuaaug ucuugcaaaa uccaauagaa guauugcagc uuccuucucu ggcucaaggg   1860

cugaguuaag ugaaaggaaa aacagcacaa uggugaccac ugauaaaggc uuuauuaggu   1920

auaucugagg aaguggguca caugaaaugu aaaaagggaa ugagguuuuu guuguuuuuu   1980

ggaaguaaag gcaaacauaa auauuaccau gaugaauucu agugaaauga ccccuugacu   2040

uugcuuuucu uaauacagau auuuacugag aggaacuauu uuuauaacac aagaaaaauu   2100

uacaauugau uaaaaguauc caugucuugg auacauacgu aucuauagag cuggcaugua   2160

auucuuccuc uauaaagaau agguauagga aagacugaau aaaaauggag ggauaucccc   2220

uuggauuuca cuugcauugu gcaauaagca aagaaggguu gauaaaaguu cuugaucaaa   2280

aaguucaaag aaaccagaau uuuagacagc aagcuaaaua aauauuguaa aauugcacua   2340

uauuagguua aguauuauuu agguauuaua auaugcuuug uaaauuuuau auuccaaaua   2400

uugcucaaua uuuuucaucu auuaaauuaa uuucuagugu aaauaaguag cuucuauauc   2460

ugucuuaguc uauuauaauu guaaggagua aaauuaaaug aauagucugc agguauaaau   2520

uugaacaaug cauagaugau cgaaaauuac ggaaaaucau agggcagaga ggugugaaga   2580

uucaucauua ugugaaauuu ggaucuuucu caaauccuug cugaaauuua ggaugguucu   2640

cacuguuuuu cugugcugau aguacccuuu ccaaggugac cuucaggggg auuaaccuuc   2700

cuagcucaag caaugagcua aaaggagccu uaugcaugau cuucccacau aucaaaauaa   2760

cuaaaaggca cugaguuugg cauuuuucug ccugcucugc uaagaccuuu uuuuuuuuuu   2820

acuuucauua uaacauauua uacaugacau uauacaaaaa ugauuaaaau auauuaaaac   2880

aacaucaaca auccaggaua uuuuucuaua aaacuuuuua aaaauaauug uaucuauaua   2940

uucaauuuua cauccuuuuu caaaggcuuu guuuuucuaa aggcuuuguu uuccuuuuua   3000
```

uuauuuuuuu cuuuuuuauu uuuuugagac agucuugcuc ugucgcucag gcuggagugc 3060
aguggcacga ucucagcuca cugcaaccuc cuccucccag guucaaguga uucuuguuca 3120
ucagccuccc gaguagcugg gacuacaggc augugccacu augcccagcu aauuuuugua 3180
cuuuuaguag agacaggguu ucaccacauu ggucaggcug gucuugaaau gcuggcguca 3240
agugaucugc cugccuccgc cucacaaagc acugggauua caggcaugaa ucuggccuua 3300
cguaauauau uuucuuaaug gcugcauaau aucacaucaa auaggcauuu uucaaaccuc 3360
uuuccuuauu aaacauguag acuauaucca uuuuuuacua aaauaaauaa cauuucagau 3420
aauaucuuug cacugauaau guugccaagc cauuucuaaa gugaccuuau caauuuaauu 3480
accauuggau gaggguguug cuuucaucgc accauuguag auugucuuuu uuauuucaau 3540
uugcguuuau uuauaacugg uugcaaaggu acacagaaca cacgcuccuu caacuuaucu 3600
uugauaaacc caagcaagga uacaaaaagu uggacgacau ugaguagagu caugguauac 3660
ggugcugacc cuacaguauc aguggaaaag auaaggaaaa ugucacuacu caccuauguu 3720
augcaaaaca guuaggugug cuggggcugg auacugcucu uuuacuugag cauugguuga 3780
uuaaaguuua gguaccaucc aggcuggucu agagaagucu uuggaguuaa ccaugcucuu 3840
uuuguuaaag aagagaguaa uguguuuauc cuggcucaua guccgucacc gaaaauagaa 3900
aaugccaucc auagguaaaa ugcugaccua uagaaaaaaa ugaacucuac uuuuauagcc 3960
uaguaaaaau gcucuaccug aguaguuaaa agcaauucau gaagccugaa gcuaaagagc 4020
acucugaugg uuuuggcaua auagcugcau uuccagaccu gaccuuuggc cccaaccaca 4080
agugcuccaa gccccaccag cugaccaaag aaagcccaag uucuccuucu guccuuccca 4140
caaccucccu gcucccaaaa cuaugaaauu aauuugacca uauuaacaca gcugacuccu 4200
ccaguuuacu uaagguagaa agaaugaguu uacaacagau gaaaauaagu gcuuugggcg 4260
aacuguauuc cuuuuaacag auccaaacua uuuuacauuu aaaaaaaaag uuaaacuaaa 4320
cuucuuuacu gcugauaugu uuccuguauu cuagaaaaau uuuuacacuu ucacauuauu 4380
uuuguacacu uuccccaugu uaagggauga uggcuuuuau aaaugugauu ucauuaaaug 4440
uuacuuuaaa aaua 4454

<210> SEQ ID NO 35
<211> LENGTH: 3150
<212> TYPE: RNA
<213> ORGANISM: HUMAN

<400> SEQUENCE: 35
ccacaaaggg cacuuggccc cagggcuagg agagcgaggg gagagcacag ccacccgccu 60
cggcggcccg ggacucggcu cgacucgccg gagaaugcgc ccgaggacga cggggcgcca 120
gagccgcggu gcuuucaacu ggcgagcgcg aaugggggug cacuggagua aggcagagug 180
augcgggggg gcaacucgcc uggcaccgag aucgccgccg ugcccuuccc uggacccggc 240
gucgcccagg auggcugccc cgagccaugg gccgcggcgg agcuagcgcg gagcgcccga 300
cccucgaccc ccgagucccg gagccggccc cgcgcggggc cacgcguccc ucgggcgcug 360
guuccuaagg aggacgacag caccagcuuc uccuuucucc cuucccuucc cugccccgca 420 cuccucccc ugcucgcugu uguugugugu cagcacuugg cuggggacuu cuugaacuug 480
cagggagaau aacuugcgca ccccacuuug cgccggugcc uuugccccag cggagccugc 540
uucgccaucu ccgagcccca ccgccccucc acuccucggc cuugcccgac acugagacgc 600
uguucccagc gugaaaagag agacugcgcg gccggcaccc gggagaagga ggaggcaaag 660

-continued

```
aaaaggaacg gacauucggu ccuugcgcca gguccuuuga ccagaguuuu uccaugugga    720
cgcucuuuca auggacgugu ccccgcgugc uucuuagacg gacugcgguc uccuaaaggu    780
cgaccauggu ggccgggacc cgcugucuuc uagcguugcu gcuuccccag guccuccugg    840
gcggcgcggc uggccucguu ccggagcugg gccgcaggaa guucgcggcg gcgucgucgg    900
gccgccccuc aucccagccc ucugacgagg uccugagcga guucgaguug cggcugcuca    960
gcauguucgg ccugaaacag agacccaccc ccagcaggga cgccguggug cccccuaca   1020
ugcuagaccu guaucgcagg cacucagguc agccgggcuc acccgcccca gaccaccggu   1080
uggagagggc agccagccga gccaacacug ugcgcagcuu ccaccaugaa gaaucuuugg   1140
aagaacuacc agaaacgagu gggaaaacaa cccggagauu cuucuuuaau uuaaguucua   1200
uccccacgga ggaguuuauc accucagcag agcuucaggu uuuccgagaa cagaugcaag   1260
augcuuuagg aaacaauagc aguuuccauc accgaauuaa uauuuaugaa aucauaaaac   1320
cugcaacagc caacucgaaa uuccccguga ccagacuuuu ggacaccagg uuggugaauc   1380
agaaugcaag cagguggaa aguuuugaug ucacccccgc ugugaugcgg uggacugcac   1440
agggacacgc caaccaugga uucguggugg aaguggccca cuuggaggag aaacaaggug   1500
ucuccaagag acauguuagg auaagcaggu cuuugcacca agaugaacac agcuggucac   1560
agauaaggcc auugcuagua acuuuuggcc augauggaaa agggcauccu cuccacaaaa   1620
gagaaaaacg ucaagccaaa cacaaacagc ggaaacgccu uaaguccagc uguaagagac   1680
acccuuugua cguggacuuc agugacgugg gguggaauga cuggauugug gcucccccgg   1740
gguaucacgc cuuuuacugc cacggagaau gcccuuuucc ucuggcugau caucugaacu   1800
ccacuaauca ugccauuguu cagacguugg ucaacucugu uaacucuaag auuccuaagg   1860
caugcugugu cccgacagaa cucagugcua ucucgaugcu guaccuugac gagaaugaaa   1920
agguuguauu aaagaacuau caggacaugg uuguggaggg uuguggggu cgcuaguaca   1980
gcaaaauuaa auacauaaau auauauauau auauauauuu uagaaaaaag aaaaaaacaa   2040
acaaacaaaa aaaccccacc ccaguugaca cuuuaauauu ucccaaugaa gacuuuauuu   2100
auggaaugga auggaaaaaa aaacagcuau uuugaaaaua uauuuauauc uacgaaaaga   2160
aguugggaaa acaaauauuu uaaucagaga auuauuccuu aaagauuuaa aauguauuua   2220
guuguacauu uuauaugggu ucaaccccag cacaugaagu auaaugguca gauuuauuuu   2280
guauuuauuu acuauuauaa ccacuuuuua ggaaaaaaau agcuaauuug uauuuuauaug   2340
uaaucaaaag aaguaucggg uuuguacaua auuuuccaaa aauuguaguu guuuucaguu   2400
gugugauuu aagaugaaaa gucuacaugg aagguuacuc uggcaaagug cuuagcacgu   2460
uugcuuuuuu gcagugcuac uguugaguuc acaaguucaa guccagaaaa aaaaagugga   2520
uaauccacuc ugcugacuuu caagauuauu auauuauuca auucucagga auguugcaga   2580
gugauugucc aauccaugag aauuuacauc cuuauuaggu ggaauauuug gauaagaacc   2640
agacauugcu gaucuauuau agaaacucuc cuccugcccc uuaauuuaca gaaagaauaa   2700
agcaggaucc auagaaauaa uuaggaaaac gaugaaccug caggaaagug aaugaugguu   2760
uguuguucuu cuuuccuaaa uuagugaucc cuucaaaggg gcugaucugg ccaaaguauu   2820
caauaaaacg uaagauuucu ucauuauuga uauuguggc auauauauuu aaaauugaua   2880
ucucguggcc cucaucaagg guuggaaauu uauuuguguu uuaccuuuac cucaucugag   2940
agcucuuuau ucuccaaaga acccaguuuu cuaacuuuuu gcccaacacg cagcaaaauu   3000
augcacaucg uguuucugc ccacccucug uucucugacc uaucagcuug cuuuucuuuc    3060
```

caagguugug uguuugaaca cauuucucca aauguuaaac cuauuucaga uaauaaauau 3120
caaaucucug gcauuucauu cuauaaaguc 3150

<210> SEQ ID NO 36
<211> LENGTH: 3130
<212> TYPE: RNA
<213> ORGANISM: HUMAN

<400> SEQUENCE: 36
gagucagugg cuugaaacuu uuaaaagcuc ugugcuccaa guuacaaaaa agcuuuuacg 60
agguaucagc acuuuucuuu cauuaggggg aaggcgugag gaaaguacca aacagcagcg 120
gaguuuuaaa cuuuaaauag acaggucuga gugccugaac uugccuuuuc auuuuacuuc 180
auccuccaag gaguucaauc acuuggcgug acuucacuac uuuuaagcaa aagaguggug 240
cccaggcaac augggugacu ggagcgccuu aggcaaacuc cuugacaagg uucaagccua 300
cucaacugcu ggagggaagg uguggcuguc aguacuuuuc auuuuccgaa uccugcugcu 360
ggggacagcg guugagucag ccuggggaga ugagcagucu gccuuucguu guaacacuca 420
gcaaccuggu ugugaaaaug ucugcuauga caagucuuuc ccaaucucuc augugcgcuu 480
cuggguccug cagaucauau uugugucugu acccacacuc uuguaccugg cucauguguu 540
cuaugugaug cgaaaggaag agaaacugaa caagaaagag gaagaacuca agguugccca 600
aacugauggu gucaauugugg acaugcacuu gaagcagauu gagauaaaga aguucaagua 660
cgguauugaa gagcauggua aggugaaaau gcgagggggg uugcugcgaa ccuacaucau 720
caguauccuc uucaagucua ucuuugaggu ggccuucuug cugauccagu gguacaucua 780
uggauucagc uugagugcug uuuacacuug caaaagagau cccugcccac aucaggugga 840
cuguuuccuc ucucgcccca cggagaaaac caucuucauc aucuucaugc ugguggugguc 900 cuuggugucc cuggccuuga auaucauuga acucuucuau guuuucuuca agggcguuaa 960
ggaucggguu aagggaaaga gcgacccuua ccaugcgacc aguggugcgc ugagcccugc 1020
caaagacugu gggucucaaa aauaugcuua uuucaauggc ugcuccucac caaccgcucc 1080
ccucucgccu augucuccuc cuggguacaa gcugguuacu ggcgacagaa acaauucuuc 1140
uugccgcaau uacaacaagc aagcaaguga gcaaaacugg gcuaauuaca gugcagaaca 1200
aaaucgaaug gggcaggcgg gaagcaccau cucuaacucc caugcacagc cuuuugauuu 1260
ccccgaugau aaccagaauu cuaaaaaacu agcugcugga caugaauuac agccacuagc 1320
cauuguggac cagcgaccuu caagcagagc cagcagucgu gccagcagca gaccucggcc 1380
ugaugaccug gagaucuaga uacaggcuug aaagcaucaa gauuccacuc aauuguggag 1440
aagaaaaaag gugcuguaga aagugcacca gguguuaauu uugauccggu ggagguggua 1500
cucaacagcc uuauucauga ggcuuagaaa acacaaagac auuagaauac cuagguucac 1560 uggggguga uggggguagau ggguggagag ggaggggaua agagaggugc auguugguau 1620
uuaaaguagu ggauucaaag aacuuagauu auaaauaaga guuccauuag gugauacaua 1680
gauaagggcu uuuucucccc gcaaacaccc cuaagaaugg uucuguguau gugaaugagc 1740
gggugguaau uguggcuaaa uauuuuuguu uuaccaagaa acugaaauaa uucuggccag 1800
gaauaaauac uuccugaaca ucuuaggucu uuucaacaag aaaaagacag aggauugucc 1860
uuaagucccu gcuaaaacau uccauuguua aaauuugcac uuugaaggua agcuuucuag 1920
gccugacccu ccaggugucca auggacuugu gcuacuauau uuuuuuauuc uugguaucag 1980
uuuaaaauuc agacaaggcc cacagaauaa gauuuuccau gcauuugcaa auacguauau 2040

-continued

```
ucuuuuucca uccacuugca caauaucauu accaucacuu uuucaucauu ccucagcuac   2100

uacucacauu cauuuaaugg uuucuguaaa cauuuuuaag acaguuggga ugucacuuaa   2160

cauuuuuuuu uugagcuaaa gucagggaau caagccaugc uuaauauuua acaaucacuu   2220

auaugugugu cgaagaguuu guuuuguuug ucauguauug guacaagcag auacaguaua   2280

aacucacaaa cacagauuug aaaauaaugc acauauggug uucaaauuug aaccuuucuc   2340

auggauuuuu gugguguggg ccaauauggu guuuacauua uauaauuccu gcuguggcaa   2400

guaaagcaca cuuuuuuuuu cuccuaaaau guuuuucccu guguauccua uuauggauac   2460

ugguuuuguu aauuaugauu cuuuauuuuc ucuccuuuuu uuaggauaua gcaguaaugc   2520

uauuacugaa augaauuucc uuuuucugaa auguaaucau ugaugcuuga augauagaau   2580

uuuaguacug uaaacaggcu uuagucauua augugagaga cuuagaaaaa augcuuagag   2640

uggacuauua aaugugccua aaugaauuuu gcaguaacug guauucuugg guuuuccuac   2700

uuaauacaca guaauucaga acuuguauuc uauuaugagu uuagcagucu uuuggaguga   2760

ccagcaacuu ugauguuugc acuaagauuu uauuuggaau gcaagagagg uugaaagagg   2820

auucaguagu acacauacaa cuaauuuauu ugaacuauau guugaagaca ucuaccaguu   2880

ucuccaaaug ccuuuuuuaa aacucaucac agaagauugg ugaaaaugcu gaguaugaca   2940

cuuuucuucu ugcaugcaug ucagcuacau aaacaguuuu guacaaugaa aauuacuaau   3000

uuguuugaca uuccauguua aacuacgguc auguucagcu ucauugcaug uaauguagac   3060

cuaguccauc agaucaugug uucuggagag uguucuuuau ucaauaaagu uuuaauuuag   3120

uauaaacaua                                                          3130
```

```
<210> SEQ ID NO 37
<211> LENGTH: 572
<212> TYPE: RNA
<213> ORGANISM: HUMAN

<400> SEQUENCE: 37

agacuuccuc cuucacuugc cuggacgcug cgccacaucc caccggcccu uacacugugg     60

uguccagcag cauccggcuu caugggggga cuugaacccu gcagcaggcu ccugcuccug    120

ccucuccugc uggcuguaag ugauugcagu ugcucuacgg ugagcccggg cgugcuggca    180

gggaucguga ugggagaccu ggugcugaca gugcucauug cccuggccgu guacuuccug    240

ggccggcugg ucccucgggg gcgagggggcu gcggaggcga cccggaaaca gcguaucacu    300

gagaccgagu cgccuuauca ggagcuccag ggucagaggu cggaugucua cagcgaccuc    360

aacacacaga ggccguauua caaaugagcc cgaaucauga cagucagcaa caugauaccu    420

ggauccagcc auuccugaag cccacccugc accucauucc aacuccuacc gcgauacaga    480

cccacagagu gccaucccug agagaccaga ccgcucccca auacucuccu aaaauaaaca    540

ugaagcacaa aaacaaaaaa aaaaaaaaaa aa                                  572
```

```
<210> SEQ ID NO 38
<211> LENGTH: 605
<212> TYPE: RNA
<213> ORGANISM: HUMAN

<400> SEQUENCE: 38

agacuuccuc cuucacuugc cuggacgcug cgccacaucc caccggcccu uacacugugg     60

uguccagcag cauccggcuu caugggggga cuugaacccu gcagcaggcu ccugcuccug    120

ccucuccugc uggcuguaag uggucuccgu ccuguccagg cccaggccca gagcgauugc    180
```

aguugcucua cggugagccc gggcgugcug gcagggaucg ugaugggaga ccuggugcug 240
acagugcuca uugcccuggc cguguacuuc cugggccggc ugguccc ucg ggggcgaggg 300 gcugcggagg cgacccggaa acagcguauc acugagaccg agucgccuua ucaggagcuc 360
cagggucaga ggucggaugu cuacagcgac cucaacacac agaggccgua uuacaaauga 420
gcccgaauca ugacagucag caacaugaua ccuggaucca gccauuccug aagcccaccc 480
ugcaccucau uccaacuccu accgcgauac agacccacag agugccaucc cugagagacc 540
agaccgcucc ccaauacucu ccuaaaauaa acaugaagca caaaaacaaa aaaaaaaaaa 600
aaaaa 605

<210> SEQ ID NO 39
<211> LENGTH: 608
<212> TYPE: RNA
<213> ORGANISM: HUMAN

<400> SEQUENCE: 39
agacuuccuc cuucacuugc cuggacgcug cgccacaucc caccggcccu uacacugugg 60
uguccagcag cauccggcuu caugggggga cuugaacccu gcagcaggcu ccugcuccug 120
ccucuccugc uggcuguaag uggucuccgu ccuguccagg cccaggccca gagcgauugc 180
aguugcucua cggugagccc gggcgugcug gcagggaucg ugaugggaga ccuggugcug 240
acagugcuca uugcccuggc cguguacuuc cugggccggc ugguccc ucg ggggcgaggg 300 gcugcggagg cagcgacccg gaaacagcgu aucacugaga ccgagucgcc uuaucaggag 360
cuccaggguc agaggucgga ugucuacagc gaccucaaca cacagaggcc guauuacaaa 420
ugagcccgaa ucaugacagu cagcaacaug auaccuggau ccagccauuc cugaagccca 480
cccugcaccu cauuccaacu ccuaccgcga uacagaccca cagagugcca ucccugagag 540
accagaccgc uccccaauac ucuccuaaaa uaaacaugaa gcacaaaaac aaaaaaaaaa 600
aaaaaaaa 608

<210> SEQ ID NO 40
<211> LENGTH: 575
<212> TYPE: RNA
<213> ORGANISM: HUMAN

<400> SEQUENCE: 40
agacuuccuc cuucacuugc cuggacgcug cgccacaucc caccggcccu uacacugugg 60
uguccagcag cauccggcuu caugggggga cuugaacccu gcagcaggcu ccugcuccug 120
ccucuccugc uggcuguaag ugauugcagu ugcucuacgg ugagcccggg cgugcuggca 180
gggaucguga ugggagaccu ggugcugaca gugcucauug cccuggccgu guacuuccug 240
ggccggcugg ucccucgggg gcgaggggcu gcggaggcag cgacccggaa acagcguauc 300
acugagaccg agucgccuua ucaggagcuc cagggucaga ggucggaugu cuacagcgac 360
cucaacacac agaggccgua uuacaaauga gcccgaauca ugacagucag caacaugaua 420
ccuggaucca gccauuccug aagcccaccc ugcaccucau uccaacuccu accgcgauac 480
agacccacag agugccaucc cugagagacc agaccgcucc ccaauacucu ccuaaaauaa 540
acaugaagca caaaaacaaa aaaaaaaaaa aaaaa 575

<210> SEQ ID NO 41
<211> LENGTH: 2358
<212> TYPE: RNA
<213> ORGANISM: HUMAN

<400> SEQUENCE: 41

```
aaacucacac aacaacucuu ccccgcugag aggagacagc cagugcgacu ccacccucca     60
gcucgacggc agccgccccg gccgacagcc ccgagacgac agcccggcgc gucccggucc    120
ccaccuccga ccaccgccag cgcuccaggc cccgccgcuc cccgcucgcc gccaccgcgc    180
ccuccgcucc gcccgcagug ccaaccauga ccgccgccag uaugggcccc guccgcgucg    240
ccuucguggu ccuccucgcc cucugcagcc ggccggccgu cggccagaac ugcagcgggc    300
cgugccggug cccggacgag ccggcgccgc gcugcccggc gggcgugagc cucgugcugg    360
acggcugcgg cugcugccgc gucugcgcca agcagcuggg cgagcugugc accgagcgcg    420
accccugcga cccgcacaag ggccucuucu gugacuucgg cuccccggcc aaccgcaaga    480
ucggcgugug caccgccaaa gauggugcuc ccugcaucuu cggugguacg guguaccgca    540
gcggagaguc cuuccagagc agcugcaagu accagugcac gugccuggac ggggcggugg    600
gcugcaugcc ccugugcagc auggacguuc gucugcccag cccugacugc cccuucccga    660
ggagggucaa gcugcccggg aaaugcugcg aggagugggu gugugacgag cccaaggacc    720
aaaccguggu ugggccugcc cucgcggcuu accgacugga agacacguuu ggcccagacc    780
caacuaugau uagagccaac ugccuggucc agaccacaga guggagcgcc uguuccaaga    840
ccugugggau gggcaucucc acccggguua ccaaugacaa cgccuccugc aggcuagaga    900
agcagagccg ccugugcaug gucaggccuu gcgaagcuga ccuggaagag aacauuaaga    960
agggcaaaaa gugcauccgu acucccaaaa ucuccaagcc uaucaaguuu gagcuuucug   1020
gcugcaccag caugaagaca uaccgagcua aauucugugg aguauguacc gacggccgau   1080
gcugcacccc ccacagaacc accacccugc cgguggaguu caagugcccu gacggcgagg   1140
ucaugaagaa gaacaugaug uucaucaaga ccugugccug ccauuacaac ugucccggag   1200
acaaugacau cuuugaaucg cuguacuaca ggaagaugua cggagacaug gcaugaagcc   1260
agagagugag agacauuaac ucauuagacu ggaacuugaa cugauucaca ucucauuuuu   1320
ccguaaaaau gauuucagua gcacaaguua uuuaaaucug uuuuucuaac uggggggaaaa  1380
gauucccacc caauucaaaa cauugugcca ugucaaacaa auagucuauc aaccccagac   1440
acugguuuga agaauguuaa gacuugacag uggaacuaca uuaguacaca gcaccagaau   1500
guauauuaag guguggcuuu aggagcagug ggaggguacc agcagaaagg uuaguaucau   1560
cagauagcau cuuauacgag uaauaugccu gcuauuugaa guguaauuga gaaggaaaau   1620
uuuagcgugc ucacugaccu gccuguagcc ccagugacag cuaggaugug cauucuccag   1680
ccaucaagag acugagucaa guuguuccuu aagucagaac agcagacuca gcucugacau   1740
ucugauucga augacacugu ucaggaaucg gaauccuguc gauuagacug gacagcuugu   1800
ggcaagugaa uuugccugua acaagccaga uuuuuuaaaa uuuauauugu aaauauugug   1860
ugugugugug uguguguaua uauauauaua uguacaguua ucuaaguuaa uuuaaaguug   1920
uuugugccuu uuuauuuuug uuuuuaaugc uuugauauuu caauguuagc cucaauuucu   1980
gaacaccaua gguagaaugu aaagcuuguc ugaucguuca aagcaugaaa uggauacuua   2040
uauggaaauu cugcucagau agaaugacag uccgucaaaa cagauuguuu gcaaagggga   2100
ggcaucagug uccuuggcag gcugauuucu agguaggaaa ugugguagcc ucacuuuuaa   2160
ugaacaaaug gccuuuauua aaaacugagu gacucuauau agcugaucag uuuuuucacc   2220
uggaagcauu uguuucuacu uugauaugac uguuuuucgg acaguuuauu uguugagagu   2280
gugaccaaaa guuacauguu ugcaccuuuc uaguugaaaa uaaaguguau auuuuuucua   2340
```

uaaaaaaaaa aaaaaaaa 2358

<210> SEQ ID NO 42
<211> LENGTH: 1641
<212> TYPE: RNA
<213> ORGANISM: HUMAN

<400> SEQUENCE: 42
cucccugugu ugguggagga ugucugcagc agcauuuaaa uucugggagg gcuugguugu 60
cagcagcagc aggaggaggc agagcacagc aucgucggga ccagacucgu cucaggccag 120
uugcagccuu cucagccaaa cgccgaccaa ggaaaacuca cuaccaugag aauugcagug 180
auuugcuuuu gccuccuagg caucaccugu gccauaccag uuaaacaggc ugauucugga 240
aguucugagg aaaagcagcu uuacaacaaa uacccagaug cuguggccac auggcuaaac 300
ccugacccau cucagaagca gaaucuccua gccccacaga augcugguc cucugaagaa 360 accaaugacu uuaaacaaga gacccuucca aguaagucca acgaaagcca ugaccacaug 420
gaugauaugg augaugaaga ugaugaugac cauguggaca gccaggacuc cauugacucg 480
aacgacucug augauguaga ugacacugau gauucucacc agucugauga gucucaccau 540
ucugaugaau cugaugaacu ggucacugau uuucccacgg accugccagc aaccgaaguu 600
uucacuccag uuguccccac aguagacaca uaugauggcc gaggugauag uguggguuau 660
ggacugaggu caaaaucuaa gaaguuucgc agaccugaca uccaguaccc ugaugcuaca 720
gacgaggaca ucaccucaca cauggaaagc gaggaguuga auggugcaua caaggccauc 780
cccguugccc aggaccugaa cgcgccuucu gauuggggaca gccgugggaa ggacaguuau 840
gaaacgaguc agcuggauga ccagagugcu gaaacccaca gccacaagca guccagauua 900
uauaagcgga aagccaauga ugagagcaau gagcauuccg augugauuga uagucaggaa 960
cuuuccaaag ucagccguga auuccacagc caugaauuuc acagccauga agauaugcug 1020
guuguagacc ccaaaaguaa ggaagaagau aaacaccuga aauuucguau uucucaugaa 1080
uuagauagug caucuucuga ggucaauuaa aaggagaaaa aauacaauuu cucacuuugc 1140
auuuagucaa aagaaaaaau gcuuuauagc aaaaugaaag agaacaugaa augcuucuuu 1200
cucaguuuau ugguugaaug uguaucuauu ugagucugga aauaacuaau guguuugaua 1260
auuaguuuag uuuguggcuu cauggaaacu cccuguaaac uaaaagcuuc aggguuaugu 1320
cuauguucau ucuauagaag aaaugcaaac uaucacugua uuuuaauauu uguuauucuc 1380
ucaugaauag aaauuuaugu agaagcaaac aaaauacuuu uacccacuua aaaagagaau 1440
auaacauuuu augucacuau aaucuuuugu uuuuuaaguu aguguauauu uuguugugau 1500
uaucuuuuug uggugugaau aaaucuuuua ucuugaaugu aauaagaauu ugguggugue 1560 aauugcuuau uuguuuuccc acgguugucc agcaauuaau aaaacauaac cuuuuuuacu 1620
gccuaaaaaa aaaaaaaaaa a 1641

<210> SEQ ID NO 43
<211> LENGTH: 1616
<212> TYPE: RNA
<213> ORGANISM: HUMAN

<400> SEQUENCE: 43
cucccugugu ugguggagga ugucugcagc agcauuuaaa uucugggagg gcuugguugu 60
cagcagcagc aggaggaggc agagcacagc aucgucggga ccagacucgu cucaggccag 120
uugcagccuu cucagccaaa cgccgaccaa ggaaaacuca cuaccaugag aauugcagug 180
auuugcuuuu gccuccuagg caucaccugu gccauaccag uuaaacaggc ugauucugga 240
aguucugagg aaaagcagcu uuacaacaaa uacccagaug cuguggccac auggcuaaac 300
ccugacccau cucagaagca gaaucuccua gccccacaga cccuuccaag uaaguccaac 360
gaaagccaug accacaugga ugauauggau gaugaagaug augaugacca uguggacagc 420
caggacucca uugacucgaa cgacucugau gauguagaug acacugauga uucucaccag 480
ucugaugagu cucaccauuc ugaugaaucu gaugaacugg ucacugauuu ucccacggac 540
cugccagcaa ccgaaguuuu cacuccaguu guccccacag uagacacaua ugauggccga 600
ggugauagug ugguuuaugg acugagguca aaaucuaaga aguuucgcag accugacauc 660
caguacccug augcuacaga cgaggacauc accucacaca uggaaagcga ggaguugaau 720
ggugcauaca aggccauccc cguugcccag gaccugaacg cgccuucuga uugggacagc 780
cgugggaagg acaguuauga aacgagucag cuggaugacc agagugcuga aacccacagc 840
cacaagcagu ccagauuaua uaagcggaaa gccaaugaug agagcaauga gcauuccgau 900
gugauugaua gucaggaacu uuccaaaguc agccgugaau uccacagcca ugaauuucac 960
agccaugaag auaugcuggu uguagacccc aaaaguaagg aagaagauaa acaccugaaa 1020
uuucguauuu cucaugaauu agauagugca ucuucugagg ucaauuaaaa ggagaaaaaa 1080
uacaauuucu cacuuugcau uuagucaaaa gaaaaaaugc uuuauagcaa aaugaaagag 1140
aacaugaaau gcuucuuucu caguuuauug guugaaugug uaucuauuug agucuggaaa 1200
uaacuaaugu guuugauaau uaguuuaguu uguggcuuca uggaaacucc cuguaaacua 1260
aaagcuucag gguuaugucu auguucauuc uauagaagaa augcaaacua ucacuguauu 1320
uuaauauuug uuauucucuc augaauagaa auuuauguag aagcaaacaa aauacuuuua 1380
cccacuuaaa aagagaauau aacauuuuau gucacuauaa ucuuuuguuu uuuaaguuag 1440
uguauauuuu guugugauua ucuuuuugug gugugaauaa aucuuuuauc uugaauguaa 1500
uaagaauuug gugguguaa uugcuuauuu guuuucccac gguuguccag caauuaauaa 1560
aacauaaccu uuuuuacugc cuaaaaaaaa aaaaaaaaaa aaaaaaaaaa aaaaaa 1616

<210> SEQ ID NO 44
<211> LENGTH: 1560
<212> TYPE: RNA
<213> ORGANISM: HUMAN

<400> SEQUENCE: 44
cucccugugu ugguggagga ugucugcagc agcauuuaaa uucugggagg gcuugguugu 60
cagcagcagc aggaggaggc agagcacagc aucgucggga ccagacucgu cucaggccag 120
uugcagccuu cucagccaaa cgccgaccaa ggaaaacuca cuaccaugag aauugcagug 180
auuugcuuuu gccuccuagg caucaccugu gccauaccag uuaaacaggc ugauucugga 240
aguucugagg aaaagcagaa ugcugugucc ucugaagaaa ccaaugacuu uaaacaagag 300
acccuuccaa guaaguccaa cgaaagccau gaccacaugg augauaugga ugaugaagau 360
gaugaugacc auguggacag ccaggacucc auugacucga acgacucuga ugauguagau 420
gacacugaug auucucacca gucugaugag ucucaccauu cugaugaauc ugaugaacug 480
gucacugauu uucccacgga ccugccagca accgaaguuu ucacuccagu uguccccaca 540
guagacacau augauggccg aggugauagu gugguuuaug gacugagguc aaaaucuaag 600
aaguuucgca gaccugacau ccaguacccu gaugcuacag acgaggacau caccucacac 660
auggaaagcg aggaguugaa uggugcauac aaggccaucc ccguugccca ggaccugaac 720
gcgccuucug auugggacag ccgugggaag gacaguuaug aaacgaguca gcuggaugac 780
cagagugcug aaacccacag ccacaagcag uccagauuau auaagcggaa agccaaugau 840
gagagcaaug agcauuccga ugugauugau agucaggaac uuuccaaagu cagccgugaa 900
uuccacagcc augaauuuca cagccaugaa gauaugcugg uuguagaccc caaaaguaag 960
gaagaagaua aacaccugaa auuucguauu ucucaugaau uagauagugc aucuucugag 1020
gucaauuaaa aggagaaaaa auacaauuuc ucacuuugca uuuagucaaa agaaaaaaug 1080
cuuuauagca aaaugaaaga gaacaugaaa ugcuucuuuc ucaguuuauu gguugaaugu 1140
guaucuauuu gagucuggaa auaacuaaug uguuugauaa uuaguuuagu uuguggcuuc 1200
auggaaacuc ccuguaaacu aaaagcuuca ggguuauguc uauguucauu cuauagaaga 1260
aaugcaaacu aucacuguau uuuaauauuu guuauucucu caugaauaga aauuuaugua 1320
gaagcaaaca aaauacuuuu acccacuuaa aaagagaaua uaacauuuua ugucacuaua 1380
aucuuuuguu uuuuaaguua guguauauuu uguugugauu aucuuuuugu ggugugaaua 1440
aaucuuuuau cuugaaugua auaagaauuu ggugguguca auugcuuauu uguuuuccca 1500
cgguugucca gcaauuaaua aaacauaacc uuuuuuacug ccuaaaaaaa aaaaaaaaaa 1560

<210> SEQ ID NO 45
<211> LENGTH: 1926
<212> TYPE: RNA
<213> ORGANISM: HUMAN

<400> SEQUENCE: 45
guggaugagc ugugagugcg cgcgcgugcg cggggccgcg accugugccg gcucgagccc 60
gcugggcacu cggaggcgcg cacgucguuc cccgcccucc cgccgccgcc cgcccucgcu 120
cucucgcgcu acccucccgc cgcccgcggu ccuccgucgg uucucucguu aguccacggu 180
cuggucuuca gcuacccgcc uucgucuccg aguuugcgac ucgcggaccg gcguccccgg 240
cgcgaagagg cuggacucgg auucguugcc ugagcaaugg cugccauccg gaagaaacug 300
gugauuguug gugauggagc cuguggaaag acaugcuugc ucauagucuu cagcaaggac 360
caguucccag agguguaugu gcccacagug uuugagaacu auguggcaga uaucgaggug 420
gauggaaagc agguagaguu ggcuuugugg gacacagcug ggcaggaaga uuaugaucgc 480
cugaggcccc ucuccuaccc agauaccgau guuauacuga uguguuuuuc caucgacagc 540
ccugauaguu uagaaaacau cccagaaaag uggaccccag aagucaagca uuucuguccc 600
aacgugccca ucauccuggu ugggaauaag aaggaucuuc ggaaugauga gcacacaagg 660
cgggagcuag ccaagaugaa gcaggagccg gugaaaccug aagaaggcag agauauggca 720
aacaggauug gcgcuuuugg guacauggag uguucagcaa agaccaaaga uggagugaga 780
gagguuuuug aaauggcuac gagagcugcu cugcaagcua gacgugggaa gaaaaaaucu 840
gggugccuug ucuugugaaa ccuugcugca agcacagccc uuaugcgguu aauuuugaag 900
ugcuguuuau uaaucuuagu guaugauuac uggccuuuuu cauuuaucua uaauuuaccu 960
aagauuacaa aucagaaguc aucuugcuac caguauuuag aagccaacua ugauuauuaa 1020
cgauguccaa cccgucuggc ccaccagggu ccuuuugaca cugcucuaac agcccuccuc 1080
ugcacuccca ccugacacac caggcgcuaa uucaaggaau uucuuaacuu cuugcuucuu 1140
ucuagaaaga gaaacaguug guaacuuuug ugaauuaggc uguaacuacu uuauaacuaa 1200
cauguccugc cuauuaucug ucagcugcaa gguacucugg ugagucacca cuucagggcu 1260
uuacuccgua acagauuuug uuggcauagc ucuggggugg gcaguuuuuu gaaaaugggc 1320

-continued ucaaccagaa aagcccaagu ucaugcagcu guggcagagu uacaguucug ugguuucaug 1380
uuaguuaccu uauaguuacu guguaauuag ugccacuuaa uguauguuac caaaaauaaa 1440
uauaucuacc ccagacuaga uguaguauuu uuuguauaau uggauuuccu aauacuguca 1500
uccucaaaga aaguguauug guuuuuuaaa aaagaaagug uauuuggaaa uaaagucaga 1560
uggaaaauuc auuuuuuaaa uucccguuuu gucacuuuuu cugauaaaag auggccauau 1620
uaccccuuuu cggccccaug uaucucagua ccccauggag cugggcuaag uaaauaggaa 1680
uugguuucac gccugaggca auuagacacu uuggaagaug gcauaaccug ucucaccugg 1740
acuuaagcau cuggcucuaa uucacagugc ucuuuucucc ucacuguauc cagguucccu 1800
cccagaggag ccaccaguuc ucaugggugg cacucagucu cucuucucuc cagcugacua 1860
aacuuuuuuu cuguaccagu uaauuuuucc aacuacuaau agaauaaagg caguuuucua 1920
aaaaaa 1926

<210> SEQ ID NO 46
<211> LENGTH: 5693
<212> TYPE: RNA
<213> ORGANISM: HUMAN

<400> SEQUENCE: 46
gcagagcugc agaggcaccg gacgagagag ggcuccgcgg gcccagcugg cagccaggcc 60
ggagacaagu ugcagucccg ggcucuggug acgccguggc cgcagcugga agaggaaaac 120
aaggaucaga uuggagaagu gauuuaucua agaucccaca guggacuggc agcagcacug 180
agaccucagc cuagucuccu gaucccccaag cagggcccug ccuaaggaac acacucugca 240
gagugcuggg ccaaagcagg guuuuccaac uaaucuuaga agguaaaguc caugaagggu 300
cuccauuuug ggacauucua aucccugagc cccuauuauu uucaucaugg gcuucugccu 360
ggcucuagca uggacacuuc ugguuggggc auggaccccu cugggagcuc agaaccccau 420
uucgugggag gugcagcgau uugaugggug guacaacaac cucauggagc acagaugggg 480
cagcaaaggc ucccggcugc agcgccuggu cccagccagc uaugcagaug gcguguacca 540
gcccuuggga gaaccccacc ugcccaaccc ccgagaccuu agcaacacca ucucaagggg 600
cccugcaggg cuggccuccc ugagaaaccg cacaguguug gggucuucu uuggcuauca 660 cgugcuuuca gaccugguga gcguggaaac ucccggcugc cccgccgagu uccucaacau 720
ucgcaucccg cccggagacc ccauguucga ccccgaccag cgcggggacg uggugcugcc 780
cuuccagaga agccgcuggg accccgagac cggacggagu cccagcaauc cccgggaccc 840
ggccaaccag gugacgggcu ggcuggacgg cagcgccauc uaugguuccu cgcauuccug 900
gagcgacgcg cugcggagcu ucuccagggg acagcuggcg ucggggcccg accccgcuuu 960
uccccgagac ucgcagaacc cccugcucau gugggcggcg cccgaccccg ccaccgggca 1020
gaacgggccc cgggggcugu acgccuucgg ggcagagaga gggaaccggg aacccuuccu 1080
gcaggcgcug ggccugcucu gguuccgcua ccacaaccug ugggcgcaga ggcuggcccg 1140
ccagcaccca gacugggagg acgaggagcu guuccagcac gcacgcaaga gggucaucgc 1200
caccuaccag aacaucgcug uguaugagug gcugcccagc uuccugcaga aaacacuccc 1260
ggaguauaca ggauaccggc cauuucugga ccccagcauc uccucagagu ucguggcggc 1320
cucugagcag uuccugucca ccauggugcc cccuggcguc uacaugagaa augccagcug 1380
ccacuuccag gggggucauca aucggaacuc aagugucucc agagcucucc gggucugcaa 1440
cagcuacugg agccgugagc acccaagccu acaaagugcu gaagaugugg augcacugcu 1500

-continued gcugggcaug gccucccaga ucgcagagcg agaggaccau guguugguug aagaugugcg 1560
ggauuucugg ccugggccac ugaaguuuuc ccgcacagac caccuggcca gcugccugca 1620
gcggggccgg gaucugggcc ugcccucuua caccaaggcc agggcagcac ugggcuuguc 1680
ucccauuacc cgcuggcagg acaucaaccc ugcacucucc cggagcaaug acacuguacu 1740
ggaggccaca gcugcccugu acaaccagga cuuauccugg cuagagcugc ucccuggggg 1800
acuccuggag agccaccggg acccuggacc ucuguucagc accaucgucc uugaacaauu 1860
ugugcggcua cgggauggug accgcuacug guuugagaac accaggaaug ggcuguucuc 1920
caagaaggag auugaagaaa uccgaaauac cacccugcag gacgugcugg ucgcuguuau 1980
caacauugac cccagugcuc ugcagcccaa ugucuuuguc uggcauaaag gagaccccug 2040
uccgcagccg agacagcuca gcacugaagg ccugccagcg ugugcucccu cuguuguucg 2100
ugacuauuuu gagggcagug gauuuggcuu cggggucacc aucgggaccc ucuguugcuu 2160
cccuuuggug agccugcuca gugccuggau uguugcccgg cuccggauga gaaauuucaa 2220
gaggcuccag ggccaggacc gccagagcau cgugucugag aagcucgugg gaggcaugga 2280
agcuuuggaa uggcaaggcc acaaggagcc cugccggccc gugcuugugu accugcagcc 2340
cgggcagauc cguguggguag auggcaggcu caccgugcuc cgcaccaucc agcugcagcc 2400
uccacagaag gucaacuucg uccuguccag caaccgugga cgccgcacuc ugcugcucaa 2460
gauccccaag gaguaugacc uggugcugcu guuuaacuug gaggaagagc ggcaggcgcu 2520
gguggaaaau cuccggggag cucugaagga gagcggguug agcauccagg agugggagcu 2580
gcgggagcag gagcugauga gagcagcugu gacacgggag cagcggaggc accuccugga 2640
gaccuuuuuc aggcaccuuu ucucccaggu gcuggacauc aaccaggccg acgcagggac 2700
ccugccccug gacuccuccc agaaggugcg ggaggcccug accugugagc ugagcagggc 2760
cgaguuugcc gagucccugg gccucaagcc ccaggacaug uuuguggagu ccauguucuc 2820
ucuggcugac aaggauggca auggcuaccu guccuuccga gaguuccugg acauccuggu 2880
ggucuucaug aaaggcucuc cugaggaaaa gucucgccuu auguuccgca uguacgacuu 2940
ugaugggaau ggccucauuu ccaaggauga guucaucagg augcugagau ccuucaucga 3000
gaucuccaac aacugccugu ccaaggccca gcuggcugag gugguggagu ccauguuccg 3060
ggagucggga uuccaggaca aggaggaacu gacaugggaa gauuuucacu ucaugcugcg 3120
ggaccacaau agcgagcucc gcuucacgca gcucugugucc aaaggggugg aggugccuga 3180
agucaucaag gaccucugcc ggcgagccuc cuacaucagc caggauaauga ucugucccuc 3240
ucccagagug agugcccgcu guucccgcag cgacauugag acugaguuga caccucagag 3300
acugcagugc cccauggaca cagacccucc ccaggagauu cggcggaggu uuggcaagaa 3360
gguaacguca uuccagcccu ugcuguucac ugaggcgcac cgagagaagu uccaacgcag 3420
cugucuccac cagacggugc aacaguucaa gcgcuucauu gagaacuacc ggcgccacau 3480
cggcugcgug gccguguucu acgccaucgc ugggggggcuu uuccuggaga gggccuacua 3540
cuacgccuuu gccgcacauc acacgggcau cacagacacc acccgcgugg gaaucauccu 3600
gucgcggggc acagcagcca gcaucucuuu cauguucucc uacaucuugc ucaccaugug 3660
ccgcaaccuc aucaccuucc ugcgagaaac cuuccucaac cgcuacgugc ccuucgacgc 3720
cgccguggac uuccaucgcc ucauugccuc caccgccauc guccucacag ucuuacacag 3780
uguggggccau guggugaaug uguaccuguu cuccaucagc cccccucagcg uccucucuug 3840
ccucuuuccu ggccucuucc augaugaugg gucugagcuc ccccagaagu auuacuggug 3900

```
guucuuccag accguaccag gccucacggg gguugugcug cuccugaucc uggccaucau   3960
guaugucuuu gccucccacc acuuccgccg ccgcaguuuc cggggcuucu ggcugaccca   4020
ccaccucuac auccugcucu auguccugcu caucauccau gguagcuuug cccugaucca   4080
gcugccccgu uuccacaucu ucuuccuggu cccagcaauc aucuaugggg gcgacaagcu   4140
ggugagccug agccggaaga agguggagau cagcguggug aaggcggagc ugcugcccuc   4200
aggagugacc caccugcggu uccagcggcc ccagggcuuu gaguacaagu cagggcagug   4260
ggugcggauc gcuugccugg cucuggggac caccgaguac caccccuuca cacugaccuc   4320
ugcgccccau gaggacacgc uuagccugca cauccgggca gcagggcccu ggaccacucg   4380
ccucagggag aucuacucag ccccgacggg ugacagaugu gccagauacc caaagcugua   4440
ccuugaugga ccauuuggag agggccacca ggaguggcau aaguuugagg ugucaguguu   4500
agugggaggg ggcauugggg ucaccccuuu ugccuccauc cucaaagacc uggucuucaa   4560
gucauccguc agcugccaag uguucuguaa gaagaucuac uucaucuggg ugacgcggac   4620
ccagcgucag uuugaguggc uggcugacau cauccgagag guggaggaga augaccacca   4680
ggaccuggug ucugugcaca ucuacaucac ccagcuggcu gagaaguucg accucaggac   4740
cacuaugcug uacaucugug agcggcacuu ccagaagguu cugaaccgga gucuauucac   4800
aggccugcgc uccaucaccc acuuuggccg ucccccuuu gagcccuucu ucaacucccu   4860
gcaggagguc cacccccagg uccggaagau cgggguguuu agcuguggcc ccccuggcau   4920
gaccaagaau guggaaaagg ccugucagcu caucaacagg caggaccgga cucacuucuc   4980
ccaccauuau gagaacuucu aggccccugc ccgggggguuc ugcccacugc ccaguugagc   5040
agagguuuga gcccacaccu caccucuguu cuuccuauuu cuggcugccu cagccuucuc   5100
ugauuuccca ccucccaacc uuguuccagg uggccauagu cagucaccau gugugggcuc   5160
agggaccccc aggaccagga ugugucucag ccuggagaaa ugguggggggg gcagugucua   5220
gggacuagag ugagaaguag gggagcuacu gauuuggggc aaagugaaac cucugcuucc   5280
agacuucaga aacaaaucuc agaagacaag cugaccugac aaguacuaug ugugugcaug   5340
ucuguaugug uguuggggcg gugaguguaa ggaugcagug ggagcaugga ugcuggcauc   5400
uuagaacccu cccuacuccc auaccuccuc cucuucuggg cuccccacug ucagacgggc   5460
uggcaaaugc cuugcaggag guagaggcug gacccauggc aagccauuua cagaaaccca   5520
cucggcaccc cagucuaaca ccacaacuaa uuucacccaa gguuuuaagc acguucuuuc   5580
aucagacccu ggcccaauac cuauguaugc aaugcuccuc agcccucuuc ucccugcucc   5640
aguagucucc cuuccaaaua aaucacuuuu cugccuuaaa aaaaaaaaaa aaa          5693
```

<210> SEQ ID NO 47
<211> LENGTH: 5501
<212> TYPE: RNA
<213> ORGANISM: HUMAN

<400> SEQUENCE: 47

```
gcagagcugc agaggcaccg gacgagagag ggcuccgcgg gcccagcugg cagccaggcc     60
ggagacaagu ugcagucccg ggcucuggug acgccgugge cgcagggucu ccauuuuggg    120
acauucuaau cccugagccc cuauuauuuu caucaugggc uucugccugg cucuagcaug    180
gacacuucug guuggggcau ggaccccucu gggagcucag aaccccauuu cgugggaggu    240
gcagcgauuu gauggguggu acaacaaccu cauggagcac agaugggca gcaaaggcuc    300
ccggcugcag cgccuggucc cagccagcua ugcagauggc guguaccagc ccuugggaga    360
```

-continued

```
accccaccug cccaaccccc gagaccuuag caacaccauc ucaaggggcc cugcagggcu    420
ggccucccug agaaaccgca caguguuggg ggucuucuuu ggcuaucacg ugcuuucaga    480
ccuggugagc guggaaacuc ccggcugccc cgccgaguuc cucaacauuc gcaucccgcc    540
cggagacccc auguucgacc ccgaccagcg cggggacgug gugcugcccu uccagagaag    600
ccgcugggac cccgagaccg gacggagucc cagcaauccc cgggacccgg ccaaccaggu    660
gacgggcugg cuggacggca gcgccaucua ugguuccucg cauuccugga gcgacgcgcu    720
gcggagcuuc uccaggggac agcuggcguc ggggcccgac cccgcuuuuc cccgagacuc    780
gcagaacccc cugcucaugu gggcggcgcc cgaccccgcc accgggcaga acgggccccg    840
ggggcuguac gccuucgggg cagagagagg gaaccgggaa cccuuccugc aggcgcuggg    900
ccugcucugg uuccgcuacc acaaccugug ggcgcagagg cuggcccgcc agcacccaga    960
cugggaggac gaggagcugu uccagcacgc acgcaagagg gucaucgcca ccuaccagaa   1020
caucgcugug uaugaguggc ugcccagcuu ccugcagaaa acacucccgg aguauacagg   1080
auaccggcca uuucuggacc ccagcaucuc cucagaguuc guggcggccu cugagcaguu   1140
ccuguccacc augguguccc cuggcgucua caugagaaau gccagcugcc acuuccaggg   1200
ggucaucaau cggaacucaa gugucuccag agcucuccgg gucugcaaca gcuacuggag   1260
ccgugagcac ccaagccuac aaagugcuga agauguggau gcacugcugc ugggcauggc   1320
cucccagauc gcagagcgag aggaccaugu guugguugaa gaugugcggg auuucuggcc   1380
ugggccacug aaguuucccc gcacagacca ccuggccagc ugccugcagc ggggccggga   1440
ucugggccug cccucuuaca ccaaggccag ggcagcacug ggcuugucuc ccauuacccg   1500
cuggcaggac aucaacccug cacucucccg gagcaaugac acuguacugg aggccacagc   1560
ugcccuguac aaccaggacu uauccuggcu agagcugcuc ccugggggac uccuggagag   1620
ccaccgggac ccuggaccuc uguucagcac caucguccuu gaacaauuug ugcggcuacg   1680
ggauggugac cgcuacuggu uugagaacac caggaauggg cuguucucca agaaggagau   1740
ugaagaaauc cgaaauacca cccugcagga cgugcugguc gcuguuauca acauugaccc   1800
cagugcucug cagcccaaug ucuuugucug gcauaaagga gaccccuguc cgcagccgag   1860
acagcucagc acugaaggcc ugccagcgug ugcucccucu guuguucgug acuauuuuga   1920
gggcagugga uuuggcuucg ggucaccau cgggacccuc uguugcuucc cuuuggugag   1980
ccugcucagu gccuggauug uugcccggcu ccggaugaga aauuucaaga ggcuccaggg   2040
ccaggaccgc cagagcaucg ugucugagaa gcucguggga ggcauggaag cuuuggaaug   2100
gcaaggccac aaggagcccu gccggcccgu gcuuguguac cugcagcccg ggcagauccg   2160
ugugguagau ggcaggcuca ccgugcuccg caccauccag cugcagccuc cacagaaggu   2220
caacuucguc cuguccagca accguggacg ccgcacucug cugcucaaga uccccaagga   2280
guaugaccug gugcugcugu uuaacuugga ggaagagcgg caggcgcugg uggaaaaucu   2340
ccggggagcu cugaaggaga gcggguugag cauccaggag ugggagcugc gggagcagga   2400
gcugaugaga gcagcuguga cacgggagca gcggaggcac cuccuggaga ccuuuuucag   2460
gcaccuuuuc ucccaggugc uggacaucaa ccaggccgac gcagggaccc ugccccugga   2520
cuccucccag aaggugcggg aggcccugac cugugagcug agcagggccg aguuugccga   2580
gucccugggc cucaagcccc aggacauguu uguggagucc auguucucuc uggcugacaa   2640
ggauggcaau ggcuaccugu ccuuccgaga guuccuggac auccuggugg ucuucaugaa   2700
aggcucuccu gaggaaaagu cucgccuuau guuccgcaug uacgacuuug augggaaugg   2760
```

-continued

```
ccucauuucc aaggaugagu ucaucaggau gcugagaucc uucaucgaga ucuccaacaa   2820
cugccugucc aaggcccagc uggcugaggu gguggagucc auguuccggg agucgggauu   2880
ccaggacaag gaggaacuga caugggaaga uuuucacuuc augcugcggg accacaauag   2940
cgagcuccgc uucacgcagc ucugugucaa aggggguggag gugccugaag ucaucaagga   3000
ccucugccgg cgagccuccu acaucagcca ggauaugauc ugucccucuc ccagagugag   3060
ugcccgcugu ucccgcagcg acauugagac ugaguugaca ccucagagac ugcagugccc   3120
cauggacaca gacccucccc aggagauucg gcggagguuu ggcaagaagg uaacgucauu   3180
ccagcccuug cuguucacug aggcgcaccg agagaaguuc caacgcagcu gucuccacca   3240
gacggugcaa caguucaagc gcuucauuga gaacuaccgg cgccacaucg gcugcguggc   3300
cguguucuac gccaucgcug gggggcuuuu ccuggagagg gccuacuacu acgccuuugc   3360
cgcacaucac acgggcauca cagacaccac ccgcguggga aucauccugu cgcggggcac   3420
agcagccagc aucucuuuca uguucuccua caucuugcuc accaugugcc gcaaccucau   3480
caccuuccug cgagaaaccu uccucaaccg cuacgugccc uucgacgccg ccguggacuu   3540
ccaucgccuc auugccucca ccgccaucgu ccucacaguc uuacacagug ugggccaugu   3600
ggugaaugug uaccuguucu ccaucagccc ccucagcguc cucucuugcc ucuuuccugg   3660
ccucuuccau gaugaugggu cugagcuccc ccagaaguau uacugguggu ucuuccagac   3720
cguaccaggc cucacggggg uugugcugcu ccugauccug gccaucaugu augucuuugc   3780
cucccaccac uuccgccgcc gcaguuuccg gggcuucugg cugacccacc accucuacau   3840
ccugcucuau guccugcuca ucauccaugg uagcuuugcc cugauccagc ugccccguuu   3900
ccacaucuuc uuccuggucc cagcaaucau cuauggggggc gacaagcugg ugagccugag   3960
ccggaagaag guggagauca gcguggugaa ggcggagcug cugcccucag gagugaccca   4020
ccugcgguuc cagcggcccc agggcuuuga guacaaguca gggcaguggg ugcggaucgc   4080
uugccuggcu cuggggacca ccgaguacca ccccuucaca cugaccucug cgccccauga   4140
ggacacgcuu agccugcaca uccgggcagc agggcccugg accacucgcc ucagggagau   4200
cuacucagcc ccgacgggug acagaugugc cagauaccca aagcuguacc uugauggacc   4260
auuuggagag ggccaccagg aguggcauaa guuugaggug ucaguguuag ugggaggggg   4320
cauuggggguc accccuuuug ccuccauccu caaagaccug gucuucaagu cauccgucag   4380
cugccaagug uucuguaaga agaucuacuu caucugggug acgcggaccc agcgucaguu   4440
ugaguggcug gcugacauca uccgagaggu ggaggagaau gaccaccagg accuggugucc   4500
ugugcacauc uacaucaccc agcuggcuga gaaguucgac cucaggacca cuaugcugua   4560
caucugugag cggcacuucc agaagguucu gaaccggagu cuauucacag gccugcgcuc   4620
caucacccac uuuggccguc cccccuuuga gcccuucuuc aacucccugc aggaggucca   4680
cccccagguc cggaagaucg ggguguuuag cuguggcccc ccuggcauga ccaagaaugu   4740
ggaaaaggcc ugucagcuca ucaacaggca ggaccggacu cacuucuccc accauuauga   4800
gaacuucuag gccccugccc gggggguucug cccacugccc aguugagcag agguuugagc   4860
ccacaccuca ccucuguucu uccuauuucu ggcugccuca gccuucucug auuucccacc   4920
ucccaaccuu guuccaggug gccauaguca gucaccaugu gugggcucag ggacccccag   4980
gaccaggaug ugucucagcc uggagaaaug gugggggggc agugucuagg gacuagagug   5040
agaaguaggg gagcuacuga uuuggggcaa agugaaaccu cugcuuccag acuucagaaa   5100
caaaucucag aagacaagcu gaccugacaa guacuaugug ugugcauguc uguaugugug   5160
```

-continued uuggggcggu gaguguaagg augcaguggg agcauggaug cuggcaucuu agaacccucc 5220
cuacucccau accuccuccu cuucugggcu ccccacuguc agacgggcug gcaaaugccu 5280
ugcaggaggu agaggcugga cccauggcaa gccauuuaca gaaacccacu cggcacccca 5340
gucuaacacc acaacuaauu ucacccaagg uuuuaagcac guucuuucau cagacccugg 5400
cccaauaccu auguaugcaa ugcuccucag cccucuucuc ccugcuccag uagucucccu 5460
uccaaauaaa ucacuuuucu gccuuaaaaa aaaaaaaaaa a 5501

<210> SEQ ID NO 48
<211> LENGTH: 4390
<212> TYPE: RNA
<213> ORGANISM: HUMAN

<400> SEQUENCE: 48
ugagugggca gagcugaccc ggugcgggug ggagucaggg cgcccggaaa acccggcucu 60
ggguagcaga ccccgcccgg gcuggcucgg cgccgggccu ucgggcuucc acucagucuu 120
ugacccucgg uccucgcuca gcggcccggc aggccgcaca acuguaaccg cugccccggc 180
cgccgcccgc uccuucucgg uccggcgggc acagagcgca gcgcggcggg gccggcggca 240
uggcuguguc cuggaggagc uggcucgcca acgaaggggu uaaacaccuc ugccuguuca 300
ucuggcucuc caugaauguc cugcuuuucu ggaaaaccuu cuugcuguau aaccaagggc 360
cagaguauca cuaccuccac cagauguugg ggcuaggauu gugucuaagc agagccucag 420
caucuguucu uaaccucaac ugcagccuua uccuuuuacc caugugccga acacucuugg 480
cuuaccuccg aggaucacag aagguuccaa gcaggagaac caggagauug uuggauaaaa 540
gcagaacauu ccauauuacc ugugguguua cuaucuguau uuucucaggc gugcaugugg 600
cugcccaucu ggugaaugcc cucaacuucu cagugaauua cagugaagac uuuguugaac 660
ugaaugcagc aagauaccga gaugaggauc cuagaaaacu ucucuucaca acuguuccug 720
gccugacagg ggucugcaug gugguggugc uauuccucau gaucacagcc ucuacauaug 780
caauaagagu uucuaacuau gauaucuucu gguauacuca uaaccucuuc uuugucuucu 840
acaugcugcu gacguugcau guuucaggag ggcugcugaa guaucaaacu aauuuagaua 900
cccacccucc cggcugcauc agucuuaacc gaaccagcuc ucagaauauu uccuuaccag 960
aguauuucuc agaacauuuu caugaaccuu ucccugaagg auuuucaaaa ccggcagagu 1020
uuacccagca caaauuugug aagauuugua uggaagagcc cagauuccaa gcuaauuuuc 1080
cacagacuug gcuuuggauu ucuggaccuu ugugccugua cugugccgaa agacuuuaca 1140
gguauauccg gagcaauaag ccagucacca ucauuucggu cauaagucau cccucagaug 1200
ucauggaaau ccgaaugguc aaagaaaauu uuaaagcaag accuggucag uauauuacuc 1260
uacauugucc caguguaucu gcauuagaaa aucauccauu uacccucaca auguguccaa 1320
cugaaaccaa agcaacauuu gggguucauc uuaaaauagu aggagacugg acagaacgau 1380
uucgagauuu acuacugccu ccaucuaguc aagacuccga aauucugccc uucauucaau 1440
cuagaaauua ucccaagcug uauauugaug guccuuuugg aaguccauuu gaggaaucac 1500
ugaacuauga ggucagccuc ugcguggcug gaggcauugg aguaacucca uuugcaucaa 1560
uacucaacac ccuguuggau gacuggaaac cauacaagcu uagaagacua uacuuuauuu 1620
ggguaugcag agauauccag uccuuccguu gguuugcaga uuuacucugu auguugcaua 1680
acaaguuuug gcaagagaac agaccugacu augucaacau ccagcuguac cucagucaaa 1740
cagaugggau acagaagaua auuggagaaa aauaucaugc acugaauuca agacuguuua 1800

-continued

```
uaggacgucc ucgguggaaa cuuuuguuug augaaauagc aaaauauaac agaggaaaaa   1860
caguuggugu uuucuguugu ggacccaauu cacuauccaa gacucuucau aaacugagua   1920
accagaacaa cucauauggg acaagauuug aauacaauaa agagucuuuc agcugaaaac   1980
uuuugccaug aagcaggacu cuaaagaagg aaugagugca auuucuaaga cuuugaaacu   2040
cagcggaauc aaucagcugu guuaugccaa agaauaguaa gguuuucuua uuuaugauua   2100
uuuaaaaugg aaaugugaga auguggcaag augaccguca cauuacaugu uuaaucugga   2160
aaccaaagag acccugaaga auauuugaug ugaugauuca cuuuucaguu cucaaauuaa   2220
aagaaaacug uuagaugcac acuguugauu uucauggugg auucaagaac ucccuaguga   2280
ggagcugaac uugcucaauc uaaggcugau ugucguguuc cucuuuaaau uguuuuuggu   2340
ugaacaaaug caagauugaa caaaauuaaa aauucauuga agcugaaauu ccauuuucug   2400
uguuguguau aaacagagua gcuuuaauuu gcaagcacuc caggcaaaua uauuagaugu   2460
uugaaaacac agcacaagac ucuguauuga uacggguacu uugugucaau aucuaaucgu   2520
cuccacuacu uaugcuaaua ccucuauuug auaucugaag acuauaugcu aacugaaccu   2580
uccucaaaug uuguuauagu aucuauuuuu auauauuuuu uucuuuuuau uccucucucu   2640
agggaaauau gccuucccuu agcaugcauu agacauaaug auuuaauagg ucccuuucau   2700
cuucauuuaa aucuaucacu auugcauggu aaugaaaaua uuccuacuau aaauuauaaa   2760
gggauauaua uauauggaua uauauaugua uauacacaua uauauauaca cacacacaca   2820
cauauauaua uauauauaua uauauacaca uauacuaaua acuuucccu uuuuucagca    2880
uuuuugucuc uauuauuauu auuguuuuuu ucccagguag gguuugucuu aggcuguagc   2940
cucuaaggau aguuaguuaa uuugcacuuu gagaccaaag gacaucaugu gugucaguag   3000
ggacugaaua uaagauuuau cuccuuugcc acacauuggu uuaugaugga gacauugaaa   3060
gucuagucau auuccugaac aguaaaaccu guauuuuacc uuuuaaguaa gaggaaauau   3120
gauauucuua uucaaacuua aguuuagaau ccagaauauu acugucgcac uuuuugguau   3180
ccugaguuuc cauagggaac uauuggguuu aaagucaccg uuggaacuac acugugugau   3240
cuuauaaacu uauguucccu ggcuaucaua uucuuggcuc agaacaauau uucccauuac   3300
uaucuuaaga auuaaggcau ucauggcuca cgccuguaau cccggcacuu ugggaggcca   3360
aggcaggugg aucacgaggu cagaguucaa gaccagccug accaaguugg ugaaacccca   3420
ucgcuacuaa aaauacaaau auuaggcggg uguggugccg ggugccuaua aucccaacua   3480
cucgggagac ugaggcaaag aaucgcuuga acccggugg cggagguugc agugagccaa    3540
gauugcacca cugcacucca gccuggguga cagagcaaga uuccaucuca aaaaaaaaaa   3600
aaaaaaaaaa aaaaaagaau uaaagcauuc auacaguuua gugauuuugu uuaguagucg   3660
gcuaucaauu gcuaucaaau auaacacugc ugaaaucagc agugugacuu accuugccau   3720
uguuaaaaug uuacauaaaa cauaacauga uagaugcuaa ggccuuuuuu ugcuauaauu   3780
caccaauagc aaucaagcau gcuaacccau acugaaugau auuuacuugu agauauuucu   3840
uccuuuccuu gaaauucucc uuucuaugga aagaagauga acccaaaaaa gugauaggaa   3900
auguggaaug cucaugcaga uuuagcucug aaggcauauu uaauaacuag uaugucuuga   3960
caacagucuu uagauuaaaa agaauuuuca uggaaacauu uaacagaaag aacuaguaaa   4020
aagacacuuu gaguuagucc aggcuuaaug ugcaauacug acucuauacu gaucauaauu   4080
uauuuaugcg aucauauuaa uagaccuaau uucauuaaaa cagguagaag auuuuucaaa   4140
agaaagauga uguuucaaag cuggucugcc auucuagaug agccuccuug cuuauuuaag   4200
```

```
uuccaguagg uguucaaaug uuaaaauguua aacauagguc aucuuugcuu cugcagggcu   4260

ucaucuugca uguuuaagag aacuuuguuu uauuuugagg gauuauuucu cuggggauca   4320

uucuuauaau acaagccuua aaucacuaau uuuaguagca auaaaauguua aaauugaaaa   4380

aaaaaaaaaa                                                           4390
```

<210> SEQ ID NO 49
<211> LENGTH: 4270
<212> TYPE: RNA
<213> ORGANISM: HUMAN

<400> SEQUENCE: 49

```
ugagugggca gagcugaccc ggugcgggug ggagucaggg cgcccggaaa acccggcucu     60

ggguagcaga ccccgcccgg gcuggcucgg cgccgggccu ucgggcuucc acucagucuu    120

ugacccucgg uccucgcuca gcggcccggc aggccgcaca acuguaaccg cugccccggc    180

cgccgcccgc uccuucucgg uccggcgggc acagagcgca gcgcggcggg gccggcggca    240

uggcugugucc cuggaggagc uggcucgcca acgaaggggu uaaacaccuc ugccuguuca    300

ucuggcucuc caugaauguc cugcuuuucu ggaaaaccuu cuugcuguau aaccaagggc    360

cagaguauca cuaccuccac cagauguugg ggcuaggauu gugucuaagc agagccucag    420

caucuguucu uaaccucaac ugcagccuua uccuuuuacc caugugccga acacucuugg    480

cuuaccuccg aggaucacag aagguuccaa gcaggagaac caggagauug uuggauaaaa    540

gcagaacauu ccauauuacc uguggugua cuaucuguau uuucucaggc gugcaugugg    600

cugcccaucu ggugaaugcc cucaacuucu cagugaauua cagugaagac uuuguugaac    660

ugaaugcagc aagauaccga gaugaggauc cuagaaaacu ucucuucaca acuguuccug    720

gccugacagg ggucugcaug guggugugc uauuccucau gaucacagcc ucuacauaug    780

caauaaagagu uucuaacuau gauaucuucu gguauacuca uaaccucuuc uuugucuucu    840

acaugcugcu gacguugcau guuucaggag ggcugcugaa guaucaaacu aauuuagaua    900

cccacccucc cggcugcauc agucuuaacc gaaccagcuc ucagaauauu uccuuaccag    960

aguauuucuc agaacauuuu caugaaccuu ucccugaagg auuuucaaaa ccggcagagu   1020

uuacccagca caaauuugug aagauuugua uggaagagcc cagauuccaa gcuaauuuuc   1080

cacagacuug gcuuuggauu ucuggaccuu ugugccugua cugugccgaa agacuuuaca   1140

gguauauccg gagcaauaag ccagucacca ucauuucggu cauaagucau cccucagaug   1200

ucauggaaau ccgaaugguc aaagaaaauu uuaaagcaag accuggucag uauauuacuc   1260

uacauugucc caguguaucu gcauuagaaa aucauccauu uacccucaca augugucaa    1320

cugaaaccaa agcaacauuu gggguucauc uuaaaauagu aggagacugg acagaacgau   1380

uucgagauuu acuacugccu ccaucuaguc aagacuccga aauucugccc uucauucaau   1440

cuagaaauua ucccaaggau gacuggaaac cauacaagcu uagaagacua uacuuuauuu   1500

ggguaugcag agauauccag uccuuccguu gguuugcaga uuuacucugu auguugcaua   1560

acaaguuuug gcaagagaac agaccugacu augucaacau ccagcuguac cucagucaaa   1620

cagaugggau acagaagaua auuggagaaa aauaucaugc acugaauuca agacuguuua   1680

uaggacgucc ucgguggaaa cuuuuguuug augaaauagc aaaauauaac agaggaaaaa   1740

caguuggugu uuucuguugu ggacccaauu cacuauccaa gacucuucau aaacugagua   1800

accagaacaa cucauauggg acaagauuug aauacaauaa agagucuuuc agcugaaaac   1860

uuuugccaug aagcaggacu cuaaagaagg aaugagugca auuucuaaga cuuugaaacu   1920
```

-continued

```
cagcggaauc aaucagcugu guuaugccaa agaauaguaa gguuuucuua uuuaugauua   1980

uuuaaaaugg aaaugugaga auguggcaag augaccguca cauuacaugu uuaaucugga   2040

aaccaaagag acccugaaga auauuugaug ugaugauuca cuuuucaguu cucaaauuaa   2100

aagaaaacug uuagaugcac acuguugauu uucauggugg auucaagaac ucccuaguga   2160

ggagcugaac uugcucaauc uaaggcugau ugucguguuc cucuuuaaau uguuuuuggu   2220

ugaacaaaug caagauugaa caaaauuaaa aauucauuga agcugaaauu ccauuuucug   2280

uguuguguau aaacagagua gcuuuaauuu gcaagcacuc caggcaaaua uauuagaugu   2340

uugaaaacac agcacaagac ucuguauuga uacggguacu uugugucaau aucuaaucgu   2400

cuccacuacu uaugcuaaua ccucuauuug auaucugaag acuauaugcu aacugaaccu   2460

uccucaaaug uuguuauagu aucuauuuuu auauauuuuu uucuuuuuau uccucucucu   2520

agggaaauau gccuucccuu agcaugcauu agacauaaug auuuaauagg ucccuuucau   2580

cuucauuuaa aucuaucacu auugcauggu aaugaaaaua uuccuacuau aaauuauaaa   2640

gggauauaua uauauggaua uauauaugua uauacacaua uauauauaca cacacacaca   2700

cauauauaua uauauauaua uauauacaca uauacuaaua acuuuucccu uuuuucagca   2760

uuuuugucuc uauuauuauu auuguuuuuu ucccagguag gguuugucuu aggcuguagc   2820

cucuaaggau aguuaguuaa uuugcacuuu gagaccaaag gacaucaugu gugucaguag   2880

ggacugaaua uaagauuuau cuccuuugcc acacauuggu uuaugaugga gacauugaaa   2940

gucuagucau auuccugaac aguaaaaccu guauuuuacc uuuuaaguaa gaggaaauau   3000

gauauucuua uucaaacuua aguuuagaau ccagaauauu acugucgcac uuuuugguau   3060

ccugaguuuc cauagggaac uauuggguuu aaagucaccg uuggaacuac acugugugau   3120

cuuauaaacu uauguucccu ggcuaucaua uucuuggcuc agaacaauau uucccauuac   3180

uaucuuaaga auuaaggcau ucauggcuca cgccuguaau cccggcacuu ugggaggcca   3240

aggcaggugg aucacgaggu cagaguucaa gaccagccug accaaguugg ugaaacccca   3300

ucgcuacuaa aaauacaaau auuaggcggg uguggugg cg ggugccuaua aucccaacua   3360

cucgggagac ugaggcaaag aaucgcuuga acccggaggg cggagguugc agugagccaa   3420

gauugcacca cugcacucca gccugggaga cagagcaaga uuccaucuca aaaaaaaaaa   3480

aaaaaaaaaa aaaaaagaau uaaagcauuc auacaguuua gugauuuugu uuaguagucg   3540

gcuaucaauu gcuaucaaau auaacacugc ugaaaucagc agugugacuu accuugccau   3600

uguuaaaaug uuacauaaaa cauaacauga uagaugcuaa ggccuuuuuu ugcuauaauu   3660

caccaauagc aaucaagcau gcuaacccau acugaaugau auuuacuugu agauauuucu   3720

uccuuuccuu gaaauucucc uuucuaugga aagaagauga acccaaaaaa gugauaggaa   3780

auguggaaug cucaugcaga uuuagcucug aaggcauauu uaauaacuag uaugucuuga   3840

caacagucuu uagauuaaaa agaauuuuca uggaaacauu uaacagaaag aacuaguaaa   3900

aagacacuuu gaguuagucc aggcuuaaug ugcaauacug acucuauacu gaucauaauu   3960

uauuuaugcg aucauauuaa uagaccuaau uucauuaaaa cagguagaag auuuuucaaa   4020

agaaagauga uguuucaaag cuggucugcc auucuagaug agccuccuug cuuauuuaag   4080

uuccaguagg uguucaaaug uuaaauguua aacauagguc aucuuugcuu cugcagggcu   4140

ucaucuugca uguuuaagag aacuuuguuu uauuuugagg gauuauuucu cuggggauca   4200

uucuuauaau acaagccuua aaucacuaau uuuaguagca auaaaauguua aaauugaaaa   4260

aaaaaaaaaa                                                          4270
```

<210> SEQ ID NO 50
<211> LENGTH: 4615
<212> TYPE: RNA
<213> ORGANISM: HUMAN

<400> SEQUENCE: 50
acacuucacu caaauggcug gcugcagcug gugcuaguua uggucuggga ucucagauga 60
ggcugcuaag ccgaaugugu uguuacuccu uuacaucguc ucuccacaug gcuugaacuu 120
cucacagcau gccugcugga uucgaagaga uggcauucaa gugcuuaaaa aucaagaaga 180
cccucaccag gugccagcgu cuagacauug gauuuuccag ccuccagaac uuacuucuag 240
ucuaguugga gaaacaaccu agaaaaugca ccaacaaaug gggcacaaua acuacucuga 300
gagagagugg cacacagugg acgcaaagaa gagguuccug augcagcugg gaagagucua 360
caugggccuc uagcaggaga agauacuggu cuugaguuug gagacuaagu aagcaucucc 420
agugucgaau agguaccugg gucaacucca cacacuucuc acucuucacu ggaccucugg 480
uacaagauug agaggauucc uauuacuuac aaacagacua guucaucugg cucuccauga 540
auguccugcu uuucuggaaa accuucuugc uguauaacca agggccagag uaucacuacc 600
uccaccagau guuggggcua ggauuguguc uaagcagagc cucagcaucu guucuuaacc 660
ucaacugcag ccuuauccuu uuacccaugu gccgaacacu cuuggcuuac cuccgaggau 720
cacagaaggu uccaagcagg agaaccagga gauuguugga uaaaagcaga acauuccaua 780
uuaccugugg uguuacuauc uguauuuucu caggcgugca uguggcugcc caucugguga 840
augcccucaa cuucucagug aauuacagug aagacuuugu ugaacugaau gcagcaagau 900
accgagauga ggauccuaga aaacuucucu ucacaacugu uccuggccug acaggggucu 960
gcaugguggu ggugcuauuc cucaugauca cagccucuac auaugcaaua agaguuucua 1020
acuaugauau cuucugguau acucauaacc ucuucuuugu cuucuacaug cugcugacgu 1080
ugcauguuuc aggagggcug cugaaguauc aaacuaauuu agauacccac ccucccggcu 1140
gcaucagucu uaaccgaacc agcucucaga auauuuccuu accagaguau uucucagaac 1200
auuuucauga accuuucccu gaaggauuuu caaaaccggc agaguuuacc cagcacaaau 1260
uugugaagau uuguauggaa gagcccagau uccaagcuaa uuuuccacag acuuggcuuu 1320
ggauuucugg accuuugugc cuguacugug ccgaaagacu uuacagguau auccggagca 1380
auaagccagu caccaucauu ucggucauaa gucaucccuc agaugucaug gaaauccgaa 1440
uggucaaaga aaauuuuaaa gcaagaccug gucaguauau uacucuacau ugucccagug 1500
uaucugcauu agaaaaucau ccauuuaccc ucacaaugug uccaacugaa accaaagcaa 1560
cauuuggggu ucaucuuaaa auaguaggag acuggacaga acgauuucga gauuuacuac 1620
ugccuccauc uagucaagac uccgaaauuc ugcccuucau ucaaucuaga aauuauccca 1680
agcuguauau ugauggaccu uuuggaaguc cauuugagga aucacugaac uaugagguca 1740
gccucugcgu ggcuggaggc auuggaguaa cuccauuugc aucaauacuc aacacccugu 1800
uggaugacug gaaaccauac aagcuuagaa gacuauacuu uauuugggua ugcagagaua 1860
uccaguccuu ccguugguuu gcagauuuac ucuguauguu gcauaacaag uuuuggcaag 1920
agaacagacc ugacuauguc aacauccagc uguaccucag ucaaacagau gggauacaga 1980
agauaauugg agaaaaauau caugcacuga auucaagacu guuuauagga cguccucggu 2040
ggaaacuuuu guuugaugaa auagcaaaau auaacagagg aaaaacaguu gguguuuucu 2100
guuguggacc caauucacua uccaagacuc uucauaaacu gaguaaccag aacaacucau 2160

-continued

```
augggacaag auuugaauac aauaaagagu cuuucagcug aaaacuuuug ccaugaagca   2220
ggacucuaaa gaaggaauga gugcaauuuc uaagacuuug aaacucagcg gaaucaauca   2280
gcuguguuau gccaaagaau aguaagguuu ucuuauuuau gauuauuuaa aauggaaaug   2340
ugagaaugug gcaagaugac cgucacauua cauguuuaau cuggaaacca aagagacccu   2400
gaagaauauu ugaugugaug auucacuuuu caguucucaa auuaaaagaa aacuguuaga   2460
ugcacacugu ugauuuucau gguggauuca agaacucccu agugaggagc ugaacuugcu   2520
caaucuaagg cugauugucg uguuccucuu uaaauuguuu uugguugaac aaaugcaaga   2580
uugaacaaaa uuaaaaauuc auugaagcug aaauuccauu uucuguguug uguauaaaca   2640
gaguagcuuu aauuugcaag cacuccaggc aaauauauua gauguuugaa aacacagcac   2700
aagacucugu auugauacgg guacuuugug ucaauaucua aucgucucca cuacuuaugc   2760
uaauaccucu auuugauauc ugaagacuau augcuaacug aaccuuccuc aaauguuguu   2820
auaguaucua uuuuuauaua uuuuuuucuu uuuauuccuc ucucuaggga aauaugccuu   2880
cccuuagcau gcauuagaca uaaugauuua auaggucccu uucaucuuca uuuaaaucua   2940
ucacuauugc augguaauga aaauauuccu acuauaaauu auaaagggau auauauauau   3000
ggauauauau auguauauac acauauauau auacacacac acacacauau auauauauau   3060
auauauauau acacauauac uaauaacuuu ucccuuuuuu cagcauuuuu gucucuauua   3120
uuauuauugu uuuuuuccca gguaggguuu gucuuaggcu guagccucua aggauaguua   3180
guuaauuugc acuuugagac caaaggacau caugugugug aguagggacu gaauauaaga   3240
uuuaucuccu uugccacaca uugguuuaug auggagacau ugaaagucua gucauauucc   3300
ugaacaguaa aaccuguauu uuaccuuuua aguaagagga aauaugauau ucuuauucaa   3360
acuuaaguuu agaauccaga auauuacugu cgcacuuuuu gguauccuga guuuccauag   3420
ggaacuauug gguuuaaagu caccguugga acuacacugu gugaucuuau aaacuuaugu   3480
ucccuggcua ucauauucuu ggcucagaac aauauuuccc auuacuaucu uaagaauuaa   3540
ggcauucaug gcucacgccu guaaucccgg cacuuuggga ggccaaggca gguggaucac   3600
gaggucagag uucaagacca gccugaccaa guuggugaaa ccccaucgcu acuaaaaaua   3660
caaauauuag gcgggugugg uggcgggugc cuauaauccc aacuacucgg gagacugagg   3720
caaagaaucg cuugaacccg gugggcggag guugcaguga gccaagauug caccacugca   3780
cuccagccug ggugacagag caagauucca ucucaaaaaa aaaaaaaaaa aaaaaaaaaa   3840
agaauuaaag cauucauaca guuuagugau uuuguuuagu agucggcuau caauugcuau   3900
caaauauaac acugcugaaa ucagcagugu gacuuaccuu gccauuguua aaauguuaca   3960
uaaaacauaa caugauagau gcuaaggccu uuuuuugcua uaauucacca auagcaauca   4020
agcaugcuaa cccauacuga augauauuua cuuguagaua uuucuuccuu uccuugaaau   4080
ucuccuuucu auggaaagaa gaugaaccca aaaaagugau aggaaaugug gaaugcucau   4140
gcagauuuag cucugaaggc auauuuaaua acuaguaugu cuugacaaca gucuuuagau   4200
uaaaaagaau uuucauggaa acauuuaaca gaaagaacua guaaaaagac acuuugaguu   4260
aguccaggcu uaaugugcaa uacugacucu auacugauca uaauuuauuu augcgaucau   4320
auuaauagac cuaauuucau uaaaacaggu agaagauuuu ucaaaagaaa gaugauguuu   4380
caaagcuggu cugccauucu agaugagccu ccuugcuuau uuaaguucca guagguguuc   4440
aaauguuaaa uguuaaacau aggucaucuu ugcuucugca gggcuucauc uugcauguuu   4500
aagagaacuu uguuuuauuu ugagggauua uuucucuggg gaucauucuu auaauacaag   4560
```

-continued ccuuaaauca cuaauuuuag uagcaauaaa uguuaaaauu gaaaaaaaaa aaaaa 4615

<210> SEQ ID NO 51
<211> LENGTH: 2529
<212> TYPE: RNA
<213> ORGANISM: HUMAN

<400> SEQUENCE: 51
gcugauagca caguucuguc cagagaagga aggcagaaua aacuuauuca uucccaggaa 60
cucuuggggu aggugugugu uuuucacauc uuaaaggcuc acagacccug cgcuggacaa 120
auguuccauu ccugaaggac cucuccagaa uccggauugc ugaaucuucc cuguugccua 180
gaagggcucc aaaccaccuc uugacaaugg gaaacugggu gguuaaccac ugguuuucag 240
uuuuguuucu gguuguuugg uuagggcuga auguuuuccu guuuguggau gccuuccuga 300
aauaugagaa ggccgacaaa uacuacuaca caagaaaaau ccuugggguca acauuggccu 360 gugcccgagc gucugcucuc ugcuugaauu uuaacagcac gcugauccug cuuccugugu 420
gucgcaaucu gcuguccuuc cugaggggca ccugcucauu uugcagccgc acacugagaa 480
agcaauugga ucacaaccuc accuuccaca agcugguggc cuauaugauc ugccuacaua 540
cagcuauuca caucauugca caccuguuua acuuugacug cuauagcaga agccgacagg 600
ccacagaugg cucccuugcc uccauucucu ccagccuauc ucaugaugag aaaaaggggg 660
guucuuggcu aaaucccauc caguccgaa acacgacagu ggaguaugug acauucacca 720
gcauugcugg ucucacugga gugaucauga caauagccuu gauucucaug guaacuucag 780
cuacugaguu cauccggagg aguuauuuug aagucuucug guauacucac caccuuuuua 840
ucuucuauau ccuuggcuua gggauucacg gcauuggugg aauuguccgg ggucaaacag 900
aggagagcau gaaugagagu cauccucgca agugugcaga gucuuuugag augugggaug 960
aucgugacuc ccacuguagg cgcccuaagu uugaagggca uccccccugag ucuuggaagu 1020 ggauccuugc accggucauu cuuuauaucu gugaaaggau ccuccgguuu uaccgcuccc 1080
agcagaaggu ugugauuacc aagguuguua ugcacccauc caaaguuuug gaauugcaga 1140
ugaacaagcg uggcuucagc auggaagugg ggcaguauau cuuuguuaau ugccccucaa 1200
ucucucuccu ggaauggcau ccuuuuacuu ugaccucugc uccagaggaa gauuucuucu 1260
ccauucauau ccgagcagca ggggacugga cagaaaaucu cauaagggcu uucgaacaac 1320
aauauucacc aauucccagg auugaagugg augguccuu uggcacagcc agugaggaug 1380
uuuuccagua ugaaguggcu gugcugguug gagcaggaau uggggucacc cccuuugcuu 1440
cuaucuugaa auccaucugg uacaaauucc agugugcaga ccacaaccuc aaaacaaaaa 1500
agaucuauuu cuacuggauc ugcagggaga caggugccuu uuccugguuc aacaaccugu 1560
ugacuucccu ggaacaggag auggaggaau uaggcaaagu ggguuuucua aacuaccguc 1620
ucuuccucac cggaugggac agcaauauug uuggucaugc agcauuaaac uuugacaagg 1680
ccacugacau cgugacaggu cugaaacaga aaaccuccuu ugggagacca augugggaca 1740
augaguuuuc uacaauagcu accucccacc ccaagucugu agugggaguu uucuuaugug 1800
gcccucggac uuuggcaaag agccugcgca aaugcugucu ccgauauucc agucuggauc 1860
cuagaaaggu ucaauucuac uucaacaaag aaaauuuuug aguuauagga auaaggacgg 1920
uaaucugcau uuugucucuu uguaucuuca guaauuuacu uggucucguc agguuugagc 1980
agucacuuua ggauaagaau gugccucuca agccuugacu cccugguauu cuuuuuuuga 2040
uugcauucaa cuucguuacu ugagcuucag caacuuaaga acuucugaag uucuuaaagu 2100
ucugaaguuc uuaaagccca uggauccuuu cucagaaaaa uaacuguaaa ucuuucugga 2160
cagccaugac uguagcaagg cuugauagca gagguuuggu gguucagagu uauacaacua 2220
aucccaggug auuuuaucaa uuccaguguu accaucuccu gaguuuuggu uuguaaucuu 2280
uugucccucc caccccaca gaagauuucu aaguagggug acuuuuuaaa uaaaaauuua 2340
uugaauaauu aaugauaaaa cauaauaaua aacauaaaua auaaacaaaa uuaccgagaa 2400
ccccaucccc auauaacacc aacaguguac auguuuacug ucacuuuuga uauggucuua 2460
uccaguguga acagcaauuu auucuuauuu uugcucauca aaaaauaaag gauuuucuuc 2520
uucacuuga 2529

<210> SEQ ID NO 52
<211> LENGTH: 2382
<212> TYPE: RNA
<213> ORGANISM: HUMAN

<400> SEQUENCE: 52
gcugauagca caguucuguc cagagaagga aggcagaaua aacuuauuca uucccaggaa 60
cucuuggggu aggugugugu uuuucacauc uuaaaggcuc acagacccug cgcuggacaa 120
auguuccauu ccugaaggac cucuccagaa uccggauugc ugaaucuucc cuguugccua 180
gaagggcucc aaaccaccuc uugacaaugg gaaacugggu gguuaaccac ugguuuucag 240
uuuuguuucu gguuguuugg uuagggcuga auguuuuccu guuuguggau gccuuccuga 300
aauaugagaa ggccgacaaa uacuacuaca caagaaaaau ccuuggguca acauuggccu 360
gugcccgagc gucugcucuc ugcuugaauu uuaacagcac gcugauccug cuuccugugu 420
gucgcaaucu gcuguccuuc cugaggggca ccugcucauu uugcagccgc acacugagaa 480
agcaauugga ucacaaccuc accuuccaca agcugguggc cuauaugauc ugccuacaua 540
cagcuauuca caucauugca caccuguuua acuuugacug cuauagcaga agccgacagg 600
ccacagaugg cucccuugcc uccauucucu ccagccuauc ucaugaugag aaaaaggggg 660
guucuuggcu aaaucccauc caguccegaa acacgacagu ggaguaugug acauucacca 720
gcauugcugg ucucacugga gugaucauga caauagccuu gauucucaug guaacuucag 780
cuacugaguu cauccggagg aguuauuuug aagucuucug guauacucac caccuuuuua 840
ucuucuauau ccuuggcuua gggauucacg gcauuggugg aauuguccgg ggucaaacag 900
aggagagcau gaaugagagu cauccucgca agugugcaga gucuuuugag augugggaug 960
aucgugacuc ccacuguagg cgcccuaagu uugaagggca ucccccugag ucuuggaagu 1020
ggauccuugc accggucauu cuuuauaucu gugaaaggau ccuccgguuu uaccgcuccc 1080
agcagaaggu ugugauuacc aagguuguua ugcacccauc caaaguuuug gaauugcaga 1140
ugaacaagcg uggcuucagc auggaagugg ggcaguauau cuuuguuaau ugccccucaa 1200
ucucucuccu ggaauggcau ccuuuuacuu ugaccucugc uccagaggaa gauuucuucu 1260
ccauucauau ccgagcagca ggggacugga cagaaaaucu cauaagggcu uucgaacaac 1320
aauauucacc aauucccagg auugaagugg augguccuu uggcacagcc agugaggaug 1380
uuuuccagua ugaaguggcu gugcugguug gagcaggaau uggggucacc cccuuugcuu 1440
cuaucuugaa auccaucugg uacaaauucc agugugcaga ccacaaccuc aaaacaaaaa 1500
agguugguca ugcagcauua aacuuugaca aggccacuga caucgugaca ggucugaaac 1560
agaaaaccuc cuuugggaga ccaaugugg acaaugaguu uucuacaaua gcuaccuccc 1620
accccaaguc uguagugga guuuucuuau guggcccucg gacuuuggca aagagccugc 1680
gcaaaugcug ucaccgauau uccagucugg auccuagaaa gguucaauuc uacuucaaca 1740
aagaaaauuu uugaguuaua ggaauaagga cgguaaucug cauuuugucu cuuuguaucu 1800
ucaguaauuu acuuggucuc gucagguuug agcagucacu uuaggauaag aaugugccuc 1860
ucaagccuug acucccuggu auucuuuuuu ugauugcauu caacuucguu acuugagcuu 1920
cagcaacuua agaacuucug aaguucuuaa aguucugaag uucuuaaagc ccauggaucc 1980
uuucucagaa aaauaacugu aaaucuuucu ggacagccau gacuguagca aggcuugaua 2040
gcagagguuu gguggguucag aguuauacaa cuaaucccag gugauuuuau caauuccagu 2100
guuaccaucu ccugaguuuu gguuuguaau cuuuugucce ucccaccccc acagaagauu 2160
ucuaaguagg gugacuuuuu aaauaaaaau uuauugaaua auuaaugaua aaacauaaua 2220
auaaacauaa auaauaaaca aaauuaccga gaaccccauc cccauauaac accaacagug 2280
uacauguuua cugucacuuu ugauauggue uuauccagug ugaacagcaa uuuauucuua 2340
uuuuugcuca ucaaaaaaua aaggauuuuc uucuucacuu ga 2382

<210> SEQ ID NO 53
<211> LENGTH: 4353
<212> TYPE: RNA
<213> ORGANISM: HUMAN

<400> SEQUENCE: 53
auuggaagaa gaagcauagu auagaagaaa ggcaaacaca acacauucaa ccucugccac 60
cauggggaac ugggcuguga augaggggcu cuccauuuuu gucauucugg uuuggcuggg 120
guugaacguc uuccucuuug ucugguauua ccggguuuau gauauuccac cuaaguucuu 180
uuacacaaga aaacuucuug ggucagcacu ggcacuggcc agggccccug cagccugccu 240
gaauuucaac ugcaugcuga uucucuugcc agucugucga aaucugcugu ccuuccucag 300
ggguuccagu gcgugcugcu caacaagagu ucgaagacaa cuggacagga aucucaccuu 360
ucauaaaaug guggcaugga ugauugcacu ucacucugcg auucacacca uugcacaucu 420
auuuaaugug gaauggugug ugaaugcccg agucaauaau ucugauccuu auucaguagc 480
acucucugaa cuuggagaca ggcaaaauga aaguuaucuc aauuuugcuc gaaagagaau 540
aaagaacccu gaaggaggcc uguaccuggc ugugacccug uuggcaggca ucacuggagu 600
ugucaucacg cugugccuca uauuaauuau cacuuccucc accaaaacca uccggagguc 660
uuacuuugaa gucuuuuggu acacacauca ucucuuugug aucuucuuca uuggccuugc 720
cauccaugga gcugaacgaa uuguacgugg gcagaccgca gagaguuugg cugugcauaa 780
uauaacaguu ugugaacaaa aaaucucaga augggggaaaa auaaaggaau gcccaauccc 840
ucaguuugcu ggaaacccuc cuaugacuug gaaauggaua gugggguccca uguuucugua 900 ucucugugag agguuggugc gguuuuggcg aucucaacag aaggugguca ucaccaaggu 960
ggucacucac ccuuucaaaa ccaucgagcu acagaugaag aagaaggggu ucaaaaugga 1020 aguggggacaa uacauuuuug ucaagugccc aaaggugucc aagcuggagu ggcacccuuu 1080
uacacugaca uccgccccug aggaagacuu cuuuaguauc cauauccgca ucguugggga 1140
cuggacagag gggcuguuca augcuuugg cugugauaag caggaguuuc aagaugcgug 1200
gaaacuaccu aagauagcgg uugaugggcc cuuuggcacu gccagugaag auguguucag 1260
cuaugaggug gugauguuag ugggagcagg gauuggggguc acacccuucg cauccauucu 1320
caagucaguc ugguacaaau auugcaauaa cgccaccaau cugaagcuca aaaagaucua 1380
cuucuacugg cugugccggg acacacaugc cuuugagugg uuugcagauc ugcugcaacu 1440

-continued gcuggagagc cagaugcagg aaaggaacaa ugccggcuuc cucagcuaca acaucuaccu 1500
cacuggcugg gaugagucuc aggccaauca cuuugcugug caccaugaug aggagaaaga 1560
ugugaucaca ggccugaaac aaaagacuuu guauggacgg cccaacuggg auaaugaauu 1620
caagacaauu gcaagucaac acccuaauac cagaauagga guuuuccucu guggaccuga 1680
agccuuggcu gaaacccuga guaaacaaag caucuccaac ucugagucug gcccucgggg 1740
agugcauuuc auuuucaaca aggaaaacuu cuaacuuguc ucuuccauga ggaaauaaau 1800
gugguugug cugccaaaug cucaaauaau gcuaauugau aauauaaaua cccccugcuu 1860
aaaaauggac aaaaagaaac uauaauguaa ugguuuuccc uuaaaggaau gucaaagauu 1920
guuugauagu gauaaguuac auuuaugugg agcucuaugg uuuugagagc acuuuuacaa 1980
acauuauuuc auuuuuuucc ucucaguaau gucaguggaa guuagggaaa agauucuugg 2040
acucaauuuu agaaucaaaa gggaaaggau caaaagguuc aguaacuucc cuaagauuau 2100
gaaacuguga ccagaucuag cccaucuuac uccagguuug auacucuuuc cacaauacug 2160
agcugccuca gaauccucaa aaucaguuuu uauauucccc aaaagaagaa ggaaaccaag 2220
gaguagcuau auauuucuac uuugugucau uuuugccauc auuauuauca uacugaagga 2280
aauuuuccag aucauuagga cauaauacau guugagagug ucucaacacu uauuagugac 2340
aguauugaca ucugagcaua cuccaguuua cuaauacagc aggguaacug ggccagaugu 2400
ucuuucuaca gaagaauauu ggauugauug gaguuaaugu aauacucauc auuuaccacu 2460
gugcuuggca gagagcggau acucaaguaa guuuuguuaa augaaugaau gaauuuagaa 2520
ccacacaaug ccaagauaga auuaauuuaa agccuuaaac aaaauuuauc uaaagaaaua 2580
acuucuauua cugucauaga ccaaaggaau cugauucucc cuagggucaa gaacaggcua 2640
aggauacuaa ccaauaggau ugccugaagg guucugcaca uucuuauuug aagcaugaaa 2700
aaagaggguu ggagguggag aauuaaccuc cugccaugac ucuggcucau cuaguccugc 2760
uccuugugcu auaaaauaaa ugcagacuaa uuuccugccc aaaguggucu ucuccagcua 2820
gcccuuauga auauugaacu uaggaauugu gacaaauaug uaucugauau ggucauuugu 2880
uuuaaauaac acccaccccu uauuuuccgu aaauacacac acaaaaugga ucgcaucugu 2940
gugacuaaug guuuauuugu auuauaucau caucaucauc cuaaaauuaa caacccagaa 3000
acaaaaaucu cuauacagag aucaaauuca cacucaauag uauguucuga auauauguuc 3060
aagagagagu cucuaaauca cuguuagugu ggccaagagc aggguuuucu uuuuguucuu 3120
agaacugcuc ccauuucugg gaacuaaaac caguuuuauu ugccccaccc cuuggagcca 3180
caaauguuua gaacucuuca acuucgguaa ugaggaagaa ggagaaagag cugggggaag 3240
ggcagaagac ugguuuagga ggaaaaggaa auaaggagaa aagagaaugg gagagugaga 3300
gaaaauaaaa aaggcaaaag ggagagagag gggaaggggg ucucauauug gucauucccu 3360
gccccagauu ucuuaaaguu ugauauguau agaauauaau ugaaggaggu auacacauau 3420
ugauguuguu uugauuaucu augguauuga aucuuuuaaa aucuggucac aaauuuugau 3480
gcugaggggg auuauucaag ggacuaggau gaacuaaaua agaacucagu uguucuuugu 3540
cauacuacua uuccuuucgu cucccagaau ccucagggca cugaggguag gucugacaaa 3600
uaaggccugc ugugcgaaua uagccuuucu gaaauguacc aggaugguuu cugcuuagag 3660
acacuuaggu ccagccuguu cacacugcac cucagguauc aauucaucua uucaacagau 3720
auuuauugug uuauuacuau gagucaggcu cuguuuauug uuucaauucu uuacaccaaa 3780
guaugaacug gagaggguac cucaguuaua aggagucuga gaauauuggc ccuuucuaac 3840

-continued cuaugugcau aauuaaaacc agcuucauuu guugcuccga gaguguuucu ccaagguuuu 3900
cuaucuucaa aaccaacuaa guuaugaaag uagagagauc ugcccugugu uauccaguua 3960
ugagauaaaa aaugaauaua agagugcuug ucauuauaaa aguuuccuuu uuuauucucu 4020
caagccacca gcugccagcc accagcagcc agcugccagc cuagcuuuuu uuuuuuuuuu 4080
uuuuuuuuag cacuuaguau uuagcauuua uuaacaggua cucuaagaau gaugaagcau 4140
uguuuuuaau cuuaagacua ugaagguuuu ucuuaguucu ucugcuuuug caauuguguu 4200
ugugaaauuu gaauacuugc aggcuuugua ugugaauaau ucuagcgggg gaccugggag 4260
auaauuccua cggggaauuc uuaaaacugu gcucaacuau uaaaaugaau gagcuuucaa 4320
aaaaaaaaaa aaaaaaaaaa aaaaaaaaaa aaa 4353

<210> SEQ ID NO 54
<211> LENGTH: 2582
<212> TYPE: RNA
<213> ORGANISM: HUMAN

<400> SEQUENCE: 54
guugcugggu gucccagggc cugaggcagg acgguacucc gcugacaccu ucccuuucgg 60
ccuugagguu cccagccugg uggccccagg acguuccggu cgcauggcag agugcuacgg 120
acgacgccua ugaagcccuu aguccuucua guugcgcuuu ugcuauggcc uucgucugug 180
ccggcuuauc cgaggucuca auccauugcg cccaggcugg uaugcaguca uguuguaucu 240
ggaauuggug gguucuuggu cucacugacu ucaagaauga agccgcagac ccucgugcac 300
caugagugcc gaggaggaug ccaggugggu ccggugggug acucagcagu uuaagaccau 360
ugcaggagaa gauggggaga ucagccugca agaauucaaa gcagcucugc augugaaaga 420
guccuucuuu gcagagcgau ucuuugcccu auuugacucc gauagaagug gcaccaucac 480
ccuccaggag cugcaggagg cacugacccu gcucauccau ggcagcccca uggacaaacu 540
caaauuccuc uuccaggugu augacaucga ugugugugca cggcaggggg cgucugcagg 600
uacagagugg ggugcugggg caggcccgca cugggcuuca uccccacucg ggacaggcag 660
uggcuccauu gacccggaug agcugcgcac ugugcugcag ucgugucugc gcgagagcgc 720
caucucgcug ccugacgaga agcuggacca gcugacgcug gcgcucuucg aaucggccga 780
cgcggacggc aacggggcca ucaccuucga ggagcuccgg gacgagcugc agcgcuuccc 840
cggagucaug gagaaccuga ccaucagcgc ugcccacugg cugacggccc ccgcccccg 900 cccacgcccg cgccggccgc gccagcugac ccgcgccuac uggcacaacc accgcagcca 960
gcuguucugc cuggccaccu augcaggccu ccacgugcug cucuucgggc uggcggccag 1020
cgcgcaccgg gaccucggcg ccagcgucau gguggccaag ggcuguggcc agugccucaa 1080
cuucgacugc agcuucaucg cggugcugau gcucagacgc ugccucaccu ggcugcgggc 1140
cacguggcug gcucaagucc uaccacugga ccagaacauc caguuccacc agcuuauggg 1200 cuacgguggua guggggcugu cccucgugca cacuguggcu cacacuguga acuuuguacu 1260
ccaggcucag gcggaggcca gcccuuucca guucugggag cugcugcuca ccacgaggcc 1320
uggcauuggc uggguacacg guucggccuc cccgacaggu gucgcucugc ugcugcugcu 1380
ccuccucaug uucaucugcu ccaguuccug cauccgcagg aguggccacu uugagguguu 1440
cuauuggacu caccuguccu accuccucgu guggcuucug cucaucuuuc augggcccaa 1500
cuucuggaag uggcugcugg ugccuggaau cuuguuuuuc cuggagaagg ccaucggacu 1560
ggcagugucc cgcauggcag ccgugugcau cauggaaguc aaccuccucc ccuccaaggu 1620

-continued

```
cacucaucuc cucaucaagc ggcccccuuu uuuucacuau agaccuggug acuacuugua   1680

ucugaacauc cccaccauug cucgcuauga guggcacccc uucaccauca gcagugcucc   1740

ugagcagaaa gacacuaucu ggcugcacau ucggucccaa ggccagugga caaacaggcu   1800

guaugagucc uucaaggcau cagacccacu gggccguggu ucuaagaggc ugucgaggag   1860

ugugacaaug agaaagaguc aaaggucguc caagggcucu gagauacuuu uggagaaaca   1920

caaauucugu aacaucaagu gcuacaucga ugggccuuau gggacccccca cccgcaggau   1980

cuuugccucu gagcaugccg ugcucaucgg ggcaggcauc ggcaucaccc ccuuugcuuc   2040

cauucugcag aguaucaugu acaggcacca gaaaagaaag cauacuugcc ccagcugcca   2100

gcacuccugg aucgaaggug uccaagacaa caugaagcuc cauaaggugg acuuuaucug   2160

gaucaacaga gaccagcggu cuuucgagug guuugugagc cugcugacua aacuggagau   2220

ggaccaggcc gaggaggcuc aauacggccg cuuccuggag cugcauaugu acaugacauc   2280

ugcacugggc aagaaugaca ugaaggccau uggccugcag auggcccuug accuccuggc   2340

caacaaggag aagaaagacu ccaucacggg gcugcagacg cgcacccagc cugggcggcc   2400

ugacuggagc aaggguguucc agaaaguggc ugcugagaag aagggcaagg ugcaggucuu   2460

cuucugugggc uccccagcuc uggccaaggu gcugaagggc cauugugaga aguucggcuu   2520

cagauuuuuc caagagaauu ucuagccuca ccucuccaag cucugcccca aguccacacc   2580

au                                                                  2582
```

<210> SEQ ID NO 55
<211> LENGTH: 6428
<212> TYPE: RNA
<213> ORGANISM: HUMAN

<400> SEQUENCE: 55

```
ggucuguccu gagccgacac cugcacagug gcgagaccaa ggacccagag agaaagguga     60

gagugcagcc ggggaggcug aggaucggcg gagcuggaag agugagggug aaggcaagaa    120

guagagcaca gaagcaaaga uuuuaagagg aaagaagaca ucugaaccca acaccacccu    180

aaaccacagg cugcaggguu ggcaugcucc gugcaagacc agaggcacug augcuccugg    240

gagcucuucu gacuggaucc cugggguccau cgggcaauca ggacgcacuc ucacugcccu    300

gggaagugca gcgcuaugac ggcugguuua acaaccugag gcaccacgag cguggugcug    360

uuggcugccg guugcagcgc cgcguaccag ccaauuacgc cgacggugug uaucaggcuc    420

uggaggagcc gcagcugccc aacccgcgcc ggcucagcaa cgcagccacg cggggcauag    480

ccggccugcc gucgcuccac aaccgcaccg uacugggggu cuucuuuggc uaccauguuc    540

uuuccgacgu ggugagcgug gaaacgcccg guugccccgc cgaguuccuc aacauccgca    600

ucccaccugg agaccccgug uucgaccccg accagcgcgg ggacguggug cugcccuucc    660

agaggagccg cugggacccc gagaccggac ggaguccccag caaccccccgg gaccuggcca    720

accaggugac gggcuggcug gacggcagcg ccaucuaugg cuccucgcac uccuggagcg    780

acgcgcugcg gagcuucucg gggggacagc uggcgucggg gcccgacccc gcuuuccccc    840

gagacucgca gaacccccug cucaugugggg cggcgcccga ccccgccacc gggcagaacg    900

ggccccgggg gcuguacgcc uucggggcag agagagggaa ccgggaaccc uuccugcagg    960

cgcugggccu gcucugguuc cgcuaccaca accugugggc gcagaggcug gcccgccagc   1020

acccagacug ggaggacgag gagcuguucc agcacgcacg caagagggguc aucgccaccu   1080

accagaacau cgcuguguau gaguggcugc ccagcuuccu gcagaaaaca cucccggagu   1140
```

-continued

```
auacaggaua ccguccuuuc cuagacccca gcaucucccc ggaauuugug guggccucug   1200
agcaguucuu cucuaccaug gugcccccug gugucuacau gagaaaugcc agcugucauu   1260
uccggaaggu ccugaacaag gguuuucaaa gcucccaagc ucucaggguc ugcaacaacu   1320
acuggauucg ggagaacccc aaucugaaca guacccagga ggugaaugag cugcugcugg   1380
gaauggccuc ccagauuucg gaguuggagg acaacauagu gguugaagau cugagggauu   1440
acuggccugg cccuggcaaa uucucccgua cagacuaugu ggccagcagc auccaacgug   1500
gccgagauau ggggcugccc agcuauagcc aggcccugcu ggccuuuggg cuggacaucc   1560
caaggaacug gagugaucuc aacccuaaug uggacccccca ggugcuggag gccacagcug   1620
cccuguacaa ccaggaccua ucccagcuag agcugcuccu ugggggggcuc cuggagagcc   1680
auggggaccc uggaccccug uucagugcca uuguccucga ccaguuugua cggcugcggg   1740
auggugaccg cuacugguuu gagaacacca ggaaugggcu guucuccaag aaggagauug   1800
aagacauccg aaauaccacc cugcgggacg ugcuggucgc uguuaucaac auugacccca   1860
gugcccugca gcccaauguc uuugucuggc auaaaggugc acccugcccu caaccuaagc   1920
agcucacaac ugacggccug ccccagugug caccccugac ugugcuugac uucuuugaag   1980
gcagcagccc ugguuuugcc aucaccauca uugcucucug cugccuuccc uuagugaguc   2040
ugcuucucuc uggaguggug gccuauuucc ggggccgaga acacaagaag cuacaaaaga   2100
aacucaaaga gagcgugaag aaggaagcag ccaaagaugg agugccagcg auggaguggc   2160
caggccccaa ggagaggagc agucccauca ucauccagcu gcugucagac aggugucugc   2220
agguccugaa caggcaucuc acugugcucc guguggucca gcugcagccu cugcagcagg   2280
ucaaccucau ccuguccaac aaccgaggau gccgcacccu gcugcucaag aucccuaagg   2340
aguaugaccu ggugcugcug uuuaguucug aagaggaacg ggcgccuuu gugcagcagc   2400
uaugggacuu cugcgugcgc ugggcucugg gccuccaugu ggcugagaug agcgagaagg   2460
agcuauuuag gaaggcugug acaaagcagc agcgggaacg cauccuggag aucuucuuca   2520
gacaccuuuu ugcucaggug cuggacauca accaggccga cgcagggacc cugccccugg   2580
acuccuccca gaaggugcgg gaggcccuga ccugcgagcu gagcagggcc gaguuugccg   2640
agucccuggg ccucaagccc caggacaugu uuguggaguc cauguucucu cuggcugaca   2700
aggauggcaa uggcuaccug uccuuccgag aguuccugga cauccuggug gucuucauga   2760
aaggcucccc agaggauaag ucccgucuaa uguuuaccau guaugaccug gaugagaaug   2820
gcuuccucuc caaggacgaa uucuucacca ugaugcgauc cuucaucgag aucuccaaca   2880
acugccuguc caaggcccag cuggccgagg ugguggaguc uauguuccgg gagucgggau   2940
uccaggacaa ggaggagcug acaugggagg auuuucacuu caugcugcgg gaccaugaca   3000
gcgagcuccg cuucacgcag cucuguguca aagguggagg uggaggugga aaugguauua   3060
gagauaucuu uaaacaaaac aucagcuguc gagucucguu caucacucgg acaccugggg   3120
agcgcuccca cccccaggga cuggggcccc cugccccaga agccccagag cugggaggcc   3180
cuggacugaa gaagagguuu ggcaaaaagg cagcagugcc cacuccccgg cuguacacag   3240
aggcgcugca agagaagaug cagcgaggcu uccuagccca aaagcugcag caguacaagc   3300
gcuucgugga gaacuaccgg aggcacaucg ugugugugcc aaucuucucg gccaucugug   3360
uuggcguguu ugcagaucgu gcuuacuacu auggcuuugc cucgccaccc ucggacauug   3420
cacagaccac ccucguggc aucauccugu cacgaggcac ggcggccagc guccuccuuca   3480
uguucucuua uaucuugcuc accaugugcc gcaaccucau aaccuuccug cgagagacuu   3540
```

-continued

```
uccucaaccg cuaugugccu uuugaugccg caguggacuu ccaccgcugg aucgccaugg   3600
cugcuguugu ccuggccauu uugcacagug cuggccacgc agucaauguc uacaucuucu   3660
cagucagccc acucagccug cuggccugca uauuccccaa cgucuuugug aaugaugggu   3720
ccaagcuucc ccagaaguuc uauuggugggu ucuuccagac cgucccaggu augacaggug   3780
ugcuucugcu ccugguccug gccaucaugu augucuucgc cucccaccac uuccgccgcc   3840
gcagcuuccg gggcuucugg cugacccacc accucuacau ccugcucuau gcccugcuca   3900
ucauccaugg cagcuaugcu cugauccagc ugcccacuuu ccacaucuac uuccuggucc   3960
cggcaaucau cuauggaggu gacaagcugg ugagccugag ccggaagaag guggagauca   4020
gcguggugaa ggcggagcug cugcccucag gagugaccua ccugcaauuc cagaggcccc   4080
aaggcuuuga guacaaguca ggacaguggg ugcggaucgc cugccuggcu cuggggacca   4140
ccgaguacca ccccuucaca cugaccuccg cgccccauga ggacacacuc agccugcaca   4200
uccgggcagu ggggcccugg accacucgcc ucagggagau cuacucaucc ccaaagggca   4260
auggcugugc uggauaccca aagcuguacc uugauggacc guuuggagag ggccaucagg   4320
aguggcauaa auuugaggug ucaguguugg ugggaggggg cauuggggguc acccccuuug   4380
ccuccauccu caaagaccug gucuucaagu cauccuuggg cagccaaaug cuguguaaga   4440
agaucuacuu caucugggug acacggaccc agcgucaguu ugaguggcug gcugacauca   4500
uccaagaggu ggaggagaac gaccaccagg accuggugucc ugugcacauu uaugucaccc   4560
agcuggcuga gaaguucgac cucaggacca ccaugcuaua caucugcgag cggcacuucc   4620
agaaagugcu gaaccggagu cuguucacgg gccugcgcuc caucacccac uuuggccguc   4680
cccccuucga gcccuucuuc aacucccugc aggaggucca cccacaggug cgcaagaucg   4740
gggugutcag cugcggcccu ccaggaauga ccaagaaugu agagaaggcc ugucagcucg   4800
ucaacaggca ggaccgagcc cacuucaugc accacuauga gaacuucuga gccuguccuc   4860
ccuggcugcu gcuuccagua uccugccuuc ucuucugugc accuaaguug cccagcccug   4920
cuggcaaucu cuccaucaga auccaccuua ggccucagcu ggagggcugc agagccccuc   4980
ccaauauugg gagaauauug acccagacaa uuauacaaau gagaaaaggc aggagacuau   5040
guucuacaau ugcagugcau gaugauuaua aguccaccug uuuaucaacg gcaccauucc   5100
ugcagcccuc cagacuuccu gcccuuagca agugcgcaac cagucaggau cucccaaaga   5160
agauaaagac cacuccucac cccagcucaa gccauggcag gcguggcaag caaagugggg   5220
aggagacagu cccugcuugu gacaagugug gaggugaaaa gguacaauag ugcuugucuc   5280
cgauagcucc ccacaucucu aauugacuuc cacaaaaucg augcguugcu uugguauuug   5340
cuuggacuga cauuugaggg aggaggaggc ugggauccuc uggcugagaa ucuccucaga   5400
gcccagugca gaagcuguga ugcuuagaac cuggacagcc cgacugccuc aacucugucu   5460
ccaggucuau ucccuccagc uccaaaagga gcagcccuac uucuaccccu ucccgucccc   5520
aaagugucag caacuuugag gagggcacca ggaaacaaag augccucccc agcccugaua   5580
uucuugaugu caccagugau acccacugcc cugaccccug ggcaggcccc ucucugcauc   5640
uacuggagug gucccugggc ucuggggcug aaggauucca gccucucugc cagauauuca   5700
guacucgauc ucaauucccc ucuuccacaa gaguugggug accagcuguc cuaguuugcc   5760
caggacucuc ccuguuuuag cacugaaagu cucuugcccc aggaaacccc aucagucca    5820
ggcagauugg gacagcuggu caccuuacgc aagagccagg cugaaacauc cccuccauac   5880
ucagcucuuu aacuuuucuu uuccuuuuuc aucgggcucu uuccuaaaaa gcugagcugu   5940
```

-continued

```
aaaauauuuu acaucgaggu auaauaaaua aucauguaca uguuuuacca ccacccaggu   6000

caagacauag aauguuucaa cauuuccauc accccagaaa cuccccuugu acccccuucc   6060

acuucgucuc cccuagcucc uagaagcaac cacugaugug auuucuacca aauccaguuu   6120

ugguccuacu aaauauacuc uuuugagacu ggccucuuuu acucaccaua augccuuugu   6180

aauucaucca ugcuguugug uguaucagca guuuguuccu uuucauugcu gaguaguauu   6240

cuauuguaga gauguaccac aguuuguuua uucuucuguu gauggacguu uggguuguuu   6300

cuaauuuuga augauuauaa auaaaaauuc ugugaguguu cuuguaaaaa aaaaaaaaaa   6360

aaaaaaaaaa aaaaaaaaaa aaaaaaaaaa aaaaaaaaaa aaaaaaaaaa aaaaaaaaaa   6420

aaaaaaaa                                                            6428


<210> SEQ ID NO 56
<211> LENGTH: 1587
<212> TYPE: RNA
<213> ORGANISM: HUMAN

<400> SEQUENCE: 56

cauucuucuu cuuccuccca gcagcucugc cuggaagucc cccaaucccu gugcuccugc     60

ccccagaucg ugggcuuggg ggacagcaag aaagcugcaa aggacucagc uggggcggcu    120

ccacaaggac cccacaggcu ugagguguug ccaggauucu aucccagggg guuuucuggg    180

ucccccagag cccucucaag cacggggagg cagaagggca cucgcccauu ucaggaaucu    240

gcagccugga agccacagcc auggcaggcc cccgauaccc aguuucagug caaggggcag    300

cccuggugca gaucaagagg cuccaaacgu uugccuucuc ugugcgcugg ucagacggca    360

gcgacaccuu cgugcgcagg aguugggacg aauucaggca gcucaagacc cucaaggaga    420

ccuucccggu ggaggcgggc cugcugcgga gaucugaccg cguucuccca aagcuucucg    480

augcaccacu guugggacgc gugggggcgca cgagccgcgg ccuggcgcgc cugcagcugu    540

uggaaaccua uucucggagg cugcuggcga cugcagagcg cguggcacgg agcccgacga    600

ucacuggcuu cuucgcaccg caaccccugg accuggagcc cgcgcugcca cccggcagcc    660

gggugauccu gcccacccca gaggagcagc cucuuucucg cgcugcgggc cgccucucca    720

uccacagucu ggaggcucag agccugcgcu gccugcagcc cuucuguacc caggacacgc    780

gggauaggcc uuuucaggcg caggcccagg agagccugga cgugcugcug cggcaccccu    840

caggcuggug gcugguggag aacgaagacc ggcagaccgc cugguuucca gcgcccuacc    900

uggaggaggc ggcccccggc caaggccggg agggaggccc gucccuaggg agcagcgguc    960

cccaguucug ugcuucccgc gccuacgaga gcagccgcgc agaugagcug uccgugcccg   1020

cgggggcgcg cgugcgcgug uuggaaacgu cagaccgcgg cugguggcua ugcagguacg   1080

gcgaccgggc gggccuacuc cccgcggugc ugcugcggcc ggaagggcug ggcgcucucc   1140

ugagcgggac ggggguuccgu ggaggagacg acccggcggg ugaggcccgg ggcuucccug   1200

aacccuccca ggccaccgcc ccuccccccca ccgugcccac ccgaccuucg ccgggcgcca   1260

uccagagccg cugcugcacc gucacacgca gggcccugga gcggcgccca cggcgccagg   1320

gccgcccucg agggugcgug gacucugugc cgcaccccac gacggagcag ugagcgcgag   1380

gaucccgaug aggggaugga ccgcgccauc ccagggcugg ggaggagcgg ggagggcgga   1440

ucucccuggc cagcagggau gggagggggc cauuugcugu uccucugagu aaagcuuguu   1500

cugcaugaaa aaaaaaaaaa aaaaaaaaaa aaaaaaaaaa aaaaaaaaaa aaaaaaaaaa   1560

aaaaaaaaaa aaaaaaaaaa aaaaaaa                                       1587
```

<210> SEQ ID NO 57
<211> LENGTH: 1132
<212> TYPE: RNA
<213> ORGANISM: HUMAN

<400> SEQUENCE: 57
agccauggca ggcccccgau acccaguuuc agugcaaggg gcagcccugg ugcagaucaa 60
gaggcuccaa acguuugccu ucucugugcg cuggucagac ggcagcgaca ccuucgugcg 120
caggaguugg gacgaauuca ggcagcucaa gaagacccuc aaggagaccu ucccggugga 180
ggcgggccug cugcggagau cugaccgcgu ucucccaaag cuucucgaug caccacuguu 240
gggacgcgug gggcgcacga gccgcggccu ggcgcgccug cagcuguugg aaaccuauuc 300
ucggaggcug cuggcgacug cagagcgcgu ggcacggagc ccgacgauca cuggcuucuu 360
cgcaccgcaa ccccuggacc uggagcccgc gcugccaccc ggcagccggg ugauccugcc 420
caccccagag gagcagccuc uuucucgcgc ugcgggccgc cucuccaucc acagucugga 480
ggcucagagc cugcgcugcc ugcagcccuu cuguacccag gacacgcggg auaggccuuu 540
ucaggcgcag gcccaggaga gccuggacgu gcugcugcgg caccccucag gcugguggcu 600
gguggagaac gaagaccggc agaccgccug guuuccagcg cccuaccugg aggaggcggc 660
cccgggccaa ggccgggagg gaggcccguc ccuagggagc agcgguccc aguucugugc 720 uucccgcgcc uacgagagca gccgcgcaga ugagcugucc gugcccgcgg gggcgcgcgu 780
gcgcguguug gaaacgucag accgcggcug guggcuaugc agguacggcg accgggcggg 840
ccuacucccc gcggugcugc ugcggccgga agggcugggc gcucuccuga gcgggacggg 900
guuccgugga ggagacgacc cggcggguga ggcccggggc uucccugaac ccucccaggc 960
caccgccccu ccccccaccg ugcccacccg accuucgccg ggcgccaucc agagccgcug 1020
cugcaccguc acacgcaggg cccuggagcg gcgcccacgg cgccagggcc gcccucgagg 1080
gugcguggac ucugugccgc accccacgac ggagcaguga gcgcgaggau cc 1132

<210> SEQ ID NO 58
<211> LENGTH: 1147
<212> TYPE: RNA
<213> ORGANISM: HUMAN

<400> SEQUENCE: 58
agccauggca ggcccccgau acccaguuuc agugcaaggg gcagcccugg ugcagaucaa 60
gaggcuccaa acguuugccu ucucugugcg cuggucagac ggcagcgaca ccuucgugcg 120
caggaguugg gacgaauuca ggcagcucaa gaagacccuc aaggagaccu ucccggugga 180
ggcgggccug cugcggagau cugaccgcgu ucucccaaag cuucucgguc aggccagccu 240
ggaugcacca cuguugggac gcguggggcg cacgagccgc ggccuggcgc gccugcagcu 300
guuggaaacc uauucucgga ggcugcuggc gacugcagag cgcguggcac ggagcccgac 360
gaucacuggc uucuucgcac cgcaaccccu ggaccuggag cccgcgcugc cacccggcag 420
ccgggugauc cugcccaccc cagaggagca gccucuuucu cgcgcugcgg gccgccucuc 480
cauccacagu cuggaggcuc agagccugcg cugccugcag cccuucugua cccaggacac 540
gcgggauagg ccuuuucagg cgcaggccca ggagagccug gacgugcugc ugcggcaccc 600
cucaggcugg uggcuggugg agaacgaaga ccggcagacc gccugguuuc cagcgcccua 660
ccuggaggag gcggccccgg gccaaggccg ggagggaggc ccgucccuag ggagcagcgg 720
uccccaguuc ugugcuuccc gcgccuacga gagcagccgc gcagaugagc uguccgugcc 780

-continued

```
cgcgggggcg cgcgugcgcg uguuggaaac gucagaccgc ggcugguggc uaugcaggua    840

cggcgaccgg gcgggccuac uccccgcggu gcugcugcgg ccggaagggc ugggcgcucu    900

ccugagcggg acgggguucc guggaggaga cgacccggcg ggugaggccc ggggcuuccc    960

ugaacccucc caggccaccg ccccuccccc caccgugccc acccgaccuu cgccgggcgc   1020

cauccagagc cgcugcugca ccgucacacg cagggcccug gagcggcgcc cacggcgcca   1080

gggccgcccu cgagggugcg uggacucugu gccgcacccc acgacggagc agugagcgcg   1140

aggaucc                                                             1147
```

<210> SEQ ID NO 59
<211> LENGTH: 1409
<212> TYPE: RNA
<213> ORGANISM: HUMAN

<400> SEQUENCE: 59

```
cgacuuccuc uuuccagugc auuuaaggcg cagccuggaa gugccaggga gcacuggagg     60

ccacccaguc augggggaca ccuucauccg ucacaucgcc cugcugggcu uugagaagcg    120

cuucguaccc agccagcacu auguguacau guuccuggug aaauggcagg accugucgga    180

gaaggugguc uaccggcgcu ucaccgagau cuacgaguuc cauaaaaccu uaaaagaaau    240

guucccuauu gaggcagggg cgaucaaucc agagaacagg aucaucccccc accucccagc    300

ucccaagugg uuugacgggc agcgggccgc cgagaaccgc cagggcacac uuaccgagua    360

cugcggcacg cucaugagcc ugcccaccaa gaucuccegc uguccccacc uccucgacuu    420

cuucaaggug cgcccugaug accucaagcu ccccacggac aaccagacaa aaaagccaga    480

gacauacuug augcccaaag auggcaagag uaccgcgaca gacaucaccg gccccaucau    540

ccugcagacg uaccgcgcca uugccaacua cgagaagacc ucgggcuccg agauggcucu    600

guccacgggg gacguggugg aggucguaga gaagagcgag agcgguuggu gguucuguca    660

gaugaaagca aagcgaggcu ggaucccagc guccuuccuc gagccccugg acaguccuga    720

cgagacggaa gacccugagc ccaacuaugc aggugagcca uacgucgcca ucaaggccua    780

cacugcugug gagggggacg aggugucccu gcucgagggu gaagcuguug aggucauuca    840

caagcuccug gacggcuggu gggucaucag gaaagacgac gucacaggcu acuucccguc    900

cauguaccug caaaagucag ggcaagacgu gucccaggcc caacgccaga ucaagcgggg    960

ggcgccgccc cgcaggucgu ccauccgcaa cgcgcacagc auccaccagc ggucgcggaa   1020

gcgccucagc caggacgccu aucgccgcaa cagcguccgu uuucugcagc agcgacgccg   1080

ccaggcgcgg ccgggaccgc agagccccgg gagcccgcuc gaggaggagc ggcagacgca   1140

gcgcucuaaa ccgcagccgg cggugccccc gcggccgagc gccgaccuca uccugaaccg   1200

cugcagcgag agcaccaagc ggaagcuggc gucugccguc ugaggcugga gcgcaguccc   1260

cagcuagcgu cucggcccuu gccgccccgu gccuguacau acguguucua uagagccugg   1320

cgucuggacg ccgagggcag ccccgacccc uguccagcgc ggcucccgcc acccucaaua   1380

aauguugcuu ggaguggaaa aaaaaaaaa                                     1409
```

<210> SEQ ID NO 60
<211> LENGTH: 1650
<212> TYPE: RNA
<213> ORGANISM: HUMAN

<400> SEQUENCE: 60

```
cggggungca ccuggcgcuu ggcgcccgca ccucugcccg ccucggagac cccgcagccc     60
```

cgcgccgccg ccuggccccg gccccggccc cuccgcggga uccuggcccc uccucgagcg 120
ccgccaccgg ccgccauggc cucucugggg gaccuggugc gcgccuggca ccugggcgcg 180
caggcugugg aucgugggga cugggcccgc gccuugcacc ucuucucggg cgucccggcg 240
ccgcccgcca ggcugugcuu caacgcgggc ugcgugcacc ugcuggccgg ggaccccgag 300
gccgcgcugc gggcauuuga ccaagccgug accaaggaca ccugcauggc gguuggcuuc 360
uuccagcgag gaguggccaa cuuccagcug gcaagguucc aggaggcucu gucugacuuc 420
uggcuggccc uggagcagcu gaggggccac gcugccaucg acuacacgca gcugggccug 480
cgguucaagc ugcaagccug ggaggugcua cacaaugugg cgucggcaca gugccagcug 540
gggcucugga cagaggcggc cagcagccua agggaggcca uguccaagug gccggagggg 600
ucccugaaug gccuggacuc agcccuggac caagugcaga gacggggcuc acugccgcca 660
cggcaggucc ccaggggcga ggucuuccgg ccccaccggu ggcaccugaa gcacuuggag 720
cccguggauu uccugggcaa ggccaaggug guggccucug ccauccccga cgaccagggc 780
uggggcgucc gcccucagca gccacaggga ccaggagcga accaugaugc cagguccccua 840
aucauggacu ccccaagagc uggcacccac cagggccccc ucgaugcaga gacagagguc 900
ggugcugacc gcugcacguc gacugccuac caggagcaga ggccccaggu ggagcaaguu 960
ggcaaacagg cuccucucuc cccagggcug ccggcaaugg gggggccugg ccccggcccc 1020
ugugaggacc ccgcgggugc ugggggagca ggugcagggg gcuccgagcc ccuggugacu 1080
gucaccgugc agugcgccuu cacaguggcc cugagggcac gaagaggagc cgaccugucc 1140
agccugcggg cacugcuggg ccaagcccuc ccucaccagg cccagcuugg gcaacucagu 1200
uaccuagccc caggugagga cgggcacugg guccccaucc ccgaggagga gucgcugcag 1260
agggccuggc aggacgcagc ugccugcccc agggggcugc agcugcagug caggggagcc 1320
gggggucggc cgguccucua ccaggguggug gcccagcaca gcuacuccgc ccaggggcca 1380
gaggaccugg gcuuccgaca gggggacacg guggacgucc ugugugaaga gcccgauguc 1440
ccccuugcag uggaccaggc auggcuggag ggccacugug acggccgcau cggcaucuuc 1500
cccaagugcu ucgugguccc cgccggcccu cggaugucag gagcccccgg ccgccugccc 1560
cgaucccagc agggagauca gcccuaauga ugcuguguccc augaugcuuu uaauaaaaac 1620
aacccccacu gcaaaaaaaa aaaaaaaaaa 1650

<210> SEQ ID NO 61
<211> LENGTH: 2429
<212> TYPE: RNA
<213> ORGANISM: HUMAN

<400> SEQUENCE: 61
acacuccacc ccuacucgcc cucucucucu cugcuucuuu ccuuuucucu cucaugguag 60
gguuaugagu caguugccaa aaggugggga cauuuccuga ugcauuugca acacugagaa 120
guuaucuuaa gggaggcugg gccccauucu acucaucugg cccagaaagu gaacaccuug 180
ggggccacua aggcagcccu gcuaggggag acgcuccaac cugucuucuc ucugucuccu 240
ggcagcucuc uuggccuccu aguuucuacc uaaucauguc ccugguggag gccaucagcc 300
ucuggaauga aggggugcug gcagcggaca agaaggacug gaagggagcc cuggaugccu 360
ucagugccgu ccaggacccc cacucccgga uuugcuucaa cauuggcugc auguacacua 420
uccugaagaa caugacugaa gcagagaagg ccuuuaccag aagcauuaac cgagacaagc 480
acuuggcagu ggcuuacuuc caacgaggga ugcucuacua ccagacagag aaauaugauu 540
uggcuaucaa agaccuuaaa gaagccuuga uucagcuucg agggaaccag cugauagacu 600
auaagauccu ggggcuccag uucaagcugu uugccuguga gguguuauau aacauugcuu 660
ucauguaugc caagaaggag gaauggaaaa aagcugaaga acaguuagca uuggccacga 720
gcaugaaguc ugagcccaga cauuccaaaa ucgacaaggc gauggagugu gucuggaagc 780
agaagcuaua ugagccagug gugaucccug ugggcaagcu guuucgacca aaugagagac 840
aaguggcuca gcuggccaag aaggauuacc uaggcaaggc gacggucgug gcaucugugg 900
uggaucaaga caguuucucu ggguuugccc cucugcaacc acaggcagcu gagccuccac 960
ccagaccgaa aaccccagag aucuucaggg cucuggaagg ggaggcucac cgugugcuau 1020
uuggguuugu gccugagaca aaagaagagc uccaggucau gccagggaac auugucuuug 1080
ucuugaagaa gggcaaugau aacugggcca cggucauguu caacgggcag aaggggcuug 1140
uucccugcaa cuaccuugaa ccaguugagc ugcggaucca cccucagcag cagccccagg 1200
aggaaagcuc uccgcagucc gacaucccag cuccuccuag uuccaaagcc ccuggaagac 1260
cccagcuguc accaggccag aaacaaaaag aagagccuaa ggaagugaag cucaguguuc 1320
ccaugcccua cacacucaag gugcacuaca aguacacggu agucaugaag acucagcccg 1380
ggcuccccua cagccagguc cgggacaugg ugucuaagaa acuggagcuc cggcuggaac 1440
acacuaagcu gagcuaucgg ccucgggaca gcaaugagcu ggugccccuu ucagaagaca 1500
gcaugaagga ugccuggggc caggugaaaa acuacugccu gacucugugg ugugagaaca 1560
caguggguga ccaaggcuuu ccagaugaac ccaaggaaag ugaaaaagcu gaugcuaaua 1620
accagacaac agaaccucag cuuaagaaag gcagccaagu ggaggcacuc uucaguuaug 1680
aggcuaccca accagaggac cuggaguuuc aggaaggggga uauaauccug guguuaucaa 1740
aggugaauga agaauggcug gaaggggagu gcaaagggaa ggugggcauu uuccccaaag 1800
uuuuuguuga agacugcgca acuacagauu uggaaagcac ucggagagaa gucuaggaug 1860
uuucacaaac uacaaagcug aagaaaauga agcccuauua cuuguuugua agauuuagca 1920
cccuucugcu guauacugua cugagacauu acaguuugga aguguuaacu auuuauuccc 1980
uguuaaaauu uaaccuacua gacaaugaug ugaguaccca ggaugauuuc cuggggcaca 2040
gugggugagg agauggggac aggugaaugg aggaguuagg ggagaggaaa aguggaugga 2100
agugucugga aagggcacga gagagucuuc cagguacuga uccuguuucu ugcucugagu 2160
gcuagcuagc cagcuguguu cacacuguaa acauucauca agcuguacau uuggugcacu 2220 uuucugugc auaccacaau aaaaaaaaac cuagcaucuu acaaaaacaa gacacccaag 2280
uccaggccca aggaguaagu acaaauauuc cuguuucuga accauuacug uaauuggcuc 2340
uuaaggcuug aaguaaccuu auagguuacu cauaaggcau auacaaauaa acuuguuugu 2400
uuucuuuuuu caaaaaaaaa aaaaaaaaa 2429

<210> SEQ ID NO 62
<211> LENGTH: 2256
<212> TYPE: RNA
<213> ORGANISM: HUMAN

<400> SEQUENCE: 62
acucuagguc acggguuuca uuugggacca guagccuagu cuuucagccu ucaggcuguu 60
uuuggcuuga agcucucuug gccuccuagu uucuaccuaa ucaugucccu gguggaggcc 120
aucagccucu ggaaugaagg ggugcuggca gcggacaaga aggacuggaa gggagcccug 180
gaugccuuca gugccgucca ggacccccac ucccggauuu gcuucaacau uggcugcaug 240
uacacuaucc ugaagaacau gacugaagca gagaaggccu uuaccagaag cauuaaccga 300
gacaagcacu uggcaguggc uuacuuccaa cgagggaugc ucuacuacca gacagagaaa 360
uaugauuugg cuaucaaaga ccuuaaagaa gccuugauuc agcuucgagg gaaccagcug 420
auagacuaua agauccuggg gcuccaguuc aagcuguuug ccugugaggu guuauauaac 480
auugcuuuca uguaugccaa gaaggaggaa uggaaaaaag cugaagaaca guuagcauug 540
gccacgagca ugaagucuga gcccagacau uccaaaaucg acaaggcgau ggagugugu c 600 uggaagcaga agcuauauga gccagugguga aucccugugg gcaagcuguu ucgaccaaau 660
gagagacaag uggcucagcu ggccaagaag gauuaccuag gcaaggcgac ggucguggca 720 ucugugggugg aucaagacag uuucucuggg uuugccccuc ugcaaccaca ggcagcugag 780
ccuccaccca gaccgaaaac cccagagauc uucagggcuc uggaagggga ggcucaccgu 840
gugcuauuug gguuugugcc ugagacaaaa gaagagcucc aggucaugcc agggaacauu 900
gucuuugucu ugaagaaggg caaugauaac ugggccacgg ucauguucaa cgggcagaag 960
gggcuuguuc ccugcaacua ccuugaacca guugagcugc ggauccaccc ucagcagcag 1020
ccccaggagg aaagcucucc gcaguccgac aucccagcuc cuccuaguuc caaagcccc u 1080 ggaagacccc agcugucacc aggccagaaa caaaaagaag agccuaagga agugaagcuc 1140
aguguuccca ugcccuacac acucaaggug cacuacaagu acacgguagu caugaagacu 1200
cagcccgggc uccccuacag ccagguccgg gacauggugu cuaagaaacu ggagcuccgg 1260
cuggaacaca cuaagcugag cuaucggccu cgggacagca augagcuggu gccccuuuca 1320
gaagacagca ugaaggaugc cuggggccag gugaaaaacu acugccugac ucugugggugu 1380 gagaacacag ugggugacca aggcuuucca gaugaaccca aggaaaguga aaaagcugau 1440
gcuaauaacc agacaacaga accucagcuu aagaaaggca gccaagugga ggcacucuuc 1500
aguuaugagg cuacccaacc agaggaccug gaguuucagg aaggggauau aauccuggug 1560
uuaucaaagg ugaaugaaga auggcuggaa ggggagugca aagggaaggu gggcauuuuc 1620
cccaaaguuu uuguugaaga cugcgcaacu acagauuugg aaagcacucg gagagaaguc 1680
uaggauguuu cacaaacuac aaagcugaag aaaaugaagc ccuauuacuu guuuguaaga 1740
uuuagcaccc uucugcugua uacuguacug agacauuaca guuuggaagu guuaacuauu 1800
uauucccugu uaaaauuuaa ccuacuagac aaugauguga guacccagga ugauuuccug 1860
gggcacagug ggugaggaga uggggacagg ugaauggagg aguuagggga gaggaaaagu 1920
ggauggaagu gucuggaaag ggcacgagag agucuuccag guacugaucc uguuucuugc 1980
ucugagugcu agcuagccag cuguguucac acuguaaaca uucaucaagc uguacauuug 2040
gugcacuuuu cugugucaua ccacaauaaa aaaaaaccua gcaucuuaca aaaacaagac 2100
acccaagucc aggcccaagg aguaaguaca aauauuccug uuucugaacc auuacuguaa 2160
uuggcucuua aggcuugaag uaaccuuaua gguuacucau aaggcauaua caaauaaacu 2220
uguuuguuuu cuuuuuucaa aaaaaaaaaa aaaaaa 2256

<210> SEQ ID NO 63
<211> LENGTH: 4976
<212> TYPE: RNA
<213> ORGANISM: HUMAN

<400> SEQUENCE: 63
gggcgggcgg gccgcaggcu gucgggcugg ggcugaggcu gaggcugagg uugaggcggc 60
ggcggcggcg gccgggugcc cgggacagcg acgcagcgcg ccggcggccg cgacagggcc 120
agcgagagcc ccgcagcccg ccgcagcugc cgccucgccg cggccgggcc ggagagcacg 180
gcggcgggag cgcggccuua ggaggcggcc ggagcggugg gcacagcucg gcgcggagcg 240
uccugucagg cggcggccga gggcgucgcg gacucucccc gcgaugaugc cgaugauauu 300
aacuguuuuc uugagcaaca augaacagau uuuaacagaa guuccuauaa caccggaaac 360
aaccugucga gauguuguag aauuuugcaa ggaaccugga gaaggcagcu gccauuuagc 420
ugaaguguggg aggggaaaug aacgucccau acccuuugau cauaugaugu acgaacaucu 480
ucagaaaugg gguccacgga gggaagaagu gaaauuuuuc cuucgacacg aggacucccc 540
aacugagaac agugaacaag guggccguca gacccaagag caacgaacuc agagaaaugu 600
aauaaaugua ccuggagaaa aacguacuga aaaugggguu gggaauccac guguugaacu 660
uacccucuca gagcuccaag auauggcagc uaggcaacag cagcagauug aaaaucagca 720
gcagauguug guugccaagg aacagcguuu acauuuucua aagcaacagg agcgccguca 780
gcagcagucu auuucugaaa augaaaagcu ucagaaauug aaagaacgag uugaagccca 840
ggagaacaag cugaagaaaa uucgugcaau gagaggacaa gucgacuaca gcaaaaucau 900
gaacggcaau cugucugcug aaauagaaag guucagugcc auguuccagg aaaagaagca 960
ggaaguacag acugcaauuu uaaggguuga ucagcuuagu cagcaauugg aagauuuaaa 1020
gaaaggaaaa cugaaugggu uccagucuua caauggcaaa uugacgggac cagcggcggu 1080
ggaguuaaaa agacuguacc aagaacuaca gauucguaac caacuuaacc aggaacaaaa 1140
uucaaaacuu cagcagcaga aggaacucuu aaauaagcgc aacauggagg uggccaugau 1200
ggacaagcga aucagugaac ugcgugaacg ucucuauggg aaaaaaauuc agcugaaccg 1260
ugugaauggc acgucaucac cacagucccc ucugagcaca ucgggcaggg ucgcugcugu 1320
ggggccuuau auccagguuc ccagugccgg aagcuuuccu gugcuggggg acccuauaaa 1380
gccccagucu cucaguauug ccucaaaugc ugcucaugga agauccaaau ccgcuaauga 1440
uggaaacugg ccaacauuaa aacagaauuc uagcucuucc gugaaaccag ugcagguggc 1500
cggugcagac uggaaggauc cgagcgugga ggggucuguc aagcagggca cugucuccag 1560
ccagccugug cccuucucag cacugggacc cacggagaag ccgggcaucg agauugguaa 1620
agugccaccu cccaucccgg guguaggcaa gcagcugccu ccaagcuaug ggacauaccc 1680
aaguccuaca ccucugggguc cugggucgac aagcucccug gaaaggagga aggaaggcag 1740
cuugcccagg cccagugcag gccugccaag ucgacagagg cccacccugc ugcccgccac 1800
aggcagcacc ccccagccag gcuccucaca acagauucag cagaggauuu ccguaccgcc 1860
aagucccacg uacccgccag cgggaccacc ugcauuucca gcuggggaca gcaagccuga 1920
acucccacug acaguggcca uuaggccuuu ccuggcugau aaagggucaa ggccacaguc 1980
ucccaggaaa ggaccccaga cagugaauuc aaguuccaua uacuccaugu accuccagca 2040
agccacacca ccuaagaauu accagccggc agcacacagc gccuuaaaua agucaguuaa 2100
agcaguguau gguaagcccg uuuuaccuuc ggguucaacc ucuccaucgc cgcugccguu 2160
ucuucacggg ucacugucca cgggcacacc acagccucag ccaccuucag aaaguacuga 2220
gaaagagccu gagcaggaug gccccgccgc ccccgcagau ggcagcaccg uggagagccu 2280
gccacggcca cucagcccca ccaagcucac gcccaucgug cauucgccac ugcgcuacca 2340
gagugaugca gaccuggagg cccuccgcag gaagcuggcc aacgcgcccc ggccccugaa 2400
aaagcgcagc uccaucacag agcccgaggg ccccggcggg cccaacaucc agaagcugcu 2460
guaccagcgc uucaacaccc uggccggugg cauggagggc accccuuucu accagcccag 2520

-continued

```
ccccucccag gacuucaugg gcaccuuggc cgauguggac aauggaaaca ccaaugccaa   2580
uggaaaccug gaagagcucc ccccugccca gcccacagcc ccacuccccg cugagccugc   2640
cccgucauca gaugccaaug auaaugaguu accuuccccc gaaccagagg agcucaucug   2700
uccccaaacc acccaccaaa cugccgagcc ggcagaggac aauaacaaca acguggccac   2760
gguccccacc acggagcaga ucccgagucc uguggcugag gccccaucuc caggggaaga   2820
gcaggucccu ccagcaccuc uucccccugc cagccacccu ccugccaccu ccacgaacaa   2880
gcggaccaac uugaagaagc ccaacucgga gcggacgggg cacgggcuga gaguccgguu   2940
uaacccccug gcacugcucc uagacgcguc ucuggaagga gaguucgauc uggugcagag   3000
gaucaucuau gagguggaag aucccagcaa gcccaacgac gaagggauca ccccacugca   3060
caacgccguc ugcgccggcc accaucacau cgugaaguuc cugcuggauu uuggugucaa   3120
cgugaaugcu gcugauagug auggauggac gccgcugcac ugcgcugccu cuuguaacag   3180
cguucaccuc ugcaaacagc ugguggagag uggugccgcc auuuuugccu caaccauaag   3240
cgacauugaa acugcugcag acaaguguga ggagauggag gaaggcuaca uccagugcuc   3300
ccaguuucua uauggggugc aggaaaagcu gggugugaug aacaaaggug uggcguaugc   3360
ucugugggac uacgaggccc agaacaguga cgagcugucc uuccacgaag ggggacgcccu   3420
caccauccug aggcgcaagg acgaaagcga gacugagugg uggugggcuc gccuuggaga   3480
ccgggagggc uaugugccca aaaaccugcu ggggcuguau ccacggauca aaccccgaca   3540
gcgaacacuc gccugaacuu ccuuuuggag caccgcaugg ucuugccagc uaccaggagc   3600
cacuuaagag auuauugugc uguuuuccag gaaagcugca gcuagaaaau ggucuuaaug   3660
gugcucacuu uagcagacag cguccacaau gugaauccua caguuuccag gugaggcccu   3720
uucuccaguu ugcccauuaa cugggagagg uacuuucgcc uccaaggacu gaauuuugcc   3780
aauuacuaua aauccaaaua aauacccacu uucaaaacac ccaccccucu ugccauuaag   3840
aagucccaua acccccgguu gguugccagu gaagacagaa gcucuuacug acuuggcccc   3900
gaggccauca cccccuccag cagugaacac uguccgccgc ugugaggccu gcuccccugc   3960
gaccgcccug ccccccguca ccgaaucgga cacucauccu uucucacacu ucccacacau   4020
gauccuucuu cccuucauca ccaaaggagc cucuguaugg aaacaugucc aguguugcug   4080
cccagugugu augccuccca guacccacuc ugcucggccg ccuuggggggu uccgcuuccu   4140
guuccaguuc accuaaaggc ugauugugca ggcccagcac uguggcugga cugccgcgcc   4200
acgggcacca ggaccccuaa gaccaaguga caacugggag agccucagca uauacucuuc   4260
uccuccgauc ucacagccug ucaugcugcu cagugugguu cucaccccug caagcucaaa   4320
uucaguuccc ugaauggagu cagguugcugg aggccguggc agcggagggu gguuggggguu   4380
ggggcugggg guggacuggu gugagggcag accagggcca gguagacggg gcuguuuggu   4440
gccugaagga uggcagacgc cugguggucag gaggggccgc caccaaggag cagcagcugg   4500
ggcagaggag cuggggucag gggccacccc ucucugccga ucucccugcc ugggcuggcu   4560
gugaggccac cuuuguccca ggcccagccu caaggcaagg agggcgcuuc acugaggugu   4620
gaauuguacg uacaggcuuu uuauauacca aaaguauuuu uugacuagac cauucaaagc   4680
uacccgaacu auguuggaaa uuuuuuuuuu cucauuaaaa uacaggcccu uaggcucuau   4740
uuuucaugua ugagucgugu guaauuuaug uaaaaaugug uguacagacu cacugaugca   4800
gcacuguagc ccaucaccuu ggagcacuga cuguacauag ugugguguaag aaaagugaac   4860
gcccuuguag agcagcccga ccacaggagc auggccgcug ccagcccaga cgcugcugac   4920
```

-continued gcuguguaaa ugugcacaau aaacccgucu caccccggca aaaaaaaaaa aaaaaa 4976

<210> SEQ ID NO 64
<211> LENGTH: 2205
<212> TYPE: RNA
<213> ORGANISM: HUMAN

<400> SEQUENCE: 64
gcgcacgccg gccgcgccca cgugaccggu ccgggugcaa acacgcgggu cagcugaucc 60
ggcccaacug cggcgucauc ccggcuauaa gcgcacggcc ucggcgaccc ucuccgaccc 120
ggccgccgcc gccaugcagc ccuccagccu ucugccgcuc gcccucugcc ugcuggcugc 180
acccgccucc gcgcucguca ggaucccgcu gcacaaguuc acguccaucc gccggaccau 240
gucggagguu gggggcucug uggaggaccu gauugccaaa ggccccgucu caaaguacuc 300
ccaggcggug ccagccguga ccgaggggcc cauucccgag gugcucaaga acuacaugga 360
cgcccaguac uacggggaga uuggcaucgg gacgcccccc cagugcuuca cagucgucuu 420
cgacacgggc uccuccaacc ugugggaccc cuccauccac ugcaaacugc uggacaucgc 480
uugcuggauc caccacaagu acaacagcga caaguccagc accuacguga agaaugguac 540
cucguuugac auccacuaug gcucgggcag ccucuccggg uaccugagcc aggacacugu 600
gucggugccc ugccagucag cgucgucagc cucugcccug ggcgguguca aaguggagag 660
gcaggucuuu ggggaggcca ccaagcagcc aggcaucacc uucaucgcag ccaaguucga 720
uggcauccug ggcauggccu acccccgcau cuccgucaac aacgugcugc ccgucuucga 780
caaccugaug cagcagaagc ugguggacca gaacaucuuc uccuucuacc ugagcaggga 840
cccagaugcg cagccugggg gugagcugau gcugggugc acagacucca aguauuacaa 900 gguucucug uccuaccuga augucacccg caaggccuac uggcagguc accuggacca 960 gguggaggug gccagcgggc ugacccugug caaggagggc ugugaggcca uuguggacac 1020
aggcacuucc cucauggugg gcccggugga ugaggugcgc gagcugcaga aggccaucgg 1080
ggccgugccg cugauucagg gcgaguacau gauccccugu gagaaggugu ccacccugcc 1140
cgcgaucaca cugaagcugg gaggcaaagg cuacaagcug uccccagagg acuacacgcu 1200
caaggugucg caggccggga agacccucug ccugagcggc uucaugggca uggacauccc 1260
gccacccagc gggccacucu ggauccuggg cgacgucuuc aucggccgcu acuacacugu 1320
guuugaccgu gacaacaaca gggugggcuu cgccgaggcu gcccgccucu aguucccaag 1380
gcguccgcgc gccagcacag aaacagagga gagucccaga gcaggaggcc ccuggcccag 1440
cggccccucc cacacacacc cacacacucg cccgcccacu guccugggcg cccuggaagc 1500
cggcggccca agcccgacuu gcuguuuugu ucugugguuu uccccucccu ggguucagaa 1560
augcugccug ccugucuguc ucuccaucug uuuggugggg guagagcuga uccagagcac 1620
agaucuguuu cgugcauugg aagaccccac ccaagcuugg cagccgagcu cguguauccu 1680
ggggcucccu ucaucuccag ggaguccccu ccccggcccu accagcgccc gcugggcuga 1740
gccccuaccc cacaccaggc cguccucccg ggcccucccu uggaaaccug cccugccuga 1800
gggccccucu gcccagcuug ggcccagcug ggcucugcca cccuaccugu ucaguguccc 1860
gggcccguug aggaugaggc cgcuagaggc cugaggauga gcuggaagga gugagagggg 1920
acaaaaccca ccuuguugga gccugcaggg uggugcuggg acugagccag ucccaggggc 1980
auguauuggc cuggaggugg gguugggauu gggggcuggu gccagccuuc cucugcagcu 2040
gaccucuguu guccucccu ugggcggcug agagccccag cugacaugga aauacaguug 2100
uuggccuccg gccucccuc aaaaaaaaaa aaaaaaaaaa aaaaaaaaaa aaaaaaaaaa 2160
aaaaaaaaaa aaaaaaaaaa aaaaaaaaaa aaaaaaaaaa aaaaa 2205

<210> SEQ ID NO 65
<211> LENGTH: 1492
<212> TYPE: RNA
<213> ORGANISM: HUMAN

<400> SEQUENCE: 65
cgggcgacag cagggccgcg gugcagiguc cgacccgaga guugcggccu gagucaccgg 60
ccccgcccuc cggagccgga cgcugcggga ggcccgggag cggcagugga accgacuccc 120
agaacuccgg acgugugcgg cgcagugagu cgcagccaug uuccugguua acucguucuu 180
gaagggcggc ggcggcggcg gcgggggagg cgggggccug gguggggggcc ugggaaaugu 240 gcuuggaggc cugaucagcg gggccggggg cggcggcggc ggcggcggcg gcggcggcgg 300
ugguggaggc ggcgguggcg guggaacggc caugcgcauc cuaggcggag ucaucagcgc 360
caucagcgag gcggcugcgc aguacaaccc ggagcccccg cccccacgca cacauuacuc 420
caacauugag gccaacgaga gugaggaggu ccggcaguuc cggagacucu uugcccagcu 480
ggcuggagau gacauggagg ucagcgccac agaacucaug aacauucuca auaagguugu 540
gacacgacac ccugaucuga agacugaugg uuuuggcauu gacacauguc gcagcauggu 600
ggccgugaug gauagcgaca ccacaggcaa gcugggcuuu gaggaauuca aguacuugug 660
gaacaacauc aaaagguggc aggccauaua caaacaguuc gacacugacc gaucagggac 720
cauuugcagu agugaacucc caggugccuu ugaggcagca ggguuccacc ugaaugagca 780
ucucuauaac augaucaucc gacgcuacuc agaugaaagu gggaacaugg auuuugacaa 840
cuucaucagc ugcuugguca ggcuggacgc cauguuccgu gccuucaaau cucuugacaa 900
agauggcacu ggacaaaucc aggugaacau ccaggagugg cugcagcuga cuauguauuc 960
cugaacugga gccccagacc cgccccccuca cugccuugcu auaggaguca ccuggagccu 1020
cggucucucc cagggccgau ccugucugca gucacaucuu uguggggccu gcugacccac 1080
aagcuuuugu ucucucagua cuuguuaccc agcuucucaa cauccagggc ccaauuugcc 1140
cugccuggag uucccccugg cucuaggaca cucuaacaag cucuguccac gggucucccc 1200
auucccacca ggcccugcac acacccacuc cguaaccucu ccccuguacc ugugccaagc 1260
cuagcacuug ugaugccucc augccccgag ggcccucucu caguucuggg aggaugacuc 1320 caguccugc acgcccuggc acacccuuca cgguugcuac ccaggcggcc aagcuccaga 1380
ccgugccaga cccaggugcc ccagugccuu ugucuauauu cugcucccag ccugccaggc 1440
ccaggaggaa auaaacaugc cccaguugcu gaucucuaaa aaaaaaaaaa aa 1492

<210> SEQ ID NO 66
<211> LENGTH: 1489
<212> TYPE: RNA
<213> ORGANISM: HUMAN

<400> SEQUENCE: 66
cgggcgacag cagggccgcg gugcagiguc cgacccgaga guugcggccu gagucaccgg 60
ccccgcccuc cggagccgga cgcugcggga ggcccgggag cggcagugga accgacuccc 120
agaacuccgg acgugugcgg cgugagucgc agccauguuc cugguuaacu cguucuugaa 180
gggcggcggc ggcggcggcg ggggaggcgg gggccugggu gggggccugg gaaaugugcu 240
uggaggccug aucagcgggg ccgggggcgg cggcggcggc ggcggcggcg gcggcggugg 300
uggaggcggc gguggcggug gaacggccau gcgcauccua ggcggaguca ucagcgccau 360
cagcgaggcg gcugcgcagu acaacccgga gcccccgccc ccacgcacac auuacuccaa 420
cauugaggcc aacgagagug aggagguccg gcaguuccgg agacucuuug cccagcuggc 480
uggagaugac auggagguca gcgccacaga acucaugaac auucucaaua agguugugac 540
acgacacccu gaucugaaga cugaugguuu uggcauugac acaugucgca gcauggugge 600 cgugauggau agcgacacca caggcaagcu gggcuuugag gaauucaagu acuuguggaa 660
caacaucaaa agguggcagg ccauauacaa acaguucgac acugaccgau cagggaccau 720
uugcaguagu gaacucccag gugccuuuga ggcagcaggg uuccaccuga augagcaucu 780
cuauaacaug aucauccgac gcuacucaga ugaaaguggg aacauggauu uugacaacuu 840
caucagcugc uuggucaggc uggacgccau guuccgugcc uucaaaucuc uugacaaaga 900
uggcacugga caaauccagg ugaacaucca ggaguggcug cagcugacua uguauuccug 960
aacuggagcc ccagacccgc cccccucacug ccuugcuaua ggagucaccu ggagccucgg 1020
ucucucccag ggccgauccu gucugcaguc acaucuuugu ggggccugcu gacccacaag 1080
cuuuuguucu cucaguacuu guuacccagc uucucaacau ccagggccca auuugcccug 1140
ccuggaguuc ccccuggcuc uaggacacuc uaacaagcuc uguccacggg ucuccccauu 1200
cccaccaggc ccugcacaca cccacuccgu aaccucuccc cuguaccugu gccaagccua 1260
gcacuuguga ugccuccaug ccccgagggc ccucucucag uucugggagg augacuccag 1320
ucccugcacg cccuggcaca cccuucacgg uugcuaccca ggcggccaag cuccagaccg 1380
ugccagaccc aggugcccca gugccuuugu cuauauucug cucccagccu gccaggccca 1440
ggaggaaaua aacaugcccc aguugcugau cucuaaaaaa aaaaaaaaa 1489

<210> SEQ ID NO 67
<211> LENGTH: 2586
<212> TYPE: RNA
<213> ORGANISM: HUMAN

<400> SEQUENCE: 67 gauuggggguu uuccccuccc augugcucaa gacuggcgcu aaaaguuuug agcuucucaa 60
aagucuagag ccaccgucca gggagcaggu agcugcuggg cuccggggac acuuugcguu 120
cgggcuggga gcgugcuuuc cacgacggug acacgcuucc cuggauuggc agccagacug 180
ccuuccgggu cacugccaug gaggagccgc agucagaucc uagcgucgag cccccucuga 240
gucaggaaac auuuucagac cuauggaaac uacuuccuga aaacaacguu cugucccccu 300
ugccguccca agcaauggau gauuugaugc uguccccgga cgauauugaa caaugguuca 360
cugaagaccc agguccagau gaagcuccca gaaugccaga ggcugcuccc cccguggccc 420
cugcaccagc agcuccuaca ccggcggccc cugcaccagc cccccuccugg ccccugucau 480 cuucuguccc uucccagaaa accuaccagg gcagcuacgg uuuccgucug ggcuucuugc 540
auucugggac agccaagucu gugacuugca cguacucccc ugcccucaac aagauguuuu 600
gccaacuggc caagaccugc ccugugcagc ugugggguuga uuccacaccc ccgcccggca 660
cccgcguccg cgccauggcc aucuacaagc agucacagca caugacggag guugugaggc 720 gcugcccccca ccaugagcgc ugcucagaua gcgauggucu ggccccuccu cagcaucuua 780
uccgagugga aggaaauuug cguguggagu auuuggauga cagaaacacu uuucgacaua 840
gugugguggu gcccuaugag ccgccugagg uuggcucuga cuguaccacc auccacuaca 900
acuacaugug uaacaguucc ugcaugggcg gcaugaaccg gaggcccauc cucaccauca 960
ucacacugga agacuccagu gguaaaucuac ugggacggaa cagcuuugag gugcguguuu 1020
gugccugucc ugggagagac cggcgcacag aggaagagaa ucuccgcaag aaaggggagc 1080
cucaccacga gcugccccca gggagcacua agcgagcacu gcccaacaac accagcuccu 1140
cuccccagcc aaagaagaaa ccacuggaug gagaauauuu cacccuucag auccgugggc 1200
gugagcgcuu cgagauguuc cgagagcuga augaggccuu ggaacucaag gaugcccagg 1260
cugggaagga gccagggggg agcagggcuc acuccagcca ccugaagucc aaaaaggguc 1320
agucuaccuc ccgccauaaa aaacucaugu ucaagacaga agggccugac ucagacugac 1380
auucuccacu ucuuguuccc cacugacagc cuccccaccc caucucuccc uccccugcca 1440
uuuuggguuu ugggucuuug aacccuugcu ugcaauaggu gugcgucaga agcacccagg 1500
acuuccauuu gcuuuguccc ggggcuccac ugaacaaguu ggccugcacu ggugucuugu 1560
uguggggagg aggaugggga guaggacaua ccagcuuaga uuuuaagguu uuuacuguga 1620
gggauguuug ggagauguaa gaaauguucu ugcaguuaag gguuaguuua caaucagcca 1680
cauucuaggu aggggcccac uucaccguac uaaccaggga agcugucccu cacuguugaa 1740
uuuucucuaa cuucaaggcc cauaucugug aaaugcuggc auuugcaccu accucacaga 1800
gugcauugug aggguuaaug aaauaaugua caucuggccu ugaaaccacc uuuuauuaca 1860
uggggucuag aacuugaccc ccuugagggu gcuuguuccc ucucccuguu ggucggugggg 1920 uugguaguuu cuacaguugg gcagcugguu agguagaggg aguugucaag ucucugcugg 1980
cccagccaaa cccugucuga caaccucuug gugaaccuua guaccuaaaa ggaaaucuca 2040
ccccauccca cacccuggag gauuucaucu cuuguauaug augaucugga uccaccaaga 2100
cuuguuuuau gcucaggguc aauuucuuuu uucuuuuuuu uuuuuuuuuu ucuuuuucuu 2160
ugagacuggg ucucgcuuug uugcccaggc uggaguggag uggcgugauc uuggcuuacu 2220
gcagccuuug ccuccccggc ucgagcaguc cugccucagc cuccggagua gcugggacca 2280
cagguucaug ccaccauggc cagccaacuu uugcauguuu uguagagaug gggucucaca 2340
guguugccca ggcuggucuc aaacuccugg gcucaggcga uccaccuguc ucagccuccc 2400
agagugcugg gauuacaauu gugagccacc acguccagcu ggaaggguca acaucuuuua 2460
cauucugcaa gcacaucugc auuuucaccc cacccuuccc cuccuucucc cuuuuuauau 2520
cccauuuuua uaucgaucuc uuauuuuaca auaaaacuuu gcugccaccu gugugucuga 2580
ggggug 2586

<210> SEQ ID NO 68
<211> LENGTH: 2583
<212> TYPE: RNA
<213> ORGANISM: HUMAN

<400> SEQUENCE: 68 gauuggggu uuccccuccc augugcucaa gacuggcgcu aaaaguuuug agcuucucaa 60
aagucuagag ccaccgucca gggagcaggu agcugcuggg cuccggggac acuuugcguu 120
cgggcuggga gcgugcuuuc cacgacggug acacgcuucc cuggauuggc cagacugccu 180
uccgggucac ugccauggag gagccgcagu cagauccuag cgucgagccc ccucugaguc 240
aggaaacauu uucagaccua uggaaacuac uuccugaaaa caacguucug ucccccuugc 300
cgucccaagc aauggaugau uugaugcugu ccccggacga uauugaacaa ugguucacug 360
aagacccagg uccagaugaa gcucccagaa ugccagaggc ugcucccccc guggccccug 420
caccagcagc uccuacaccg gcggccccug caccagcccc cuccuggccc cugucaucuu 480

```
cugucccuuc ccagaaaacc uaccagggca gcuacgguuu ccgucugggc uucuugcauu     540

cugggacagc caagucugug acuugcacgu acuccccugc ccucaacaag auguuuugcc     600

aacuggccaa gaccugcccu gugcagcugu ggguugauuc cacacccccg cccggcaccc     660

gcguccgcgc cauggccauc uacaagcagu cacagcacau gacggagguu gugaggcgcu     720

gcccccacca ugagcgcugc ucagauagcg augguccggc cccuccucag caucuuaucc     780

gaguggaagg aaauuugcgu guggaguauu uggaugacag aaacacuuuu cgacauagug     840

uggugugcc cuaugagccg ccugagguug gcucugacug uaccaccauc cacuacaacu     900

acauguguaa caguuccugc augggcggca ugaaccggag gcccauccuc accaucauca     960

cacuggaaga cuccaguggu aaucuacugg gacggaacag cuuugaggug cguguuugug    1020

ccuguccugg gagagaccgg cgcacagagg aagagaaucu ccgcaagaaa ggggagccuc    1080

accacgagcu gcccccaggg agcacuaagc gagcacugcc caacaacacc agcuccucuc    1140

cccagccaaa gaagaaacca cuggauggag aauauuucac ccuucagauc cgugggcgug    1200

agcgcuucga gauguuccga gagcugaaug aggccuugga acucaaggau gcccaggcug    1260

ggaaggagcc aggggggagc agggcucacu ccagccaccu gaaguccaaa aagggucagu    1320

cuaccucccg ccauaaaaaa cucauguuca agacagaagg gccugacuca gacugacauu    1380

cuccacuucu uguuccccac ugacagccuc ccaccccau cucucccucc ccugccauuu    1440

uggguuuugg gucuuugaac ccuugcuugc aauaggugug cgucagaagc acccaggacu    1500

uccauuugcu uugucccggg gcuccacuga acaaguuggc cugcacuggu guuuuguugu    1560

ggggaggagg auggggagua ggacauacca gcuuagauuu uaagguuuuu acugugaggg    1620

auguuuggga gauguaagaa auguucuugc aguuaagggu uaguuuacaa ucagccacau    1680

ucuagguagg ggcccacuuc accguacuaa ccagggaagc ugucccucac uguugaauuu    1740

ucucuaacuu caaggcccau aucugugaaa ugcuggcauu ugcaccuacc ucacagagug    1800

cauugugagg guuaaugaaa uaauguacau cuggccuuga aaccaccuuu uauuacaugg    1860

ggucuagaac uugacccccu ugagggugcu uguucccucu cccuguuggu cgguggguug    1920

guaguuucua caguugggca gcugguuagg uagagggagu ugucaagucu cugcuggccc    1980

agccaaaccc ugucugacaa ccucuuggug aaccuuagua ccuaaaagga aaucucaccc    2040

caucccacac ccuggaggau uucaucucuu guauaugaug aucuggaucc accaagacuu    2100

guuuuaugcu cagggucaau uucuuuuuuc uuuuuuuuuu uuuuuuuucu uuuucuuuga    2160

gacuggggucu cgcuuuguug cccaggcugg aguggagugg cgugaucuug gcuuacugca    2220

gccuuugccu ccccggcucg agcaguccug ccucagccuc cggaguagcu gggaccacag    2280

guucaugcca ccauggccag ccaacuuuug cauguuuugu agagaugggg ucucacagug    2340

uugcccaggc uggucucaaa cuccugggcu caggcgaucc accugucuca gccucccaga    2400

gugcugggau uacaauugug agccaccacg uccagcugga agggucaaca ucuuuuacau    2460

ucugcaagca caucugcauu uucaccccac ccuuccccuc cuucucccuu uuuauauccc    2520

auuuuuauau cgaucucuua uuuuacaaua aaacuuugcu gccaccugug ugucugaggg    2580

gug                                                                  2583
```

<210> SEQ ID NO 69
<211> LENGTH: 2719
<212> TYPE: RNA
<213> ORGANISM: HUMAN

<400> SEQUENCE: 69

-continued gauuggggguu uuccccuccc augugcucaa gacuggcgcu aaaaguuuug agcuucucaa 60
aagucuagag ccaccgucca gggagcaggu agcugcuggg cuccggggac acuuugcguu 120
cgggcuggga gcgugcuuuc cacgacggug acacgcuucc cuggauuggc agccagacug 180
ccuuccgggu cacugccaug gaggagccgc agucagaucc uagcgucgag cccccucuga 240
gucaggaaac auuuucagac cuauggaaac uacuuccuga aaacaacguu cugucccccu 300 ugccgucccca agcaauggau gauuugaugc uguccccgga cgauauugaa caaugguuca 360
cugaagaccc agguccagau gaagcuccca gaaugccaga ggcugcuccc cccguggccc 420
cugcaccagc agcuccuaca ccggcggccc cugcaccagc cccccuccugg ccccugucau 480 cuucugucc uucccagaaa accuaccagg gcagcuacgg uuuccgucug ggcuucuugc 540
auucugggac agccaagucu gugacuugca cguacucccc ugcccucaac aagauguuuu 600
gccaacuggc caagaccugc ccugugcagc ugugggguuga uuccacaccc ccgcccggca 660
cccgcguccg cgccauggcc aucuacaagc agucacagca caugacggag guugugaggc 720
gcugccccca ccaugagcgc ugcucagaua gcgauggucu ggccccuccu cagcaucuua 780
uccgagugga aggaaauuug cgugugggagu auuuggauga cagaaacacu uuucgacaua 840 guguggugu gcccuaugag ccgccugagg uuggcucuga cuguaccacc auccacuaca 900
acuacaugug uaacaguucc ugcaugggcg gcaugaaccg gaggcccauc cucaccauca 960
ucacacugga agacuccagu gguaaucuac ugggacggaa cagcuuugag gugcguguuu 1020
gugccugucc ugggagagac cggcgcacag aggaagagaa ucuccgcaag aaaggggagc 1080
cucaccacga gcugccccca gggagcacua agcgagcacu gcccaacaac accagcuccu 1140
cuccccagcc aaagaagaaa ccacuggaug gagaauauuu cacccuucag gaccagacca 1200
gcuuucaaaa agaaaauugu uaaagagagc augaaaaugg uucuaugacu uugccugaua 1260
cagaugcuac uugacuuacg augguguuac uuccugauaa acucgucgua aguugaaaau 1320
auuauccgug ggcgugagcg cuucgagaug uuccgagagc ugaaugaggc cuuggaacuc 1380
aaggaugccc aggcugggaa ggagccaggg gggagcaggg cucacuccag ccaccugaag 1440
uccaaaaagg gucagucuac cucccgccau aaaaaacuca uguucaagac agaagggccu 1500
gacucagacu gacauucucc acuucuuguu ccccacugac agccucccac ccccaucucu 1560 cccucccccug ccauuuuggg uuuugggucu uugaacccuu gcuugcaaua ggugugcguc 1620
agaagcaccc aggacuucca uuugcuuugu cccggggcuc cacugaacaa guuggccugc 1680
acugguguuu uguugugggg aggaggaugg ggaguaggac auaccagcuu agauuuuaag 1740
guuuuuacug ugagggaugu uugggagaug uaagaaaugu ucuugcaguu aaggguuagu 1800
uuacaaucag ccacauucua gguaggggcc cacuucaccg uacuaaccag ggaagcuguc 1860
ccucacuguu gaauuuucuc uaacuucaag gcccauaucu gugaaaugcu ggcauuugca 1920
ccuaccucac agagugcauu gugagggguua augaaauaau guacaucugg ccuugaaacc 1980
accuuuuauu acauggggguc uagaacuuga cccccuugag ggugcuuguu cccucucccu 2040
guuggucggu ggguugguag uuucuacagu ugggcagcug guuagguaga gggaguuguc 2100
aagucucugc uggcccagcc aaacccuguc ugacaaccuc uuggugaacc uuaguaccua 2160
aaaggaaauc ucaccccauc ccacacccug gaggauuuca ucucuuguau augaugaucu 2220
ggauccacca agacuuguuu uaugcucagg gucaauuucu uuuuucuuuu uuuuuuuuuu 2280
uuuucuuuuu cuuugagacu gggucucgcu uuguugccca ggcuggagug gaguggcgug 2340
aucuuggcuu acugcagccu uugccucccc ggcucgagca guccugccuc agccuccgga 2400

```
guagcuggga ccacagguuc augccaccau ggccagccaa cuuuugcaug uuuuguagag   2460

auggggucuc acaguguugc ccaggcuggu cucaaacucc ugggcucagg cgauccaccu   2520

gucucagccu cccagagugc ugggauuaca auugugagcc accacgucca gcuggaaggg   2580

ucaacaucuu uuacauucug caagcacauc ugcauuuuca ccccacccuu ccccuccuuc   2640

ucccuuuuua uaucccauuu uuauaucgau cucuuauuuu acaauaaaac uuugcugcca   2700

ccuguguguc ugaggggug                                                 2719
```

```
<210> SEQ ID NO 70
<211> LENGTH: 2646
<212> TYPE: RNA
<213> ORGANISM: HUMAN

<400> SEQUENCE: 70

gauuggggUU uuccccuccc augugcucaa gacuggcgcu aaaaguuuug agcuucucaa     60
```

```
aagucuagag ccaccgucca gggagcaggu agcugcuggg cuccggggac acuuugcguu    120

cgggcuggga gcgugcuuuc cacgacggug acacgcuucc cuggauuggc agccagacug    180

ccuuccgggu cacugccaug gaggagccgc agucagaucc uagcgucgag cccccucuga    240

gucaggaaac auuuucagac cuauggaaac uacuuccuga aaacaacguu cuguccccu    300

ugccguccca agcaauggau gauuugaugc uguccccgga cgauauugaa caaugguuca    360

cugaagaccc agguccagau gaagcuccca gaaugccaga ggcugcuccc cccguggccc    420

cugcaccagc agcuccuaca ccggcggccc cugcaccagc cccuccuggg ccccugucau    480

cuucuguccc uucccagaaa accuaccagg gcagcuacgg uuuccgucug ggcuucuugc    540

auucugggac agccaagucu gugacuugca cguacucccc ugcccucaac aagauguuuu    600

gccaacuggc caagaccugc ccugugcagc ugugggguuga uuccacaccc ccgcccggca    660

cccgcguccg cgccauggcc aucuacaagc agucacagca caugacggag guugugaggc    720

gcugccccca ccaugagcgc ugcucagaua gcgauggucu ggccccuccu cagcaucuua    780

uccgagugga aggaaauuug cguguggagu auuuggauga cagaaacacu uuucgacaua    840

gugugguggu gcccuaugag ccgccugagg uuggcucuga cuguaccacc auccacuaca    900

acuacaugug uaacaguucc ugcaugggcg gcaugaaccg gaggcccauc cucaccauca    960

ucacacugga agacuccagu gguaaucuac ugggacggaa cagcuuugag gugcguguuu   1020

gugccugucc ugggagagac cggcgcacag aggaagagaa ucuccgcaag aaaggggagc   1080

cucaccacga gcugccccca gggagcacua agcgagcacu gcccaacaac accagcuccu   1140

cuccccagcc aaagaagaaa ccacuggaug gagaauauuu cacccuucag augcuacuug   1200

acuuacgaug guguuacuuc cugauaaacu cgucguaagu ugaaaauauu auccgugggc   1260

gugagcgcuu cgagauguuc cgagagcuga augaggccuu ggaacucaag gaugcccagg   1320

cugggaagga gccagggggg agcagggcuc acuccagcca ccugaagucc aaaaagggguc   1380

agucuaccuc ccgccauaaa aaacucaugu ucaagacaga agggccugac ucagacugac   1440

auucuccacu ucuuguuccc cacugacagc cucccacccc caucucuccc ucccugcca   1500

uuuuggguuu ugggucuuug aacccuugcu ugcaauaggu gugcgucaga agcacccagg   1560

acuuccauuu gcuuuguccc ggggcuccac ugaacaaguu ggccugcacu ggugu uuugu   1620

ugugggggagg aggaugggga guaggacaua ccagcuuaga uuuuaagguu uuuacuguga   1680

gggauguuug ggagauguaa gaaauguucu ugcaguuaag gguuaguuua caaucagcca   1740

cauucuaggu aggggcccac uucaccguac uaaccaggga agcuguccu cacuguugaa   1800
```

-continued uuuucucuaa cuucaaggcc cauaucugug aaaugcuggc auuugcaccu accucacaga 1860
gugcauugug aggguuaaug aaauaaugua caucuggccu ugaaaccacc uuuuauuaca 1920
uggggucuag aacuugaccc ccuugagggu gcuuguuccc ucucccuguu ggucggu ggg 1980 uugguaguuu cuacaguugg gcagcugguu agguagaggg aguugucaag ucucugcugg 2040
cccagccaaa cccugucuga caaccucuug gugaaccuua guaccuaaaa ggaaaucuca 2100
ccccauccca cacccuggag gauuucaucu cuuguauaug augaucugga uccaccaaga 2160
cuuguuuuau gcucaggguc aauuucuuuu uucuuuuuuu uuuuuuuuuu ucuuuuucuu 2220
ugagacuggg ucucgcuuug uugcccaggc uggaguggag uggcgugauc uuggcuuacu 2280
gcagccuuug ccuccccggc ucgagcaguc cugccucagc cuccggagua gcugggacca 2340
cagguucaug ccaccauggc cagccaacuu uugcauguuu uguagagaug gggucucaca 2400
guguugccca ggcuggucuc aaacuccugg gcucaggcga uccaccuguc ucagccuccc 2460
agagugcugg gauuacaauu gugagccacc acguccagcu ggaaggguca acaucuuuua 2520
cauucugcaa gcacaucugc auuuucaccc cacccuuccc cuccuucucc cuuuuuauau 2580
cccauuuuua uaucgaucuc uuauuuuaca auaaaacuuu gcugccaccu gugugucuga 2640
ggggug 2646

<210> SEQ ID NO 71
<211> LENGTH: 2271
<212> TYPE: RNA
<213> ORGANISM: HUMAN

<400> SEQUENCE: 71
ugaggccagg agauggaggc ugcagugagc ugugaucaca ccacugugcu ccagccugag 60
ugacagagca agacccuauc ucaaaaaaaa aaaaaaaaaa gaaaagcucc ugaggugaag 120
acgccaacuc ucucuagcuc gcuagugggu ugcaggaggu gcuuacgcau guuuguuucu 180
uugcugccgu cuuccaguug cuuuaucugu ucacuugugc ccugacuuuc aacucugucu 240
ccuuccucuu ccuacaguac uccccugccc ucaacaagau guuuugccaa cuggccaaga 300
ccugcccugu gcagcugugg guugauucca cacccccgcc cggcacccgc guccgcgcca 360
uggccaucua caagcaguca cagcacauga cggagguugu gaggcgcugc cccccaccaug 420 agcgcugcuc agauagcgau ggucuggccc cuccucagca ucuuauccga guggaaggaa 480
auuugcgugu ggaguauuug gaugacagaa acacuuuucg acauagugug guggugcccu 540
augagccgcc ugagguuggc ucugacugua ccaccaucca cuacaacuac auguguaaca 600
guuccugcau gggcggcaug aaccggaggc ccauccucac caucaucaca cuggaagacu 660
ccagugguaa ucuacuggga cggaacagcu uugaggugcg uguuugugcc uguccuggga 720
gagaccggcg cacagaggaa gagaaucucc gcaagaaagg ggagccucac cacgagcugc 780
ccccagggag cacuaagcga gcacugccca acaacaccag cuccucuccc cagccaaaga 840
agaaaccacu ggauggagaa uauuucaccc uucagauccg ugggcgugag cgcuucgaga 900
uguuccgaga gcugaaugag gccuuggaac ucaaggaugc ccaggcuggg aaggagccag 960
gggggagcag ggcucacucc agccaccuga aguccaaaaa gggucagucu accuccccgcc 1020 auaaaaaacu cauguucaag acagaagggc cugacucaga cugacauucu ccacuucuug 1080
uuccccacug acagccuccc acccccaucu cucccucccc ugccauuuug gguuuugggu 1140
cuuugaaccc uugcuugcaa uaggugugcg ucagaagcac ccaggacuuc cauuugcuuu 1200
gucccggggc uccacugaac aaguuggccu gcacuggugu uuuguugugg ggaggaggau 1260

```
ggggaguagg acauaccagc uuagauuuua agguuuuuac ugugagggau guuugggaga   1320
uguaagaaau guucuugcag uuaaggguua guuuacaauc agccacauuc uagguagggg   1380
cccacuucac cguacuaacc agggaagcug ucccucacug uugaauuuuc ucuaacuuca   1440
aggcccauau cugugaaaug cuggcauuug caccuaccuc acagagugca uugugagggu   1500
uaaugaaaua auguacaucu ggccuugaaa ccaccuuuua uuacaugggg ucuagaacuu   1560
gacccccuug agggugcuug uucccucucc cuguuggucg gugggguuggu aguuucuaca   1620
guugggcagc ugguuaggua gagggaguug ucaagucucu gcuggcccag ccaaacccug   1680
ucugacaacc ucuuggugaa ccuuaguacc uaaaaggaaa ucucacccca ucccacaccc   1740
uggaggauuu caucucuugu auaugaugau cuggauccac caagacuugu uuuaugcuca   1800
gggucaauuu cuuuuuucuu uuuuuuuuuu uuuuuucuuu uucuuugaga cugggucucg   1860
cuuuguugcc caggcuggag uggaguggcg ugaucuuggc uuacugcagc cuuugccucc   1920
ccggcucgag caguccugcc ucagccuccg gaguagcugg gaccacaggu ucaugccacc   1980
auggccagcc aacuuuugca uguuuuguag agaugggguc ucacaguguu gcccaggcug   2040
gucucaaacu ccugggcuca ggcgauccac cugucucagc cucccagagu gcugggauua   2100
caauugugag ccaccacguc cagcuggaag ggucaacauc uuuuacauuc ugcaagcaca   2160
ucugcauuuu caccccaccc uuccccuccu ucucccuuuu uauaucccau uuuuauaucg   2220
aucucuuauu uuacaauaaa acuuugcugc caccugugug ucugaggggu g            2271
```

```
<210> SEQ ID NO 72
<211> LENGTH: 2404
<212> TYPE: RNA
<213> ORGANISM: HUMAN

<400> SEQUENCE: 72

ugaggccagg agauggaggc ugcagugagc ugugaucaca ccacugugcu ccagccugag     60
ugacagagca agacccuauc ucaaaaaaaa aaaaaaaaaa gaaaagcucc ugagguguag    120
acgccaacuc ucucuagcuc gcuagugggu ugcaggaggu gcuuacgcau guuuguuucu    180
uugcugccgu cuuccaguug cuuuaucugu ucacuugugc ccugacuuuc aacucugucu    240
ccuuccucuu ccuacaguac uccccugccc ucaacaagau guuuugccaa cuggccaaga    300
ccugcccugu gcagcugugg guugauucca cacccccgcc cggcacccgc guccgcgcca    360
uggccaucua caagcaguca cagcacauga cggagguugu gaggcgcugc ccccaccaug    420
agcgcugcuc agauagcgau ggucuggccc cuccucagca ucuuauccga guggaaggaa    480
auuugcgugu ggaguauuug gaugacagaa acacuuuucg acauagugug guggugcccu    540
augagccgcc ugagguuggc ucugacugua ccaccaucca cuacaacuac auguguaaca    600
guuccugcau gggcggcaug aaccggaggc ccauccucac caucaucaca cuggaagacu    660
ccagugguaa ucuacuggga cggaacagcu uugaggugcg uguuugugcc uguccuggga    720
gagaccggcg cacagaggaa gagaaucucc gcaagaaagg ggagccucac cacgagcugc    780
ccccagggag cacuaagcga gcacugccca acaacaccag cuccucuccc cagccaaaga    840
agaaaccacu ggauggagaa uauuucaccc uucaggacca gaccagcuuu caaaaagaaa    900
auuguuaaag agagcaugaa aaugguucua ugacuuugcc ugauacagau gcuacuugac    960
uuacgauggu guuacuuccu gauaaacucg ucguaaguug aaaauauuau ccgugggcgu   1020
gagcgcuucg agauguuccg agagcugaau gaggccuugg aacucaagga ugcccaggcu   1080
gggaaggagc caggggggag cagggcucac uccagccacc ugaaguccaa aaagggucag   1140
```

ucuaccuccc gccauaaaaa acucauguuc aagacagaag ggccugacuc agacugacau 1200
ucuccacuuc uuguucccca cugacagccu cccaccccca ucucucccuc cccugccauu 1260
uuggguuuug ggucuuugaa cccuugcuug caauaggugu gcgucagaag cacccaggac 1320
uuccauuugc uuugucccgg ggcuccacug aacaaguugg ccugcacugg uguuuuguug 1380
uggggaggag gauggggagu aggacauacc agcuuagauu uuaagguuuu uacugugagg 1440
gauguuuggg agauguaaga aauguucuug caguuaaggg uuaguuuaca aucagccaca 1500
uucuagguag gggcccacuu caccguacua accagggaag cugucccuca cuguugaauu 1560
uucucuaacu ucaaggccca uaucugugaa augcuggcau uugcaccuac cucacagagu 1620
gcauugugag gguuaaugaa auaauguaca ucuggccuug aaaccaccuu uuauuacaug 1680
gggucuagaa cuugaccccc uugagggugc uuguucccuc ucccuguugg ucgguggguu 1740
gguaguuucu acaguugggc agcugguuag guagagggag uugucaaguc ucugcuggcc 1800
cagccaaacc cugucugaca accucuuggu gaaccuuagu accuaaaagg aaaucucacc 1860
ccaucccaca cccuggagga uuucaucucu uguauaugau gaucuggauc caccaagacu 1920
uguuuuaugc ucagggucaa uuucuuuuuu cuuuuuuuuu uuuuuuuuuc uuuuucuuug 1980
agacuggguc ucgcuuuguu gcccaggcug gaguggagug gcgugaucuu ggcuuacugc 2040
agccuuugcc uccccggcuc gagcaguccu gccucagccu ccggaguagc ugggaccaca 2100
gguucaugcc accauggcca gccaacuuuu gcauguuuug uagagauggg gucucacagu 2160
guugcccagg cuggucucaa acuccugggc ucaggcgauc caccugucuc agccucccag 2220
agugcuggga uuacaauugu gagccaccac guccagcugg aagggucaac aucuuuuaca 2280
uucugcaagc acaucugcau uuucacccca cccuuccccu ccuucucccu uuuuauaucc 2340
cauuuuuaua ucgaucucuu auuuuacaau aaaacuuugc ugccaccugu gugucugagg 2400
ggug 2404

<210> SEQ ID NO 73
<211> LENGTH: 2331
<212> TYPE: RNA
<213> ORGANISM: HUMAN

<400> SEQUENCE: 73
ugaggccagg agauggaggc ugcagugagc ugugaucaca ccacugugcu ccagccugag 60
ugacagagca agacccuauc ucaaaaaaaa aaaaaaaaaa gaaaagcucc ugaggugaag 120
acgccaacuc ucucuagcuc gcuagugggu ugcaggaggu gcuuacgcau guuuguuucu 180
uugcugccgu cuuccaguug cuuuaucugu ucacuugugc ccugacuuuc aacucugucu 240
ccuuccucuu ccuacaguac uccccugccc ucaacaagau guuuugccaa cuggccaaga 300
ccugcccugu gcagcugugg guugauucca cacccccgcc cggcacccgc guccgcgcca 360
uggccaucua caagcaguca cagcacauga cggagguugu gaggcgcugc ccccaccaug 420
agcgcugcuc agauagcgau ggucuggccc cuccucagca ucuuauccga guggaaggaa 480
auuugcgugu ggaguauuug gaugacagaa acacuuuucg acauagugug guggugcccu 540
augagccgcc ugagguuggc ucugacugua ccaccaucca cuacaacuac auguguaaca 600
guuccugcau gggcggcaug aaccggaggc ccauccucac caucaucaca cuggaagacu 660
ccagugguaa ucuacuggga cggaacagcu uugaggugcg uguuugugcc uguccuggga 720
gagaccggcg cacagaggaa gagaaucucc gcaagaaagg ggagccucac cacgagcugc 780
ccccagggag cacuaagcga gcacugccca acaacaccag cuccucuccc cagccaaaga 840

```
agaaaccacu ggauggagaa uauuucaccc uucagaugcu acuugacuua cgauggugu u    900

acuuccugau aaacucgucg uaaguugaaa auauuauccg ugggcgugag cgcuucgaga    960

uguuccgaga gcugaaugag gccuuggaac ucaaggaugc ccaggcuggg aaggagccag   1020

gggggagcag ggcucacucc agccaccuga aguccaaaaa gggucagucu accucccgcc   1080

auaaaaaacu cauguucaag acagaagggc cugacucaga cugacauucu ccacuucuug   1140

uuccccacug acagccuccc acccccaucu cucccucccc ugccauuuug gguuuugggu   1200

cuuugaaccc uugcuugcaa uaggugugcg ucagaagcac ccaggacuuc cauuugcuuu   1260

gucccggggc uccacugaac aaguuggccu gcacuggugu uuuguugugg ggaggaggau   1320

ggggaguagg acauaccagc uuagauuuua agguuuuuac ugugagggau guuugggaga   1380

uguaagaaau guucuugcag uuaaggguua guuuacaauc agccacauuc uagguagggg   1440

cccacuucac cguacuaacc agggaagcug ucccucacug uugaauuuuc ucuaacuuca   1500

aggcccauau cugugaaaug cuggcauuug caccuaccuc acagagugca uugugagggu   1560

uaaugaaaua auguacaucu ggccuugaaa ccaccuuuua uuacaugggg ucuagaacuu   1620

gacccccuug agggugcuug uucccucucc cuguuggucg gugggu uggu aguuucuaca   1680

guugggcagc ugguuaggua gagggaguug ucaagucucu gcuggcccag ccaaacccug   1740

ucugacaacc ucuuggugaa ccuuaguacc uaaaaggaaa ucucacccca ucccacaccc   1800

uggaggauuu caucucuugu auaugaugau cuggauccac caagacuugu uuuaugcuca   1860

gggucaauuu cuuuuuucuu uuuuuuuuuu uuuuuucuuu uucuuugaga cugggucucg   1920

cuuuguugcc caggcuggag uggaguggcg ugaucuuggc uuacugcagc cuuugccucc   1980

ccggcucgag caguccugcc ucagccuccg gaguagcugg gaccacaggu ucaugccacc   2040

auggccagcc aacuuuugca uguuuuguag agaugggguc ucacaguguu gcccaggcug   2100

gucucaaacu ccugggcuca ggcgauccac cugucucagc cucccagagu gcugggauua   2160

caauugugag ccaccacguc cagcuggaag ggucaacauc uuuuacauuc ugcaagcaca   2220

ucugcauuuu caccccaccc uuccccuccu ucucccuuuu uauaucccau uuuuauaucg   2280

aucucuuauu uuacaauaaa acuuugcugc caccugugug ucugaggggu g            2331
```

<210> SEQ ID NO 74
<211> LENGTH: 2550
<212> TYPE: RNA
<213> ORGANISM: HUMAN

<400> SEQUENCE: 74

```
cguggauccc gagaaagagg cgcaggacga ggaggcagaa cccgacuggc gcguagagca     60

gcagcacgag caguaggaag cagucacccg gaagccuggg ggcgagaggc gaagugguca    120

ggcgccgaag gccgagagca cgcggggauc ggucucuucc cgccgggucu cuuaccggug    180

cgagucaaag agccgcuccg gccccggccc ugagggaagc uccauaacug cugcuucagg    240

agcgcccggc cgucgccgcc gccgccauuu ucgcgcccgg ccgcaggggc ucuugggaag    300

gcggagucuu ugggcauccg cccgggguga ggggacccga aguccugagg cgcgccggaa    360

gggcuagcgg ucccagcaua ccccgcggcc ccuugggccg ucucacaacu cgcguccggc    420

ggagaccaca auucccggca uucgugggc agggaggagu cggccucccg gaauccuggu    480

cccggcgugc acuucugaag gacuucaggu accggcgugc cccgcguccu acuguccgcc    540

ugcucgcguc cugggugccg ccucugagua gggcgggcga ggaggcagcc aaggcggagc    600

ugauggcugc gccgagggcg gggcggggug caggcuggag ccuucgggca uggcgggcuu    660
```

-continued

```
ugggggggcau ucgcuggggg aggagacccc guuugacccc ugaccuccgg gcccugcuga    720
cgucaggaac uucugacccc cgggcccgag ugacuuaugg gacccccagu cucugggccc    780
gguugucugu uggggucacu gaaccccgag caugccugac gucugggacc ccgggucccc    840
gggcacaacu gacugcggug accccagaua ccaggacccg ggaggccuca gagaacucug    900
gaacccguuc gcgcgcgugg cuggcggugg cgcugggcgc uggggggggca gugcuguugu    960
uguuguggggg cgggggucgg gguccuccgg ccguccucgc cgccgucccu agcccgccgc   1020
ccgcuucucc ccggagucag uacaacuuca ucgcagaugu gguggagaag acagcaccug   1080
ccguggucua uaucgagauc cuggaccggc acccuuucuu gggccgcgag gucccuaucu   1140
cgaacggcuc aggauucgug guggcugccg augggcucau ugucaccaac gcccaugugg   1200
uggcugaucg gcgcagaguc cgugugagac ugcuaagcgg cgacacguau gaggccgugg   1260
ucacagcugu ggaucccgug gcagacaucg caacgcugag gauucagacu aaggagccuc   1320
uccccacgcu gccucuggga cgcucagcug auguccggca aggggaguuu guuguugcca   1380
ugggaagucc cuuugcacug cagaacacga ucacauccgg cauuguuagc ucugcucagc   1440
guccagccag agaccuggga cucccccaaa ccaaugugga auacauucaa acugaugcag   1500
cuauugauuu uggaaacucu ggaggucccc ugguuaaccu ggauggggag gugauuggag   1560
ugaacaccau gaaggucaca gcuggaaucu ccuuugccau cccuucugau cgucuucgag   1620
aguuucugca ucgugggggaa aagaagaauu ccuccuccgg aaucaguggg ucccagcggc   1680
gcuacauugg ggugaugaug cugacccuga gucccagcau ccuugcugaa cuacagcuuc   1740
gagaaccaag cuuucccgau guucagcaug guguacucau ccauaaaguc auccugggcu   1800
ccccugcaca ccgggcuggu cugcggccug gugaugugau uuuggccauu ggggagcaga   1860
ugguacaaaa ugcugaagau guuuaugaag cuguucgaac ccaaucccag uuggcagugc   1920
agauccggcg gggacgagaa acacugaccu uauauguggac cccugagguc acagaaugaa   1980
uagaucacca agaguaugag gcuccugcuc ugauuuccuc cuugccuuuc uggcugaggu   2040
ucugagggca ccgagacaga ggguuaaaug aaccaguggg ggcaggucccc uccaaccacc   2100
agcacugacu ccugggcucu gaagaaucac agaaacacuu uuuauauaaa auaaaaauuau   2160
accuagcaac auauuauagu aaaaaaugag gugggagggc uggaucuuuu cccccaccaa   2220
aaggcuagag guaaagcugu aucccccuaa acuuagggga gauacuggag cugaccaucc   2280
ugaccuccua uuaaagaaaa ugagcugcug ccaucuuuug ugggcaguua gucaggugcu   2340
gcucuuugug guguggguggg cucuggucug uucugcucgg ugcugggccu gggagcaaag   2400
auucccaugc uuggcuacag auacugacag cuggccucug aaggagggug aaaacuucug   2460
cuugacaguu ccacauccau agugcauggu cugaugagug cgguugcuga caugguuuc   2520
uugguaagcu ccugagguaa uggcagccuc                                      2550
```

<210> SEQ ID NO 75
<211> LENGTH: 2259
<212> TYPE: RNA
<213> ORGANISM: HUMAN

<400> SEQUENCE: 75

```
cguggauccc gagaaagagg cgcaggacga ggaggcagaa cccgacuggc gcguagagca     60
gcagcacgag caguaggaag cagucacccg gaagccuggg ggcgagaggc gaagugguca    120
ggcgccgaag gccgagagca cgcggggauc ggucucuucc cgccgggucu cuuaccggug    180
cgagucaaag agccgcuccg gccccggccc ugagggaagc uccauaacug cugcuucagg    240
```

```
agcgcccggc cgucgccgcc gccgccauuu ucgcgcccgg ccgcaggggc ucuugggaag    300

gcggagucuu ugggcauccg cccgggguga ggggacccga aguccugagg cgcgccggaa    360

gggcuagcgg ucccagcaua ccccgcggcc ccuugggccg ucucacaacu cgcguccggc    420

ggagaccaca auucccggca uucguggggc agggaggagu cggccucccg gaauccuggu    480

cccggcgugc acuucugaag gacuucaggu accggcgugc cccgcguccu acuguccgcc    540

ugcucgcguc cugggugccg ccucugagua gggcgggcga ggaggcagcc aaggcggagc    600

ugauggcugc gccgagggcg gggcggggug caggcuggag ccuucgggca uggcgggcuu    660

ugggggggcau ucgcuggggg aggagacccc guuugacccc ugaccuccgg gcccugcuga    720

cgucaggaac uucugacccc cgggcccgag ugacuuaugg gacccccagu cucugggccc    780

gguugucugu uggggucacu gaaccccgag caugccugac gucugggacc ccgggucccc    840

gggcacaacu gacugcggug accccagaua ccaggacccg ggaggccuca gagaacucug    900

gaacccguuc gcgcgcgugg cuggcggugg cgcugggcgc uggggggggca gugcuguugu    960

uguuguuggggg cgggggucgg gguccuccgg ccguccucgc cgccgucccu agcccgccgc   1020

ccgcuucucc ccggagucag uacaacuuca ucgcagaugu gguggagaag acagcaccug   1080

ccguggucua uaucgagauc cuggaccggc acccuuucuu gggccgcgag gucccuaucu   1140

cgaacggcuc aggauucgug guggcugccg augggcucau ugucaccaac gcccaugugg   1200

uggcugaucg gcgcagaguc cgugugagac ugcuaagcgg cgacacguau gaggccgugg   1260

ucacagcugu ggaucccgug gcagacaucg caacgcugag gauucagacu aaguuuggaa   1320

acucuggagg uccccugguu aaccuggaug gggaggugau uggagugaac accaugaagg   1380

ucacagcugg aaucuccuuu gccaucccuu cugaucgucu ucgagaguuu cugcaucgug   1440

gggaaaagaa gaauuccucc uccggaauca gugggucca gcggcgcuac auuggggguga   1500

ugaugcugac ccugaguccc agggcugguc ugcggccugg ugaugugauu uuggccauug   1560

gggagcagau gguacaaaau gcugaagaug uuuaugaagc uguucgaacc caaucccagu   1620

uggcagugca gauccggcgg ggacgagaaa cacugaccuu auaugugacc ccugagguca   1680

cagaaugaau agaucaccaa gaguaugagg cuccugcucu gauuuccucc uugccuuucu   1740

ggcugagguu cugagggcac cgagacagag gguuaaauga accagugggg gcaggucccu   1800

ccaaccacca gcacugacuc cugggcucug aagaaucaca gaaacacuuu uuauauaaaa   1860

uaaaauuaua ccuagcaaca uauuauagua aaaaaugagg ugggagggcu ggaucuuuuc   1920

ccccaccaaa aggcuagagg uaaagcugua ucccccuaaa cuuaggggag auacuggagc   1980

ugaccauccu gaccuccuau uaaagaaaau gagcugcugc caucuuuugu gggcaguuag   2040

ucaggugcug cucuuugugg ugugguggc ucugggucugu ucugcucggu gcugggccug   2100

ggagcaaaga uucccaugcu uggcuacaga uacugacagc uggccucuga aggagggguga   2160

aaacuucugc uugacaguuc cacauccaua gugcaugguc ugaugagugc gguugcugac   2220

auggguuucu ugguaagcuc cugagguaau ggcagccuc                          2259
```

<210> SEQ ID NO 76
<211> LENGTH: 2606
<212> TYPE: RNA
<213> ORGANISM: HUMAN

<400> SEQUENCE: 76

```
cuuuccgccc ucuccccgcc uccuuuucgg gcgucccgag gccgcucccc aaccgacaac     60

caagaccccg caggccacgc agcccuggag ccgaggcccc ccgacggcgg aggcgcccgc    120
```

```
gggucccua cagccaaggu cccugagugc cagagguggu gguguugcuu aucuucugga    180
accccaugca gccagauccc aggccuagcg gggcuggggc cugcugccga uuccugcccc   240
ugcagucaca gugcccugag ggggcagggg acgcggugau guacgccucc acugagugca   300
aggcggaggu gacgcccucc cagcauggca accgcaccuu cagcuacacc cuggaggauc   360
auaccaagca ggccuuuggc aucaugaacg agcugcggcu cagccagcag cugugugacg   420
ucacacugca ggucaaguac caggaugcac cggccgccca guucauggcc cacaaggugg   480
ugcuggccuc auccagcccu gucuucaagg ccauguucac caacgggcug cgggagcagg   540
gcauggaggu gguguccauu gaggguaucc accccaaggu cauggagcgc cucauugaau   600
ucgccuacac ggccuccauc uccaugggcg agaagugugu ccuccacguc augaacggug   660
cugucaugua ccagaucgac agcguugucc gugccugcag ugacuuccug gugcagcagc   720
uggaccccag caaugccauc ggcaucgcca acuucgcuga gcagauuggc uguguggagu   780
ugcaccagcg ugcccgggag uacaucuaca ugcauuuugg ggagguggcc aagcaagagg   840
aguucuucaa ccugucccac ugccaacugg ugacccucau cagccgggac gaccugaacg   900
ugcgcugcga guccgagguc uuccacgccu gcaucaacug ggucaaguac gacugcgaac   960
agcgacgguu cuacguccag gcgcugcugc gggccgugcg cugccacucg uugacgccga  1020
acuuccugca gaugcagcug cagaagugcg agauccugca guccgacucc cgcugcaagg  1080
acuaccuggu caagaucuuc gaggagcuca cccugcacaa gcccacgcag gugaugcccu  1140
gccgggcgcc caagguggge cgccugaucu acaccgcggg cggcuacuuc cgacagucgc  1200
ucagcuaccu ggaggcuuac aaccccagug acggcaccug gcuccgguug gcggaccugc  1260
aggugccgcg gagcggccug gccggcugcg ugguggggcgg gcuguuguac gccgugggcg  1320
gcaggaacaa cucgcccgac ggcaacaccg acuccagcgc ccuggacugu uacaacccca  1380
ugaccaauca guggucgccc ugcgccccca ugagcgugcc ccguaaccgc aucggggugg  1440
gggucaucga uggccacauc uaugccgucg gcggcuccca cggcugcauc caccacaaca  1500
guguggagag guaugagcca gagcgggaug aguggcacuu gguggcccca augcugacac  1560
gaaggaucgg ggugggcgug gcuguccuca aucgucuccu uuaugccgug gggggcuuug  1620
acgggacaaa ccgccuuaau ucagcugagu guuacuaccc agagaggaac gaguggcgaa  1680
ugaucacagc aaugaacacc auccgaagcg gggcaggcgu cugcguccug cacaacugua  1740
ucuaugcugc ugggggcuau gaugguoagg accagcugaa cagcguggag cgcuacgaug  1800
uggaaacaga gacguggacu uucguagccc ccaugaagca ccggcgaagu gcccuggggga  1860
ucacugucca ccaggggaga aucuacgucc uuggaggcua ugauggucac acguuccugg  1920
acagugugga guguuacgac ccagauacag acaccuggag cgaggugacc cgaaugacau  1980
cgggccggag uggggugggc guggcuguca ccauggagcc cugccggaag cagauugacc  2040
agcagaacug uaccuguuga ggcacuuuug uuucuugggc aaaaauacag uccaaugggg  2100
aguaucauug uuuuuguaca aaaaccggga cuaaaagaaa agacagcacu gcaaauaacc  2160
caucuuccgg gaagggaggc caggaugccu caguguuaaa augacaucuc aaaagaaguc  2220
caaagcggga aucaugugcc ccucagcgga gccccgggag uguccaagac agccuggcug  2280
ggaaaggggg uguggaaaga gcaggcuucc aggagagagg cccccaaacc cucuggccgg  2340
guaauaggcc ugggucccac ucacccaugc cggcagcugu caccauguga uuuauucuug  2400
gauaccuggg agggggccaa ugggggccuc agggggaggc cccccucugga aaugugguuc  2460
ccagggaugg gccuguacau agaagccacc ggauggcacu uccccaccgg auggacaguu  2520
```

-continued auuuuguuga uaaguaaccc uguaauuuuc caaggaaaau aaagaacaga cuaacuagug 2580
ucuuucaccc ugaaaaaaaa aaaaaa 2606

<210> SEQ ID NO 77
<211> LENGTH: 2577
<212> TYPE: RNA
<213> ORGANISM: HUMAN

<400> SEQUENCE: 77
ucugcuuagu cauggugacc ugcgcgcgcu ccgcgccucc cccacgcgca gcgauggagg 60
cgccggggcu cgggcggugg aggcggagcc ggagcgcggc cauggcgggg ucccugagug 120
ccagaggugg ugguguugcu uaucuucugg aaccccaugc agccagaucc caggccuagc 180
ggggcugggg ccugcugccg auuccugccc cugcagucac agugcccuga gggggcaggg 240
gacgcgguga uguacgccuc cacugagugc aaggcggagg ugacgcccuc ccagcauggc 300
aaccgcaccu ucagcuacac ccuggaggau cauaccaagc aggccuuugg caucaugaac 360
gagcugcggc ucagccagca gcugugugac gucacacugc aggucaagua ccaggaugca 420
ccggccgccc aguucauggc ccacaaggug gugcuggccu cauccagccc ugucuucaag 480
gccauguuca ccaacgggcu gcgggagcag ggcauggagg ugguguccau ugaggguauc 540
caccccaagg ucauggagcg ccucauugaa uucgccuaca cggccuccau cuccaugggc 600
gagaagugug uccuccacgu caugaacggu gcugucaugu accagaucga cagcguuguc 660
cgugccugca gugacuuccu ggugcagcag cuggacccca gcaaugccau cggcaucgcc 720
aacuucgcug agcagauugg cuguguggag uugcaccagc gugcccggga guacaucuac 780
augcauuuug gggagguggc caagcaagag gaguucuuca accuguccca cugccaacug 840
gugacccuca ucagccggga cgaccugaac gugcgcugcg aguccgaggu cuuccacgcc 900
ugcaucaacu gggucaagua cgacugcgaa cagcgacggu ucuacgucca ggcgcugcug 960
cgggccgugc gcugccacuc guugacgccg aacuuccugc agaugcagcu gcagaagugc 1020
gagauccugc aguccgacuc ccgcugcaag gacuaccugg ucaagaucuu cgaggagcuc 1080
acccugcaca agcccacgca ggugaugccc ugccgggcgc ccaagguggg ccgccugauc 1140
uacaccgcgg gcggcuacuu ccgacagucg cucagcuacc uggaggcuua caaccccagu 1200
gacggcaccu ggcuccgguu ggcggaccug caggugccgc ggagcggccu ggccggcugc 1260 gugguggcg ggcuguugua cgccgugggc ggcaggaaca acucgcccga cggcaacacc 1320
gacuccagcg cccuggacug uuacaacccc augaccaauc aguggucgcc cugcgccccc 1380
augagcgugc cccguaaccg caucggggug ggggucaucg auggccacau cuaugccguc 1440
ggcggcuccc acggcugcau ccaccacaac aguguggaga gguaugagcc agagcgggau 1500
gaguggcacu ugguggcccc aaugcugaca cgaaggaucg gggugggcgu ggcuguccuc 1560
aaucgucucc uuuaugccgu ggggggcuuu gacgggacaa accgccuuaa uucagcugag 1620
uguuacuacc cagagaggaa cgaguggcga augaucacag caaugaacac cauccgaagc 1680
ggggcaggcg ucugcguccu gcacaacugu aucuaugcug cugggggcua ugauggucag 1740
gaccagcuga acagcgugga gcgcuacgau guggaaacag agacguggac uuucguagcc 1800
cccaugaagc accggcgaag ugcccugggg aucacugucc accaggggag aaucuacguc 1860
cuuggaggcu augaugguca cacguuccug gacagugugg aguguuacga cccagauaca 1920
gacaccugga gcgaggugac ccgaaugaca ucgggccgga gugggguggg cguggcuguc 1980
accauggagc ccugccggaa gcagauugac cagcagaacu guaccuguug aggcacuuuu 2040
guuucuuggg caaaaauaca guccaauggg gaguaucauu guuuuuguac aaaaaccggg 2100
acuaaaagaa aagacagcac ugcaaauaac ccaucuuccg ggaagggagg ccaggaugcc 2160
ucaguguuaa aaugacaucu caaaagaagu ccaaagcggg aaucaugugc cccucagcgg 2220
agccccggga guguccaaga cagccuggcu gggaaagggg guguggaaag agcaggcuuc 2280
caggagagag gcccccaaac ccucuggccg gguaauaggc cuggguccca cucacccaug 2340
ccggcagcug ucaccaugug auuuauucuu ggauaccugg gagggggcca augggggccu 2400
cagggggagg cccccucugg aaaugugguu cccagggaug ggccuguaca uagaagccac 2460
cggauggcac uuccccaccg gauggacagu uauuuuguug auaaguaacc cuguaauuuu 2520
ccaaggaaaa uaaagaacag acuaacuagu gucuuucacc cugaaaaaaa aaaaaaa 2577

<210> SEQ ID NO 78
<211> LENGTH: 3493
<212> TYPE: RNA
<213> ORGANISM: HUMAN

<400> SEQUENCE: 78
agagaagagg cuccacguug ggcggggaug gggccugaaa cugucugggu cugagcuggg 60
gagcggaagc cacuuguccc ucucccuccc caggacuucu gugacuccug ggccacagag 120
guccaaccag gcuaagggcc uggggauacc cccugccugg cccccuugcc caaacuggca 180 gggggccag gcugggcagc agccccucuu ucaccucaac uauggaucuc cugcccccca 240
agcccaagua caauccacuc cggaaugagu cucugucauc gcuggaggaa ggggcuucug 300
gguccacccc cccggaggag cugccuuccc caucagcuuc aucccugggg cccauccugc 360
cuccucugcc uggggacgau agucccacua cccugugcuc cuucuucccc cggaugagca 420
accugaggcu ggccaacccg gcugggggc gcccagggc uaagggggag ccaggaaggg 480
cagcugauga uggggagggg aucguagggg cagccaugcc agacucaggc cccccuaccc 540
uccuccagga caugaacaag cugaguggag gcggcgggcg caggacucgg guggaagggg 600
gccagcuugg gggcgaggag uggacccgcc acgggagcuu ugucaauaag cccacgcggg 660
gcuggcugca ucccaacgac aaagucaugg gacccggggu uuccuacuug guucgguaca 720
uggguugugu ggagguccuc cagucaaugc gugcccugga cuucaacacc cggacucagg 780
ucaccaggga ggccaucagu cuggugugug aggcugugcc gggugcuaag ggggcgacaa 840
ggaggagaaa gcccuguagc cgcccgcuca gcucuauccu ggggaggagu aaccugaaau 900
uugcuggaau gccaaucacu cucaccgucu ccaccagcag ccucaaccuc auggccgcag 960
acugcaaaca gaucaucgcc aaccaccaca ugcaaucuau cucauuugca uccggcgggg 1020
auccggacac agccgaguau gucgccuaug uugccaaaga cccugugaau cagagagccu 1080
gccacauucu ggagugucc gaagggcuug cccaggaugu caucagcacc auuggccagg 1140
ccuucgaguu gcgcuucaaa caauaccuca ggaacccacc caaacugguc accccucaug 1200
acaggauggc uggcuuugau ggcucagcau gggaugagga ggaggaagag ccaccugacc 1260
aucaguacua uaaugacuuc ccggggaagg aacccccuu gggggggug guagacauga 1320 ggcuucggga aggagccgcu ccagggcug cucgacccac ugcacccaau gcccagaccc 1380
ccagccacuu gggagcuaca uugccuguag gacagccugu ugggggagau ccagaagucc 1440
gcaaacagau gccaccucca ccacccuguc caggcagaga gcuuuuugau gaucccuccu 1500
augucaacgu ccagaaccua gacaaggccc ggcaagcagu gggugguggcu gggcccccca 1560 auccugcuau caauggcagu gcaccccggg accuguuuga caugaagccc uucgaagaug 1620
cucuucgcgu gccuccaccu ccccagucgg uguccauggc ugagcagcuc cgaggggagc 1680
ccugguucca ugggaagcug agccggcggg aggcugaggc acugcugcag cucaaugggg 1740
acuuccuggu acgggagagc acgaccacac cuggccagua ugugcucacu ggcuugcaga 1800
gugggcagcc uaagcauuug cuacuggugg acccugaggg uguggguucgg acuaaggauc 1860 accgcuuuga aagugucagu caccuuauca gcuaccacau ggacaaucac uugcccauca 1920
ucucugcggg cagcgaacug ugucuacagc aaccugugga gcggaaacug ugaucugccc 1980
uagcgcucuc uuccagaaga ugcccuccaa uccuuuccac ccuauucccu aacucucggg 2040
accucguuug ggaguguucu gugggcuugg ccuuguguca gagcugggag uagcauggac 2100
ucuggguuuc auauccagcu gagugagagg guuugaguca aaagccuggg ugagaauccu 2160
gccucucccc aaacauuaau caccaaagua uuaauguaca gaguggcccc ucaccugggc 2220
cuuuccugug ccaaccugau gccccuuccc caagaaggug agugcuuguc auggaaaaug 2280
uccuguggug acaggcccag uggaacaguc acccuucugg gcaaggggga acaaaucaca 2340
ccucugggcu ucaggguauc ccagaccccu cucaacaccc gcccccccca uguuuaaacu 2400
uugugccuuu gaccaucucu uaggucuaau gauauuuuau gcaaacaguu cuuggacccc 2460
ugaauucaau gacagggaug ccaacaccuu cuuggcuucu gggaccugug uucuugcuga 2520
gcacccucuc cgguuugggu ugggauaaca gaggcaggag uggcagcugu ccccucuccc 2580
uggggauaug caacccuuag agauugcccc agagccccac ucccggccag gcgggagaug 2640
gaccccuccc uugcucagug ccuccuggcc ggggccccuc accccaaggg gucuguauau 2700
acauuucaua aggccugccc ucccauguug caugccuaug uacucuacgc caaagugcag 2760
cccuuccucc ugaagccucu gcccugccuc ccuuucuggg agggcggggu gggggugacu 2820
gaauuugggc cucuuguaca guuaacucuc ccagguggau uuguggagg ugagaaaagg 2880 ggcauugaga cuauaaagca guagacaauc cccacauacc aucuguagag uuggaacugc 2940
auucuuuuaa aguuuuauau gcauauauuu uagggcugua gacuuacuuu ccuauuuucu 3000
uuuccauugc uuauucuuga gcacaaaaug auaaucaauu auuacauuua uacaucaccu 3060
uuuugacuuu uccaagcccu uuuacagcuc uuggcauuuu ccucgccuag gccugugagg 3120
uaacugggau cgcaccuuuu auaccagaga ccugaggcag augaaauuua uuuccaucua 3180
ggacuagaaa aacuuggguc ucuuaccgcg agacugagag gcagaaguca gcccgaaugc 3240
cugucaguuu cauggagggg aaacgcaaaa ccugcaguuc cugaguaccu ucuacaggcc 3300
cggcccagcc uaggcccggg guggccacac cacagcaagc cggccccccc ucuuuuggcc 3360
uuguggauaa gggagaguug accguuuuca uccuggccuc cuuuugcugu uuggauguuu 3420
ccacgggucu cacuuauacc aaagggaaaa cucuucauua aaguccguau uucuucuaaa 3480
aaaaaaaaaa aaa 3493

<210> SEQ ID NO 79
<211> LENGTH: 3195
<212> TYPE: RNA
<213> ORGANISM: HUMAN

<400> SEQUENCE: 79
acugccuuug ugcgcgaucu cgcgcugcca uuggcuaacu cgggaaagug ggaagcguga 60
aggagggacc cugagguaga gggucagggg uuagugaggc cggaagugag uguaauaaag 120
uuucuccagg gaggcagggc ccggggagaa aguuggagcg guaaccuaag cuggcagugg 180
cgugauccgg caccaaaucg gcccgcggug cggugcggag acuccaugag gcccuggaca 240

-continued ugaacaagcu gaguggaggc ggcgggcgca ggacucgggu ggaagggggc cagcuugggg 300
gcgaggagug gacccgccac gggagcuuug ucaauaagcc cacgcggggc uggcugcauc 360
ccaacgacaa agucauggga cccggggguuu ccuacuuggu ucgguacaug gguugugugg 420
agguccucca gucaaugcgu gcccuggacu ucaacacccg gacucagguc accagggagg 480
ccaucagucu ggugugugag gcugugccgg gugcuaaggg ggcgacaagg aggagaaagc 540
ccuguagccg cccgcucagc ucuauccugg ggaggaguaa ccugaaauuu gcuggaaugc 600
caaucacucu caccgucucc accagcagcc ucaaccucau ggccgcagac ugcaaacaga 660
ucaucgccaa ccaccacaug caaucuaucu cauuugcauc cggcggggau ccggacacag 720
ccgaguaugu cgccuauguu gccaaagacc cugugaauca gagagccugc cacauucugg 780
agugucccga agggcuugcc caggauguca ucagcaccau uggccaggcc uucgaguugc 840
gcuucaaaca auaccucagg aacccaccca aacuggucac cccucaugac aggauggcug 900
gcuuugaugg cucagcaugg gaugaggagg aggaagagcc accugaccau caguacuaua 960
augacuuccc ggggaaggaa ccccccuugg ggggggugggu agacaugagg cuucgggaag 1020
gagccgcucc aggggcugcu cgacccacug cacccaaugc ccagaccccc agccacuugg 1080
gagcuacauu gccuguagga cagccuguug ggggagaucc agaaguccgc aaacagaugc 1140
caccuccacc acccugucca gcaggcagag agcuuuuuga ugaucccucc uaugucaacg 1200
uccagaaccu agacaaggcc cggcaagcag ugggguggugc ugggcccccc aauccugcua 1260
ucaauggcag ugcaccccgg gaccuguuug acaugaagcc cuucgaagau gcucuucgcg 1320
ugccuccacc uccccagucg guguccaugg cugagcagcu ccgaggggag cccugguucc 1380
augggaagcu gagccggcgg gaggcugagg cacugcugca gcucaauggg gacuuccugg 1440
uacgggagag cacgaccaca ccuggccagu augugcucac uggcuugcag agugggcagc 1500
cuaagcauuu gcuacuggug gacccugagg guguggguucg gacuaaggau caccgcuuug 1560
aaagugucag ucaccuuauc agcuaccaca uggacaauca cuugcccauc aucucugcgg 1620
gcagcgaacu gugucuacag caaccugugg agcggaaacu gugaucugcc cuagcgcucu 1680
cuuccagaag augcccucca auccuuucca cccuauuccc uaacucucgg gaccucguuu 1740
gggaguguuc ugugggcuug gccuugugucc agagcuggga guagcaugga cucuggguuu 1800
cauauccagc ugagugagag gguuugaguc aaaagccugg gugagaaucc ugccucuccc 1860
caaacauuaa ucaccaaagu auuaauguac agaguggccc cucaccuggg ccuuuccugu 1920
gccaaccuga ugccccuucc ccaagaaggu gagugcuugu cauggaaaau guccugugggu 1980 gacaggccca guggaacagu cacccuucug ggcaaggggg aacaaaucac accucugggc 2040
uucaggguau cccagacccc ucucaacacc cgcccccccc auguuuaaac uuugugccuu 2100
ugaccaucuc uuaggucuaa ugauauuuua ugcaaacagu ucuuggaccc cugaauucaa 2160
ugacagggau gccaacaccu ucuuggcuuc ugggaccugu guucuugcug agcacccucu 2220
ccgguuuggg uugggauaac agaggcagga guggcagcug uccccucucc cuggggauau 2280
gcaacccuua gagauugccc cagagcccca cucccggcca ggcgggagau ggacccucc 2340 cuugcucagu gccuccuggc cggggccccu caccccaagg ggucuguaua uacauuucau 2400
aaggccugcc cucccauguu gcaugccuau guacucuacg ccaaagugca gcccuuccuc 2460
cugaagccuc ugcccugccu cccuuucugg gagggcgggg ugggggugac ugaauuuggg 2520
ccucuuguac aguuaacucu cccaggugga uuuuguggag gugagaaaag gggcauugag 2580
acuauaaagc aguagacaau ccccacauac caucuguaga guuggaacug cauucuuuua 2640

-continued aaguuuuaua ugcauauauu uuagggcugu agacuuacuu ucccuauuuuc uuuuccauug 2700 cuuauucuug agcacaaaau gauaaucaau uauuacauuu auacaucacc uuuuugacuu 2760
uuccaagccc uuuuacagcu cuuggcauuu ucccucgccua ggccugugag guaacuggga 2820
ucgcaccuuu uauaccagag accugaggca gaugaaauuu auuuccaucu aggacuagaa 2880
aaacuugggu cucuuaccgc gagacugaga ggcagaaguc agcccgaaug ccugucaguu 2940
ucauggaggg gaaacgcaaa accugcaguu ccugaguacc uucuacaggc ccggcccagc 3000
cuaggcccgg gguggccaca ccacagcaag ccggcccccc cucuuuuggc cuuguggaua 3060
agggagaguu gaccguuuuc auccuggccu ccuuuugcug uuuggauguu uccacggguc 3120
ucacuuauac caaagggaaa acucuucauu aaaguccgua uuucuucuaa aaaaaaaaaa 3180
aaaaaaaaaa aaaaa 3195

<210> SEQ ID NO 80
<211> LENGTH: 3496
<212> TYPE: RNA
<213> ORGANISM: HUMAN

<400> SEQUENCE: 80
agagaagagg cuccacguug ggcggggaug gggccugaaa cugucugggu cugagcuggg 60
gagcggaagc cacuuguccc ucucccuccc caggacuucu gugacuccug ggccacagag 120
guccaaccag gcuaagggcc uggggauacc cccugccugg cccccuugcc caaacuggca 180
ggggggccag gcugggcagc agccccucuu ucaccucaac uauggaucuc cugcccccca 240
agcccaagua caauccacuc cggaaugagu cucugucauc gcuggaggaa ggggcuucug 300
gguccacccc cccggaggag cugccuuccc caucagcuuc aucccugggg cccauccugc 360
cuccucugcc uggggacgau agucccacua cccugugcuc cuucuucccc cggaugagca 420
accugaggcu ggccaacccg gcugggggggc gcccagggguc uaagggggag ccaggaaggg 480
cagcugauga uggggagggg aucguagggg cagccaugcc agacucaggc ccccuacccc 540
uccuccagga caugaacaag cugaguggag gcggcgggcg caggacucgg guggaagggg 600
gccagcuugg gggcgaggag uggacccgcc acgggagcuu ugucaauaag cccacgcggg 660
gcuggcugca ucccaacgac aaagucaugg gacccggggu uuccuacuug guucgguaca 720
uggguugugu ggagguccuc cagucaaugc gugcccugga cuucaacacc cggacucagg 780
ucaccaggga ggccaucagu cuggugugug aggcugugcc gggugcuaag gggcgacaa 840 ggaggagaaa gcccuguagc cgcccgcuca gcucuauccu ggggaggagu aaccugaaau 900
uugcuggaau gccaaucacu cucaccgucu ccaccagcag ccucaaccuc auggccgcag 960
acugcaaaca gaucaucgcc aaccaccaca ugcaaucuau cucauuugca uccggcgggg 1020
auccggacac agccgaguau gucgccuaug uugccaaaga cccugugaau cagagagccu 1080
gccacauucu ggagugucccc gaagggcuug cccaggaugu caucagcacc auuggccagg 1140
ccuucgaguu gcgcuucaaa caauaccuca ggaacccacc caaacugguc accccucaug 1200
acaggauggc uggcuuugau ggcucagcau gggaugagga ggaggaagag ccaccugacc 1260
aucaguacua uaaugacuuc ccggggaagg aacccccuu ggggggggug guagacauga 1320
ggcuucggga aggagccgcu ccaggggcug cucgacccac ugcacccaau gcccagaccc 1380
ccagccacuu gggagcuaca uugccuguag gacagccugu ugggggagau ccagaagucc 1440
gcaaacagau gccaccucca ccacccuguc cagcaggcag agagcuuuuu gaugaucccu 1500
ccuaugucaa cguccagaac cuagacaagg cccggcaagc agugggguggu gcugggcccc 1560 ccaauccugc uaucaauggc agugcacccc gggaccuguu ugacaugaag cccuucgaag 1620
augcucuucg cgugccucca ccucccccagu cggugucccau ggcugagcag cuccgagggg 1680
agcccugguu ccaugggaag cugagccggc gggaggcuga ggcacugcug cagcucaaug 1740
gggacuuccu gguacgggag agcacgacca caccuggcca guaugugcuc acuggcuugc 1800
agagugggca gccuaagcau uugcuacugg uggacccuga gggugugguu cggacuaagg 1860
aucaccgcuu ugaaaguguc agucaccuua ucagcuacca cauggacaau cacuugccca 1920
ucaucucugc gggcagcgaa cugugucuac agcaaccugu ggagcggaaa cugugaucug 1980
cccuagcgcu cucuuccaga agaugcccuc caauccuuuc cacccuauuc ccuaacucuc 2040
gggaccucgu uugggagugu ucugugggcu uggccuugug ucagagcugg gaguagcaug 2100
gacucugggu uucauaucca gcugagugag aggguuugag ucaaaagccu gggugagaau 2160
ccugccucuc cccaaacauu aaucaccaaa guauuaaugu acagaguggc cccucaccug 2220
ggccuuuccu gugccaaccu gaugccccuu ccccaagaag gugagugcuu gucauggaaa 2280
auguccugug gugacaggcc caguggaaca gucacccuuc ugggcaaggg ggaacaaauc 2340
acaccucugg gcuucagggu aucccagacc ccucucaaca cccgcccccc ccauguuuaa 2400
acuuugugcc uuugaccauc ucuuaggucu aaugauauuu uaugcaaaca guucuuggac 2460
cccugaauuc aaugacaggg augccaacac cuucuuggcu ucugggaccu guguucuugc 2520
ugagcacccu cuccgguuug gguugggaua acagaggcag gaguggcagc uguccccucu 2580
cccuggggau augcaacccu uagagauugc cccagagccc cacucccggc caggcgggag 2640
auggaccccu cccuugcuca gugccuccug gccggggccc cucaccccaa ggggucugua 2700
uauacauuuc auaaggccug cccucccaug uugcaugccu auguacucua cgccaaagug 2760
cagcccuucc uccugaagcc ucugcccugc cucccuuucu gggagggcgg ggugggggug 2820
acugaauuug ggccucuugu acaguuaacu cucccaggug gauuuugugg aggugagaaa 2880
aggggcauug agacuauaaa gcaguagaca auccccacau accaucugua gaguuggaac 2940
ugcauucuuu uaaaguuuua uaugcauaua uuuuagggcu guagacuuac uuuccuauuu 3000
ucuuuuccau ugcuuauucu ugagcacaaa augauaauca auuauuacau uuauacauca 3060
ccuuuuugac uuuuccaagc ccuuuuacag cucuuggcau uuuccucgcc uaggccugug 3120
agguaacugg gaucgcaccu uuuauaccag agaccugagg cagaugaaau uuauuuccau 3180
cuaggacuag aaaaacuugg gucucuuacc gcgagacuga gaggcagaag ucagcccgaa 3240
ugccugucag uuucauggag gggaaacgca aaaccugcag uuccugagua ccuucuacag 3300
gcccggccca gccuaggccc ggggugccca caccacagca agccggcccc cccucuuuug 3360
gccuugugga uaagggagag uugaccguuu ucauccuggc cuccuuuugc uguuuggaug 3420
uuuccacggg ucucacuuau accaaaggga aaacucuuca uuaaaguccg uauuucuucu 3480
aaaaaaaaaa aaaaaa 3496

<210> SEQ ID NO 81
<211> LENGTH: 3192
<212> TYPE: RNA
<213> ORGANISM: HUMAN

<400> SEQUENCE: 81
acugccuuug ugcgcgaucu cgcgcugcca uuggcuaacu cgggaaagug ggaagcguga 60
aggagggacc cugagguaga gggucagggg uuagugaggc cggaagugag uguaauaaag 120
uuucuccagg gaggcagggc ccggggagaa aguuggagcg guaaccuaag cuggcagugg 180

-continued

```
cgugauccgg caccaaaucg gcccgcggug cggugcggag acuccaugag gcccuggaca    240
ugaacaagcu gaguggaggc ggcgggcgca ggacucgggu ggaagggggc cagcuugggg    300
gcgaggagug gacccgccac gggagcuuug ucaauaagcc cacgcggggc uggcugcauc    360
ccaacgacaa agucauggga cccgggguuu ccuacuuggu ucgguacaug gguugugugg    420
agguccucca gucaaugcgu gcccuggacu ucaacacccg gacucagguc accagggagg    480
ccaucagucu ggugugugag gcugugccgg gugcuaaggg ggcgacaagg aggagaaagc    540
ccuguagccg cccgcucagc ucuauccugg ggaggaguaa ccugaaauuu gcuggaaugc    600
caaucacucu caccgucucc accagcagcc ucaaccucau ggccgcagac ugcaaacaga    660
ucaucgccaa ccaccacaug caaucuaucu cauuugcauc cggcggggau ccggacacag    720
ccgaguaugu cgccuauguu gccaaagacc cugugaauca gagagccugc cacauucugg    780
agugucccga agggcuugcc caggauguca ucagcaccau uggccaggcc uucgaguugc    840
gcuucaaaca auaccucagg aacccaccca aacuggucac cccucaugac aggauggcug    900
gcuuugaugg cucagcaugg gaugaggagg aggaagagcc accugaccau caguacuaua    960
augacuuccc ggggaaggaa ccccccuugg gggggguggu agacaugagg cuucgggaag   1020
gagccgcucc aggggcugcu cgacccacug cacccaaugc ccagaccccc agccacuugg   1080
gagcuacauu gccuguagga cagccuguug ggggagaucc agaaguccgc aaacagaugc   1140
caccuccacc acccugucca ggcagagagc uuuuugauga ucccuccuau gucaacgucc   1200
agaaccuaga caaggcccgg caagcagugg guggugcugg gcccccccaau ccugcuauca   1260
auggcagugc accccgggac cuguuugaca ugaagcccuu cgaagaugcu cuucgcgugc   1320
cuccaccucc ccagucggug uccauggcug agcagcuccg aggggagccc ugguuccaug   1380
ggaagcugag ccggcgggag gcugaggcac ugcugcagcu caaugggac uuccugguac   1440
gggagagcac gaccacaccu ggccaguaug ugcucacugg cuugcagagu gggcagccua   1500
agcauuugcu acugguggac ccugagggug ugguucggac uaaggaucac cgcuuugaaa   1560
gugucaguca ccuuaucagc uaccacaugg acaaucacuu gcccaucauc ucugcgggca   1620
gcgaacugug ucuacagcaa ccuguggagc ggaaacugug aucugcccua gcgcucucuu   1680
ccagaagaug cccuccaauc cuuuccaccc uauucccuaa cucucgggac cucguuuggg   1740
aguguucugu gggcuuggcc uugugucaga gcugggagua gcauggacuc uggguuucau   1800
auccagcuga gugagagggu uugagucaaa agccugggug agaauccugc cucuccccaa   1860
acauuaauca ccaaaguauu aauguacaga guggccccuc accugggccu uuccugugcc   1920
aaccugaugc cccuucccca agaaggugag ugcuugucau ggaaaauguc cugugugac   1980
aggcccagug gaacagucac ccuucugggc aagggggaac aaaucacacc ucugggcuuc   2040
aggguauccc agaccccucu caacacccgc cccccccaug uuuaaacuuu gugccuuuga   2100
ccaucucuua ggucuaauga uauuuuaugc aaacaguucu uggaccccug aauucaauga   2160
cagggaugcc aacaccuucu uggcuucugg gaccuguguu cuugcugagc acccucuccg   2220
guuuggguug ggauaacaga ggcaggagug gcagcugucc ccucucccug gggauaugca   2280
acccuuagag auugccccag agccccacuc ccggccaggc gggagaugga ccccucccuu   2340
gcucagugcc uccuggccgg ggccccucac cccaaggggu cuguauauac auuucauaag   2400
gccugcccuc ccauguugca ugccuaugua cucuacgcca aagugcagcc cuuccuccug   2460
aagccucugc ccugccuccc uuucugggag ggcgggggugg gggugacuga auuugggccu   2520
cuuguacagu uaacucuccc agguggauuu uguggaggug agaaaagggg cauugagacu   2580
```

```
auaaagcagu agacaauccc cacauaccau cuguagaguu ggaacugcau ucuuuuaaag   2640

uuuuauaugc auauauuuua gggcuguaga cuuacuuucc uauuuucuuu uccauugcuu   2700

auucuugagc acaaaaugau aaucaauuau uacauuuaua caucaccuuu uugacuuuuc   2760

caagcccuuu uacagcucuu ggcauuuucc ucgccuaggc cugugaggua acugggaucg   2820

caccuuuuau accagagacc ugaggcagau gaaauuuauu uccaucuagg acuagaaaaa   2880

cuugggucuc uuaccgcgag acugagaggc agaagucagc ccgaaugccu gucaguuuca   2940

uggaggggaa acgcaaaacc ugcaguuccu gaguaccuuc uacaggcccg gcccagccua   3000

ggcccggggu ggccacacca cagcaagccg gccccccuc uuuuggccuu guggauaagg   3060

gagaguugac cguuuucauc cuggccuccu uuugcuguuu ggauguuucc acgggucuca   3120

cuuauaccaa agggaaaacu cuucauuaaa guccguauuu cuucuaaaaa aaaaaaaaaa   3180

aaaaaaaaaa aa                                                       3192
```

<210> SEQ ID NO 82
<211> LENGTH: 1208
<212> TYPE: RNA
<213> ORGANISM: HUMAN

<400> SEQUENCE: 82

```
ggcggcgaca gggagggagg aagccuagga guccgccgcg ggacggaggc cugggggaac     60

ugggaguuca gcuuucugca gagggccacu aggaaccucg gauugcccac ggaagccagc    120

cacuuucuuu gacaguccag cccaccuccu cuucugcccg gagaagcucc aggggcugcc    180

uuugugauca cagcaucuuc acaaggacca aaggaaaaua agauuucuug uaagaacacc    240

gugaccacau cuuuaaaaug acccauuucg uggcucccac aagauuuaca ccuccacacu    300

gaggccggaa gugguuuugc cccuauaaaa cauggcgaaa agcuuucuug ucuccaagga    360

aacgccacgu aaugagucaa agcuguggcg cacgcgcaga aguacaagcu accggaagug    420

auggcgcccc uacuaaagcc uuggggguuag uacgcgugcg cagcaguuuc uuccgacagu    480

uguguugugc caauggugga gaagaaaacu ucgguucgcu cccaggaccc cgggcagcgg    540

cgggugcugg accgggcugc ccggcagcgu cgcaucaacc ggcagcugga ggcccuggag    600

aaugacaacu uccaggauga cccccacgcg ggacucccuc agcucggcaa gagacugccu    660

caguuugaug acgaugcgga cacuggaaag aaaaagaaga aaacccgagg ugaucauuuu    720

aaacuucgcu uccgaaaaaa cuuucaggcc cuguuggagg agcagaacuu gagugugccc    780

gagggcccua acuaccugac ggccugugcg ggaccccau cgcggcccca gcgccccuuc    840

ugugcugucu guggcuuccc aucccccuac accuguguca gcugcggugc ccgguacugc    900

acugugcgcu gucuggggac ccaccaggag accaggugug ugaaguggac ugugugagcc    960

ugggcauucc cagagaggaa gggccgcugu gcacugcccg gccuucagaa agacagaauu   1020

ucaucaccca augcaggggg agcucuuccu ggaccaaggg aggagccgcu cauucaccca   1080

acaaaacugu gucuuaucug ccaggaaaga ccagccucac uccugggaac ugucuggcag   1140

guaggcuggg cccccagug cuguuagaau aaaaagccuc gugccggaaa aaaaaaaaaa   1200

aaaaaaaa                                                            1208
```

<210> SEQ ID NO 83
<211> LENGTH: 1017
<212> TYPE: RNA
<213> ORGANISM: HUMAN

<400> SEQUENCE: 83

-continued

```
gaguauuuga ggcucggagc caccgccccg ccggcgcccg cagcaccucc ucgccagcag     60

ccguccggag ccagccaacg agcggaaaau ggcagacaau uuuucgcucc augaugcguu    120

aucugggucu ggaaacccaa acccucaagg auggccuggc gcauggggga accagccugc    180

uggggcaggg ggcuacccag gggcuuccua uccuggggcc uaccccgggc aggcaccccc    240

aggggcuuau ccuggacagg caccuccagg cgccuacccu ggagcaccug gagcuuaucc    300

cggagcaccu gcaccuggag ucuacccagg gccacccagc ggcccugggg ccuacccauc    360

uucuggacag ccaagugcca ccggagccua cccugccacu ggccccuaug gcgccccugc    420

ugggccacug auugugccuu auaaccugcc uuugccuggg ggaguggugc cucgcaugcu    480

gauaacaauu cugggcacgg ugaagcccaa ugcaaacaga auugcuuuag auuuccaaag    540

agggaaugau guugccuucc acuuuaaccc acgcuucaau gagaacaaca ggagagucau    600

uguuugcaau acaaagcugg auaauaacug ggggaaggaa gaaagacagu cgguuuuccc    660

auuugaaagu gggaaaccau ucaaaauaca aguacugguu gaaccugacc acuucaaggu    720

ugcagugaau gaugcucacu uguugcagua caaucaucgg guuaaaaaac ucaaugaaau    780

cagcaaacug ggaauuucug gugacauaga ccucaccagu gcuucauaua ccaugauaua    840

aucugaaagg ggcagauuaa aaaaaaaaaa agaaucuaaa ccuuacaugu guaaagguuu    900

cauguucacu gugagugaaa auuuuuacau ucaucaauau cccucuugua agucaucuac    960

uuaauaaaua uuacagugaa uuaccugucu caauauguca aaaaaaaaaa aaaaaaa     1017
```

<210> SEQ ID NO 84
<211> LENGTH: 1973
<212> TYPE: RNA
<213> ORGANISM: HUMAN

<400> SEQUENCE: 84

```
gugugcaaau agaggaauaa auagcagggc agcaacuaug ucuggagguc auugucuuuc     60

cugucucagu aguaaucaau cacugcuuau cuucaaaaac ccagaguagg ggaugggggca   120

guuagugggg acagagggca gaugggguaag auucagagca caggcuagug ugacggaagu   180

uuaaacuugu gaguuaaaua ggguuuggca aucuagcugg auagcauccc ugccccuuga    240

agagauguuu uuguggcgcc acacuacuga cuuaggcaua augccuagag auggauuaga    300

acugcacaau gaacuagugg ugagguucag uuuaauggaa auuggugaaa gcuuuuagga    360

uaaaaugaua aucuuuguuu cuuucaggaa aauggcagac aauuuuucgg uaaguguuuu    420

augccuguuu cuuccccuug aucagcucca caugguugag gguuggggggu uuuguuuuua   480

ccaugacuuu cccuuuucac ucucccacug cguggcuucc ccuggacuca uuuguccaau    540

gagggcuugc aagcuggagc cuuguuuuuc cagcagcaga uuugggaaga aagccaggca    600

gagcgaggcc ugggacucac ucacaguaac ccuuucacca aaaggcccag ggcggaaggg    660

aguggacucu gccggcagga gcugagaaau cccucugagua gcgggaagug cgguacaguc   720

ugggcauucu gauguuugug auuguuuuuc ucacggugau gaaaaaguau gugcuauaag    780

uagaggagcg cuaacuccug acuugagcua auuaugaaaa ugcagcccuc ccugaucuga    840

gacguuggga ggcaagaaua aagugaaaaa guauauguaa ucccaacauc uaauuuuagu    900

cuuagaaacu caaacuauua auaaguggaa aaaguuuaau gauaugcaug uaaugccuuu    960

gccauauucc ucuccuucuu agaucacaua uuccuauuuu ccugaaaauu cugcuuuuga   1020

gaaugcuuuc ugucccguaa uuguguaugu cuuucuuucc agcuccauga ugcguuaucu   1080

gggucuggaa acccaaaccc ucaaggaugg ccuggcgcau gggggaacca gccugcuggg   1140
```

-continued

```
gcagggggcu acccaggggc uuccuauccu ggggccuacc ccgggcaggc acccccaggg   1200

gcuuauccug gacaggcacc uccaggcgcc uacccuggag caccuggagc uuaucccgga   1260

gcaccugcac cuggagucua cccagggcca cccagcggcc cuggggccua cccaucuucu   1320

ggacagccaa gugccaccgg agccuacccu gccacuggcc ccuauggcgc cccugcuggg   1380

ccacugauug ugccuuauaa ccugccuuug ccugggggag uggugccucg caugcugaua   1440

acaauucugg gcacggugaa gcccaaugca aacagaauug cuuuagauuu ccaaagaggg   1500

aaugauguug ccuuccacuu uaacccacgc uucaaugaga acaacaggag agucauuguu   1560

ugcaauacaa agcuggauaa uaacugggga agggaagaaa gacagucggu uuucccauuu   1620

gaaaguggga aaccauucaa aauacaagua cugguugaac cugaccacuu caagguugca   1680

gugaaugaug cucacuuguu gcaguacaau caucggguua aaaaacucaa ugaaaucagc   1740

aaacugggaa uuucugguga cauagaccuc accagugcuu cauauaccau gauauaaucu   1800

gaaaggggca gauuaaaaaa aaaaaaagaa ucuaaaccuu acauguguaa agguuucaug   1860

uucacuguga gugaaaauuu uuacauucau caauaucccu cuuguaaguc aucuacuuaa   1920

uaaauauuac agugaauuac cugucucaau augucaaaaa aaaaaaaaaa aaa          1973
```

<210> SEQ ID NO 85
<211> LENGTH: 744
<212> TYPE: RNA
<213> ORGANISM: HUMAN

<400> SEQUENCE: 85

```
gaguauuuga ggcucggagc caccgccccg ccggcgcccg cagcaccucc ucgccagcag     60

ccguccggag ccagccaacg agcggaaaau ggcagacaau uuuucgcucc augaugcguu    120

aucugggucu ggaaacccaa acccucaagg auggccuggc gcauggggga accagccugc    180

uggggcaggg ggcuacccag gggcuuccua uccuggggcc uaccccgggc aggcaccccc    240

aggggcuuau ccuggacagg caccuccagg cgccuacccu ggagcaccug gagcuuaucc    300

cggagcaccu gcaccuggag ucuacccagg gccacccagc ggcccugggg ccuacccauc    360

uucuggacag ccaagugcca ccggagccua cccugccacu ggccccuaug gcgccccugc    420

ugggccacug auugugccuu auaaccugcc uuugccuggg ggaguggugc cucgcaugcu    480

gauaacaauu cugggcacgg ugaagcccaa ugcaaacaga auugcuuuag auuuccaaag    540

agggaaugau guugccuucc acuuuaaccc acgcuucaau gagaacaaca ggagagucau    600

uguuugcacu uacaugugua aagguuucau guucacugug agugaaaauu uuuacauuca    660

ucaauauccc ucuuguaagu caucuacuua auaaauauua cagugaauua ccugucucaa    720

uaugucaaaa aaaaaaaaaa aaaa                                           744
```

<210> SEQ ID NO 86
<211> LENGTH: 3503
<212> TYPE: RNA
<213> ORGANISM: HUMAN

<400> SEQUENCE: 86

```
gcugguguca gagcccggcg agcgcuggca guuccgcggc ggggaugcug aggagcgcug     60

gguccgggag cagcccuggc cccugcggac uuccgaggcc gugaaaaccc cugcgcugcg    120

gcccuuccca ggcccccgag gccguucgcc guucccgaag cccgacuggg ggaagagucc    180

agcaccaaag cggccguucu cggauuccgg agcguucugg agccccgaga gacgccccgg    240

gguucuagaa gcuccccggc ggcgcccagu cccggcuuca uucgggcguc ccuccgaaac    300
```

-continued

```
ccacucgggu gcacgggucg ucggcgagcc gcgaccgggu ccuggcgcgc accaugaucg    360
uggcggacuc cgagugccgc gcagagcuca aggacuaccu gcgguucgcc ccgggcggcg    420
ucggcgacuc gggccccgga gaggagcaga gggagagccg ggcucggcga ggcccucgag    480
ggcccagcgc cuucaucccc guggaggagg uccuucggga gggggcugag agccucgagc    540
agcaccuggg gcuggaggca cugauguccu cugggcgagu agacaaccug gcagugguga    600
ugggccugca cccugacuac uuuaccagcu ucuggcgccu gcacuaccug cugcugcaca    660
cggauggucc cuuggccagc uccuggcgcc acuacauugc caucauggcu gccgcccgcc    720
aucaguguuc uuaccuggua ggcucccaca uggccgaguu ucugcagacu gguggugacc    780
cugaguggcu gcugggccuc caccgggccc ccgagaagcu gcgcaaacuc agcgagauca    840
acaaguugcu ggcgcaucgg ccauggcuca ucaccaagga acacauccag gccuugcuga    900
agaccggcga gcacacuugg ucccuggccg agcucauuca ggcucugguc cugcucaccc    960
acugccacuc gcucuccucc uucguguuug gcuguggcau ccucccugag ggggaugcag   1020
auggcagccc ugcccccag gcaccuacac ccccuaguga acagagcagc cccccaagca   1080
gggacccguu gaacaacucu gggggcuuug agucugcccg cgacguggag gcgcugaugg   1140
agcgcaugca gcagcugcag gagagccugc ugcgggauga ggggacgucc caggaggaga   1200
uggagagccg cuuugagcug gagaagucag agagccugcu ggugaccccc ucagcugaca   1260
uccuggagcc cucuccacac ccagacaugc ugugcuuugu ggaagacccu acuuucggau   1320
augaggacuu cacucggaga ggggcucagg cacccccuac cuuccgggcc caggauuaua   1380
ccugggaaga ccauggcuac ucgcugaucc agcggcuuua cccugagggu gggcagcugc   1440
uggaugagaa guuccaggca gccuauagcc ucaccuacaa uaccaucgcc augcacagug   1500
guguggacac cuccgugcuc cgcagggcca ucuggaacua uauccacugc gucuuuggca   1560
ucagauauga ugacuaugau uauggggagg ugaaccagcu ccuggagcgg aaccucaagg   1620
ucuauaucaa gacaguggcc ugcuacccag agaagaccac ccgaagaaug uacaaccucu   1680
ucuggaggca cuuccgccac ucagagaagg uccacgugaa cuugcugcuc cuggaggcgc   1740
gcaugcaagc cgcucugcug uacgcccucc gugccaucac ccgcuacaug accugacucc   1800
ugagcaggac cugggcccgg uucagcuccc cacaaggacu ucucugucug gagacagccc   1860
cagacccuuu ugugucccau gcccacccuc cccacgcugc agugggcuug ugugugaugu   1920
gcagucccga agccacaccc ucccuuuucc ucacuggaau ggacaguuca uugcacugac   1980
ucugggaucu cagcccugcu ccugggagcu ggaagagcac uuggagaucc uaagggacca   2040
cacccuuccu ccuuccccug cccacagagg cagagggcac aggaaagaag ccgggccaag   2100
cucggaauua augugccaca aguguugugg ccuuccugaa cugggaaguc ccuggcuggc   2160
ccccggggga gaggggcaaa ugccuccggg acugacacuc caggcagcuu ugccuucucu   2220
ccccugucau uuccagauuu cauuaccucc uacuugccau ucacccauca augugaaagu   2280
cagggucaca gcuggucugu guguccaguu cccuaaaagc cuguucuguu gggcagccug   2340
aggcuguugc ccgaauccua guucaguuuu uugacuuccu uugcccuuuu ucccuuuucu   2400
ccaugcuuaa uggugugagg cgucaggaga gaggccaagu acauaaaaaa aaaaaaagca   2460
gauuaucucu agagaguuug agccuuugcu ggucacauug ccuucugaag aggagggagu   2520
auuagauuau aaauccucuu uauuuugguc cuuuaugcuu gagguuccaa ccuggagcca   2580
caguguguga gaggaggagg agagggagaa uucuguucuc ccagagcugc accugccucg   2640
cagaggccag caccccacuc uccugccucc aguggcccug ccgcagaugu cucccaaaaa   2700
```

```
guugagccuu ucuagauggc uuagguggca ccauggcuca gcaggagggg cgggaggcac   2760

cagggguucuu guuuggaccc ugccccuggg ccauggccag gugaccaugg cuacauugcc   2820

aaaccucuga cugccacagc ugcagacuga gaggguggguu cugaguccccc acaaugucug   2880

aagcugcccc ugggauucuc aggccaaccu gccaacagca agcggauuuu cuugcaagau   2940

cagggacccc auuucugcag ccagugucuc cugggugccu ucugaggacu cccaccccca   3000

ucccaguauc ucaucugucc ccucuccugg ggcuuaagug gguugcuucc aggcagaagc   3060

agccaaggac cgauuccagg cacuuucugu agcaaaugac ugugaauuac gacuucucuu   3120

gcccuucuuc uagcagucug ugccuccucu cugaccaguu uggagggcac ugaagaaagg   3180

caagggccgu gcugcugcug ggcggggcag gagaggagcc uggccagugu gccacauuaa   3240

auacccgugc aggcgcggag aagcaaccgg cacccccuuc cggccugaaa gcccucccug   3300

caagaaggug ugcaggagag aagaggcccc ggcaugggga ucuggguucu agagggcaug   3360

ugaugacugu aaauguucac uggguggguua gggaguggua uccaguguuc aagugcagaa   3420

aucuuuggcu uugcuaccag uuccauauga ugagaaauaa acguucgcug agguuuuguu   3480

ucauaaaaaa aaaaaaaaaa aaa                                             3503
```

<210> SEQ ID NO 87
<211> LENGTH: 2217
<212> TYPE: RNA
<213> ORGANISM: HUMAN

<400> SEQUENCE: 87

```
ccccgccgcc gccgcccuuc gcgcccuggg ccaucucccu cccaccuccc uccgcggagc     60

agccagacag cgagggcccc ggccgggggc agggggggacg ccccguccgg ggcacccccc    120

cggcucugag ccgcccgcgg ggccggccuc ggcccggagc ggaggaagga gucgccgagg    180

agcagccuga ggccccagag ucugagacga gccgccgccg cccccgccac ugcggggagg    240

agggggagga ggagcgggag gagggacgag cuggucggga gaagaggaaa aaaacuuuug    300

agacuuuucc guugccgcug ggagccggag gcgcggggac cucuuggcgc gacgcugccc    360

cgcgaggagg caggacuugg ggaccccaga ccgccucccu uugccgccgg ggacgcuugc    420

ucccucccug cccccuacac ggcgucccuc aggcgccccc auuccggacc agcccucggg    480

agucgccgac ccggccuccc gcaaagacuu uuccccagac cucgggcgca cccccugcac    540

gccgccuuca uccccggccu gucuccugag cccccgcgca uccuagaccc uuucuccucc    600

aggagacgga ucucucuccg accugccaca gauccccuau ucaagaccac ccaccuucug    660

guaccagauc gcgcccaucu agguuauuuc cgugggauac ugagacaccc ccgguccaag    720

ccucccccucc accacugcgc ccuucucccu gaggaccuca gcuuucccuc gaggcccucc    780

uaccuuuugc cgggagaccc ccagccccug caggggcggg gccuccccac cacaccagcc    840

cuguucgcgc ucucggcagu gccggggggc gccgccuccc ccaugccgcc cuccgggcug    900

cggcugcugc cgcugcugcu accgcugcug uggcuacugg ugcugacgcc uggccggccg    960

gccgcgggac uauccaccug caagacuauc gacauggagc uggugaagcg gaagcgcauc   1020

gaggccaucc gcggccagau ccuguccaag cugcggcucg ccagccccccc gagccagggg   1080

gaggugccgc ccggcccgcu gcccgaggcc gugcucgccc uguacaacag cacccgcgac   1140

cggguggccg gggagagugc agaaccggag cccgagccug aggccgacua cuacgccaag   1200

gaggucaccc gcgugcuaau gguggaaacc cacaacgaaa ucuaugacaa guucaagcag   1260

aguacacaca gcauauauau guucuucaac acaucagagc uccgagaagc gguaccugaa   1320
```

cccguguugc ucucccgggc agagcugcgu cugcugaggc ucaaguuaaa aguggagcag 1380
cacguggagc uguaccagaa auacagcaac aauuccuggc gauaccucag caaccggcug 1440
cuggcaccca gcgacucgcc agagugguua ucuuuugaug ucaccggagu ugugcggcag 1500
ugguugagcc guggagggga aauugagggc uuucgccuua gcgcccacug cuccugugac 1560
agcagggaua acacacugca aguggacauc aacggguuca cuaccggccg ccgaggugac 1620
cuggccacca uucauggcau gaaccggccu uuccugcuuc ucauggccac cccgcuggag 1680
agggcccagc aucugcaaag cucccggcac cgccgagccc uggacaccaa cuauugcuuc 1740
agcuccacgg agaagaacug cugcgugcgg cagcuguaca uugacuuccg caaggaccuc 1800
ggcuggaagu ggauccacga gcccaagggc uaccaugcca acuucugccu cgggcccugc 1860
cccuacauuu ggagccugga cacgcaguac agcaaggucc uggcccugua caaccagcau 1920
aacccgggcg ccucggcggc gccgugcugc gugccgcagg cgcuggagcc gcugcccauc 1980
guguacuacg ugggccgcaa gcccaaggug gagcagcugu ccaacaugau cgugcgcucc 2040
ugcaagugca gcugaggucc cgccccgccc cgccccgccc cggcaggccc ggccccaccc 2100
cgccccgccc ccgcugccuu gcccaugggg gcuguauuua aggacacccg ugccccaagc 2160
ccaccugggg ccccauuaaa gauggagaga ggacugcgga aaaaaaaaaa aaaaaaa 2217

<210> SEQ ID NO 88
<211> LENGTH: 2503
<212> TYPE: RNA
<213> ORGANISM: HUMAN

<400> SEQUENCE: 88
cgcucuuauu ggccagggga cgguagcugc aggacucugc ucuccugcgg ccaugggcca 60
ggguugggcu acugcaggac uucccagccu ccucuuccug cugcucugcu acgggcaccc 120
ucugcugguc cccagccagg aggcauccca acaggugaca gucacccaug ggacaagcag 180
ccaggcaaca accagcagcc agacaaccac ccaccaggcg acggcccacc agacaucagc 240
ccagagccca aaccugguga cugaugaggc ugaggccagc aaguuugugg aggaauauga 300
ccggacaucc cagguggugu ggaacgagua ugccgaggcc aacuggaacu acaacaccaa 360
caucaccaca gagaccagca agauucugcu gcagaagaac augcaaauag ccaaccacac 420
ccugaaguac ggcacccagg ccaggaaguu ugaugugaac caguugcaga acaccacuau 480
caagcggauc auaaagaagg uucaggaccu agaacgggca gcacugccug cccaggagcu 540
ggaggaguac aacaagaucc uguuggauau ggaaaccacc uacagcgugg ccacugugug 600
ccacccgaau ggcagcugcc ugcagcucga gccagaucug acgaauguga uggccacguc 660
ccggaaauau gaagaccugu uaugggcaug ggagggcugg cgagacaagg cggggagagc 720
cauccuccag uuuuacccga aauacgugga acucaucaac caggcugccc ggcucaaugg 780
cuauguagau gcaggggacu cguggagguc uauguacgag acaccauccc uggagcaaga 840
ccuggagcgg cucuuccagg agcugcagcc acucuaccuc aaccugcaug ccuacgugcg 900
ccgggcccug caccgucacu acggggccca gcacaucaac cuggaggggc ccauuccugc 960
ucaccugcug gggaacaugu gggcgcagac cugguccaac aucuaugacu ugguggugcc 1020
cuucccuuca gcccccucga uggacaccac agaggcuaug cuaaagcagg gcuggacgcc 1080
caggaggaug uuuaaggagg cugaugauuu cuucaccucc cuggggcugc ugcccgugcc 1140
uccugaguuc uggaacaagu cgaugcugga gaagccaacc gacgggcggg agguggucug 1200
ccacgccucg gccugggacu ucuacaacgg caaggacuuc cggaucaagc agugcaccac 1260

-continued cgugaacuug gaggaccugg ugguggccca ccacgaaaug ggccacaucc aguauuucau 1320
gcaguacaaa gacuuaccug uggccuugag ggagggugcc aaccccggcu uccaugaggc 1380
cauuggggac gugcuagccc ucucaguguc uacgcccaag caccugcaca gucucaaccu 1440
gcugagcagu gaggguggca gcgacgagca ugacaucaac uuucugauga agauggcccu 1500
ugacaagauc gccuuuaucc ccuucagcua ccucgucgau caguggcgcu ggaggguauu 1560
ugauggaagc aucaccaagg agaacuauaa ccaggagugg uggagccuca ggcugaagua 1620
ccagggccuc ugcccccag ugcccaggac ucaaggugac uuugacccag gggccaaguu 1680
ccacauuccu ucuagcgugc cuuacaucag guacuuuguc agcuucauca uccaguucca 1740
guuccacgag gcacugugcc aggcagcugg ccacacgggc cccugcaca agugugacau 1800 cuaccagucc aaggaggccg ggcagcgccu ggcgaccgcc augaagcugg gcuucaguag 1860
gccguggccg gaagccaugc agcugaucac gggccagccc aacaugagcg ccucggccau 1920
guugagcuac uucaagccgc ugcuggacug gcuccgcacg gagaacgagc ugcaugggga 1980
gaagcugggc uggccgcagu acaacuggac gccgaacucc gcucgcucag aagggcccu 2040 cccagacagc ggccgcguca gcuuccuggg ccuggaccug gaugcgcagc aggcccgcgu 2100
gggccagugg cugcugcucu uccugggcau cgcccugcug guagccaccc ugggccucag 2160
ccagcggcuc uucagcaucc gccaccgcag ccuccaccgg cacucccacg ggccccaguu 2220
cggcuccgag guggagcuga gacacuccug aggugacccg gcugggucgg cccugcccaa 2280
gggccuccca ccagagacug ggaugggaac acugguggc agcugaggac acacccaca 2340 ccccagccca cccugcuccu ccugcccugu cccuguccc cuccccuccc aguccuccag 2400
accaccagcc gccccagccc cuucucccag cacacggcug ccugacacug agcccaccu 2460 cuccaagucu cucugugaau acaauuaaag guccugcccu ccc 2503

<210> SEQ ID NO 89
<211> LENGTH: 4195
<212> TYPE: RNA
<213> ORGANISM: HUMAN

<400> SEQUENCE: 89
gccgagcacc gcgcaccgcg ucaugggggc cgccucgggc cgccgggggc cggggcugcu 60
gcugccgcug ccgcugcugu ugcugcugcc gccgcagccc gcccuggcgu uggaccccgg 120
gcugcagccc ggcaacuuuu cugcugacga ggccgggggcg cagcucuucg cgcagagcua 180
caacuccagc gccgaacagg ugcuguucca gagcguggcc gccagcuggg cgcacgacac 240
caacaucacc gcggagaaug caaggcgcca ggaggaagca gcccugcuca gccaggaguu 300
ugcggaggcc uggggccaga aggccaagga gcuguaugaa ccgaucuggc agaacuucac 360
ggacccgcag cugcgcagga ucaucggagc ugugcgcacc cugggcucug ccaaccugcc 420
ccuggcuaag cggcagcagu acaacgcccu gcuaagcaac augagcagga ucuacuccac 480
cgccaagguc ugccucccca acaagacugc caccugcugg ucccuggacc cagaucucac 540
caacauccug gcuuccucgc gaagcuacgc caugcuccug uuugccuggg agggcuggca 600
caacgcugcg ggcaucccgc ugaaaccgcu guacgaggau uucacugccc ucagcaauga 660
agccuacaag caggacggcu ucacagacac gggggccuac uggcgcuccu gguacaacuc 720
ccccaccuuc gaggacgauc uggaacaccu cuaccaacag cuagagcccc ucuaccugaa 780
ccuccaugcc uucguccgcc gcgcacugca ucgccgauac ggagacagau acaucaaccu 840
caggggaccc aucccugcuc aucugcuggg agacaugugg gcccagagcu gggaaaacau 900

-continued

```
cuacgacaug guggugccuu ucccagacaa gcccaaccuc gaugucacca guacuaugcu    960
gcagcagggc uggaacgcca cgcacauguu ccgggugca gaggaguucu ucaccucccu   1020
ggagcucucc cccaugccuc ccgaguucug ggaagggucg augcuggaga agccggccga   1080
cgggcgggaa guggugugcc acgccucggc uugggacuuc uacaacagga aagacuucag   1140
gaucaagcag ugcacacggg ucacgaugga ccagcucucc acagugcacc augagauggg   1200
ccauauacag uacuaccugc aguacaagga ucugcccguc ucccugcguc gggggccaa    1260
ccccggcuuc caugaggcca uuggggacgu gcuggcgcuc ucggucucca cuccugaaca   1320
ucugcacaaa aucggccugc uggaccgugu caccaaugac acggaaagug acaucaauua   1380
cuugcuaaaa auggcacugg aaaaaauugc cuuccugccc uuuggcuacu ugguggacca   1440
guggcgcugg ggggucuuua gugggcguac ccccccuucc cgcuacaacu ucgacuggug   1500
guaucuucga accaaguauc aggggaucug uccuccuguu acccgaaacg aaacccacuu   1560
ugaugcugga gcuaaguuuc auguuccaaa ugugacacca uacaucaggu acuuugugag   1620
uuuuguccug caguuccagu uccaugaagc ccugugcaag gaggcaggcu augagggccc   1680
acugcaccag ugugacaucu accgguccac caaggcaggg gccaagcucc ggaaggugcu   1740
gcaggcuggc ucccuccaggc ccuggcagga ggugcugaag gacauggucg gcuuagaugc   1800
ccuggaugcc cagccgcugc ucaaguacuu ccagccaguc acccaguggc ugcaggagca   1860
gaaccagcag aacggcgagg uccugggcug gcccgaguac caguggcacc cgccguugcc   1920
ugacaacuac ccggagggca uagaccuggu gacugaugag gcugaggcca gcaaguuugu   1980
ggaggaauau gaccggacau cccagguggu guggaacgag uaugccgagg ccaacuggaa   2040
cuacaacacc aacaucacca cagagaccag caagauucug cugcagaaga acaugcaaau   2100
agccaaccac acccugaagu acggcaccca ggccaggaag uuugauguga accaguugca   2160
gaacaccacu aucaagcgga ucauaaagaa gguucaggac cuagaacggg cagcacugcc   2220
ugcccaggag cuggaggagu acaacaagau ccuguuggau auggaaacca ccuacagcgu   2280
ggccacugug ugccacccga auggcagcug ccugcagcuc gagccagauc ugacgaaugu   2340
gauggccacg ucccggaaau augaagaccu guuaugggca ugggagggcu ggcgagacaa   2400
ggcggggaga gccauccucc aguuuaccc gaaauacgug gaacucauca accaggcugc    2460
ccggcucaau ggcuauguag augcagggga cucguggagg ucuauguacg agacaccauc   2520
ccuggagcaa gaccuggagc ggcucuucca ggagcugcag ccacucuacc ucaaccugca   2580
ugccuacgug cgccgggccc ugcaccguca cuacggggcc cagcacauca accuggaggg   2640
gcccauuccu gcucaccugc uggggaacau gugggcgcag accuggucca acaucuauga   2700
cuugguggug cccuucccuu cagccccuc gauggacacc acagaggcua ugcuaaagca    2760
gggcuggacg cccaggagga uguuuaagga ggcugaugau uucuucaccu cccuggggcu   2820
gcugcccgug ccuccugagu ucuggaacaa gucgaugcug gagaagccaa ccgacgggcg   2880
ggagguggu c ugccacgccu cggccuggga cuucuacaac ggcaaggacu uccggaucaa  2940
gcagugcacc accgugaacu uggaggaccu gguggguggcc caccacgaaa ugggccacau  3000
ccaguauuuc augcaguaca aagacuuacc uguggccuug agggagggug ccaaccccgg   3060
cuuccaugag gccauugggg acgugcuagc ccucucagug ucuacgccca agcaccugca   3120
cagucucaac cugcugagca gugagggugg cagcgacgag caugacauca acuuucugau   3180
gaagauggcc cuugacaaga ucgccuuuau ccccuucagc uaccucgucg aucaguggcg   3240
cuggagggua uuugauggaa gcaucaccaa ggagaacuau aaccaggagu gguggagccu   3300
```

-continued

```
caggcugaag uaccagggcc ucugcccccc agugcccagg acucaaggug acuuugaccc   3360

aggggccaag uuccacauuc cuucuagcgu gccuuacauc agguacuuug ucagcuucau   3420

cauccaguuc caguuccacg aggcacugug ccaggcagcu ggccacacgg gcccccugca   3480

caagugugac aucuaccagu ccaaggaggc cgggcagcgc cuggcgaccg ccaugaagcu   3540

gggcuucagu aggccguggc cggaagccau gcagcugauc acgggccagc ccaacaugag   3600

cgccucggcc auguugagcu acuucaagcc gcugcuggac uggcuccgca cggagaacga   3660

gcugcauggg gagaagcugg gcuggccgca guacaacugg acgccgaacu ccgcucgcuc   3720

agaagggccc cucccagaca gcggccgcgu cagcuuccug ggccuggacc uggaugcgca   3780

gcaggcccgc gugggccagu ggcugcugcu cuuccugggc aucgcccugc ugguagccac   3840

ccugggccuc agccagcggc ucuucagcau ccgccaccgc agccuccacc ggcacuccca   3900

cgggccccag uucggcuccg agguggagcu gagacacucc ugaggugacc cggcugggug   3960

ggcccugccc aagggccucc caccagagac ugggauggga acacuggugg gcagcugagg   4020

acacacccca caccccagcc cacccugcuc cuccugcccu gucccugucc cccucccuc    4080

ccaguccucc agaccaccag ccgccccagc cccuucuccc agcacacggc ugccugacac   4140

ugagccccac cucuccaagu cucucuguga auacaauuaa agguccugcc cuccc        4195
```

<210> SEQ ID NO 90
<211> LENGTH: 760
<212> TYPE: RNA
<213> ORGANISM: HUMAN

<400> SEQUENCE: 90

```
gaggaaccga gaggcugaga cuaacccaga aacauccaau ucucaaacug aagcucgcac     60

ucucgccucc agcaugaaag ucucugccgc ccuucugugc cugcugcuca uagcagccac    120

cuucauuccc caagggcucg cucagccaga ugcaaucaau gccccaguca ccugcuguua    180

uaacuucacc aauaggaaga ucucagugca gaggcucgcg agcuauagaa gaaucaccag    240

cagcaagugu cccaaagaag cugugaucuu caagaccauu guggccaagg agaucugugc    300

ugaccccaag cagaaguggg uucaggauuc cauggaccac cuggacaagc aaacccaaac    360

uccgaagacu ugaacacuca cuccacaacc caagaaucug cagcuaacuu auuuuccccu    420

agcuuucccc agacacccug uuuuauuuua uuauaaugaa uuuuguuugu ugaugugaaa    480

cauuaugccu uaaguaaugu uaauucuuau uuaaguuauu gauguuuuaa guuuaucuuu    540

caugguacua guguuuuuua gauacagaga cuuggggaaa uugcuuuucc ucuugaacca    600

caguucuacc ccugggaugu uuugaggguc uuugcaagaa ucauuaauac aaagaauuuu    660

uuuuaacauu ccaaugcauu gcuaaaauau uauuguggaa augaauauuu uguaacuauu    720

acaccaaaua aauauauuuu uguacaaaaa aaaaaaaaaa                          760
```

<210> SEQ ID NO 91
<211> LENGTH: 1916
<212> TYPE: RNA
<213> ORGANISM: HUMAN

<400> SEQUENCE: 91

```
gaguuugaaa cugcucgcac uuggcuucaa agcuggcucu uggaaauuga gcggagagcg     60

acgcgguugu uguagcugcc gcugcggccg ccgcggaaua auaagccggg aucuaccaua    120

cccauugacu aacuauggaa gauuauacca aaauagagaa aauuggagaa gguaccuaug    180

gaguugugua uaaggguaga cacaaaacua caggucaagu gguagccaug aaaaaaauca    240
```

```
gacuagaaag ugaagaggaa gggguuccua guacugcaau ucgggaaauu ucucuauuaa    300

aggaacuucg ucauccaaau auagucaguc uucaggaugu gcuuaugcag gauuccaggu    360

uauaucucau cuuugaguuu cuuuccaugg aucugaagaa auacuuggau ucuaucccuc    420

cuggucagua cauggauucu ucacuuguua agaguuauuu auaccaaauc cuacagggga    480

uuguguuuug ucacucuaga agaguucuuc acagagacuu aaaaccucaa aaucucuuga    540

uugaugacaa aggaacaauu aaacuggcug auuuuggccu ugccagagcu uuuggaauac    600

cuaucagagu auauacacau gagguaguaa cacucuggua cagaucucca gaaguauugc    660

uggggucagc ucguuacuca acuccaguug acauuuggag uauaggcacc auauuugcug    720

aacuagcaac uaagaaacca cuuuuccaug ggauucaga aauugaucaa cucuucagga    780

uuuucagagc uuugggcacu cccaauaaug aaguguggcc agaaguggaa ucuuuacagg    840

acuauaagaa uacauuuccc aaauggaaac caggaagccu agcaucccau gucaaaaacu    900

uggaugaaaa uggcuuggau uugcucucga aaauguuaau cuaugaucca gccaaacgaa    960

uuucuggcaa aauggcacug aaucauccau auuuuaauga uuuggacaau cagauuaaga   1020

agauguagcu uucugacaaa aaguuuccau auguuauauc aacagauagu uguguuuuua   1080

uuguuaacuc uugucuauuu uugucuuaua uauauuucuu uguuaucaaa cuucagcugu   1140

acuucgucuu cuaauuucaa aaauauaacu uaaaaaugua aauauucuau augaauuuaa   1200

auauaauucu guaaaugugu guaggucuca cuguaacaac uauuuguuac uauaauaaaa   1260

cuauaauauu gaugucagga aucaggaaaa aauuugaguu ggcuuaaauc aucucagucc   1320

uuauggcagu uuuauuuucc uguaguugga acuacuaaaa uuuaggaaaa ugcuaaguuc   1380

aaguuucgua augcuuugaa guauuuuuau gcucugaaug uuuaaauguu cucaucaguu   1440

ucuugccaug uuguuaacua uacaaccugg cuaaagauga auauuuuucu acugguauuu   1500

uaauuuuuga ccuaaauguu uaagcauucg gaaugagaaa acuauacaga uuugagaaau   1560

gaugcuaaau uuauaggagu uuucaguaac uuaaaaagcu aacaugagag caugccaaaa   1620

uuugcuaagu cuuacaaaga ucaagggcug uccgcaacag ggaagaacag uuuugaaaau   1680

uuaugaacua ucuuauuuuu agguagguuu ugaaagcuuu uugucuaagu gaauucuuau   1740

gccuugguca gaguaauaac ugaaggaguu gcuuaucuug gcuuucgagu cugaguuuaa   1800

aacuacacau uuugacauag uguuuauuag cagccaucua aaaaggcucu aauguauauu   1860

uaacuaaaau uacuagcuuu gggaauuaaa cuguuuaaca aauaaaaaaa aaaaaa       1916
```

<210> SEQ ID NO 92
<211> LENGTH: 1636
<212> TYPE: RNA
<213> ORGANISM: HUMAN

<400> SEQUENCE: 92

```
gaucuaccau acccauugac uaacuaugga agauuauacc aaaauagaga aaauuggaga     60

agguaccuau ggaguugugu auaaggguag acacaaaacu acaggucaag ugguagccau    120

gaaaaaaauc agacuagaaa gugaagagga aggggguuccu aguacugcaa uucgggaaau    180

uucucuauua aaggaacuuc gucauccaaa uauagucagu cuucaggaug ugcuuaugca    240

ggauuccagg uuauaucuca ucuuugaguu ucuuuccaug gaucugaaga aauacuugga    300

uucuaucccu ccuggucagu acauggauuc uucacuuguu aagguaguaa cacucuggua    360

cagaucucca gaaguauugc uggggucagc ucguuacuca acuccaguug acauuuggag    420

uauaggcacc auauuugcug aacuagcaac uaagaaacca cuuuuccaug ggauucaga    480
```

-continued aauugaucaa cucuucagga uuuucagagc uuugggcacu cccaauaaug aaguguggcc 540
agaaguggaa ucuuuacagg acuauaagaa uacauuuccc aaauggaaac caggaagccu 600
agcaucccau gucaaaaacu uggaugaaaa uggcuuggau uugcucucga aaauguuaau 660
cuaugaucca gccaaacgaa uuucuggcaa aauggcacug aaucauccau auuuuaauga 720
uuuggacaau cagauuaaga agauguagcu uucugacaaa aaguuuccau auguuauauc 780
aacagauagu uguguuuuua uuguuaacuc uugucuauuu uugucuuaua uauauuucuu 840
uguuaucaaa cuucagcugu acuucgucuu cuaauuucaa aaauauaacu uaaaaaugua 900
aauauucuau augaauuuaa auauaauucu guaaaugugu guaggucuca cuguaacaac 960
uauuuguuac uauaauaaaa cuauaauauu gaugucagga aucaggaaaa aauuugaguu 1020
ggcuuaaauc aucucagucc uuauggcagu uuuauuuucc uguaguugga acuacuaaaa 1080
uuuaggaaaa ugcuaaguuc aaguuucgua augcuuugaa guauuuuuau gcucugaaug 1140
uuuaaauguu cucaucaguu ucuugccaug uuguuaacua uacaaccugg cuaaagauga 1200
auauuuuucu acugguauuu uaauuuuuga ccuaaaauguu uaagcauucg gaaugagaaa 1260
acuauacaga uuugagaaau gaugcuaaau uuauaggagu uuucaguaac uuaaaaagcu 1320
aacaugagag caugccaaaa uuugcuaagu cuuacaaaga ucaagggcug uccgcaacag 1380
ggaagaacag uuuugaaaau uuaugaacua ucuuauuuuu agguagguuu ugaaagcuuu 1440
uugucuaagu gaauucuuau gccuugguca gaguaauaac ugaaggaguu gcuuaucuug 1500
gcuuucgagu cugaguuuaa aacuacacau uuugacauag uguuuauuag cagccaucua 1560
aaaaggcucu aauguauauu uaacuaaaau uacuagcuuu gggaauuaaa cuguuuaaca 1620
aauaaaaaaa aaaaaa 1636

<210> SEQ ID NO 93
<211> LENGTH: 1943
<212> TYPE: RNA
<213> ORGANISM: HUMAN

<400> SEQUENCE: 93
guagcugccg cugcggccgc cgcggaauaa uaagccgggu acaguggcug gggucagggu 60
cgugucuagg ggacggccga gggccucgga gggcgaguau ugaggaacgg gguccucuaa 120
gaaggccgga cuggaggauc uaccauaccc auugacuaac uauggaagau uauaccaaaa 180
uagagaaaau uggagaaggu accuauggag uuguguauaa ggguagacac aaaacuacag 240
gucaaguggu agccaugaaa aaaaucagac uagaaaguga agaggaaggg guuccuagua 300
cugcaauucg ggaaauuucu cuauuaaagg aacuucguca uccaaauaua gucagucuuc 360
aggaugugcu uaugcaggau uccagguuau aucucaucuu ugaguuucuu uccauggauc 420
ugaagaaaua cuuggauucu aucccuccug gucaguacau ggauucuuca cuuguuaaga 480
guuauuuaua ccaaauccua caggggauug uguuuuguca cucuagaaga guucuucaca 540
gagacuuaaa accucaaaau cucuugauug augacaaagg aacaauuaaa cuggcugauu 600
uuggccuugc cagagcuuuu ggaauaccua ucagaguaua uacacaugag gcaauaacac 660
ucugguacag aucuccagaa guauugcugg ggucagcucg uuacucaacu ccaguugaca 720
uuuggaguau aggcaccaua uuugcugaac uagcaacuaa gaaaccacuu uuccaugggg 780
auucagaaau ugaucaacuc uucaggauuu ucagagcuuu gggcacuccc aauaaugaag 840
uguggccaga aguggaaucu uuacaggacu auaagaauac auuucccaaa uggaaaccag 900
gaagccuagc aucccauguc aaaaacuugg augaaaaugg cuuggauuug cucucgaaaa 960

```
uguuaaucua ugauccagcc aaacgaauuu cuggcaaaau ggcacugaau cauccauauu   1020

uuaaugauuu ggacaaucag auuaagaaga uguagcuuuc ugacaaaaag uuuccauaug   1080

uuauaucaac agauaguugu guuuuuauug uuaacucuug ucuauuuuug ucuuauauau   1140

auuucuuugu uaucaaacuu cagcuguacu ucgucuucua auuucaaaaa uauaacuuaa   1200

aaauguaaau auucuauaug aauuuaaaua uaauucugua aaugugugua ggucucacug   1260

uaacaacuau uuguuacuau aauaaaacua uaauauugau gucaggaauc aggaaaaaau   1320

uugaguuggc uuaaaucauc ucaguccuua uggcaguuuu auuuuccugu aguuggaacu   1380

acuaaaauuu aggaaaaugc uaaguucaag uuucguaaug cuuugaagua uuuuuaugcu   1440

cugaauguuu aaauguucuc aucaguuucu ugccauguug uuaacuauac aaccuggcua   1500

aagaugaaua uuuuucuacu gguauuuaa uuuuugaccu aaauguuuaa gcauucggaa   1560

ugagaaaacu auacagauuu gagaaaugau gcuaaauuua uaggaguuuu caguaacuua   1620

aaaagcuaac augagagcau gccaaaauuu gcuaagucuu acaaagauca agggcugucc   1680

gcaacaggga agaacaguuu ugaaaauuua ugaacuaucu uauuuuuagg uagguuuuga   1740

aagcuuuuug ucuaagugaa uucuuaugcc uuggucagag uaauaacuga aggaguugcu   1800

uaucuuggcu uucgagucug aguuuaaaac uacacauuuu gacauagugu uuauuagcag   1860

ccaucuaaaa aggcucuaau guauauuuaa cuaaaauuac uagcuuuggg aauuaaacug   1920

uuuaacaaau aaaaaaaaaa aaa                                            1943
```

<210> SEQ ID NO 94
<211> LENGTH: 561
<212> TYPE: RNA
<213> ORGANISM: HUMAN

<400> SEQUENCE: 94

```
accacagugg uguccgagaa gucaggcacg uagcucagcg gcggccgcgg cgcgugcguc     60

ugugccucug cgcgggucuc cugguccuuc ugccaucaug ccgauguuca ucguaaacac    120

caacgugccc cgcgccuccg ugccggacgg guuccucucc gagcucaccc agcagcuggc    180

gcaggccacc ggcaagcccc cccaguacau cgcggugcac gugguccegg accagcucau    240

ggccuucggc ggcuccagcg agccgugcgc gcucugcagc cugcacagca ucggcaagau    300

cggcggcgcg cagaaccgcu ccuacagcaa gcugcugugc ggccugcugg ccgagcgccu    360

gcgcaucagc ccggacaggg ucuacaucaa cuauuacgac augaacgcgg ccaauguggg    420

cuggaacaac uccaccuucg ccuaagagcc gcagggaccc acgcugucug cgcuggcucc    480

acccgggaac ccgccgcacg cuguguucua ggcccgccca ccccaaccuu cuggugggga    540

gaaauaaacg guuuagagac u                                              561
```

<210> SEQ ID NO 95
<211> LENGTH: 5114
<212> TYPE: RNA
<213> ORGANISM: HUMAN

<400> SEQUENCE: 95

```
agguggugca acgccuggcc cggcccaucc caucccggcc acccgggcag cgggaccagg     60

cgucuggggc acagcaugcg gggcguguggg ccgcccccgg uguccgcccu gcugucggcg    120

cuggggaugu cgacguacaa gcgggccacg cuggacgagg aggaccuggu ggacucgcuc    180

uccgagggcg acgcauaccc caacggccug cagguggaacu uccacagccc ccggaguggc    240

cagaggugcu gggcugcacg gacccaggug gagaagcggc ugguggguguu ggugguacuu    300
```

-continued

```
cuggcggcag gacugguggc cugcuuggca gcacugggca uccaguacca gacaagaucc     360
cccucugugu gccugagcga agcuuguguc ucagugacca gcuccaucuu gagcuccaug     420
gaccccacag uggaccccug ccaugacuuc uucagcuacg ccuguggggg cuggaucaag     480
gccaacccag ucccugaugg ccacucacgc ugggggaccu ucagcaaccu cugggaacac     540
aaccaagcaa ucaucaagca ccuccucgaa aacuccacgg ccagcgugag cgaggcagag     600
agaaaggcgc aaguauacua ccgugcgugc augaacgaga ccaggaucga ggagcucagg     660
gccaaaccuc uaauggaguu gauugagagg cucgggggcu ggaacaucac agguccuugg     720
gccaaggaca acuuccagga cacccugcag gugguccaccg cccacuaccg caccucaccc    780
uucuucucug ucuaugucag ugccgauucc aagaacucca acagcaacgu gauccaggug     840
gaccagucug gccugggcuu gcccucgaga gacuauuacc ugaacaaaac ugaaaacgag     900
aaggugcuga ccggauaucu gaacuacaug guccagcugg ggaagcugcu gggcggcggg     960
gacgaggagg ccauccggcc ccagaugcag cagaucuugg acuuugagac ggcacuggcc    1020
aacaucacca ucccacagga gaagcgccgu gaugaggagc ucaucuacca caaagugacg    1080
gcagccgagc ugcagaccuu ggcacccgcc aucaacuggu ugccuuuucu caacaccauc    1140
uucuaccccg uggagaucaa ugaauccgag ccuauugugg ucuaugacaa ggaauaccuu    1200
gagcagaucu ccacucucau caacaccacc gacagaugcc ugcucaacaa cuacaugauc    1260
uggaaccugg ugcggaaaac aagcuccuuc cuugaccagc gcuuucagga cgccgaugag    1320
aaguucaugg aagucaugua cgggaccaag aagaccuguc uuccucgcug gaaguuuugc    1380
gugagugaca cagaaaacaa ccugggcuuu gcguugggcc ccauguuugu caaagcaacc    1440
uucgccgagg acagcaagag cauagccacc gagaucaucc uggagauuaa gaaggcauuu    1500
gaggaaagcc ugagcacccu gaaguggaug gaugaggaaa cccgaaaauc agccaaggaa    1560
aaggccgaug ccaucuacaa caugauagga uaccccaacu ucaucaugga ucccaaggag    1620
cuggacaaag uguuuaauga cuacacugca guuccagacc ucuacuuuga aaaugccaug    1680
cgguuuuuca acuucucaug gagggucacu gccgaucagc ucaggaaagc cccccaacaga   1740
gaucagugga gcaugacccc gcccauggug aacgccuacu acucgcccac caagaaugag    1800
auuguguuuc cggccgggau ccugcaggca ccauucuaca cacgcuccuc acccaaggcc    1860
uuaaacuuug guggcauagg ugucgucgug ggccaugagc ugacucaugc uuuugaugau    1920
caaggacggg aguaugacaa ggacgggaac cuccggccau gguggaagaa cucauccgug    1980
gaggccuuca agcgucagac cgagugcaug guagagcagu acagcaacua cagcgugaac    2040
ggggagccgg ugaacgggcg gcacacccug ggggagaaca ucgccgacaa cgggggucuc    2100
aaggcggccu aucgggcuua ccagaacugg gugaagaaga acggggcuga gcacucgcuc    2160
cccacccugg gccucaccaa uaaccagcuc uucuuccugg gcuuugcaca ggucuggugc    2220
uccguccgca caccugagag cucccacgaa ggccucauca ccgaucccca cagccccucu    2280
cgcuuccggg ucaucggcuc ccucuccaau uccaaggagu ucucagaaca cuuccgcugc    2340
ccaccuggcu cacccaugaa cccgccucac aagugcgaag ucugguaagg acgaagcgga    2400
gagagccaag acggaggagg ggaaggggcu gaggacgaga cccccaucca gccuccaggg    2460
cauugcucag cccgcuuggc cacccggggc ccugcuuccu cacacuggcg gguuuucagc    2520
cggaaccgag cccauggugu uggcucucaa cgugacccgc agucugaucc ccugugaaga    2580
gccggacauc ccaggcacac gugugcgcca ccuucagcag gcauucgggu gcugggcugg    2640
uggcucauca ggccugggcc ccacacugac aagcgccaga uacgccacaa auaccacugu    2700
```

-continued

```
gucaaaugcu uucaagauau auuuuugggg aaacuauuuu uuaaacacug uggaauacac   2760
uggaaaucuu cagggaaaaa cacauuuaaa cacuuuuuuu uuuaaggaaa gaauugguau   2820
auuuauuaug uucuguuuuu cuaaauaacc uguggacaag ggaagcccca cugauuuacu   2880
cccucucuuc cccacucccu gugaggcugg gcugaggcac ggaucccugg gccacagagc   2940
aagucuccaa aucagacagc ugccucagcc ccugggaugu gugauuucag cuccugucac   3000
cucaugcaag ggcguggaga ccaguagagg uguggaggcc aggcagagag aggagccugc   3060
ucugcggggg gcccagcuca ugggcacugc cccuucagcu agccugccuc cguccccuga   3120
guccaacagu gggagcccua gcugggaagu ucugaucccc aaagccacag caggggacug   3180
auggcuauag cagaaugagg ucgggucagg acccucaaac accaucuggg aacaccaagc   3240
acccugaauc gagacugcag gagcccugcg gggugagacu gugucagaga uacacugcug   3300
gccacaagug uccccucuca gucccaccuu uucgggcugu cccaugucua ucucaggggc   3360
ccguuaccuc ucugcagcag ucccccaucc cagccacacc agggucuguc cggccaaccc   3420
ucuuccccag ggaaaggaga aaagagaaaa caggcugggc ccgguggcuc acuccuguaa   3480
ucccagcacu uugggagguu gaggugggcg gaucaccuga ggucaggagu uugagaccag   3540
ccuggccaac guggugaaac cccaucucua cuaaaaaaaa uuacaaaaau uagccgggag   3600
uggugguggg caccuguaau cccaguuacu cgggaggcug aggcaagaga aucucuugag   3660
cucaggaggc agagguugca gugagcugag auugcgccac ugcacuccag ccugggugac   3720
agagggagac uccgucccaa aaaaaagaaa agagaaacag cugucaccuc ccgcaggacc   3780
caaauccucu cucugagcac cgucauccac cacauggcug ggccuggcuc ccaggaccag   3840
uccaguccuc uagugccuua ucugaggcug cagccgccag ucuccacccc aaggagacag   3900
ccccugcucc uagaugcccu uggccuccgc agugcagccc ccaggugucc ugacugaagc   3960
acaggccaua gccccauuuc cccggugccu gcagggcuaa ccuccacggg agcccaggag   4020
cucuggccgg cagguccaug gcacagggca ucggaagacu gcaaaacugc uggacuuacc   4080
cugggcugca guccauuguc ggccccuggg uugaaucaag auaguacuug cagcuagaug   4140
gaugcuuuua gccaggggac auugugaggg gaagauuccu ccacccaguc uggccugugg   4200
ugucugucuc cucccugaga ccacagcuuc uccaguagca gacucauggg cgccaccaag   4260
uggaagcacc uggagcggcc ucugccaucc agugggggaag ccaggccccg agacggaggu   4320
gggggcagca cgugcccucc acagccaccg cuuucccgcc ucagcagccc aggccuccug   4380
gcccagcccu gccuggacag ugcucucccc ucacccggga agcuggaauc cuccugcccg   4440
agaggaagca gacggcacag ggacaccccu gccaccuugg gaucugccuc caagcuggug   4500
caggguaucg agaguggauu ccagauggag guccuggucc cagcacgcag caguccuggu   4560
agcucugcag aggagacagg aacccgagaa guagcugaag cagaagccag ccgcaguccc   4620
cuugccacau agaggcgggc uucucccagc cauggugucc ccucugccuc cccuccccccg   4680
acccuccugc cuuccgcgug gaggguggug guccuguagu gucagcacca gcaccauggg   4740
cuuggacccc cucccuggac acaggcaggu guccuagggc ugggggugca gcccgaggga   4800
auggagacca cacucauggc ucaggucugc cggggccggc agggggguugg ggaagaagag   4860
ggcucaggcc cagcaggggu ggaagccccu gccacugcca cuacccgcuc cagagcuuua   4920
aggaaaauga agugagaccc cuccccuuag gccuggggag ccauagggcu ggcuucucug   4980
ugggugcgug gacguggggu ugggagcugg gaaucuauuu uuuguauuau guuuugagcu   5040
acuguaguuu uggcguggca cuauuguaau ggaaauaaaa uacuuguacg gagggcaaaa   5100
```

-continued aaaaaaaaaa aaaa 5114

<210> SEQ ID NO 96
<211> LENGTH: 5105
<212> TYPE: RNA
<213> ORGANISM: HUMAN

<400> SEQUENCE: 96
guguccaggc cggggcgggg cgcggcggcg gcggcgccag ggucggggcc gcuuccccau 60
ucgggcgcga gagccaugga ggcgcugagg gaguccgugc ugcauuuggc cuugcagaug 120
ucgacguaca agcgggccac gcuggacgag gaggaccugg uggacucgcu cuccgagggc 180
gacgcauacc ccaacggccu gcaggugaac uuccacagcc cccggagugg ccagaggugc 240
ugggcugcac ggacccaggu ggagaagcgg cugguggugu ugguggua cu ucuggcggca 300 ggacuggugg ccugcuuggc agcacugggc auccaguacc agacaagauc cccucugug 360 ugccugagcg aagcuugugu cucagugacc agcuccaucu ugagcuccau ggaccccaca 420
guggaccccu gccaugacuu cuucagcuac gccuguggggg gcuggaucaa ggccaaccca 480
gucccugaug gccacucacg cugggggacc uucagcaacc ucugggaaca caaccaagca 540
aucaucaagc accuccucga aaacuccacg gccagcguga gcgaggcaga gagaaaggcg 600
caaguauacu accgugcgug caugaacgag accaggaucg aggagcucag ggccaaaccu 660
cuaauggagu ugauugagag gcucgggggc uggaacauca caggucccug ggccaaggac 720
aacuuccagg acacccugca gguggucacc gcccacuacc gcaccucacc cuucuucucu 780
gucuauguca gugccgauuc caagaacucc aacagcaacg ugauccaggu ggaccagucu 840
ggccugggcu ugcccucgag agacuauuac cugaacaaaa cugaaaacga gaaggugcug 900
accggauauc ugaacuacau gguccagcug ggaagcugc ugggcggcgg ggacgaggag 960
gccauccggc cccagaugca gcagaucuug gacuuugaga cggcacuggc caacaucacc 1020
aucccacagg agaagcgccg ugaugaggag cucaucuacc acaaagugac ggcagccgag 1080
cugcagaccu uggcacccgc caucaacugg uugccuuuuc ucaacaccau cuucuacccc 1140
guggagauca augaauccga gccuauugug gucuaugaca aggaauaccu ugagcagauc 1200
uccacucuca ucaacaccac cgacagaugc cugcucaaca acuacaugau cuggaaccug 1260
gugcggaaaa caagcuccuu ccuugaccag cgcuuucagg acgccgauga gaaguucaug 1320
gaagucaugu acgggaccaa gaagaccugu cuuccucgcu ggaaguuuug cgugagugac 1380
acagaaaaca accugggcuu ugcguugggc cccauguuug ucaaagcaac cuucgccgag 1440
gacagcaaga gcauagccac cgagaucauc cuggagauua agaaggcauu ugaggaaagc 1500
cugagcaccc ugaaguggau ggaugaggaa acccgaaaau cagccaagga aaaggccgau 1560
gccaucuaca acaugauagg auaccccaac uucaucaugg aucccaagga gcuggacaaa 1620
guguuuaaug acuacacugc aguuccagac cucuacuuug aaaaugccau gcgguuuuuc 1680
aacuucucau ggagggucac ugccgaucag cucaggaaag cccccaacag agaucagugg 1740
agcaugaccc cgcccauggu gaacgccuac uacucgccca ccaagaauga gauuguguuu 1800
ccggccggga uccugcaggc accauucuac acacgcuccu cacccaaggc cuuaaacuuu 1860
gguggcauag gugucgucgu gggccaugag cugacucaug cuuuugauga ucaaggacgg 1920
gaguaugaca aggacgggaa ccuccggcca ugguggaaga acucauccgu ggaggccuuc 1980
aagcgucaga ccgagugcau gguagagcag uacagcaacu acagcgugaa cggggagccg 2040
gugaacgggc ggcacacccu gggggagaac aucgccgaca acgggggucu caaggcggcc 2100

-continued

```
uaucgggcuu accagaacug ggugaagaag aacggggcug agcacucgcu ccccacccug   2160
ggccucacca auaaccagcu cuucuuccug ggcuuugcac aggucuggug cuccguccgc   2220
acaccugaga gcucccacga aggccucauc accgaucccc acagccccuc ucgcuuccgg   2280
gucaucggcu cccucuccaa uuccaaggag uucucagaac acuuccgcug cccaccuggc   2340
ucacccauga acccgccuca caagugcgaa gucugguaag gacgaagcgg agagagccaa   2400
gacggaggag gggaaggggc ugaggacgag acccccaucc agccuccagg gcauugcuca   2460
gcccgcuugg ccacccgggg cccugcuucc ucacacuggc ggguuuucag ccggaaccga   2520
gcccauggug uuggcucuca acgugacccg cagucugauc cccugugaag agccggacau   2580
cccaggcaca cgugugcgcc accuucagca ggcauucggg ugcugggcug guggcucauc   2640
aggccugggc cccacacuga caagcgccag auacgccaca aauaccacug ugucaaaugc   2700
uuucaagaua uauuuuuggg gaaacuauuu uuuaaacacu guggaauaca cuggaaaucu   2760
ucagggaaaa acacauuuaa acacuuuuuu uuuuaaggaa agaauuggua uauuuauuau   2820
guucuguuuu ucuaaauaac cuguggacaa gggaagcccc acugauuuac ucccucucuu   2880
ccccacuccc ugugaggcug ggcugaggca cggaucccug ggccacagag caagucucca   2940
aaucagacag cugccucagc cccugggaug ugugauuuca gcuccuguca ccucaugcaa   3000
gggcguggag accaguagag guguggaggc caggcagaga gaggagccug cucugcgggg   3060
ggcccagcuc augggcacug ccccuucagc uagccugccu ccguccccug aguccaacag   3120
ugggagcccu agcugggaag uucugauccc caaagccaca gcaggggacu gauggcuaua   3180
gcagaaugag gucgggucag gacccucaaa caccaucugg gaacaccaag cacccugaau   3240
cgagacugca ggagcccugc ggggugagac ugugucagag auacacugcu ggccacaagu   3300
guccccucuc agucccaccu uuucgggcug ucccaugucu aucucagggg cccguuaccu   3360
cucugcagca gucccccauc ccagccacac cagggucugu ccggccaacc cucuucccca   3420
gggaaaggag aaaagagaaa acaggcuggg cccgguggcu cacuccugua aucccagcac   3480
uuugggaggu ugaggugggc ggaucaccug aggucaggag uuugagacca gccuggccaa   3540
cguggugaaa ccccaucucu acuaaaaaaa auuacaaaaa uuagccggga gugguggugg   3600
gcaccuguaa ucccaguuac ucgggaggcu gaggcaagag aaucucuuga gcucaggagg   3660
cagagguugc agugagcuga gauugcgcca cugcacucca gccugggugu cagagggaga   3720
cuccguccca aaaaaaagaa aagagaaaca gcugucaccu cccgcaggac ccaaauccuc   3780
ucucugagca ccgucaucca ccacauggcu gggccuggcu cccaggacca guccaguccu   3840
cuagugccuu aucugaggcu gcagccgcca gucuccaccc caaggagaca gccccugcuc   3900
cuagaugccc uuggccuccg cagugcagcc cccagguguc cugacugaag cacaggccau   3960
agccccauuu ccccggugcc ugcagggcua accuccacgg gagcccagga gcucuggccg   4020
gcagguccau ggcacagggc aucggaagac ugcaaaacug cuggacuuac ccugggcugc   4080
aguccauugu cggccccugg guugaaucaa gauaguacuu gcagcuagau ggaugcuuuu   4140
agccagggga cauugugagg ggaagauucc uccacccagu cuggccugug gugucugucu   4200
ccucccugag accacagcuu cuccaguagc agacucaugg gcgccaccaa guggaagcac   4260
cuggagcggc cucugccauc caguggggaa gccaggcccc gagacggagg ugggggcagc   4320
acgugcccuc cacagccacc gcuuucccgc cucagcagcc caggccuccu ggcccagccc   4380
ugccuggaca gugcucuccc cucacccggg aagcuggaau ccuccugccc gagaggaagc   4440
agacggcaca gggacacccc ugccaccuug ggaucugccu ccaagcuggu gcagguauc    4500
```

-continued

```
gagaguggau uccagaugga gguccugguc ccagcacgca gcaguccugg uagcucugca   4560

gaggagacag gaacccgaga aguagcugaa gcagaagcca gccgcagucc ccuugccaca   4620

uagaggcggg cuucucccag ccauggugc cccucugccu ccccuccccc gacccuccug   4680

ccuuccgcgu ggaggguggu gguccuguag ugucagcacc agcaccaugg gcuuggaccc   4740

ccucccugga cacaggcagg uguccuaggg cugggggugc agcccgaggg aauggagacc   4800

acacucaugg cucaggucug ccggggccgg cagggggguug gggaagaaga gggcucaggc   4860

ccagcagggg uggaagcccc ugccacugcc acuacccgcu ccagagcuuu aaggaaaaug   4920

aagugagacc ccucccccuua ggccugggga gccauagggc uggcuucucu gugggugcgu   4980

ggacgugggg uugggagcug ggaaucuauu uuuuguauua uguuuugagc uacuguaguu   5040

uuggcguggc acuauuguaa uggaaauaaa auacuuguac ggagggcaaa aaaaaaaaaa   5100

aaaaa                                                               5105
```

<210> SEQ ID NO 97
<211> LENGTH: 5259
<212> TYPE: RNA
<213> ORGANISM: HUMAN

<400> SEQUENCE: 97

```
guacucacug gaugccugca aguccaaaca uccuguucuu uuuugaacuc cucacuggag     60

aaacagggaa aagcuguagu uuuuuccuuc cacucauauc gagugacaca aaaaaacaag    120

ccugucgggg ccgagcugcu ugacucucug auguuuggga gcagauccga gcagcugagc    180

agggguggcug uuccuuuccu ggauuagggc ugaaucugug ggaaccagac caccccugag    240

acaggaggca gcccugaugc cucuccaggg ccugggccug cagcggaacc ccuuccucca    300

agggaagcgg ggcccggggc ucacgucuuc cccgccccuc cugccuccuu cccugcaggu    360

gaacuuccac agcccccgga guggccagag gugcugggcu gcacggaccc agguggagaa    420

gcggcuggug guguuggugg uacuucuggc ggcaggacug guggccugcu uggcagcacu    480

gggcauccag uaccagacaa gaucccccuc ugugugccug agcgaagcuu gugucucagu    540

gaccagcucc aucuugagcu ccauggaccc cacaguggac cccugccaug acuucuucag    600

cuacgccugu gggggcugga ucaaggccaa cccagucccu gauggccacu cacgcugggg    660

gaccuucagc aaccucuggg aacacaacca agcaaucauc aagcaccucc ucgaaaacuc    720

cacggccagc gugagcgagg cagagagaaa ggcgcaagua uacuaccgug cgugcaugaa    780

cgagaccagg aucgaggagc ucagggccaa accucuaaug gaguugauug agaggcucgg    840

gggcuggaac aucacagguc ccugggccaa ggacaacuuc caggacaccc ugcagguggu    900

caccgcccac uaccgcaccu cacccuucuu cucugucuau gucagugccg auuccaagaa    960

cuccaacagc aacgugaucc agguggacca gucuggccug ggcuugcccu cgagagacua   1020

uuaccugaac aaaacugaaa acgagaaggu gcugaccgga uaucugaacu acauggucca   1080

gcuggggaag cugcugggcg gcggggacga ggaggccauc cggccccaga ugcagcagau   1140

cuuggacuuu gagacggcac uggccaacau caccauccca caggagaagc gccgugauga   1200

ggagcucauc uaccacaaag ugacggcagc cgagcugcag accuuggcac ccgccaucaa   1260

cugguugccu uuucucaaca ccaucuucua ccccguggag aucaaugaau ccgagccuau   1320

uguggucuau gacaaggaau accuugagca gaucuccacu cucaucaaca ccaccgacag   1380

augccugcuc aacaacuaca ugaucuggaa ccuggugcgg aaaacaagcu ccuuccuuga   1440

ccagcgcuuu caggacgccg augagaaguu cauggaaguc auguacggga ccaagaagac   1500
```

-continued

```
cugucuuccu cgcuggaagu uuugcgugag ugacacagaa aacaaccugg gcuuugcguu   1560
gggccccaug uuugucaaag caaccuucgc cgaggacagc aagagcauag ccaccgagau   1620
cauccuggag auuaagaagg cauuugagga aagccugagc acccugaagu ggauggauga   1680
ggaaacccga aaaucagcca aggaaaaggc cgaugccauc uacaacauga uaggauaccc   1740
caacuucauc auggauccca aggagcugga caaagugguu aaugacuaca cugcaguucc   1800
agaccucuac uuugaaaaug ccaugcgguu uuucaacuuc ucauggaggg ucacugccga   1860
ucagcucagg aaagccccca acagagauca guggagcaug accccgccca uggugaacgc   1920
cuacuacucg cccaccaaga augagauugu guuuccggcc gggauccugc aggcaccauu   1980
cuacacacgc uccucaccca aggccuuaaa cuuuggugc auaggugucg ucgugggcca   2040
ugagcugacu caugcuuuug augaucaagg acgggaguau gacaaggacg ggaaccuccg   2100
gccauggugg aagaacucau ccguggaggc cuucaagcgu cagaccgagu gcaugguaga   2160
gcaguacagc aacuacagcg ugaacgggga gccggugaac gggcggcaca cccuggggga   2220
gaacaucgcc gacaacgggg gucucaaggc ggccuaucgg gcuuaccaga acugggugaa   2280
gaagaacggg gcugagcacu cgcuccccac ccugggccuc accaauaacc agcucuucuu   2340
ccugggcuuu gcacaggucu ggugcuccgu ccgcacaccu gagagcuccc acgaaggccu   2400
caucaccgau ccccacagcc ccucucgcuu ccgggucauc ggcuccccucu ccaauuccaa   2460
ggaguucuca gaacacuucc gcugcccacc uggcucaccc augaacccgc cucacaagug   2520
cgaagucugg uaaggacgaa gcggagagag ccaagacgga ggaggggaag gggcugagga   2580
cgagaccccc auccagccuc cagggcauug cucagcccgc uuggccaccc ggggcccugc   2640
uuccucacac uggcggguuu ucagccggaa ccgagcccau gguguuggcu cucaacguga   2700
cccgcagucu gauccccugu gaagagccgg acaucccagg cacacgugug cgccaccuuc   2760
agcaggcauu cgggugcugg gcugguggcu caucaggccu gggcccccaca cugacaagcg   2820
ccagauacgc cacaaauacc acugugucaa augcuuucaa gauauauuuu uggggaaacu   2880
auuuuuuaaa cacuguggaa uacacuggaa aucuucaggg aaaaacacau uuaaacacuu   2940
uuuuuuuuaa ggaaagaauu gguauauuua uuauguucug uuuuucuaaa uaaccugugg   3000
acaagggaag ccccacugau uuacucccuc ucuuccccac ucccugugag gcugggcuga   3060
ggcacggauc ccugggccac agagcaaguc uccaaaucag acagcugccu cagcccccugg   3120
gaugugugau uucagcuccu gucaccucau gcaagggcgu ggagaccagu agaggugugg   3180
aggccaggca gagagaggag ccugcucugc gggggggccca gcucaugggc acugccccuu   3240
cagcuagccu gccuccgucc ccugagucca acagugggag cccuagcugg gaaguucuga   3300
uccccaaagc cacagcaggg gacugauggc uauagcagaa ugaggucggg ucaggacccu   3360
caaacaccau cugggaacac caagcacccu gaaucgagac ugcaggagcc cugcggggug   3420
agacugu guc agagauacac ugcuggccac aagugucccc ucucaguccc accuuuucgg   3480
gcugucccau gucuaucuca ggggcccguu accucucugc agcagucccc caucccagcc   3540
acaccagggu cuguccggcc aacccucuuc cccagggaaa ggagaaaaga gaaaacaggc   3600
ugggcccggu ggcucacucc uguaauccca gcacuuuggg agguugaggu gggcggauca   3660
ccugagguca ggaguuugag accagccugg ccaacguggu gaaaccccau cucuacuaaa   3720
aaaaauuaca aaaauuagcc gggaguggug gugggcaccu guaaucccag uuacucggga   3780
ggcugaggca agagaaucuc uugagcucag gaggcagagg uugcagugag cugagauugc   3840
gccacugcac uccagccugg gugacagagg gagacuccgu cccaaaaaaa agaaaagaga   3900
```

aacagcuguc accucccgca ggacccaaau ccucucucug agcaccguca uccaccacau 3960
ggcugggccu ggcucccagg accaguccag uccucuagug ccuuaucuga ggcugcagcc 4020
gccagucucc accccaagga gacagccccu gcuccuagau gcccuuggcc uccgcagugc 4080
agcccccagg uguccugacu gaagcacagg ccauagcccc auuuccccgg ugccugcagg 4140
gcuaaccucc acgggagccc aggagcucug gccggcaggu ccauggcaca gggcaucgga 4200
agacugcaaa acugcuggac uuacccuggg cugcagucca uugucggccc cuggguugaa 4260
ucaagauagu acuugcagcu agauggaugc uuuuagccag gggacauugu gaggggaaga 4320
uuccuccacc cagucuggcc uguggugucu gucuccuccc ugagaccaca gcuucuccag 4380
uagcagacuc augggcgcca ccaaguggaa gcaccuggag cggccucugc cauccagugg 4440
ggaagccagg ccccgagacg gaggugggg cagcacgugc ccuccacagc caccgcuuuc 4500
ccgccucagc agcccaggcc uccuggccca gcccugccug gacagugcuc uccccucacc 4560
cgggaagcug gaauccuccu gcccgagagg aagcagacgg cacagggaca ccccugccac 4620
cuugggaucu gccuccaagc uggugcaggg uaucgagagu ggauuccaga uggagguccu 4680
ggucccagca cgcagcaguc cugguagcuc ugcagaggag acaggaaccc gagaaguagc 4740
ugaagcagaa gccagccgca guccccuugc cacauagagg cgggcuucuc ccagccaugg 4800
uguccccucu gccuccccuc ccccgacccu ccugccuucc gcguggaggg uggugguccu 4860
guagugucag caccagcacc augggcuugg accccccuccc uggacacagg caggugucuu 4920
agggcugggg gugcagcccg agggaaugga gaccacacuc auggcucagg ucugccgggg 4980
ccggcagggg guuggggaag aagagggcuc aggcccagca gggguggaag ccccugccac 5040
ugccacuacc cgcuccagag cuuuaaggaa aaugaaguga gaccccuccc cuuaggccug 5100
gggagccaua gggcuggcuu cucugugggu gcguggacgu gggguuggga gcugggaauc 5160
uauuuuuugu auuauguuuu gagcuacugu aguuuuggcg uggcacuauu guaauggaaa 5220
uaaaauacuu guacggaggg caaaaaaaaa aaaaaaaaa 5259

<210> SEQ ID NO 98
<211> LENGTH: 5154
<212> TYPE: RNA
<213> ORGANISM: HUMAN

<400> SEQUENCE: 98
acucggcgcc gaagccgcga gcucgcccgc uggagcugag cgcgccgccu gggccaggca 60
gccgagccgu ccgagcagcu gggcugggag cagggaaccc ggagcuggga aucgggagcc 120
gggcgcgggg agcugcgcga agccggggcg gagcacgcga gcuaugaugu cgacguacaa 180
gcgggccacg cuggacgagg aggaccuggu ggacucgcuc uccgagggcg acgcauaccc 240
caacggccug caggugaacu uccacagccc ccggaguggc cagaggugcu gggcugcacg 300
gacccaggug gagaagcggc ugguggguguu ggugguacuu cuggcggcag gacugguggc 360
cugcuuggca gcacugggca uccaguacca gacaagaucc cccucugugu gccugagcga 420 agcuugugc ucagugacca gcuccaucuu gagcuccaug gaccccacag uggaccccug 480
ccaugacuuc uucagcuacg ccugugggg cuggaucaag gccaacccag ucccugaugg 540
ccacucacgc ugggggaccu ucagcaaccu cugggaacac aaccaagcaa ucaucaagca 600
ccuccucgaa aacuccacgg ccagcgugag cgaggcagag agaaaggcgc aaguauacua 660
ccgugcgugc augaacgaga ccaggaucga ggagcucagg gccaaaccuc uaauggaguu 720
gauugagagg cucgggggcu ggaacaucac aggucccugg gccaaggaca acuuccagga 780

```
cacccugcag guggucaccg cccacuaccg caccucaccc uucuucucug ucuaugucag    840
ugccgauucc aagaacucca acagcaacgu gauccaggug gaccagucug gccugggcuu    900
gcccucgaga gacuauuacc ugaacaaaac ugaaacgag aaggugcuga ccggauaucu     960
gaacuacaug guccagcugg ggaagcugcu gggcggcggg gacgaggagg ccauccggcc   1020
ccagaugcag cagaucuugg acuuugagac ggcacuggcc aacaucacca ucccacagga   1080
gaagcgccgu gaugaggagc ucaucuacca caaagugacg gcagccgagc ugcagaccuu   1140
ggcacccgcc aucaacuggu ugccuuuucu caacaccauc uucuaccccg uggagaucaa   1200
ugaauccgag ccuauugugg ucuaugacaa ggaauaccuu gagcagaucu ccacucucau   1260
caacaccacc gacagaugcc ugcucaacaa cuacaugauc uggaaccugg ugcggaaaac   1320
aagcuccuuc cuugaccagc gcuuucagga cgccgaugag aaguucaugg aagucaugua   1380
cgggaccaag aagaccuguc uuccucgcug gaaguuuugc gugagugaca cagaaaacaa   1440
ccugggcuuu gcguugggcc ccauguuugu caaagcaacc uucgccgagg acagcaagag   1500
cauagccacc gagaucaucc uggagauuaa gaaggcauuu gaggaaagcc ugagcacccu   1560
gaaguggaug gaugaggaaa cccgaaaauc agccaaggaa aaggccgaug ccaucuacaa   1620
caugauagga uaccccaacu caucauggga ucccaaggag cuggacaaag uguuaauga    1680
cuacacugca guuccagacc ucuacuuuga aaaugccaug cgguuuuuca acuucucaug   1740
gagggucacu gccgaucagc ucaggaaagc ccccaacaga gaucagugga gcaugacccc   1800
gcccauggug aacgccuacu acucgcccac caagaaugag auugguuuc cggccgggau    1860
ccugcaggca ccauucuaca cacgcuccuc acccaaggcc uuaaacuuug guggcauagg   1920
ugucgucgug ggccaugagc ugacucaugc uuuugaugau caaggacggg aguaugacaa   1980
ggacgggaac cuccggccau gguggaagaa cuccauccgu gaggccuuca agcgucagac   2040
cgagugcaug guagagcagu acagcaacua cagcgugaac ggggagccgg ugaacgggcg   2100
gcacacccug ggggagaaca ucgccgacaa cgggggucuc aaggcggccu aucgggcuua   2160
ccagaacugg gugaagaaga acggggcuga gcacucgcuc cccacccugg gccucaccaa   2220
uaaccagcuc uucuuccugg gcuuugcaca ggucuggugu ccgucegca caccugagag   2280
cucccacgaa ggccucauca ccgauccccca gccccucu cgcuucgggg ucaucggcuc   2340
ccucuccaau uccaaggagu ucucagaaca cuuccgcugc ccaccuggcu cacccaugaa   2400
cccgccucac aagugcgaag ucugguaagg acgaagcgga gagagccaag acggaggagg   2460
ggaagggggcu gaggacagaga cccccauccg gccuccagggg cauugcucag cccgcuuggc   2520
cacccggggc ccugcuuccu cacacuggcg gguuucagc cggaaccgag cccauggugu   2580
uggcucucaa cgugacccgc agucugaucc ccgugaaga gccggacauc ccaggcacac   2640
gugugcgcca ccuucagcag gcauucgggu gcgggcugg uggcucauca ggccugggcc   2700
ccacacugac aagcgccaga uacgccacaa auaccacugu ucaaaugcu ucaagauau    2760
auuuugggg aaacuauuuu uuaaacacug uggaauacac uggaaaucuu cagggaaaaa   2820
cacauuuaaa cacuuuuuuu uuuaaggaaa gaauugguau auuuauuaug uucguuuuu    2880
cuaaauaacc uguggacaag ggaagcccca cugauuuacu cccucucuuc cccacucccu   2940
gugaggcugg gcugagcac ggaucccugg gccacagagc aagucccaa aucagacagc     3000
ugccucagcc ccugggaugu gugauuucag cuccugucac cucaugcaag ggcguggaga   3060
ccaguagagg uguggaggcc aggcagagag aggagccugc ucugcggggg gcccagcuca   3120
ugggcacugc cccuucagcu agccugccuc cguccccuga guccaacagu gggagcccua   3180
```

-continued

```
gcugggaagu ucugaucccc aaagccacag caggggacug auggcuauag cagaaugagg   3240

ucgggucagg acccucaaac accaucuggg aacaccaagc acccugaauc gagacugcag   3300

gagcccugcg gggugagacu gugucagaga uacacugcug gccacaagug uccccucuca   3360

gucccaccuu uucgggcugu cccaugucua ucucaggggc ccguuaccuc ucugcagcag   3420

ucccccaucc cagccacacc agggucuguc cggccaaccc ucuuccccag ggaaaggaga   3480

aaagagaaaa caggcugggc ccgguggcuc acuccuguaa ucccagcacu uugggagguu   3540

gaggugggcg gaucaccuga ggucaggagu uugagaccag ccuggccaac guggugaaac   3600

cccaucucua cuaaaaaaaa uuacaaaaau uagccgggag ugguggugg caccuguaau   3660

cccaguuacu cgggaggcug aggcaagaga aucucuugag cucaggaggc agagguugca   3720

gugagcugag auugcgccac ugcacuccag ccugggugac agagggagac uccgucccaa   3780

aaaaaagaaa agagaaacag cugucaccuc ccgcaggacc caaauccucu cucugagcac   3840

cgucauccac cacauggcug ggccuggcuc ccaggaccag uccaguccuc uagugccuua   3900

ucugaggcug cagccgccag ucuccacccc aaggagacag ccccugcucc uagaugcccu   3960

uggccuccgc agugcagccc ccaggugucc ugacugaagc acaggccaua gccccauuuc   4020

cccggugccu gcagggcuaa ccuccacggg agcccaggag cucuggccgg cagguccaug   4080

gcacagggca ucggaagacu gcaaaacugc uggacuuacc cugggcugca guccauuguc   4140

ggccccuggg uugaaucaag auaguacuug cagcuagaug gaugcuuuua gccaggggac   4200

auugugaggg gaagauuccu ccacccaguc uggccugugg ugucugucuc cucccugaga   4260

ccacagcuuc uccaguagca gacucauggg cgccaccaag uggaagcacc uggagcggcc   4320

ucugccaucc aguggggaag ccaggccccg agacggaggu gggggcagca cgugcccucc   4380

acagccaccg cuuucccgcc ucagcagccc aggccuccug gcccagcccu gccuggacag   4440

ugcucucccc ucacccggga agcuggaauc cuccugcccg agaggaagca gacggcacag   4500

ggacaccccu gccaccuugg gaucugccuc caagcuggug cagguaucg agaguggauu    4560

ccagauggag guccuggucc cagcacgcag caguccuggu agcucugcag aggagacagg   4620

aacccgagaa guagcugaag cagaagccag ccgcaguccc cuugccacau agaggcgggc   4680

uucucccagc cauggugucc ccucugccuc cccucccccg acccuccugc cuuccgcgug   4740

gaggguggug guccuguagu gucagcacca gcaccauggg cuuggacccc cucccuggac   4800

acaggcaggu guccuagggc ugggggugca gcccgaggga auggagacca cacucauggc   4860

ucaggucugc cggggccggc aggggguugg ggaagaagag ggcucaggcc cagcaggggu   4920

ggaagccccu gccacugcca cuacccgcuc cagagcuuua aggaaaauga agugagaccc   4980

cuccccuuag gccuggggag ccauagggcu ggcuucucug ugggugcgug gacgugggu    5040

ugggagcugg gaaucuauuu uuuguauuau guuuugagcu acuguaguuu uggcguggca   5100

cuauuguaau ggaaauaaaa uacuuguacg gagggcaaaa aaaaaaaaaa aaaa         5154
```

<210> SEQ ID NO 99
<211> LENGTH: 2117
<212> TYPE: RNA
<213> ORGANISM: HUMAN

<400> SEQUENCE: 99

```
ggagcuguuu acccccacuc uaauaggggu ucaauauaaa aagccggcag agagcugucc     60

aagucagacg cgccucugca ucugcgccag gcgaacgggu ccugcgccuc cugcaguccc    120

agcucuccac cgccgcgugc gccugcagac gcuccgcucg cugccuucuc uccuggcagg    180
```

cgcugccuuu ucucccguu aaaagggcac uugggcugaa ggaucgcuuu gagaucugag 240
gaacccgcag cgcuuugagg gaccugaagc uguuuuucuu cguuuuccuu uggguucagu 300
uugaacggga gguuuuugau cccuuuuuuu cagaauggau uauuugcuca ugauuuucuc 360
ucugcuguuu guggcuugcc aaggagcucc agaaacagca gucuuaggcg cugagcucag 420
cgcggugggu gagaacggcg gggagaaacc cacucccagu ccacccuggc ggcuccgccg 480
guccaagcgc ugcuccugcu cgucccugau ggauaaagag ugugucuacu ucugccaccu 540
ggacaucauu ugggucaaca cucccgagca cguuguuccg uauggacuug gaagcccuag 600
guccaagaga gccuuggaga auuuacuucc cacaaaggca acagaccgug agaauagaug 660
ccaaugugcu agccaaaaag acaagaagug cuggaauuuu ugccaagcag gaaaagaacu 720
cagggcugaa gacauuaugg agaaagacug gaauaaucau aagaaaggaa aagacuguuc 780
caagcuuggg aaaaagugua uuuaucagca guuagugaga ggaagaaaaa ucagaagaag 840
uucagaggaa caccuaagac aaaccagguc ggagaccaug agaaacagcg ucaaaucauc 900
uuuucaugau cccaagcuga aaggcaagcc cuccagagag cguuauguga cccacaaccg 960
agcacauugg ugacagaccu ucggggccug ucugaagcca uagccuccac ggagagcccu 1020
guggccgacu cugcacucuc cacccuggcu gggaucagag caggagcauc cucugcuggu 1080
uccugacugg caaaggacca gcguccucgu ucaaaacauu ccaagaaagg uuaaggaguu 1140
cccccaacca ucuucacugg cuuccaucag ugguaacugc uuuggucucu ucuuucaucu 1200
ggggaugaca auggaccucu cagcagaaac acacagucac auucgaauuc ggguggcauc 1260
cuccggagag agagagagga aggagauucc acacaggggu ggaguuucug acgaagaucc 1320
uaagggagug uuugugucug acucaggcgc cuggcacauu ucagggagaa acuccaaagu 1380
ccacacaaag auuuucuaag gaaugcacaa auugaaaaca cacucaaaag acaaacaugc 1440
aaguaaagaa aaaaaaaaga aagacuuuug uuuaaauuug uaaaaugcaa aacugaauga 1500
aacuguuacu accauaaauc aggauauguu ucaugaauau gagucuaccu caccuauauu 1560
gcacucuggc agaaguauuu cccacauuua auuauugccu ccccaaacuc uucccacccc 1620
ugcugccccu uccuccaucc cccauacuaa auccuagccu cguagaaguc uggucuaaug 1680
ugucagcagu agauauaaua uuuucauggu aaucuacuag cucugaucca uaagaaaaaa 1740
aagaucauua aaucaggaga uucccugucc uugauuuuug gagacacaau gguauagggu 1800
uguuuaugaa auauauugaa aaguaagugu uuguuacgcu uuaaagcagu aaaauuauuu 1860
uccuuuauau aaccggcuaa ugaaagaggu uggauugaau uuugauguac uuauuuuuuu 1920
auagauauuu auauucaaac aauuuauucc uuauauuuac cauguuaaau aucuguuugg 1980
gcaggccaua uuggucuaug uauuuuuaaa auauguauuu cuaaaugaaa uugagaacau 2040
gcuuuguuuu gccugucaag guaaugacuu uagaaaauaa auauuuuuuu ccuuacugua 2100
aaaaaaaaaa aaaaaaa 2117

<210> SEQ ID NO 100
<211> LENGTH: 1194
<212> TYPE: RNA
<213> ORGANISM: HUMAN

<400> SEQUENCE: 100
ggggccgcgc ggcugccugg gaggcuccgg gccagccgcg guccagagcg cgcgagguuc 60
ggggagcucg gccaggcugc ugguaccugc guccgcccgg cgagcaggac aggcugcuuu 120
gguuugugac cuccaggcag gacggccauc cucuccagaa ugaagaucuu cuugccagug 180

-continued

```
cugcuggcug cccuucuggg uguggagcga gccagcucgc ugaugugcuu cuccugcuug    240
aaccagaaga gcaaucugua cugccugaag ccgaccaucu gcuccgacca ggacaacuac    300
ugcgugacug ugucugcuag ugccggcauu gggaaucucg ugacauuugg ccacagccug    360
agcaagaccu guuccccggc cugccccauc ccagaaggcg ucaauguugg uguggcuucc    420
augggcauca gcugcugcca gagcuuucug ugcaauuuca gugcggccga uggcgggcug    480
cgggcaagcg ucacccugcu gggugccggg cugcugcuga gccugcugcc ggcccugcug    540
cgguuuggcc ccugaccgcc cagacccugu cccccgaucc cccagcucag gaaggaaagc    600
ccagccccuuu cuggauccca caguguaugg gagccccuga cuccucacgu gccugaucug    660
ugcccuuggu cccaggucag gcccaccccc ugcaccucca ccugccccag ccccugccuc    720
ugccccaagu ggggccagcu gcccucacuu cuggggugga ugaugugacc uuccuugggg    780
gacugcggaa gggacgaggg uucccuggag ucuuacgguc caacaucagg accaaguccc    840
auggacaugc ugacaggguc cccagggaga ccgugucagu agggaugugu gccuggcugu    900
guacgugggu gugcagugca cgugagagca cguggcggcu ucugggggcc auguuugggg    960
agggaggugu gccagcagcc uggagagccu caguccugu agcccccugc ccuggcacag   1020
cugcaugcac uucaagggca gccuuugggg guuggggguuu cugccacuuc cgggucuagg   1080
cccugcccca aauccagcca guccugcccc agcccacccc cacauuggag cccuccugcu   1140
gcuuuggugc cucaaauaaa uacagauguc ccccagaaaa aaaaaaaaaa aaaa         1194


<210> SEQ ID NO 101
<211> LENGTH: 1189
<212> TYPE: RNA
<213> ORGANISM: HUMAN

<400> SEQUENCE: 101

ggggccgcgc ggcugccugg gaggcuccgg gccagccgcg guccagagcg cgcgagguuc     60
ggggagcucg gccaggcugc ugguaccugc guccgcccgg cggacaggcu gcuuugguuu    120
gugaccucca ggcaggacgg ccauccucuc cagaaugaag aucuucuugc cagugcugcu    180
ggcugcccuu cugggugugg agcgagccag cucgcugaug ugcuucuccu gcuugaacca    240
gaagagcaau cuguacugcc ugaagccgac caucugcucc gaccaggaca acuacugcgu    300
gacugugucu gcuagugccg gcauugggaa ucucgugaca uuuggccaca gccugagcaa    360
gaccuguucc ccggccugcc ccaucccaga aggcgucaau guuggugugg cuuccauggg    420
caucagcugc ugccagagcu uucugugcaa uuucagugcg gccgauggcg ggcugcgggc    480
aagcgucacc cugcugggug ccgggcugcu gcugagccug cugccggccc ugcugcgguu    540
uggccccuga ccgcccagac ccuguccccc gaucccccag cucaggaagg aaagcccagc    600
ccuuucugga ucccacagug uaugggagcc ccugacuccu cacgugccug aucugugccc    660
uuggucccag gucaggccca cccccugcac cuccaccugc cccagccccu gccucugccc    720
caaguggggc cagcugcccu cacuucuggg guggaugaug ugaccuuccu ugggggacug    780
cggaagggac gaggguuccc uggagucuua cgguccaaca ucaggaccaa gucccaugga    840
caugcugaca gggucccag ggagaccgug ucaguaggga ugugugccug gcuguguacg    900
ugggugugca gugcacguga gagcacgugg cggcuucugg gggccauguu uggggaggga    960
ggugugccag cagccuggag agccucaguc ccuguagccc ccugcccugg cacagcugca   1020
ugcacuucaa gggcagccuu uggggguugg gguuucugcc acuuccgggu cuaggcccug   1080
ccccaaaucc agccaguccu gccccagccc acccccacau uggagcccuc cugcugcuuu   1140
```

ggugccucaa auaaauacag augucccca gaaaaaaaaa aaaaaaaaa 1189

<210> SEQ ID NO 102
<211> LENGTH: 10384
<212> TYPE: RNA
<213> ORGANISM: HUMAN

<400> SEQUENCE: 102
gcgcccgggc cgccggccgg gcccgggccu gggggcgggg cgggaagacg gcggccggga 60
guguuuucag uuccgccucc aaucgcccau ucccccucuuc cccucccagc ccccuccauc 120
ccaucggaag aggaaggaac aaaaggaccc ggaccccccg gaucugacgg ggcgggaccu 180
ggcgccaccu ugcagguucg auacaagagg cuguuuuccu agcguggcuu gcugccuuug 240
guaagaacau gucguccauc uugccauuca cgccgccagu ugugaagaga cugcugggau 300
ggaagaaguc agcugguggg ucuggaggag caggcggagg agagcagaau gggcaggaag 360 aaaagguggug ugagaaagca gugaaaaguc ugguagaagaa gcuaaagaaa acaggacgau 420
uagaugagcu ugagaaagcc aucaccacuc aaaacuguaa uacuaaaugu guuaccauac 480
caagcacuug cucugaaauu uggggacuga guacaccaaa uacgauagau caguggggaua 540 caacaggccu uuacagcuuc ucugaacaaa ccaggucucu ugauggucgu cuccagguau 600
cccaucgaaa aggauugcca cauguuauau auugccgauu auggcgcugg ccugaucuuc 660
acagucauca ugaacucaag gcaauugaaa acugcgaaua ugcuuuuaau cuuaaaaagg 720
augaaguaug uguaaacccu uaccacuauc agagaguuga gacaccaguu uugccuccag 780
uauuagugcc ccgacacacc gagauccuaa cagaacuucc gccucuggau gacuauacuc 840
acuccauucc agaaaacacu aacuucccag caggaauuga gccacagagu aauuauauuc 900
cagaaacgcc accuccugga uauaucagug aagauggaga aacaagugac caacaguuga 960
aucaaaguau ggacacaggc ucuccagcag aacuaucucc uacuacucuu uccccuguua 1020
aucauagcuu ggauuuacag ccaguuacuu acucagaacc ugcauuuugg uguucgauag 1080
cauauuauga auuaaaucag aggguuggag aaaccuucca ugcaucacag cccucacuca 1140
cuguagaugg cuuuacagac ccaucaaauu cagagagguu cugcuuaggu uuacucucca 1200
auguuaaccg aaaugccacg guagaaauga caagaaggca uauaggaaga ggagugcgcu 1260
uauacuacau aggugggggaa guuuuugcug agugccuaag ugauagugca aucuuugugc 1320
agagccccaa uuguaaucag agauauggcu ggcacccugc aacaguguguu aaaauuccac 1380 caggcuguaa ucugaagauc uucaacaacc aggaauuugc ugcucuucug gcucagucug 1440
uuaaucaggg uuuugaagcc gucuaucagc uaacuagaau gugcaccaua agaaugaguu 1500
uugugaaagg gugggggagca gaauaccgaa ggcagacggu aacaaguacu ccuugcugga 1560
uugaacuuca ucugaaugga ccucuacagu gguuggacaa aguauuaacu cagaugggau 1620
ccccuucagu gcguugcuca agcaugucau aaagcuucac caaucaaguc ccaugaaaag 1680
acuuaaugua acaacucuuc ugucauagca uugugugugg ucccuaugga cuguuuacua 1740
uccaaaaguu caagagagaa aacagcacuu gaggucucau caauuaaagc accuugugga 1800
aucuguuucc uauauuugaa uauuagaugg gaaaauuagu gucuagaaau acucucccau 1860
uaaagaggaa gagaagauuu uaaagacuua augaugucuu auugggcaua aaacugagug 1920
ucccaaaggu uuauuaauaa caguaguagu uauguguaca gguaauguau caugauccag 1980
uaucacagua uugugcuguu uauauacauu uuuaguuugc auagaugagg ugugugugug 2040
cgcugcuucu ugaucuaggc aaaccuuuau aaaguugcag uaccuaaucu guuauuccca 2100

-continued

```
cuucucuguu auuuuugugu gucuuuuuua auauauaaua uauaucaaga uuuucaaauu   2160
auuuagaagc agauuuuccu guagaaaaac uaauuuuucu gccuuuuacc aaaaauaaac   2220
ucuuggggga agaaaagugg auuaacuuuu gaaauccuug accuuaaugu guucaguggg   2280
gcuuaaacag ucauucuuuu ugugguuuuu uguuuuuuuu uguuuuuuuu uuuaacugcu   2340
aaaucuuauu auaaggaaac cauacugaaa accuuuccaa gccucuuuuu uccauuccca   2400
uuuuuguccu cauaaucaaa acagcauaac augacaucau caccaguaau aguugcauug   2460
auacugcugg caccaguuaa uucugggaua caguaagaau ucauauggag aaagucccuu   2520
ugucuuaugc ccaaauuuca acaggaauaa uuggcuugua uaaucuagca gucuguugau   2580
uuauccuucc accucauaaa aaaugcauag guggcaguau aauuauuuuc agggauaugc   2640
uagaauuacu uccacauauu uaucccuuuu uaaaaaagcu aaucuauaaa uaccguuuuu   2700
ccaaagguau uuuacaauau uucaacagca gaccuucugc ucuucgagua guuugauuug   2760
guuuaguaac cagauugcau uaugaaaugg gccuuuugua aauguaauug uuucugcaaa   2820
auaccuagaa aagugaugcu gagguaggau cagcagauau gggccaucug uuuuuaaagu   2880
auguuguauu caguuuauaa auugauuguu auucuacaca uaauuaugaa uucagaauuu   2940
uaaaaauugg gggaaaagcc auuuauuuag caaguuuuuu agcuuauaag uuaccugcag   3000
ucugagcugu ucuuaacuga uccugguuuu gugauugaca auauuucaug cucuguagug   3060
agaggagauu uccgaaacuc uguugcuagu ucauucugca gcaaauaauu auuaugucug   3120
auguugacuc auugcaguuu aaacauuucu ucuuguuugc aucuuaguag aaauggaaaa   3180
uaaccacucc uggucgucuu uucauaaauu uucauauuuu ugaagcuguc uuugguacuu   3240
guucuuugaa aucauaucca ccugucucua uagguaucau uuucaauacu uucaacauuu   3300
ggugguuuuc uauuggguac uccccauuuu ccuauauuug uguguauaug uauguguuca   3360
uguaaauuug guauaguaau uuuuuauuca uucaacaaau auuuauuguu caccuguuug   3420
uaccaggaac uuuucuuagu cuuuggguaa aggugaacaa gacaacuaca guuccugccu   3480
uugcugagac agcaguuaca cuaacccuua auuaucuuac uugucuauga aggagauaaa   3540
cagguacug uacuggagaa uaacagaugg gaugcuucag guaggacauc aaggaaagcc   3600
ucuaaggaaa ggaugcauga gcuaacaccu gacauuaaag aagcaagcca agugaggagc   3660
caggggagau aagcauuccu ggcaaagaga auagcaucaa augcaaaaag guucacacua   3720
aaggaaacuc cugauuaggu auuaaugcuu uauacagaaa ccucuauaca aauccaaacu   3780
ugaagaucag aaugguucua caguucauaa cauuuugaag guggccuuau uuugugauag   3840
ucugcuucau gugauucuca cuaacauauc uccuuccuca accuuugcug uaaaaauuuc   3900
auuugcacca caucaguacu acuuaauuua acaagcuuuu guuguguaag cucucacugu   3960
uuuagugccc ugcugcuugc uuccagacuu ugugcugucc aguaauuaug ucuuccacua   4020
cccaucuugu gagcagagua aauguccuag guaauaccac uaucaggccu guaggagaua   4080
cucaguggag ccucugcccu ucuuuuucuu acuugagaac uuguaauggu guuagggaac   4140
aguuguaggg gcagaaaaca acucugaaag ugguagaagg uccugaucuu gguggguuacu   4200
cuugcauuac uguguuaggu caagcagugc cuacuaugcu guuucaguag uggagcgcau   4260
cucuacaguu cugaugcgau uuuucuguac aguaugaaau ugggacucaa cucuuugaaa   4320
acaccuauug agcaguuaua ccuguugagc aguuuacuuc cugguuguaa uuacauuugu   4380
gugaaugugu uugaugcuuu uuaacgagau gauguuuuuu guauuuuauc uacuguggcc   4440
ugauuuuuuu uuuguuuucu gccccucccc ccauuuauag guguggguuu cauuuuucua   4500
```

-continued

```
agugauagaa uccccucuuu guugaauuuu ugucuuuauu uaaauuagca acauuacuua   4560
ggauuuauuc uucacaauac uguuaauuuu cuaggaauga ugaccugaga accgaauggc   4620
caugcuuucu aucacauuuc uaagaugagu aauauuuuuu ccaguagguu ccacagagac   4680
accuuggggg cuggcuuagg ggaggcuguu ggaguucuca cugacuuagu ggcauauuua   4740
uucuguacug aagaacugca uggggguucu uuuggaaaga guuucauugc uuuaaaaaga   4800
agcucagaaa gucuuuauaa ccacugguca acgauuagaa aaauauaacu ggauuuaggc   4860
cuaccuucug gaauaccgcu gauugugcuc uuuuuauccu acuuuaaaga agcuuucaug   4920
auuagauuug agcuauauca guuauaccga uuauaccuua uaauacacau ucaguuagua   4980
aacauuuauu gaugccuguu guuugcccag ccacugugau ggauauugaa uaauaaaaag   5040
augacuagga cggggcccug acccuugagc ugugcuuggu cuuguagagg uuguguuuuu   5100
uuuccucagg accugucacu uuggcagaag gaaaucugcc uaauuuuucu ugaaagcuaa   5160
auuuucuuug uaaguuuuua caaauuguuu aauaccuagu uguauuuuuu accuuaagcc   5220
acauugaguu uugcuugauu ugucugucuu uuaaacacug ucaaaugcuu ucccuuuugu   5280
uaaaaauuau uuaauuucac uuuuuuugug cccuugucaa uuuaagacua agacuuugaa   5340
gguaaaacaa acaaacaaac aucagucuua gucucuugcu aguugaaauc aaauaaaaga   5400
aaauauauac ccaguugguu ucucuaccuc uuaaaagcuu cccauauaua ccuuuaagau   5460
ccuucucuuu uuucuuuaac uacuaaauag guucagcauu uauucagugu uagauacccu   5520
cuucgucuga ggguggcgua gguuuauguu gggauauaaa guaacacaag acaaucuuca   5580
cuguacauaa aauaugucuu cauguacagu cuuuacuuua aaagcugaac auuccaauuu   5640
gcgccuuccc ucccaagccc cugcccacca aguaucucuu uagauaucua gucuguggac   5700
augaacaaug aauacuuuuu ucuuacucug aucgaaggca uugauacuua gacauaucaa   5760
acauuucuuc cuuucauaug cuuuacuuug cuaaaucuau uauauucauu gccugaauuu   5820
uauucuuccu uucuaccuga caacacacau ccagguggua cuugcugguu auccucuuuc   5880
uuguuagccu uguuuuuugu uuuuuuuuuu uuuuuuugag agggagucuc gcucuguugc   5940
ccaaccugga gugcaguggu gcgaucuugg uucacugcaa gcuccgccuc ccggguucac   6000
gccaugcuuc ugccucagcc ucccaaguag cugggacuac aggcgcccac caccacacuc   6060
ggcuaauuuu uuguauuuuu aguagagacg ggguuucacc guguuggcca ggauggucuc   6120
gaucuccuga ccucgugauc uguccaccuc ggcuucccaa agugcuggga uuacaggcau   6180
gagccaccgc gcccagccua gccauauuuu uaucugcaua uaucagaaug uuucucuccu   6240
uugaacuuau uaacaaaaaa ggaacaugcu uuucauaccu agaguccuaa uuucuucauc   6300
augaagguug cuauucaaau ugaucaauca uuuuaauuuu acaaauggcu caaaaaauucu   6360
guucaguaaa ugucuuugug acuggcaaau ggcauaaauu auguuuaaga uuaugaacuu   6420
uucugacagu ugcagccaau guuuucccua cgauaccaga uuuccaucuu ggggcauauu   6480
ggauuguugu auuuaagaca gucagaauaa ugauagugug uggucuccag agguagucag   6540
aauccugcua uugaguucuu uuuauaucuu ccuuuucaau uuuuuauuac cauuuuguuu   6600
guuuagacua cacuuuguag ggauugaggg gcaaauuauc ucuuggagug gaauuccugu   6660
guuuugagcc uuacaaccag gaaauaugag cuauacuaga uagccucaug auagcauuua   6720
cgauaagaac uuaucucgug uguucaugua auuuuuugag uaggaacugu uuuaucuuga   6780
auauuguagc uaacuauaua uagcagaacu gccucagucu uuuuaagaag gaaauaaaua   6840
auauaugugu augaauuuau auauacauau acacucauag acaaacuuaa caguuggggu   6900
```

```
cauucuaaca guuaaaacaa uuguuccauu guuuaaaucu cagauccugg uaaaauguuc   6960
uuaauuuguc uguguacauu uuccuuucau ggacagacca uuggaguaca uuaauuuucu   7020
uaaucugcca uuuggcaguu cauuuaauau accauuuuuu ggcaacuugg uaacuaagaa   7080
ucacagccaa aauuuguuaa caucaaagaa agcucugcca uauaccccgu uacuaaauua   7140
uuauacaucc agcagauucu gggauguacu aacuuagggu uaacuuuguu guuguugaua   7200
auacuagauu gcucccucuu uaauucuucu ucuggugcaa gguugcugcu uaaguuaccc   7260
ugggaaauac uacuacaagg ucaaauuuuc uaguaucuua cagccugauu gaaggugauu   7320
cagaucuuug cucaauauaa auggauuuuc caagauucuc ugggccaucc uugacccaca   7380
ggugaucucg cuggaguaua uuaacuuaac uucagugcca guugguuugg ugccaugaga   7440
uccauaauga auccagaacu ucaccauugc uuagauauaa gagucccuug gaagaauaau   7500
gccacugaug augggggguca gaagguguau uaacucaaca uagagggcuu uuagauuuuu   7560
cuucaaaaaa auuucgagaa aaguauucuu uuacccucca aacaguuaac agcucuuagu   7620
uucuccaaau augcucuuug auuuacuuau uuuuaauuaa agaugguaau uuauugaaca   7680
augaaauccg uaauauauug auuuaaggac aaaagugaag uuuuagaauu auaaaaguac   7740
uuaaauauua uauauuuucc auuucauaau uguuuuccuu ucucuguggc uuuaaaguuu   7800
uugacuauuu uacaauguua aucacuaggu aacuugccau auuucugguu cuauauuaag   7860
uucuauccuu uauaaugcug uuauuauaaa gcugguuuuu agcauuuguc uguagcaaua   7920
gaaauuuuac uaagucucug uucucccagu aaguuuuuuc uuuucucagu aagucccuaa   7980
gaaaacauuu guuugccacu cuuacuauuc ccaaucuugg auuguucgag cugaaaaaaa   8040
auuugaugag aaacaggagg auccuuuucu ggugaauaua gguuccugcu uuaagaaugu   8100
ggaaauccau ugcuuuauau aacuaauaua cacacagauu aauuaaaauu gugagaaaua   8160
auucacacau gacaaguagg uaacaugcau gaguuuugaa uuuuuuuaaa aacccaacug   8220
uuugacaaaa uauagaaccc aaauugguac uuucuuagac caguguaacc ucacaccuca   8280
guuuugcuuu uccaacccug acuugaaagg cauauuugua ucuuuuuauu agugauagug   8340
aagcugugac acuaaccuuu uauacaaaag aguaaagaaa gaaaaacuac agcgauuaag   8400
augagaacag uucugcaguu guugaacuag aucacagcau uguaggcaga auaaaaaaug   8460
uucauaucug agaauauucc uuucgccauc uuuucccaag gccagaccuc cugguggagc   8520
acaguuaaaa guaacauucu gggccuuugu aaucggaggg cugugucucc agcuggcagc   8580
cuuuguuuua auauauaaug caggacugug gaaaacaguu ggcauagaau auuuucaccu   8640
aaaaaagaaa gaaaagacau acaaaacugg auuaauugca aaaagagaau acaguaaaau   8700
accauauaac uggacaaagc uagaagaacc uuuagaagau uugucugaaa acagauuuca   8760
agagugagcu uuuauacacu gcucacuaau uugcuugauu acuaccaacu cuucuuaaag   8820
uuaacacguu uaagguauuu cuggacuucc uagccuuuua gcaagcuuag aggaacuagc   8880
cauuagcuag ugauguaaaa auauuuuggg gacugaugcc cuuaaagguu augcccuuga   8940
aaguucuuac cuuuucucua gugauauuaa ggaacgagug gguaguguuc ucagggugac   9000
cagcugcccu aaagugccug ggauugaggg uuucccugga ugcgggacuu ucccuggaua   9060
caaaacuuuu agcagaguuu uguauauaug uggauuuuuc ugauaaguag cacaucagag   9120
gccuuaacca cugcccaaaa gcgauucucc auugagagua cauaucuuga acuuaagaaa   9180
uucauuugcu cugauuuuua aucuuguaaa guuuuugcua aacucaaaac aagucccagg   9240
cacaccagaa ggagcugacc accuuaggug uucuugugau uuauccuuac uucccuaugu   9300
```

-continued ugucauaguu gcuucuaaac ucagcugcac uauggcuguc aacauuucug auacuuauug 9360
ggauaugugc cauccaguca uuuaguacuu ugaauggaac augagauuua uaacacaggu 9420
aauagcugaa gguaccagua ugguggugag acucacacuu agugauccag cuaagguaac 9480
ugauguuaua auggaacaga gaagaggcca acuagauagc uaaguucuuc ugaaccuaug 9540
uguauaugua aguacaaauc augcguccuu augggguuaa acuuaaucug aaauuuacau 9600
uuuucauagu aaaaggaaac caauuguugc agauuucuuu ucuugugagg aaauacaugg 9660
ccuuugaugc ucuggcgucu acugcauuuc ccagucuguu cugcucgaga agccagaaug 9720
uguuguuaac auuuuuccgu gaauguugug uuaaaaugau uaaaugcauc agccaauggc 9780
aagugaagga auuggguguc cugaugcaga cugagcaguu ucucucaauu guagccucau 9840
acucauaagg ugcuuaccag cuagaacauu gagcacguga ggugagauuu uuuuucucug 9900
auggcauuaa cuuuguaaug caauaugaug gaugcagacc cuguucuugu uucccucugg 9960
aaguccuuag uggcugcauc cuuggugcac ugugauggag auauuaaaug uguucuuugu 10020
gagcuuucgu ucuaugauug ucaaaaguac gaugugguuc cuuuuuuauu uuuauuaaac 10080
aaugagcuga ggcuuuauua cagcugguuu ucaaguuaaa auuguugaau acugaugucu 10140
uucucccacc uacaccaaau auuuuagucu auuuaaagua caaaaaaagu ucugcuuaag 10200
aaaacauugc uuacaugucc ugugauuucu ggucaauuuu uauauauauu ugugugcauc 10260
aucuguaugu gcuuucacuu uuuaccuugu uugcucuuac cuguguuaac agcccuguca 10320
ccguugaaag guggacaguu uuccuagcau uaaaagaaag ccauuugagu uguuuaccau 10380
guua 10384

<210> SEQ ID NO 103
<211> LENGTH: 10531
<212> TYPE: RNA
<213> ORGANISM: HUMAN

<400> SEQUENCE: 103
gggaggcggg gcgggccgua ggcaaaggga ggugggggagg cgguggccgg cgacuccccg 60
cgccccgcuc gcccccggc ccuucccgcg gugcucggcc ucguuccuuu ccuccuccgc 120
ucccuccguc uuccauaccc gccccgcgcg gcuuucggcc ggcgugccuc gcgcccuaac 180
gggcggcugg aggcgccaau cagcgggcgg cagggugcca gccccggggc ugcgccggcg 240
aaucggcggg gcccgcggcc cagggguggca ggcgggucua cccgcgcggc cgcggcggcg 300
gagaagcagc ucgccagcca gcagcccgcc agccgccggg agguucgaua caagaggcug 360
uuuuccuagc guggcuugcu gccuuuggua agaacauguc guccaucuug ccauucacgc 420
cgccaguugu gaagagacug cugggaugga agaagucagc uggugggucu ggaggagcag 480
gcggaggaga gcagaauggg caggaagaaa agugguguga gaaagcagug aaaagucugg 540
ugaagaagcu aaagaaaaca ggacgauuag augagcuuga gaaagccauc accacucaaa 600
acuguaauac uaaaugugguu accauaccaa gcacuugcuc ugaaauuugg ggacugagua 660
caccaaauac gauagaucag ugggauacaa caggccuuua cagcuucucu gaacaaacca 720
ggucucuuga uggucgucuc cagguauccc aucgaaaagg auugccacau guuauauauu 780
gccgauuaug gcgcuggccu gaucuucaca gucaucauga acucaaggca auugaaaacu 840
gcgaauaugc uuuuaaucuu aaaaaggaug aaguaugugu aaacccuuac cacuaucaga 900
gaguugagac accaguuuug ccuccaguau uagugccccg acacaccgag auccuaacag 960
aacuuccgcc ucuggaugac uauacucacu ccauuccaga aaacacuaac uucccagcag 1020

-continued

```
gaauugagcc acagaguaau uauauuccag aaacgccacc uccuggauau aucagugaag   1080
auggagaaac aagugaccaa caguugaauc aaaguaugga cacaggcucu ccagcagaac   1140
uaucuccuac uacucuuucc ccuguuaauc auagcuugga uuuacagcca guuacuuacu   1200
cagaaccugc auuuuggugu ucgauagcau auuaugaauu aaaucagagg guuggagaaa   1260
ccuuccaugc aucacagccc ucacucacug uagauggcuu uacagaccca ucaaauucag   1320
agagguucug cuuagguuua cucuccaaug uuaaccgaaa ugccacggua gaaaugacaa   1380
gaaggcauau aggaagagga gugcgcuuau acuacauagg uggggaaguu uuugcugagu   1440
gccuaaguga uagugcaauc uuugugcaga gccccaauug uaaucagaga uauggcuggc   1500
acccugcaac aguguguaaa auuccaccag gcuguaaucu gaagaucuuc aacaaccagg   1560
aauuugcugc ucuucuggcu cagucuguua aucaggguuu ugaagccguc uaucagcuaa   1620
cuagaaugug caccauaaga augaguuuug ugaaagggug gggagcagaa uaccgaaggc   1680
agacgguaac aaguacuccu ugcuggauug aacuucaucu gaauggaccu cuacaguggu   1740
uggacaaagu auuaacucag augggauccc cuucagugcg uugcucaagc augucauaaa   1800
gcuucaccaa ucaaguccca ugaaaagacu uaauguaaca acucuucugu cauagcauug   1860
ugugugguccc cuauggacug uuuacuaucc aaaaguucaa gagagaaaac agcacuugag   1920
gucucaucaa uuaaagcacc uuguggaauc uguuuccuau auuugaauau uagaugggaa   1980
aauuaguguc uagaaauacu cucccauuaa agaggaagag aagauuuuaa agacuuaaug   2040
augucuuauu gggcauaaaa cugaguguccc caaagguuua uuaauaacag uaguaguuau   2100
guguacaggu aauguaucau gauccaguau cacaguauug ugcuguuuau auacauuuuu   2160
aguuugcaua gaugaggugu gugugugcgc ugcuucuuga ucuaggcaaa ccuuuauaaa   2220
guugcaguac cuaaucuguu auucccacuu cucuguuauu uuugugugucc uuuuuuaaua   2280
uauaauauau aucaagauuu ucaaauuauu uagaagcaga uuuuccugua gaaaaacuaa   2340
uuuuucugcc uuuuaccaaa aauaaacucu ugggggaaga aaaguggauu aacuuuugaa   2400
auccuugacc uuaauguguu cagugggggcu uaaacaguca uucuuuuugu gguuuuuugu   2460
uuuuuuuugu uuuuuuuuuu aacugcuaaa ucuuauuaua aggaaaccau acugaaaacc   2520
uuuccaagcc ucuuuuuucc auucccauuu uuguccucau aaucaaaaca gcauaacaug   2580
acaucaucac caguaauagu ugcauugaua cugcuggcac caguuaaauc ugggauacag   2640
uaagaauuca uauggagaaa gucccuuugu cuuaugccca aauuucaaca ggaauaauug   2700
gcuuguauaa ucuagcaguc uguugauuua uccuucccacc ucauaaaaaa ugcauaggug   2760
gcaguauaau uauuuucagg gauaugcuag aauuacuucc acauauuuau cccuuuuuaa   2820
aaaagcuaau cuauaaauac cguuuuucca aagguauuuu acaauauuuc aacagcagac   2880
cuucugcucu ucgaguaguu ugauuugguu uaguaaccag auugcauuau gaaaugggcc   2940
uuuuguaaau guaauuguuu cugcaaaaua ccuagaaaag ugaugcugag guaggaucag   3000
cagauauggg ccaucuguuu uuaaaguaug uuguauucag uuuauaaauu gauuguuauu   3060
cuacacauaa uuaugaauuc agaauuuuaa aaauuggggg aaaagccauu uauuuagcaa   3120
guuuuuuagc uuauaaguua ccugcagucu gagcuguucu uaacugaucc ugguuuugug   3180
auugacaaua uuucaugcuc uguagugaga ggagauuucc gaaacucugu ugcuaguuca   3240
uucugcagca aauaauuauu augucugaug uugacucauu gcaguuuaaa cauuucuucu   3300
uguuugcauc uuaguagaaa uggaaaauaa ccacuccugg ucgucuuuuc auaaaauuuc   3360
auauuuuuga agcugucuuu gguacuuguu cuuugaaauc auauccaccu gucucuauag   3420
```

guaucauuuu caauacuuuc aacauuuggu gguuuucuau uggguacucc ccauuuuccu 3480
auauuugugu guauauguau guguucaugu aaauuuggua uaguaauuuu uuauucauuc 3540
aacaaauauu uauuguucac cuguuuguac caggaacuuu ucuuagucuu uggguaaagg 3600
ugaacaagac aacuacaguu ccugccuuug cugagacagc aguuacacua acccuuaauu 3660
aucuuacuug ucuaugaagg agauaaacag gguacuguac uggagaauaa cagaugggau 3720
gcuucaggua ggacaucaag gaaagccucu aaggaaagga ugcaugagcu aacaccugac 3780
auuaaagaag caagccaagu gaggagccag gggagauaag cauuccuggc aaagagaaua 3840
gcaucaaaug caaaaagguu cacacuaaag gaaacuccug auuagguauu aaugcuuuau 3900
acagaaaccu cuauacaaau ccaaacuuga agaucagaau gguucuacag uucauaacau 3960
uuugaaggug gccuuauuuu gugauagucu gcuucaugug auucucacua acauaucucc 4020
uuccucaacc uuugcuguaa aaauuucauu ugcaccacau caguacuacu uaauuuaaca 4080
agcuuuuguu guguaagcuc ucacuguuuu agugcccugc ugcuugcuuc cagacuuugu 4140
gcuguccagu aauuaugucu uccacuaccc aucuugugag cagaguaaau guccuaggua 4200
auaccacuau caggccugua ggagauacuc aguggagccu cugcccuucu uuuucuuacu 4260
ugagaacuug uaaugguguu agggaacagu uguaggggca gaaaacaacu cugaaagugg 4320
uagaaggucc ugaucuuggu gguuacucuu gcauuacugu guuaggucaa gcagugccua 4380
cuaugcuguu ucaguagugg agcgcaucuc uacaguucug augcgauuuu ucuguacagu 4440
augaaauugg gacucaacuc uuugaaaaca ccuauugagc aguuauaccu guugagcagu 4500
uuacuuccug guuguaauua cauuugugug aauguguuug augcuuuuua acgagaugau 4560
guuuuuugua uuuuaucuac uguggccuga uuuuuuuuuu guuuucugcc ccucccccca 4620
uuuauaggug ugguuuucau uuuucuaagu gauagaaucc ccucuuuguu gaauuuuugu 4680
cuuuauuuaa auuagcaaca uuacuuagga uuuauucuuc acaauacugu uaauuuucua 4740
ggaaugauga ccugagaacc gaauggccau gcuuucuauc acauuucuaa gaugaguaau 4800
auuuuuucca guagguucca cagagacacc uugggggcug gcuuaggggga ggcuguugga 4860 guucucacug acuuaguggc auauuuauuc uguacugaag aacugcaugg gguuucuuuu 4920
ggaaagaguu ucauugcuuu aaaaagaagc ucagaaaguc uuuauaacca cuggucaacg 4980
auuagaaaaa uauaacugga uuuaggccua ccuucuggaa uaccgcugau ugugcucuuu 5040
uuauccuacu uuaaagaagc uuucaugauu agauuugagc uauaucaguu auaccgauua 5100
uaccuuauaa uacacauuca guuaguaaac auuuauugau gccuguuguu ugcccagcca 5160
cugugaugga uauugaauaa uaaaaagaug acuaggacgg ggcccugacc cuugagcugu 5220
gcuuggucuu guagagguug uguuuuuuuu ccucaggacc ugucacuuug gcagaaggaa 5280
aucugccuaa uuuuucuuga aagcuaaauu uucuuuguaa guuuuuacaa auuguuuaau 5340
accuaguugu auuuuuuacc uuaagccaca uugaguuuug cuugauuugu cugucuuuua 5400
aacacuguca aaugcuuucc cuuuuguuaa aauuauuuua auuucacuuu uuuugugccc 5460
uugucaauuu aagacuaaga cuuugaaggu aaaacaaaca aacaaacauc agucuuaguc 5520
ucuugcuagu ugaaaucaaa uaaaagaaaa uauauaccca guugguuucu cuaccucuua 5580
aaagcuuccc auauauaccu uuaagauccu ucucuuuuuu cuuuaacuac uaaauaggu 5640 cagcauuuau ucaguguuag auacccucuu cgucugaggg uggcguaggu uuauguuggg 5700
auauaaagua acacaagaca aucuucacug uacauaaaau augucuucau guacagucuu 5760
uacuuuaaaa gcugaacauu ccaauuugcg ccuucccucc caagccccug cccaccaagu 5820

-continued

```
aucucuuuag auaucuaguc uguggacaug aacaaugaau acuuuuuucu uacucugauc   5880
gaaggcauug auacuuagac auaucaaaca uuucuuccuu ucauaugcuu uacuuugcua   5940
aaucuauuau auucauugcc ugaauuuuau ucuuccuuuc uaccugacaa cacacaucca   6000
ggugguacuu gcugguuauc cucuuucuug uuagccuugu uuuuuguuuu uuuuuuuuuu   6060
uuuugagagg gagucucgcu cuguugccca accuggagug caguggugcg aucuugguuc   6120
acugcaagcu ccgccucccg gguucacgcc augcuucugc cucagccucc caaguagcug   6180
ggacuacagg cgcccaccac cacacucggc uaauuuuuug uauuuuuagu agagacgggg   6240
uuucaccgug uuggccagga uggucucgau cuccugaccu cgugaucugu ccaccucggc   6300
uucccaaagu gcugggauua caggcaugag ccaccgcgcc cagccuagcc auauuuuuau   6360
cugcauauau cagaauguuu cucuccuuug aacuuauuaa caaaaaagga acaugcuuuu   6420
cauaccuaga guccuaauuu cuucaucaug aagguugcua uucaaauuga ucaaucauuu   6480
uaauuuuaca aauggcucaa aaauucuguu caguaaaugu cuuugugacu ggcaaauggc   6540
auaaauuaug uuuaagauua ugaacuuuuc ugacaguugc agccaauguu uucccuacga   6600
uaccagauuu ccaucuuggg gcauauugga uuguuguauu uaagacaguc agaauaauga   6660
uagugugugg ucuccagagg uagucagaau ccugcuauug aguucuuuuu auaucuuccu   6720
uuucaauuuu uuauuaccau uuuguuuguu uagacuacac uuuguaggga uugaggggca   6780
aauuaucucu uggaguggaa uuccuguguu uugagccuua caaccaggaa auaugagcua   6840
uacuagauag ccucaugaua gcauuuacga uaagaacuua ucucgugugu ucauguaauu   6900
uuuugaguag gaacuguuuu aucuugaaua uuguagcuaa cuauauauag cagaacugcc   6960
ucagucuuuu uaagaaggaa auaaauaaua uauguguaug aauuuauaua uacauauaca   7020
cucauagaca aacuuaacag uuggggucau ucuaacaguu aaaacaauug uuccauuguu   7080
uaaaucucag auccugguaa aauguucuua auuugucugu guacauuuuc cuuucaugga   7140
cagaccauug gaguacauua auuuucuuaa ucugccauuu ggcaguucau uuaauauacc   7200
auuuuuuggc aacuugguaa cuaagaauca cagccaaaau uuguuaacau caaagaaagc   7260
ucugccauau accccguuac uaaauuauua uacauccagc agauucuggg auguacuaac   7320
uuaggguuaa cuuuguuguu guugauaaua cuagauugcu cccucuuuaa uucuucuucu   7380
ggugcaaggu ugcugcuuaa guuacccugg gaaauacuac uacaagguca aauuuucuag   7440
uaucuuacag ccugauugaa ggugauucag aucuuugcuc aauauaaaug gauuuuccaa   7500
gauucucugg gccauccuug acccacaggu gaucucgcug gaguauauua acuuaacuuc   7560
agugccaguu gguuuggugc caugagaucc auaaugaauc cagaacuuca ccauugcuua   7620
gauauaagag ucccuuggaa gaauaaugcc acugaugaug ggggucagaa gguguauuaa   7680
cucaacauag agggcuuuua gauuuuucuu caaaaaaauu ucgagaaaag uauucuuuua   7740
cccuccaaac aguuaacagc ucuuaguuuc uccaaauaug cucuuugauu uacuuauuuu   7800
uaauuaaaga ugguaauuua uugaacaaug aaauccguaa uauauugauu uaaggacaaa   7860
agugaaguuu uagaauuaua aaaguacuua aauauuauau auuuuccauu ucauaauugu   7920
uuuccuuucu cuguggcuuu aaaguuuuug acuauuuuac aauguuaauc acuagguaac   7980
uugccauauu ucugguucua uauuaaguuc uauccuuuau aaugcuguua uuauaaagcu   8040
gguuuuuagc auuugucugu agcaauagaa auuuuacuaa gucucuguuc ucccaguaag   8100
uuuuuucuuu ucucaguaag ucccuaagaa aacauuuguu ugccacucuu acuauuccca   8160
aucuuggauu guucgagcug aaaaaaaauu ugaugagaaa caggaggauc cuuuucuggu   8220
```

-continued

```
gaauauaggu uccugcuuua agaaugugga aauccauugc uuuauauaac uaauauacac   8280
acagauuaau uaaaauugug agaaauaauu cacacaugac aaguagguaa caugcaugag   8340
uuuugaauuu uuuuaaaaac ccaacuguuu gacaaaauau agaacccaaa uugguacuuu   8400
cuuagaccag uguaaccuca caccucaguu uugcuuuucc aacccugacu ugaaaggcau   8460
auuuguaucu uuuuauuagu gauagugaag cugugacacu aaccuuuuau acaaaagagu   8520
aaagaaagaa aaacuacagc gauuaagaug agaacaguuc ugcaguuguu gaacuagauc   8580
acagcauugu aggcagaaua aaaaauguuc auaucugaga auauuccuuu cgccaucuuu   8640
ucccaaggcc agaccuccug guggagcaca guuaaaagua acauucuggg ccuuuguaau   8700
cggagggcug ugucuccagc uggcagccuu uguuuuaaua uauaaugcag gacuguggaa   8760
aacaguuggc auagaauauu uucaccuaaa aaagaaagaa aagacauaca aaacuggauu   8820
aauugcaaaa agagaauaca guaaaauacc auauaacugg acaaagcuag aagaaccuuu   8880
agaagauuug ucugaaaaca gauuucaaga gugagcuuuu auacacugcu cacuaauuug   8940
cuugauuacu accaacucuu cuuaaaguua acacguuuaa gguauuucug gacuuccuag   9000
ccuuuuagca agcuuagagg aacuagccau uagcuaguga uguaaaaaua uuuuggggac   9060
ugaugcccuu aaagguuaug cccuugaaag uucuuaccuu uucucuagug auauuaagga   9120
acgagugggu aguguucuca gggugaccag cugcccuaaa gugccuggga uugaggguuu   9180
cccuggaugc gggacuuucc cuggauacaa aacuuuuagc agaguuuugu auauaugugg   9240
auuuuucuga uaaguagcac aucagaggcc uuaaccacug cccaaaagcg auucuccauu   9300
gagaguacau aucuugaacu uaagaaauuc auuugcucug auuuuuaauc uuguaaaguu   9360
uuugcuaaac ucaaaacaag ucccaggcac accagaagga gcugaccacc uuagguguuc   9420
uugugauuua uccuuacuuc ccuauguugu cauaguugcu ucuaaacuca gcugcacuau   9480
ggcugucaac auuucugaua cuuauuggga uaugugccau ccagucauuu aguacuuuga   9540
auggaacaug agauuuauaa cacagguaau agcugaaggu accaguaugg uggugagacu   9600
cacacuuagu gauccagcua agguaacuga uguuauaaug gaacagagaa gaggccaacu   9660
agauagcuaa guucuucuga accuaugugu auauguaagu acaaaucaug cguccuuaug   9720
ggguuaaacu uaaucugaaa uuuacauuuu ucauaguaaa aggaaaccaa uuguugcaga   9780
uuucuuuucu ugugaggaaa uacauggccu uugaugcucu ggcgucuacu gcauuuccca   9840
gucuguucug cucgagaagc cagaaugugu uguuaacauu uuuccgugaa uguuguguua   9900
aaaugauuaa augcaucagc caauggcaag ugaaggaauu ggguguccug augcagacug   9960
agcaguuucu cucaauugua gccucauacu cauaaggugc uuaccagcua gaacauugag  10020
cacgugaggu gagauuuuuu uucucugaug gcauuaacuu uguaaugcaa uaugauggau  10080
gcagacccug uucuuguuuc ccucuggaag uccuuagugg cugcauccuu ggugcacugu  10140
gauggagaua uuaaaugugu ucuuugugag cuuucguucu augauuguca aaaguacgau  10200
gugguuccuu uuuuauuuuu auuaaacaau gagcugaggc uuuauuacag cugguuuuca  10260
aguuaaaauu guugaauacu gaugucuuuc ucccaccuac accaaauauu uuagucuauu  10320
uaaaguacaa aaaaaguucu gcuuaagaaa acauugcuua cauguccugu gauuucuggu  10380
caauuuuuau auauauuugu gugcaucauc uguaugugcu uucacuuuuu accuuguuug  10440
cucuuaccug uguuaacagc ccugucaccg uugaaaggug gacaguuuuc cuagcauuaa  10500
aagaaagcca uuugaguugu uuaccauguu a                                 10531
```

<210> SEQ ID NO 104

<211> LENGTH: 10444
<212> TYPE: RNA
<213> ORGANISM: HUMAN

<400> SEQUENCE: 104
gccgggaggc ggggcgggcc guaggcaaag ggaggugggg aggcggugge cggcgacucc 60 ccgcgccccg cucgcccccc ggcccuuccc gcggugcucg gccucguucc uuuccuccuc 120
cgcucccucc gucuuccaua cccgccccgc gcggcuuucg gccggcgugc cucgcgcccu 180
aacgggcggc uggaggcgcc aaucagcggg cggcagggug ccagccccgg ggcugcgccg 240
gcgaaucggc ggggcccgcg gcccagggug gcaggcgggu cuacccgcgc ggccgcggcg 300
gcggagaagc agcucgccag ccagcagccc gccagccgcc gggagguucg auacaagagg 360
cuguuuuccu agcguggcuu gcugccuuug guaagaacau gucguccauc uugccauuca 420
cgccgccagu ugugaagaga cugcugggau ggaagaaguc agcuggugg ucuggaggag 480 caggcggagg agagcagaau gggcaggaag aaaaguggug ugagaaagca gugaaaaguc 540
uggugaagaa gcuaaagaaa acaggacgau uagaugagcu ugagaaagcc aucaccacuc 600
aaaacuguaa uacuaaaugu guuaccauac caaggucucu ugauggucgu cuccagguau 660
cccaucgaaa aggauugcca cauguuauau auugccgauu auggcgcugg ccugaucuuc 720
acagucauca ugaacucaag gcaauugaaa acugcgaaua ugcuuuuaau cuuaaaaagg 780
augaaguaug uguaaacccu uaccacuauc agagaguuga gacaccaguu uugccuccag 840
uauuagugcc ccgacacacc gagauccuaa cagaacuucc gccucuggau gacuauacuc 900
acuccauucc agaaaacacu aacuucccag caggaauuga gccacagagu aauuauauuc 960
cagaaacgcc accuccugga uauaucagug aagauggaga aacaagugac caacaguuga 1020
aucaaaguau ggacacaggc ucuccagcag aacuaucucc uacuacucuu uccccuguua 1080
aucauagcuu ggauuuacag ccaguuacuu acucagaacc ugcauuuugg uguucgauag 1140
cauauuauga auuaaaucag aggguuggag aaaccuucca ugcaucacag cccucacuca 1200
cuguagaugg cuuuacagac ccaucaaauu cagagagguu cugcuuaggu uuacucucca 1260
auguuaaccg aaaugccacg guagaaauga caagaaggca uauaggaaga ggagugcgcu 1320
uauacuacau aggugggggaa guuuuugcug agugccuaag ugauagugca aucuuugugc 1380
agagccccaa uuguaaucag agauauggcu ggcacccugc aacagugugu aaaauuccac 1440
caggcuguaa ucugaagauc uucaacaacc aggaauuugc ugcucuucug gcucagucug 1500
uuaaucaggg uuuugaagcc gucuaucagc uaacuagaau gugcaccaua agaaugaguu 1560
uugugaaagg gugggggagca gaauaccgaa ggcagacggu aacaaguacu ccuugcugga 1620
uugaacuuca ucugaaugga ccucuacagu gguuggacaa aguauuaacu cagaugggau 1680
ccccuucagu gcguugcuca agcaugucau aaagcuucac caaucaaguc ccaugaaaag 1740
acuuaaugua acaacucuuc ugucauagca uugugugugg ucccuaugga cuguuuacua 1800
uccaaaaguu caagagagaa aacagcacuu gaggucucau caauuaaagc accuugugga 1860
aucuguuucc uauauuugaa uauuagaugg gaaaauuagu gucuagaaau acucucccau 1920
uaaagaggaa gagaagauuu uaaagacuua augaugucuu auugggcaua aaacugagug 1980
ucccaaaggu uuauuaauaa caguaguagu uauguguaca gguaauguau caugauccag 2040
uaucacagua uugugcuguu uauauacauu uuuaguuugc auagaugagg ugugugugug 2100
cgcugcuucu ugaucuaggc aaaccuuuau aaaguugcag uaccuaaucu guuauuccca 2160
cuucucuguu auuuuugugu gucuuuuuua auauauaaua uauaucaaga uuuucaaauu 2220

```
auuuagaagc agauuuuccu guagaaaaac uaauuuuucu gccuuuuacc aaaaauaaac   2280
ucuuggggga agaaaagugg auuaacuuuu gaaauccuug accuuaaugu guucaguggg   2340
gcuuaaacag ucauucuuuu ugugguuuuu uguuuuuuuu uguuuuuuuu uuuaacugcu   2400
aaaucuuauu auaaggaaac cauacugaaa accuuuccaa gccucuuuuu uccauuccca   2460
uuuuuguccu cauaaucaaa acagcauaac augacaucau caccaguaau aguugcauug   2520
auacugcugg caccaguuaa uucugggaua caguaagaau ucauauggag aaagucccuu   2580
ugucuuaugc ccaaauuuca acaggaauaa uuggcuugua uaaucuagca gucuguugau   2640
uuauccuucc accucauaaa aaaugcauag guggcaguau aauuauuuuc agggauaugc   2700
uagaauuacu uccacauauu uaucccuuuu uaaaaaagcu aaucuauaaa uaccguuuuu   2760
ccaaagguau uuuacaauau uucaacagca gaccuucugc ucuucgagua guuugauuug   2820
guuuaguaac cagauugcau uaugaaaugg gccuuuugua aauguaauug uuucugcaaa   2880
auaccuagaa aagugaugcu gagguaggau cagcagauau gggccaucug uuuuuaaagu   2940
auguuguauu caguuuauaa auugauuguu auucuacaca uaauuaugaa uucagaauuu   3000
uaaaaauugg gggaaaagcc auuuauuuag caaguuuuuu agcuuauaag uuaccugcag   3060
ucugagcugu ucuuaacuga uccugguuuu gugauugaca auauuucaug cucuguagug   3120
agaggagauu uccgaaacuc uguugcuagu ucauucugca gcaaauaauu auuaugucug   3180
auguugacuc auugcaguuu aaacauuucu ucuuguuugc aucuuaguag aaauggaaaa   3240
uaaccacucc uggucgucuu uucauaaauu uucauauuuu ugaagcuguc uuugguacuu   3300
guucuuugaa aucauaucca ccugucucua uagguaucau uuucaauacu uucaacauuu   3360
gguggguuuuc uauuggguac uccccauuuu ccuauauuug uguguauaug uauguguuca   3420
uguaaauuug guauaguaau uuuuuauuca uucaacaaau auuuauuguu caccuguuug   3480
uaccaggaac uuuucuuagu cuuuggguaa aggugaacaa gacaacuaca guuccugccu   3540
uugcugagac agcaguuaca cuaacccuua auuaucuuac uugucuauga aggagauaaa   3600
cagggguacug uacuggagaa uaacagaugg gaugcuucag guaggacauc aaggaaagcc   3660
ucuaaggaaa ggaugcauga gcuaacaccu gacauuaaag aagcaagcca agugaggagc   3720
caggggagau aagcauuccu ggcaaagaga auagcaucaa augcaaaaag guucacacua   3780
aaggaaacuc cugauuaggu auuaaugcuu uauacagaaa ccucuauaca aauccaaacu   3840
ugaagaucag aaugguucua caguucauaa cauuuugaag guggccuuau uuugugauag   3900
ucugcuucau gugauucuca cuaacauauc uccuuccuca accuuugcug uaaaaauuuc   3960
auuugcacca caucaguacu acuuaauuua acaagcuuuu guuguguaag cucucacugu   4020
uuuagugccc ugcugcuugc uuccagacuu ugugcugucc aguaauuaug ucuuccacua   4080
cccaucuugu gagcagagua aauguccuag guaauaccac uaucaggccu guaggagaua   4140
cucaguggag ccucugcccu ucuuuuucuu acuugagaac uuguaauggu guuagggaac   4200
aguuguaggg gcagaaaaca acucugaaag ugguagaagg uccugaucuu ggugguuacu   4260
cuugcauuac uguguuaggu caagcagugc cuacuaugcu guuucaguag uggagcgcau   4320
cucuacaguu cugaugcgau uuuucuguac aguaugaaau ugggacucaa cucuuugaaa   4380
acaccuauug agcaguuaua ccuguugagc aguuuacuuc cugguuguaa uuacauuugu   4440
gugaaugugu uugaugcuuu uuaacgagau gauguuuuuu guauuuuauc uacuguggcc   4500
ugauuuuuuu uuuguuuucu gccccucccc ccauuuauag guguugguuuu cauuuuucua   4560
agugauagaa uccccucuuu guugaauuuu ugucuuuauu uaaauuagca acauuacuua   4620
```

-continued

```
ggauuuauuc uucacaauac uguuaauuuu cuaggaauga ugaccugaga accgaauggc   4680
caugcuuucu aucacauuuc uaagaugagu aauauuuuuu ccaguagguu ccacagagac   4740
accuuggggg cuggcuuagg ggaggcuguu ggaguucuca cugacuuagu ggcauauuua   4800
uucuguacug aagaacugca uggggguucu uuuggaaaga guuucauugc uuuaaaaaga   4860
agcucagaaa gucuuuauaa ccacugguca acgauuagaa aaauauaacu ggauuuaggc   4920
cuaccuucug gaauaccgcu gauugugcuc uuuuuauccu acuuuaaaga agcuuucaug   4980
auuagauuug agcuauauca guuauaccga uuauaccuua uaauacacau ucaguuagua   5040
aacauuuauu gaugccuguu guuugcccag ccacugugau ggauauugaa uaauaaaaag   5100
augacuagga cggggcccug acccuugagc ugugcuuggu cuuguagagg uuguguuuuu   5160
uuuccucagg accugucacu uuggcagaag gaaaucugcc uaauuuuucu ugaaagcuaa   5220
auuuucuuug uaaguuuuua caaauuguuu aauaccuagu uguauuuuuu accuuaagcc   5280
acauugaguu uugcuugauu ugucugucuu uuaaacacug ucaaaugcuu ucccuuuugu   5340
uaaaauuauu uuaauuucac uuuuuuugug cccuugucaa uuuaagacua agacuuugaa   5400
gguaaaacaa acaaacaaac aucagucuua gucucuugcu aguugaaauc aaauaaaaga   5460
aaauauauac ccaguugguu ucucuaccuc uuaaaagcuu cccauauaua ccuuuaagau   5520
ccuucucuuu uuucuuuaac uacuaaauag guucagcauu uauucagugu uagauacccu   5580
cuucgucuga ggguggcgua gguuuauguu gggauauaaa guaacacaag acaaucuuca   5640
cuguacauaa aauaugucuu cauguacagu cuuuacuuua aaagcugaac auuccaauuu   5700
gcgccuuccc ucccaagccc cugcccacca aguaucucuu uagauaucua gucuguggac   5760
augaacaaug aauacuuuuu ucuuacucug aucgaaggca uugauacuua gacauaucaa   5820
acauuucuuc cuuucauaug cuuuacuuug cuaaaucuau uauauucauu gccugaauuu   5880
uauucuuccu uucuaccuga caacacacau ccagguggua cuugcugguu auccucuuuc   5940
uuguuagccu uguuuuuugu uuuuuuuuuu uuuuuuugag agggagucuc gcucuguugc   6000
ccaaccugga gugcaguggu gcgaucuugg uucacugcaa gcuccgccuc ccggguucac   6060
gccaugcuuc ugccucagcc ucccaaguag cugggacuac aggcgcccac caccacacuc   6120
ggcuaauuuu uuguauuuuu aguagagacg ggguuucacc guguuggcca ggauggucuc   6180
gaucuccuga ccucgugauc uguccaccuc ggcuucccaa agugcuggga uuacaggcau   6240
gagccaccgc gcccagccua gccauauuuu uaucugcaua uaucagaaug uuucucuccu   6300
uugaacuuau uaacaaaaaa ggaacaugcu uuucauaccu agaguccuaa uuucuucauc   6360
augaagguug cuauucaaau ugaucaauca uuuuaauuuu acaaauggcu caaaaaauucu   6420
guucaguaaa ugucuuugug acuggcaaau ggcauaaauu auguuuaaga uuaugaacuu   6480
uucugacagu ugcagccaau guuuucccua cgauaccaga uuuccaucuu ggggcauauu   6540
ggauuguugu auuuaagaca gucagaauaa ugauagugug uggucuccag agguagucag   6600
aauccugcua uugaguucuu uuuauaucuu ccuuuucaau uuuuuauuac cauuuuguuu   6660
guuuagacua cacuuuguag ggauugaggg gcaaauuauc ucuuggagug gaauuccugu   6720
guuuugagcc uuacaaccag gaaauaugag cuauacuaga uagccucaug auagcauuua   6780
cgauaagaac uuaucucgug uguucaugua auuuuuugag uaggaacugu uuuaucuuga   6840
auauuguagc uaacuauaua uagcagaacu gccucagucu uuuuaagaag gaaauaaaua   6900
auauaugugu augaauuuau auauacauau acacucauag acaaacuuaa caguuggggu   6960
cauucuaaca guuaaaacaa uuguuccauu guuuaaaucu cagauccugg uaaaauguuc   7020
```

-continued

```
uuaauuuguc uguguacauu uuccuuucau ggacagacca uuggaguaca uuaauuuucu   7080
uaaucugcca uuuggcaguu cauuuaauau accauuuuuu ggcaacuugg uaacuaagaa   7140
ucacagccaa aauuuguuaa caucaaagaa agcucugcca uauaccccgu uacuaaauua   7200
uuauacaucc agcagauucu gggauguacu aacuuagggu uaacuuuguu guuguugaua   7260
auacuagauu gcucccucuu uaauucuucu ucuggugcaa gguugcugcu uaaguuaccc   7320
ugggaaauac uacuacaagg ucaaauuuuc uaguaucuua cagccugauu gaaggugauu   7380
cagaucuuug cucaauauaa auggauuuuc caagauucuc ugggccaucc uugacccaca   7440
ggugaucucg cuggaguaua uuaacuuaac uucagugcca guugguuugg ugccaugaga   7500
uccauaauga auccagaacu ucaccauugc uuagauauaa gagucccuug gaagaauaau   7560
gccacugaug augggggguca gaagguguau uaacucaaca uagagggcuu uuagauuuuu   7620
cuucaaaaaa auuucgagaa aaguauucuu uuacccucca aacaguuaac agcucuuagu   7680
uucuccaaau augcucuuug auuuacuuau uuuuaauuaa agaugguaau uuauugaaca   7740
augaaauccg uaauauauug auuuaaggac aaaagugaag uuuuagaauu auaaaaguac   7800
uuaaauauua uauauuuucc auuucauaau uguuuuccuu ucucuguggc uuuaaaguuu   7860
uugacuauuu uacaauguua aucacuaggu aacuugccau auuucugguu cuauauuaag   7920
uucuauccuu uauaaugcug uuauuauaaa gcugguuuuu agcauuuguc uguagcaaua   7980
gaaauuuuac uaagucucug uucucccagu aaguuuuuuc uuuucucagu aagucccuaa   8040
gaaaacauuu guuugccacu cuuacuauuc ccaaucuugg auuguucgag cugaaaaaaa   8100
auuugaugag aaacaggagg auccuuuucu ggugaauaua gguuccugcu uuaagaaugu   8160
ggaaauccau ugcuuuauau aacuaauaua cacacagauu aauuaaaauu gugagaaaua   8220
auucacacau gacaaguagg uaacaugcau gaguuuugaa uuuuuuuaaa aacccaacug   8280
uuugacaaaa uauagaaccc aaauugguac uuucuuagac caguguaacc ucacaccuca   8340
guuuugcuuu uccaacccug acuugaaagg cauauuugua ucuuuuuauu agugauagug   8400
aagcugugac acuaaccuuu uauacaaaag aguaaagaaa gaaaaacuac agcgauuaag   8460
augagaacag uucugcaguu guugaacuag aucacagcau uguaggcaga auaaaaaaug   8520
uucauaucug agaauauucc uuucgccauc uuuucccaag gccagaccuc cugguggagc   8580
acaguuaaaa guaacauucu gggccuuugu aaucggaggg cugugucucc agcuggcagc   8640
cuuuguuuua auauauaaug caggacugug gaaaacaguu ggcauagaau auuuucaccu   8700
aaaaaagaaa gaaaagacau acaaaacugg auuaauugca aaaagagaau acaguaaaau   8760
accauauaac uggacaaagc uagaagaacc uuuagaagau uugucugaaa acagauuuca   8820
agagugagcu uuuauacacu gcucacuaau uugcuugauu acuaccaacu cuucuuaaag   8880
uuaacacguu uaagguauuu cuggacuucc uagccuuuua gcaagcuuag aggaacuagc   8940
cauuagcuag ugauguaaaa auauuuuggg gacugaugcc cuuaaagguu augcccuuga   9000
aaguucuuac cuuuucucua gugauauuaa ggaacgagug gguaguguuc ucagggugac   9060
cagcugcccu aaagugccug ggauugaggg uuucccugga ugcgggacuu ucccuggaua   9120
caaaacuuuu agcagaguuu uguauauaug uggauuuuuc ugauaaguag cacaucagag   9180
gccuuaacca cugcccaaaa gcgauucucc auugagagua cauaucuuga acuuaagaaa   9240
uucauuugcu cugauuuuua aucuuguaaa guuuuugcua aacucaaaac aagucccagg   9300
cacaccagaa ggagcugacc accuuaggug uucuugugau uuauccuuac uucccuaugu   9360
ugucauaguu gcuucuaaac ucagcugcac uauggcuguc aacauuucug auacuuauug   9420
```

ggauaugugc cauccaguca uuuaguacuu ugaauggaac augagauuua uaacacaggu 9480
aauagcugaa gguaccagua ugguggugag acucacacuu agugauccag cuaagguaac 9540
ugauguuaua auggaacaga gaagaggcca acuagauagc uaaguucuuc ugaaccuaug 9600
uguauaugua aguacaaauc augcguccuu augggguuaa acuuaaucug aaauuuacau 9660
uuuucauagu aaaaggaaac caauuguugc agauuucuuu ucuugugagg aaauacaugg 9720
ccuuugaugc ucuggcgucu acugcauuuc ccagucuguu cugcucgaga agccagaaug 9780
uguuguuaac auuuuuccgu gaauguugug uuaaaaugau uaaaugcauc agccaauggc 9840
aagugaagga auugggugu c cugaugcaga cugagcaguu ucucucaauu guagccucau 9900
acucauaagg ugcuuaccag cuagaacauu gagcacguga ggugagauuu uuuuucucug 9960
auggcauuaa cuuuguaaug caauaugaug gaugcagacc cuguucuugu uucccucugg 10020
aaguccuuag uggcugcauc cuuggugcac ugugauggag auauuaaaug uguucuuugu 10080
gagcuuucgu ucuaugauug ucaaaaguac gaugugguuc cuuuuuuauu uuuauuaaac 10140
aaugagcuga ggcuuuauua cagcugguuu ucaaguuaaa auuguugaau acugaugucu 10200
uucucccacc uacaccaaau auuuuagucu auuuaaagua caaaaaaagu ucugcuuaag 10260
aaaacauugc uuacaugucc ugugauuucu ggucaauuuu uauauauauu ugugugcauc 10320
aucuguaugu gcuuucacuu uuuaccuugu uugcucuuac cuguguuaac agcccuguca 10380
ccguugaaag guggacaguu uuccuagcau uaaaagaaag ccauuugagu uguuuaccau 10440
guua 10444

<210> SEQ ID NO 105
<211> LENGTH: 6256
<212> TYPE: RNA
<213> ORGANISM: HUMAN

<400> SEQUENCE: 105
gcggccgccg ccuccgcccc gcguucgggg ccuucccgac ccugcacugc ugccguccgc 60
ccgcccggcc gcucuucucu ucgccguggg agccgcuccg ggcgcagggc cgcgcgccga 120
gccccgcagg cugcagcgcc gcggcccggc ccggcgcccc ggcaacuucg ccgagaguug 180
aggcgaaguu ugggcgaccg cggcaggccc cggccgagcu ccccucugcg cccccggcgu 240
cccgucgagc ccagccccgc cgggggcgcu ccucgccgcc cgcgcgcccu ccccagccau 300
gucguccauc cugccuuuca cucccccgau cgugaagcgc cugcugggcu ggaagaaggg 360
cgagcagaac gggcaggagg agaaauggug cgagaaggcg gucaagagcc uggucaagaa 420
acucaagaag acggggcagc uggacgagcu ggagaaggcc aucaccacgc agaacgucaa 480
caccaagugc aucaccaucc ccaggucccu ggauggccgg uugcaggugu cccaucggaa 540
ggggcucccu caugucaucu acugccgccu guggcgaugg ccagaccugc acagccacca 600
cgagcuacgg gccauggagc ugugugaguu cgccuucaau augaagaagg acgaggucug 660
cgugaauccc uaccacuacc agagaguaga gacaccaguu cuaccuccug uguuggugcc 720
acgccacaca gagaucccgg ccgaguuccc cccacuggac gacuacagcc auuccauccc 780
cgaaaacacu aacuuccccg caggcaucga gccccagagc aauauuccag agaccccacc 840
cccuggcuac cugagugaag auggagaaac cagugaccac cagaugaacc acagcaugga 900
cgcagguucu ccaaaccuau ccccgaaucc gauguccccca gcacauaaua acuuggaccu 960
gcagccaguu accuacugcg agccggccuu cugguguucc aucuccuacu acgagcugaa 1020
ccagcgcguc ggggagacau uccacgccuc gcagccaucc augacugugg auggcuucac 1080
cgaccccucc aauucggagc gcuucugccu agggcugcuc uccaauguca acaggaaugc 1140
agcaguggag cugacacgga gacacaucgg aagaggcgug cggcucuacu acaucggagg 1200
ggaggucuuc gcagagugcc ucagugacag cgcuauuuuu guccagucuc ccaacuguaa 1260
ccagcgcuau ggcuggcacc cggccaccgu cugcaagauc ccaccaggau gcaaccugaa 1320
gaucuucaac aaccaggagu ucgcugcccu ccuggcccag ucggucaacc agggcuuuga 1380
ggcugucuac caguugaccc gaaugugcac cauccgcaug agcuucguca aaggcugggg 1440
agcggaguac aggagacaga cugugaccag uacccccugc uggauugagc ugcaccugaa 1500
ugggccuuug caguggcuug acaagguccu cacccagaug ggcuccccaa gcauccgcug 1560
uuccagugug ucuuagagac aucaaguaug guaggggagg gcaggcuugg ggaaaauggc 1620
caugcaggag guggagaaaa uuggaacucu acucaaccca uuguugucaa ggaagaagaa 1680
aucuuucucc cucaacugaa ggggugcacc caccuguuuu cugaaacaca cgagcaaacc 1740
cagaggugga uguuaugaac agcugugucu gccaaacaca uuuacccuuu ggccccacuu 1800
ugaagggcaa gaaauggcgu cugcucuggu ggcuuaagug agcagaacag guaguauuac 1860
accaccggcc cccuccccc agacucuuuu uuugagugac agcuuucugg gaugucacag 1920
uccaaccaga aacaccccuc ugucuaggac ugcagugugg aguucaccuu ggaagggcgu 1980
ucuagguagg aagagcccgc agggccaugc agaccucaug cccagcucuc ugacgcuugu 2040
gacagugccu cuuccaguga acauucccag cccagccccg ccccgccccg ccccaccacu 2100
ccagcagacc uugccccuug ugagcuggau agacuuggga uggggaggga gggaguuuug 2160
ucugucuccc uccccucuca gaacauacug auugggaggu gcguguucag cagaaccugc 2220
acacaggaca gcgggaaaaa ucgaugagcg ccaccucuuu aaaaacucac uuacguuugu 2280
ccuuuuucac uuugaaaagu uggaaggauc ugcugaggcc cagugcauau gcaauguaua 2340
gugucuauua ucacauuaau cucaaagaga uucgaaugac gguaaguguu cucaugaagc 2400
aggaggcccu ugucguggga uggcauuugg ucucaggcag caccacacug ggugcgucuc 2460
cagucaucug uaagagcuug cuccagauuc ugaugcauac ggcuauauug guuuauguag 2520
ucaguugcau ucauuaaauc aacuuuauca uaugcucuuu uaaauguuug guuuauauau 2580
uuucuuuaaa aauccugggc uggcacauug acugggaaac cugagugaga cccagcaacu 2640
gcuucucucc cuucucucuc cugaggugaa gcuuuuccag guuuuguuga agagauaccu 2700
gccagcacuu cugcaagcug aaauuuacag aagcaaauuc accagaaggg aaacaucuca 2760
ggccaacaua ggcaaaugaa aagggcuauu aaaauauuuu uacaccuuug aaaauugcag 2820
gcuugguaca aagaggucug ucaucuuccc ccugggauau aagaugaucu agcucccggu 2880
agaggaucac cggugacaac uauagcaguu guauugugua acaaguacug cucccagcag 2940
caauuaggga gaaaacuagu cuaaauuauu ucaacuggaa aaaagaaaaa agaguccucu 3000
ucuuucccca gccuuuugca gaacacagua gacagaacug ccaccuucaa uugguacuuu 3060
auucuuugcu gcuguuuuug uauaaaauga ccuaucccac guuuuugcau gaauuuauag 3120
caggaaaaau caagggauuu ccuauggaag uccugcuuua uuccagguga agggaaggaa 3180
guguauauac uuuuggcaag ucauacagcu caaaugugau gagauuucug auguuagagg 3240
gagauggaga ggcuuccuga ugccucaucu gcaggguccu gugccucuga aguucuagcc 3300
augagguuuc cagguaggac agcugcuccc caagccuccu gaggacacag gaagagacgg 3360
aaggagcacc uugacagacu ugugugaguc uucucgaagg aggguugacu cagaacccag 3420
agacaauaca aaaccccuca cuuccucuga gagggccaaa ugcugugagu cugaaguaug 3480

-continued

```
ugccuggugu gaaaugaucu auggccuguu ucuuacacag gaagccccu gaaccuccug   3540
uacauguguu cauguuccca gccagcucug agacccagga accaaauauu ccauuuuggc   3600
uucugcuaga gcagucaugg uuccucuccu aaaagccaug ggcagcaguu uccgagggcc   3660
ugcaugaucc accugcugca cgauccuaug agggcuuccu guggcacaca gcccucuggg   3720
ugcuugggaa cuagcuucag gcacagccug auucuggugua uccagugauc uauggaaguc   3780
gugucuuacu ccaggugaag ggggaaaaaa aaagccuaua cuuuggcagg uuaugaacuu   3840
ugaaugugau gaaaugacac guuuggcugc auuuggaugg ugucuuagaa cccucauugc   3900
ucagaccuga aggcuacuuc uaggagcaug aaguuugagu uuuguguuuu uccaaaggau   3960
acuuccuugg cccuuuuucu uuauugacua gaccaccaga ggaggaugug ugggauugua   4020
ggcaaaccca ccuguggcau cacugaaaau aaauuugauc auaccuaaga gguuaggaaa   4080
uggugccauu cccaccuuag agugcuacau aggugcuuug ggcguaugua acauuagugu   4140
ccuuccuuga agccacaagc uaguuuucuu aguuuuaaaa uccuguugua ugaauggcau   4200
uuguauauua aaacacuuuu uuaaaggaca guugaaaagg gcaagaggaa accagggcag   4260
uucuagagga gugcugguga cuggauagca guuuuaagug gcguucaccu agucaacacg   4320
accgcgugug uugccccugc ccugggcucc ccgccaugac aucuucaccu ugcagcuugu   4380
gcugagacug acccaagugc agcuagcacu gggacacaga uccuugucuu cagcaccuuc   4440
caaggagcca acuuuuauuc ccuuuccucu cuccccuccc caccucgcuu cuucccaauu   4500
uaguaacuua gaugcuucca gcacauacgu agguagcuac cccagccggu uuggauuaca   4560
ggccugugcu ggaacaucau cucaguuggc caccuuccug gcaggcugua gaccugacau   4620
uuugagacaa gccuagaguc aggagcaggg acuuugacuc uuaggaagag cacacaugag   4680
ggcaaggcug cuggcagacg ucuccauugu ccuuauguug ucuguguugu auuuuuuuuu   4740
uuuuauugac cauggugauu auuuuuuuaa accaucguua auauacugaa gugagcuaua   4800
gcacauauca ugugcuuagu uuguuuauuu uucuccaucu ccccuuggcu uccuagaguu   4860
uggacauauu ccaggcuaaa ugcuuuuacu caagacuaca gaaagguuug aaguagugug   4920
ugcauggcau gcacguaugu aaguaaucug gggaagaagc aaagaucugu uucauucuua   4980
gccucaggcc ucaugagggu cuccacaggg ccggagcuca gguuacacca cuccuucguc   5040
cuuacaggag auguagggag aagaaucugc aggcugcuug uaggacuguu caccaagggg   5100
gauaccagca gcaagagagu gcacccguuu agcccuggac ccuguuucuu acugugugac   5160
uuggcuagag uugggaguuc ccccaaaaua aacgugucc cauuuuacca gaaccaaacc   5220
ucaacacagc gaagcuguac ugucuuugug uggcaaagau guucccuugu aggccccuuu   5280
cagguaaccg ucuucacaau guauuuucau cacaguuuaa ggagcaucag ccgcuucuca   5340
agugguuagg gaaagcagaa aaacguacgc aagaggacau ggauccaaaa ugaugaugaa   5400
gcaucuccca uggggaggug augguggga gaugaugggc uaaacaggca acuuuucaaa   5460
aacacagcua ucauagaaaa gaaacuugcc ucauguaaac uggauugaga aauucucagu   5520
gauucugcaa uggauuuuuu uuuaaugcag aaguaaugua uacucuagua uucuggugu u  5580
uuuauauuua uguaauaauu ucuuaaaacc auucagacag auaacuauuu aauuuuuuuu   5640
aagaaaguug gaaaggucuc uccucccaag gacaguggcu ggaagaguug gggcacagcc   5700
aguucugaau guuggguggag gguguagugg cuuuuuggcu cagcauccag aaacaccaaa   5760
ccaggcuggc uaaacaagug gccgcgugua aaaacagaca gcucugaguc aaaucugggc   5820
ccuuccacaa ggguccucug aaccaagccc cacucccuug cuagggguga aagcauuaca   5880
```

-continued gagagaugga gccaucuauc caagaagccu ucacucaccu ucacugcugc uguugcaacu 5940
cggcuguucu ggacucugau gugugugag ggaugggaa uagaacauug acuguguuga 6000
uuaccuucac uauucggcca gccugaccuu uuaauaacuu uguaaaaagc auguauguau 6060
uuauaguguu uuagauuuuu cuaacuuuua uaucuuaaaa gcagagcacc uguuuaagca 6120
uuguaccccu auuguuaaag auuugugucc ucucauuccc ucucuuccuc uuguaagugc 6180
ccuucuaaua aacuuuucau ggaaaagcuc cugugccagg agcucagucu gaaaaaaaaa 6240
aaaaaaaaaa aaaaaa 6256

<210> SEQ ID NO 106
<211> LENGTH: 5997
<212> TYPE: RNA
<213> ORGANISM: HUMAN

<400> SEQUENCE: 106
aaauaugagc uugugcuugc uggaggagga ugacagagga gccugcugcu gaguucacug 60
gugcuggggu uaggucacug cugggcugaa gcgcacugac cauaagagca acaugugggc 120
aagagccgcg gcacuggggu aauuuauugc cgccgcucgc uucaccagga accccacacg 180
cuggguuccc acaggaugcg acauucccac aggaugggac aacugcaugg aaacccacac 240
ucgggccugu guugagcaac cacguuugag ucccuggaug gccgguugca ggugucccau 300
cggaaggggc ucccucaugu caucuacugc cgccuguggc gauggccaga ccugcacagc 360
caccacgagc uacgggccau ggagcugugu gaguucgccu ucaauaugaa gaaggacgag 420
gucugcguga aucccuacca cuaccagaga guagagacac caguucuacc uccuguguug 480
gugccacgcc acacagagau cccggccgag uucccccac uggacgacua cagccauucc 540
auccccgaaa acacuaacuu ccccgcaggc aucgagcccc agagcaauau uccagagacc 600
ccacccccug gcuaccugag ugaagaugga gaaaccagug accaccagau gaaccacagc 660
auggacgcag guucuccaaa ccuaucccccg aauccgaugu ccccagcaca uaauaacuug 720
gaccugcagc caguuaccua cugcgagccg gccuucuggu gcuccaucuc cuacuacgag 780
cugaaccagc gcgucgggga gacauuccac gccucgcagc cauccaugac uguggauggc 840
uucaccgacc ccuccaauuc ggagcgcuuc ugccuagggc ugcucuccaa ugucaacagg 900
aaugcagcag uggagcugac acggagacac aucggaagag gcgugcggcu cuacuacauc 960
ggaggggagg ucuucgcaga gugccucagu gacagcgcua uuuuugucca gucucccaac 1020
uguaaccagc gcuauggcug gcacccggcc accgucugca agaucccacc aggaugcaac 1080
cugaagaucu ucaacaacca ggaguucgcu gcccuccugg cccagucggu caaccagggc 1140
uuugaggcug ucuaccaguu gacccgaaug ugcaccaucc gcaugagcuu cgucaaaggc 1200
uggggagcgg aguacaggag acagacugug accaguaccc ccugcuggau ugagcugcac 1260
cugaaugggc cuuugcagug gcuugacaag guccucaccc agaugggcuc cccaagcauc 1320
cgcuguucca gugugucuua gagacaucaa guaugguagg ggagggcagg cuuggggaaa 1380
auggccaugc aggaggugga gaaaauugga acucuacuca acccauuguu gucaaggaag 1440
aagaaaucuu ucucccucaa cugaaggggu gcacccaccu guuuucugaa acacacgagc 1500
aaacccagag guggauguua ugaacagcug ugucugccaa acacauuuac ccuuuggccc 1560
cacuuugaag ggcaagaaau ggcgucugcu cugguggcuu aagugagcag aacagguagu 1620
auuacaccac cggcccccuc cccccagacu cuuuuuuuga gugacagcuu ucugggaugu 1680
cacaguccaa ccagaaacac cccucugucu aggacugcag uguggaguuc accuuggaag 1740

-continued

```
ggcguucuag guaggaagag cccgcagggc caugcagacc ucaugcccag cucucugacg   1800
cuugugacag ugccucuucc agugaacauu cccagcccag ccccgccccg ccccgcccca   1860
ccacuccagc agaccuugcc ccuugugagc uggauagacu ugggaugggg agggagggag   1920
uuuugucugu cucccucccc ucucagaaca uacugauugg gaggugcgug uucagcagaa   1980
ccugcacaca ggacagcggg aaaaaucgau gagcgccacc ucuuuaaaaa cucacuuacg   2040
uuuguccuuu uucacuuuga aaaguuggaa ggaucugcug aggcccagug cauaugcaau   2100
guauaguguc uauuaucaca uuaaucucaa agagauucga augacgguaa guguucucau   2160
gaagcaggag gcccuugucg ugggauggca uuuggucuca ggcagcacca cacugggugc   2220
gucuccaguc aucuguaaga gcuugcucca gauucugaug cauacggcua uauugguuua   2280
uguagucagu ugcauucauu aaaucaacuu uaucauaugc ucuuuuaaau guuugguuua   2340
uauauuuucu uuaaaaaucc ugggcuggca cauugacugg gaaaccugag ugagacccag   2400
caacugcuuc ucucccuucu cucuccugag gugaagcuuu uccagguuuu guugaagaga   2460
uaccugccag cacuucugca agcugaaauu uacagaagca aauucaccag aagggaaaca   2520
ucucaggcca acauaggcaa augaaaaggg cuauuaaaau auuuuuacac cuuugaaaau   2580
ugcaggcuug guacaaagag gucugucauc uucccccugg gauauaagau gaucuagcuc   2640
ccgguagagg aucaccggug acaacuauag caguuguauu guguaacaag uacugcuccc   2700
agcagcaauu agggagaaaa cuagucuaaa uuauuucaac uggaaaaaag aaaaaagagu   2760
ccucuucuuu ucccagccuu uugcagaaca caguagacag aacugccacc uucaauuggu   2820
acuuuauucu uugcugcugu uuuuguauaa aaugaccuau cccacguuuu ugcaugaauu   2880
uauagcagga aaaaucaagg gauuuccuau ggaaguccug cuuuauucca ggugaaggga   2940
aggaagugua uauacuuuug gcaagucaua cagcucaaau gugaugagau uucugauguu   3000
agagggagau ggagaggcuu ccugaugccu caucugcagg guccugugcc ucugaaguuc   3060
uagccaugag guuuccaggu aggacagcug cucccccaagc cuccugagga cacaggaaga   3120
gacggaagga gcaccuugac agacuugugu gagucuucuc gaaggagggu ugacucagaa   3180
cccagagaca auacaaaacc ccucacuucc ucugagaggg ccaaaugcug ugagucugaa   3240
guaugugccu ggugugaaau gaucuauggc cuguuucuua cacaggaagc ccccugaacc   3300
uccuguacau guguucaugu ucccagccag cucugagacc caggaaccaa auauuccauu   3360
uuggcuucug cuagagcagu caugguuccu cuccuaaaag ccaugggcag caguuuccga   3420
gggccugcau gauccaccug cugcacgauc cuaugagggc uuccuguggc acacagcccu   3480
cugggugcuu gggaacuagc uucaggcaca gccugauucu ggugauccag ugaucuaugg   3540
aagucguguc uuacuccagg ugaaggggga aaaaaaaagc cuauacuuug gcagguuaug   3600
aacuuugaau gugaugaaau gacacguuug gcugcauuug gauggugucu uagaacccuc   3660
auugcucaga ccugaaggcu acuucuagga gcaugaaguu ugaguuuugu guuuuuccaa   3720
aggauacuuc cuuggcccuu uuucuuuauu gacuagacca ccagaggagg augugugggga   3780
uuguaggcaa acccaccugu ggcaucacug aaaauaaauu ugaucauacc uaagagguua   3840
ggaaauggug ccauucccac cuuagagugc uacauaggug cuuugggcgu auguaacauu   3900
aguguccuuc cuugaagcca caagcuaguu uucuuaguuu uaaaauccug uuguaugaau   3960
ggcauuugua uauuaaaaca cuuuuuuaaa ggacaguuga aaagggcaag aggaaaccag   4020
ggcaguucua gaggagugcu ggugacugga uagcaguuuu aaguggcguu caccuaguca   4080
acacgaccgc guguguugcc ccugcccugg gcucccccgcc augacaucuu caccuugcag   4140
```

cuugugcuga gacugaccca agugcagcua gcacugggac acagauccuu gucuucagca 4200
ccuuccaagg agccaacuuu uauucccuuu ccucucuccc cuccccaccu cgcuucuucc 4260
caauuuagua acuuagaugc uuccagcaca uacguaggua gcuaccccag ccgguuugga 4320
uuacaggccu gugcuggaac aucaucucag uuggccaccu uccuggcagg cuguagaccu 4380
gacauuuuga gacaagccua gagucaggag cagggacuuu gacucuuagg aagagcacac 4440
augagggcaa ggcugcuggc agacgucucc auuguccuua uguugucugu guuguauuuu 4500
uuuuuuuuua uugaccaugg ugauuauuuu uuuaaaccau cguuaaauaua cugaagugag 4560 cuauagcaca uaucaugugc uuaguuuguu uauuuuucuc caucucccu uggcuuccua 4620 gaguuuggac auauuccagg cuaaaugcuu uuacucaaga cuacagaaag guuugaagua 4680
gugugugcau ggcaugcacg uauguaagua aucuggggaa gaagcaaaga ucuguuucau 4740
ucuuagccuc aggccucaug agggucucca cagggccgga gcucagguua caccacuccu 4800
ucguccuuac aggagaugua gggagaagaa ucugcaggcu gcuuguagga cuguucacca 4860
agggggauac cagcagcaag agagugcacc cguuuagccc uggacccugu uucuuacugu 4920
gugacuuggc uagaguuggg aguuccccca aaauaaacgu guccccauuu uaccagaacc 4980
aaaccucaac acagcgaagc uguacugucu uugugugca aagauguucc cuuguaggcc 5040
ccuuucaggu aaccgucuuc acaauguauu uucaucacag uuuaaggagc aucagccgcu 5100
ucucaagugg guagggaaag cagaaaaacg uacgcaagag gacauggauc caaaaugaug 5160
augaagcauc ucccaugggg aggugauggu ggggagauga ugggcuaaac aggcaacuuu 5220
ucaaaaacac agcuaucaua gaaaagaaac uugccucaug uaaacuggau ugagaaauuc 5280
ucagugauuc ugcaauggau uuuuuuuuaa ugcagaagua auguauacuc uaguauucug 5340
guguuuuuau auuuauguaa uaauuucuua aaaccauuca gacagauaac uauuuaauuu 5400
uuuuuaagaa aguuggaaag gucucuccuc ccaaggacag uggcuggaag aguuggggca 5460
cagccaguuc ugaauguugg uggagggugu aguggcuuuu uggcucagca uccagaaaca 5520
ccaaaccagg cuggcuaaac aaguggccgc guguaaaaac agacagcucu gagucaaauc 5580
ugggcccuuc cacaaggguc cucugaacca agccccacuc ccuugcuagg ggugaaagca 5640
uuacagagag auggagccau cuauccaaga agccuucacu caccuucacu gcugcuguug 5700
caacucggcu guucuggacu cugaugugug uggagggaug gggaauagaa cauugacugu 5760
guugauuacc uucacuauuc ggccagccug accuuuuaau aacuuuguaa aaagcaugua 5820
uguauuuaua guguuuuaga uuuuucuaac uuuuauaucu uaaaagcaga gcaccuguuu 5880
aagcauugua ccccuauugu uaaagauuug uguccucuca uuccccucucu uccucuugua 5940 agugcccuuc uaauaaacuu uucauggaaa agcuccugug ccaggagcuc agucuga 5997

<210> SEQ ID NO 107
<211> LENGTH: 5808
<212> TYPE: RNA
<213> ORGANISM: HUMAN

<400> SEQUENCE: 107
acaaacaugu cuugccugca cccuaggcaa acguggaaag gcgcagcucu gguacaccgg 60
aaagcauggu ggaugggggag gucccuggau ggccgguugc aggugucca ucggaagggg 120 cucccucaug ucaucuacug ccgccugugg cgauggccag accugcacag ccaccacgag 180
cuacgggcca uggagcugug ugaguucgcc uucaauauga agaaggacga ggucugcgug 240
aaucccuacc acuaccagag aguagagaca ccaguucuac cuccuguguu ggugccacgc 300

-continued

```
cacacagaga ucccggccga guucccccca cuggacgacu acagccauuc cauccccgaa    360
aacacuaacu uccccgcagg caucgagccc cagagcaaua uuccagagac cccacccccu    420
ggcuaccuga gugaagaugg agaaaccagu gaccaccaga ugaaccacag cauggacgca    480
gguucuccaa accuaucccc gaauccgaug uccccagcac auaauaacuu ggaccugcag    540
ccaguuaccu acugcgagcc ggccuucugg ugcuccaucu ccuacuacga gcugaaccag    600
cgcgucgggg agacauucca cgccucgcag ccauccauga cuguggaugg cuucaccgac    660
cccuccaauu cggagcgcuu cugccuaggg cugcucucca augucaacag gaaugcagca    720
guggagcuga cacggagaca caucggaaga ggcgugcggc ucuacuacau cggaggggag    780
gucuucgcag agugccucag ugacagcgcu auuuuugucc agucucccaa cuguaaccag    840
cgcuauggcu ggcacccggc caccgucugc aagaucccac caggaugcaa ccugaagauc    900
uucaacaacc aggaguucgc ugcccuccug gcccagucgg ucaaccaggg cuuugaggcu    960
gucuaccagu ugacccgaau gugcaccauc cgcaugagcu ucgucaaagg cuggggagcg   1020
gaguacagga gacagacugu gaccaguacc cccugcugga uugagcugca ccugaauggg   1080
ccuuugcagu ggcuugacaa gguccucacc cagaugggcu ccccaagcau ccgcuguucc   1140
agugugucuu agagacauca aguaugguag gggagggcag gcuuggggaa aauggccaug   1200
caggaggugg agaaaauugg aacucuacuc aacccauugu ugucaaggaa gaagaaaucu   1260
uucucccuca acugaagggg ugcacccacc uguuuucuga aacacacgag caaacccaga   1320
gguggauguu augaacagcu gugucugcca aacacauuua cccuuuggcc ccacuuugaa   1380
gggcaagaaa uggcgucugc ucugguggcu uaagugagca gaacagguag uauuacacca   1440
ccggccccccu cccccagac ucuuuuuuug agugacagcu uucugggaug ucacagucca   1500
accagaaaca ccccucuguc uaggacugca guguggaguu caccuuggaa gggcguucua   1560
gguaggaaga gcccgcaggg ccaugcagac cucaugccca gcucucugac gcuugugaca   1620
gugccucuuc cagugaacau ucccagccca gccccgcccc gccccgcccc accacuccag   1680
cagaccuugc cccuugugag cuggauagac uugggauggg gagggaggga guuuugucug   1740
ucucccuccc cucucagaac auacugauug ggaggugcgu guucagcaga accugcacac   1800
aggacagcgg gaaaaaucga ugagcgccac cucuuuaaaa acucacuuac guuuguccuu   1860
uuucacuuug aaaaguugga aggaucugcu gaggcccagu gcauaugcaa uguauagugu   1920
cuauuaucac auuaaucuca aagagauucg aaugacggua aguguucuca ugaagcagga   1980
ggcccuuguc gugggauggc auuuggucuc aggcagcacc acacugggug cgucuccagu   2040
caucuguaag agcuugcucc agauucugau gcauacggcu auauugguuu auguagucag   2100
uugcauucau uaaaucaacu uuaucauaug cucuuuuaaa uguuugguuu auauauuuuc   2160
uuuaaaaauc cugggcuggc acauugacug ggaaaccuga gugagaccca gcaacugcuu   2220
cucucccuuc ucucuccuga ggugaagcuu uuccagguuu uguugaagag auaccugcca   2280
gcacuucugc aagcugaaau uuacagaagc aaauucacca gaagggaaac aucucaggcc   2340
aacauaggca aaugaaaagg gcuauuaaaa uauuuuuaca ccuuugaaaa uugcaggcuu   2400
gguacaaaga ggucugucau cuuccccccug ggauauaaga ugaucuagcu cccgguagag   2460
gaucaccggu gacaacuaua gcaguuguau uguguaacaa guacugcucc cagcagcaau   2520
uagggagaaa acuagucuaa auuauuucaa cuggaaaaaa gaaaaaagag uccucuucuu   2580
uucccagccu uuugcagaac acaguagaca gaacugccac cuucaauugg uacuuuauuc   2640
uuugcugcug uuuuuguaua aaaugaccua ucccacguuu uugcaugaau uuauagcagg   2700
```

-continued

```
aaaaaucaag ggauuuccua uggaaguccu gcuuuauucc aggugaaggg aaggaagugu   2760
auauacuuuu ggcaagucau acagcucaaa ugugaugaga uuucugaugu uagagggaga   2820
uggagaggcu uccugaugcc ucaucugcag gguccugugc cucugaaguu cuagccauga   2880
gguuuccagg uaggacagcu gcucccccaag ccuccugagg acacaggaag agacggaagg   2940
agcaccuuga cagacuugug ugagucuucu cgaaggaggg uugacucaga acccagagac   3000
aauacaaaac cccucacuuc cucugagagg gccaaaugcu gugagucuga aguaugugcc   3060
uggugugaaa ugaucuaugg ccuguuucuu acacaggaag cccccugaac cuccuguaca   3120
uguguucaug uucccagcca gcucugagac ccaggaacca aauauuccau uuuggcuucu   3180
gcuagagcag ucaugguucc ucuccuaaaa gccaugggca gcaguuuccg agggccugca   3240
ugauccaccu gcugcacgau ccuaugaggg cuuccugugg cacacagccc ucugggugcu   3300
ugggaacuag cuucaggcac agccugauuc uggugaucca gugaucuaug gaagucgugu   3360
cuuacuccag gugaaggggg aaaaaaaaag ccuauacuuu ggcagguuau gaacuuugaa   3420
ugugaugaaa ugacacguuu ggcugcauuu ggauggugc uuagaacccu cauugcucag   3480
accugaaggc uacuucuagg agcaugaagu uugaguuuug uguuuuucca aaggauacuu   3540
ccuuggcccu uuuucuuuau ugacuagacc accagaggag gauguguggg auuguaggca   3600
aacccaccug uggcaucacu gaaaauaaau uugaucauac cuaagagguu aggaaauggu   3660
gccauuccca ccuuagagug cuacauaggu gcuuugggcg uauguaacau uaguguccuu   3720
ccuugaagcc acaagcuagu uuucuuaguu uuaaaauccu guuguaugaa uggcauuugu   3780
auauuaaaac acuuuuuuaa aggacaguug aaaagggcaa gaggaaacca gggcaguucu   3840
agaggagugc uggugacugg auagcaguuu uaaguggcgu ucaccuaguc aacacgaccg   3900
cgugguuugc cccugcccug ggcuccccgc caugacaucu ucaccuugca gcuugugcug   3960
agacugaccc aagugcagcu agcacuggga cacagauccu ugucuucagc accuuccaag   4020
gagccaacuu uuauucccuu uccucucucc ccuccccacc ucgcuucuuc ccaauuuagu   4080
aacuuagaug cuuccagcac auacguaggu agcuacccca gccgguuugg auuacaggcc   4140
ugugcuggaa caucaucuca guuggccacc uuccuggcag gcuguagacc ugacauuuug   4200
agacaagccu agagucagga gcagggacuu ugacucuuag gaagagcaca caugagggca   4260
aggcugcugg cagacgucuc cauuguccuu auguugucug uguuguauuu uuuuuuuuuu   4320
auugaccaug gugauuauuu uuuuaaacca ucguuaauau acugaaguga gcuauagcac   4380
auaucaugug cuuaguuugu uuauuuuucu ccaucucccc uuggcuuccu agaguuugga   4440
cauauuccag gcuaaaugcu uuuacucaag acuacagaaa gguuugaagu agugugugca   4500
uggcaugcac guauguaagu aaucugggga agaagcaaag aucuguuuca uucuuagccu   4560
caggccucau gagggucucc acagggccgg agcucagguu acaccacucc uucguccuua   4620
caggagaugu agggagaaga aucugcaggc ugcuuguagg acuguucacc aaggggggaua   4680
ccagcagcaa gagagugcac ccguuuagcc cuggacccug uuucuuacug ugugacuugg   4740
cuagaguugg gaguuccccc aaaauaaacg uguccccauu uuaccagaac caaaccucaa   4800
cacagcgaag cuguacuguc uuugugugc aaagauguuc ccuuguaggc cccuuucagg   4860
uaaccgucuu cacaauguau uuucaucaca guuuaaggag caucagccgc uucucaagug   4920
gguagggaaa gcagaaaaac guacgcaaga ggacauggau ccaaaaugau gaugaagcau   4980
cucccauggg gaggugaugg uggggagaug augggcuaaa caggcaacuu uucaaaaaca   5040
cagcuaucau agaaaagaaa cuugccucau guaaacugga uugagaaauu cucagugauu   5100
```

cugcaaugga uuuuuuuuua augcagaagu aauguauacu cuaguauucu gguguuuuua 5160
uauuuaugua auaauuucuu aaaaccauuc agacagauaa cuauuuaauu uuuuuuaaga 5220
aaguuggaaa ggucucuccu cccaaggaca guggcuggaa gaguuggggc acagccaguu 5280
cugaauguug guggagggug uaguggcuuu uuggcucagc auccagaaac accaaaccag 5340
gcuggcuaaa caaguggccg cguguaaaaa cagacagcuc ugagucaaau cugggcccuu 5400
ccacaagggu ccucugaacc aagccccacu cccuugcuag gggugaaagc auuacagaga 5460
gauggagcca ucuauccaag aagccuucac ucaccuucac ugcugcuguu gcaacucggc 5520
uguucuggac ucugaugugu guggagggau ggggaauaga acauugacug uguugauuac 5580
cuucacuauu cggccagccu gaccuuuuaa uaacuuugua aaaagcaugu auguauuuau 5640
aguguuuuag auuuuucuaa cuuuuauauc uuaaaagcag agcaccuguu uaagcauugu 5700
accccuauug uuaaagauuu guguccucuc auucccucuc uuccucuugu aagugcccuu 5760
cuaauaaacu uuucauggaa aagcuccugu gccaggagcu cagucuga 5808

<210> SEQ ID NO 108
<211> LENGTH: 5441
<212> TYPE: RNA
<213> ORGANISM: HUMAN

<400> SEQUENCE: 108
cuucucagau ccuuugcggg uagcccuggc gucccgcgga gaccccaccc ccuggcuacc 60
ugagugaaga uggagaaacc agugaccacc agaugaacca cagcauggac gcagguucuc 120
caaaccuauc cccgaauccg auguccccag cacauaauaa cuuggaccug cagccaguua 180
ccuacugcga gccggccuuc uggugcucca ucuccuacua cgagcugaac cagcgcgucg 240
gggagacauu ccacgccucg cagccaucca ugacugugga uggcuucacc gaccccucca 300
auucggagcg cuucugccua gggcugcucu ccaaugucaa caggaaugca gcaguggagc 360
ugacacggag acacaucgga agaggcgugc ggcucuacua caucggaggg gaggucuucg 420
cagagugccu cagugacagc gcuauuuuug uccagucucc caacuguaac cagcgcuaug 480
gcuggcaccc ggccaccguc ugcaagaucc caccaggaug caaccugaag aucuucaaca 540
accaggaguu cgcugcccuc cuggcccagu cggucaacca gggcuuugag gcugucuacc 600
aguugacccg aaugugcacc auccgcauga gcuucgucaa aggcugggga gcggaguaca 660
ggagacagac ugugaccagu accccccugcu ggauugagcu gcaccugaau gggccuuugc 720
aguggcuuga caagguccuc acccagaugg gcuccccaag cauccgcugu uccagugugu 780
cuuagagaca ucaaguaugg uaggggaggg caggcuuggg gaaaauggcc augcaggagg 840
uggagaaaau uggaacucua cucaacccau uguugucaag gaagaagaaa ucuuucuccc 900
ucaacugaag gggugcaccc accuguuuuc ugaaacacac gagcaaaccc agagguggau 960
guuaugaaca gcugugucug ccaaacacau uuacccuuug gccccacuuu gaagggcaag 1020
aaauggcguc ugcucuggug gcuuaaguga gcagaacagg uaguauuaca ccaccggccc 1080
ccucccccca gacucuuuuu uugagugaca gcuuucuggg augucacagu ccaaccagaa 1140
acaccccucu gucuaggacu gcagugugga guucaccuug gaagggcguu cuagguagga 1200
agagcccgca gggccaugca gaccucaugc ccagcucucu gacgcuugug acagugccuc 1260
uuccagugaa cauucccagc ccagccccgc cccgccccgc cccaccacuc cagcagaccu 1320
ugccccuugu gagcuggaua gacuugggau ggggagggag ggaguuuugu cugucucccu 1380
ccccucucag aacauacuga uugggaggug cguguucagc agaaccugca cacaggacag 1440

-continued

```
cgggaaaaau cgaugagcgc caccucuuua aaaacucacu uacguuuguc cuuuuucacu   1500
uugaaaaguu ggaaggaucu gcugaggccc agugcauaug caauguauag ugucuauuau   1560
cacauuaauc ucaaagagau ucgaaugacg guaaguguuc ucaugaagca ggaggcccuu   1620
gucgugggau ggcauuuggu cucaggcagc accacacugg gugcgucucc agucaucugu   1680
aagagcuugc uccagauucu gaugcauacg gcuauauugg uuuauguagu caguugcauu   1740
cauuaaauca acuuuaucau augcucuuuu aaauguuugg uuuauauauu uucuuuaaaa   1800
auccugggcu ggcacauuga cugggaaacc ugagugagac ccagcaacug cuucucuccc   1860
uucucucucc ugaggugaag cuuuuccagg uuuuguugaa gagauaccug ccagcacuuc   1920
ugcaagcuga aauuuacaga agcaaauuca ccagaaggga aacaucucag gccaacauag   1980
gcaaaugaaa agggcuauua aaauauuuuu acaccuuuga aaauugcagg cuugguacaa   2040
agaggucugu caucuucccc cugggauaua agaugaucua gcucccggua gaggaucacc   2100
ggugacaacu auagcaguug uauuguguaa caaguacugc ucccagcagc aauuagggag   2160
aaaacuaguc uaaauuauuu caacuggaaa aaagaaaaaa gaguccucuu cuuuucccag   2220
ccuuuugcag aacacaguag acagaacugc caccuucaau ugguacuuua uucuuugcug   2280
cuguuuuugu auaaaaugac cuaucccacg uuuuugcaug aauuuauagc aggaaaaauc   2340
aagggauuuc cuauggaagu ccugcuuuau uccaggugaa gggaaggaag uguauauacu   2400
uuuggcaagu cauacagcuc aaaugugaug agauuucuga uguuagaggg agauggagag   2460
gcuuccugau gccucaucug cagggucccug ugccucugaa guucuagcca ugagguuucc   2520
agguaggaca gcugcucccc aagccuccug aggacacagg aagagacgga aggagcaccu   2580
ugacagacuu gugugagucu ucucgaagga ggguugacuc agaacccaga gacaauacaa   2640
aaccccucac uuccucugag agggccaaau gcugugaguc ugaaguaugu gccuggugug   2700
aaaugaucua uggccuguuu cuuacacagg aagcccccug aaccuccugu acauguguuc   2760
auguucccag ccagcucuga gacccaggaa ccaaauauuc cauuuuggcu ucugcuagag   2820
cagucauggu uccucuccua aaagccaugg gcagcaguuu ccgagggccu gcaugaucca   2880
ccugcugcac gauccuauga gggcuuccug uggcacacag cccucugggu gcuugggaac   2940
uagcuucagg cacagccuga uucuggugau ccagugaucu auggaagucg ugucuuacuc   3000
caggugaagg gggaaaaaaa aagccuauac uuuggcaggu uaugaacuuu gaaugugaug   3060
aaaugacacg uuuggcugca uuuggauggu gucuuagaac ccucauugcu cagaccugaa   3120
ggcuacuucu aggagcauga aguuugaguu uuguguuuuu ccaaaggaua cuuccuuggc   3180
ccuuuuucuu uauugacuag accaccagag gaggaugugu gggauuguag gcaaacccac   3240
cuguggcauc acugaaaaua aauuugauca uaccuaagag guuaggaaau gguggccauuc   3300
ccaccuuaga gugcuacaua ggugcuuugg gcguauguaa cauuaguguc cuuccuugaa   3360
gccacaagcu aguuuucuua guuuuaaaau ccuguuguau gaauggcauu uguauauuaa   3420
aacacuuuuu uaaaggacag uugaaaaggg caagaggaaa ccagggcagu ucuagaggag   3480
ugcuggugac uggauagcag uuuuaagugg cguucaccua gucaacacga ccgcgugugu   3540
ugccccugcc cugggcuccc cgccaugaca ucuucaccuu gcagcuugug cugagacuga   3600
cccaagugca gcuagcacug ggacacagau ccuugucuuc agcaccuucc aaggagccaa   3660
cuuuuauucc cuuuccucuc uccccucccc accucgcuuc uucccaauuu aguaacuuag   3720
augcuuccag cacauacgua gguagcuacc ccagccgguu uggauuacag gccugugcug   3780
gaacaucauc ucaguuggcc accuuccugg caggcuguag accugacauu uugagacaag   3840
```

ccuagaguca ggagcaggga cuuugacucu uaggaagagc acacaugagg gcaaggcugc 3900
uggcagacgu cuccauuguc cuuauguugu cuguguugua uuuuuuuuuu uuuauugacc 3960
auggugauua uuuuuuuaaa ccaucguuaa uauacugaag ugagcuauag cacauaucau 4020
gugcuuaguu uguuuauuuu ucuccaucuc cccuuggcuu ccuagaguuu ggacauauuc 4080
caggcuaaau gcuuuuacuc aagacuacag aaagguuuga aguagugugu gcauggcaug 4140
cacguaugua aguaaucugg ggaagaagca aagaucuguu ucauucuuag ccucaggccu 4200
caugaggguc uccacagggc cggagcucag guuacaccac uccuucgucc uuacaggaga 4260
uguagggaga agaaucugca ggcugcuugu aggacuguuc accaaggggg auaccagcag 4320
caagagagug cacccguuua gcccuggacc cuguuucuua cugugugacu uggcuagagu 4380
ugggaguucc cccaaaauaa acgugucccc auuuuaccag aaccaaaccu caacacagcg 4440
aagcuguacu gucuuugugu ggcaaagaug uucccuugua ggccccuuuc agguaaccgu 4500
cuucacaaug uauuuucauc acaguuuaag gagcaucagc cgcuucucaa gugggguaggg 4560 aaagcagaaa aacguacgca agaggacaug gauccaaaau gaugaugaag caucucccau 4620
ggggagguga uggugggggag augaugggcu aaacaggcaa cuuuucaaaa acacagcuau 4680
cauagaaaag aaacuugccu cauguaaacu ggauugagaa auucucagug auucugcaau 4740
ggauuuuuuu uuaaugcaga aguaauguau acucuaguau ucugguguuu uuauauuuau 4800
guaauaauuu cuuaaaacca uucagacaga uaacuauuua auuuuuuuua agaaaguugg 4860
aaaggucucu ccucccaagg acaguggcug gaagaguugg ggcacagcca guucugaaug 4920
uugguggagg guguaguggc uuuuuggcuc agcauccaga aacaccaaac caggcuggcu 4980
aaacaagugg ccgcguguaa aaacagacag cucugaguca aaucugggcc cuuccacaag 5040
gguccucuga accaagcccc acucccuugc uaggggugaa agcauuacag agagauggag 5100
ccaucuaucc aagaagccuu cacucaccuu cacugcugcu guugcaacuc ggcuguucug 5160
gacucugaug uguguggagg gaugggggaau agaacauuga cuguguugau uaccuucacu 5220
auucggccag ccugaccuuu uaauaacuuu guaaaaagca uguauguauu uauaguguuu 5280
uagauuuuuc uaacuuuuau aucuuaaaag cagagcaccu guuuaagcau uguaccccua 5340
uuguuaaaga uuugugucu cucauucccu cucuuccucu uguaagugcc cuucuaauaa 5400
acuuuucaug gaaaagcucc ugugccagga gcucagucug a 5441

<210> SEQ ID NO 109
<211> LENGTH: 6475
<212> TYPE: RNA
<213> ORGANISM: HUMAN

<400> SEQUENCE: 109
ggcgaggcga gguuugcugg ggugaggcag cggcgcggcc gggccgggcc gggccacagg 60
cgguggcggc gggaccaugg aggcggcggu cgcugcuccg cgucccccggc ugcuccuccu 120 cgugcuggcg gcggcggcgg cggcggcggc ggcgcugcuc ccgggggcga cggcguuaca 180
guguuucugc caccucugua caaaagacaa uuuuacuugu gugacagaug ggcucugcuu 240
ugucucuguc acagagacca cagacaaagu uauacacaac agcaugugua uagcugaaau 300
ugacuuaauu ccucgagaua ggccguuugu augugcaccc ucuucaaaaa cugggucugu 360
gacuacaaca uauugcugca aucaggacca uugcaauaaa auagaacuuc caacuacugu 420
aaagucauca ccuggccuug guccugugga acuggcagcu gucauugcug gaccagugug 480
cuucgucugc aucucacuca uguugauggu cuauaucugc cacaaccgca cugucauuca 540

-continued

```
ccaucgagug ccaaaugaag aggacccuuc auuagaucgc ccuuuuauuu cagaggguac     600
uacguugaaa gacuuaauuu augauaugac aacgucaggu ucuggcucag guuuaccauu     660
gcuuguucag agaacaauug cgagaacuau uguguuacaa gaaagcauug gcaaaggucg     720
auuuggagaa guuuggagag gaaaguggcg gggagaagaa guugcuguua agauauucuc     780
cucuagagaa gaacguucgu gguuccguga ggcagagauu uaucaaacug uaauguuacg     840
ucaugaaaac auccugggau uuauagcagc agacaauaaa gacaauggua cuuggacuca     900
gcucugguug gugucagauu aucaugagca uggaucccuu uuugauuacu uaaacagaua     960
cacaguuacu guggaaggaa ugauaaaacu ugcucugucc acggcgagcg gucuugccca    1020
ucuucacaug gagauuguug guacccaagg aaagccagcc auugcucaua gagauuugaa    1080
aucaaagaau aucuugguaa agaagaaugg aacuugcugu auugcagacu uaggacuggc    1140
aguaagacau gauucagcca cagauaccau ugauauugcu ccaaaccaca gagugggaac    1200
aaaaagguac auggccccug aaguucucga ugauuccaua aauaugaaac auuuugaauc    1260
cuucaaacgu gcugacaucu augcaauggg cuuaguauuc ugggaaauug cucgacgaug    1320
uuccauuggu ggaauucaug aagauuacca acugccuuau uaugaucuug uaccuucuga    1380
cccaucaguu gaagaaauga gaaaaguugu uugugaacag aaguuaaggc caaauauccc    1440
aaacagaugg cagagcugug aagccuugag aguaauggcu aaaauuauga gagaauguug    1500
guaugccaau ggagcagcua ggcuuacagc auugcggauu aagaaaacau uaucgcaacu    1560
cagucaacag gaaggcauca aaauguaauu cuacagcuuu gccugaacuc uccuuuuuuc    1620
uucagaucug cuccugggguu uuaauuuggg aggucaauug uucuaccuca cugagaggga    1680
acagaaggau auugcuuccu uuugcagcag uguaauaaag ucaauuaaaa acuucccagg    1740
auuucuuugg acccaggaaa cagccaugug gguccuuucu gugcacuaug aacgcuucuu    1800
ucccaggaca gaaaaugugu agucuaccuu uauuuuuuau uaacaaaacu uguuuuuuaa    1860
aaagaugauu gcuggucuua acuuuaggua acucugcugu gcuggagauc aucuuuaagg    1920
gcaaaggagu uggauugcug aauuacaaug aaacaugucu uauuacuaaa gaaagugauu    1980
uacuccuggu uaguacauuc ucagaggauu cugaaccacu agaguuuccu ugauucagac    2040
uuugaaugua cuguucuaua guuuuucagg aucuuaaaac uaacacuuau aaaacucuua    2100
ucuugagucu aaaaaugacc ucauauagua gugaggaaca uaauucaugc aauuguauuu    2160
uguauacuau uauuguucuu ucacuuauuc agaacauuac augccuucaa aaugggaaug    2220
uacuauacca guaagugcca cuucuguguc uuucuaaugg aaaugaguag aauugcugaa    2280
agucucuaug uuaaaaccua uaguguuuga auucaaaaag cuuauuuauc uggguaaccc    2340
aaacuuuuuc uguuuuguuu uuggaagggu uuuuguggua ugucauuugg uauucuauuc    2400
ugaaaaugcc uuucuccuac caaaaugugc uuaagccacu aaagaaauga aguggcauua    2460
auuaguaaau uauuagcaug gucauguuug aauauucuca caucaagcuu uugcauuuua    2520
auuguguugu cuaaguauac uuuuaaaaaa ucaaguggca cucuagaugc uuauaguacu    2580
uuaauauuug uagcauacag acuaauuuuu cuaaaaggga aagucugucu agcugcuugu    2640
gaaaaguuau gugguauucu guaagccauu uuuuucuuua ucuguucaaa gacuuauuuu    2700
uuaagacaug aauuacauuu aaaauuagaa uaugguuaau auuaaauaau aggccuuuuu    2760
cuaggaaggc gaagguaguu aauaauuuga auagauaaca gaugugcaag aaagucacau    2820
uuguuaugua uguaggagua aacguucggu ggauccucug ucuuuguaac ugagguuaga    2880
gcuagugugg uuuugagguc ucacuacacu uugaggaagg cagcuuuuaa uucaguguuu    2940
```

ccuuaugugu gcguacauug caacugcuua cauguaauuu auguaaugca uucagugcac 3000
ccuuguuacu ugggagaggu gguagcuaaa gaacauucug aguauagguu uuucuccauu 3060
uacagauguc uuuggucaaa uauugaaagc aaacuuguca uggucuucuu acauuaaguu 3120
gaaacuagcu uauaauaacu gguuuuuacu uccaaugcua ugaagucucu gcagggcuuu 3180
uacaguuuuc gaaguccuuu uaucacugug aucuuauucu gaggggagaa aaaacuauca 3240
uagcucugag gcaagacuuc gacuuuauag ugcuaucagu uccccgauac agggucagag 3300
uaacccauac aguauuuugg ucaggaagag aaaguggcca uuuacacuga augaguugca 3360
uucugauaau gucuuaucuc uuauacguag aauaaaauug aaagacuauu ugaucuuaaa 3420
accaaaguaa uuuuagaaug agugacauau uacauaggaa uuuaguguca auuucaugug 3480
uuuaaaaaca ucaugggaaa aaugcuuaga gguuacuauu uugacuacaa aguugaguuu 3540
uuuucuguag uuaccauaau uucauugaag caaaugaaug aguuugagag guuuguuuuu 3600
auaguugugu uguauuacuu guuuaauaau aaucucuaau ucugugauca gguacuuuuu 3660
uugugggggu uuuuuuuuug uuuuuuuuuu uuuguuguug uuuuugggcc auuucuaagc 3720
cuaccagauc ugcuuuauga aauccagggg accaaugcau uuuaucacua aaacuauuuu 3780
uauauaauuu uaagaauaua ccaaaaguug ucugauuuaa aguuguaaua caugauuucu 3840
cacuuucaug uaagguuauc cacuuuugcu gaagauauuu uuuauugaau caaagauuga 3900
guuacaauua uacuuuucuu accuaagugg auaaaaugua cuuuugauga aucagggaau 3960
uuuuuuaaag uuggaguuua guucuaaauu gacuuuacgu auuacugcag uuaauuccuu 4020
uuuuggcuag ggaugguuug auaaaccaca auuggcugau auugaaaaug aaagaaacuu 4080 aaaaggugg auggaucaug auuacugucg auaacugcag auaaauuuga uuagaguaau 4140
aauuuuguca uuuaaaaaca caguuguuua uacugcccau ccuaggaugc ucaccuucca 4200
agauucaacg uggcuaaaac aucuucuggu aaauugugcg uccauauuca uuuugucagu 4260
agccaggaga aaugggaug ggggaaauac gacuuaguga ggcauagaca ucccuggucc 4320
auccuuucug ucuccagcug uuucuuggaa ccugcucucc ugcuugcugg ucccugacgc 4380
agagaccguu gccuccccca cagccguuug acugaaggcu gcucuggaga ccuagaguaa 4440
aacggcugau ggaaguugug ggacccacuu ccauuuccuu cagucauuag agguggaagg 4500
gaggggucuc caaguuugga gauugagcag augaggcuug ggaugcccu gcuuugacuu 4560 cagccaugga ugaggagugg gauggcagca agguggcucc uguggcagug gaguugugcc 4620
agaaacagug gccaguugua ucgccuauaa gacaggguaa ggucugaaga gcugagccug 4680
uaauucugcu guaauaauga uagugcucaa gaagugccuu gaguuggugu acagugccau 4740
ggccaucaag aaucccagau uucagguuuu auuacaaaau guaaguggc acuuggcgau 4800 uuuguaguac augcaugagu uaccuuuuuu cucuaugucu gagaacuguc agauuaaaac 4860
aagauggcaa agagaucguu agagugcaca acaaaaucac uaucccauua gacacaucau 4920
caaaagcuua uuuuuauucu ugcacuggaa gaaucguaag ucaacuguuu cuugaccaug 4980
gcaguguucu ggcuccaaau gguagugauu ccaaauaaug guucuguuaa cacuuuggca 5040
gaaaaugcca gcucagauau uuugagauac uaaggauuau cuuuggacau guacugcagc 5100
uucuugucuc uguuuuggau uacuggaaua cccaugggcc cucucaagag ugcuggacuu 5160
cuaggacauu aagaugauug ucaguacauu aaacuuuuca aucccauuau gcaaucuugu 5220
uuguaaaugu aaacuucuaa aaauauggu aauaacauuc aaccuguuua uuacaacuua 5280
aaaggaacuu cagugaauuu guuuuuauuu uuuaacaaga uuugugaacu gaauaucaug 5340
aaccauguuu ugauaccccu uuuucacguu gugccaacgg aauagggugu uugauauuuc 5400
uucauauguu aaggagaugc uucaaaaugu caauugcuuu aaacuuaaau uaccucucaa 5460
gagaccaagg uacauuuacc ucauugugua uauaauguuu aauauuuguc agagcauucu 5520
ccagguuugc aguuuuauuu cuauaaagua uggguauuau guugcucagu uacucaaaug 5580
guacuguauu guuuauauuu guaccccaaa uaacaucguc uguacuucu guuuucugua 5640 uuguauuugu gcaggauucu uuaggcuuua ucaguguaau cucugccuuu uaagauaugu 5700
acagaaaaug uccauauaaa uuuccauuga agucgaauga uacugagaag ccuguaaaga 5760
ggagaaaaaa acauaagcug uguuucccca uaaguuuuuu uaaauuguau auuguauuug 5820
uaguaauauu ccaaaagaau guaaauagga aauagaagag ugaugcuuau guuaaguccu 5880
aacacuacag uagaagaaug gaagcagugc aaauaaauua cauuuuuccc aagugccagu 5940
ggcauauuuu aaaauaaagu guauacguug gaaugaguca ugccauaugu aguugcugua 6000
gauggcaacu agaaccuuug aguuacaaga gucuuuagaa guuuucuaac ccugccuagu 6060
gcaaguuaca auauuauagc guguucgggg agugcccucc ugucugcagg ugugucucug 6120
ugccuggggg cuuuucucca caugcuuagg ggugugggguc uuccauuggg gcaugaugga 6180
ccugucuaca ggugaucucu guugccuuug ggucagcaca uuuguuaguc uccugggggu 6240
gaaaacuugg cuuacaagag aacuggaaaa augaugagau gugguacccca aacccuugau 6300 ugacucuggg gaggggcuuu gugaauagga uugcucucac auuaaagaua guuacuucaa 6360
uuugaaggcu ggauuuaggg auuuuuuuuu uuccuuauaa caaagacauc accaggauau 6420
gaagcuuuug uugaaaguug gaaaaaaagu gaaauuaaag acauucccag acaaa 6475

<210> SEQ ID NO 110
<211> LENGTH: 6244
<212> TYPE: RNA
<213> ORGANISM: HUMAN

<400> SEQUENCE: 110
ggcgaggcga gguuugcugg ggugaggcag cggcgcggcc gggccgggcc gggccacagg 60
cgguggcggc gggaccaugg aggcggcggu cgcugcuccg cguccccggc ugcuccuccu 120
cgugcuggcg gcggcggcgg cggcggcggc ggcgcugcuc ccgggggcga cggcguuaca 180
guguuucugc caccucugua caaaagacaa uuuuacuugu gugacagaug ggcucugcuu 240
ugucucuguc acagagacca cagacaaagu uauacacaac agcaugugua uagcugaaau 300
ugacuuaauu ccucgagaua ggccguuugu augugcaccc ucuucaaaaa cugggucugu 360
gacuacaaca uauugcugca aucaggacca uugcaauaaa auagaacuuc caacuacugg 420
uuuaccauug cuuguucaga gaacaauugc gagaacuauu guguuacaag aaagcauugg 480
caaaggucga uuuggagaag uuuggagagg aaaguggcgg ggagaagaag uugcuguuaa 540
gauauucucc ucuagagaag aacguucgug guuccgugag gcagagauuu aucaaacugu 600
aauguuacgu caugaaaaca uccugggauu uauagcagca gacaauaaag acaaugguac 660
uuggacucag cucugguugg ugucagauua ucaugagcau ggaucccuuu uugauuacuu 720
aaacagauac acaguuacug uggaaggaau gauaaaacuu gcucugucca cggcgagcgg 780
ucuugcccau cuucacaugg agauuguugg uacccaagga aagccagcca uugcucauag 840
agauuugaaa ucaaagaaua ucuugguaaa gaagaaugga acuugcugua uugcagacuu 900
aggacuggca guaagacaug auucagccac agauaccauu gauauugcuc caaaccacag 960
agugggaaca aaaagguaca uggccccuga aguucucgau gauuccauaa auaugaaaca 1020
uuuugaaucc uucaaacgug cugacaucua ugcaaugggc uuaguauucu gggaaauugc 1080
ucgacgaugu uccauuggug gaauucauga agauuaccaa cugccuuauu augaucuugu 1140
accuucugac ccaucaguug aagaaaugag aaaaguuguu ugugaacaga aguuaaggcc 1200
aaauauccca aacagauggc agagcuguga agccuugaga guaauggcua aaauuaugag 1260
agaauguugg uaugccaaug gagcagcuag gcuuacagca uugcggauua agaaaacauu 1320
aucgcaacuc agucaacagg aaggcaucaa aauguaauuc uacagcuuug ccugaacucu 1380
ccuuuuuucu ucagaucugc uccuggguuu uaauuuggga ggucaauugu ucuaccucac 1440
ugagagggaa cagaaggaua uugcuuccuu uugcagcagu guaauaaagu caauuaaaaa 1500
cuucccagga uuucuuugga cccaggaaac agccaugugg guccuuucug ugcacuauga 1560
acgcuucuuu cccaggacag aaaaugugua gucuaccuuu auuuuuuauu aacaaaacuu 1620
guuuuuuaaa aagaugauug cuggucuuaa cuuuagguaa cucugcugug cuggagauca 1680
ucuuuaaggg caaaggaguu ggauugcuga auuacaauga aacaugucuu auuacuaaag 1740
aaagugauuu acuccugguu aguacauucu cagaggauuc ugaaccacua gaguuuccuu 1800
gauucagacu uugaauguac uguucuauag uuuuucagga ucuuaaaacu aacacuuaua 1860
aaacucuuau cuugagucua aaaaugaccu cauauaguag ugaggaacau aauucaugca 1920
auuguauuuu guauacuauu auuguucuuu cacuuauuca gaacauuaca ugccuucaaa 1980
augggauugu acuauaccag uaagugccac uucugugucu uucuaaugga aaugaguaga 2040
auugcugaaa gucucuaugu uaaaaccuau aguguuugaa uucaaaaagc uuauuuaucu 2100
ggguaaccca aacuuuuucu guuuuguuuu uggaagggu uuuguggguau gucauuuggu 2160
auucuauucu gaaaaugccu uucuccuacc aaaaugugcu uaagccacua aagaaaugaa 2220
guggcauuaa uuaguaaauu auuagcaugg ucauguuuga auauucucac aucaagcuuu 2280
ugcauuuuaa uuguguuguc uaaguauacu uuuaaaaaau caaguggcac ucuagaugcu 2340
uauaguacuu uaauauuugu agcauacaga cuaauuuuuc uaaaagggaa agucugucua 2400
gcugcuugug aaaaguuaug ugguauucug uaagccauuu uuuucuuuau cuguucaaag 2460
acuuauuuuu uaagacauga auuacauuua aaauuagaau augguuaaua uuaaauaaua 2520
ggccuuuuuc uaggaaggcg aagguaguua auaauuugaa uagauaacag augugcaaga 2580
aagucacauu uguuauguau guaggaguaa acguucggug gauccucugu cuuuguaacu 2640
gagguuagag cuaguguggu uuugaggucu cacuacacuu ugaggaaggc agcuuuuaau 2700
ucaguguuuc cuuaugugug cguacauugc aacugcuuac auguaauuua uguaaugcau 2760
ucagugcacc cuuguuacuu gggagaggug guagcuaaag aacauucuga guauagguuu 2820
uucuccauuu acagaugucu uugguccaaau auugaaagca aacuugucau ggucuucuua 2880
cauuaaguug aaacuagcuu auaauaacug guuuuuacuu ccaaugcuau gaagucucug 2940
cagggcuuuu acaguuuucg aaguccuuuu aucacuguga ucuuauucug aggggagaaa 3000
aaacuaucau agcucugagg caagacuucg acuuuauagu gcuaucaguu ccccgauaca 3060
gggucagagu aacccauaca guauuuuggu caggaagaga aaguggccau uuacacugaa 3120
ugaguugcau ucugauaaug ucuuaucucu uauacguaga auaaauuuga aagacuauuu 3180
gaucuuaaaa ccaaaguaau uuuagaauga gugacauauu acauaggaau uuagugucaa 3240
uuucaugugu uuaaaaacau caugggaaaa augcuuagag guuacuauuu ugacuacaaa 3300
guugaguuuu uuucuguagu uaccauaauu ucauugaagc aaaugaauga guuugagagg 3360
uuuguuuuua uaguuguguu guauuacuug uuuaauaaua aucucuaauu cugugaucag 3420

-continued

```
guacuuuuuu uguggggguu uuuuuuuugu uuuuuuuuuu uuguuguugu uuuugggcca   3480
uuucuaagcc uaccagaucu gcuuuaugaa auccagggga ccaaugcauu uuaucacuaa   3540
aacuauuuuu auauaauuuu aagaauauac caaaaguugu cugauuuaaa guuguaaauac  3600
augauuucuc acuuucaugu aagguuaucc acuuuugcug aagauauuuu uuauugaauc   3660
aaagauugag uuacaauuau acuuuucuua ccuaagugga uaaaauguac uuuugaugaa   3720
ucagggaauu uuuuuaaagu uggaguuuag uucuaaauug acuuuacgua uuacugcagu   3780
uaauuccuuu uuuggcuagg gaugguuuga uaaaccacaa uuggcugaua uugaaaauga   3840
aagaaacuua aaagguggga uggaucauga uuacugucga uaacugcaga uaaauuugau   3900
uagaguaaua auuuugucau uuaaaaacac aguuguuuau acugcccauc cuaggaugcu   3960
caccuuccaa gauucaacgu ggcuaaaaca ucuucuggua aauugugcgu ccauauucau   4020
uuugucagua gccaggagaa auggggaugg gggaaauacg acuuagugag gcauagacau   4080
cccuggucca uccuuucugu cuccagcugu uucuuggaac cugcucuccu gcuugcuggu   4140
cccugacgca gagaccguug ccucccccac agccguuuga cugaaggcug cucuggagac   4200
cuagaguaaa acggcugaug gaaguugugg gacccacuuc cauuuccuuc agucauuaga   4260
gguggaaggg aggggucucc aaguuuggag auugagcaga ugaggcuugg gaugccccug   4320
cuuugacuuc agccauggau gaggaguggg auggcagcaa gguggcuccu guggcagugg   4380
aguugugcca gaaacagugg ccaguuguau cgccuauaag acaggguaag gucugaagag   4440
cugagccugu aauucugcug uaauaaugau agugcucaag aagugccuug aguuggugua   4500
cagugccaug gccaucaaga aucccagauu ucagguuuua uuacaaaaug uaagugguca   4560
cuuggcgauu uuguaguaca ugcaugaguu accuuuuuuc ucuaugucug agaacuguca   4620
gauuaaaaca agauggcaaa gagaucguua gagugcacaa caaaaucacu aucccauuag   4680
acacaucauc aaaagcuuau uuuuauucuu gcacuggaag aaucguaagu caacuguuuc   4740
uugaccaugg caguguucug gcuccaaaug guagugauuc caaauaaugg uucuguuaac   4800
acuuuggcag aaaaugccag cucagauauu uugagauacu aaggauuauc uuuggacaug   4860
uacugcagcu ucuugucucu guuuuggauu acuggaauac ccaugggccc ucucaagagu   4920
gcuggacuuc uaggacauua agaugauugu caguacauua aacuuuucaa ucccauuaug   4980
caaucuuguu uguaaaugua aacuucuaaa aauaugguua auaacauuca accuguuuau   5040
uacaacuuaa aaggaacuuc agugaauuug uuuuuauuuu uuaacaagau uugugaacug   5100
aauaucauga accauguuuu gauaccccuu uuucacguug ugccaacgga auaggguguu   5160
ugauauuucu ucauauguua aggagaugcu ucaaaauguc aauugcuuua aacuuaaauu   5220
accucucaag agaccaaggu acauuuaccu cauuguguau auaauguuua auauuuguca   5280
gagcauucuc cagguuugca guuuuauuuc uauaaaguau ggguauuaug uugcucaguu   5340
acucaaaugg uacuguauug uuuauauuug uaccccaaau aacaucgucu guacuuucug   5400
uuuucuguau uguauuugug caggauucuu uaggcuuuau caguguaauc ucugccuuuu   5460
aagauaugua cagaaaaugu ccauauaaau uuccauugaa gucgaaugau acugagaagc   5520
cuguaaagag gagaaaaaaa cauaagcugu guuuccccau aaguuuuuuu aaauuguaua   5580
uuguauuugu aguaauauuc caaaagaaug uaaauaggaa auagaagagu gaugcuuaug   5640
uuaaguccua acacuacagu agaagaaugg aagcagugca aauaaauuac auuuuuccca   5700
agugccagug gcauauuuua aaauaaagug uauacguugg aaugagucau gccauaugua   5760
guugcuguag auggcaacua gaaccuuuga guuacaagag ucuuuagaag uuuucuaacc   5820
```

-continued cugccuagug caaguuacaa uauuauagcg uguucgggga gugcccuccu gucugcaggu 5880
gugucucugu gccugggggc uuuucuccac augcuuaggg guguggggucu uccauugggg 5940 caugauggac cugucuacag gugaucucug uugccuuugg gucagcacau uuguuagucu 6000
ccugggggug aaaacuuggc uuacaagaga acuggaaaaa ugaugagaug ugguccccaa 6060
acccuugauu gacucugggg aggggcuuug ugaauaggau ugcucucaca uuaaagauag 6120
uuacuucaau uugaaggcug gauuuaggga uuuuuuuuuu uccuuauaac aaagacauca 6180
ccaggauaug aagcuuuugu ugaaaguugg aaaaaaagug aaauuaaaga cauucccaga 6240
caaa 6244

<210> SEQ ID NO 111
<211> LENGTH: 4978
<212> TYPE: RNA
<213> ORGANISM: HUMAN

<400> SEQUENCE: 111
gguuuccgga gcugcggcgg cgcagacugg gagggggagc cgggggguucc gacgucgcag 60 ccgagggaac aagccccaac cggauccugg acaggcaccc cggcuuggcg cugucucucc 120
cccucggcuc ggagaggccc uucggccuga gggagccucg ccgcccgucc ccggcacacg 180
cgcagccccg gccucucggc cucugccgga gaaacaguug ggaccccuga uuuuagcagg 240
auggcccaau ggaaucagcu acagcagcuu gacacacggu accuggagca gcuccaucag 300
cucuacagug acagcuuccc aauggagcug cggcaguuuc uggccccuug gauugagagu 360
caagauuggg cauaugcggc cagcaaagaa ucacaugcca cuuugguguu ucauaaucuc 420
cugggagaga uugaccagca guauagccgc uuccugcaag agucgaaugu ucucuaucag 480
cacaaucuac gaagaaucaa gcaguuucuu cagagcaggu aucuugagaa gccaauggag 540
auugcccgga uuguggcccg gugccugugg gaagaaucac gccuucuaca gacugcagcc 600
acugcggccc agcaaggggg ccaggccaac caccccacag cagccguggu gacggagaag 660
cagcagaugc uggagcagca ccuucaggau guccggaaga gagugcagga ucuagaacag 720
aaaaugaaag ugguagagaa ucuccaggau gacuuugauu ucaacuauaa aacccucaag 780
agucaaggag acaugcaaga ucugaaugga aacaaccagu cagugaccag gcagaagaug 840
cagcagcugg aacagaugcu cacugcgcug gaccagaugc ggagaagcau cgugagugag 900
cuggcggggc uuuugucagc gauggaguac gugcagaaaa cucucacgga cgaggagcug 960
gcugacugga agaggcggca acagauugcc ugcauuggag gcccgcccaa caucugccua 1020
gaucggcuag aaaacuggau aacgucauua gcagaaucuc aacuucagac ccgucaacaa 1080
auuaagaaac uggaggaguu gcagcaaaaa guuuccuaca aaggggaccc cauuguacag 1140
caccggccga ugcuggagga gagaaucgug gagcuguuua gaaacuuaau gaaaagugcc 1200
uuuguggugg agcggcagcc cugcaugccc augcauccug accggccccu cgucaucaag 1260
accggcgucc aguucacuac uaaagucagg uugcugguca aauucccuga guugaauuau 1320
cagcuuaaaa uuaaagugug cauugacaaa gacucugggg acguugcagc ucucagagga 1380
ucccggaaau uuaacauucu gggcacaaac acaaaaguga ugaacaugga agaauccaac 1440
aacggcagcc ucucugcaga auucaaacac uugacccuga gggagcagag augugggaau 1500
gggggccgag ccaauuguga ugcuucccug auugugacug aggagcugca ccugaucacc 1560
uuugagaccg agguguauca ccaaggccuc aagauugacc uagagaccca cuccuugcca 1620
guugugguga ucuccaacau cugucagaug ccaaaugccu gggcguccau ccugugguac 1680

-continued

```
aacaugcuga ccaacaaucc caagaaugua aacuuuuuua ccaagccccc aauuggaacc   1740
ugggaucaag uggccgaggu ccugagcugg caguucuccu ccaccaccaa gcgaggacug   1800
agcaucgagc agcugacuac acuggcagag aaacucuugg gaccuggugu gaauuauuca   1860
gggugucaga ucacaugggc uaaauuuugc aaagaaaaca uggcuggcaa gggcuucucc   1920
uucugggucu ggcuggacaa uaucauugac cuugugaaaa aguacauccu ggcccuuugg   1980
aacgaagggu acaucauggg cuuuaucagu aaggagcggg agcgggccau cuugagcacu   2040
aagccuccag gcaccuuccu gcuaagauuc agugaaagca gcaaagaagg aggcgucacu   2100
uucacuuggg uggagaagga caucagcggu aagacccaga uccaguccgu ggaaccauac   2160
acaaagcagc agcugaacaa caugucauuu gcugaaauca ucaugggcua uaagaucaug   2220
gaugcuacca auauccuggu gucuccacug gucuaucucu auccugacau ucccaaggag   2280
gaggcauucg gaaaguauug ucggccagag agccaggagc auccugaagc ugacccaggu   2340
agcgcugccc cauaccugaa gaccaaguuu aucuguguga caccaacgac cugcagcaau   2400
accauugacc ugccgauguc cccccgcacu uuagauucau ugaugcaguu uggaaauaau   2460
ggugaaggug cugaacccuc agcaggaggg caguuugagu cccucaccuu ugacauggag   2520
uugaccucgg agugcgcuac cucccccaug ugaggagcug agaacggaag cugcagaaag   2580
auacgacuga ggcgccuacc ugcauucugc caccccucac acagccaaac cccagaucau   2640
cugaaacuac uaacuuugug guuccagauu uuuuuuaauc uccuacuucu gcuaucuuug   2700
agcaaucugg gcacuuuuaa aaauagagaa augagugaau gugggugauc ugcuuuuauc   2760
uaaaugcaaa uaaggaugug uucucugaga cccaugauca ggggaugugg cgggggggugg   2820
cuagagggag aaaaaggaaa ugucuugugu uguuuuguuc cccugcccuc cuuucucagc   2880
agcuuuuugu uauuguuguu guuguucuua gacaagugcc uccuggugcc ugcggcaucc   2940
uucugccugu uucuguaagc aaaugccaca ggccaccuau agcuacauac uccuggcauu   3000
gcacuuuuua accuugcuga cauccaaaua gaagauagga cuaucuaagc ccuagguuuc   3060
uuuuuaaauu aagaaauaau aacaauuaaa gggcaaaaaa cacuguauca gcauagccuu   3120
ucuguauuua agaaacuuaa gcagccgggc augguggcuc acgccuguaa ucccagcacu   3180
uugggaggcc gaggcggauc auaaggucag gagaucaaga ccauccuggc uaacacggug   3240
aaaccccguc ucuacuaaaa guacaaaaaa uuagcugggu gugguggugg gcgccuguag   3300
ucccagcuac ucgggaggcu gaggcaggag aaucgcuuga accugagagg cggagguugc   3360
agugagccaa aauugcacca cugcacacug cacuccaucc ugggcgacag ucugagacuc   3420
ugucucaaaa aaaaaaaaaa aaaaaagaaa cuucaguuaa cagccuccuu ggugcuuuaa   3480
gcauucagcu uccuucaggc ugguaauuua uauaaucccu gaaacgggcu ucaggucaaa   3540
cccuuaagac aucugaagcu gcaaccuggc cuuuggugu u gaaauaggaa gguuuaagga   3600
gaaucuaagc auuuuagacu uuuuuuuaua aauagacuua uuuuccuuug uaauguauug   3660
gccuuuuagu gaguaaggcu gggcagaggg ugcuuacaac cuugacuccc uuucucccug   3720
gacuugaucu gcuguuucag aggcuagguu guuucugugg gugccuuauc agggcuggga   3780
uacuucugau ucuggcuucc uuccugcccc acccucccga ccccaguccc ccugauccug   3840
cuagaggcau gucuccuugc gugucuaaag gucccucauc cuguuuguuu uaggaauccu   3900
ggucucagga ccucauggaa gaagaggggg agagaguuac agguuggaca ugaugcacac   3960
uauggggccc cagcgacgug ucugguugag cucagggaau augguucuua gccaguuucu   4020
uggugauauc caguggcacu uguaauggcg ucuucauuca guucaugcag ggcaaaggcu   4080
```

uacugauaaa cuugagucug cccucguaug agggguguaua ccuggccucc cucugaggcu 4140
ggugacuccu cccugcuggg gccccacagg ugaggcagaa cagcuagagg gccuccccgc 4200
cugcccgccu uggcuggcua gcucgccucu ccugugcgua ugggaacacc uagcacgugc 4260
uggaugggcu gccucugacu cagaggcaug gccggauuug gcaacucaaa accaccuugc 4320
cucagcugau cagaguuucu guggaauucu guuuguuaaa ucaaauuagc uggucucuga 4380
auuaaggggg agacgaccuu cucuaagaug aacaggguuc gccccagucc uccugccugg 4440
agacaguuga ugugucaugc agagcucuua cuucuccagc aacacucuuc aguacauaau 4500
aagcuuaacu gauaaacaga auauuuagaa aggugagacu ugggcuuacc auuggguuua 4560
aaucauaggg accuagggcg aggguucagg gcuucucugg agcagauauu gucaaguuca 4620
uggccuuagg uagcauguau cuggucuuaa cucugauugu agcaaaaguu cugagaggag 4680
cugagcccug uuguggccca uuaaagaaca ggguccucag gcccugcccg cuuccugucc 4740
acugcccccu ccccaucccc agcccagccg agggaauccc gugguugcu uaccuaccua 4800 uaaggugguu uauaagcugc uguccuggcc acugcauuca aauuccaaug uguacuucau 4860
aguguaaaaa uuuauauuau ugugagguuu uuugucuuuu uuuuuuuuuu uuuuuuuugg 4920
uauauugcug uaucuacuuu aacuuccaga aauaaacguu auauaggaac cguaaaaa 4978

<210> SEQ ID NO 112
<211> LENGTH: 4953
<212> TYPE: RNA
<213> ORGANISM: HUMAN

<400> SEQUENCE: 112
gguuuccgga gcugcggcgg cgcagacugg gagggggagc cgggggguucc gacgucgcag 60 ccgagggaac aagccccaac cggauccugg acaggcaccc cggcuuggcg cugucucucc 120
cccucggcuc ggagaggccc uucggccuga gggagccucg ccgcccgucc ccggcacacg 180
cgcagccccg gccucucggc cucugccgga gaaacaggau ggcccaaugg aaucagcuac 240
agcagcuuga cacacgguac cuggagcagc uccaucagcu cuacagugac agcuucccaa 300
uggagcugcg gcaguuucug gccccuugga uugagaguca agauugggca uaugcggcca 360
gcaaagaauc acaugccacu uuggguguuuc auaaucuccu gggagagauu gaccagcagu 420
auagccgcuu ccugcaagag ucgaauguuc ucuaucagca caaucuacga agaaucaagc 480
aguuucuuca gagcagguau cuugagaagc caauggagau ugcccggauu guggcccggu 540
gccuguggga agaaucacgc cuucuacaga cugcagccac ugcggcccag caaggggggc 600
aggccaacca ccccacagca gccgugguga cggagaagca gcagaugcug gagcagcacc 660
uucaggaugu ccggaagaga gugcaggauc uagaacagaa aaugaaagug guagagaauc 720
uccaggauga cuuugauuuc aacuauaaaa cccucaagag ucaaggagac augcaagauc 780
ugaauggaaa caaccaguca gugaccaggc agaagaugca gcagcuggaa cagaugcuca 840
cugcgcugga ccagaugcgg agaagcaucg ugagugagcu ggcgggggcuu uugucagcga 900 uggaguacgu gcagaaaacu cucacggacg aggagcuggc ugacuggaag aggcggcaac 960
agauugccug cauuggaggc ccgcccaaca ucugccuaga ucggcuagaa aacuggauaa 1020
cgucauuagc agaaucucaa cuucagaccc gucaacaaau uaagaaacug gaggaguugc 1080
agcaaaaagu uuccuacaaa ggggacccca uuguacagca ccggccgaug cuggaggaga 1140
gaaucgugga gcuguuuaga aacuuaauga aaagugccuu ugugguggag cggcagcccu 1200
gcaugcccau gcauccugac cggccccucg ucaucaagac cggcguccag uucacuacua 1260
aagucagguu gcuggucaaa uucccugagu ugaauuauca gcuuaaaauu aaagugugca 1320
uugacaaaga cucuggggac guugcagcuc ucagaggauc ccggaaauuu aacauucugg 1380
gcacaaacac aaaagugaug aacauggaag aauccaacaa cggcagccuc ucugcagaau 1440
ucaaacacuu gacccugagg gagcagagau gugggaaugg gggccgagcc aauugugaug 1500
cuucccugau ugugacugag gagcugcacc ugaucaccuu ugagaccgag guguaucacc 1560
aaggccucaa gauugaccua gagacccacu ccuugccagu uguggugauc uccaacaucu 1620
gucagaugcc aaaugccugg gcguccaucc ugugguacaa caugcugacc aacaauccca 1680
agaauguaaa cuuuuuuacc aagcccccaa uuggaaccug ggaucaagug gccgaggucc 1740
ugagcuggca guucuccucc accaccaagc gaggacugag caucgagcag cugacuacac 1800
uggcagagaa acucuuggga ccugguguga auuauucagg gugucagauc acaugggcua 1860
aauuuugcaa agaaaacaug gcuggcaagg gcuucuccuu cugggucugg cuggacaaua 1920
ucauugaccu ugugaaaaag uacauccugg cccuuuggaa cgaagggguac aucaugggcu 1980 uuaucaguaa ggagcgggag cgggccaucu ugagcacuaa gccuccaggc accuuccugc 2040
uaagauucag ugaaagcagc aaagaaggag gcgucacuuu cacuugggug gagaaggaca 2100
ucagcgguaa gacccagauc caguccgugg aaccauacac aaagcagcag cugaacaaca 2160
ugucauuugc ugaaaucauc augggcuaua agaucaugga ugcuaccaau auccuggugu 2220
cuccacuggu cuaucucuau ccugacauuc ccaaggagga ggcauucgga aaguauuguc 2280
ggccagagag ccaggagcau ccugaagcug acccaggcgc ugccccauac cugaagacca 2340
aguuuaucug ugugacacca acgaccugca gcaauaccau ugaccugccg auguccccc 2400 gcacuuuaga uucauugaug caguuuggaa auaaugguga aggugcugaa cccucagcag 2460
gagggcaguu ugagucccuc accuuugaca uggaguugac cucggagugc gcuaccuccc 2520
ccaugugagg agcugagaac ggaagcugca gaaagauacg acugaggcgc cuaccugcau 2580
ucugccaccc cucacacagc caaaccccag aucaucugaa acuacuaacu uugugguucc 2640
agauuuuuuu uaaucuccua cuucugcuau cuuugagcaa ucugggcacu uuuaaaaaua 2700
gagaaaugag ugaauguggg ugaucugcuu uuaucuaaau gcaaauaagg auguguucuc 2760
ugagacccau gaucagggga uguggcgggg gguggcuaga gggagaaaaa ggaaaugucu 2820
uguguuguuu uguuccccug cccuccuuuc ucagcagcuu uuuguuauug uuguuguugu 2880
ucuuagacaa gugccuccug gugccugcgg cauccuucug ccuguuucug uaagcaaaug 2940
ccacaggcca ccuauagcua cauacuccug gcauugcacu uuuuaaccuu gcugacaucc 3000
aaauagaaga uaggacuauc uaagcccuag guuucuuuuu aaauuaagaa auaauaacaa 3060
uuaaagggca aaaaacacug uaucagcaua gccuuucugu auuuaagaaa cuuaagcagc 3120
cgggcauggu ggcucacgcc uguaauccca gcacuuuggg aggccgaggc ggaucauaag 3180
gucaggagau caagaccauc cuggcuaaca cggugaaacc ccgucucuac uaaaaguaca 3240
aaaaauuagc ugggugugggu ggugggcgcc uguaguccca gcuacucggg aggcugaggc 3300
aggagaaucg cuugaaccug agaggcggag guugcaguga gccaaaauug caccacugca 3360
cacugcacuc cauccugggc gacagucuga gacucugucu caaaaaaaaa aaaaaaaaaa 3420
agaaacuuca guuaacagcc uccuuggugc uuuaagcauu cagcuuccuu caggcuggua 3480
auuuauauaa ucccugaaac gggcuucagg ucaaacccuu aagacaucug aagcugcaac 3540
cuggccuuug guguugaaau aggaagguuu aaggagaauc uaagcauuuu agacuuuuuu 3600
uuauaaauag acuuauuuuc cuuuguaaug uauuggccuu uuagugagua aggcugggca 3660
gagggugcuu acaaccuuga cucccuuucu cccuggacuu gaucugcugu uucagaggcu 3720
agguuguuuc ugugggugcc uuaucagggc ugggauacuu cugauucugg cuuccuuccu 3780
gccccacccu cccgacccca guccccccuga uccugcuaga ggcaugucuc cuugcguguc 3840
uaaagguccc ucauccuguu uguuuuagga auccuggucu caggaccuca uggaagaaga 3900
gggggagaga guuacagguu ggacaugaug cacacuaugg ggccccagcg acgugucugg 3960
uugagcucag ggaauauggu ucuuagccag uuucuuggug auauccagug gcacuuguaa 4020
uggcgucuuc auucaguuca ugcagggcaa aggcuuacug auaaacuuga gucugcccuc 4080
guaugagggu guauaccugg ccucccucug aggcugguga cuccucccug cuggggcccc 4140
acaggugagg cagaacagcu agagggccuc cccgccugcc cgccuuggcu ggcuagcucg 4200
ccucuccugu gcguauggga acaccuagca cgugcuggau gggcugccuc ugacucagag 4260
gcauggccgg auuuggcaac ucaaaaccac cuugccucag cugaucagag uuucugugga 4320
auucuguuug uuaaaucaaa uuagcugguc ucugaauuaa gggggagacg accuucucua 4380
agaugaacag gguucgcccc aguccuccug ccuggagaca guugaugugu caugcagagc 4440
ucuuacuucu ccagcaacac ucuucaguac auaauaagcu uaacugauaa acagaauauu 4500
uagaaaggug agacuugggc uuaccauugg guuuaaauca uagggaccua gggcgagggu 4560
ucagggcuuc ucuggagcag auauugucaa guucauggcc uuagguagca uguaucuggu 4620
cuuaacucug auuguagcaa aaguucugag aggagcugag cccuguugug gcccauuaaa 4680
gaacaggguc cucaggcccu gcccgcuucc uguccacugc ccccucccca uccccagccc 4740
agccgaggga aucccguggg uugcuuaccu accuauaagg ugguuuauaa gcugcugucc 4800
uggccacugc auucaaauuc caauguguac uucauagugu aaaaauuuau auuauuguga 4860
gguuuuuugu cuuuuuuuuu uuuuuuuuuu uuugguauau ugcuguaucu acuuuaacuu 4920
ccagaaauaa acguuauaua ggaaccguaa aaa 4953

<210> SEQ ID NO 113
<211> LENGTH: 4819
<212> TYPE: RNA
<213> ORGANISM: HUMAN

<400> SEQUENCE: 113
cgcugucucu cccccucggc ucggagaggc ccuucggccu gagggagccu cgccgcccgu 60
ccccggcaca cgcgcagccc cggccucucg gccucugccg gagaaacagu ugggaccccu 120
gauuuuagca ggauggccca auggaaucag cuacagcagc uugacacacg guaccuggag 180
cagcuccauc agcucuacag ugacagcuuc ccaauggagc ugcggcaguu ucuggccccu 240
uggauugaga gucaagauug ggcauaugcg gccagcaaag aaucacaugc cacuuuggug 300
uuucauaauc uccugggaga gauugaccag caguauagcc gcuuccugca agagucgaau 360
guucucuauc agcacaaucu acgaagaauc aagcaguuuc uucagagcag guaucuugag 420
aagccaaugg agauugcccg gauuguggcc cggugccugu gggaagaauc acgccuucua 480
cagacugcag ccacugcggc ccagcaaggg ggccaggcca accaccccac agcagccgug 540
gugacggaga agcagcagau gcuggagcag caccuucagg auguccggaa gagagugcag 600
gaucuagaac agaaaaugaa agugguagag aaucuccagg augacuuuga uuucaacuau 660
aaaacccuca agagucaagg agacaugcaa gaucugaaug gaaacaacca gucagugacc 720
aggcagaaga ugcagcagcu ggaacagaug cucacugcgc uggaccagau gcggagaagc 780
aucgugagug agcuggcggg gcuuuuguca gcgauggagu acgugcagaa aacucucacg 840

-continued

```
gacgaggagc uggcugacug gaagaggcgg caacagauug ccugcauugg aggcccgccc    900
aacaucugcc uagaucggcu agaaaacugg auaacgucau uagcagaauc ucaacuucag    960
acccgucaac aaauuaagaa acuggaggag uugcagcaaa aaguuuccua caaaggggac   1020
cccauuguac agcaccggcc gaugcuggag gagagaaucg uggagcuguu uagaaacuua   1080
augaaaagug ccuuuguggu ggagcggcag cccugcaugc ccaugcaucc ugaccggccc   1140
cucgucauca agaccggcgu ccaguucacu acuaaaguca gguugcuggu caaauucccu   1200
gaguugaauu aucagcuuaa aauuaaagug ugcauugaca aagacucugg ggacguugca   1260
gcucucagag gaucccggaa auuuaacauu cugggcacaa acacaaaagu gaugaacaug   1320
gaagaaucca acaacggcag ccucucugca gaauucaaac acuugacccu gagggagcag   1380
agauguggga augggggccg agccaauugu gaugcuuccc ugauugugac ugaggagcug   1440
caccugauca ccuuugagac cgagguguau caccaaggcc ucaagauuga ccuagagacc   1500
cacuccuugc caguuguggu gaucuccaac aucugucaga ugccaaaugc cugggcgucc   1560
auccuguggu acaacaugcu gaccaacaau cccaagaaug uaaacuuuuu uaccaagccc   1620
ccaauuggaa ccugggauca aguggccgag guccugagcu ggcaguucuc cuccaccacc   1680
aagcgaggac ugagcaucga gcagcugacu acacuggcag agaaacucuu gggaccuggu   1740
gugaauuauu cagggguguca gaucacaugg gcuaaauuuu gcaaagaaaa cauggcuggc   1800
aagggcuucu ccuucugggu cuggcuggac aauaucauug accuugugaa aaaguacauc   1860
cuggcccuuu ggaacgaagg guacaucaug ggcuuuauca guaaggagcg ggagcgggcc   1920
aucuugagca cuaagccucc aggcaccuuc cugcuaagau ucagugaaag cagcaaagaa   1980
ggaggcguca cuuucacuug gguggagaag gacaucagcg guaagaccca gauccagucc   2040
guggaaccau acacaaagca gcagcugaac aacaugucau uugcugaaau caucaugggc   2100
uauaagauca uggaugcuac caauauccug gugucuccac uggucuaucu cuauccugac   2160
auucccaagg aggaggcauu cggaaaguau ugucggccag agagccagga gcauccugaa   2220
gcugacccag guagcgcugc cccauaccug aagaccaagu uuaucugugu gacaccauuc   2280
auugaugcag uuuggaaaua auggugaagg ugcugaaccc ucagcaggag ggcaguuuga   2340
gucccucacc uuugacaugg aguugaccuc ggagugcgcu accuccccca ugugaggagc   2400
ugagaacgga agcugcagaa agauacgacu gaggcgccua ccugcauucu gccacccuc   2460
acacagccaa accccagauc aucugaaacu acuaacuuug ugguuccaga uuuuuuuuaa   2520
ucuccuacuu cugcuaucuu ugagcaaucu gggcacuuuu aaaaauagag aaaugaguga   2580
auguggguga ucugcuuuua ucuaaaugca aauaaggaug uguucucuga gacccaugau   2640
caggggaugu ggcgggggggu ggcuagaggg agaaaaagga aaugucuugu guuguuuugu   2700
uccccugccc uccuuucuca gcagcuuuuu guuauuguug uuguuguucu uagacaagug   2760
ccuccuggug ccugcggcau ccuucugccu guuucuguaa gcaaaugcca caggccaccu   2820
auagcuacau acuccuggca uugcacuuuu uaaccuugcu gacauccaaa uagaagauag   2880
gacuaucuaa gcccuagguu ucuuuuuaaa uuaagaaaua auaacaauua aagggcaaaa   2940
aacacuguau cagcauagcc uuucuguauu uaagaaacuu aagcagccgg gcauggugggc   3000
ucacgccugu aaucccagca cuuugggagg ccgaggcgga ucauaagguc aggagaucaa   3060
gaccauccug gcuaacacgg ugaaaccccg ucucuacuaa aaguacaaaa aauuagcugg   3120
guguggugggu gggcgccugu agucccagcu acucgggagg cugaggcagg agaaucgcuu   3180
gaaccugaga ggcggagguu gcagugagcc aaaauugcac cacugcacac ugcacuccau   3240
```

ccugggcgac agucugagac ucugucucaa aaaaaaaaaa aaaaaaaaga aacuucaguu 3300
aacagccucc uuggugcuuu aagcauucag cuuccuucag gcugguaauu uauauaaucc 3360
cugaaacggg cuucagguca aacccuuaag acaucugaag cugcaaccug gccuuuggug 3420
uugaaauagg aagguuuaag gagaaucuaa gcauuuuaga cuuuuuuuua uaaauagacu 3480
uauuuuccuu uguaauguau uggccuuuua gugaguaagg cugggcagag ggugcuuaca 3540
accuugacuc ccuuucuccc uggacuugau cugcuguuuc agaggcuagg uuguuucugu 3600
gggugccuua ucagggcugg gauacuucug auucuggcuu ccuuccugcc ccacccuccc 3660
gaccccaguc ccccugaucc ugcuagaggc augucuccuu gcgugucuaa aggucccuca 3720
uccuguuugu uuuaggaauc cuggucucag gaccucaugg aagaagaggg ggagagaguu 3780
acagguugga caugaugcac acuaugggc cccagcgacg ugucugguug agcucaggga 3840
auaugguucu uagccaguuu cuuggugaua uccaguggca cuuguaaugg cgucuucauu 3900
caguucaugc agggcaaagg cuuacugaua aacuugaguc ugcccucgua ugagggugua 3960
uaccuggccu cccucugagg cuggugacuc cucccugcug gggccccaca ggugaggcag 4020
aacagcuaga gggccucccc gccugcccgc cuuggcuggc uagcucgccu cuccugugcg 4080
uaugggaaca ccuagcacgu gcuggauggg cugccucuga cucagaggca uggccggauu 4140
uggcaacuca aaaccaccuu gccucagcug aucagaguuu cuguggaauu cuguuuguua 4200
aaucaaauua gcuggucucu gaauuaaggg ggagacgacc uucucuaaga ugaacagggu 4260
ucgccccagu ccuccugccu ggagacaguu gaugugucau gcagagcucu uacuucucca 4320
gcaacacucu ucaguacaua auaagcuuaa cugauaaaca gaauauuuag aaaggugaga 4380
cuugggcuua ccauuggguu uaaaucauag ggaccuaggg cgaggguuca gggcuucucu 4440
ggagcagaua uugucaaguu cauggccuua gguagcaugu aucuggucuu aacucugauu 4500
guagcaaaag uucugagagg agcugagccc uguuguggcc cauuaaagaa cagggguccuc 4560 aggcccugcc cgcuuccugu ccacugcccc cuccccaucc ccagcccagc cgagggaauc 4620 ccgugggguug cuuaccuacc uauaaggugg uuuauaagcu gcuguccugg ccacugcauu 4680
caaauuccaa uguguacuuc auaguguaaa aauuuauauu auugugaggu uuuuugucuu 4740
uuuuuuuuuu uuuuuuuuuu gguauauugc uguaucuacu uuaacuucca gaaauaaacg 4800
uuauauagga accguaaaa 4819

<210> SEQ ID NO 114
<211> LENGTH: 837
<212> TYPE: RNA
<213> ORGANISM: HUMAN

<400> SEQUENCE: 114
gcuccuccug cacaccuccc ucgcucuccc acaccacugg caccaggccc cggacacccg 60
cucugcugca ggagaauggc uacucaucac acgcugugga ugggacuggc ccugcugggg 120
gugcugggcg accugcaggc agcaccggag gcccaggucu ccgugcagcc caacuuccag 180
caggacaagu uccuggggcg cugguucagc gcgggccucg ccuccaacuc gagcuggcuc 240
cgggagaaga aggcggcguu guccaugugc aagucugugg uggccccugc cacggauggu 300
ggccucaacc ugaccuccac cuuccucagg aaaaaccagu gugagacccg aaccaugcug 360
cugcagcccg cggggucccu cggcuccuac agcuaccgga gucccccacug gggcagcacc 420 uacuccgugu caguggugga gaccgacuac gaccaguacg cgcugcugua cagccagggc 480
agcaagggcc cuggcgagga cuuccgcaug gccacccucu acagccgaac ccagaccccc 540
agggcugagu uaaaggagaa auucaccgcc uucugcaagg cccagggcuu cacagaggau 600
accauugucu uccugcccca aaccgauaag ugcaugacgg aacaauagga cuccccaggg 660
cugaagcugg gaucccggcc agccaggaga cccccacgcu cuggaugucu cugcucuguu 720
ccuuccccga gccccugccc cggcuccccg ccaaagcaac ccugcccacu caggcuucau 780
ccugcacaau aaacuccgga agcaagucag uaaaaaaaaa aaaaaaaaaa aaaaaaa 837

<210> SEQ ID NO 115
<211> LENGTH: 3417
<212> TYPE: RNA
<213> ORGANISM: HUMAN

<400> SEQUENCE: 115
cggaggcagc gagaaagcgc agccaggcgg cugcucggcg uucucucagg ugacugcucg 60
gaguucuccc aguguuuggu guugcaagca ggauccaaag gagaccuaua gugacuccca 120
ggagcucuua gugaccaagu gaagguaccu guggggcuca uugugcccau ugcucuuuca 180
cugcuuucaa cugguaguug ugggguugaag cacuggacaa ugccacauac uuuguggaug 240
gugugggucu ugggggucau caucagccuc uccaaggaag aauccuccaa ucaggcuucu 300
cugucuugug accgcaaugg uaucugcaag ggcagcucag gaucuuuaaa cuccauuccc 360
ucagggcuca cagaagcugu aaaaagccuu gaccugucca acaacaggau caccuacauu 420
agcaacagug accuacagag gugugugaac cuccaggcuc uggugcugac auccaaugga 480
auuaacacaa uagaggaaga uucuuuuucu ucccugggca gucuugaaca uuuagacuua 540
uccuauaauu acuuaucuaa uuuaucgucu uccugguuca agccccuuuc uucuuuaaca 600
uucuuaaacu uacugggaaa uccuuacaaa acccuagggg aaacaucucu uuuuucucau 660
cucacaaaau ugcaaauccu gagaguggga aauauggaca ccuucacuaa gauucaaaga 720
aaagauuuug cuggacuuac cuuccuugag gaacuugaga uugaugcuuc agaucuacag 780
agcuaugagc caaaaaguuu gaagucaauu cagaauguaa gucaucugau ccuucauaug 840
aagcagcaua uuuuacugcu ggagauuuuu guagauguua caaguuccgu ggaauguuug 900
gaacugcgag auacugauuu ggacacuuuc cauuuuucag aacuauccac uggugaaaca 960
aauucauuga uuaaaaaguu uacauuuaga aaugugaaaa ucaccgauga aaguuuguuu 1020
cagguuauga aacuuuugaa ucagauuucu ggauuguuag aauuagaguu ugaugacugu 1080
acccuuaaug gaguugguaa uuuuagagca ucugauaaug acagaguuau agauccaggu 1140
aaaguggaaa cguuaacaau ccggaggcug cauauuccaa gguuuuacuu auuuuaugau 1200
cugagcacuu uauauucacu uacagaaaga guuaaaagaa ucacaguaga aaacaguaaa 1260
guuuuucugg uuccuuguuu acuuucacaa cauuuaaaau cauuagaaua cuuggaucuc 1320
agugaaaauu ugaugguuga agaauacuug aaaaauucag ccugugagga ugccuggccc 1380
ucucuacaaa cuuuaauuuu aaggcaaaau cauuuggcau cauuggaaaa aaccggagag 1440
acuuugcuca cucugaaaaa cuugacuaac auugauauca guaagaauag uuuucauucu 1500
augccugaaa cuugucagug gccagaaaag augaaauauu ugaacuuauc cagcacacga 1560
auacacagug uaacaggcug cauucccaag acacuggaaa uuuuagaugu uagcaacaac 1620
aaucucaauu uauuuucuuu gaauuugccg caacucaaag aacuuuauau uuccagaaau 1680
aaguugauga cucuaccaga ugccucccuc uuacccaugu uacuaguauu gaaaaucagu 1740
aggaaugcaa uaacuacguu uucuaaggag caacuugacu cauuucacac acugaagacu 1800
uuggaagcug guggcaauaa cuucauuugc uccugugaau uccucuccuu cacucaggag 1860

```
cagcaagcac uggccaaagu cuugauugau uggccagcaa auuaccugug ugacucucca   1920

ucccaugugc guggccagca gguucaggau guccgccucu cggugucgga augucacagg   1980

acagcacugg ugucuggcau gugcugugcu cuguuccugc ugauccugcu cacggggguc   2040

cugugccacc guuuccaugg ccugugguau augaaaauga ugugggccug gcuccaggcc   2100

aaaaggaagc ccaggaaagc ucccagcagg aacaucugcu augaugcauu uguuucuuac   2160

agugagcggg augccuacug gguggagaac cuuauggucc aggagcugga gaacuucaau   2220

ccccccuuca aguuguguca ucauaagcgg gacuucauuc cuggcaagug gaucauugac   2280

aauaucauug acuccauuga aaagagccac aaaacugucu uugugcuuuc ugaaaacuuu   2340

gugaagagug aguggugcaa guaugaacug gacuucuccc auuuccgucu uuuugaugag   2400

aacaaugaug cugccauucu cauucuucug gagcccauug agaaaaaagc cauuccccag   2460

cgcuucugca agcugcggaa gauaaugaac accaagaccu accuggagug gcccauggac   2520

gaggcucagc gggaaggauu uuggguaaau cugagagcug cgauaaaguc cuagguuccc   2580

auauuuaaga ccagucuuug ucuaguuggg aucuuuaugu cacuaguuau aguuaaguuc   2640

auucagacau aauuauauaa aaacuacgug gauguaccgu cauuugagga cuugcuuacu   2700

aaaacuacaa aacuucaaau uuugucuggg gugcuguuuu auaaacauau gccagauuua   2760

aaaauugguu uuugguuuuu cuuuuuucua ugagauaacc augaucauaa gucuauuacu   2820

gauaucugaa uauagucccu ugguauccaa gggaauuggu ugcaggaucc ucguggauau   2880

caaaauucau agaugaucaa gucccuuaua agaguggcau aguauuugca uauaaccugu   2940

guacauucuc cuguauacuu uaaaucaucu cuagauuacu uaugauaccc aauacaaugu   3000

aaauacuaug uaaauaguug uacugucuuu uuauuuauau uauuauuguu auuuuuuauu   3060

uucaaaauuu uuaaaacaua cuuuugaucc acaguugguu gacuucaugg augcagaacc   3120

cauggauaua gagggccaac uguaaucugu agcaacuggc uuaguucauu aggaaacagc   3180

acaaaugaac uuaagauucu caaugacugu gucauucuuu cuuccugcua agagacuccu   3240

cuguggccac aaaaggcauu cucuguccua ccuagcuguc acuucucugu gcagcugauc   3300

ucaagagcaa caaggcaaag uauuuggggc acuccccaaa acuuguugcu auuccuagaa   3360

aaaagugcug uguauuuccu auuaaacuuu acaggaugag aaaaaaaaaa aaaaaaa      3417
```

<210> SEQ ID NO 116
<211> LENGTH: 19
<212> TYPE: RNA
<213> ORGANISM: Artificial
<220> FEATURE:
<223> OTHER INFORMATION: Chemically synthesized

<400> SEQUENCE: 116

```
gaagaaaauu uccgcaaaa                                                 19
```

<210> SEQ ID NO 117
<211> LENGTH: 19
<212> TYPE: RNA
<213> ORGANISM: Artificial
<220> FEATURE:
<223> OTHER INFORMATION: Chemically synthesized

<400> SEQUENCE: 117

```
uuuugcggaa auuuucuuc                                                 19
```

<210> SEQ ID NO 118
<211> LENGTH: 19
<212> TYPE: RNA

-continued

```
<213> ORGANISM: Artificial
<220> FEATURE:
<223> OTHER INFORMATION: Chemically synthesized

<400> SEQUENCE: 118

gagaauauuu cacccuuca                                     19


<210> SEQ ID NO 119
<211> LENGTH: 19
<212> TYPE: RNA
<213> ORGANISM: Artificial
<220> FEATURE:
<223> OTHER INFORMATION: Chemically synthesized

<400> SEQUENCE: 119

ugaaggguga aauauucuc                                     19
```